(12) United States Patent
Shioda et al.

(10) Patent No.: US 9,560,850 B2
(45) Date of Patent: Feb. 7, 2017

(54) TETRAZOLINONE COMPOUND AND USE THEREOF

(71) Applicant: SUMITOMO CHEMICAL COMPANY, LIMITED, Tokyo (JP)

(72) Inventors: Takayuki Shioda, Takarazuka (JP); Sadayuki Arimori, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 11 days.

(21) Appl. No.: 14/654,575

(22) PCT Filed: Dec. 24, 2013

(86) PCT No.: PCT/JP2013/085307
§ 371 (c)(1),
(2) Date: Jun. 22, 2015

(87) PCT Pub. No.: WO2014/104384
PCT Pub. Date: Jul. 3, 2014

(65) Prior Publication Data
US 2015/0336908 A1   Nov. 26, 2015

(30) Foreign Application Priority Data
Dec. 27, 2012   (JP) ................................ 2012-284305

(51) Int. Cl.
*A01N 43/713* (2006.01)
*C07D 257/04* (2006.01)

(52) U.S. Cl.
CPC ........... *A01N 43/713* (2013.01); *C07D 257/04* (2013.01)

(58) Field of Classification Search
None
See application file for complete search history.

(56) References Cited

U.S. PATENT DOCUMENTS

| 6,583,090 | B1 | 6/2003 | Gewehr et al. |
| 7,056,941 | B1 | 6/2006 | Muller et al. |
| 2004/0242895 | A1 | 12/2004 | Yanagi et al. |
| 2015/0031733 | A1 | 1/2015 | Yoshimoto et al. |
| 2015/0051171 | A1 | 2/2015 | Yoshimoto et al. |
| 2015/0203511 | A1 | 7/2015 | Arimori et al. |
| 2015/0223460 | A1 | 8/2015 | Arimori et al. |
| 2015/0299146 | A1 | 10/2015 | Hasegawa et al. |

FOREIGN PATENT DOCUMENTS

| CN | 1370153 A | 9/2002 |
| JP | 9208565 A | 8/1997 |
| JP | 2002506060 A | 2/2002 |
| JP | 2003509415 A | 3/2003 |
| WO | 9636229 A1 | 11/1996 |
| WO | 0119803 A1 | 3/2001 |
| WO | 2013092224 A1 | 6/2013 |
| WO | 2013162072 A1 | 10/2013 |
| WO | 2013162077 A1 | 10/2013 |
| WO | 2014051161 A1 | 4/2014 |
| WO | 2014051165 A1 | 4/2014 |
| WO | 2014084223 A1 | 6/2014 |
| WO | 2014104268 A1 | 7/2014 |
| WO | 2014104382 A1 | 7/2014 |
| WO | 2014175465 A1 | 10/2014 |
| WO | 2014192953 A1 | 12/2014 |
| WO | 2015005499 A1 | 1/2015 |
| WO | 2015016372 A1 | 2/2015 |
| WO | 2015016373 A1 | 2/2015 |

OTHER PUBLICATIONS

Communication dated Jan. 12, 2016 from the Intellectual Property Office of the P.R. China issued in corresponding Application No. 201380067789.6.
English Translation of International Preliminary Report on Patentability dated Jun. 30, 2015 from the International Searching Authority in counterpart International application No. PCT/JP2013/085307.
Communication dated Apr. 15, 2016 from the European Patent Office issued in corresponding Application No. 13866807.4.

*Primary Examiner* — Alicia L Otton
(74) *Attorney, Agent, or Firm* — Sughrue Mion, PLLC

(57) ABSTRACT

Disclosed is a tetrazolinone compound having a high pest control effect and represented by the formula (1):

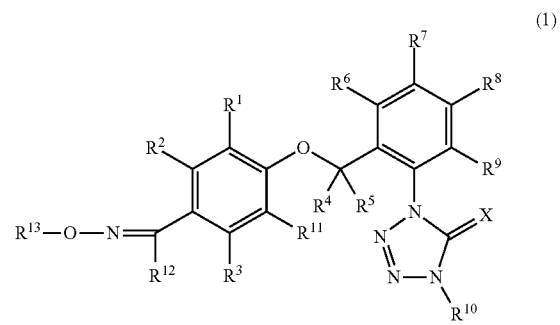

wherein $R^1$, $R^2$, $R^3$, and $R^{11}$ each represent a halogen atom, a C1-C6 alkyl group, or the like; $R^4$ and $R^5$ each represent a hydrogen atom, a halogen atom, a C1-C3 alkyl group, or the like; $R^6$ represents a C1-C3 alkyl group which may have a halogen atom(s) or the like; $R^7$, $R^8$, and $R^9$ each represent a hydrogen atom, a halogen atom, or the like; $R^{10}$ represents a C1-C3 alkyl group or the like; $R^{12}$ represents a C1-C6 alkyl group, a C3-C6 cycloalkyl group, or the like, and $R^{13}$ represents a C1-C6 alkyl group, a C2-C6 alkenyl group, or the like.

9 Claims, No Drawings

TETRAZOLINONE COMPOUND AND USE THEREOF

CROSS REFERENCE TO RELATED APPLICATIONS

This application is a National Stage of International Application No. PCT/JP2013/085307 filed Dec. 24, 2013, claiming priority based on Japanese Patent Application No. 2012-284305 filed Dec. 27, 2012, the contents of all of which are incorporated herein by reference in their entirety.

TECHNICAL FIELD

The present invention relates to a tetrazolinone compound and its applications.

BACKGROUND ART

Various types of chemicals have been developed so far to control pests and put to practical use. However, these chemicals are not always satisfactory.

In the meantime, a compound represented by 1-{2-[2-methyl-4-(1-methoxyimino-ethyl)-phenoxymethyl]-phenyl}-4-methyl-1,4-dihydrotetrazol-5-one (the following formula (A)) is known as a compound having a tetrazolinone ring (see JP-A-09-208565).

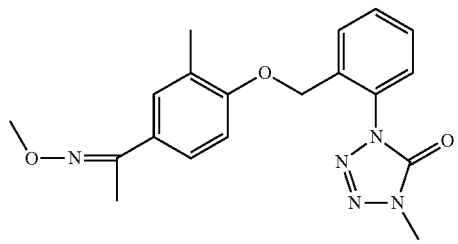

(A)

DISCLOSURE OF THE INVENTION

The present invention provides a compound having a high control effect on pests.

The present inventors have studied to find a compound having a high control effect on pests, and, as the result, found that a tetrazolinone compound represented by the following formula (1) has a high control effect on pests, and thereby completed the present invention.

The compound of the present invention (hereinafter referred to as "compound of the present invention") is a tetrazolinone compound represented by the formula (1).

[1] A tetrazolinone compound represented by the formula (1):

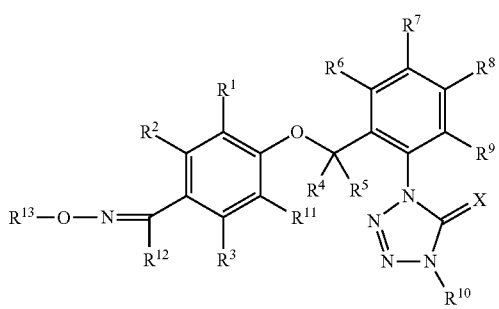

(1)

wherein $R^1$, $R^2$, $R^3$, and $R^{11}$ each represent a hydrogen atom, a halogen atom, a cyano group, a nitro group, an amino group, a hydroxy group, a thiol group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a C3-C12 trialkylsilyl group, a C2-C6 alkylcarbonyl group, a C2-C6 alkoxycarbonyl group, or a C2-C9 alkylaminocarbonyl group,
a C1-C6 alkyl group which may have a group selected from the group $P^1$, or
a C3-C6 cycloalkyl group which may have a group selected from the group $P^1$;

$R^4$ and $R^5$ each represent a hydrogen atom, a halogen atom, or a C1-C3 alkyl group;

$R^6$ represents a C1-C4 alkyl group which may have a halogen atom(s), a halogen atom, a C1-C4 alkoxy group which may have a halogen atom(s), a C2-C4 alkenyl group, a C2-C4 haloalkenyl group, a C2-C4 alkynyl group, a C2-C4 haloalkynyl group, a C1-C4 alkylthio group, a C1-C4 haloalkylthio group, a C3-C6 cycloalkyl group or a C3-C6 halocycloalkyl group, a cyano group, a nitro group, a C1-C4 alkylsulfinyl group, a C1-C4 alkylsulfonyl group, a C1-C4 haloalkylsulfinyl group, a C1-C4 haloalkylsulfonyl group, a C1-C6 alkylamino group, or a C1-C6 haloalkylamino group;

$R^7$, $R^8$, and $R^9$ each represent a hydrogen atom, a halogen atom, a C1-C3 alkyl group, a C1-C3 haloalkyl group, a C2-C3 alkenyl group, a C2-C3 haloalkenyl group, a C1-C3 alkoxy group, or a C1-C3 haloalkoxy group;

$R^{10}$ represents a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;

X represents an oxygen atom or a sulfur atom;

$R^{12}$ represents
a C1-C6 alkyl group which may have a group selected from the group $P^1$,
a C3-C6 cycloalkyl group which may have a group selected from the group $P^1$,
a phenyl group which may have a group selected from the group $P^2$,
a hydrogen atom, a halogen atom, a cyano group, a nitro group, an amino group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C6 cycloalkenyl group, a C3-C6 halocycloalkenyl group, a C1-C8 alkylamino group, a C3-C12 trialkylsilyl group, a C2-C6 alkylcarbonyl group, a C2-C6 alkoxycarbonyl group, or a C2-C9 alkylaminocarbonyl group;

$R^{13}$ represents a C1-C8 alkyl group, a C1-C8 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C3-C6 cycloalkenyl group, or a C3-C6 halocycloalkenyl group, or
a benzyl group which may have a group selected from the group $P^2$;

Group $P^1$: Group consisting of a halogen atom, a cyano group, a C3-C6 cycloalkyl group, a C3-C6 halocycloalkyl group, a C1-C4 alkoxy group, a C1-C4 haloalkoxy group, a C1-C4 alkylthio group, and a C1-C4 haloalkylthio group; and Group P²: Group consisting of a halogen atom, a cyano group, an amino group, a hydroxy group, thiol group, a C1-C6 alkyl group, a C1-C6 haloalkyl group, a C3-C6 cycloalkyl group, a C3-C6 halocycloalkyl group, a C2-C6 alkenyl group, a C2-C6 haloalkenyl group, a C2-C6 alkynyl group, a C1-C6 alkoxy group, a C1-C6 haloalkoxy group, a C1-C8 alkylamino group, a C1-C6 alkylthio group, a C1-C6 haloalkylthio group, a C1-C6 alkylsulfinyl group, a C1-C6 alkylsulfonyl group, a pentafluorosulfanyl group, a C3-C12 trialkylsilyl group, a C2-C6 alkylcarbonyl group, a C2-C6 alkoxycarbonyl group, and a C2-C9 alkylaminocarbonyl group.

[2] The tetrazolinone compound according to the above [1], wherein $R^1$ is a C1-C3 alkyl group which may have a halogen atom(s), a halogen atom, a C3-C5 cycloalkyl group, a C1-C3 alkoxy group, a C2-C3 alkynyl group, a C2-C3 haloalkynyl group, a C3-C5 halocycloalkyl group, or a C1-C3 haloalkoxy group, $R^2$, $R^4$, $R^5$, $R^7$, $R^8$, $R^9$, and $R^{11}$ are each a hydrogen atom;

$R^3$ is a halogen atom, a C1-C3 alkyl group, a C1-C3 haloalkyl group, or a hydrogen atom;

$R^6$ is a C1-C3 alkyl group which may have a halogen atom(s) a halogen atom, a C1-C3 alkoxy group which may have a halogen atom(s), a C2-C4 alkenyl group, a C2-C4 haloalkenyl group, a C2-C4 alkynyl group, a C2-C4 haloalkynyl group, a C1-C4 alkylthio group, a C1-C4 haloalkyl thio group, a C3-C6 cycloalkyl group, or a C3-C6 halocycloalkyl group;

$R^{10}$ is a methyl group; and

X is an oxygen atom.

[3] The tetrazolinone compound according to the above [1] or [2], wherein $R^{12}$ is a C1-C6 alkyl group which may have a halogen atom(s), a C3-C6 cycloalkyl group which may have a halogen atom(s), a phenyl group which may have a group selected from the group P³, a C2-C6 alkenyl group, a C2-C6 haloalkynyl group, a C1-C6 alkoxy group, a C1-C6 haloalkoxy group, or a C3-C6 halocycloalkyl group; and Group P³: Group consisting of a hydrogen atom, a halogen atom, a C1-C3 alkyl group, and a C1-C3 haloalkyl group.

[4] The tetrazolinone compound according to anyone of the above [1] to [3], wherein $R^{13}$ is a C1-C6 alkyl group which may have a halogen atom(s), a C2-C6 alkenyl group, a C2-C6 haloalkenyl group, a C2-C6 alkynyl group, a C2-C6 haloalkynyl group, a C3-C6 cycloalkyl group, a C3-C6 cycloalkenyl group, or a benzyl group which may have a group selected from the group P³.

[5] The tetrazolinone compound according to anyone of the above [1] to [4], wherein $R^{12}$ is a C1-C6 alkyl group which may have a halogen atom(s), a C3-C6 cycloalkyl group which may have a halogen atom(s), a phenyl group, or a hydrogen atom.

[6] The tetrazolinone compound according to anyone of the above [1] to [5], wherein $R^{13}$ is a C1-C6 alkyl group which may have a halogen atom(s), a C2-C6 alkenyl group, a C2-C6 alkynyl group, a benzyl group, or a C3-C6 cycloalkyl group.

[7] The tetrazolinone compound according to anyone of the above [1] to [6], wherein $R^1$ is a C1-C3 alkyl group which may have a halogen atom(s), or a halogen atom;

$R^3$ is a hydrogen atom or a methyl group; and $R^6$ is a C1-C3 alkyl group which may have a halogen atom(s), a C1-C3 alkoxy group which may have a halogen atom(s), a cyclopropyl group, or a halogen atom.

[8] A pest control agent comprising the tetrazolinone compound according to any one of the [1] to [7] above.

[9] A pest control method comprising treating plants or soils with an effective amount of the tetrazolinone compound as defined in any one of the [1] to [7] above.

[10] Use of the tetrazolinone compound as defined in any one of the above [1] to [7] to control pests.

Pests can be controlled by the present invention.

MODE FOR CARRYING OUT THE INVENTION

The details of the substituents in this description are shown below.

Examples of the halogen atom include a fluorine atom, chlorine atom, bromine atom, and iodine atom.

The C1-C8 alkyl group represents a linear or branched C1-C8 alkyl group and examples of the alkyl group include, for example, a methyl group, ethyl group, propyl group, isopropyl group, butyl group, isobutyl group, sec-butyl group, tert-butyl group, pentyl group, neopentyl group, hexyl group, heptyl group, and octyl group.

The C1-C6 alkyl group represents a linear or branched C1-C6 alkyl group and examples of the alkyl group include, for example, a methyl group, ethyl group, propyl group, isopropyl group, butyl group, isobutyl group, sec-butyl group, tert-butyl group, pentyl group, neopentyl group, and hexyl group.

Examples of the C1-C3 alkyl group include, for example, a methyl group, ethyl group, propyl group, or isopropyl group.

The C1-C8 haloalkyl group represents a linear or branched C1-C8 alkyl group in which at least one of hydrogen atoms is substituted with a halogen atom. Examples of the C1-C8 haloalkyl groups include, for example, a monofluoromethyl group, monochloromethyl group, dichloromethyl group, difluoromethyl group, trifluoromethyl group, trichloromethyl group, tribromomethyl group, 2,2,2-trifluoroethyl group, 2,2,2-trichloroethyl group, pentafluoroethyl group, chlorofluoromethyl group, dichlorofluoromethyl group, chlorodifluoromethyl group, 2,2-difluoroethyl group, 2-chloro-2-fluoroethyl group, 2-chloro-2,2-difluoroethyl group, 2,2-dichloro-2-fluoroethyl group, 2-fluoropropyl group, 3-fluoropropyl group, 2,2-difluoropropyl group, 3,3,3-trifluoropropyl group, 1-(fluoromethyl)-2-fluoroethyl group, 4-fluorobutyl group, and 2,2-difluorohexyl group.

The C1-C6 haloalkyl group represents a linear or branched C1-C6 alkyl group in which at least one of hydrogen atoms is substituted with a halogen atom. Examples of the C1-C6 haloalkyl groups include, for example, a monofluoromethyl group, monochloromethyl group, dichloromethyl group, difluoromethyl group, trifluoromethyl group, trichloromethyl group, tribromomethyl group, 2,2,2-trifluoroethyl group, 2,2,2-trichloroethyl group, pentafluoroethyl group, chlorofluoromethyl group, dichlorofluoromethyl group, chlorodifluoromethyl group, 2,2-difluoroethyl group, 2-chloro-2-fluoroethyl group, 2-chloro-2,2-difluoroethyl group, 2,2-dichloro-2-fluoroethyl group, 2-fluoropropyl group, 3-fluoropropyl group, 2,2-difluoropropyl group, 3,3,3-trifluoropropyl group, 1-(fluoromethyl)-2-fluoroethyl group, 4-fluorobutyl group, and 2,2-difluorohexyl group.

Examples of the C1-C3 haloalkyl group include, for example, a chloromethyl group, dichloromethyl group, fluoromethyl group, difluoromethyl group, chlorofluoromethyl group, dichlorofluoromethyl group, chlrodifluoromethyl group, trifluoromethyl group, trichloromethyl group, tribromomethyl group, 2-fluoroethyl group, 2,2-difluoroethyl group, 2,2,2-trifluoroethyl group, 2-chloroethyl group, 2,2-dichloroethyl group, 2,2,2-trichloroethyl group, pentafluoroethyl group, pentachloroethyl group, 2-chloro-2-fluoroethyl group, 2-chloro-2,2-difluoroethyl group, 2-fluoropropyl group, 3-fluoropropyl group, 2,2-difluoropropyl group, 2,3-difluoropropyl group, 3,3,3-trifluoropropyl group, heptafluoropropyl group, and 1-(fluoromethyl)-2-fluoroethyl group.

The C1-C6 alkyl group which may have a halogen atom(s) represents a C1-C6 alkyl group which may be linear or branched and in which a hydrogen atom(s) may be substituted with a halogen atom(s). Examples of the C1-C6 alkyl group include, for example, a methyl group, ethyl group, propyl group, isopropyl group, butyl group, isobutyl group, sec-butyl group, tert-butyl group, pentyl group, neopentyl group, hexyl group, monofluoromethyl group, monochloromethyl group, dichloromethyl group, difluoromethyl group, trifluoromethyl group, trichloromethyl group, tribromomethyl group, 2,2,2-trifluoroethyl group, 2,2,2-trichloroethyl group, pentafluoroethyl group, chlorofluoromethyl group, dichlorofluoromethyl group, chlorodifluoromethyl group, 2,2-difluoroethyl group, 2-chloro-2-fluoroethyl group, 2-chloro-2,2-difluoroethyl group, 2,2-dichloro-2-fluoroethyl group, 2-fluoropropyl group, 3-fluoropropyl group, 2,2-difluoropropyl group, 3,3,3-trifluoropropyl group, 1-(fluoromethyl)-2-fluoroethyl group, 4-fluorobutyl group, and 2,2-difluorohexyl group.

The C1-C4 alkyl group which may have a halogen atom(s) represents a C1-C4 alkyl group which may be linear or branched and in which a hydrogen atom(s) may be substituted with a halogen atom(s). Examples of the C1-C4 alkyl group which may have a halogen atom(s) include, for example, a methyl group, ethyl group, propyl group, isopropyl group, butyl group, isobutyl group, sec-butyl group, tert-butyl group, chloromethyl group, dichloromethyl group, fluoromethyl group, difluoromethyl group, chlorofluoromethyl group, dichlorofluoromethyl group, chlorodifluoromethyl group, trifluoromethyl group, trichloromethyl group, tribromomethyl group, 2-fluoroethyl group, 2,2-difluoroethyl group, 2,2,2-trifluoroethyl group, 2-chloroethyl group, 2,2-dichloroethyl group, 2,2,2-trichloroethyl group, pentafluoroethyl group, pentachloroethyl group, 2-chloro-2-fluoroethyl group, 2-chloro-2,2-difluoroethyl group, 2-fluoropropyl group, 3-fluoropropyl group, 2,2-difluoropropyl group, 2,3-difluoropropyl group, 3,3,3-trifluoropropyl group, heptafluoropropyl group, 1-(fluoromethyl)-2-fluoroethyl group, and 4-fluorobutyl group.

The C1-C3 alkyl group which may have a halogen atom(s) represents a C1-C3 alkyl group which may be linear or branched and in which a hydrogen atom(s) may be substituted with a halogen atom(s). Examples of the C1-C3 alkyl group which may have a halogen atom(s) include, for example, a methyl group, ethyl group, propyl group, isopropyl group, chloromethyl group, dichloromethyl group, fluoromethyl group, difluoromethyl group, chlorofluoromethyl group, dichlorofluoromethyl group, chlorodifluoromethyl group, trifluoromethyl group, trichloromethyl group, tribromomethyl group, 2-fluoroethyl group, 2,2-difluoroethyl group, 2,2,2-trifluoroethyl group, 2-chloroethyl group, 2,2-dichloroethyl group, 2,2,2-trichloroethyl group, pentafluoroethyl group, pentachloroethyl group, 2-chloro-2-fluoroethyl group, 2-chloro-2,2-difluoroethyl group, 2-fluoropropyl group, 3-fluoropropyl group, 2,2-difluoropropyl group, 2,3-difluoropropyl group, 3,3,3-trifluoropropyl group, heptafluoropropyl group, and 1-(fluoromethyl)-2-fluoroethyl group.

The C3-C6 cycloalkyl group represents a C3-C6 cyclic alkyl group and includes, for example, a cycloalkyl group having an alkyl group or groups. Examples of the C3-C6 cycloalkyl group include, for example, a cyclopropyl group, cyclobutyl group, cyclopentyl group, cyclohexyl group, 1-methylcyclopropyl group, 2-methylcyclopropyl group, 2,2-dimethylcyclopropyl group, and 2,3-dimethylcyclopropyl group.

The C3-C5 cycloalkyl group represents C3-C5 cyclic alkyl groups and includes cycloalkyl groups having alkyl groups. Examples of the C3-C5 cycloalkyl group include, for example, a cyclopropyl group, cyclobutyl group, cyclopentyl group, 1-methylcyclopropyl group, 2-methylcyclopropyl group, 2,2-dimethylcyclopropyl group, and 2,3-dimethylcyclopropyl group.

The C3-C6 halocycloalkyl group represents a C3-C6 cycloalkyl group in which at least one hydrogen atom is substituted with a halogen atom. Examples of the C3-C6 halocycloalkyl group include, for example, a 1-fluorocyclopropyl group, 2-fluorocyclopropyl group, 2,2-difluorocyclopropyl group, 1-chlorocyclopropyl group, 2-chloro-2-fluorocyclopropyl group, 2,2-dichlorocyclopropyl group, 2,2-dibromocyclopropyl group, 2,2-difluoro-1-methylcyclopropyl group, 2,2-dichloro-1-methylcyclopropyl group, 2,2-dibromo-1-methylcyclopropyl group, 1-(trifluoromethyl)cyclopropyl group, 2,2,3,3-tetrafluorocyclobutyl group, 1-fluorocyclobutyl group, 1-chlorocyclobutyl group, 2,2,3,3-tetrafluorocyclobutyl group, 2-chlorocyclopentyl group, 3-chlorocyclopentyl group, 3,3-difluorocyclopentyl group, 1-fluorocyclohexyl group, 2,2-difluorocyclohexyl group, 3,3-difluorocyclohexyl group, and 4,4-difluorocyclohexyl group.

The C3-C5 halocycloalkyl group represents a C3-C5 cycloalkyl group in which at least one hydrogen atom is substituted with a halogen atom. Examples of the C3-C5 halocycloalkyl group include, for example, a 1-fluorocyclopropyl group, 2-fluorocyclopropyl group, 2,2-difluorocyclopropyl group, 1-chlorocyclopropyl group, 2-chloro-2-fluorocyclopropyl group, 2,2-dichlorocyclopropyl group, 2,2-dibromocyclopropyl group, 2,2-difluoro-1-methylcyclopropyl group, 2,2-dichloro-1-methylcyclopropyl group, 2,2-dibromo-1-methylcyclopropyl group, 1-(trifluoromethyl)cyclopropyl group, 2,2,3,3-tetrafluorocyclobutyl group, 2,2,3,3-tetrafluorocyclobutyl group, 2-chlorocyclopentyl group, and 3-chlorocyclopentyl group.

The C3-C6 cycloalkyl group which may have a halogen atom(s) represents a C1-C6 cyclic alkyl group in which a hydrogen atom(s) may be substituted with a halogen atom(s). Examples of the C3-C6 cycloalkyl group include, for example, a cyclopropyl group, cyclobutyl group, cyclopentyl group, cyclohexyl group, 1-methylcyclopropyl group, 2-methylcyclopropyl group, 2,2-dimethylcyclopropyl group, 2,3-dimethylcyclopropyl group, 1-fluorocyclopropyl group, 2-fluorocyclopropyl group, 2,2-difluorocyclopropyl group, 1-chlorocyclopropyl group, 2-chloro-2-fluorocyclopropyl group, 2,2-dichlorocyclopropyl group, 2,2-dibromocyclopropyl group, 2,2-difluoro-1-methylcyclopropyl group, 2,2-dichloro-1-methylcyclopropyl group, 2,2-dibromo-1-methylcyclopropyl group, 1-(trifluoromethyl)cyclopropyl group, 2,2,3,3-tetrafluorocyclobutyl group, 1-fluorocyclobutyl group, 1-chlorocyclobutyl group, 2,2,3,3-tetrafluorocyclobutyl group, 2-chlorocyclopentyl group, 3-chlorocyclopentyl group, 3,3-difluorocyclopentyl group, 1-fluorocyclohexyl group, 2,2-difluorocyclohexyl group, 3,3-difluorocyclohexyl group, and 4,4-difluorocyclohexyl group.

The C3-C6 cycloalkenyl group represents a C3-C6 cyclic alkenyl group and includes a cycloalkenyl groups having an alkyl group. Examples of the C3-C6 cycloalkenyl group include, for example, a cyclopropenyl group, cyclobutenyl group, cyclopentenyl group, cyclohexenyl group, and 2-methylcyclopentenyl group.

The C3-C6 halocycloalkenyl group represents a C3-C6 cycloalkenyl group in which at least one hydrogen atom is substituted with a halogen atom. Examples of the C3-C6 halocycloalkenyl group include, for example, 1-fluorocyclopropenyl group, 2-chlorocyclobutenyl group, 2-chlorocyclopentenyl group, and 2-chlorocyclohexenyl group.

The C2-C6 alkenyl group represents a linear or branched C2-C6 alkenyl group. Examples of the C2-C6 alkenyl group include, for example, a vinyl group, 1-propenyl group, isopropenyl group, 2-propenyl group, 1-butenyl group, 1-methyl-1-propenyl group, 2-butenyl group, 1-methyl-2-propenyl group, 3-butenyl group, 2-methyl-1-propenyl group, 2-methyl-2-propenyl group, 1,3-butadienyl group, 1-pentenyl group, 1-ethyl-2-propenyl group, 2-pentenyl group, 1-methyl-1-butenyl group, 3-pentenyl group, 1-methyl-2-butenyl group, 4-pentenyl group, 1-methyl-3-butenyl group, 3-methyl-1-butenyl group, 1,2-dimethyl-2-propenyl group, 1,1-dimethyl-2-propenyl group, 2-methyl-2-butenyl group, 3-methyl-2-butenyl group, 1,2-dimethyl-1-propenyl group, 2-methyl-3-butenyl group, 3-methyl-3-butenyl group, 1,3-pentadienyl group, 1-vinyl-2-propenyl group, 1-hexenyl group, and 5-hexenyl group.

The C2-C6 haloalkenyl group represents a linear or branched C2-C6 alkenyl groups in which at least one hydrogen atom is substituted with a halogen atom. Examples of the C2-C6 haloalkenyl group include, for example, a 2-chlorovinyl group, 2-bromovinyl group, 2-iodovinyl group, 3-chloro-2-propenyl group, 3-bromo-2-propenyl group, 1-chloromethylvinyl group, 2-bromo-1-methylvinyl group, 1-trifluoromethylvinyl group, 3,3,3-trichloro-1-propenyl group, 3-bromo-3,3-difluoro-1-propenyl group, 2,3,3,3-tetrachloro-1-propenyl group, 1-trifluoromethyl-2,2-difluorovinyl group, 2-chloro-2-propenyl group, 3,3-difluoro-2-propenyl group, 2,3,3-trichloro-2-propenyl group, 4-bromo-3-chloro-3,4,4-trifluoro-1-butenyl group, 1-bromomethyl-2-propenyl group, 3-chloro-2-butenyl group, 4,4,4-trifluoro-2-butenyl group, 4-bromo-4,4-difluoro-2-butenyl group, 3-bromo-3-butenyl group, 3,4,4-trifluoro-3-butenyl group, 3,4,4-tribromo-3-butenyl group, 3-bromo-2-methyl-2-propenyl group, 3,3-difluoro-2-methyl-2-propenyl group, 3,3,3-trifluoro-2-methyl-1-propenyl group, 3-chloro-4,4,4-trifluoro-2-butenyl group, 3,3,3-trifluoro-1-methyl-1-propenyl group, 3,4,4-trifluoro-1,3-butadienyl group, 3,4-dibromo-1-pentenyl group, 4,4-difluoro-3-methyl-3-butenyl group, 3,3,4,4,5,5,5-heptafluoro-1-pentenyl group, 5,5-difluoro-4-pentenyl group, 4,5,5-trifluoro-4-pentenyl group, 3,4,4,4-tetrafluoro-3-trifluoromethyl-1-butenyl group, 4,4,4-trifluoro-3-methyl-2-butenyl group, 3,5,5-trifluoro-2,4-pentadienyl group, 4,4,5,5,6,6,6-heptafluoro-2-hexenyl group, 3,4,4,5,5-hexafluoro-3-trifluoromethyl-1-pentenyl group, 4,5,5,5-tetrafluoro-4-trifluoromethyl-2-pentenyl group, 5-bromo-4,5,5-trifluoro-4-trifluoromethyl-2-pentenyl group.

Examples of the C2-C4 alkenyl group include, for example, a vinyl group, 1-propenyl group, isopropenyl group, 2-propenyl group, 1-butenyl group, 1-methyl-1-propenyl group, 2-butenyl group, 1-methyl-2-propenyl group, 3-butenyl group, 2-methyl-1-propenyl group, and 2-methyl-2-propenyl group.

The C2-C4 haloalkenyl group represents a linear or branched C2-C4 alkenyl group in which at least one hydrogen atom is substituted with a halogen atom. Examples of the C2-C4 haloalkenyl group include, for example, 2-chlorovinyl group, 2-bromovinyl group, 2-iodovinyl group, 3-chloro-2-propenyl group, 3-bromo-2-propenyl group, 1-chloromethylvinyl group, 2-bromo-1-methylvinyl group, 1-trifluoromethylvinyl group, 3,3,3-trichloro-1-propenyl group, 3-bromo-3,3-difluoro-1-propenyl group, 2,3,3,3-tetrachloro-1-propenyl group, 1-trifluoromethyl-2,2-difluorovinyl group, 2-chloro-2-propenyl group, 3,3-difluoro-2-propenyl group, 2,3,3-trichloro-2-propenyl group, 4-bromo-3-chloro-3,4,4-trifluoro-1-butenyl group, 1-bromomethyl-2-propenyl group, 3-chloro-2-butenyl group, 4,4,4-trifluoro-2-butenyl group, 4-bromo-4,4-difluoro-2-butenyl group, 3-bromo-3-butenyl group, 3,4,4-trifluoro-3-butenyl group, 3,4,4-tribromo-3-butenyl group, 3-bromo-2-methyl-2-propenyl group, 3,3-difluoro-2-methyl-2-propenyl group, 3,3,3-trifluoro-2-methyl-1-propenyl group, 3-chloro-4,4,4-trifluoro-2-butenyl group, 3,3,3-trifluoro-1-methyl-1-propenyl group, and 3,4,4-trifluoro-1,3-butadienyl group.

Examples of the C2-C3 alkenyl group include, for example, a vinyl group, 1-propenyl group, isopropenyl group, and 2-propenyl group.

Examples of the C2-C3 haloalkenyl group include, for example, 2-chlorovinyl group, 2-bromovinyl group, 2-iodovinyl group, 3-chloro-2-propenyl group, 3-bromo-2-propenyl group, 1-chloromethylvinyl group, 2-bromo-1-methylvinyl group, 1-trifluoromethylvinyl group, 3,3,3-trichloro-1-propenyl group, 3-bromo-3,3-difluoro-1-propenyl group, 2,3,3,3-tetrachloro-1-propenyl group, 1-trifluoromethyl-2,2-difluorovinyl group, 2-chloro-2-propenyl group, 3,3-difluoro-2-propenyl group, and 2,3,3-trichloro-2-propenyl group.

The C2-C6 alkynyl group represents a C2-C6 alkynyl group which may be linear or branched. Examples of the C2-C6 alkynyl group include, for example, an ethynyl group, propargyl group, 1-butyn-3-yl group, 3-methyl-1-butyn-3-yl group, 2-butynyl group, 3-butynyl group, 2-pentynyl group, 3-pentynyl group, 4-pentynyl group, 1-hexynyl group, and 5-hexynyl group.

The C2-C6 haloalkynyl group represents a linear or branched C2-C6 alkynyl group in which at least one hydrogen atom is substituted with a halogen atom. Examples of the C2-C6 haloalkynyl group include, for example, fluoroethynyl group, 3-fluoro-2-bromovinyl group, 3-chloro-2-propynyl group, 3-bromo-2-propynyl group, 3-iodo-2-propynyl group, 3-chloro-1-propynyl group, 5-chloro-4-pentynyl group, 3,3,3-trifluoro-1-propynyl group, 3,3-difluoro-1-propynyl group, 4,4,4-trifluoro-2-butynyl group, perfluoro-2-butynyl group, perfluoro-2-pentynyl group, perfluoro-3-pentynyl group, and perfluoro-1-hexynyl group.

Examples of the C2-C4 alkynyl group include, for example, an ethynyl group, 2-propynyl group, 2-butynyl group, and 3-butynyl group.

The C2-C4 haloalkynyl group represents a linear or branched C2-C4 alkynyl group in which at least one hydrogen atom is substituted with a halogen atom. Examples of the C2-C4 haloalkynyl group include, for example, a fluoroethynyl group, 3-fluoro-2-propynyl group, and 4,4,4-trifluoro-2-butynyl group.

Examples of the C2-C3 alkynyl group include, for example, an ethynyl group, 1-propynyl group, and 2-propynyl group.

Examples of the C2-C3 haloalkynyl group include, for example, a fluoroethynyl group, 3-fluoro-2-propynyl group, 3-chloro-2-propynyl group, 3-bromo-2-propynyl group, 3-iodo-2-propynyl group, 3-chloro-1-propynyl group, 3,3,3-trifluoro-1-propynyl group, and 3,3-difluoro-1-propynyl group.

The C1-C6 alkoxy group represents a C1-C6 alkoxy group which may be linear or branched. Examples of the C1-C6 alkoxy group include, for example, a methoxy group, ethoxy group, propyloxy group, isopropyloxy group, butyloxy group, isobutyloxy group, sec-butyloxy group, tert-butyloxy group, pentyloxy group, isoamyloxy group, neopentyloxy group, 2-pentyloxy group, 3-pentyloxy group, 2-methylbutyloxy group, hexyloxy group, isohexyloxy group, 3-methylpentyloxy group, and 4-methylpentyloxy group.

The C1-C4 alkoxy group represents a C1-C4 alkoxy group which may be linear or branched. Examples of the C1-C4 alkoxy group include, for example, a methoxy group, ethoxy group, propyloxy group, isopropyloxy group, butyloxy group, isobutyloxy group, sec-butyloxy group, and tert-butyloxy group.

Examples of the C1-C3 alkoxy group include, for example, a methoxy group, ethoxy group, propyloxy group, and isopropyloxy group.

The C1-C6 haloalkoxy group represents a linear or branched C1-C6 alkoxy group in which at least one hydrogen atom is substituted with a halogen atom. Examples of the C1-C6 haloalkoxy group include, for example, a trifluoromethoxy group, trichloromethoxy group, chloromethoxy group, dichloromethoxy group, fluoromethoxy group, difluoromethoxy group, chlorofluoromethoxy group, dichlorofluoromethoxy group, chlorodifluoromethoxy group, pentafluoroethoxy group, pentachloroethoxy group, 2,2,2-trichloroethoxy group, 2,2,2-trifluoroethoxy group, 2,2,2-tribromoethoxy group, 2,2,2-triiodoethoxy group, 2-fluoroethoxy group, 2-chloroethoxy group, 2,2-difluoroethoxy group, 2-chloro-2-fluoroethoxy group, 2-chloro-2,2-difluoroethoxy group, heptafluoropropoxy group, heptachloropropoxy group, heptabromopropoxy group, heptaiodopropoxy group, 3,3,3-trifluoropropoxy group, 3,3,3-trichloropropoxy group, 3,3,3-tribromopropoxy group, 3,3,3-triiodopropoxy group, 2-fluoropropoxy group, 3-fluoropropoxy group, 2,2-difluoropropoxy group, 2,3-difluoropropoxy group, 2-chloropropoxy group, 3-chloropropoxy group, 2,3-dichloropropoxy group, 2-bromopropoxy group, 3-bromopropoxy group, 3,3,3-trifluoropropoxy group, nonafluorobutoxy group, nonachlorobutoxy group, nonabromobutoxy group, nonaiodobutoxy group, perfluoropentyloxy group, perchloropentyloxy group, perbromopentyloxy group, perfluorohexyloxy group, perchlorohexyloxy group, perbromohexyloxy group, and periodohexyloxy group.

The C1-C4 haloalkoxy group represents a linear or branched C1-C4 alkoxy group in which at least one hydrogen atom is substituted with a halogen atom. Examples of the C1-C4 haloalkoxy group include, for example, a trifluoromethoxy group, trichloromethoxy group, chloromethoxy group, dichloromethoxy group, fluoromethoxy group, difluoromethoxy group, chlorofluoromethoxy group, dichlorofluoromethoxy group, chlorodifluoromethoxy group, pentafluoroethoxy group, pentachloroethoxy group, 2,2,2-trichloroethoxy group, 2,2,2-trifluoroethoxy group, 2,2,2-tribromoethoxy group, 2,2,2-triiodoethoxy group, 2-fluoroethoxy group, 2-chloroethoxy group, 2,2-difluoroethoxy group, 2-chloro-2-fluoroethoxy group, 2-chloro-2,2-difluoroethoxy group, heptafluoropropoxy group, heptachloropropoxy group, heptabromopropoxy group, heptaiodopropoxy group, 3,3,3-trifluoropropoxy group, 3,3,3-trichloropropoxy group, 3,3,3-tribromopropoxy group, 3,3,3-triiodopropoxy group, 2-fluoropropoxy group, 3-fluoropropoxy group, 2,2-difluoropropoxy group, 2,3-difluoropropoxy group, 2-chloropropoxy group, 3-chloropropoxy group, 2,3-dichloropropoxy group, 2-bromopropoxy group, 3-bromopropoxy group, 3,3,3-trifluoropropoxy group, nonafluorobutoxy group, nonachlorobutoxy group, nonabromobutoxy group, and nonaiodobutoxy group.

The C1-C3 haloalkoxy group represents a linear or branched C1-C3 alkoxy group in which at least one hydrogen atom is substituted with a halogen atom. Examples of the C1-C3 haloalkoxy group include, for example, a trifluoromethoxy group, trichloromethoxy group, chloromethoxy group, dichloromethoxy group, fluoromethoxy group, difluoromethoxy group, chlorofluoromethoxy group, dichlorofluoromethoxy group, chlorodifluoromethoxy group, pentafluoroethoxy group, pentachloroethoxy group, 2,2,2-trichloroethoxy group, 2,2,2-trifluoroethoxy group, 2,2,2-tribromoethoxy group, 2,2,2-triiodoethoxy group, 2-fluoroethoxy group, 2-chloroethoxy group, 2,2-difluoroethoxy group, 2,2,2-trifluoroethoxy group, 2-chloro-2-fluoroethoxy group, 2-chloro-2,2-difluoroethoxy group, heptafluoropropoxy group, heptachloropropoxy group, heptabromopropoxy group, heptaiodopropoxy group, 3,3,3-trifluoropropoxy group, 3,3,3-trichloropropoxy group, 3,3,3-tribromopropoxy group, 3,3,3-triiodopropoxy group, 2-fluoropropoxy group, 3-fluoropropoxy group, 2,2-difluoropropoxy group, 2,3-difluoropropoxy group, 2-chloropropoxy group, 3-chloropropoxy group, 2,3-dichloropropoxy group, 2-bromopropoxy group, 3-bromopropoxy group, and 3,3,3-trifluoropropoxy group.

The C1-C4 alkoxy group which may have a halogen atom(s) represents a C1-C4 alkoxy group which may be linear or branched and in which hydrogen atom(s) may be substituted with a halogen atom(s). Examples of the C1-C4 alkoxy groups which may have a halogen atom(s) include, for example, a methoxy group, ethoxy group, propyloxy group, isopropyloxy group, butyloxy group, isobutyloxy group, sec-butyloxy group, tert-butyloxy group, trifluoromethoxy group, trichloromethoxy group, chloromethoxy group, dichloromethoxy group, fluoromethoxy group, difluoromethoxy group, chlorofluoromethoxy group, dichlorofluoromethoxy group, chlorodifluoromethoxy group, pentafluoroethoxy group, pentachloroethoxy group, 2,2,2-trichloroethoxy group, 2,2,2-trifluoroethoxy group, 2,2,2-tribromoethoxy group, 2,2,2-triiodoethoxy group, 2-fluoroethoxy group, 2-chloroethoxy group, 2,2-difluoroethoxy group, 2,2,2-trifluoroethoxy group, 2-chloro-2-fluoroethoxy group, 2-chloro-2,2-difluoroethoxy group, heptafluoropropoxy group, heptachloropropoxy group, heptabromopropoxy group, heptaiodopropoxy group, 3,3,3-trifluoropropoxy group, 3,3,3-trichloropropoxy group, 3,3,3-tribromopropoxy group, 3,3,3-triiodopropoxy group, 2-fluoropropoxy group, 3-fluoropropoxy group, 2,2-difluoropropoxy group, 2,3-difluoropropoxy group, 2-chloropropoxy group, 3-chloropropoxy group, 2,3-dichloropropoxy group, 2-bromopropoxy group, 3-bromopropoxy group, 2,3,3-trifluoropropoxy group, nonafluorobutoxy group, nonachlorobutoxy group, nonabromobutoxy group, and nonaiodobutoxy group.

The C1-C3 alkoxy group which may have a halogen atom(s) represents a C1-C3 alkoxy group which may be linear or branched and in which hydrogen atom(s) may be substituted with a halogen atom(s). Examples of the C1-C3 alkoxy group which may have a halogen atom(s) include, for example, a methoxy group, ethoxy group, propyloxy group, isopropyloxy group, trifluoromethoxy group, trichloromethoxy group, chloromethoxy group, dichloromethoxy group, fluoromethoxy group, difluoromethoxy group, chlorofluoromethoxy group, dichlorofluoromethoxy group, chlorodifluoromethoxy group, pentafluoroethoxy group, pentachloroethoxy group, 2,2,2-trichloroethoxy group, 2,2,2-trifluoroethoxy group, 2,2,2-tribromoethoxy group, 2,2,2-triiodoethoxy group, 2-fluoroethoxy group, 2-chloroethoxy group, 2,2-difluoroethoxy group, 2,2,2-trifluoroethoxy group, 2-chloro-2-fluoroethoxy group, 2-chloro-2,2-difluoroethoxy group, heptafluoropropoxy group, heptachloropropoxy group, heptabromopropoxy group, heptaiodopropoxy group, 3,3,3-trifluoropropoxy group, 3,3,3-trichloropropoxy group, 3,3,3-tribromopropoxy group, 3,3,3-triiodopropoxy group, 2-fluoropropoxy group, 3-fluoropropoxy group, 2,2-difluoropropoxy group, 2,3-difluoropropoxy group, 2-chloropropoxy group, 3-chloropropoxy group, 2,3-dichloropropoxy group, 2-bromopropoxy group, 3-bromopropoxy group, and 2,3,3-trifluoropropoxy group.

The C1-C6 alkylthio group represents a C1-C6 alkylthio group which may be linear or branched. Examples of the C1-C6 alkylthio group include, for example, a methylthio group, ethylthio group, n-propylthio group, isopropylthio group, n-butylthio group, sec-butylthio group, tert-butylthio group, n-pentylthio group, isopentylthio group, neopentylthio group, n-hexylthio group, isohexylthio group, and sec-hexylthio group.

The C1-C6 haloalkylthio group represents a linear or branched C1-C6 alkylthio group in which at least one hydrogen atom is substituted with a halogen atom. Examples of the C1-C6 haloalkylthio group include, for example, a monofluoromethylthio group, difluoromethylthio group, trifluoromethylthio group, trichloromethylthio group, tribromomethylthio group, triiodomethylthio group, chlorofluoromethylthio group, pentafluoroethylthio group, pentachloroethylthio group, pentabromoethylthio group, pentaiodoethylthio group, 2,2,2-trichloroethylthio group, 2,2,2-trifluoroethylthio group, 2,2,2-tribromoethylthio group, 2,2,2-triiodoethylthio group, 2,2-difluoroethylthio group, heptafluoropropylthio group, heptachloropropylthio group, heptabromopropylthio group, heptaiodopropylthio group, 3,3,3-trifluoropropylthio group, 3,3,3-trichloropropylthio group, 3,3,3-tribromopropylthio group, 3,3,3-triiodopropylthio group, 2,2-difluoropropylthio group, 2,3,3-trifluoropropylthio group, nonafluorobutylthio group, nonachlorobutylthio group, nonabromobutylthio group, nonaiodobutylthio group, perfluoropentylthio group, perchloropentyl group, perbromopentyl group, perfluorohexylthio group, perchlorohexylthio group, perbromohexylthio group, and periodohexylthio group.

Examples of the C1-C4 alkylthio group include, for example, a methylthio group, ethylthio group, n-propylthio group, isopropylthio group, n-butylthio group, isobutylthio group, and tert-butylthio group.

The C1-C4 haloalkylthio group represents a linear or branched C1-C4 alkylthio group in which at least one hydrogen atom is substituted with a halogen atom. Examples of the C1-C4 haloalkylthio group include, for example, a monofluoromethylthio group, difluoromethylthio group, trifluoromethylthio group, trichloromethylthio group, tribromomethylthio group, triiodomethylthio group, chlorofluoromethylthio group, pentafluoroethylthio group, pentachloroethylthio group, pentabromoethylthio group, pentaiodoethylthio group, 2,2,2-trichloroethylthio group, 2,2,2-trifluoroethylthio group, 2,2,2-trifluoroethylthio group, 2,2,2-tribromoethylthio group, 2,2,2-triiodoethylthio group, 2,2-difluoroethylthio group, and 1-(trifluoromethyl)-2,2,2-trifluoroethylthio group.

The C1-C8 alkylamino group represents an amino group having linear or branched C1-C8 alkyl group in which one or two hydrogen atoms on nitrogen atom are substituted with the same or different C1-C4 alkyl group or groups. Examples of the C1-C8 alkylamino group include, for example, a methylamino group, ethylamino group, propylamino group, isopropylamino group, N,N-dimethylamino group, N,N-diethylamino group, N-ethyl-N-methylamino group, butylamino group, N,N-dibutylamino group, and N-sec-buty-N-methylamino group.

The C1-C6 alkylamino group represents an amino group having a linear or branched C1-C6 alkyl group in which one or two hydrogen atoms on nitrogen atom are substituted with the same or different C1-C3 alkyl group or groups. Examples of the C1-C6 alkylamino group include, for example, a methylamino group, ethylamino group, propylamino group, isopropylamino group, N,N-dimethylamino group, N,N-diethylamino group, and N-ethyl-N-methylamino group.

The C1-C8 haloalkylamino group represents a C1-C8 alkylamino group in which one or more hydrogen atoms are substituted with a halogen atom(s). Examples of the C1-C8 haloalkylamino group include, for example, a 2,2,2-trifluoroethylamino group, N,N-(2,2-ditrifluoroethyl)-amino group, N,N-(2,2-ditrichloroethyl)-amino group, and pentafluoropropylamino group.

The C1-C6 haloalkylamino group represents a C1-C6 alkylamino group in which one or more hydrogen atoms are substituted with a halogen atom(s). Examples of the C1-C6 haloalkylamino group include, for example, a 2,2,2-trifluoroethylamino group, N,N-(2,2-ditrifluoroethyl)-amino group, N,N-(2,2-ditrichloroethyl)-amino group, and pentafluoropropylamino group.

The C2-C6 alkylcarbonyl group represents a C2-C6 alkylcarbonyl group having a linear or branched C1-05 alkyl group. Examples of the C2-C6 alkylcarbonyl group include, for example, a methylcarbonyl group, ethylcarbonyl group, n-propylcarbonyl group, isopropylcarbonyl group, pivaloyl group, n-butylcarbonyl group, and n-pentylcarbonyl group.

The C2-C6 alkoxycarbonyl group represents a C2-6 alkoxycarbonyl group having a linear or branched C1-05 alkyl group. Examples of the C2-C6 alkoxycarbonyl group include, for example, a methoxycarbonyl group, ethoxycarbonyl group, propyloxycarbonyl group, isopropyloxycarbonyl group, butyloxycarbonyl group, isobutyloxycarbonyl group, sec-butyloxycarbonyl group, tert-butyloxycarbonyl group, pentyloxycarbonyl group, isoamyloxycarbonyl group, neopentyloxycarbonyl group, 2-pentyloxycarbonyl group, 3-pentyloxycarbonyl group, and 2-methylbutyloxycarbonyl group.

The C2-C9 alkylaminocarbonyl group represents an aminoarbonyl group in which one or two hydrogen atoms on the nitrogen atom are substituted with the same or different and linear or branched C1-C4 alkyl group(s). Examples of the C2-C9 alkylaminocarbonyl group include, for example, a methylaminocarbonyl group, ethylaminocarbonyl group, propylaminocarbonyl group, isopropylaminocarbonyl group, butylaminocarbonyl group, N,N-dimethylaminocarbonyl group, N,N-diethylaminocarbonyl group, N,N-dipropylaminocarbonyl group, and N,N-disiopropylaminocarbonyl group.

The C3-C12 trialkylsilyl group represents an alkylsilyl group in which three hydrogen atoms on the silyl group are substituted with the same or different C1-C4 alkyl group(s), the alkyl groups being linear or branched. Examples of the C3-C12 trialkylsilyl group include, for example, a trimethylsilyl group, tert-butyl-dimethylsilyl group, triethylsilyl group, isopropyldimethylsilyl group, and triisopropylsilyl group.

The C1-C6 alkylsulfonyl group represents an alkylsulfonyl group having a linear or branched C1-C6 alkyl group. Examples of the C1-C6 alkylsulfonyl group include, for example, a methylsulfonyl group, ethylsulfonyl group, propylsulfonyl group, isopropylsulfonyl group, butylsulfonyl group, isobutylsulfonyl group, sec-butylsulfonyl group, pentylsulfonyl group, isoamylsulfonyl group, neopentylsulfonyl group, 2-pentylsulfonyl group, 3-pentylsulfonyl group, 2-methylbutylsulfonyl group, hexylsulfonyl group, isohexylsulfonyl group, 3-methylpentylsulfonyl group, and 4-methylpentylsulfonyl group.

The C1-C4 alkylsulfonyl group represents an alkylsulfonyl group having a linear or branched C1-C4 alkyl group. Examples of the C1-C4 alkylsulfonyl group include, for example, a methylsulfonyl group, ethylsulfonyl group, propylsulfonyl group, isopropylsulfonyl group, butylsulfonyl group, isobutylsulfonyl group, and sec-butylsulfonyl group.

The C1-C6 haloalkylsulfonyl group represents a linear or branched C1-C6 alkylsulfonyl group in which at least one hydrogen atom is substituted with a halogen atom. Examples of the C1-C6 haloalkylsulfonyl group include, for example, a trifluoromethylsulfonyl group, trichloromethylsulfonyl group, tribromomethylsulfonyl group, triiodomethylsulfonyl group, pentafluoroethylsulfonyl group, pentachloroethylsulfonyl group, pentabromoethylsulfonyl group, pentaiodoethylsulfonyl group, 2,2,2-trichloroethylsulfonyl group, 2,2,2-trifluoroethylsulfonyl group, 2,2,2-tribromoethylsulfonyl group, 2,2,2-triiodoethylsulfonyl group, heptafluoropropylsulfonyl group, heptachloropropylsulfonyl group, heptabromopropylsulfonyl group, heptaiodopropylsulfonyl group, 3,3,3-trifluoropropylsulfonyl group, 3,3,3-trichloropropylsulfonyl group, 3,3,3-tribromopropylsulfonyl group, 3,3,3-triiodopropylsulfonyl group, nonafluorobutylsulfonyl group, nonachlorobutylsulfonyl group, nonabromobutylsulfonyl group, nonaiodobutylsulfonyl group, perfluoropentylsulfonyl group, perchloropentylsulfonyl group, perbromopentylsulfonyl group, perfluorohexylsulfonyl group, perchlorohexylsulfonyl group, perbromohexylsulfonyl group, and periodohexylsulfonyl group.

The C1-C4 haloalkylsulfonyl group represents a linear or branched C1-C4 alkylsulfonyl group in which at least one hydrogen atom is substituted with a halogen atom. Examples of the C1-C4 haloalkylsulfonyl group include, for example, a trifluoromethylsulfonyl group, trichloromethylsulfonyl group, tribromomethylsulfonyl group, triiodomethylsulfonyl group, pentafluoroethylsulfonyl group, pentachloroethylsulfonyl group, pentabromoethylsulfonyl group, pentaiodoethylsulfonyl group, 2,2,2-trichloroethylsulfonyl group, 2,2,2-trifluoroethylsulfonyl group, 2,2,2-tribromoethylsulfonyl group, 2,2,2-triiodoethylsulfonyl group, heptafluoropropylsulfonyl group, heptachloropropylsulfonyl group, heptabromopropylsulfonyl group, heptaiodopropylsulfonyl group, 3,3,3-trifluoropropylsulfonyl group, 3,3,3-trichloropropylsulfonyl group, 3,3,3-tribromopropylsulfonyl group, 3,3,3-triiodopropylsulfonyl group, nonafluorobutylsulfonyl group, nonachlorobutylsulfonyl group, nonabromobutylsulfonyl group, and nonaiodobutylsulfonyl group.

The C1-C6 alkylsulfinyl group represents linear or branched C1-C6 alkylsulfinyl group. Examples of the C1-C6 alkylsulfinyl group include, for example, a methylsulfinyl group, ethylsulfinyl group, propylsulfinyl group, isopropylsulfinyl group, butylsulfinyl group, isobutylsulfinyl group, sec-butylsulfinyl group, pentylsulfinyl group, isoamylsulfinyl group, neopentylsulfinyl group, 2-pentylsulfinyl group, 3-pentylsulfinyl group, 2-methylbutylsulfinyl group, hexylsulfinyl group, isohexylsulfinyl group, 3-methylpentylsulfinyl group, and 4-methylpentylsulfinyl group.

The C1-C4 alkylsulfinyl group represents a linear or branched C1-C4 alkylsulfinyl group. Examples of the C1-C4 alkylsulfinyl group include, for example, a methylsulfinyl group, ethylsulfinyl group, propylsulfinyl group, isopropylsulfinyl group, butylsulfinyl group, isobutylsulfinyl group, and sec-butylsulfinyl group.

The C1-C6 haloalkylsulfinyl group represents a linear or branched C1-C6 alkylsulfinyl group in which at least one hydrogen atom is substituted with a halogen atom. Examples of the C1-C6 haloalkylsulfinyl groups include, for example, a trifluoromethylsulfinyl group, trichloromethylsulfinyl group, tribromomethylsulfinyl group, triiodomethylsulfinyl group, pentafluoroethylsulfinyl group, pentachloroethylsulfinyl group, pentabromoethylsulfinyl group, pentaiodoethylsulfinyl group, 2,2,2-trichloroethylsulfinyl group, 2,2,2-trifluoroethylsulfinyl group, 2,2,2-tribromoethylsulfinyl group, 2,2,2-triiodoethylsulfinyl group, heptafluoropropylsulfinyl group, heptachloropropylsulfinyl group, heptabromopropylsulfinyl group, heptaiodopropylsulfinyl group, 3,3,3-trifluoropropylsulfinyl group, 3,3,3-trichloropropylsulfinyl group, 3,3,3-tribromopropylsulfinyl group, 3,3,3-triiodopropylsulfinyl group, nonafluorobutylsulfinyl group, nonachlorobutylsulfinyl group, nonabromobutylsulfinyl group, nonaiodobutylsulfinyl group, perfluoropentylsulfinyl group, perchloropentylsulfinyl group, perbromopentylsulfinyl group, perfluorohexylsulfinyl group, perchlorohexylsulfinyl group, perbromohexylsulfinyl group, and periodohexylsulfinyl group.

The C1-C4 haloalkylsulfinyl group represents a linear or branched C1-C4 alkylsulfinyl group in which at least one hydrogen atom is substituted with a halogen atom. Examples of the C1-C4 haloalkylsulfinyl groups include, for example, a trifluoromethylsulfinyl group, trichloromethylsulfinyl group, tribromomethylsulfinyl group, triiodomethylsulfinyl group, pentafluoroethylsulfinyl group, pentachloroethylsulfinyl group, pentabromoethylsulfinyl group, pentaiodoethylsulfinyl group, 2,2,2-trichloroethylsulfinyl group, 2,2,2-trifluoroethylsulfinyl group, 2,2,2-tribromoethylsulfinyl group, 2,2,2-triiodoethylsulfinyl group, heptafluoropropylsulfinyl group, heptachloropropylsulfinyl group, heptabromopropylsulfinyl group, heptaiodopropylsulfinyl group, 3,3,3-trifluoropropylsulfinyl group, 3,3,3-trichloropropylsulfinyl group, 3,3,3-tribromopropylsulfinyl group, 3,3,3-triiodopropylsulfinyl group, nonafluorobutylsulfinyl group, nonachlorobutylsulfinyl group, nonabromobutylsulfinyl group, and nonaiodobutylsulfinyl group.

The C1-C6 alkyl group which may have a group selected from the group $P^1$ represents a C1-C6 alkyl group in which hydrogen atom(s) bonded with the carbon atom(s) may be substituted with one or more atoms or groups selected from the group $P^1$. When the C1-C6 alkyl group has two or more atoms or groups selected from the group $P^1$, these atoms or groups selected from the group $P^1$ may be the same or different.

Examples of the C1-C6 alkyl group having a group selected from the group $P^1$ include, for example, a fluoromethyl group, difluoromethyl group, trifluoromethyl group, chloromethyl group, dichloromethyl group, trichloromethyl group, tribromomethyl group, chlorofluoromethyl group, dichlorofluoromethyl group, chlorodifluoromethyl group, 2,2,2-trifluoroethyl group, 2,2,2-trichloroethyl group, 3,3,3-trifluoropropyl group, 2,2-difluoroethyl group, 1,1-difluoroethyl group, 2-chloro-2-fluoroethyl group, 2-chloro-2,2-difluoroethyl group, 2,2-dichloro-2-fluoroethyl group, pentafluoroethyl group, 2-fluoropropyl group, 3-fluoropropyl group, 2,2-difluoropropyl group, 3,3,3-trifluoropropyl group, 1-(fluoromethyl)-2-fluoroethyl group, heptafluoroisopropyl group, 1,1,2,2-tetrafluoroethyl group, 2,2,3,3,3-pentafluoropropyl group, 4-fluorobutyl group, 2,2,3,3,3-pentafluorobutyl group, 2,2-difluorohexyl group, cyclopropylmethyl group, cyclopropylethyl group, cyclopropylpropyl group, cyclopropylbutyl group, cyclopropylpentyl group, cyclopropylhexyl group, cyclobutylmethyl group, cyclobutylethyl group, cyclobutylpropyl group, cyclobutylbutyl group, cyclopentylmethyl group, cyclopentylethyl group, cyclopentylpropyl group, cyclohexylethyl group, cyclohexylpropyl group, 1-fluorocyclopropylmethyl group, 1-fluorocyclopropylethyl group, 1-fluorocyclopropylpropyl group, 2,2-difluorocyclopropylmethyl group, 2,2-difluorocyclopropylethyl group, 2,2-difluorocyclopropylpropyl group, pentafluorocyclopropylmethyl group, pentafluorocyclopropylethyl group, pentafluorocyclopropylpropyl group, 1-chlorocyclopropylmethyl group, 1-chlorocyclopropylethyl group, 1-chlorocyclopropylpropyl group, 2,2-dichlorocyclopropylmethyl group, 2,2-dichlorocyclopropylethyl group, 2,2-dichlorocyclopropylpropyl group, pentachlorocyclopropylmethyl group, pentachlorocyclopropylethyl group, pentachlorocyclopropylpropyl group, 1-fluorocyclobutylmethyl group, 1-fluorocyclobutylethyl group, 1-fluorocyclobutylpropyl group, 2,2-difluorocyclobutylmethyl group, 2,2-difluorocyclobutylethyl group, 2,2-difluorocyclobutylpropyl group, 1-chlorocyclobutylmethyl group, 1-chlorocyclobutylethyl group, 1-chlorocyclobutylpropyl group, 2,2-dichlorocyclobutylmethyl group, 2,2-dichlorocyclobutylethyl group, 2,2-dichlorocyclobutylpropyl group, 1-fluorocyclopentylmethyl group, 1-fluorocyclopentylethyl group, 1-fluorocyclopentylpropyl group, 2,2-difluorocyclopentylmethyl group, 2,2-difluorocyclopentylethyl group, 2,2-difluorocyclopentylpropyl group, 3,3-difluorocyclopentylmethyl group, 3,3-difluorocyclopentylpropyl group, 3,3-difluorocyclopentylpropyl group, 1-chlorocyclopentylethyl group, 1-chlorocyclopentylethyl group, 1-chlorocyclopentylpropyl group, 2,2-dichlorocyclopentylmethyl group, 2,2-dichlorocyclopentylethyl group, 2,2-dichlorocyclopentylpropyl group, 3,3-dichlorocyclopentylmethyl group, 3,3-dichlorocyclopentylethyl group, 3,3-dichlorocyclopentylpropyl group, 1-fluorocyclohexylmethyl group, 1-fluorocyclohexylethyl group, 1-fluorocyclohexylpropyl group, 2,2-difluorocyclohexylmethyl group, 2,2-difluorocyclohexylethyl group, 2,2-difluorocyclohexylpropyl group, 3,3-difluorocyclohexylmethyl group, 3,3-difluorocyclohexylethyl group, 3,3-difluorocyclohexylpropyl group, 4,4-difluorocyclohexylmethyl group, 4,4-difluorocyclohexylethyl group, 4,4-difluorocyclohexylpropyl group, 1-chlorocyclohexylmethyl group, 1-chlorocyclohexylethyl group, 1-chlorocyclohexylpropyl group, 2,2-dichlorocyclohexylmethyl group, 2,2-dichlorocyclohexylethyl group, 2,2-dichlorocyclohexylpropyl group, 3,3-dichlorocyclohexylmethyl group, 3,3-dichlorocyclohexylethyl group, 3,3-dichlorocyclohexylpropyl group, methoxymethyl group, ethoxymethyl group, isopropoxymethyl group, tert-butoxymethyl group, 2-methoxyethyl group, 2-ethoxyethyl group, 2-tert-butoxyethyl group, 3-methoxypropyl group, 3-ethoxypropyl group, trifluoromethoxymethyl group, 2-trifluoromethoxyethyl group, 3-trifluoromethoxypropyl group, 4-trifluoromethoxybutyl group, difluoromethoxymethyl group, difluoromethoxymethyl group, 2-difluoromethoxyethyl group, 2-pentafluoroethoxyethyl group, 3-pentafluoroethoxypropyl group, 1,1,2,2-tetrafluoroethoxymethyl group, 2-(1,1,2,2-tetrafluoroethoxy)-ethyl group, methylthiomethyl group, 2-methylthioethyl group, 3-methylthiopropyl group, ethylthiomethyl group, 2-ethylthioethyl group, 3-ethylthiopropyl group, tert-butylthiomethyl group, 2-(tert-butylthio)-ethyl group, 3-(tert-butylthio)-propyl group, trifluoromethylthiomethyl group, 2-trifluoromethylthioethyl group, trifluoromethylthiopropyl group, cyanomethyl group, 2-cyanoethyl group, 3-cyanopropyl group, 1-cyanoethyl group, 2-cyano-2-methylethyl group, and 2-cyano-2, methylpropyl group. Similarly, examples of the C1-C6 alkyl group having no group selected from the group $P^1$ include, for example, those given as examples in the explanations of the C1-C6 alkyl group above.

The C3-C6 cycloalkyl group which may have a group selected from the group $P^1$ represents a C3-C6 cycloalkyl group in which hydrogen atom(s) bonded with carbon atom(s) may be substituted with one or more atoms or groups selected from the group $P^1$. When the C3-C6 cycloalkyl group has two or more atoms or groups selected from the group $P^1$, these atoms or groups selected from the group $P^1$ may be the same or different.

Examples of the C3-C6 cycloalkyl group having a group selected from the group $P^1$ include, for example, 1-fluorocyclopropyl group, 2,2-difluorocyclopropyl group, 1-chloro-2-fluorocyclopropyl group, 2,2-dichlorocyclopropyl group, 2,2-dibromocyclopropyl group, 2,2-difluoro-1-methylcyclopropyl group, 2,2-dichloro-1-methylcyclopropyl group, 2,2-dibromo-1-methylcyclopropyl group, 2,2,3,3-tetrafluorocyclobutyl group, 2,2,3,3-tetrafluorocyclobutyl group, 2-chlorocyclopentyl group, 3-chlorocyclopentyl group, 3,3-difluorocyclopentyl group, 1-fluorocyclohexyl group, 2,2-difluorocyclohexyl group, 3,3-difluorocyclohexyl group, 4,4-difluorocyclohexyl group, 1-cyclopropylcyclopropyl group, 2-cyclopropylcyclopropyl group, 2,2-bis-cyclopropyl-cyclopropyl group, 2,3-bis-cyclopropyl-cyclopropyl group, 1-cyclopropylcyclobutyl group, 1-cyclobutylcyclobutyl group, 2-cyclopropylcyclobutyl group, 1-cyclopropylcyclopentyl group, 2-cyclopropylcyclopentyl group, 1-(1-fluorocyclopropyl)-cyclopropyl group, 1-(2,2-difluorocyclopropyl)-cyclopropyl group, 1-(1-chlorocyclopropyl)-cyclopropyl group, 1-(2,2-dichlorocyclopropyl)-cyclopropyl group, 1-methoxycyclopropyl group, 1-methoxycyclobutyl group, 1-methoxycyclopentyl group, 1-methoxycyclohexyl group, 2-methoxycyclopropyl group, 2-methoxycyclobutyl group, 2-methoxycyclopentyl group, 2-methoxycyclohexyl group, 2-ethoxycyclopropyl group, 2-ethoxycyclobutyl group, 2-ethoxycyclopentyl group, 2-ethoxycyclohexyl group, 1-ethoxycyclopropyl group, 1-ethoxycyclobutyl group, 1-ethoxycyclopentyl group, 1-ethoxycyclohexyl group, 1-isopropoxycyclopropyl group, 1-isopropoxycyclobutyl group, 1-isopropoxycyclopentyl group, 1-isopropoxycyclohexyl group, 1-trifluoromethoxycyclopropyl group, 2-trifluoromethoxycyclopropyl group, 1-difluoromethoxycyclopropyl group, 2-difluoromethoxycyclopropyl group, 1-(2,2-difluoroethoxy)-cyclopropyl group, 2-(2,2-difluoroethoxy)-cyclopropyl group, 1-methylthiocyclopropyl group, 1-ethylthiocyclopropyl group, 2-methylthiocyclopropyl group, 2-ethylthiocyclopropyl group, 1-trifluoromethylthiocyclopropyl group, 2-trifluoromethylthiocyclopropyl group, 1-cyanocyclopropyl group, 2-cyanocyclopropyl group, and 2,2-dicyanocyclopropyl group. Similarly, examples of the C3-C6 cycloalkyl groups having no group selected from the group $P^1$ include those given as examples in the explanations of the above C3-C6 cycloalkyl group.

The phenyl group which may have a group selected from the group $P^2$ represents a phenyl group in which hydrogen atom(s) bonded with carbon atom(s) may be substituted with one or more atoms or groups selected from the group $P^2$. When the phenyl group has two or more atoms or groups selected from the group $P^2$, these atoms or groups selected from the group $P^2$ may be the same or different.

Examples of the phenyl group having a group selected from the group $P^2$ include a phenyl group, 2-methylphenyl group, 3-methylphenyl group, 4-methylphenyl group, 2-ethylphenyl group, 3-ethylphenyl group, 3-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, 4-trifluorophenyl group, 2-methoxyphenyl group, 3-methoxyphenyl group, 4-methoxyphenyl group, 2-ethoxyphenyl group, 3-ethoxyphenyl group, 4-ethoxyphenyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,3,4,5,6-pentafluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-fluoro-4-chlorophenyl group, 2-chloro-4-fluorophenyl group, 2-fluoro-4-methylphenyl group, and 2-methyl-4-fluorophenyl group.

The benzyl group which may have a group selected from the group $P^2$ represents a benzyl group in which hydrogen atom(s) on the benzene ring may be substituted with one or more atoms or groups selected from the group $P^2$. When the benzyl group has two or more atoms or groups selected from the group $P^2$, these atoms or groups selected from the group $P^2$ may be the same or different.

Examples of the benzyl group which may have a group selected from the group $P^2$ include, for example, a benzyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-cyanobenzyl group, 3-cyanobenzyl group, 4-cyanobenzyl group, 2-aminobenzyl group, 3-aminobenzyl group, 4-aminobenzyl group, 2-methylbenzyl group, 3-methylbenzyl group, 4-methylbenzyl group, 2-ethylbenzyl group, 3-ethylbenzyl group, 4-ethylbenzyl group, 2-propylbenzyl group, 3-propylbenzyl group, 4-propylbenzyl group, 2-cyclopropylbenzyl group, 3-cyclopropylbenzyl group, 4-cyclopropylbenzyl group, 2-trifluorobenzyl group, 3-trifluorobenzyl group, 4-trifluorobenzyl group, 2-methoxybenzyl group, 3-methoxybenzyl group, 4-methoxybenzyl group, 2-dimethylaminobenzyl group, 3-dimethylaminobenzyl group, 4-dimethylaminobenzyl group, 2-acetylbenzyl group, 3-acetylbenzyl group, 4-acetylbenzyl group, 2,3-difluorobenzyl group, 2,4-difluorobenzyl group, 2,5-difluorobenzyl group, 2,6-difluorobenzyl group, 3,4-difluorobenzyl group, 3,5-difluorobenzyl group, 2,3,4,5,6-pentafluorobenzyl group, 2,3-dichlorobenzyl group, 2,4-dichlorobenzyl group, 2,5-dichlorobenzyl group, 2,6-dichlorobenzyl group, 3,4-dichlorobenzyl group, 3,5-dichlorobenzyl group, 2-fluoro-4-chlorobenzyl group, 2-chloro-4-fluorobenzyl group, 2-fluoro-4-methylbenzyl group, and 2-methyl-4-fluorobenzyl group.

The phenyl group which may have a group selected from the group $P^3$ represents a phenyl group in which hydrogen atom(s) bonded with carbon atom(s) may be substituted with one or more atoms or groups selected from the group $P^3$. When the phenyl group has two or more atoms or groups selected from the group $P^3$, these atoms or groups selected from the group $P^3$ may be the same or different.

Examples of the phenyl group having a group selected from the group $P^3$ include, for example, a phenyl group, 2-methylphenyl group, 3-methylphenyl group, 4-methylphenyl group, 2-ethylphenyl group, 3-ethylphenyl group, 3-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluoromethylphenyl group, 3-trifluoromethylphenyl group, 4-trifluoromethylphenyl group, 2,3-difluorophenyl group, 2,4-difluorophenyl group, 2,5-difluorophenyl group, 2,6-difluorophenyl group, 3,4-difluorophenyl group, 3,5-difluorophenyl group, 2,3,4,5,6-pentafluorophenyl group, 2,3-dichlorophenyl group, 2,4-dichlorophenyl group, 2,5-dichlorophenyl group, 2,6-dichlorophenyl group, 3,4-dichlorophenyl group, 3,5-dichlorophenyl group, 2-fluoro-4-chlorophenyl group, 2-chloro-4-fluorophenyl group, 2-fluoro-4-methylphenyl group, and 2-methyl-4-fluorophenyl group.

The benzyl group which may have a group selected from the group $P^3$ represents a benzyl group in which hydrogen atom(s) bonded with carbon atom(s) may be substituted with one or more atoms or groups selected from the group $P^3$. When the benzyl group has two or more atoms or groups selected from the group $P^3$, these atoms or groups selected from the group $P^3$ may be the same or different.

Examples of the benzyl group which may have a group selected from the group $P^3$ include, for example, a benzyl group, 2-methylbenzyl group, 3-methylbenzyl group, 4-methylbenzyl group, 2-ethylbenzyl group, 3-ethylbenzyl group, 4-ethylbenzyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-trifluorobenzyl group, 3-trifluorobenzyl group, 4-trifluorobenzyl group, 2,3-difluorobenzyl group, 2,4-difluorobenzyl group, 2,5-difluorobenzyl group, 2,6-difluorobenzyl group, 3,4-difluorobenzyl group, 3,5-difluorobenzyl group, 2,3,4,5,6-pentafluorobenzyl group, 2,3-dichlorobenzyl group, 2,4-dichlorobenzyl group, 2,5-dichlorobenzyl group, 2,6-dichlorobenzyl group, 3,4-dichlorobenzyl group, 3,5-dichlorobenzyl group, 2-fluoro-4-chlorobenzyl group, 2-chloro-4-fluorobenzyl group, 2-fluoro-4-methylbenzyl group, and 2-methyl-4-fluorobenzyl group.

Examples of the benzyl group which may have a halogen atom(s) include, for example, a benzyl group, 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2,3-difluorobenzyl group, 2,4-difluorobenzyl group, 2,5-difluorobenzyl group, 2,6-difluorobenzyl group, 3,4-difluorobenzyl group, 3,5-difluorobenzyl group, 2,3,4,5,6-pentafluorobenzyl group, 2,3-dichlorobenzyl group, 2,4-dichlorobenzyl group, 2,5-dichlorobenzyl group, 2,6-dichlorobenzyl group, 3,4-dichlorobenzyl group, 3,5-dichlorobenzyl group, 2-fluoro-4-chlorobenzyl group, and 2-chloro-4-fluorobenzyl group.

Embodiments of the compound of the present invention include, for example, Compound of formula (1) having the substituent or substituents as shown below.

Compound wherein $R^1$ is a hydrogen atom, methyl group, ethyl group, propyl group, methoxy group, trifluoromethyl group, cyclopropyl group, 2-propenyl group, chlorine atom, or bromine atom;

Compound wherein $R^2$ is a methyl group, ethyl group, fluorine atom, chlorine atom, bromine atom, or iodine atom;

Compound wherein $R^3$ is a methyl group, ethyl group, fluorine atom, chlorine atom, bromine atom, or iodine atom;

Compound wherein $R^4$ is a hydrogen atom or fluorine atom;

Compound wherein $R^5$ is a hydrogen atom or fluorine atom;

Compound wherein $R^7$ is a hydrogen atom or fluorine atom;

Compound wherein $R^8$ is a hydrogen atom or fluorine atom;

Compound wherein $R^9$ is a hydrogen atom or fluorine atom;

Compound wherein $R^{11}$ is a hydrogen atom or fluorine atom;

Compound wherein $R^1$ is a methyl group, ethyl group, trifluoromethyl group, chlorine atom, or bromine atom;

Compound wherein $R^4$ is a hydrogen atom;

Compound wherein $R^5$ is a hydrogen atom;

Compound wherein $R^7$ is a hydrogen atom;

Compound wherein $R^8$ is a hydrogen atom;

Compound wherein $R^9$ is a hydrogen atom;

Compound wherein $R^{11}$ is a hydrogen atom;

Compound wherein $R^2$ is a hydrogen atom;

Compound wherein $R^3$ is a hydrogen atom or methyl group;

Compound wherein $R^{10}$ is a methyl group, ethyl group, difluoromethyl group, or 2,2-difluoroethyl group;

Compound wherein $R^{10}$ is a methyl group;

Compound wherein X is an oxygen atom;

Compound wherein X is a sulfur atom;

Compound wherein $R^6$ is a methyl group, ethyl group, methoxy group, or cyclopropyl group;

Compound wherein $R^6$ is a C1-C3 alkyl group which may have a halogen atom(s), C1-C3 alkoxy group which may have a halogen atom(s), cyclopropyl group, or a halogen atom;

Compound wherein $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group;

Compound wherein $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group;

Compound wherein $R^{12}$ is a methyl group, ethyl group, cyclopropyl group, or phenyl group;

Compound wherein $R^{12}$ is a methyl group, ethyl group, propyl group, isopropyl group, butyl group, neopentyl group, cyclopropyl group, cyclohexyl group, or phenyl group;

Compound wherein $R^{12}$ is an ethyl group, propyl group, isopropyl group, butyl group, neopentyl group, cyclopropyl group, cyclohexyl group, phenyl group, trifluoromethyl group, 2-propenyl group, or 1-cyclohexenyl group;

Compound wherein $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group;

Compound wherein $R^{12}$ is a C1-C6 alkyl group which may have a halogen atom(s), C3-C6 cycloalkyl group which may have a halogen atom(s), phenyl group, or hydrogen atom;

Compound wherein $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or a phenyl group which may have a group selected from the group $P^2$;

Compound wherein $R^{13}$ is a methyl group, ethyl group, 2,2-dimethylethyl group, 2-propenyl group, 2-propynyl, or benzyl group;

Compound wherein $R^{13}$ is a methyl group, ethyl group, 2,2-dimethylethyl group, butyl group, 2-propenyl group, 3-propynyl group, benzyl group, 2-chlorobenzyl group, 3-chlorobenzyl, or 4-chlorobenzyl group;

Compound wherein $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^{13}$ is a C1-C6 alkyl group which may have a halogen atom, C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or a benzyl group which may have a group selected from the group $P^3$;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), a halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 haloalkylthio group, C1-C4 haloalkylthio group, C3-C6 cycloalkyl group, or C3-C6 halocycloalkyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a C1-C6 alkyl group which may have a halogen atom(s), C2-C6 alkenyl group, C2-C6 alkynyl group, a benzyl group, or C3-C6 cycloalkyl group;

Compound wherein $R^1$ is a C1-C3 alkyl group which may have a halogen atom(s), a halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), a halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a methyl group, ethyl group, 2,2-dimethylethyl group, butyl group, 2-propenyl group, 3-propenyl group, benzyl group, 2-chlorobenzyl group, 3-chlorobenzyl group, or 4-chlorobenzyl group;

Compound wherein $R^1$ is a C1-C3 alkyl group which may have a halogen atom(s), a halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), a halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a methyl group, ethyl group, 2,2-dimethylethyl group, 2-propenyl group, 2-propynyl group, or benzyl group.

Compound wherein $R^1$ is a C1-C3 alkyl group which may have a halogen atom(s), a halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a C1-C3 alkyl group which may have a halogen atom(s), a halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), a halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a C1-C6 alkyl group which may have a halogen atom(s), C3-C6 cycloalkyl group which may have a halogen atom(s), a phenyl group, or a hydrogen atom, and $R^{13}$ is a methyl group, ethyl group, 2,2-dimethylethyl group, butyl group, 2-propenyl group, 3-propenyl group, benzyl group, 2-chlorobenzyl group, 3-chlorobenzyl group, or 4-chlorobenzyl group;

Compound wherein $R^1$ is a C1-C3 alkyl group which may have a halogen atom(s), a halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a methyl group, ethyl group, 2,2-dimethylethyl group, 2-propenyl group, 2-propynyl group, or benzyl group;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a methyl group, ethyl group, 2,2-dimethylethyl group, 2-propenyl group, 2-propynyl group, or benzyl group;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a C1-C6 alkyl group which may have a halogen atom(s), C2-C6 alkenyl group, C2-C6 haloalkenyl group, C2-C6 alkinyl group, C2-C6 haloalkinyl group, C3-C6 cycloalkyl group, C3-C6 cycloalkenyl group, or benzyl group which may have a group selected from the group $P^3$;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a C1-C6 alkyl group which may have a halogen atom(s), C2-C6 alkenyl group, C2-C6 alkinyl group, benzyl group, or C3-C6 cycloalkyl group;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a C1-C3 alkyl group which may have a halogen atom(s), halogen atom, C3-C5 cycloalkyl group, C1-C3 alkoxy group, C2-C3 alkynyl group, C2-C3 haloalkynyl group, C3-C5 halocycloalkyl group, or C1-C3 haloalkoxy group, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), halogen atom, C1-C3 alkoxy group which may have a halogen atom(s), C2-C4 alkenyl group, C2-C4 haloalkenyl group, C2-C4 alkynyl group, C2-C4 haloalkynyl group, C1-C4 alkylthio group, C1-C4 haloalkylthio group, C3-C6 cycloalkyl group, or C3-C6 halocycloalkyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a methyl group, ethyl group, 2,2-dimethylethyl group, 2-propenyl group, 2-propynyl group, or benzyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a methyl group, ethyl group, 2,2-dimethylethyl group, 2-propenyl group, 2-propynyl group, or benzyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a methyl group, ethyl group, 2,2-dimethylethyl group, 2-propenyl group, 2-propynyl group, or benzyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a methyl group, ethyl group, 2,2-dimethylethyl group, 2-propenyl group, 2-propynyl group, or benzyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a C1-C6 alkyl group which may have a halogen atom(s), C2-C6 alkenyl group, C2-C6 alkynyl group, benzyl group or C3-C6 cycloalkyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a hydrogen atom, methyl group, ethyl group, propyl group, methoxy group, trifluoromethyl group, cyclopropyl group, 2-propenyl group, chlorine atom, or bromine atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, halogen atom, C2-C3 alkenyl group, or C2-C3 alkynyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a methyl group, ethyl group, 2,2-dimethylethyl group, 2-propenyl group, 2-propynyl group, or benzyl group;

Compound wherein $R^1$ is a C1-C3 alkyl group which may have a halogen atom(s) or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a C1-C3 alkyl group which may have a halogen atom(s) or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s) C1-C3 alkoxy group which may have a halogen atom(s), cyclopropyl group, or a halogen atom, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$; and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$; and $R^{13}$ is a methyl group, ethyl group, 2,2-dimethylethyl group, 2-propenyl group, 2-propynyl group, or benzyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s) C1-C3 alkoxy group which may have a halogen atom(s), cyclopropyl group, or a halogen atom, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or hydrogen atom, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s) C1-C3 alkoxy group which may have a halogen atom(s), cyclopropyl group, or a halogen atom, $R^{13}$ is a methyl group, X is an oxygen atom, $R^{12}$ is a C1-C6 alkyl group which may have a halogen atom(s) C3-C6 cycloalkyl group which may have a halogen atom(s), phenyl group, or hydrogen atom, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s) C1-C3 alkoxy group which may have a halogen atom(s), cyclopropyl group, or a halogen atom, $R^{13}$ is a methyl group, X is an oxygen atom, $R^{12}$ is a C1-C6 alkyl group which may have a halogen atom(s), C3-C6 cycloalkyl group which may have a halogen atom(s), phenyl group, or hydrogen atom, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or hydrogen atom, and $R^{13}$ is a methyl group, ethyl group, 2,2-dimethylethyl group, 2-propenyl group, 2-propynyl group, or benzyl group;

Compound wherein $R^1$ is a C1-C3 alkyl group which may have a halogen atom(s) or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a C1-C3 alkyl group which may have a halogen atom(s) or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s) C1-C3 alkoxy group which may have a halogen atom(s), cyclopropyl group, or a halogen atom, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a methyl group, ethyl group, 2,2-dimethylethyl group, 2-propenyl group, 2-propynyl group, or benzyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s) C1-C3 alkoxy group which may have a halogen atom(s), cyclopropyl group, or a halogen atom, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s) C1-C3 alkoxy group which may have a halogen atom(s), cyclopropyl group, or a halogen atom, $R^{13}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a C1-C6 alkyl group which may have a halogen atom(s) C2-C6 alkenyl group, C2-C6 alkynyl group, benzyl group, or C3-C6 cycloalkyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s) C1-C3 alkoxy group which may have a halogen atom(s), cyclopropyl group, or a halogen atom, $R^{13}$ is a methyl group, X is an oxygen atom, $R^{12}$ is a methyl group, propyl group, isopropyl group, butyl group, neopentyl group, cyclopropyl group, cyclohexyl group, or phenyl group, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a C1-C3 alkyl group which may have a halogen atom(s), or a halogen atom, $R^4$, $R^5$, $R^7$, $R^8$, $R^9$, and $R^{11}$ are each a hydrogen atom, $R^2$ and $R^3$ are each a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a methyl group, ethyl group, 2,2-dimethylethyl group, 2-propenyl group, 2-propynyl group, or benzyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a C1-C6 alkyl group, C1-C6 haloalkyl group, C2-C6 alkenyl group, C2-C6 haloalkynyl group, C1-C6 alkoxy group, C1-C6 haloalkoxy group, C3-C6 cycloalkyl group, C3-C6 halocycloalkyl group, or phenyl group which may have a group selected from the group $P^2$, and $R^{13}$ is a methyl group, ethyl group, 2,2-dimethylethyl group, 2-propenyl group, 2-propynyl group, or benzyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a methyl group, trifluoromethyl group, chlorine atom, or bromine atom, $R^2$, $R^4$, $R^5$, $R^3$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a methyl group, trifluoromethyl group, chlorine atom, or bromine atom, $R^2$, $R^4$, $R^5$, $R^3$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a C1-C6 alkyl group which may have a halogen atom(s), C3-C6 cycloalkyl group which may have a halogen atom(s), phenyl group, or a hydrogen atom, and $R^{13}$ is a methyl group, ethyl group, 2,2-dimethylethyl group, 2-propenyl group, 2-propynyl group, or benzyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a C1-C6 alkyl group which may have a halogen atom(s), C2-C6 alkenyl group, C2-C6 haloalkenyl group, C2-C6 alkynyl group, C2-C6 haloalkynyl group, C3-C6 cycloalkyl group, C3-C6 cycloalkenyl group, or benzyl group which may have a group selected from the group $P^3$;

Compound wherein $R^1$ is a methyl group, trifluoromethyl group, chlorine atom, or bromine atom, $R^2$, $R^4$, $R^5$, $R^3$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is an ethyl group, propyl group, isopropyl group, butyl group, neopentyl group, cyclopropyl group, cyclohexyl group, phenyl group, trifluoromethyl group, 2-propenyl group, 1-cyclohexenyl group, 2-methylphenyl group, 3-methylphenyl group, 4-methylphenyl group, 2-ethylphenyl group, 3-ethylphenyl group, 4-ethylphenyl group, 2-fluorophenyl group, 3-fluorophenyl group, 4-fluorophenyl group, 2-chlorophenyl group, 3-chlorophenyl group, 4-chlorophenyl group, 2-bromophenyl group, 3-bromophenyl group, 4-bromophenyl group, 2-trifluorophenyl group, 3-trifluorophenyl group, or 4-trifluorophenyl group, and $R^{13}$ is a methyl group, ethyl group, 2,2-dimethylethyl group, 2-propenyl group, 2-propynyl group, or benzyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a C1-C6 alkyl group which may have a halogen atom(s), a C2-C6 alkenyl group, C2-C6 haloalkenyl group, C2-C6 alkynyl group, C2-C6 haloalkynyl group, C3-C6 cycloalkyl group, C3-C6 cycloalkenyl group, or a benzyl group which may have a group selected from the group $P^3$.

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a C1-C6 alkyl group which may have a halogen atom(s), C2-C6 alkenyl group, C2-C6 alkynyl group, benzyl group, or C3-C6 cycloalkyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a methyl group, ethyl group, 2,2-dimethylethyl group, butyl group, 2-propenyl group, 3-propynyl group, benzyl group, 2-chlorobenzyl group, 3-chlorobenzyl group, or 4-chlorobenzyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, ethyl group, methoxy group, or cyclopropyl group, $R^{10}$ is a methyl group, X is an oxygen atom, $R^{12}$ is a methyl group, ethyl group, propyl group, isopropyl group, butyl group, neopentyl group, cyclopropyl group, cyclohexyl group, or phenyl group, and $R^{13}$ is a methyl group, ethyl group, 2,2-dimethylethyl group, 2-propenyl group, 2-propynyl group, or benzyl group;

Compound wherein $R^1$ is a C1-C6 alkyl group, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a C1-C3 alkyl group, X is an oxygen atom, $R^{12}$ is a C1-C6 alkyl group, C3-C6 cycloalkyl group, phenyl group, or hydrogen atom, and $R^{13}$ is a C1-C8 alkyl group, benzyl group which may have a halogen atom(s), C2-C6 alkenyl group, or C2-C6 alkynyl group;

Compound wherein $R^1$ is a C1-C3 alkyl group, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkoxy group which may have a halogen atom(s), $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a cyclopropyl group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a halogen atom, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methyl group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is an ethyl group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a methoxy group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is an ethoxy group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a trifluoromethyl group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a difluoromethyl group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a chloro group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a bromo group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a fluoro group, $R^{10}$ is a methyl group, X is an oxygen atom, $R^{12}$ is a C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a C1-C6 alkyl group, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a C3-C6 cycloalkyl group, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a phenyl group, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a methyl group, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is an ethyl group, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is an isopropyl group, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is a neopentyl group, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a C1-C6 alkyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a benzyl group which may have a halogen atom(s);

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a C2-C6 alkenyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a methyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is an ethyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a 2-propenyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a 2-propynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a benzyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom or methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a 2,2-dimethylethyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a hydrogen atom, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a methyl group, trifluoromethyl group, chlorine atom, or bromine atom, $R^2$, $R^4$, $R^5$, $R^7$, $R^8$, $R^9$, and $R^{11}$ are each a hydrogen atom, $R^3$ is a methyl group, $R^6$ is a C1-C3 alkyl group which may have a halogen atom(s), C1-C3 alkoxy group which may have a halogen atom(s), cyclopropyl group, or a halogen atom, $R^{10}$ is a methyl group, X is an oxygen atom, $R^{12}$ is C1-C6 alkyl group, C3-C6 cycloalkyl group, phenyl group, or hydrogen atom, and $R^{13}$ is a C1-C6 alkyl group, benzyl group which may have a halogen atom(s), C2-C6 alkenyl group, or C2-C6 alkynyl group;

Compound wherein $R^1$ is a C1-C6 alkyl group which may have a halogen atom(s), hydrogen atom, halogen atom, C1-C6 alkoxy group, C3-C6 cycloalkyl group, or nitro group, $R^2$ and $R^3$ are each a hydrogen atom or C1-C6 alkyl group, $R^4$, $R^5$, $R^7$, $R^8$, and $R^9$ are each a hydrogen atom, $R^6$ is a C1-C4 alkyl group which may have a halogen atom(s), C2-C4 alkenyl group, C1-C4 alkoxy group, C3-C6 cycloalkyl group, or a halogen atom, $R^{10}$ is a C1-C3 alkyl group, $R^{11}$ is a hydrogen atom or C1-C6 alkyl group, X is an oxygen atom, $R^{12}$ is C1-C6 alkyl group, C3-C6 cycloalkyl group, phenyl group which may have a halogen atom(s), or hydrogen atom, and $R^{13}$ is a C1-C6 alkyl group, benzyl group which may have a halogen atom(s), C2-C6 alkenyl group, or C2-C6 alkynyl group;

Although there is the case where the structural formula of a compound represents a specific isomer in this specification for convenience, the present invention embraces all active isomers including geometrical isomers, optical isomers, stereoisomers, and tautomers and mixtures of these isomers which are structurally generated from the compound and is not therefore limited to the formula described for the sake of convenience but may be either one or mixture of these isomers. Accordingly, there is the case where the compound contains an asymmetric carbon in molecules and optically active substance and racemate exist. However, any of these cases is embraced without any limitation in the present invention.

Next, a method for producing the compound of the present invention will be explained.

(Production Method A)

The compound of the present invention as shown in the formula (1) can be produced by reacting a compound (hereinafter referred to as "compound (A-1)") represented by a formula (A-1) with a compound (hereinafter referred to as "compound (A-2)") represented by a formula (A-2) in the presence of a base.

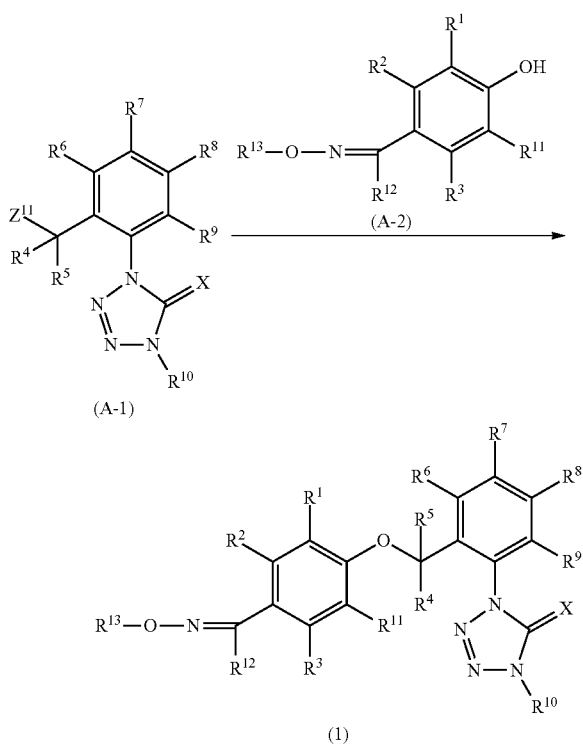

(1)

In the above formula, $R^1$, $R^2$, $R^3$, $R^4$, $R^5$, $R^6$, $R^7$, $R^8$, $R^9$, $R^{10}$, $R^{11}$, $R^{12}$, $R^{13}$, and X each have the same meaning as above and $Z^{11}$ represents a leaving group such as a chlorine atom, bromine atom, iodine atom, a methanesulfonyloxy group, trifluoromethanesulfonyloxy group, or p-toluenesulfonyloxy group.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethylsulfoxide, ketones such as acetone, methyl ethyl ketone, and methyl isobutyl ketone, nitriles such as acetonitrile and propionitrile, water and mixtures of these compounds.

Examples of the base used in this reaction include, for example, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, alkali metal hydroxides such as lithium hydroxide, sodium hydroxide, potassium hydroxide, and cesium hydroxide, alkali metal halides such as sodium fluoride, potassium fluoride, and cesium fluoride, alkali metal hydrides such as lithium hydride, sodium hydride, and potassium hydride, and alkali metal alkoxides such as sodium tert-butoxide and potassium tert-butoxide.

In the reaction, the compound (A-2) is usually used in an amount of 1 to 10 moles and the base is usually used in an amount of 1 to 10 moles per mol of the compound (A-1).

The reaction temperature in the reaction is in a range from −20 to 150° C. and the reaction time in the reaction is usually in a range from 0.1 to 24 hr.

In the reaction, sodium iodide or tetrabutylammonium iodide may be added according the need and these compounds are usually used in an amount of 0.01 to 1.2 moles per mol of the compound (A-1).

After the reaction, after-treatments including the extraction of the reaction mixture with an organic solvent and drying and concentration of the obtained organic phase may be performed to isolate the compound represented by the formula (1) of the present invention. In another method, after-treatments such as filtration and concentration of the reaction mixture may be performed to isolate the compound represented by the formula (1) of the present invention. The isolated compound of the present invention may be further purified by chromatography, recrystallization, and the like.

(Production Method B)

The compound of the present invention as shown in the formula (1) can be produced by reacting a compound (hereinafter referred to as "compound (B-1)") represented by a formula (B-1) with a compound (hereinafter referred to as "compound (B-2)") represented by a formula (B-2) in the presence of a base.

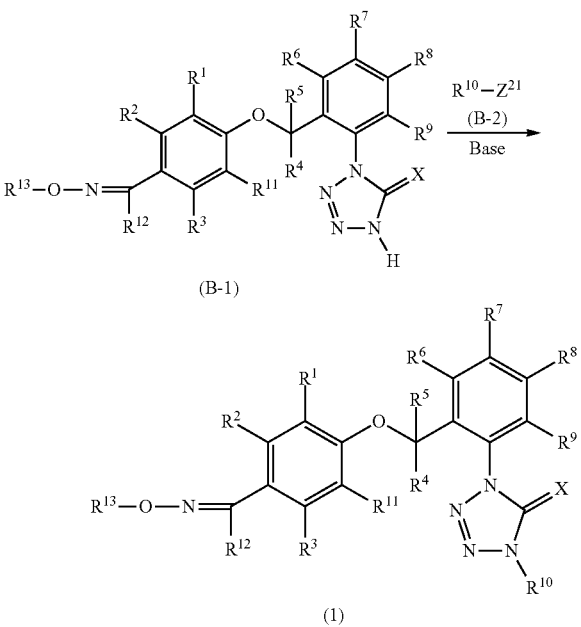

(1)

In the above formula, $R^1$, $R^2$, $R^3$, $R^4$, $R^5$, $R^6$, $R^7$, $R^8$, $R^9$, $R^{10}$, $R^{11}$, $R^{12}$, $R^{13}$, and X each have the same meaning as above and $Z^{21}$ represents a leaving group such as a chlorine atom, bromine atom, iodine atom, methane sulfonyloxy group, methoxysulfonyloxy group, trifluoromethane sulfonyloxy group, or p-toluene sulfonyloxy group.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethylsulfoxide, ketones such as acetone, methyl ethyl ketone, and methyl isobutyl ketone, nitriles such as acetonitrile and propionitrile, water and mixtures of these compounds.

As the compound (B-2) used in the reaction, a commercially available one may be usually used. Examples of the compound (B-2) may include, for example, alkyl halides such as chlorodifluoromethane, methyl bromide, ethyl bromide, n-propyl bromide, methyl iodide, ethyl iodide, n-propyl bromide, allyl bromide, cyclopropyl bromide, and 1,1-difluoro-2-iodoethane, and alkyl or aryl sulfates such as dimethyl sulfate, methyl p-toluenesulfonate, ethyl p-toluenesulfonate, n-propyl p-toluenesulfonate, methyl methanesulfonate, ethyl methanesulfonate, and n-propyl methanesulfonate.

Examples of the base used in this reaction include, for example, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, alkali metal hydroxides such as lithium hydroxide, sodium hydroxide, potassium hydroxide, and cesium hydroxide, alkali metal halides such as sodium fluoride, potassium fluoride, and cesium fluoride, alkali metal hydrides such as lithium hydride, sodium hydride, and potassium hydride, alkali metal hydrides such as lithium hydride, sodium hydride, and potassium hydride, and alkali metal alkoxides such as sodium tert-butoxide and potassium tert-butoxide.

In the reaction, the compound (B-2) is usually used in an amount of 0.5 to 10 moles and the base is usually used in an amount of 1 to 10 moles per mol of the compound (B-1).

The reaction temperature in the reaction is in a range from −20 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound represented by the formula (1) of the present invention. The isolated compound of the present invention may be further purified by chromatography, recrystallization, and the like.

(Production Method C)

Among the compounds represented by the formula (1) of the present invention, a compound (hereinafter referred to as "compound (1-S)") represented by the formula (1-S) in which X is a sulfur atom can be produced from a compound (hereinafter referred to as "compound (1-O)") wherein X is an oxygen atom among the compounds represented by the formula (1) of the present invention by a known sulfidization reaction.

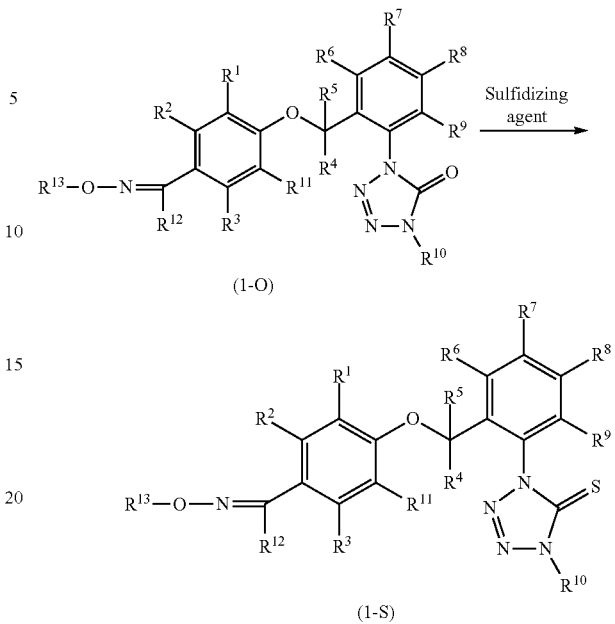

In the above formula, $R^1$, $R^2$, $R^3$, $R^4$, $R^5$, $R^6$, $R^7$, $R^8$, $R^9$, $R^{10}$, $R^{11}$, $R^{12}$, and $R^{13}$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, nitriles such as acetonitrile and propionitrile, and mixtures of these compounds.

Examples of the sulfidizing agent used in the reaction include, for example, phosphorous pentasulfide and a Lawesson's reagent (2,4-Bis(4-methoxyphenyl)-1,3,2,4-dithiadiphosphetane 2,4-disulfide).

In this reaction, the sulfidizing agent is usually used in an amount of 0.5 to 10 moles per mol of the compound (1-O).

The reaction temperature in the reaction is in a range from −20 to 150° C. and the reaction time in the reaction is usually in a range from 0.1 to 24 hr.

In the reaction, organic bases such as pyridine and triethylamine and inorganic bases such as alkali metal hydroxides and alkali metal carbonates may be added according to the need and the amount of the bases to be added is usually 0.5 to 10 moles based on the compound (1-O).

After the reaction, after-treatments including the extraction of the reaction mixture with an organic solvent and drying and concentration of the obtained organic phase may be performed to isolate the compound represented by the formula (1-S) of the present invention. The isolated compound of the present invention may be further purified by chromatography, recrystallization, and the like.

(Production Method D)

Among the compounds represented by the formula (1) of the present invention, a compound (hereinafter referred to as "compound (1-4-1)") represented by the formula (1-4-1) in which $R^6$ is $R^{41}$ can be produced by a coupling reaction between a compound (hereinafter referred to as "compound (D-1)") represented by the formula (D-1) and a compound (hereinafter referred to as "compound (D-2)") represented by the formula (D-2) in the presence of a base and a catalyst.

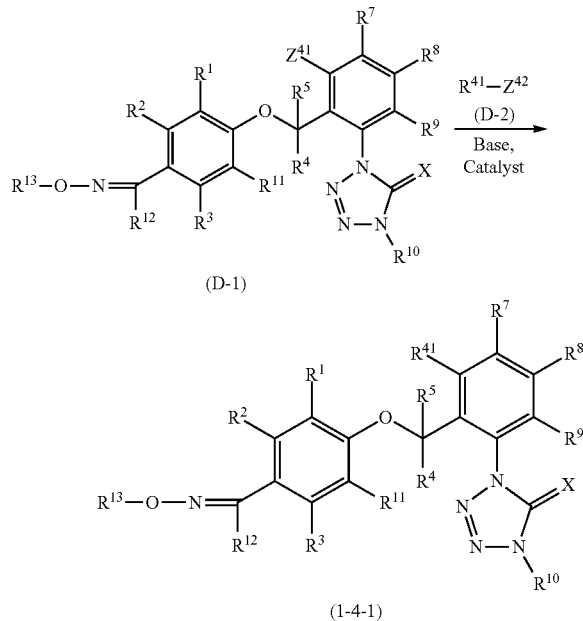

In the above formula, $R^1$, $R^2$, $R^3$, $R^4$, $R^5$, $R^7$, $R^8$, $R^9$, $R^{13}$, $R^{11}$, $R^{12}$, $R^{13}$ and X each have the same meaning as above, $Z^{41}$ represents a chlorine atom, bromine atom, iodine atom, trifluoromethane sulfonyloxy group, $R^{41}$ represents a C1-C4 alkyl group, C1-C4 haloalkyl group, C2-C4 alkenyl group, C2-C4 haloalkenyl group, C3-C6 cycloalkyl group, or C3-C6 halocycloalkyl group, and $Z^{42}$ represents $B(OH)_2$, alkoxyboryl group or trifluoroborate salt $BF_3^-K^+$.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethylsulfoxide, ketones such as acetone, methyl ethyl ketone, and methyl isobutyl ketone, nitriles such as acetonitrile and propionitrile, alcohols such as methanol, ethanol, propanol, and butanol, water and mixtures of these compounds.

As the compound (D-2) used in this reaction, a commercially available one may be used or compounds produced by a known method described in, for example, N. Miyaura and A. Suzuki, Chem. Rev., 1995, 95, 2457 and Molander et al. Acc. Chem. Res., 2007, 40, 275 may be used.

Examples of the catalyst to be used in the reaction include, for example, palladium (II) acetate, dichloro-bis-(triphenylphosphine)palladium, tetrakistriphenylphosphine palladium (0), palladium (II) acetate/triscyclohexylphosphine, bis(diphenylphosphaneferrocenyl)palladium (II) dichloride, 1,3-bis(2,6-diisopropylphenyl)imidazole-2-ylidene(1,4-naphthoquinone)palladium dimer, allyl(chloro)(1,3-dimesityl-1,3-dihydro-2H-imidazole-2-yl idene)palladium, or palladium (II) acetate/dicyclohexyl(2',4',6'-triisopropylbiphenyl-2-yl)phosphine, and tris(dibenzylideneacetone)dipalladium.

Examples of the base used in this reaction include, for example, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, alkali metal hydroxides such as lithium hydroxide, sodium hydroxide, potassium hydroxide, and cesium hydroxide, alkali metal halides such as sodium fluoride, potassium fluoride, and cesium fluoride, alkali metal hydrides such as lithium hydride, sodium hydride, and potassium hydride, alkali metal phosphates such as tripotassium phosphate, and alkali metal alkoxides such as sodium methoxide, sodium ethoxide, sodium tert-butoxide and potassium tert-butoxide.

In this reaction, the compound (D-2) is usually used in an amount of 1 to 10 moles, the base is usually used in an amount of 1 to 10 moles and the catalyst is usually used in an amount of 0.0001 to 1 mol per mol of the compound (D-1).

The reaction temperature in the reaction is in a range from 0 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound represented by the formula (1-4-1) of the present invention. In another method, after-treatments such as filtration and concentration of the reaction mixture may be performed to isolate the compound represented by the formula (1-4-1) of the present invention. The isolated compound of the present invention may be further purified by chromatography, recrystallization, and the like.

Among the compounds represented by the formula (1) of the present invention, a compound (hereinafter referred to as "compound (1-4-2)") represented by the formula (1-4-2) in which $R^7$ is $R^{42}$ can be produced by a coupling reaction between a compound (hereinafter referred to as "compound (D-3)") represented by the formula (D-3) and a compound (hereinafter referred to as "compound (D-4)") represented by the formula (D-4) in the presence of a base and a catalyst according to the method of producing the compound (1-4-1).

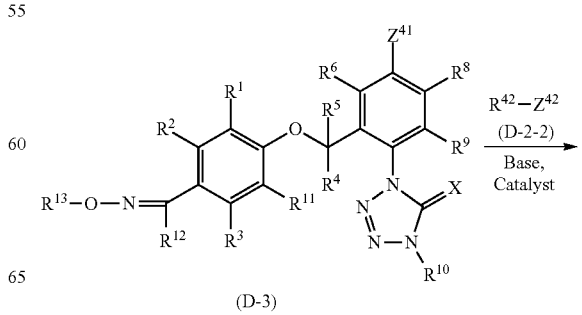

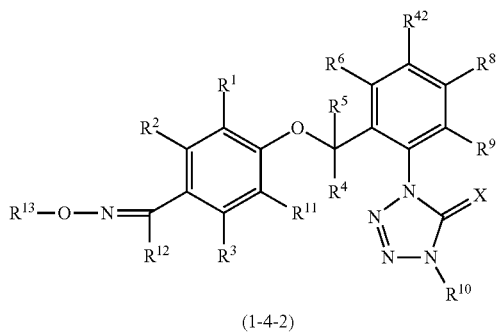

(1-4-2)

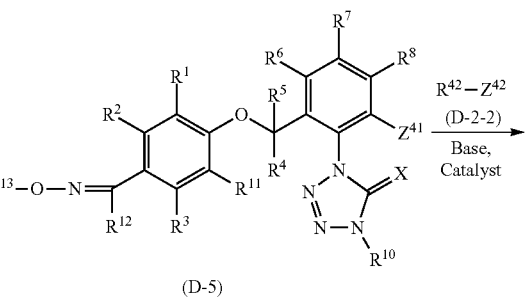

(D-5)

Among the compounds represented by the formula (1) of the present invention, a compound (hereinafter referred to as "compound (1-4-3)") represented by the formula (1-4-3) in which $R^8$ is $R^{42}$ can be produced by a coupling reaction between a compound (hereinafter referred to as "compound (D-5)") represented by the formula (D-5) and the compound (D-4) in the presence of a base and a catalyst according to the method of producing the compound (1-4-1).

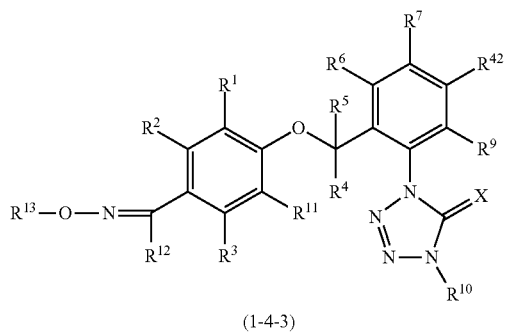

(1-4-4)

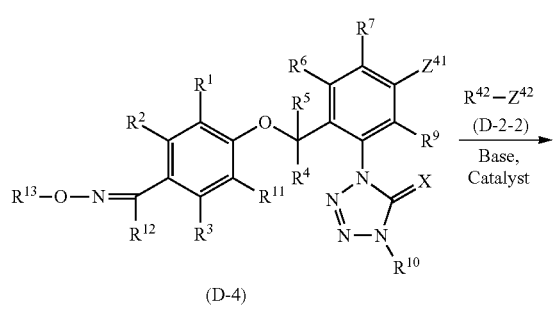

(D-4)

In the above formula, $R^1$, $R^2$, $R^3$, $R^4$, $R^5$, $R^6$, $R^7$, $R^8$, $R^{10}$, $R^{11}$, $R^{12}$, $R^{13}$, $R^{42}$, X, $Z^{41}$, and $Z^{42}$ each have the same meaning as above.

Among the compounds represented by the formula (1) of the present invention, a compound wherein $R^6$ is $R^{41}$ and one or more substituents selected from the group consisting of $R^7$, $R^8$ and $R^9$ are each $R^{42}$ can be produced according to the above production method D.

Compounds (1-4-1), (1-4-2), (1-4-3), and (1-4-4) can be produced by using other known coupling reactions in place of the coupling reaction used in the above production method D.

(Production Method E)

Among the compounds represented by the formula (1) of the present invention, a compound (hereinafter referred to as "compound (1-2)") represented by the formula (1-2) in which $R^1$ is $R^{51}$ can be produced by a coupling reaction between a compound (hereinafter referred to as "compound (E-1)") represented by the formula (E-1) and a compound (hereinafter referred to as "compound (E-2)") represented by the formula (E-2) in the presence of a base and a catalyst.

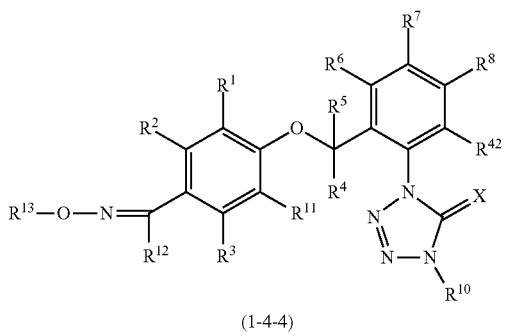

(1-4-3)

In the above formula, $R^1$, $R^2$, $R^3$, $R^4$, $R^5$, $R^6$, $R^7$, $R^9$, $R^{10}$, $R^{11}$, $R^{12}$, $R^{13}$, $R^{42}$, X, $Z^{41}$, and $Z^{42}$ each have the same meaning as above.

Among the compounds represented by the formula (1) of the present invention, a compound (hereinafter referred to as "compound (1-4-4)") represented by the formula (1-4-4) in which $R^9$ is $R^{42}$ can be produced by a coupling reaction between a compound (hereinafter referred to as "compound (D-6)") represented by the formula (D-6) and a compound (hereinafter referred to as "compound (D-4)") in the presence of a base and a catalyst according to the method of producing the compound (1-4-1).

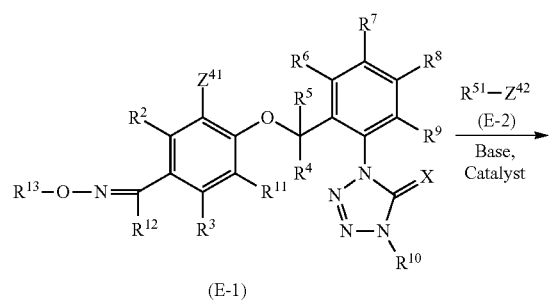

(E-1)

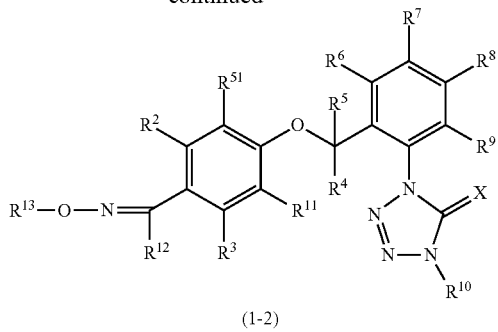

(1-2)

In the above formula, $R^2$, $R^3$, $R^4$, $R^5$, $R^6$, $R^7$, $R^8$, $R^9$, $R^{10}$, $R^{11}$, $R^{12}$, $R^{13}$, $Z^{41}$, $Z^{42}$, and X each have the same meaning as above, $R^{51}$ represents a C1-C6 alkyl group, C1-C6 haloalkyl group, C2-C6 alkenyl group, C2-C6 haloalkenyl group, C2-C6 alkynyl group, C2-C6 haloalkynyl group, C3-C6 cycloalkyl group, or C3-C6 halocycloalkyl group.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethylsulfoxide, ketones such as acetone, methyl ethyl ketone, and methyl isobutyl ketone, nitriles such as acetonitrile and propionitrile, alcohols such as methanol, ethanol, propanol, and butanol, water and mixtures of these compounds.

As the compound (E-2) used in this reaction, a commercially available one may be used or compounds produced by a known method described in, for example, N. Miyaura and A. Suzuki, Chem. Rev., 1995, 95, 2457 and Molander et al. Acc. Chem. Res., 2007, 40, 275 may be used.

Examples of the catalyst to be used in the reaction include, for example, palladium (II) acetate, dichloro-bis-(triphenylphosphine)palladium, tetrakistriphenylphosphine palladium (0), palladium (II) acetate/tricyclohexylphosphine, bis(diphenylphosphaneferrocenyl)palladium (II) dichloride, 1,3-bis(2,6-diisopropylphenyl)imidazole-2-ylidene(1,4-naphthoquinone)palladium dimer, allyl(chloro)(1,3-dimesityl-1,3-dihydro-2H-imidazole-2-yl idene)palladium, or palladium (II) acetate/dicyclohexyl(2',4',6'-triisopropylbiphenyl-2-yl)phosphine, and tris(dibenzylideneacetone)dipalladium.

Examples of the base used in this reaction include, for example, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, alkali metal hydroxides such as lithium hydroxide, sodium hydroxide, potassium hydroxide, and cesium hydroxide, alkali metal halides such as sodium fluoride, potassium fluoride, and cesium fluoride, alkali metal hydrides such as lithium hydride, sodium hydride, and potassium hydride, alkali metal phosphate such as tripotassium phosphate, and alkali metal alkoxides such as sodium methoxide, sodium ethoxide, sodium tert-butoxide and potassium tert-butoxide.

In this reaction, the compound (E-2) is usually used in an amount of 1 to 10 moles, the base is usually used in an amount of 0.5 to 10 moles, and the catalyst is usually used in an amount of 0.0001 to 1 mol per mol of the compound (E-1).

The reaction temperature in the reaction is usually in a range from 0 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound represented by the formula (1-2) of the present invention. The isolated compound of the present invention may be further purified by chromatography, recrystallization, and the like.

Among the compounds represented by the formula (1) of the present invention, a compound (hereinafter referred to as "compound (1-2-2)") represented by the formula (1-2-2) in which $R^2$ is $R^{51}$ can be produced by a coupling reaction between a compound (hereinafter referred to as "compound (E-3)") represented by the formula (E-3) and a compound (hereinafter referred to as "compound (E-2)") represented by the formula (E-2) in the presence of a base and a catalyst according to the method of producing the compound (1-2).

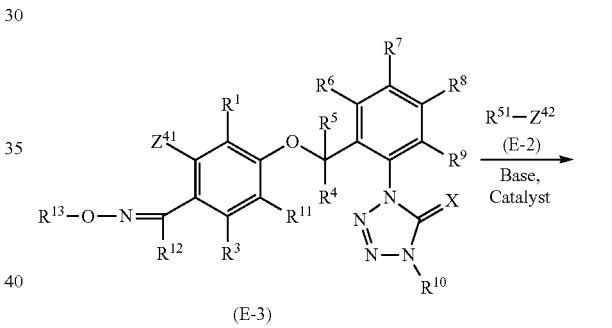

(E-3)

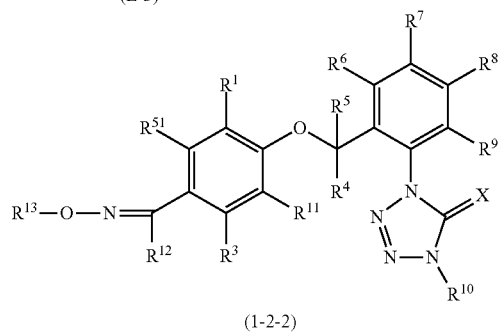

(1-2-2)

In the above formula, $R^1$, $R^3$, $R^4$, $R^5$, $R^6$, $R^7$, $R^8$, $R^9$, $R^{10}$, $R^{11}$, $R^{12}$, $R^{13}$, $R^{51}$, X, $Z^{41}$, and $Z^{42}$ each have the same meaning as above.

Among the compounds represented by the formula (1) of the present invention, a compound (hereinafter referred to as "compound (1-2-3)") represented by the formula (1-2-3) in which $R^3$ is $R^{51}$ can be produced by a coupling reaction between a compound (hereinafter referred to as "compound (E-4)") represented by the formula (E-4) and a compound (hereinafter referred to as "compound (E-2)") represented by the formula (E-2) in the presence of a base and a catalyst according to the method of producing the compound (1-2).

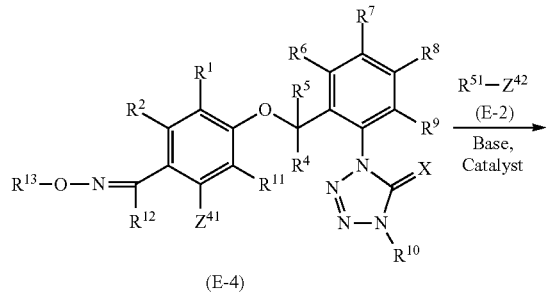

(E-4)

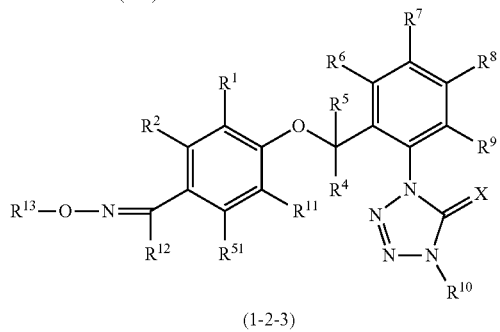

(1-2-3)

In the above formula, $R^1$, $R^2$, $R^4$, $R^5$, $R^6$, $R^7$, $R^8$, $R^9$, $R^{10}$, $R^{11}$, $R^{12}$, $R^{13}$, $R^{51}$, X, $Z^{41}$, and $Z^{42}$ each have the same meaning as above.

Among the compounds represented by the formula (1) of the present invention, a compound (hereinafter referred to as "compound (1-2-4)") represented by the formula (1-2-4) in which $R^{11}$ is $R^{51}$ can be produced by a coupling reaction between a compound (hereinafter referred to as "compound (E-5)") represented by the formula (E-5) and a compound (hereinafter referred to as "compound (E-2)") represented by the formula (E-2) in the presence of a base and a catalyst according to the method of producing the compound (1-2).

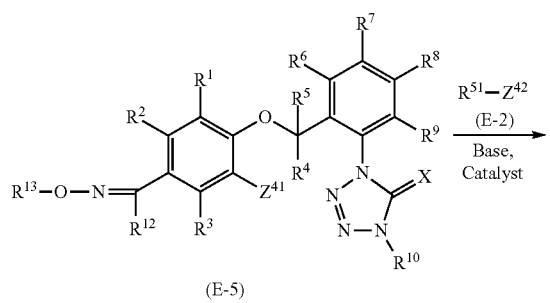

(E-5)

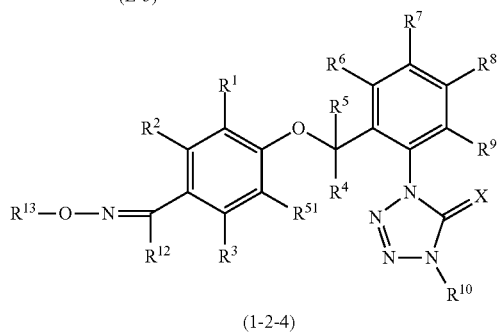

(1-2-4)

In the above formula, $R^1$, $R^2$, $R^3$, $R^4$, $R^5$, $R^6$, $R^7$, $R^8$, $R^9$, $R^{10}$, $R^{12}$, $R^{13}$, $R^{51}$, X, $Z^{41}$, and $Z^{42}$ each have the same meaning as above.

Among the compounds represented by the formula (1) of the present invention, a compound wherein one or more substituents selected from the group consisting of $R^1$, $R^2$, $R^3$, and $R^{11}$ are each $R^{51}$ can be produced according to the above production method E.

Compounds (1-2), (1-2-2), (1-2-3), and (1-2-4) can be produced by using other known coupling reactions in place of the coupling reaction used in the above production method E.

(Production Method F)

The compound represented by the formula (1) of the present invention can be produced by reacting a compound (hereinafter referred to as "compound (F-1)") represented by the formula (F-1) and a compound (hereinafter referred to as "compound (F-2)") represented by the formula (F-2) or its salt.

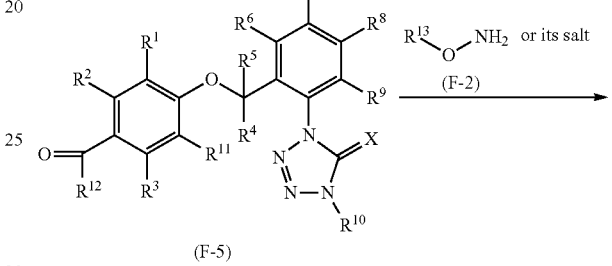

(F-5)

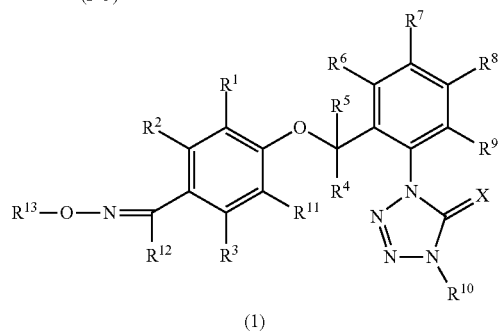

(1)

In the above formula, $R^1$, $R^2$, $R^3$, $R^4$, $R^5$, $R^6$, $R^7$, $R^8$, $R^9$, $R^{10}$, $R^{11}$, $R^{12}$, $R^{13}$, and X each have the same meaning as above.

Examples of the solvent used in the reaction include, for example, alcohols such as methanol, ethanol, propanol, and butanol, water, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, sulfoxides such as dimethylsulfoxide, and nitriles such as acetonitrile and propionitrile, and mixtures of these compounds.

Examples of the salt which can be used in the reaction include, for example, hydrochlorides, sulfates, and carbonates.

In the reaction, (F-2) or its salt is usually used in an amount of 1 to 10 moles per mol of the compound (F-1).

In the reaction, additives may be added according to the need, and examples of these additives include, for example, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, alkali metal acetates such as sodium acetate and potassium acetate, and quaternary ammonium salts such as tetra(n-butyl)ammonium hydroxide. These additives are usually used in an amount of 0.5 to 10 moles per mol of the compound (F-1).

The reaction temperature in the reaction is usually in a range from 20 to 150° C. and the reaction time in the reaction is usually in a range from 0.1 to 72 hr.

After the reaction, after-treatments including the extraction of the reaction mixture with an organic solvent and drying and concentration of the obtained organic phase may be performed to isolate the compound (1). The isolated compound of the present invention may be further purified by distillation, chromatography, recrystallization, and the like.

A method of synthesizing an intermediate compound will be explained.

(Reference Production Method XA)

A compound (hereinafter referred to as "compound (XA3)") represented by the formula (XA3) can be produced by reacting a compound (hereinafter referred to as "compound (XA1)") represented by the formula (XA1) or a compound (hereinafter referred to as "compound (XA2)") represented by the formula (XA2) with an aziding agent.

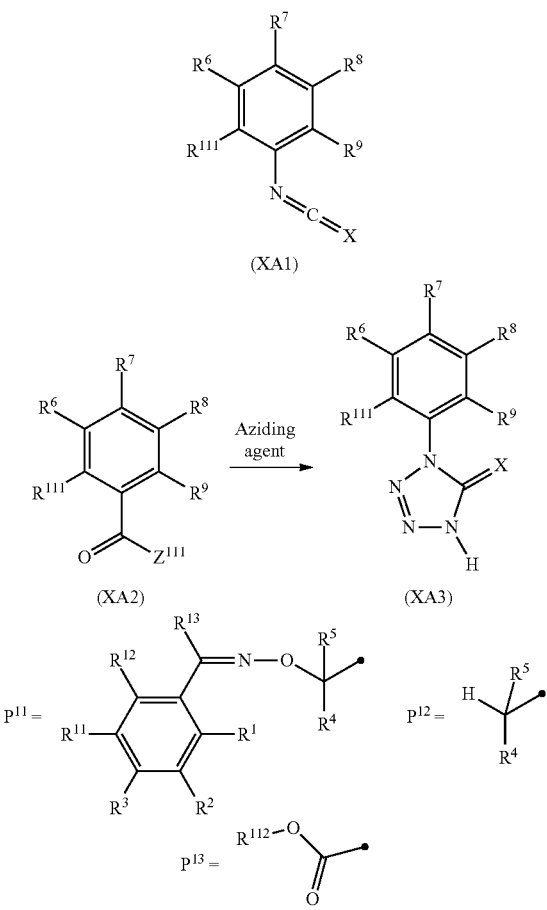

In the above formula, $R^1$, $R^2$, $R^3$, $R^4$, $R^5$, $R^6$, $R^7$, $R^8$, $R^9$, $R^{11}$, $R^{12}$, $R^{13}$, and X each have the same meaning as above, $R^{111}$ represents $P^{11}$, $P^{12}$, or $P^{13}$, $R^{112}$ represents a C1-C6 alkyl group, $Z^{111}$ represents a chlorine atom or bromine atom, and "●" shows a bonding site.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethylsulfoxide, ketones such as acetone, methyl ethyl ketone, and methyl isobutyl ketone, nitriles such as acetonitrile and propionitrile, and mixtures of these compounds.

Examples of the aziding agent to be used in the reaction include, for example, inorganic azides such as sodium azide, barium azide and lithium azide, and organic azides such as trimethylsilyl azide and diphenylphosphoryl azide.

In the reaction, the aziding agent is usually used in an amount of 1 to 10 moles per mol of the compound (XA1) or compound (XA2).

The reaction temperature in the reaction is usually in a range from −20 to 150° C. and the reaction time in the reaction is usually in a range from 0.1 to 24 hr.

In the reaction, a Lewis acid such as aluminum chloride or zinc chloride may be added according to the need and these compounds are usually used in an amount of 0.05 to 5 moles per mol of the compound (XA1) or compound (XA2).

After the reaction, after-treatments including the extraction of the reaction mixture with an organic solvent and drying and concentration of the obtained organic phase may be performed to isolate the compound (XA3). The isolated compound (XA3) may be further purified by chromatography, recrystallization, and the like.

(Reference Production Method XB)

The compound (XA1) can be produced by reacting a compound (hereinafter referred to as "compound (XB1)") represented by the formula (XB1) with an isocyanating agent.

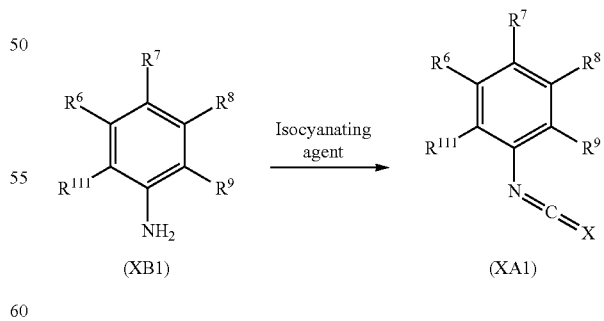

In the above formula, $R^6$, $R^7$, $R^8$, $R^9$, $R^{111}$, and X each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, esters such as ethyl acetate and methyl acetate, ketones such as acetone, methyl ethyl ketone, and methyl isobutyl ketone, nitriles such as acetonitrile and propionitrile, and mixtures of these compounds.

Examples of the isocyanating agent used in the reaction include, for example, phosgene, diphosgene, triphosgene, thiophosgene, N,N-carbodiimidazole, and N,N-thiocarbodiimidazole.

In the reaction, the isocyanating agent is usually used in an amount of 1 to 10 moles per mol of the compound (XB1).

The reaction temperature in the reaction is usually in a range from −20 to 150° C. and the reaction time in the reaction is usually in a range from 0.1 to 24 hr.

In the reaction, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate may be added according to the need. These compounds are usually used in an amount of 0.05 to 5 moles per 1 mol of the compound (XB1).

After the reaction, after-treatments including the extraction of the reaction mixture with an organic solvent and drying and concentration of the obtained organic phase may be performed to isolate the compound (XA1). The isolated compound (XA1) may be further purified by chromatography, recrystallization, and the like.

(Reference Production Method XC)

The compound (XA2) can be produced by reacting a compound (hereinafter referred to as "compound (XC1)") represented by the formula (XC1) with a halogenating agent.

Examples of the halogenating agent used in the reaction include, for example, phosphorous oxychloride, phosphorous trichloride, phosphorous pentachloride, thionyl chloride, phosphorous oxybromide, phosphorous tribromide, phosphorous pentabromide, phosphorous triiodide, oxalyl dichloride, oxalyl dibromide, triphosgene, diphosgene, phosgene, and sulfuryl chloride.

In the reaction, the halogenating agent is usually used in an amount of 1 to 10 moles per mol of the compound (XC1).

The reaction temperature in the reaction is usually in a range from −20 to 150° C. and the reaction time in the reaction is usually in a range from 0.1 to 24 hr.

In the reaction, a catalyst may be added and N, N-dimethyl formamide is given as an example of the catalyst. The catalyst is usually used in an amount of 0.001 to 1 mol per mol of the compound (XC1).

In the reaction, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate may be added according to the need. These compounds are usually used in an amount of 0.05 to 5 moles per mol of the compound (XC1).

After the reaction, after-treatments including the extraction of the reaction mixture with an organic solvent and drying and concentration of the obtained organic phase may be performed to isolate the compound (XA2). The isolated compound (XA2) may be further purified by distillation, chromatography, recrystallization, and the like.

(Reference Production Method XD)

The compound (XA1) can be produced by reacting the compound (XB1) with a carbamating agent to obtain a compound (hereinafter referred to as "compound (XD1)") represented by the formula (XD1) and then, by reacting the compound (XD1) with an isocyanating agent.

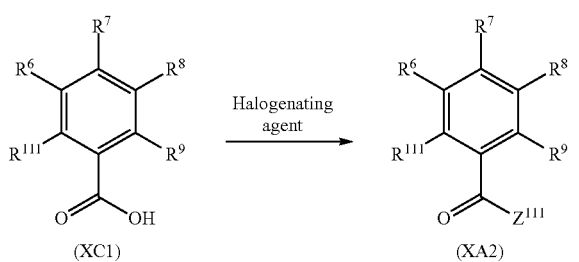

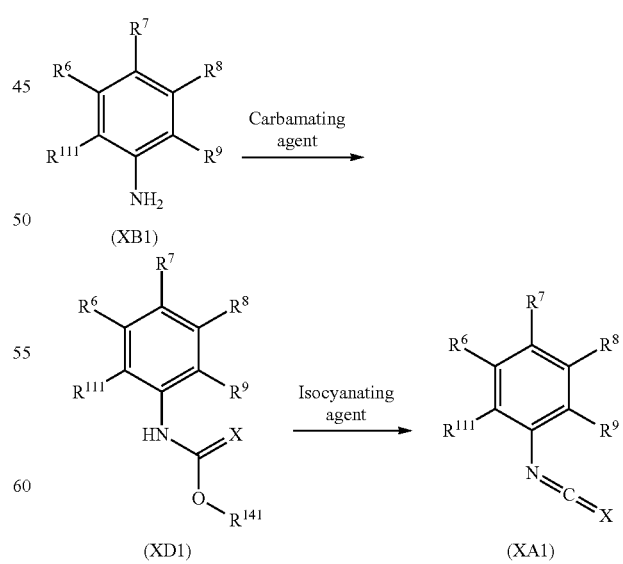

In the above formula, $R^6$, $R^7$, $R^8$, $R^9$, $R^{111}$, and $Z^{111}$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, esters such as ethyl acetate and methyl acetate, ketones such as acetone, methyl ethyl ketone, and methyl isobutyl ketone, nitriles such as acetonitrile and propionitrile, and mixtures of these compounds.

In the above formula, $R^6$, $R^7$, $R^8$, $R^9$, $R^{111}$, and X each have the same meaning as above and $R^{141}$ represents a C1-C6 alkyl group or phenyl group.

The following explanations are furnished as to a method for producing the compound (XD1) from the compound (XB1).

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethylsulfoxide, ketones such as acetone, methyl ethyl ketone, and methyl isobutyl ketone, nitriles such as acetonitrile and propionitrile, water, and mixtures of these compounds.

Examples of the carbamating agent to be used in the reaction include, for example, phenyl chlorocarbonate, methyl chlorocarbonate, ethyl chlorocarbonate, n-propyl chlorocarbonate, isopropyl chlorocarbonate, n-butyl chlorocarbonate, tert-butyl chlorocarbonate, di-tert-butyl dicarbonate, dimethyl dicarbonate, diethyl dicarbonate, phenyl chlorothioformate, methyl chlorothioformate, and ethyl chlorothioformate.

In the reaction, the carbamating agent is usually used in an amount of 1 to 10 moles per mol of the compound (XB1).

The reaction temperature in the reaction is usually in a range from −20 to 150° C. and the reaction time in the reaction is usually in a range from 0.1 to 24 hr.

In the reaction, bases including organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate may be added according to the need. These bases are usually used in an amount of 0.05 to 5 moles per mol of the compound (XB1).

After the reaction, after-treatments including the extraction of the reaction mixture with an organic solvent and drying and concentration of the obtained organic phase may be performed to isolate the compound (XD1). The isolated compound may be further purified by distillation, chromatography, recrystallization, and the like.

The following explanations are furnished as to a method for producing the compound (XA1) from the compound (XD1).

The reaction is usually carried out in a solvent.

Examples of the solvent used in the reaction include, for example, ethers such as tetrahydrofuran, dioxane, ethylene glycol dimethyl ether, and methyl tert-butyl ether, aromatic hydrocarbon such as toluene and xylene, halogenated hydrocarbon such as carbon tetrachloride, chloroform, 1,2-dichloroethane, and chlorobenzene, nitriles such as acetonitrile, acid amides such as N,N-dimethylformamide, 1,3-dimethyl-2-imidazolidinone, and N-methyl pyrrolidone, sulfoxides such as dimethylsulfoxide, ketones such as acetone, methyl ethyl ketone, and methyl isobutyl ketone, and mixtures of these compounds.

As the isocyanating agent to be used in the reaction, phosphorous pentachloride, phosphorous oxychloride, diphosphorous pentaoxide, trichlorosilane, dichlorosilane, monochlorosilane, boron trichloride, 2-chloro-1,3,2-benzodioxaborole, silane diiodide, methyl trichlorosilane, dimethyl dichlorosilane, chlorotrimethylsilane, and the like may be used.

In the reaction, the isocyanating agent is usually used in an amount of 1 to 10 moles per mol of the compound (XD1).

The reaction temperature in the reaction is usually in a range from −20 to 250° C. and the reaction time in the reaction is usually in a range from 0.1 to 24 hr.

In the reaction, bases including organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate may be added according to the need. These bases are usually used in an amount of 0.05 to 5 moles per mol of the compound (XD1).

After the reaction, after-treatments including the extraction of the reaction mixture with an organic solvent and drying and concentration of the obtained organic phase may be performed to isolate the compound (XA1). The isolated compound may be further purified by distillation, chromatography, recrystallization, and the like.

(Reference Production Method XE)

A compound (hereinafter referred to as "compound (XE2)") represented by the formula (XE2) can be produced by reacting a compound (hereinafter referred to as "compound (XE1)") represented by the formula (XE1) with hydrogen in the presence of a catalyst.

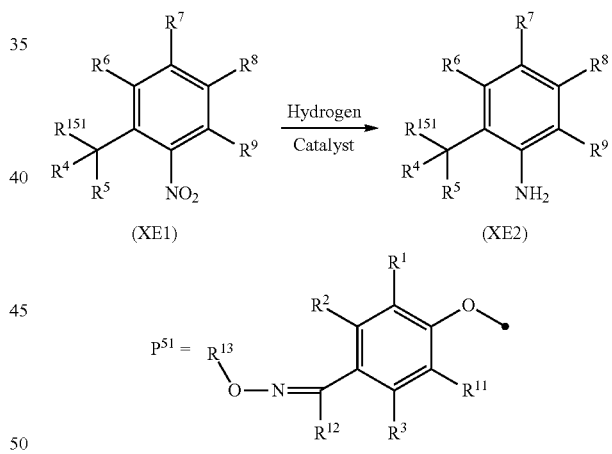

In the above formula, $R^1$, $R^2$, $R^3$, $R^4$, $R^5$, $R^6$, $R^7$, $R^8$, $R^9$, $R^{11}$, $R^{12}$, and $R^{13}$ each have the same meaning as above, $R^{151}$ represents a hydrogen atom or $P^{51}$, and ● shows a bonding site.

The reaction is usually carried out in a solvent.

Examples of the solvent used in the reaction include, for example, alcohols such as methanol, ethanol, propanol, and butanol, esters such as ethyl acetate and butyl acetate, halogenated hydrocarbon such as carbon tetrachloride, chloroform, dichloromethane, 1,2-dichloroethane, tetrachloroethane, and chlorobenzene, ethers such as diethyl ether, tetrahydrofuran, 1,4-dioxane, ethylene glycol dimethyl ether, anisole, methyl tert-butyl ether, and diisopropyl ether, hydrocarbon such as n-heptane, n-hexane, cyclohexane, n-pentane, toluene, and xylene, acetic acid, water and mixtures of these compounds.

Examples of the catalyst to be used in the reaction include, for example, palladium-carrying carbon (Pd/C), platinum-carrying carbon (Pt/C), osmium-carrying carbon (Os/C), ruthenium-carrying carbon (Ru/C), rhodium-carrying carbon (Rh/C), and Raney-nickel.

In the reaction, the catalyst is usually used in an amount of 0.1 to 1 mol and hydrogen is used in an excessive amount per mol of the compound (XE1).

The reaction temperature in the reaction is usually in a range from −20 to 150° C. and the reaction time in the reaction is usually in a range from 0.1 to 24 hr.

After the reaction, after-treatments including the concentration of the organic phase after the filtration of the catalyst may be performed to isolate the compound (XE2). The isolated compound may be further purified by distillation, chromatography, recrystallization, and the like.

(Reference Production Method XF)

The compound (XE2) can be produced by reacting the compound (XE1) with a reducing agent in the presence of an acid.

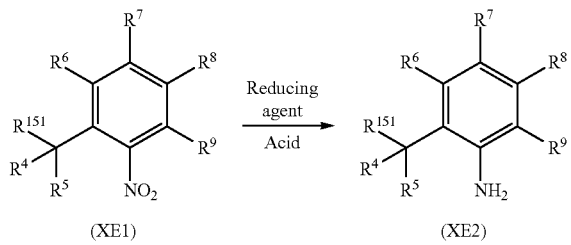

In the above formula, $R^4$, $R^5$, $R^6$, $R^7$, $R^8$, $R^9$, and $R^{151}$ each have the same meaning as above.

The reaction is usually carried out in a solvent.

Examples of the solvent used in the reaction include, for example, aliphatic carboxylic acids such as acetic acid, alcohols such as methanol and ethanol, water, and mixtures of these compounds.

Examples of the reducing agent to be used in the reaction include, for example, tin compounds such as tin chloride, zinc compounds such as zinc chloride, and iron.

Examples of the acid to be used in the reaction include, for example, hydrochloric acid, sulfuric acid, acetic acid, and an aqueous ammonium chloride solution.

In the reaction, the reducing agent is usually used in an amount of 1 to 30 moles and the acid is usually used in an amount of 1 to 100 moles per mol of the compound (XE1).

The reaction temperature in the reaction is usually in a range from −20 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (XE2). The isolated compound (XE2) may be further purified by distillation, chromatography, recrystallization, and the like.

(Reference Production Method XG)

A compound (hereinafter referred to as "compound (XG2)") represented by the formula (XG2) can be produced by reacting a compound (hereinafter referred to as "compound (XG1)") represented by the formula (XG1) with the compound (B-2) in the presence of a base.

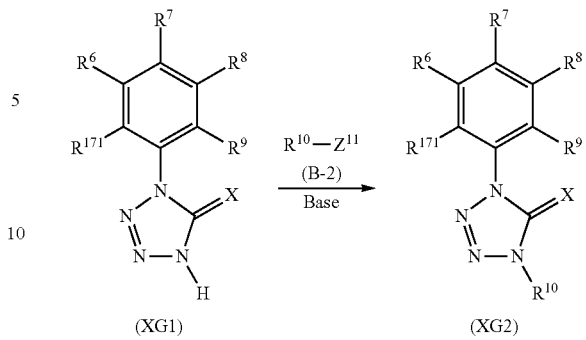

In the above formula, $R^6$, $R^7$, $R^8$, $R^9$, $R^{10}$, X, and $Z^{11}$ each have the same meaning as above, and $R^{171}$ represents $P^{12}$ or $P^{13}$.

The reaction may be carried out according to the above production method B.

(Reference Production Method XH)

A compound (hereinafter referred to as "compound (XH2)") represented by the formula (XH2) can be produced by reacting a compound (hereinafter referred to as "compound (XH1)") represented by the formula (XH1) with a halogenating agent in the presence of a radical initiator.

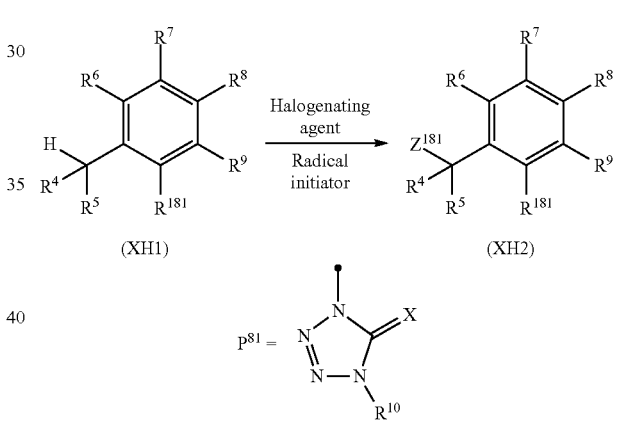

In the above formula, $R^4$, $R^5$, $R^6$, $R^7$, $R^8$, $R^9$, $R^{10}$, and X each have the same meaning as above, $R^{181}$ represents $P^{81}$ or a nitro group and $Z^{181}$ represents a chlorine atom, bromine atom, or iodine atom.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, and α,α,α-trichlorotoluene, esters such as ethyl acetate and methyl acetate, ketones such as acetone, methyl ethyl ketone, and methyl isobutyl ketone, nitriles such as acetonitrile and propionitrile, and mixtures of these compounds.

The halogenating agent which can be used in the reaction is chlorinating agents, brominating agents, and iodinating agents and examples of the halogenating agent may include, for example, chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexylbenzenesulfonimide, and N-bromophthalimide.

Examples of the radical initiator to be used in the reaction may include, for example, benzoyl peroxide, azobisisobutyronitrile (AIBN), 1,1-azobis(cyanocyclohexane), diacylperoxide, dialkyl peroxydicarbonate, tert-alkyl peroxyester, mono-peroxycarbonate, di(tert-alkylperoxy)ketal, ketone peroxide, and triethyl borane.

In the reaction, the halogenating agent is usually used in an amount of 1 to 10 moles and the radical initiator is usually used in an amount of 0.01 to 5 moles per mol of the compound (XH1).

The reaction temperature in the reaction is usually in a range from −20 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (XH2). The isolated compound may be further purified by distillation, chromatography, recrystallization, and the like.

(Reference Production Method XI)

A compound (hereinafter referred to as "compound (XI2)") represented by the formula (XI2) can be produced by a coupling reaction between a compound (hereinafter referred to as "compound (XI1)") represented by the formula (XI1) and the compound (D-2) in the presence of a base and a catalyst.

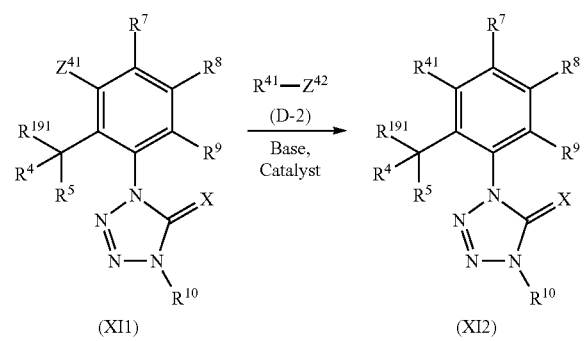

In the above formula, $R^{191}$ represents a hydrogen atom or $OR^{112}$, $R^4$, $R^5$, $R^7$, $R^8$, $R^9$, $R^{10}$, $R^{41}$, X, $Z^{41}$, and $Z^{42}$ each have the same meaning as above.

The reaction can be carried out according to the production method D.

A compound (hereinafter referred to as "compound (XI4)") represented by the formula (XI4) can be produced by a coupling reaction between a compound (hereinafter referred to as "compound (XI3)") represented by the formula (XI3) and the compound (D-4) in the presence of a base and a catalyst.

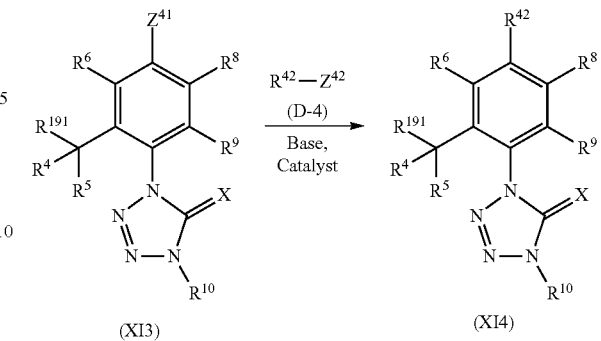

In the above formula, $R^4$, $R^5$, $R^6$, $R^8$, $R^9$, $R^{10}$, $R^{42}$, $R^{191}$, X, $Z^{41}$, and $Z^{42}$ each have the same meaning as above.

The reaction can be carried out according to the production method D.

A compound (hereinafter referred to as "compound (XI6)") represented by the formula (XI6) can be produced by a coupling reaction between a compound (hereinafter referred to as "compound (XI5)") represented by the formula (XI5) and the compound (D-4) in the presence of a base and a catalyst.

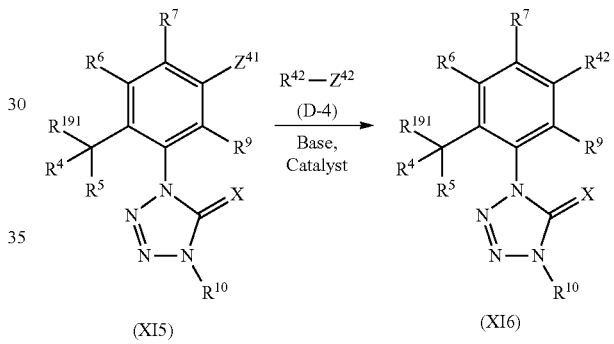

In the above formula, $R^4$, $R^5$, $R^6$, $R^7$, $R^9$, $R^{10}$, $R^{42}$, $R^{191}$, X, $Z^{41}$, and $Z^{42}$ each have the same meaning as above.

The reaction can be carried out according to the production method D.

A compound (hereinafter referred to as "compound (XI8)") represented by the formula (XI8) can be produced by a coupling reaction between a compound (hereinafter referred to as "compound (XI7)") represented by the formula (XI7) and the compound (D-4) in the presence of a base and a catalyst.

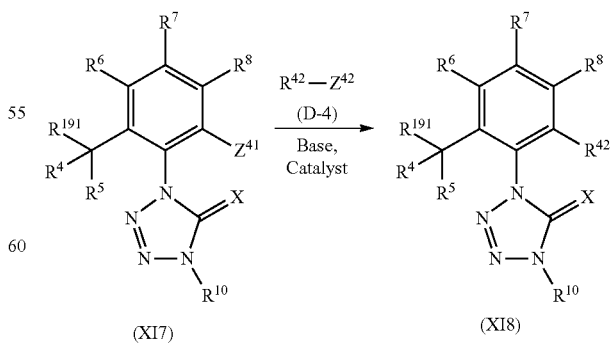

In the above formula, $R^4$, $R^5$, $R^6$, $R^7$, $R^8$, $R^{10}$, $R^{42}$, $R^{191}$, X, $Z^{41}$, and $Z^{42}$ each have the same meaning as above.

The reaction can be carried out according to the production method D.

(Reference Production Method XJ)

A compound (hereinafter referred to as "compound (XJ2)") represented by the formula (XJ2) can be produced by a coupling reaction between a compound (hereinafter referred to as "compound (XJ1)") represented by the formula (XJ1) and the compound (D-2) in the presence of a base and a catalyst.

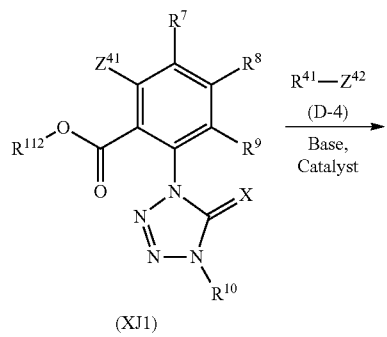

(XJ1)

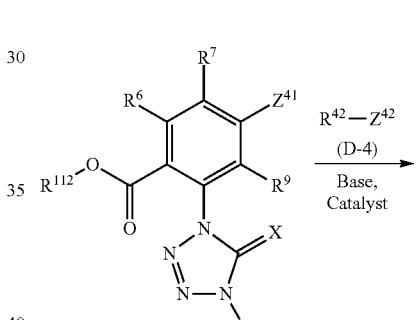

(XJ2)

In the above formula, $R^7$, $R^8$, $R^9$, $R^{10}$, $R^{41}$, $R^{112}$, X, $Z^{41}$, and $Z^{42}$ each have the same meaning as above.

The reaction can be carried out according to the production method D.

A compound (hereinafter referred to as "compound (XJ4)") represented by the formula (XJ4) can be produced by a coupling reaction between a compound (hereinafter referred to as "compound (XJ3)") represented by the formula (XJ3) and the compound (D-4) in the presence of a base and a catalyst.

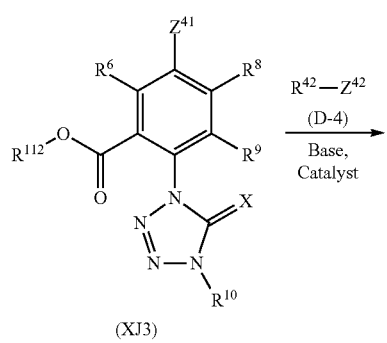

(XJ3)

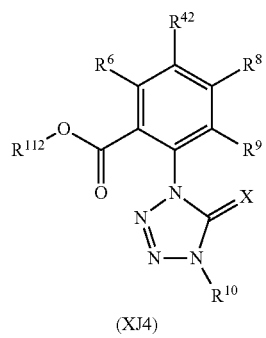

(XJ4)

In the above formula, $R^6$, $R^8$, $R^9$, $R^{10}$, $R^{42}$, $R^{112}$, X, $Z^{41}$, and $Z^{42}$ each have the same meaning as above.

The reaction can be carried out according to the production method D.

A compound (hereinafter referred to as "compound (XJ6)") represented by the formula (XJ6) can be produced by a coupling reaction between a compound (hereinafter referred to as "compound (XJ5)") represented by the formula (XJ5) and the compound (D-4) in the presence of a base and a catalyst.

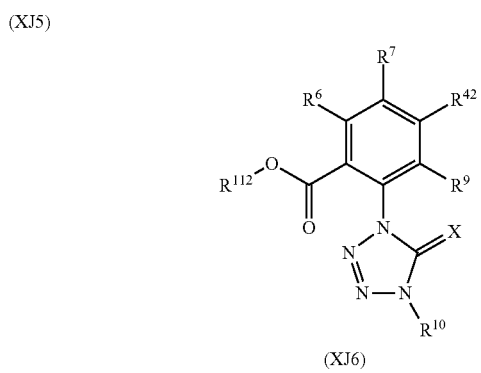

(XJ5)

(XJ6)

In the above formula, $R^6$, $R^7$, $R^9$, $R^{10}$, $R^{42}$, $R^{112}$, X, $Z^{41}$, and $Z^{42}$ each have the same meaning as above.

The reaction can be carried out according to the production method D.

A compound (hereinafter referred to as "compound (XJ8)") represented by the formula (XJ8) can be produced by a coupling reaction between a compound (hereinafter referred to as "compound (XJ7)") represented by the formula (XJ7) and the compound (D-4) in the presence of a base and a catalyst.

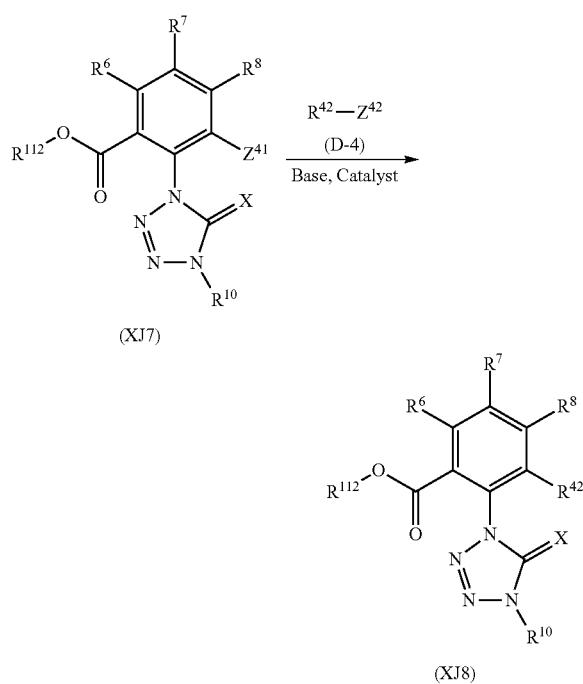

(XJ7)

(XJ8)

In the above formula, $R^6$, $R^7$, $R^8$, $R^{10}$, $R^{42}$, $R^{112}$, X, $Z^{41}$, and $Z^{42}$ each have the same meaning as above.

The reaction can be carried out according to the production method D.

(Reference Production Method XK)

A compound (hereinafter referred to as "compound (XK3)") represented by the formula (XK3) can be produced by reacting a compound (hereinafter referred to as "compound (XK1)") represented by the formula (XK1) with a compound (hereinafter referred to as "compound (XK2)") represented by the formula (XK2) in the presence of a reaction accelerator.

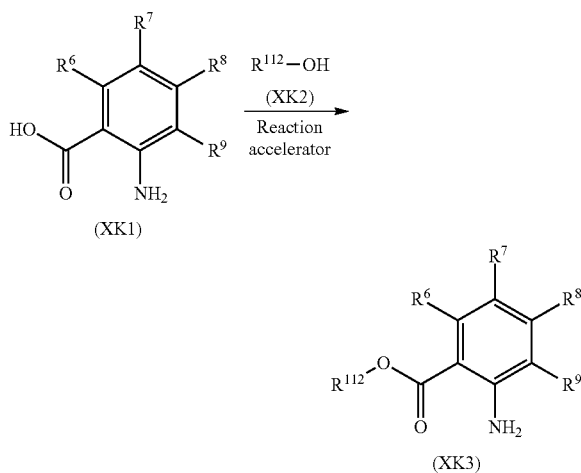

In the above formula, $R^6$, $R^9$, $R^8$, $R^9$, and $R^{112}$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethyl sulfoxide, ketones such as acetone, methyl ethyl ketone, and methyl isobutyl ketone, nitriles such as acetonitrile and propionitrile, and mixtures of these compounds. Also, the compound (XK2) may be used as the solvent.

Examples of the compound (XK2) which can be used in the reaction include, for example, methyl alcohol, ethyl alcohol, propyl alcohol, isopropyl alcohol, n-butyl alcohol, sec-butyl alcohol, t-butanol, and n-pentanol.

Examples of the reaction accelerator to be used in the reaction include, for example, acids such as hydrochloric acid, sulfuric acid, carbodiimides such as dicyclohexylcarbodiimide, diisopropylcarbodiimide, and N'-(3-dimethylaminopropyl)-N-ethylcarbodiimide, organic acids such as methane sulfonic acid and toluene sulfonic acid, Mitsunobu reaction reagents such as triphenylylphosphine/diethyl azodicarboxylate, thionyl chloride, and boron trifluoride-ethyl ether complex. The reaction accelerator is used in an amount of 0.01 to 10 moles per mol of the compound (XK1).

In the reaction, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, and alkali metal bicarbonates such as lithium bicarbonate, sodium bicarbonate, potassium bicarbonate, and cesium bicarbonate may be added and these compounds are used in an amount of 0.001 to 5 moles per mol of the compound (XK1).

In the reaction, an excess amount of the compound (XK2) is used based on the compound (XK1).

The reaction temperature in the reaction is usually in a range from −78 to 100° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (XK3). The isolated compound may be further purified by distillation, chromatography, recrystallization, and the like.

(Reference Production Method XL)

The compound (XK3) can be produced by reacting the compound (XK1) with a halogenating agent to obtain a compound (hereinafter referred to as "compound (XL1)") represented by the following formula (XL1) and then, by reacting the compound (XL1) with the compound (XK2).

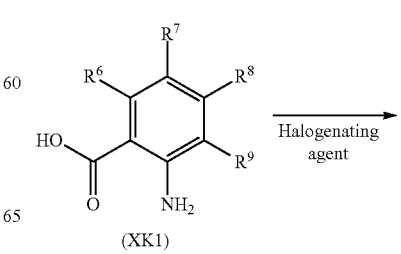

(XK1)

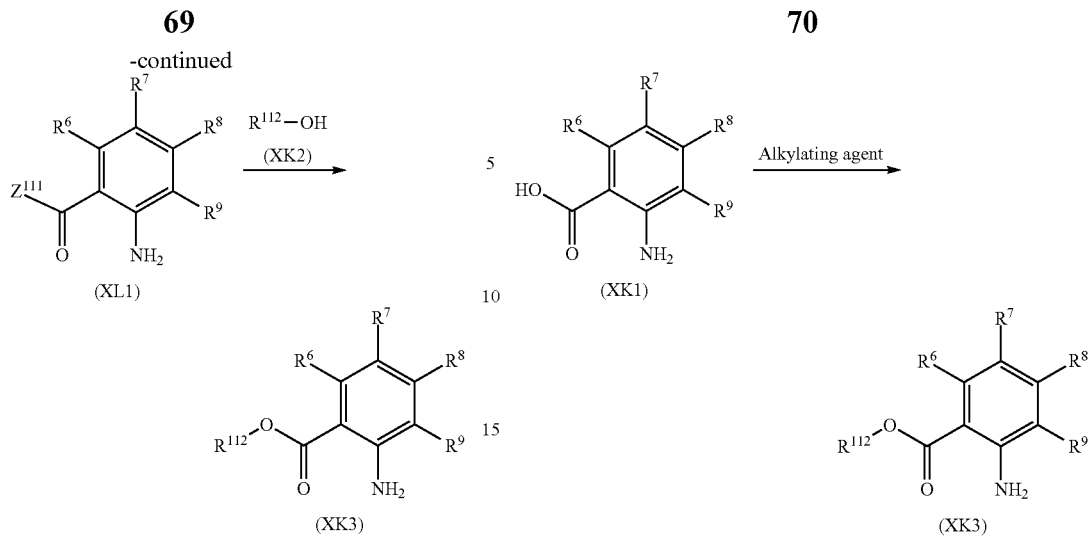

In the above formula, $R^6$, $R^7$, $R^8$, $R^9$, $R^{112}$, and $Z^{111}$ each have the same meaning as above.

A method for producing the compound (XL1) by reacting the compound (XK1) with a halogenating agent can be performed according to the Reference production method XC.

The following explanations are furnished as to a method for producing the compound (XK3) from the compound (XL1).

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethyl sulfoxide, ketones such as acetone, methyl ethyl ketone, and methyl isobutyl ketone, nitriles such as acetonitrile and propionitrile, and mixtures of these compounds. Also, the compound (XK2) may be used as the solvent.

Examples of the compound (XK2) which can be used in the reaction include, for example, methyl alcohol, ethyl alcohol, propyl alcohol, isopropyl alcohol, n-butyl alcohol, sec-butyl alcohol, t-butanol, and n-pentanol.

In the reaction, the compound (XK2) is usually used in an amount of 1 to 50 moles per mol of the compound (XL1).

The reaction temperature in the reaction is usually in a range from −78 to 100° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (XK3). The isolated compound may be further purified by distillation, chromatography, recrystallization, and the like.

(Reference Production Method XM)

The compound (XK3) can be produced by reacting the compound (XK1) with an alkylating agent.

In the above formula, $R^6$, $R^7$, $R^8$, $R^9$, and $R^{112}$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethyl sulfoxide, ketones such as acetone, methyl ethyl ketone, and methyl isobutyl ketone, nitriles such as acetonitrile and propionitrile, water, and mixtures of these compounds.

Examples of the alkylating agent which can be used in the reaction may include, for example, diazo compounds such as diazomethane, and trimethylsilyldiazomethane, alkyl halides such as chlorodifluoromethane, methyl bromide, ethyl bromide, n-propyl bromide, methyl iodide, ethyl iodide, n-propyl bromide, allyl bromide, cyclopropyl bromide, benzyl bromide, and 1,1-difluoro-2-iodoethane, and dialkyl sulfate such as dimethyl sulfate, diethyl sulfate, and di-n-propyl sulfate, and alkyl or aryl sulfates such as methyl p-toluenesulfonate, ethyl p-toluenesulfonate, n-propyl p-toluenesulfonate, methyl methanesulfonate, ethyl methanesulfonate, and n-propyl methanesulfonate.

The alkylating agent is usually used in an amount of 1 to 10 moles per mol of the compound (XK1).

In the reaction, additives may be added, if necessary and examples of these additives include, for example, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, and quaternary ammonium salts such as tetra(n-butyl)ammonium hydroxide. These compounds are usually used in an amount of 0.001 to 5 moles per mol of the compound (XK1).

The reaction temperature in the reaction is usually in a range from −78 to 100° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (XK3). The isolated compound may be further purified by distillation, chromatography, recrystallization, and the like.

(Reference Production Method XN)

A compound (hereinafter referred to as "compound (XN2)") represented by the formula (XN2) can be produced by reacting a compound (hereinafter referred to as "compound (XN1)") represented by the formula (XN1) with a reducing agent.

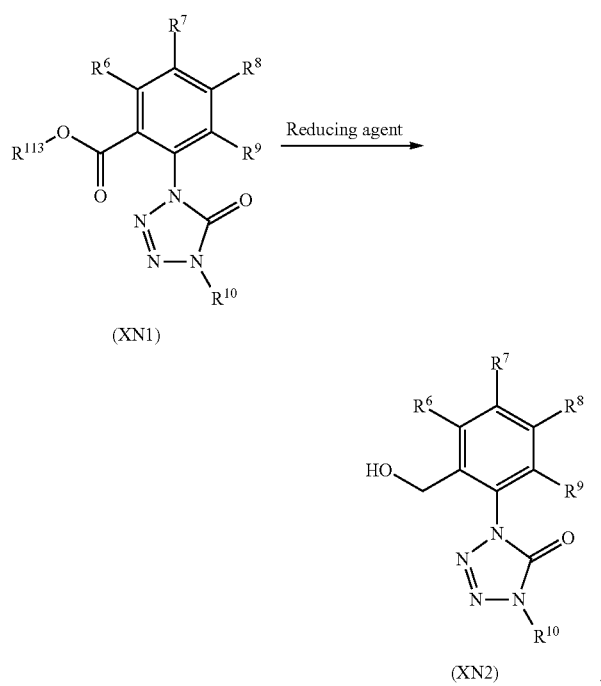

In the above formula, $R^6$, $R^7$, $R^8$, $R^9$, and $R^{10}$ each have the same meaning as above and $R^{113}$ represents a hydrogen atom or C1-C3 alkyl group.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, alcohols such as methanol, ethanol, propanol, and butanol, water, and mixtures of these compounds.

Examples of the reducing agent which can be used in the reaction include, for example, lithium triethylborohydride, aluminum diisobutylhydride, lithium aminoborohydride, lithium borohydride, sodium borohydride, borane, borane dimethylsulfide complex, and borane tetrahydrofuran complex.

In the reaction, the reducing agent is usually used in an amount of 1 to 10 moles per mol of the compound (XN1).

The reaction temperature in the reaction is usually in a range from −78 to 100° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (XN2). The isolated compound may be further purified by distillation, chromatography, recrystallization, and the like.

(Reference Production Method XO)

A compound (hereinafter referred to as "compound (XO2)") represented by the formula (XO2) can be produced by reacting a compound (hereinafter referred to as "compound (XO1)") represented by the formula (XO1) with a reducing agent.

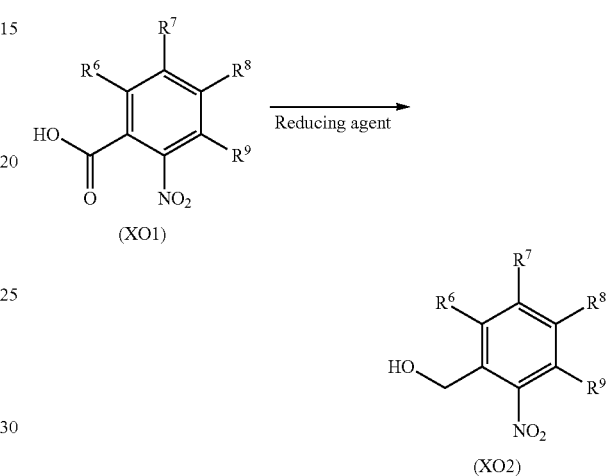

In the above formula, $R^6$, $R^7$, $R^8$, and $R^9$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, sulfoxides such as dimethylsulfoxide, nitriles such as acetonitrile and propionitrile, alcohols such as methanol, ethanol, propanol, and butanol, water, and mixtures of these compounds.

Examples of the reducing agent which can be used in this reaction include, for example, borane, borane tetrahydrofuran complex, and borane dimethylsulfide complex. Also, borane generated by mixing borohydride such as sodium borohydride or potassium borohydride with an acid such as sulfuric acid, hydrochloric acid, methanesulfonic acid, or trifluoride boron-diethyl ether complex is also used.

In the reaction, the reducing agent is usually used in an amount of 1 to 10 moles per mol of the compound (XO1).

The reaction temperature in the reaction is usually in a range from −20 to 100° C. and the reaction time in the reaction is usually in a range from 0.1 to 72 hr.

After the reaction, after-treatments including the extraction of the reaction mixture with an organic solvent and drying and concentration of the obtained organic phase may be performed to isolate the compound (XO2). The isolated compound may be further purified by distillation, chromatography, recrystallization, and the like.

(Reference Production Method XP)

A compound (hereinafter referred to as "compound (XP2)") represented by the formula (XP2) can be produced by reacting the compound (XH2) with a compound (hereinafter referred to as "compound (XP1)") represented by the formula (XP1).

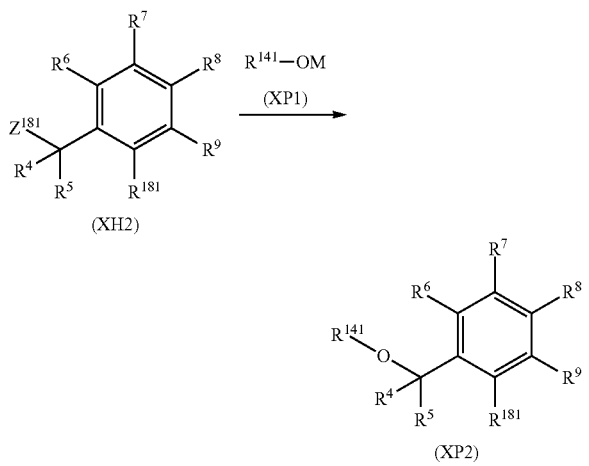

In the above formula, $R^4$, $R^5$, $R^6$, $R^7$, $R^8$, $R^9$, $R^{141}$, $R^{181}$, and $Z^{181}$ each have the same meaning as above and M represents sodium, potassium, or lithium.

The reaction is usually carried out in a solvent.

Examples of the solvent used in the reaction include, for example, ethers such as diethyl ether, tetrahydrofuran, 1,4-dioxane, ethylene glycol dimethyl ether, anisole, methyl tert-butyl ether, and diisopropyl ether, hydrocarbon such as n-heptane, n-hexane, cyclohexane, n-pentane, toluene, and xylene, halogenated hydrocarbon such as carbon tetrachloride, chloroform, dichloromethane, 1,2-dichloroethane, tetrachloroethane, and chlorobenzene, nitriles such as acetonitrile and propionitrile, acid amides such as N,N-dimethylformamide, 1,3-dimethyl-2-imidazolidinone, and N-methyl pyrrolidone, sulfoxides such as dimethylsulfoxide, ketones such as acetone, methyl ethyl ketone, and methyl isobutyl ketone, alcohols such as methanol, ethanol, propanol, and butanol, and mixtures of these compounds.

Examples of the compound (XI1) include, for example, sodium methoxide, sodium ethoxide, sodium n-propoxide, sodium n-butoxide, sodium isopropoxide, sodium sec-butoxide, sodium tert-butoxide, potassium methoxide, potassium ethoxide, potassium n-propoxide, potassium n-butoxide, potassium isopropoxide, potassium sec-butoxide, potassium tert-butoxide, and sodium phenoxide.

In the reaction, the compound (XP1) is usually used in an amount of 1 to 10 moles per mol of the compound (XH2).

In the reaction, the reaction temperature is usually in a range from −20 to 150° C. and the reaction time is usually in a range from 0.1 to 24 hr.

After the reaction, after-treatments including the extraction of the reaction mixture with an organic solvent and drying and concentration of the obtained organic phase may be performed to isolate the compound (XP2). The isolated compound may be further purified by chromatography, recrystallization, and the like.

(Reference Production Method XQ)

A compound (hereinafter referred to as "compound (XQ1)") represented by the formula (XQ1) can be produced by reacting the compound (XH2) with water in the presence of a base.

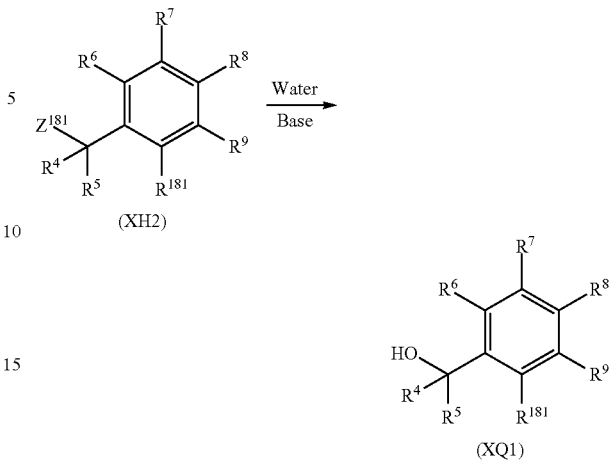

In the above formula, $R^4$, $R^5$, $R^6$, $R^7$, $R^8$, $R^9$, $R^{181}$, and $Z^{181}$ each have the same meaning as above.

The reaction is usually carried out in water or in a solvent containing water.

Examples of the solvent used in the reaction include, for example, ethers such as diethyl ether, tetrahydrofuran, 1,4-dioxane, ethylene glycol dimethyl ether, anisole, methyl tert-butyl ether, and diisopropyl ether, hydrocarbon such as n-heptane, n-hexane, cyclohexane, n-pentane, toluene, and xylene, halogenated hydrocarbon such as carbon tetrachloride, chloroform, dichloromethane, 1,2-dichloroethane, tetrachloroethane, and chlorobenzene, nitriles such as acetonitrile and propionitrile, acid amides such as N,N-dimethylformamide, 1,3-dimethyl-2-imidazolidinone, and N-methyl pyrrolidone, sulfoxides such as dimethyl sulfoxide, ketones such as acetone, methyl ethyl ketone, and methyl isobutyl ketone, alcohols such as methanol, ethanol, propanol, and butanol, and mixtures of these compounds.

Examples of the base used in the reaction include, for example, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, metal organic acid salts such as lithium formate, lithium acetate, sodium formate, sodium acetate, potassium formate, and potassium acetate, metal nitrates such as silver nitrate and sodium nitrate, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, alkali metal hydroxides such as lithium hydroxide, sodium hydroxide, potassium hydroxide, and cesium hydroxide, and alkali metal alkoxides such as sodium methoxide, sodium ethoxide, sodium tert-butoxide, and potassium tert-butoxide.

In the reaction, the base is usually used in an amount of 1 to 100 moles per mol of the compound (XH2).

In the reaction, water is usually used in an amount of 1 mol to a largely excessive ratio per mol of the compound (XH2).

The reaction temperature in the reaction is usually in a range from −20 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (XQ1). The isolated compound may be further purified by distillation, chromatography, recrystallization, and the like.

(Reference Production Method XR)

The compound (XH2) can be produced by reacting the compound (XP2) with a halogenating agent.

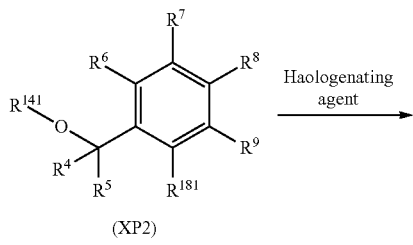

(XP2)

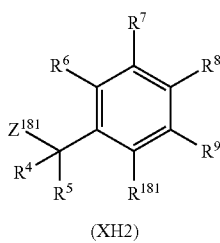

(XH2)

In the above formula, $R^4$, $R^5$, $R^6$, $R^7$, $R^8$, $R^9$, $R^{141}$, $R^{181}$, and $Z^{181}$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, halogenated hydrocarbon such as carbon tetrachloride, chloroform, dichloromethane, 1,2-dichloroethane, tetrachloroethane, and chlorobenzene, ketones such as acetone, methyl ethyl ketone, and methyl isobutyl ketone, nitriles such as acetonitrile and propionitrile, organic acids such as formic acid, acetic acid, and trifluoroacetic acid, water, and mixtures of these compounds.

Examples of the halogenating agent to be used in the reaction include, for example, hydrochloric acid, hydrobromic acid, and hydroiodic acid.

In the reaction, the halogenating agent is usually used in an amount of 1 mol or more per mol of the compound (XP2).

The reaction temperature in the reaction is usually in a range from –20 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (XH2). The isolated compound may be further purified by distillation, chromatography, recrystallization, and the like.

(Reference Production Method XS)

The compound (XH2) can be produced by reacting the compound (XQ1) with a halogenating agent.

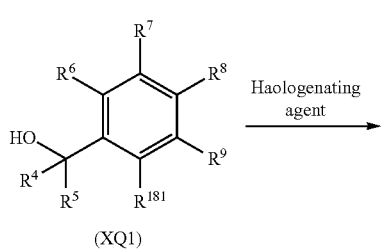

(XQ1)

-continued

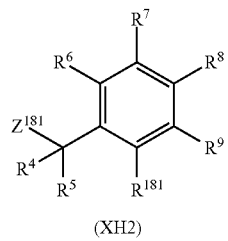

(XH2)

In the above formula, $R^4$, $R^5$, $R^6$, $R^7$, $R^8$, $R^9$, $R^{181}$, and $Z^{181}$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, esters such as ethyl acetate and methyl acetate, ketones such as acetone, methyl ethyl ketone, and methyl isobutyl ketone, nitriles such as acetonitrile and propionitrile, organic acids such as formic acid, acetic acid, and trifluoroacetic acid, water, and mixtures of these compounds.

Examples of the halogenating agent to be used in the reaction include, for example, bromine, chlorine, sulfuryl chloride, hydrochloric acid, hydrobromic acid, hydroiodic acid, boron tribromide, phosphorous tribromide, trimethylsilyl chloride, trimethylsilyl bromide, trimethylsilyl iodide, thionyl chloride, thionyl bromide, phosphorous oxychloride, phosphorous trichloride, phosphorous pentachloride, thionyl chloride, phosphorous oxybromide, phosphorous pentabromide, phosphorous triiodide, oxalyl dichloride, oxalyl dibromide, acetyl chloride, carbon tetrabromide, N-bromosuccinimide, lithium chloride, sodium iodide, and acetyl bromide.

The halogenating agent is usually used in an amount of 1 to 10 moles per mol of the compound (XQ1).

Additives may be added corresponding to the halogenating agent to be used to promote the reaction, for example, the following combinations are exemplified: zinc chloride to acetyl chloride, triphenylphosphine to carbon tetrabromide, dimethyl sulfide to N-bromosuccinimide, trifluoroborondiethyl ether complex to sodium iodide, trifluoroborondiethyl ether complex to acetyl bromide, triethylamine and methanesulfonyl chloride to lithium chloride, aluminum chloride to sodium iodide, and trimethylsilyl chloride to sodium iodide. The additive is usually used in an amount of 0.01 to 5 moles per mol of the compound (XQ1).

The reaction temperature in the reaction is usually in a range from –20 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (XH2). The isolated compound may be further purified by distillation, chromatography, recrystallization, and the like.

(Reference Production Method YA)

The compound (A-2) can be produced by reacting a compound (hereinafter referred to as "compound (YA1)") represented by the formula (YA1) with (F-2) or its salt in the presence of an acid or base.

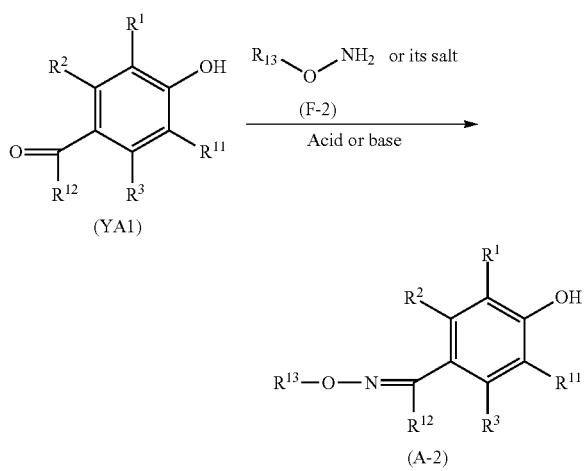

(YA1)

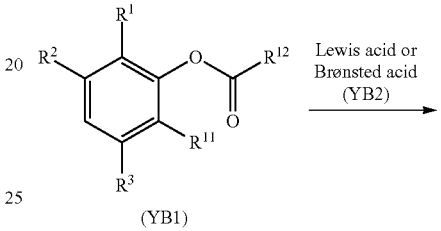

(A-2)

In the above formula, $R^1$, $R^2$, $R^3$, $R^{11}$, $R^{12}$, and $R^{13}$ each have the same meaning as above.

The reaction is usually carried out in a solvent.

Examples of the solvent used in the reaction include, for example, alcohols such as methanol, ethanol, propanol, and butanol, water, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, sulfoxides such as dimethylsulfoxide, nitriles such as acetonitrile and propionitrile, and mixtures of these compounds.

Examples of the salt which can be used in this reaction include, for example, hydrochlorides, sulfates, acetates, and carbonates.

In this reaction, (F-2) or its salt is usually used in an amount of 1 to 10 moles per mol of the compound (YA1).

Examples of the acid to be used in the reaction include, for example, hydrochloric acid, sulfuric acid, nitric acid, acetic acid, trifluoroacetic acid, and p-toluenesulfonic acid. Also, examples of the base include, for example, organic bases such as triethylamine, pyridine, N-methylmorpholine, N-methylpiperidine, 4-dimethylaminopyridine, disiopropylethylamine, lutidine, collidine, diazabicycloundecene, aqueous ammonia, and diazabicyclononene, metal hydrides such as sodium hydride and potassium hydride, metal organic acid salts such as lithium formate, lithium acetate, sodium formate, sodium acetate, potassium formate, and potassium acetate, metal nitrates such as silver nitrate and sodium nitrate, alkali metal carbonates such as lithium carbonate, sodium carbonate, potassium carbonate, and cesium carbonate, and alkali metal bicarbonates such as lithium bicarbonate, sodium bicarbonate, potassium bicarbonate, and cesium bicarbonate, alkali metal hydroxides such as lithium hydroxide, sodium hydroxide, potassium hydroxide, and cesium hydroxide, and alkali metal alkoxides such as sodium methoxide, sodium ethoxide, sodium tert-butoxide, potassium tert-butoxide.

In the reaction, the base is usually used in an amount of 1 to 10 moles per mol of the compound (YA1).

In the reaction, the acid is usually used in an amount of 0.01 to 10 moles per mol of the compound (YA1).

The reaction temperature in the reaction is usually in a range from 0 to 150° C. and the reaction time in the reaction is usually in a range from 0.1 to 72 hr.

After the reaction, after-treatments including the extraction of the reaction mixture with an organic solvent and drying and concentration of the obtained organic phase may be performed to isolate the compound (A-2). The isolated compound may be further purified by distillation, chromatography, recrystallization, and the like.

(Reference Production Method YB)

The compound (YA1) can be produced by reacting a compound (hereinafter referred to as "compound (YB1)") represented by the formula (YB1) in the presence of a Lewis acid or Brønsted acid (hereinafter, this Lewis acid or Brønsted acid is referred to as "compound (YB2)").

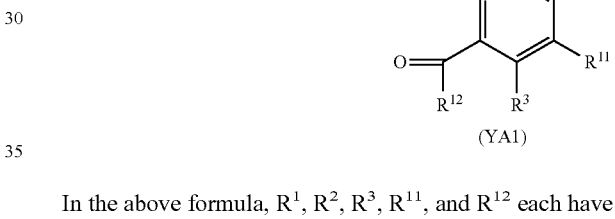

(YB1)

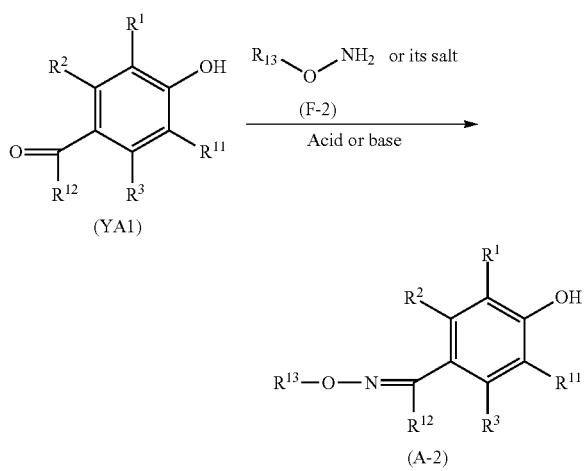

(YA1)

In the above formula, $R^1$, $R^2$, $R^3$, $R^{11}$, and $R^{12}$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, chlorobenzene, nitromethane, and mixtures of these compounds.

Examples of the Lewis acid used in the reaction include, for example, aluminum chloride and titanium tetrachloride and example of the Brønsted acid include, for example, hydrogen fluoride, and perchloric acid.

The compound (YB2) is usually used in an amount of 0.5 to 10 moles per mol of the compound (YB1).

The reaction temperature in the reaction is usually in a range from –90 to 100° C. and the reaction time in the reaction is usually in a range from 0.1 to 72 hr.

After the reaction, after-treatments including the extraction of the reaction mixture with an organic solvent and drying and concentration of the obtained organic phase may be performed to isolate the compound (YA1). The isolated compound may be further purified by distillation, chromatography, recrystallization, and the like.

(Reference Production Method YC)

The compound (YB1) can be produced by reacting a compound (hereinafter referred to as "compound (YC1)") represented by the formula (YC1) with a compound (hereinafter referred to as "compound (YC2)") represented by the formula (YC2).

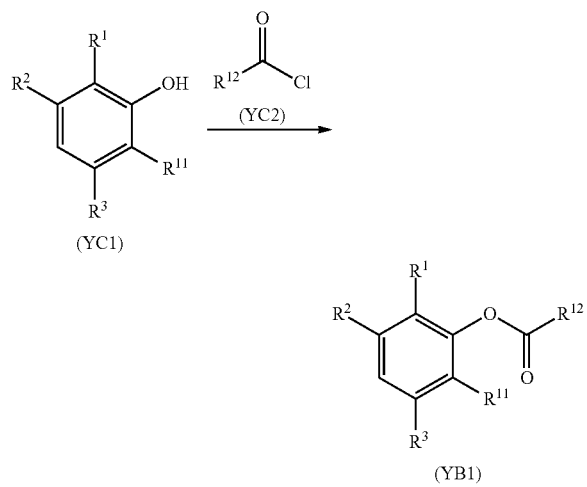

(YC1) → (YB1)

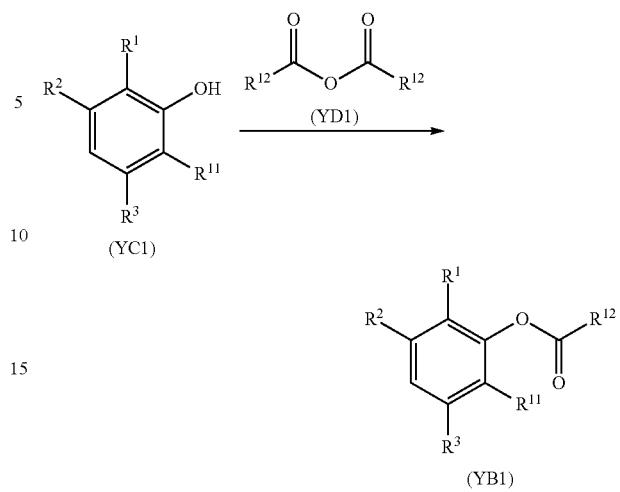

(YC1) → (YB1)

In the above formula, $R^1$, $R^2$, $R^3$, $R^{11}$, and $R^{12}$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, esters such as ethyl acetate and methyl acetate, ketones such as acetone, methyl ethyl ketone, and methyl isobutyl ketone, nitriles such as acetonitrile and propionitrile, and mixtures of these compounds.

In the reaction, additives may be added according to the need and examples of these additives include, for example, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, alkali metal acetates such as sodium acetate and potassium acetate, and quaternary ammonium salts such as tetra(n-butyl)ammonium hydroxide. These additives are usually used in an amount of 0.5 to 10 moles per mol of the compound (YC1).

In the reaction, (YC2) is usually used in an amount of 1 to 10 moles based on the compound (YC1).

The reaction temperature in the reaction is usually in a range from −20 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (YB1). The isolated compound (YB1) may be further purified by chromatography, recrystallization, and the like.

(Reference Production Method YD)

The compound (YB1) can be produced by reacting the compound (YC1) with a compound (hereinafter referred to as "compound (YD1)") represented by the formula (YD1).

In the above formula, $R^1$, $R^2$, $R^3$, $R^{11}$, and $R^{12}$ each have the same meaning as above.

The reaction is usually carried out in a solvent.

Examples of the solvent used in the reaction include, for example, hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, halogenated hydrocarbon such as carbon tetrachloride, chloroform, dichloromethane, 1,2-dichloroethane, tetrachloroethane, and chlorobenzene, esters such as ethyl acetate and methyl acetate, ketones such as acetone, methyl ethyl ketone, and methyl isobutyl ketone, nitriles such as acetonitrile and propionitrile, and mixtures of these compounds.

In the reaction, additives may be added according to the need and examples of these additives include, for example, organic bases such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, alkali metal acetates such as sodium acetate and potassium acetate, and quaternary ammonium salts such as tetra(n-butyl)ammonium hydroxide. These additives are usually used in an amount of 0.5 to 10 moles per mol of the compound (YC1).

In the reaction, (YD1) is usually used in an amount of 1 to 10 moles based on the compound (YC1).

The reaction temperature in the reaction is usually in a range from −20 to 150° C. and the reaction time in the reaction is usually in a range from 0.1 to 24 hr.

After the reaction, after-treatments including the extraction of the reaction mixture with an organic solvent and drying and concentration of the obtained organic phase may be performed to isolate the compound (YB1). The isolated compound (YB1) may be further purified by chromatography, recrystallization, and the like.

(Reference Production Method YE)

The compound (F-1) can be produced by reacting the compound (A-1) with the compound (YA1) in the presence of a base.

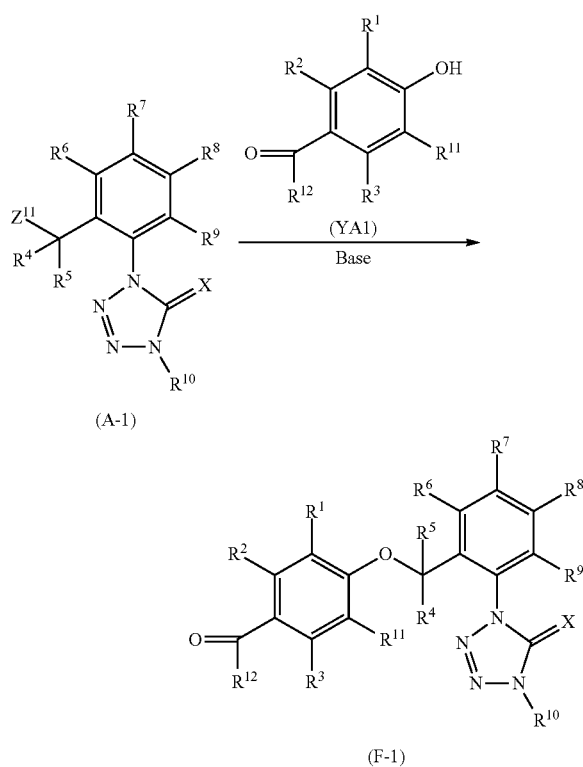

In the above formula, $R^1$, $R^2$, $R^3$, $R^4$, $R^5$, $R^6$, $R^7$, $R^8$, $R^9$, $R^{10}$, $R^{11}$, $R^{12}$, $Z^{11}$, and X each have the same meaning as above.

The reaction is usually carried out in a solvent.

Examples of the solvent used in the reaction include, for example, for example, a hydrocarbon such as n-heptane, n-hexane, cyclohexane, n-pentane, toluene, and xylene, ethers such as diethyl ether, tetrahydrofuran, 1,4-dioxane, ethylene glycol dimethyl ether, anisole, methyl tert-butyl ether, and diisopropyl ether, a halogenated hydrocarbon such as carbon tetrachloride, chloroform, dichloromethane, 1,2-dichloroethane, tetrachloroethane, and chlorobenzene, acid amides such as N,N-dimethylformamide, 1,3-dimethyl-2-imidazolidinone, and N-methyl pyrrolidone, esters such as ethyl acetate and methyl acetate, sulfoxides such as dimethylsulfoxide, ketones such as acetone, methyl ethyl ketone, and methyl isobutyl ketone, nitriles such as acetonitrile and propionitrile, water, and mixtures of these compounds.

Examples of the base to be used in the reaction include, for example, an organic base such as triethylamine, pyridine, N-methylmorpholine, N-methylpiperidine, 4-dimethylaminopyridine, disiopropylethylamine, lutidine, collidine, diazabicycloundecene, and diazabicyclononene, alkali metal carbonates such as lithium carbonate, sodium carbonate, potassium carbonate, and cesium carbonate, alkali metal bicarbonates such as lithium bicarbonate, sodium bicarbonate, potassium bicarbonate, and cesium bicarbonate, alkali metal hydroxides such as lithium hydroxide, sodium hydroxide, potassium hydroxide, and cesium hydroxide, alkali metal halides such as sodium fluoride, potassium fluoride, and cesium fluoride, alkali metal hydrides such as lithium hydride, sodium hydride, and potassium hydride, and alkali metal alkoxides such as sodium tert-butoxide and potassium tert-butoxide.

In the reaction, the base is usually used in an amount of 1 to 10 moles per mol of the compound (A-1).

In the reaction, the compound (YA1) is usually used in an amount of 0.5 to 10 moles and the base is usually used in an amount of 1 to 10 moles per mol of the compound (A-1).

The reaction temperature in the reaction is usually in a range from −20 to 150° C. and the reaction time in the reaction is usually in a range from 0.1 to 24 hr.

In the reaction, sodium iodide, tetrabutylammonium iodide, and the like may be added. These compounds are usually used in an amount of 0.01 to 1.2 moles per mol of the compound (A-1).

After the reaction, after-treatments including the extraction of the reaction mixture with an organic solvent and drying and concentration of the obtained organic phase may be performed to isolate the compound (F-1). Alternatively, the compound (F-1) can be isolated by performing after-treatments including the filtration and concentration of the reaction product. The isolated compound (F-1) may be further purified by chromatography, recrystallization, and the like.

With regard to the form used for the compound of the present invention, the compound of the present invention is usually mixed with a solid support, liquid support, surfactants and the like, preparation adjuvants such as a binder, dispersant, and stabilizer are added according to the need, and these ingredients are prepared into forms such as water-dispersible powder, water dispersible granule, flowable agent, granule, dri flowable type particle, emulsion concentrate, aqueous liquid formulation, oil formulation, smoking agent, aerosol, or microcapsules prior to use, though it may be used singly. The compound of the present invention is contained in an amount of, usually, 0.1 to 99% by weight and preferably 0.2 to 90% by weight in these formulations.

Examples of the solid support include, for example, fine powders and granules of clays (for example, kaolin, diatomaceous earth, synthetic hydrated silicon oxide, Fubasami clay, bentonite, and acid clay), talcs, other inorganic minerals (for example, sericite, quarts powder, sulfur powder, activated carbon, calcium carbonate, silica hydrate). Examples of the liquid support include, for example, water, alcohols (for example, methanol, and ethanol), ketones (for example, acetone and methyl ethyl ketone), aromatic hydrocarbon (for example, benzene, toluene, xylene, ethylbenzene, and methyl naphthalene), aliphatic hydrocarbon (for example, n-hexane, cyclohexanone, and kerosene), esters (for example, ethyl acetate and butyl acetate), nitriles (for example, acetonitrile and isobutyronitrile), ethers (for example, dioxane and diisopropyl ether), acid amides (for example, N,N-dimethylformamide (hereinafter also referred to as "DMF") and dimethylacetamide), and halogenated hydrocarbon (for example, dichloroethane, trichloroethane, and carbon tetrachloride).

Examples of the surfactant include, for example, alkyl sulfates, alkyl sulfonate, alkylaryl sulfonate, alkyl aryl ether, and polyoxyethylated compound thereof, polyoxyethylene glycol ethers, polyhydric alcohol esters, and sugar alcohol derivatives.

Examples of other preparation adjuvants include, for example, a binder, dispersant, and stabilizer, and specifically, include, for example, casein, gelatin, polysaccharides (for example, starch, gum arabic, cellulose derivatives, alginic acid), lignin derivatives, bentonite, sugars, synthetic water-soluble polymers (for example, polyvinyl alcohol, polyvinyl pyrrolidone, and polyacrylic acids), PAP (acidic isopropyl phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, fatty acids or their esters).

Examples of a method for applying the compound of the present invention include, for example, treatments on plant bodies such as spraying on stem and leaves, treatments on culture medium such as soil treatments, and treatments on seeds such as sterilization of seeds, though no particular limitation to the method as long as the compound of the present invention can be applied.

Also, the control agent of the present invention may be blended with various oils such as mineral oils and vegetable oils, surfactants, or the like prior to use. Examples of the oils and surfactants which may be blended include, for example, Nimbus (trademark), Assist (trademark), Aureo (trademark), Iharol (trademark), Silwet L-77 (trademark), BreakThru (trademark), Sundance II (trademark), Induce (trademark), Penetrator (trademark), AgriDex (trademark), Lutensol A8 (trademark), NP-7 (trademark), Triton (trademark), Nufilm (trademark), Emulgator NP7 (trademark), Emulad (trademark), TRITON X45 (trademark), AGRAL 90 (trademark), AGROTIN (trademark), ARPON (trademark), EnSpray N (trademark), and BANGLE (trademark).

Also, the control agent of the present invention may be blended or not be blended with other sterilizers, pesticides, acaricides, nematicides, or plant growth regulators prior to use.

The following compounds are given as examples of these sterilizers.

(1) Azole Germicides

For example, propiconazole, prothioconazole, triadimenol, prochloraz, penconazole, tebuconazole, flusilazole, diniconazole, bromuconazole, epoxiconazole, difenoconazole, cyproconazole, metconazole, triflumizole, tetraconazole, myclobutanil, fenbuconazole, hexaconazole, fluquinconazole, triticonazole, bitertanol, imazalil, flutriafol, simeconazole, and ipconazole;

(2) Amine Germicides

For example, fenpropimorph, tridemorph, fenpropidin, and spiroxamine;

(3) Benzimidazole Germicides

For example, carbendazim, benomyl, thiabendazole, and thiophanate-methyl;

(4) Dicarboxyimide Germicides

For example, procymidone, iprodione, and vinclozolin;

(5) Anilinopyrimidine Germicides

For example, cyprodinil, pyrimethanil, and mepanipyrim;

(6) Phenylpyrrole Germicides

For example, fenpiclonil, and fludioxonil;

(7) Strobilurin Germicides

For example, kresoxim-methyl, azoxystrobin, trifloxystrobin, fluoxastrobin, picoxystrobin, pyraclostrobin, dimoxystrobin, pyribencarb, metominostrobin, orysastrobin, enestrobin, pyraoxystrobin, pyrametostrobin, flufenoxystrobin, fenaminstrobin, enoxastrobin, coumoxystrobin, pyriminostrobin, triclopyricarb, and mandestrobin;

(8) Phenylamide Germicides

For example, metalaxyl, metalaxyl-M or mefenoxam, benalaxyl, benalaxyl-M or kiralaxyl;

(9) Carboxylic Acid Amide Germicides

For example, dimethomorph, iprovalicarb, benthivalicarb-isopropyl, mandipropamid, and valiphenal;

(10) Carboxyamide Germicides

For example, carboxin, mepronil, flutolanil, thifluzamide, furametpyr, boscalid, penthiopyrad, fluopyram, bixafen, penflufen, sedaxane, fluxapyroxad, isopyrazam, benzovindiflupyr, isofetamid, and N-[2-(3,4-difluorophenyl)phenyl]-3-trifluoromethyl pyrazine-2-carboxylic acid amide and N-(1,1,3-trimethylindane-4-yl)-1-methyl-3-difluoromethyl-pyrazole-4-carboxylic acid amide (including a racemic body, enantiomer, and mixtures of optional ratios of R-enantiomer and S-enantiomer);

(11) Other Germicides

For example, diethofencarb; thiuram; fluazinam; mancozeb; chlorothalonil; captan; dichlofluanid; folpet; quinoxyfen; fenhexanid; fanoxadon; fenamidon; zoxamide; ethaboxam; amisulbrom; cyanzofamid; metrafenone; pyriofenone; cyflufenamid; proquinazid; flusulfamide; fluopicolide; fosetyl; cymoxanil; pencycuron; tolclofos-methyl; carpropamid; diclocymet; fenoxanil; tricyclazole; pyroquilon; probenazole; isotianil; tiadinil; tebufloquin; diclomezine; kasugamycin; ferimzone; fthalide; validamycin; hydroxyisoxazole; iminoctadinec acetate; isoprothiolane; oxolinic acid; oxytetracycline; streptomycin; copper oxychloride; copper hydroxide; copper hydroxide sulfate; organocopper; sulfur; ametoctaradin; fenpyrazamine; oxathiapiprolin; 3-chloro-4-(2,6-difluorophenyl)-6-methyl-5-phenylpyrydazine; and 3-cyano-4-(2,6-difluorophenyl)-6-methyl-5-phenylpyridazine;

Examples of other pesticides like the above include, for example, the following compounds.

(1) Organic Phosphorous Compounds

For example, acephate, aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, and cadusafos;

(2) Carbamate Compounds

For example, alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, and aldicarb;

(3) Synthetic Pyrethroid Compound

For example, acrinathrin, allethrin, benfluthrin, beta-cyfluthrin, bifenthrin, cycloprothrin, cyfluthrin, cyhalothrin, cypermethrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, beta-cypermethrin, theta-cypermethrin, zeta-cypermethrin, lambda-cyhalothrin, gamma-cyhalothrin, furamethrin, tau-fluvalinate, halfenprox, protrifenbute, 2,3,5,6-tetrafluoro-4-(methoxymethyl)benzyl(EZ)-(1RS,3RS; 1RS,3SR)-2,2-dimethyl-3-prop-1-enylcyclopropanecarboxylate, 2,3,5,6-tetrafluoro-4-methylbenzyl (EZ)-(1RS,3RS; 1RS,3SR)-2,2-dimethyl-3-prop-1-enylcyclopropanecarboxylate, 2,3,5,6-tetrafluoro-4-(methoxymethyl)benzyl(1RS,3RS; 1RS,3SR)-2,2-dimethyl-3-(2-methyl-1-propenyl) cyclopropanecarboxylate;

(4) Nereistoxin Compounds

For example, cartap, bensultap, thiocyclam, monosultap, and bisultap;

(5) Neonicotinoid Compounds

For example, imidacloprid, nitenpyram, acetamiprid, thiamethoxam, thiacloprid, dinotefuran, and clothianidin;

(6) Benzoyl Urea Compounds

For example, chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, and triazuron;

(7) Phenyl Pyrazole Compounds

For example, acetoprole, ethiprole, fipronil, vaniliprole, pyriprole, and pyrafluprole;

(8) Bt-Toxin Pesticides

Spores derived from and crystal toxins produced by bacteria belonging to genus *Bacillus thuringiensis* and mixtures of them;

(9) Hydrazine Compounds

For example, chromafenozide, halofenozide, methoxyfenozide, and tebufenozide;

(10) Organic Chlorine Compounds

For example, aldrin, dieldrin, dienochlor, endosulfan, and methoxychlor;

(11) Natural Pesticides

For example, machine oil and nicotine-sulfate;

(12) Other Pesticides

For example, avermectin-B, bromopropylate, buprofezin, chlorphenapyr, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, doramectin, lepimectin, arsenic acid, benclothiaz, calcium cyanamide, calcium polysulfide, chlordane, DDT, DSP, flufenerim, flonicamid, flurimfen, formetanate, metam-ammonium, metam-sodium, methyl bromide, potassium oleate, spiromesifen, sulfur, metaflumizone, spirotetramat, pyrifluquinazone, spinetoram, chlorantraniliprole, cyantraniliprole, cyclaniliprole, sulfoxaflor, and flupyradifurone;

Examples of other acaricides (acaricidal active components) include, for example, acequinocyl, amitraz, benzoximate, bifenaate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, and cyenopyrafen;

Examples of other nematicides (nematicidal active components) include, for example, DCIP, fosthiazate, levamisol, methylisothiocyanate, morantel tartarate, imicyafos, and fluensulfone;

Examples of other plant growth regulators include, for example, the following compounds:

Ethephon, chlormequat-chloride, mepiquat-chloride, Gibberellin A represented by Gibberellin A3, abscisic acid, kinetin, benzyladenine, 1,3-diphenylurea, forchlorfenuron, thidiazuron, 4-oxo-4-(2-phenylethyl)aminobutyric acid, methyl 5-(trifluoromethyl)benzo[b]thiophene-2-carboxylate, and 5-(trifluoromethyl)benzo[b]thiophene-2-carboxylic acid.

The amount of the control agent of the present invention is usually 1 to 500 g and preferably 2 to 200 g per 1000 $m^2$ in terms of the amount of the compound of the present invention in the control agent of the present invention though it differs depending on climatic condition, preparation form, application time, applying method, applying place, subject diseases, and subject crops. Emulsions, water-dispersible powders, suspensions, and the like are generally diluted with water when they are used. In this case, the concentration of the compound of the present invention after the compound is diluted is usually 0.0005 to 2% by weight and preferably 0.005 to 1% by weight. A powder or granule formulation is usually used as it is without being diluted. In the treatments on seeds, the compound of the present invention is applied in such a manner that the amount of the compound in the control agent of the present invention is in a range from, usually 0.001 to 100 g and preferably 0.01 to 50 g.

The control agent of the present invention may be used as control agents for plant disease in crop lands such as a field, paddy field, turf, and orchard. The control agent of the present invention can control diseases generated on crops in croplands where plants given below as examples are cultivated.

In another embodiment, for example, the compound of the present invention or the control agent of the present invention can exterminate organisms and parasitic worms on vertebrate animals systemically or non-systemically by administering it to the internal parts (inside of the body) or external parts (body surface) of the vertebrate animals. Examples of an internally administration method include, for example, oral administration, rectal administration, transplantation, and subcutaneous, intramuscular, or intravenous administration by injection. Examples of external administration include, for example, dermal administration. Also, domestic animals may be made to eat the compound or the control agent of the present invention to exterminate sanitary insect pests that occur on the excrements of these animals.

When the compound of the present invention or the control agent of the present invention is used to treat animals such as domestic animals or pets on which harmful organisms parasitize, the dosage of the compound or control agent is generally 0.1 mg to 2000 mg and preferably 0.5 mg to 1000 mg in terms of the amount of effective components (the compound of the present invention or its salt) per 1 kg of the weight of the animal though it may be widely changed depending on, for example, the method of administration.

The compound of the present invention or the control agent of the present invention may be used as control agents for plant disease in crop lands such as a field, paddy field, turf, and orchard. The compound of the present invention can control diseases generated on crops in croplands where plants given below as examples are cultivated.

Crops; corn, rice, wheat, barley, rye, oat, sorghum, cotton, soybean, peanut, sarrazin, sugar beat, rape seed, sunflower, sugar cane, tobacco, and the like, Vegetables; Solanaceae vegetables (for example, eggplant, tomato, green pepper, hot pepper, potato), Cucurbitaceae vegetables (for example, cucumber, pumpkin, zucchini, watermelon, and melon), Cruciferase vegetables (for example, Japanese radish, turnip, horseradish, kohlrabi, Chinese cabbage, cabbage, brown mustard, broccoli, and cauliflower), Compositae vegetables (burdock, garland chrysanthethemum, artichoke, lettuce), Liliaceae vegetables (for example, Welsh onion, onion, garlic, and asparagus), Umbelliferase vegetables (for example, carrot, parsley, celery, and parsnip), Chenopodiaceae vegetables (for example, spinach, and Swiss chard), Labiatae vegetables (for example, Japanese mint, mint, and basil), strawberry, sweet potato, yam, aroid, flowering plant, foliage plants, and the like;

Fruit trees; Pomaceous fruits (for example, apple, common pear, Japanese pear, Chinese quince, and quince), Stone fleshy fruits (for example, peach, plum, nectarine, Japanese plum, cherry, apricot, prune), Citrus plants (for example, Satsuma mandarin, orange, lemon, lime, and grapefruits), Nuts (for example, chest nuts, walnut, hazel nut, almond, pistachio, cashew nut, macadamia nut), Berry fruits (for example, blueberry, cranberry, blackberry, and raspberry), grape, persimmon, olive, loquat, banana, coffee, date, coconut, and the like;

Trees other than fruit trees; tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, and yew), and the like.

The above "vegetables" include, for example, transgenic crops.

Examples of harmful organisms which can be controlled by the compound of the present invention include, for example, plant pathogens such as filamentous fungi, noxious arthropod such as noxious insects and noxious acari, and nematodes such as threadworms and examples of the harmful organisms may include, though not limited to, the followings.

(Rice): *Magnaporthe grisea, Cochliobolus miyabeanus, Rhizoctonia solani, Gibberella fujikuroi, Sclerophthora macrospora*; (wheat): *Erysiphe graminis, Fusarium graminearum, F. avenaceum, F. culmorum, Microdochium-nivale, Puccinia striiformis, P. graminis, P. recondita, Micronectriella nivale, Typhula* sp., *Ustilago tritici, Tilletia caries, T. controversa, Pseudocercosporella herpotrichoides, Septoria tritici, Stagonospora nodorum, Pyrenophora tritici-repentis, Rhizoctonia solani, Gaeumannomyces graminis*; (barley): *Erysiphe graminis, Fusarium graminearum, F. avenaceum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea, Ramularia collo-cygni, Rhizoctonia solani*; (corn): *Puccinia sorghi, Puccinia polysora, Setosphaeria turcica, Cochliobolus heterostrophus, Colletotrichum graminicola, Cercospora zeae-maydis, Kabatiella zeae, Phaeosphaeria maydis*; (cotton): *Colletotrichum gossypii, Ramuraria areola, Alternaria macrospora, A. gossypii*; (coffee): *Hemileia vastatrix*; (rapeseed) *Sclerotinia sclerotiorum, Alternaria brassicae, Phoma lingam*; (citrus plants): *Diaporthe citri, Elsinoe fawcetti, Penicillium digitatum, P. italicum*; (apple): *Monilinia mali, Valsa ceratosperma, Podosphaera leucotricha, Alternaria alternata* apple pathotype, *Venturia inaequalis, Glomerella cingulata*; (pear): *Venturia nashicola, V. pirina, Alternaria alternata* Japanese pear pathotype, *Gymnosporangium haraeanum*; (peach): *Monilinia fructicola, Cladosporium carpophilum, Phomopsis* sp.; (grape): *Elsinoe ampelina, Glomerella cingulata, Uncinula necator, Phakopsora ampelopsidis, Guignardia bidwellii, Plasmopara viticola*; (persimmon): *Gloeosporium kaki, Cercospora Kaki, Mycosphaerella nawae*; (cucurbitaceous fruits): *Colletotrichum lagenarium, Sphaerotheca fuliginea, Didymella bryoniae, Corynespora cassiicola, Fusarium oxysporum, Pseudoperonospora cubensis, Phytophthora* sp. *Pythium* sp.; (tomato): *Alternaria solani, Cladosporium fulvum, Pseudocercospora fuligena, Phytophthora infestans*; (eggplant): *Phomopsis vexans, Erysiphe cichoracearum*; (Cruciferous vegetables): *Alternaria japonica, Cercosporella brassicae, Plasmodiophora brassicae, Peronospora parasitica*; (Welsh onion): *Puccinia allii*; (soybean): *Cercospora kikuchii, Elsinoe glycines, Diaporthe phaseolorum* var. *sojae, Phakopsora pachyrhizi, Corynespora cassiicola, Colletotrithum glycines, C. truncatum, Rhizoctonia solani, Septoria Glycines, Cercospora sojina;* (kidney bean): *Colletotrichum lindemthianum*; (peanut): *Cercospora personata, Cercospora arachidicola, Sclerotium rolfsii*; (pea) *Erysiphe pisi*; (potato): *Alternaria solani, Phytophthora infestans, Verticillium albo-atrum, V. dahliae, V. nigrescens*; (strawberry): *Sphaerotheca humuli*; (tea): *Exobasidium reticulatum, Elsinoe leucospila, Pestalotiopsis* sp., *Colletotrichum theae-sinensis*; (tobacco): *Alternaria longipes, Erysiphe cichoracearum, Colletotrichum tabacum, Peronospora tabacina, Phytophthora nicotianae*; (sugar beat): *Cercospora beticola, Thanatephorus cucumeris, Thanatephorus cucumeris, Aphanomyces cochlioides*; (rose): *Diplocarpon rosae, Sphaerotheca pannosa*; (chrysanthemum): *Septoria chrysanthemi-indici, Puccinia horiana*; (onion): *Botrytis cinerea, B. byssoidea, Botrytis alli, Botrytis squamosa*; (various crops): *Botrytis cinerea, Sclerotinia sclerotiorum*; (Japanese radish): *Alternaria brassicicola*; (grass): *Sclerotinia homeocarpa, Rhizoctonia solani*; (banana): *Mycosphaerella fijiensis, Mycosphaerella musicola*.

Noxious insects belonging to order Hemiptera: planthoppers such as *Laodelphax striatellus, Nilaparvata lugens*, and *Sogatella furcifera*; leafhoppers such as *Nephotettix cincticeps* and *Nephotettix virescens*; aphids such as *Aphis gossypii, Myzus persicae, Brevicoryne brassicae, Macrosiphum euphorbiae, Aulacorthum solani, Rhopalosiphum padi*, and *Toxoptera citricidus*; stink bugs such as *Nezara antennata, Riptortus clavetus, Leptocorisa chinensis, Eysarcoris parvus, Halyomorpha mista*, and *Lygus lineolaris*; white flies such as *Trialeurodes vaporariorum*, and *Bemisia argentifolii*; scale insects such as *Aonidiella aurantii, Comstockaspis perniciosa, Unaspis citri, Ceroplastes rubens*, and *Icerya purchase*; lace bugs; jumping planlice.

Noxious insects belonging to order Lepidoptera: Pyralidae such as *Chilo suppressalis, Tryporyza incertulas, Cnaphalocrocis medinalis, Notarcha derogate, Plodia interpunctella, Ostrinia furnacalis, Hellula undalis*, and *Pediasia teterrellus*; Noctuidae such as *Spodoptera litura, Spodoptera exigua, Pseudaletia separate, Mamestra brassicae, Agrotis ipsilon, Plusia nigrisigna, Trichoplusia* spp., *Heliothis* spp., and *Helicoverpa* spp.; Pieridae such as *Pieris rapae*; Tortoricidae such as *Adoxophyes* spp., *Grapholita molesta, Leguminivora glycinivorella, Matsumuraeses azukivora, Adoxophyes orana fasciata, Adoxophyes* sp., *Homona magnanima, Archips fuscocupreanus*, and *Cydia pomonella*; Gracilariidae such as *Caloptilia theivora* and *Phyllonorycter ringoneella*; Carposinidae such as *Carposina niponensis*; Lyonetiidae such as *Lyonetia*; Lymantriidae such as *Lymantria* spp. and *Euproctis* spp.; Plutellidae such as *Plutella xylostella*; Gelechiidae such as *Pectinophora gossypiella* and *Phthorimaea operculella*; Arctiidae such as *Hyphantria cunea*; Tineidae such as *Tinea translucens* and *Tineola bisselliella*. Noxious insects belonging to order Thysanoptera: thrips such as *Frankliniella occidentalis, Thrips palmi, Scirtothrips dorsalis, Thrips tabaci, Frankliniella intonsa*, and *Frankliniella fusca*.

Noxious insects belonging to order Diptera: *Musca domestica, Culex pipiens pallens, Tabanus trigonus, Hylemya antiqua, Hylemya platura, Anopheles sinensis, Agromyza oryzae, Hydrellia griseola, Chlorops oryzae, Dacus cucurbitae, Ceratitis capitata*, and *Liriomyza trifolii*.

Noxious insects belonging to order Coleoptera: *Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica spp., Leptinotarsa decemlineata, Agriotes spp., Lasioderma serricorne, Anthrenus verbasci, Tribolium castaneum, Lyctus brunneus, Anoplophora malasiaca, and Tomicus piniperda.

Noxious insects belonging to order Orthopter: Locusta migratoria, Gryllotalpa africana, Oxya yezoensis, and Oxya japonica.

Noxious insects belonging to order Hymenoptera: Athalia rosae, Acromyrmex spp., and Solenopsis spp.

Nematodes: Aphelenchoides besseyi, Nothotylenchus acris, Heterodera glycines, Meloidogyne incognita, Pratylenchus penetrans, Nacobbus aberrans.

Noxious insects belonging to order Blattaria: Blattella germanica, Periplaneta fuliginosa, Periplaneta americana, Periplaneta brunnea, and Blatta orientalis.

Noxious insects belonging to order Acarina: Tetranychidae such as Tetranychus urticae, Panonychus citri, and Oligonychus spp.; Eriophyidae such as Aculops pelekassi; Tarsonemidae such as Polyphagotarsonemus latus; Tenuipalpidae, Tuckerellidae, Acaridae such as Tyrophagus putrescentiae; Pyroglyphidae such as Dermatophagoides farinae and Dermatophagoides ptrenyssnus; Cheyletidae such as Cheyletus eruditus, Cheyletus malaccensis, and Cheyletus moorei; Dermanyssidae.

Also, preparations including the compound of the present invention or its salt can be used in the fields of treatments of diseases of domestic animals and in stockbreeding and also to control organisms and parasitic worms which parasitize internally or externally on vertebrate animals, for example, a human, cattle, sheep, goat, pig, domestic fowl, dog, cat, and fish, thereby maintaining public health. Examples of these harmful organisms include, for example, Ixodes spp. (for example, Ixodes scapularis), Boophilus spp. (for example, Boophilus microplus), Amblyomma spp., Hyalomma spp., Rhipicephalus spp. (for example, Rhipicephalus sanguineus), Haemaphysalis spp. (for example, Haemaphysalis longicornis), Dermacentor spp., Ornithodoros spp. (for example, Ornithodoros moubata), Dermahyssus gallinae, Ornithonyssus sylviarum, Sarcoptes spp. (for example, Sarcoptes scabiei), Psoroptes spp., Chorioptes spp., Demodex spp., Eutrombicula spp., Aedes spp. (for example, Aedes albopictus), Anopheles spp., Culex spp., Culicodes spp., Musca spp., Hypoderma spp., Gasterophilus spp., Haematobia spp., Tabanus spp., Simulium spp., Triatoma spp., Phthiraptera (for example, Damalinia spp., Linognathus spp., Haematopinus spp.), Ctenocephalides spp. (for example, Ctenocephalides felis), Xenosylla spp., Monomorium pharaonis, and nematodes [for example, Trichostrongylus spp. (for example, Nippostrongylus brasiliensis, Trichostrongylus axei, Trichostrongylus colubriformis), Trichinella spp. (for example, Trichinella spiralis), Haemonchus contortus, Nematodirus spp. (for example, Nematodirus battus), Ostertagia circumcincta, Cooperia spp. and Hymenolepis nana].

EXAMPLES

Next, the present invention will be explained in more detail by way of examples including production examples, preparation examples, and test examples which are however not intended to be limiting of the present invention.

First, production examples will be shown.

Production Example 1

A mixture of 0.28 g of 1-(2-bromomethyl-3-methylphenyl)-4-methyl-1,4-dihydrotetrazol-5-one described in Reference production example 11, 0.22 g of 2-methyl-4-{1-(tert-butoxy)imino-ethyl}phenol described in Reference production example 59, 0.28 g of potassium carbonate, and 4 mL of acetoanilile was refluxed under heating with stirring for 4 hr. The reaction mixture was cooled to ambient temperature and filtered, and the filtrate was concentrated. The resulting residue was subjected to silica gel column chromatography to obtain 0.15 g of 1-{2-[2-methyl-4-{1-(tert-butoxy)imino-ethyl}-phenoxymethyl]-3-methyl-phenyl}-4-methyl-1,4-dihydrotetrazol-5-one (hereinafter referred to as "Compound 1 of the present invention").

Compound 1 of the present invention

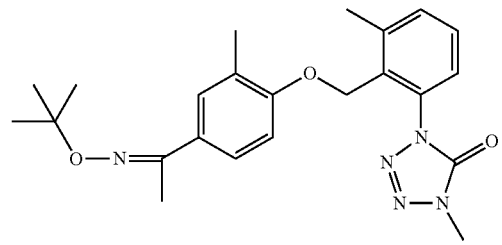 [SMILES: CC(=NOC(C)(C)C)c1ccc(OCc2c(C)cccc2-n2nnn(C)c2=O)c(C)c1]

1H-NMR (CDCl3) δ: 7.47-7.38 (4H, m), 7.29-7.25 (1H, m), 6.80 (1H, d, J=8.45 Hz), 5.05 (2H, s), 3.62 (3H, s), 2.50 (3H, s), 2.16 (3H, s), 2.10 (3H, s), 1.34 (9H, s).

Production Example 2

A mixture of 0.28 g of 1-(2-bromomethyl-3-methylphenyl)-4-methyl-1,4-dihydrotetrazol-5-one described in Reference production example 11, 0.18 g of 2-methyl-4-(1-methoxyimino-ethyl)phenol described in Reference production example 38, 0.28 g of potassium carbonate, and 4 mL of acetoanilile was refluxed under heating with stirring for 4 hr. The reaction mixture was cooled to ambient temperature and filtered, and the filtrate was concentrated. The resulting residue was subjected to silica gel column chromatography to obtain 0.25 g of 1-{2-[2-methyl-4-(1-methoxyimino-ethyl)-phenoxymethyl]-3-methyl-phenyl}-4-methyl-1,4-dihydrotetrazol-5-one (hereinafter referred to as "Compound 2 of the present invention").

Compound 2 of the present invention

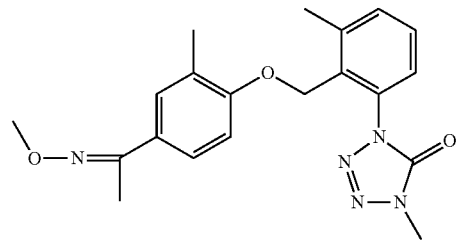 [SMILES: CON=C(C)c1ccc(OCc2c(C)cccc2-n2nnn(C)c2=O)c(C)c1]

1H-NMR (CDCl3) δ: 7.48-7.36 (4H, m), 7.30-7.25 (1H, m), 6.81 (1H, d, J=8.54 Hz), 5.05 (2H, s), 3.97 (3H, s), 3.63 (3H, s), 2.49 (3H, s), 2.18 (3H, s), 2.10 (3H, s).

Production Example 3

The same reaction as that of Production Example 1 was carried out except that 2-methyl-4-(1-ethoxyimino-ethyl) phenol described in Reference production example 57 was used in place of 2-methyl-4-{1-(tert-butoxy)imino-ethyl}phenol in Production example 1 to obtain 1-{2-[2-methyl-4-(1-ethoxyimino-ethyl)phenoxymethyl]-phenyl}-4-methyl-1,4-dihydrotetrazol-5-one (hereinafter referred to as "Compound 3 of the present invention").

Compound 3 of the present invention

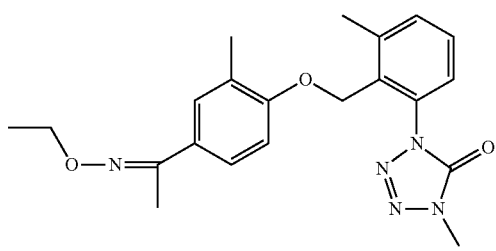 [SMILES: CCON=C(C)c1ccc(OCc2c(C)cccc2-n2nnn(C)c2=O)c(C)c1]

1H-NMR (CDCl3) δ: 7.45-7.36 (4H, m), 7.30-7.25 (1H, m), 6.81 (1H, d, J=8.54 Hz), 5.05 (2H, s), 4.22 (2H, q, J=7.07 Hz), 3.62 (3H, s), 2.49 (3H, s), 2.19 (3H, s), 2.10 (3H, s), 1.32 (3H, t, J=7.07 Hz).

Production Example 4

The same reaction as that of Production Example 2 was carried out except that 1-(2-bromomethyl-3-chlorophenyl)-4-methyl-1,4-dihydrotetrazol-5-one described in Reference production example 2 was used in place of 1-(2-bromomethyl-3-methylphenyl)-4-methyl-1,4-dihydrotetrazol-5-one in Production example 2 to obtain 1-{2-[2-methyl-4-(1-methoxyimino-ethyl)phenoxymethyl]-3-chlorophenyl}-4-methyl-1,4-dihydrotetrazol-5-one (hereinafter referred to as "Compound 4 of the present invention").

Compound 4 of the present invention

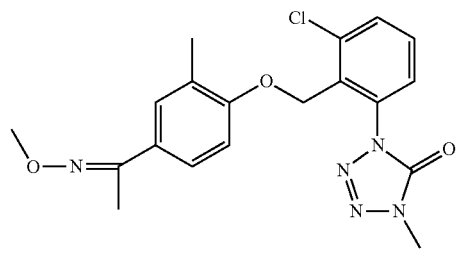 [SMILES: CON=C(C)c1ccc(OCc2c(Cl)cccc2-n2nnn(C)c2=O)c(C)c1]

1H-NMR (CDCl3) δ: 7.61 (1H, d, J=7.80 Hz), 7.47 (1H, t, J=7.80 Hz), 7.41-7.37 (3H, m), 6.81 (1H, d, J=8.54 Hz), 5.33 (2H, s), 3.96 (3H, s), 3.60 (3H, s), 2.17 (3H, s), 2.03 (3H, s).

Production Example 5

The same reaction as that of Production Example 4 was carried out except that 2-methyl-4-(1-ethoxyimino-ethyl)phenol described in Reference production example 57 was used in place of 2-methyl-4-(1-methoxyimino-ethyl)phenol in Production example 4 to obtain 1-{2-[2-methyl-4-(1-ethoxyimino-ethyl)-phenoxymethyl]-3-chlorophenyl}-4-methyl-1,4-dihydrotetrazol-5-one (hereinafter referred to as "Compound 5 of the present invention").

Compound 5 of the present invention

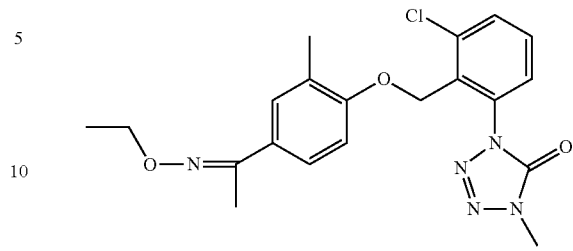

1H-NMR (CDCl3) δ: 7.61 (1H, dd, J=8.05, 1.22 Hz), 7.46 (1H, t, J=8.05 Hz), 7.43-7.36 (3H, m), 6.81 (1H, d, J=8.54 Hz), 5.33 (2H, s), 4.21 (2H, q, J=7.07 Hz), 3.60 (3H, s), 2.18 (3H, s), 2.03 (3H, s), 1.32 (3H, t, J=7.07 Hz).

Production Example 6

A mixture of 0.30 g of 1-(2-bromomethyl-3-methylphenyl)-4-methyl-1,4-dihydrotetrazol-5-one described in Reference production example 8, 0.18 g of 2-methyl-4-(1-methoxyimino-ethyl)phenol described in Reference production example 38, 0.28 g of potassium carbonate, and 4 mL of acetoanilile was refluxed under heating with stirring for 4 hr. The reaction mixture was cooled to ambient temperature and filtered, and the filtrate was concentrated. The resulting residue was subjected to silica gel column chromatography to obtain 0.28 g of 1-{2-[2-methyl-4-(1-methoxyimino-ethyl)-phenoxymethyl]-3-methoxy-phenyl}-4-methyl-1,4-dihydrotetrazol-5-one (hereinafter referred to as "Compound 6 of the present invention").

Compound 6 of the present invention

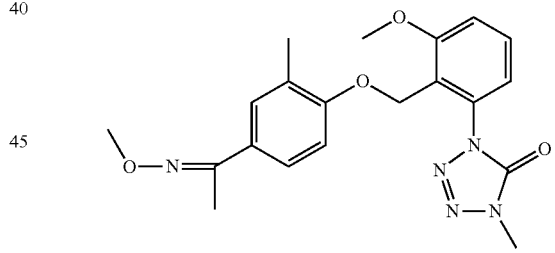

1H-NMR (CDCl3) δ: 7.46 (1H, t, J=8.17 Hz), 7.39 (1H, s), 7.35 (1H, d, J=8.54 Hz), 7.10-7.04 (2H, m), 6.84 (1H, d, J=8.17 Hz), 5.28 (2H, s), 3.96 (3H, s), 3.93 (3H, s), 3.59 (3H, s), 2.17 (3H, s), 2.00 (3H, s).

Production Example 7

The same reaction as that of Production Example 6 was carried out except that 2-methyl-4-(1-ethoxyimino-ethyl)phenol described in Reference production example 57 was used in place of 2-methyl-4-(1-methoxyimino-ethyl)phenol in Production example 6 to obtain 1-{2-[2-methyl-4-(1-ethoxyimino-ethyl)-phenoxymethyl]-3-methoxy-phenyl}-4-methyl-1,4-dihydrotetrazol-5-one (hereinafter referred to as "Compound 7 of the present invention").

Compound 7 of the present invention

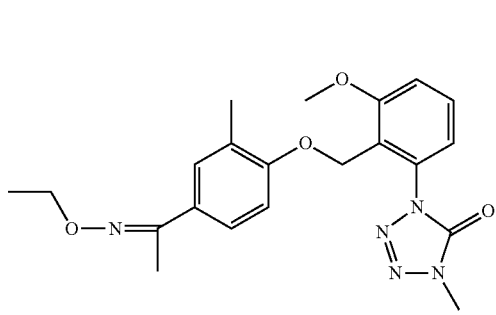 [SMILES: CCON=C(C)c1ccc(OCc2c(OC)cccc2-n2nnn(C)c2=O)c(C)c1]

1H-NMR (CDCl3) δ: 7.44 (1H, t, J=8.17 Hz), 7.42-7.37 (1H, m), 7.35 (1H, dd, J=8.54, 2.32 Hz), 7.09-7.04 (2H, m), 6.84 (1H, d, J=8.54 Hz), 5.28 (2H, s), 4.21 (2H, q, J=7.01 Hz), 3.90 (3H, s), 3.59 (3H, s), 2.18 (3H, s), 2.00 (3H, s), 1.31 (3H, t, J=7.01 Hz).

Production Example 8

The same reaction as that of Production Example 2 was carried out except that 2-chloro-4-(1-methoxyimino-ethyl)phenol described in Reference production example 91 was used in place of 2-methyl-4-(1-methoxyimino-ethyl)phenol in Production example 2 to obtain 1-{2-[2-chloro-4-(1-methoxyimino-ethyl)-phenoxymethyl]-3-methyl-phenyl}-4-methyl-1,4-dihydrotetrazol-5-one (hereinafter referred to as "Compound 8 of the present invention").

Compound 8 of the present invention

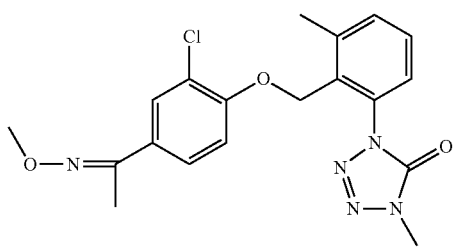 [SMILES: CON=C(C)c1ccc(OCc2c(C)cccc2-n2nnn(C)c2=O)c(Cl)c1]

1H-NMR (CDCl3) δ: 7.68-7.65 (1H, m), 7.47-7.37 (3H, m), 7.32-7.27 (1H, m), 6.86 (1H, d, J=8.69 Hz), 5.18 (2H, s), 3.97 (3H, s), 3.66 (3H, s), 2.53 (3H, s), 2.16 (3H, s).

Production Example 9

The same reaction as that of Production Example 2 was carried out except that 2-chloro-4-(1-ethoxyimino-ethyl)phenol described in Reference production example 58 was used in place of 2-methyl-4-(1-methoxyimino-ethyl)phenol in Production example 2 to obtain 1-{2-[2-chloro-4-(1-ethoxyimino-ethyl)-phenoxymethyl]-3-methyl-phenyl}-4-methyl-1,4-dihydrotetrazol-5-one (hereinafter referred to as "Compound 9 of the present invention").

Compound 9 of the present invention

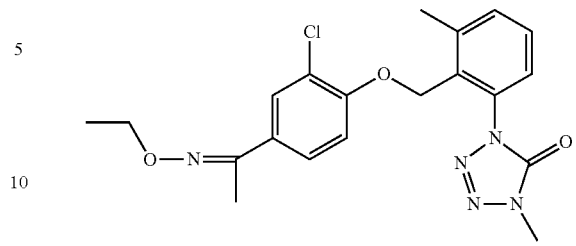

1H-NMR (CDCl3) δ: 7.69-7.65 (1H, m), 7.48-7.36 (3H, m), 7.30-7.26 (1H, m), 6.85 (1H, d, J=8.45 Hz), 5.18 (2H, s), 4.22 (2H, q, J=7.12 Hz), 3.66 (3H, s), 2.53 (3H, s), 2.17 (3H, s), 1.32 (3H, t, J=7.12 Hz).

Production Example 10

The same reaction as that of Production Example 4 was carried out except that 2-chloro-4-(1-methoxyimino-ethyl)phenol described in Reference production example 91 was used in place of 2-methyl-4-(1-methoxyimino-ethyl)phenol in Production example 4 to obtain 1-{2-[2-chloro-4-(1-methoxyimino-ethyl)-phenoxymethyl]-3-methyl-phenyl}-4-methyl-1,4-dihydrotetrazol-5-one (hereinafter referred to as "Compound 10 of the present invention").

Compound 10 of the present invention

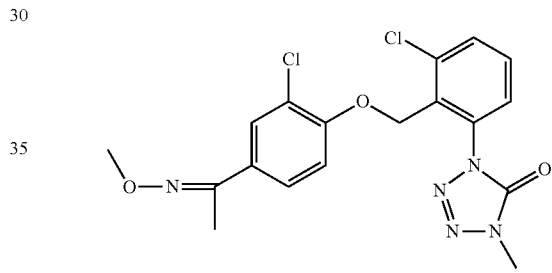

1H-NMR (CDCl3) δ: 7.64 (1H, d, J=1.46 Hz), 7.59 (1H, dd, J=7.19, 1.46 Hz), 7.48-7.41 (3H, m), 6.88 (1H, d, J=8.54 Hz), 5.53 (2H, s), 3.96 (3H, s), 3.64 (3H, s), 2.15 (3H, s).

Production Example 11

The same reaction as that of Production Example 4 was carried out except that 2-chloro-4-(1-ethoxyimino-ethyl)phenol described in Reference production example 58 was used in place of 2-methyl-4-(1-methoxyimino-ethyl)phenol in Production example 4 to obtain 1-{2-[2-chloro-4-(1-ethoxyimino-ethyl)-phenoxymethyl]-3-methyl-phenyl}-4-methyl-1,4-dihydrotetrazol-5-one (hereinafter referred to as "Compound 11 of the present invention").

Compound 11 of the present invention

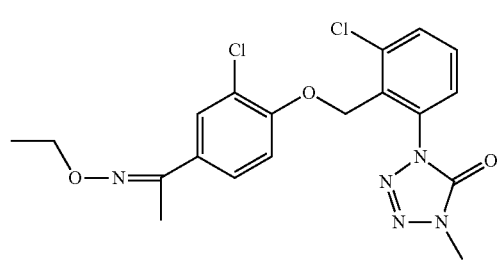 [SMILES: CCON=C(C)c1ccc(OCc2c(Cl)cccc2-n2nnn(C)c2=O)c(Cl)c1]

1H-NMR (CDCl3) δ: 7.64 (1H, d, J=2.17 Hz), 7.58 (1H, dd, J=7.12, 2.17 Hz), 7.46-7.42 (3H, m), 6.87 (1H, d, J=8.69 Hz), 5.53 (2H, s), 4.21 (2H, q, J=7.00 Hz), 3.64 (3H, s), 2.15 (3H, s), 1.31 (3H, t, J=7.00 Hz).

Production Example 12

The same reaction as that of Production Example 2 was carried out except that 1-(2-bromomethyl-3-ethylphenyl)-4-methyl-1,4-dihydrotetrazol-5-one described in Reference production example 14 was used in place of 1-(2-bromomethyl-3-methylphenyl)-4-methyl-1,4-dihydrotetrazol-5-one in Production example 2 to obtain 1-{2-[2-methyl-4-(1-methoxyimino-ethyl)-phenoxymethyl]-3-ethyl-phenyl}-4-methyl-1,4-dihydrotetrazol-5-one (hereinafter referred to as "Compound 12 of the present invention").

Compound 12 of the present invention

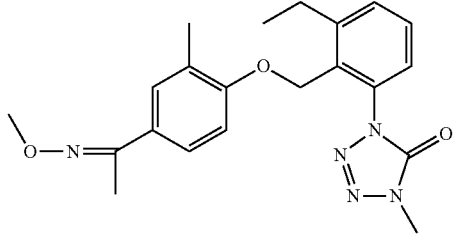 [SMILES: CCc1cccc(-n2nnn(C)c2=O)c1COc1ccc(C(C)=NOC)cc1C]

1H-NMR (CDCl3) δ: 7.49-7.34 (3H, m), 7.39 (1H, dd, J=8.41, 2.32 Hz), 7.29-7.26 (1H, m), 6.82 (1H, d, J=8.54 Hz), 5.06 (2H, s), 3.97 (3H, s), 3.59 (3H, s), 2.83 (2H, q, J=7.56 Hz), 2.18 (3H, s), 2.08 (3H, s), 1.27 (3H, t, J=7.00 Hz).

Production Example 13

A mixture of 0.31 g of 1-(2-bromomethyl-3-cyclopropylphenyl)-4-methyl-1,4-dihydrotetrazol-5-one described in Reference production example 17, 0.18 g of 2-methyl-4-(1-methoxyimino-ethyl)phenol described in Reference production example 38, 0.28 g of potassium carbonate, and 4 mL of acetoanilile was refluxed under heating with stirring for 4 hr. The reaction mixture was cooled to ambient temperature and filtered, and the filtrate was concentrated. The resulting residue was subjected to silica gel column chromatography to obtain 0.25 g of 1-{2-[2-methyl-4-(1-methoxyimino-ethyl)-phenoxymethyl]-3-cyclopropyl-phenyl}-4-methyl-1,4-dihydrotetrazol-5-one (hereinafter referred to as "Compound 13 of the present invention").

Compound 13 of the present invention

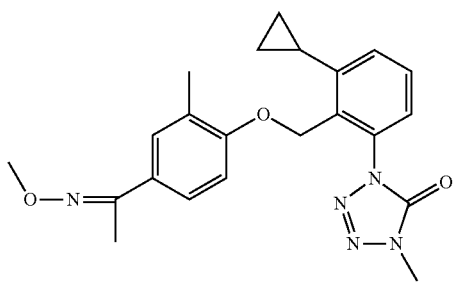

1H-NMR (CDCl3) δ: 7.46-7.36 (3H, m), 7.29-7.25 (2H, m), 6.86 (1H, d, J=8.45 Hz), 5.27 (2H, s), 3.97 (3H, s), 3.61 (3H, s), 2.18 (3H, s), 2.10-20.7 (4H, m), 0.98 (2H, td, J=5.80, 4.35 Hz), 0.76 (2H, td, J=5.80, 4.35 Hz).

Production Example 14

The same reaction as that of Production Example 2 was carried out except that 2-methoxy-4-(1-methoxyimino-ethyl)phenol described in Reference production example 85 was used in place of 2-methyl-4-(1-methoxyimino-ethyl)phenol in Production example 2 to obtain 1-{2-[2-methoxy-4-(1-methoxyimino-ethyl)-phenoxymethyl]-3-methyl-phenyl}-4-methyl-1,4-dihydrotetrazol-5-one (hereinafter referred to as "Compound 14 of the present invention").

Compound 14 of the present invention

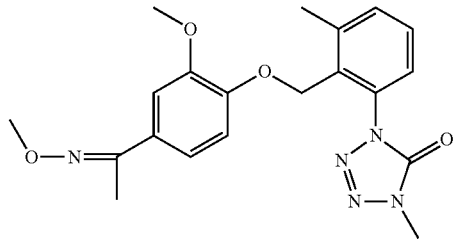 [SMILES: CON=C(C)c1ccc(OCc2c(C)cccc2-n2nnn(C)c2=O)c(OC)c1]

1H-NMR (CDCl3) δ: 7.41-7.33 (2H, m), 7.27-7.23 (2H, m), 7.06 (1H, dd, J=8.33, 2.05 Hz), 6.81 (1H, d, J=8.45 Hz), 5.13 (2H, s), 3.98 (3H, s), 3.83 (3H, s), 3.63 (3H, s), 2.51 (3H, s), 2.18 (3H, s).

Production Example 15

The same reaction as that of Production Example 2 was carried out except that 2-nitro-4-(1-methoxyimino-ethyl)phenol described in Reference production example 86 was used in place of 2-methyl-4-(1-methoxyimino-ethyl)phenol in Production example 2 to obtain 1-{2-[2-nitro-4-(1-methoxyimino-ethyl)-phenoxymethyl]-3-methyl-phenyl}-4-methyl-1,4-dihydrotetrazol-5-one (hereinafter referred to as "Compound 15 of the present invention").

Compound 15 of the present invention

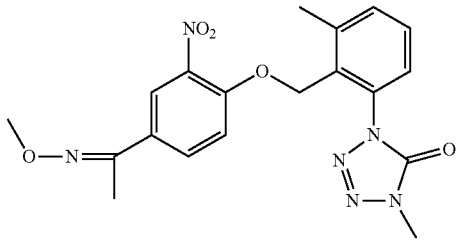

1H-NMR (CDCl3) δ: 8.08 (1H, d, J=2.20 Hz), 7.78 (1H, dd, J=8.78, 2.20 Hz), 7.44-7.38 (2H, m), 7.29 (1H, dd, J=7.32, 1.71 Hz), 6.97 (1H, d, J=8.78 Hz), 5.29 (2H, s), 3.99 (3H, s), 3.71 (3H, s), 2.55 (3H, s), 2.20 (3H, s).

Production Example 16

The same reaction as that of Production Example 2 was carried out except that 2,6-dimethyl-4-(1-methoxyimino-ethyl)phenol described in Reference production example 87 was used in place of 2-methyl-4-(1-methoxyimino-ethyl) phenol in Production example 2 to obtain 1-{2-[2,6-dimethyl-4-(1-methoxyimino-ethyl)-phenoxymethyl]-3-methyl-phenyl}-4-methyl-1,4-dihydrotetrazol-5-one (hereinafter referred to as "Compound 16 of the present invention").

Compound 16 of the present invention

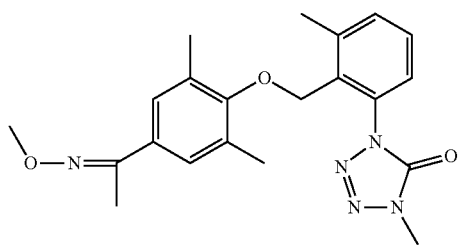 [SMILES: CON=C(C)c1cc(C)c(OCc2c(C)cccc2-n2nnn(C)c2=O)c(C)c1]

1H-NMR (CDCl3) δ: 7.43-7.37 (2H, m), 7.24-7.19 (3H, m), 4.97 (2H, s), 3.97 (3H, s), 3.62 (3H, s), 2.55 (3H, s), 2.16 (3H, s), 2.05 (6H, s).

Production Example 17

The same reaction as that of Production Example 2 was carried out except that 2-methyl-4-{1-(2-allyloxy)imino-ethyl)phenol described in Reference production example 60 was used in place of 2-methyl-4-(1-methoxyimino-ethyl)phenol in Production example 2 to obtain 1-{2-[2-methyl-4-{1-(2-allyloxy)imino-ethyl)-phenoxymethyl]-3-methyl-phenyl}-4-methyl-1,4-dihydrotetrazol-5-one (hereinafter referred to as "Compound 17 of the present invention").

Compound 17 of the present invention

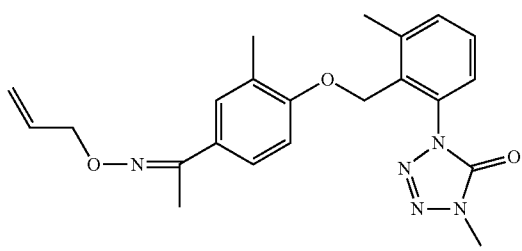 [SMILES: C=CCON=C(C)c1ccc(OCc2c(C)cccc2-n2nnn(C)c2=O)c(C)c1]

1H-NMR (CDCl3) δ: 7.44-7.38 (4H, m), 7.27 (1H, dd, J=7.19, 2.32 Hz), 6.80 (1H, d, J=8.29 Hz), 6.11-6.00 (1H, m), 5.37-5.29 (1H, m), 5.25-5.19 (1H, m), 5.05 (2H, s), 4.68 (2H, dt, J=5.61, 1.34 Hz), 3.62 (3H, s), 2.49 (3H, s), 2.21 (3H, s), 2.09 (3H, s).

Production Example 18

The same reaction as that of Production Example 2 was carried out except that 2-methyl-4-(1-benzyloxyimino-ethyl)phenol described in Reference production example 61 was used in place of 2-methyl-4-(1-methoxyimino-ethyl)phenol in Production example 2 to obtain 1-{2-[2-methyl-4-1-(1-benzyloxyimino-ethyl)-phenoxymethyl]-3-methyl-phenyl}-4-methyl-1,4-dihydrotetrazol-5-one (hereinafter referred to as "Compound 18 of the present invention").

Compound 18 of the present invention

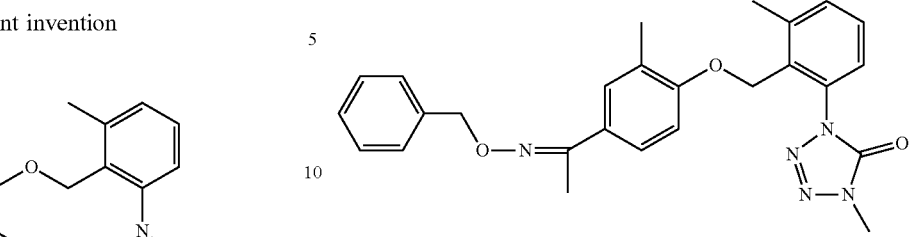

1H-NMR (CDCl3) δ: 7.45-7.26 (10H, m), 6.80 (1H, d, J=8.45 Hz), 5.22 (2H, s), 5.05 (2H, s), 3.61 (3H, s), 2.49 (3H, s), 2.23 (3H, s), 2.09 (3H, s).

Production Example 19

The same reaction as that of Production Example 2 was carried out except that 2-methyl-4-(1-methoxyimino-methyl)phenol described in Reference production example 88 was used in place of 2-methyl-4-(1-methoxyimino-ethyl)phenol in Production example 2 to obtain 1-{2-[2-methyl-4-1-(1-methoxyimino-ethyl)-phenoxymethyl]-3-methyl-phenyl}-4-methyl-1,4-dihydrotetrazol-5-one (hereinafter referred to as "Compound 19 of the present invention").

Compound 19 of the present invention

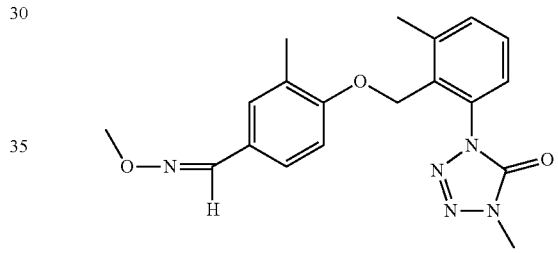

1H-NMR (CDCl3) δ: 7.97 (1H, s), 7.45-7.38 (3H, m), 7.32-7.25 (2H, m), 6.82 (1H, d, J=8.21 Hz), 5.06 (2H, s), 3.94 (3H, s), 3.61 (3H, s), 2.49 (3H, s), 2.09 (3H, s).

Production Example 20

The same reaction as that of Production Example 2 was carried out except that 2-bromo-4-(1-methoxyimino-ethyl)phenol described in Reference production example 53 was used in place of 2-methyl-4-(1-methoxyimino-ethyl)phenol in Production example 2 to obtain 1-{2-[2-bromo-4-(1-methoxyimino-ethyl)-phenoxymethyl]-3-methyl-phenyl}-4-methyl-1,4-dihydrotetrazol-5-one (hereinafter referred to as "Compound 20 of the present invention").

Compound 20 of the present invention

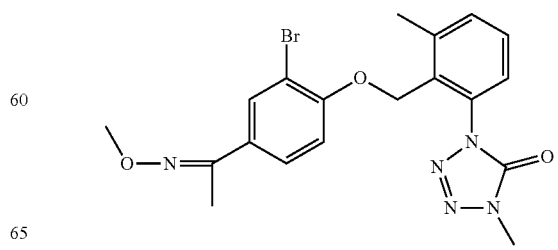

1H-NMR (CDCl3) δ: 7.84 (1H, d, J=2.17 Hz), 7.49 (1H, dd, J=8.45, 2.17 Hz), 7.45-7.37 (2H, m), 7.32-7.26 (1H, m), 6.87-6.80 (1H, m), 5.18 (2H, s), 3.97 (3H, s), 3.67 (3H, s), 2.53 (3H, s), 2.16 (3H, s).

Production Example 21

The same reaction as that of Production Example 6 was carried out except that 2-methyl-4-(1-methoxyimino-methyl)phenol described in Reference production example 88 was used in place of 2-methyl-4-(1-methoxyimino-ethyl)phenol in Production example 6 to obtain 1-{2-[2-methyl-4-(1-methoxyimino-methyl)-phenoxymethyl]-3-methoxy-phenyl}-4-methyl-1,4-dihydrotetrazol-5-one (hereinafter referred to as "Compound 21 of the present invention").

Compound 21 of the present invention

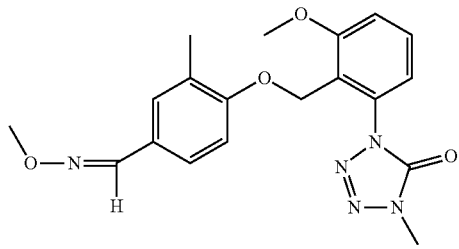

1H-NMR (CDCl3) δ: 7.88-7.80 (2H, m), 7.53 (1H, dd, J=7.07, 1.46 Hz), 7.45-7.40 (2H, m), 7.29 (1H, dd, J=6.83, 2.44 Hz), 6.93 (1H, d, J=6.10 Hz), 5.11 (2H, s), 3.63 (6H, s), 2.52 (3H, s), 2.17 (3H, s).

Production Example 22

The same reaction as that of Production Example 6 was carried out except that 2-methyl-4-(1-allyloxyimino-ethyl)phenol described in Reference production example 60 was used in place of 2-methyl-4-(1-methoxyimino-ethyl)phenol in Production example 6 to obtain 1-{2-[2-methyl-4-(1-allyloxyimino-methyl)-phenoxymethyl]-3-methoxy-phenyl}-4-methyl-1,4-dihydrotetrazol-5-one (hereinafter referred to as "Compound 22 of the present invention").

Compound 22 of the present invention

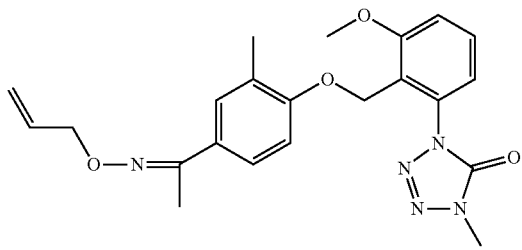 [SMILES: C=CCON=C(C)c1ccc(OCc2c(OC)cccc2-n2nnn(C)c2=O)c(C)c1]

1H-NMR (CDCl3) δ: 7.46 (1H, t, J=8.29 Hz), 7.38 (1H, s), 7.36 (1H, dd, J=8.54, 2.20 Hz), 7.10-7.04 (2H, m), 6.84 (1H, d, J=8.54 Hz), 6.11-6.00 (1H, m), 5.36-5.30 (1H, m), 5.28 (2H, s), 5.24-5.19 (1H, m), 4.67 (2H, d, J=5.61 Hz), 3.92 (3H, s), 3.59 (3H, s), 2.20 (3H, s), 2.00 (3H, s).

Production Example 23

The same reaction as that of Production Example 2 was carried out except that 2-trifluoromethyl-4-(1-methoxy-imino-ethyl)phenol described in Reference production example 89 was used in place of 2-methyl-4-(1-methoxy-imino-ethyl)phenol in Production example 2 to obtain 1-{2-[2-trifluoromethyl-4-(1-methoxyimino-ethyl)-phenoxym-ethyl]-3-methyl-phenyl}-4-methyl-1,4-dihydrotetrazol-5-one (hereinafter referred to as "Compound 23 of the present invention").

Compound 23 of the present invention

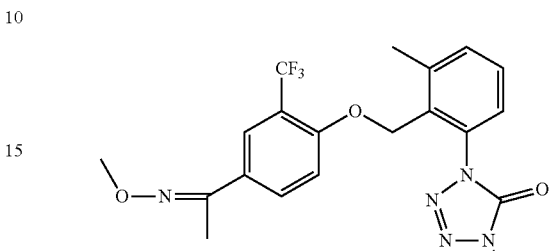

1H-NMR (CDCl3) δ: 7.79 (1H, dd, J=8.45, 2.41 Hz), 7.77-7.73 (1H, m), 7.46-7.41 (2H, m), 7.29 (1H, dd, J=7.24, 1.93 Hz), 6.87 (1H, d, J=8.54 Hz), 5.11 (2H, s), 3.62 (3H, s), 2.54 (3H, s), 2.50 (3H, s), 2.12 (3H, s).

Production Example 24

The same reaction as that of Production Example 6 was carried out except that 2-methyl-4-(1-methoxyimino-ethyl)phenol described in Reference production example 61 was used in place of 2-methyl-4-(1-methoxyimino-ethyl)phenol in Production example 6 to obtain 1-{2-[2-methyl-4-(1-benzyloxyimino-ethyl)-phenoxymethyl]-3-methoxy-phenyl}-4-methyl-1,4-dihydrotetrazol-5-one (hereinafter referred to as "Compound 24 of the present invention").

Compound 24 of the present invention

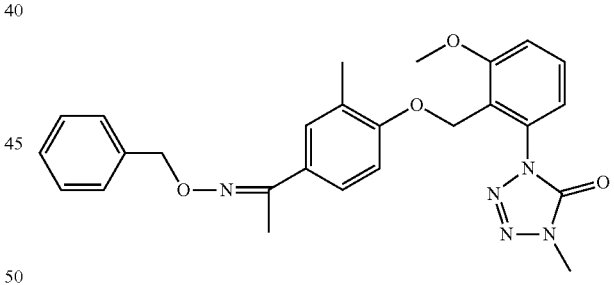

1H-NMR (CDCl3) δ: 7.45 (1H, t, J=8.45 Hz), 7.42-7.34 (6H, m), 7.33-7.27 (2H, m), 7.07 (1H, t, J=5.74 Hz), 6.84 (1H, d, J=8.45 Hz), 5.28 (2H, s), 5.21 (2H, s), 3.92 (3H, s), 3.57 (3H, s), 2.21 (3H, s), 1.99 (3H, s).

Production Example 25

The same reaction as that of Production Example 6 was carried out except that 2-nitro-4-(1-methoxyimino-ethyl)phenol described in Reference production example 86 was used in place of 2-methyl-4-(1-methoxyimino-ethyl)phenol in Production example 6 to obtain 1-{2-[2-nitro-4-(1-methoxyimino-ethyl)-phenoxymethyl]-3-methoxy-phenyl}-4-methyl-1,4-dihydrotetrazol-5-one (hereinafter referred to as "Compound 25 of the present invention").

101

Compound 25 of the present invention

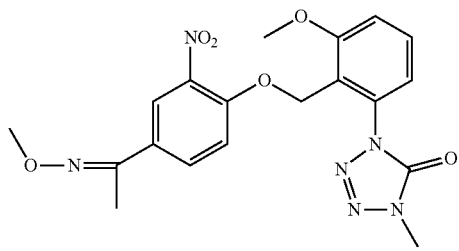 [SMILES: CON=C(C)c1ccc(OCc2c(OC)cccc2-n2nnn(C)c2=O)c([N+](=O)[O-])c1]

1H-NMR (CDCl3) δ: 8.06 (1H, d, J=2.20 Hz), 7.75 (1H, dd, J=8.78, 2.20 Hz), 7.45 (1H, t, J=8.17 Hz), 7.10-7.05 (3H, m), 5.59 (2H, s), 3.98 (3H, s), 3.96 (3H, s), 3.71 (3H, s), 2.15 (3H, s).

Production Example 26

The same reaction as that of Production Example 6 was carried out except that 2-trifluoromethyl-4-(1-methoxy-imino-ethyl)phenol described in Reference production example 89 was used in place of 2-methyl-4-(1-methoxy-imino-ethyl)phenol in Production example 6 to obtain 1-{2-[2-trifluoromethyl-4-(1-methoxyimino-ethyl)-phenoxym-ethyl]-3-methoxy-phenyl}-4-methyl-1,4-dihydrotetrazol-5-one (hereinafter referred to as "Compound 26 of the present invention").

Compound 26 of the present invention

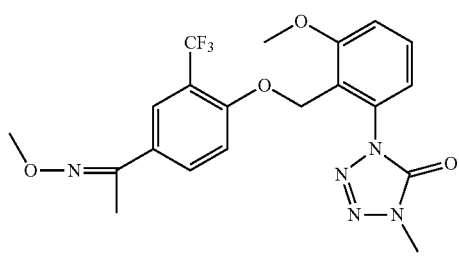

1H-NMR (CDCl3) δ: 7.79-7.77 (1H, m), 7.69 (1H, dd, J=8.69, 2.41 Hz), 7.46 (1H, t, J=8.21 Hz), 7.11 (1H, dd, J=7.97, 0.97 Hz), 7.07 (1H, d, J=8.45 Hz), 7.02 (1H, d, J=8.69 Hz), 5.49 (2H, s), 3.97 (3H, s), 3.95 (3H, s), 3.65 (3H, s), 2.16 (3H, s).

Production Example 27

The same reaction as that of Production Example 6 was carried out except that 2-bromo-4-(1-methoxyimino-ethyl) phenol described in Reference production example 53 was used in place of 2-methyl-4-(1-methoxyimino-ethyl)phenol in Production example 6 to obtain 1-{2-[2-bromo-4-(1-methoxyimino-ethyl)-phenoxymethyl]-3-methoxy-phenyl}-4-methyl-1,4-dihydrotetrazol-5-one (hereinafter referred to as "Compound 27 of the present invention").

102

Compound 27 of the present invention

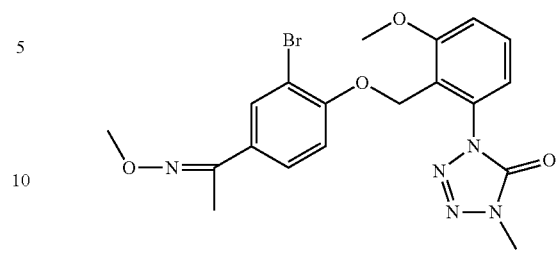

1H-NMR (CDCl3) δ: 7.80-7.76 (1H, m), 7.69 (1H, dd, J=8.69, 2.41 Hz), 7.46 (1H, t, J=8.21 Hz), 7.11 (1H, d, J=7.97 Hz), 7.07 (1H, d, J=8.45 Hz), 7.02 (1H, d, J=8.69 Hz), 5.49 (2H, s), 3.97 (3H, s), 3.95 (3H, s), 3.65 (3H, s), 2.16 (3H, s).

Production Example 28

The same reaction as that of Production Example 2 was carried out except that 2-methyl-4-(1-butoxyimino-ethyl) phenol described in Reference production example 62 was used in place of 2-methyl-4-(1-methoxyimino-ethyl)phenol in Production example 2 to obtain 1-{2-[2-methyl-4-(1-butoxyimino-ethyl)-phenoxymethyl]-3-methyl-phenyl}-4-methyl-1,4-dihydrotetrazol-5-one (hereinafter referred to as "Compound 28 of the present invention").

Compound 28 of the present invention

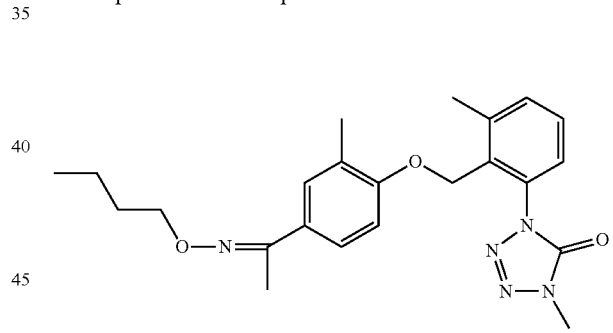

1H-NMR (CDCl3) δ: 7.45-7.35 (4H, m), 7.29-7.25 (1H, m), 6.80 (1H, d, J=8.54 Hz), 5.05 (2H, s), 4.17 (2H, t, J=6.71 Hz), 3.62 (3H, s), 2.49 (3H, s), 2.19 (3H, s), 2.10 (3H, s), 1.74-1.65 (2H, m), 1.48-1.38 (2H, m), 0.96 (3H, t, J=7.32 Hz).

Production Example 29

The same reaction as that of Production Example 6 was carried out except that 2-methyl-4-(1-butoxyimino-ethyl) phenol described in Reference production example 62 was used in place of 2-methyl-4-(1-methoxyimino-ethyl)phenol in Production example 6 to obtain 1-{2-[2-methyl-4-(1-butoxyimino-ethyl)-phenoxymethyl]-3-methoxy-phenyl}-4-methyl-1,4-dihydrotetrazol-5-one (hereinafter referred to as "Compound 29 of the present invention").

Compound 29 of the present invention

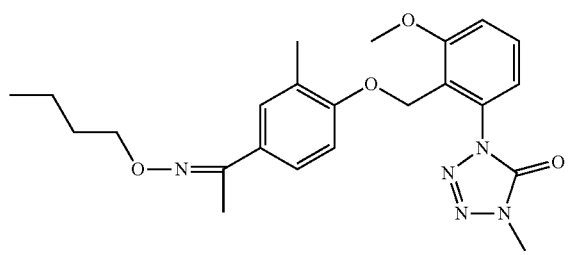 [SMILES: CCCCON=C(C)c1ccc(OCc2c(OC)cccc2-n2nnn(C)c2=O)c(C)c1]

1H-NMR (CDCl3) δ: 7.46 (1H, t, J=8.17 Hz), 7.40-7.33 (2H, m), 7.10-7.05 (2H, m), 6.84 (1H, d, J=8.29 Hz), 5.28 (2H, s), 4.16 (2H, t, J=6.71 Hz), 3.93 (3H, s), 3.59 (3H, s), 2.17 (3H, s), 2.00 (3H, s), 1.73-1.65 (2H, m), 1.47-1.37 (2H, m), 0.95 (3H, t, J=7.44 Hz).

Production Example 30

The same reaction as that of Production Example 2 was carried out except that 2-methyl-4-(1-propargyloxyimino-ethyl)phenol described in Reference production example 92 was used in place of 2-methyl-4-(1-methoxyimino-ethyl) phenol in Production example 2 to obtain 1-{2-[2-methyl-4-(1-propargyloxyimino-ethyl)-phenoxymethyl]-3-methyl-phenyl}-4-methyl-1,4-dihydrotetrazol-5-one (hereinafter referred to as "Compound 30 of the present invention").

Compound 30 of the present invention

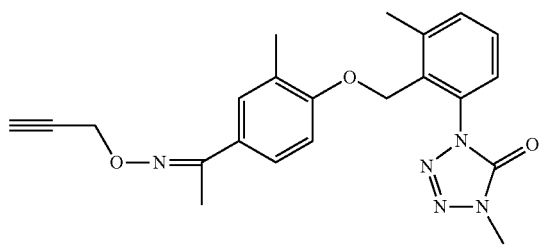 [SMILES: C#CCON=C(C)c1ccc(OCc2c(C)cccc2-n2nnn(C)c2=O)c(C)c1]

1H-NMR (CDCl3) δ: 7.47-7.38 (4H, m), 7.27 (1H, dd, J=7.12, 2.29 Hz), 6.81 (1H, d, J=8.69 Hz), 5.05 (2H, s), 4.77 (2H, d, J=2.41 Hz), 3.62 (3H, s), 2.49 (3H, s), 2.48 (1H, t, J=2.41 Hz), 2.22 (3H, s), 2.10 (3H, s).

Production Example 31

The same reaction as that of Production Example 6 was carried out except that 2-methyl-4-(1-propargyloxyimino-ethyl)phenol described in Reference production example 92 was used in place of 2-methyl-4-(1-methoxyimino-ethyl) phenol in Production example 6 to obtain 1-{2-[2-methyl-4-(1-propargyloxyimino-ethyl)-phenoxymethyl]-3-methoxy-phenyl}-4-methyl-1,4-dihydrotetrazol-5-one (hereinafter referred to as "Compound 31 of the present invention").

Compound 31 of the present invention

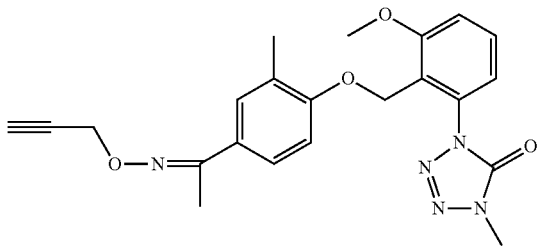 [SMILES: C#CCON=C(C)c1ccc(OCc2c(OC)cccc2-n2nnn(C)c2=O)c(C)c1]

1H-NMR (CDCl3) δ: 7.45 (1H, t, J=8.21 Hz), 7.42-7.35 (2H, m), 7.09-7.05 (2H, m), 6.85 (1H, d, J=8.45 Hz), 5.29 (2H, s), 4.76 (2H, d, J=2.41 Hz), 3.92 (3H, s), 3.58 (3H, s), 2.47 (1H, t, J=2.41 Hz), 2.20 (3H, s), 2.00 (3H, s).

Production Example 32

The same reaction as that of Production Example 13 was carried out except that 2-methoxy-4-(1-methoxyimino-ethyl)phenol described in Reference production example 85 was used in place of 2-methyl-4-(1-methoxyimino-ethyl) phenol in Production example 13 to obtain 1-{2-[2-methoxy-4-(1-methoxyimino-ethyl)-phenoxymethyl]-3-cyclopropyl-phenyl}-4-methyl-1,4-dihydrotetrazol-5-one (hereinafter referred to as "Compound 32 of the present invention").

Compound 32 of the present invention

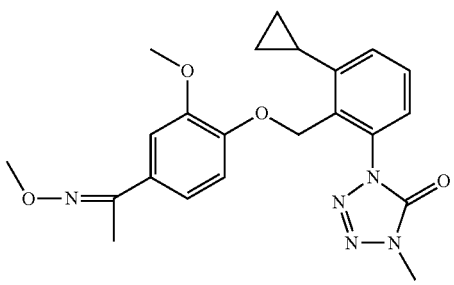

1H-NMR (CDCl3) δ: 7.39 (1H, t, J=7.80 Hz), 7.28-7.23 (3H, m), 7.06 (1H, dd, J=8.41, 2.07 Hz), 6.85 (1H, d, J=8.29 Hz), 5.38 (2H, s), 3.98 (3H, s), 3.82 (3H, s), 3.61 (3H, s), 2.19-2.15 (4H, m), 1.02-0.96 (2H, m), 0.77-0.72 (2H, m).

Production Example 33

The same reaction as that of Production Example 13 was carried out except that 2-trifluoro-4-(1-methoxyimino-ethyl) phenol described in Reference production example 89 was used in place of 2-methyl-4-(1-methoxyimino-ethyl)phenol in Production example 13 to obtain 1-{2-[2-trifluoro-4-(1-methoxyimino-ethyl)-phenoxymethyl]-3-cyclopropyl-phenyl}-4-methyl-1,4-dihydrotetrazol-5-one (hereinafter referred to as "Compound 33 of the present invention").

Compound 33 of the present invention

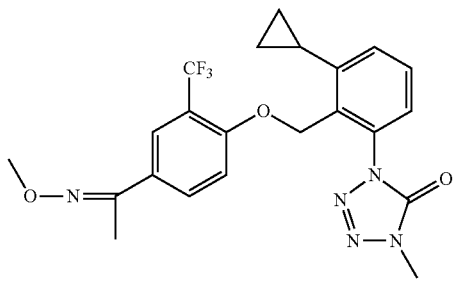 [SMILES: CON=C(C)c1ccc(OCc2c(C3CC3)cccc2-n2nnn(C)c2=O)c(C(F)(F)F)c1]

1H-NMR (CDCl3) δ: 7.84 (1H, d, J=2.17 Hz), 7.73 (1H, dd, J=8.69, 2.41 Hz), 7.44 (1H, t, J=7.85 Hz), 7.32-7.25 (2H, m), 7.00 (1H, d, J=8.69 Hz), 5.43 (2H, s), 3.98 (3H, s), 3.66 (3H, s), 2.19 (3H, s), 2.16-2.10 (1H, m), 1.02-0.96 (2H, m), 0.78-0.72 (2H, m).

Production Example 34

The same reaction as that of Production Example 13 was carried out except that 2-methyl-4-{1-(tert-butoxy)imino-ethyl)phenol described in Reference production example 59 was used in place of 2-methyl-4-(1-methoxyimino-ethyl) phenol in Production example 13 to obtain 1-{2-[2-methyl-4-{1-(tert-butoxy)imino-ethyl)-phenoxymethyl]-3-cyclopropyl-phenyl}-4-methyl-1,4-dihydrotetrazol-5-one (hereinafter referred to as "Compound 34 of the present invention").

Compound 34 of the present invention

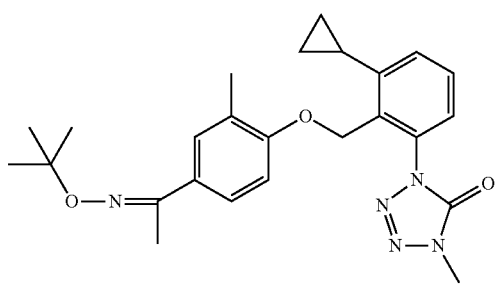 [SMILES: CC(=NOC(C)(C)C)c1ccc(OCc2c(C3CC3)cccc2-n2nnn(C)c2=O)c(C)c1]

1H-NMR (CDCl3) δ: 7.46-7.40 (3H, m), 7.28-7.25 (2H, m), 6.85 (1H, d, J=8.54 Hz), 5.27 (2H, s), 3.61 (3H, s), 2.16 (3H, s), 2.14-2.08 (4H, m), 1.34 (9H, s), 1.01-0.95 (2H, m), 0.78-0.74 (2H, m).

Production Example 35

The same reaction as that of Production Example 13 was carried out except that 2-methyl-4-{1-propargyloxyimino-ethyl)phenol described in Reference production example 92 was used in place of 2-methyl-4-(1-methoxyimino-ethyl) phenol in Production example 13 to obtain 1-{2-[2-methyl-4-{1-propargyloxyimino-ethyl)-phenoxymethyl]-3-cyclopropyl-phenyl}-4-methyl-1,4-dihydrotetrazol-5-one (hereinafter referred to as "Compound 35 of the present invention).

Compound 35 of the present invention

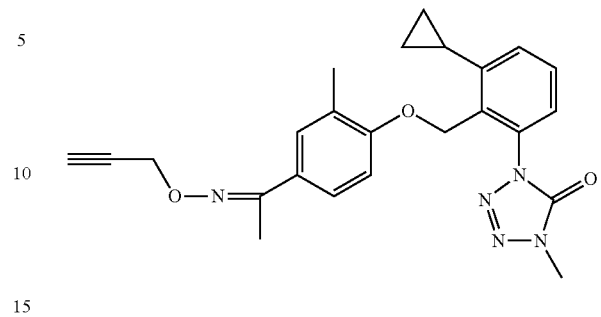

1H-NMR (CDCl3) δ: 7.46-7.40 (3H, m), 7.27 (2H, d, J=6.76 Hz), 6.86 (1H, d, J=8.45 Hz), 5.28 (2H, s), 4.77 (2H, d, J=2.41 Hz), 3.61 (3H, s), 2.47 (1H, t, J=2.41 Hz), 2.24-2.18 (4H, m), 2.22 (3H, s), 1.01-0.95 (2H, m), 0.78-0.73 (2H, m).

Production Example 36

The same reaction as that of Production Example 13 was carried out except that 2-methyl-4-{1-methoxyimino-methyl)phenol described in Reference production example 88 was used in place of 2-methyl-4-(1-methoxyimino-ethyl) phenol in Production example 13 to obtain 1-{2-[2-methyl-4-(1-methoxyimino-methyl)-phenoxymethyl]-3-cyclopropyl-phenyl}-4-methyl-1,4-dihydrotetrazol-5-one (hereinafter referred to as "Compound 36 of the present invention").

Compound 36 of the present invention

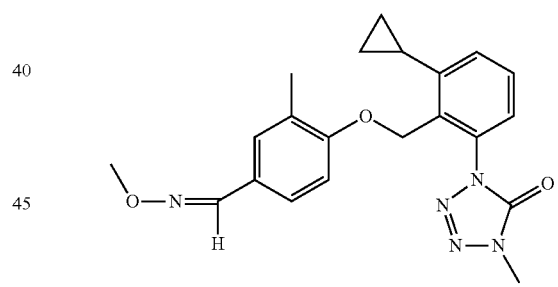

1H-NMR (CDCl3) δ: 7.98 (1H, s), 7.44 (1H, t, J=7.85 Hz), 7.41-7.39 (1H, m), 7.31 (2H, dd, J=8.45, 1.93 Hz), 7.28 (1H, s), 6.86 (1H, d, J=8.45 Hz), 5.28 (2H, s), 3.94 (3H, s), 3.60 (3H, s), 2.15-2.06 (4H, m), 1.02-0.95 (2H, m), 0.79-0.73 (2H, m).

Production Example 37

The same reaction as that of Production Example 13 was carried out except that 2-fluoro-4-{1-methoxyimino-ethyl) phenol described in Reference production example 84 was used in place of 2-methyl-4-(1-methoxyimino-ethyl)phenol in Production example 13 to obtain 1-{2-[2-fluoro-4-(1-methoxyimino-ethyl)-phenoxymethyl]-3-cyclopropyl-phenyl}-4-methyl-1,4-dihydrotetrazol-5-one (hereinafter referred to as "Compound 37 of the present invention").

Compound 37 of the present invention

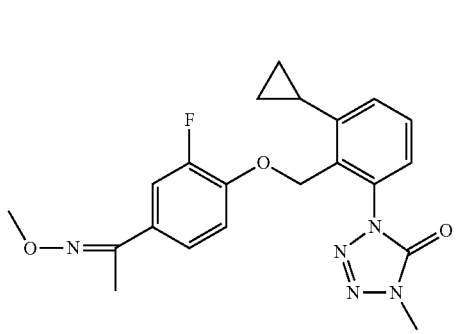 [SMILES: CON=C(C)c1ccc(OCc2c(C3CC3)cccc2-n2nnn(C)c2=O)c(F)c1]

1H-NMR (CDCl3) δ: 7.45-7.38 (2H, m), 7.31-7.25 (3H, m), 6.93 (1H, t, J=8.54 Hz), 5.38 (2H, s), 3.97 (3H, s), 3.65 (3H, s), 2.17-2.10 (4H, m), 1.04-0.98 (2H, m), 0.79-0.73 (2H, m).

Production Example 38

The same reaction as that of Production Example 2 was carried out except that 2-fluoro-4-{1-methoxyimino-ethyl)phenol described in Reference production example 84 was used in place of 2-methyl-4-(1-methoxyimino-ethyl)phenol in Production example 2 to obtain 1-{2-[2-fluoro-4-(1-methoxyimino-ethyl)-phenoxymethyl]-3-methyl-phenyl}-4-methyl-1,4-dihydrotetrazol-5-one (hereinafter referred to as "Compound 38 of the present invention").

Compound 38 of the present invention

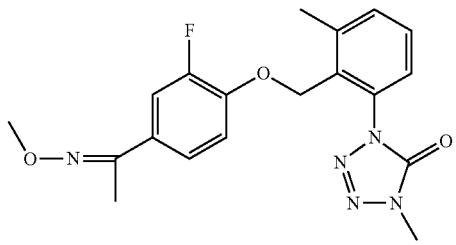

1H-NMR (CDCl3) δ: 7.45-7.36 (3H, m), 7.31-7.25 (2H, m), 6.90 (1H, t, J=8.54 Hz), 5.15 (2H, s), 3.97 (3H, s), 3.67 (3H, s), 2.52 (3H, s), 2.16 (3H, s).

Production Example 39

The same reaction as that of Production Example 6 was carried out except that 2-fluoro-4-{1-methoxyimino-ethyl)phenol described in Reference production example 84 was used in place of 2-methyl-4-(1-methoxyimino-ethyl)phenol in Production example 6 to obtain 1-{2-[2-fluoro-4-(1-methoxyimino-ethyl)-phenoxymethyl]-3-methoxy-phenyl}-4-methyl-1,4-dihydrotetrazol-5-one (hereinafter referred to as "Compound 39 of the present invention").

Compound 39 of the present invention

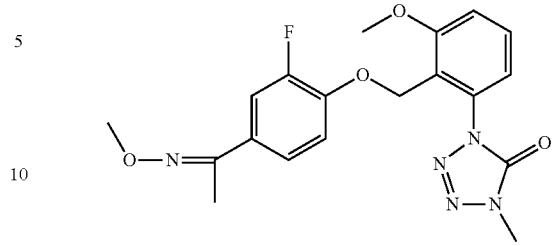

1H-NMR (CDCl3) δ: 7.45 (1H, t, J=8.17 Hz), 7.37 (1H, dd, J=12.56, 2.07 Hz), 7.27-7.23 (1H, m), 7.09-7.04 (2H, m), 6.91 (1H, t, J=8.54 Hz), 5.37 (2H, s), 3.96 (3H, s), 3.93 (3H, s), 3.64 (3H, s), 2.14 (3H, s).

Production Example 40

The same reaction as that of Production Example 13 was carried out except that 2-bromo-4-{1-methoxyimino-ethyl)phenol described in Reference production example 84 was used in place of 2-methyl-4-(1-methoxyimino-ethyl)phenol in Production example 13 to obtain 1-{2-[2-bromo-4-(1-methoxyimino-ethyl)-phenoxymethyl]-3-methoxy-phenyl}-4-methyl-1,4-dihydrotetrazol-5-one (hereinafter referred to as "Compound 40 of the present invention").

Compound 40 of the present invention

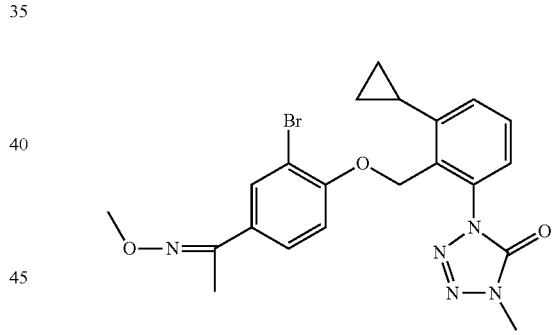

1H-NMR (CDCl3) δ: 7.83 (1H, d, J=2.20 Hz), 7.61-7.54 (1H, m), 7.49 (1H, dd, J=8.54, 2.20 Hz), 7.46-7.40 (1H, m), 7.31-7.26 (1H, m), 6.89-6.85 (1H, m), 5.43 (2H, s), 3.97 (3H, s), 3.66 (3H, s), 2.18-2.07 (4H, m), 1.04-0.95 (2H, m), 0.79-0.73 (2H, m).

Production Example 41

The same reaction as that of Production Example 13 was carried out except that 2-nitro-4-(1-methoxyimino-ethyl)phenol described in Reference production example 86 was used in place of 2-methyl-4-(1-methoxyimino-ethyl)phenol in Production example 13 to obtain 1-{2-[2-nitro-4-(1-methoxyimino-ethyl)-phenoxymethyl]-3-methoxy-phenyl}-4-methyl-1,4-dihydrotetrazol-5-one (hereinafter referred to as "Compound 41 of the present invention").

Compound 41 of the present invention

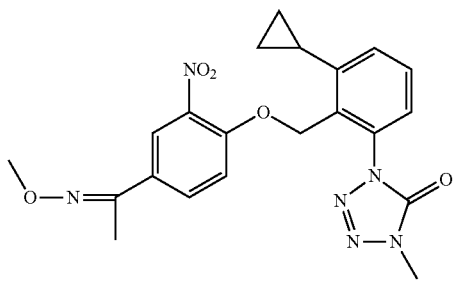 [SMILES: CON=C(C)c1ccc(OCc2c(C3CC3)cccc2-n2nnn(C)c2=O)c([N+](=O)[O-])c1]

1H-NMR (CDCl3) δ: 8.08 (1H, d, J=2.20 Hz), 7.78 (1H, dd, J=8.78, 2.20 Hz), 7.43 (1H, t, J=7.80 Hz), 7.32-7.25 (2H, m), 7.03 (1H, d, J=9.02 Hz), 5.55 (2H, s), 3.98 (3H, s), 3.69 (3H, s), 2.18-2.14 (4H, m), 1.07-1.01 (2H, m), 0.80-0.75 (2H, m).

Production Example 42

0.05 mL of hydrochloric acid (12 M) was added to a mixture of 0.38 g of 1-[2-(2-cyclopropyl-4-acetyl-phenoxymethyl)-3-methyl-phenyl]-4-methyl-1,4-dihydro-tetrazole-5-one described in Reference production example 76, 0.084 g of O-ethylhydroxyamine hydrochloride, 4 mL of ethanol and the mixture was stirred at ambient temperature for 4 hr. Saturated sodium bicarbonate water was added to the reaction mixture and the mixture was extracted three times with chloroform and washed with saturated saline. The obtained solution was dried by sodium sulfate and filtered, and then, the filtrate was concentrated. The obtained residue was subjected to silica gel chromatography to obtain 0.08 g of 1-{2-[2-cyclopropyl-4-(1-methoxyimino-ethyl)-phenoxymethyl]-3-methylphenyl}-4-methyl-1,4-dihydrotetrazol-5-one (hereinafter referred to as "compound 42 of the present invention).

Compound 42 of the present invention

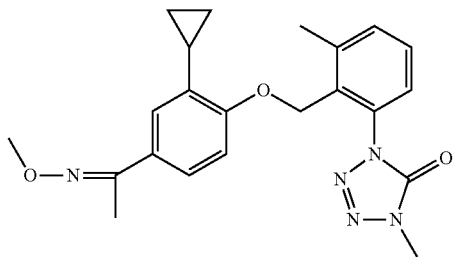 [SMILES: CON=C(C)c1ccc(OCc2c(C)cccc2-n2nnn(C)c2=O)c(C2CC2)c1]

1H-NMR (CDCl3) δ: 7.46-7.39 (3H, m), 7.30-7.25 (1H, m), 6.91-6.84 (1H, m), 6.84-6.80 (1H, m), 5.06 (2H, d, J=1.21 Hz), 3.91 (3H, s), 3.66 (3H, s), 3.63 (3H, s), 2.52 (3H, s), 2.04-1.99 (1H, m), 0.89-0.80 (2H, m), 0.64-0.53 (2H, m).

Production Example 43

The same reaction as that of Production Example 2 was carried out except that 1-(2-bromomethyl-3-bromophenyl)-4-methyl-1,4-dihydrotetrazol-5-one described in Reference production example 5 was used in place of 1-(2-bromomethyl-3-methylphenyl)-4-methyl-1,4-dihydrotetrazol-5-one in Production example 2 to obtain 1-{2-[2-methyl-4-(1-methoxyimino-ethyl)phenoxymethyl]-3-bromo-phenyl}-4-methyl-1,4-dihydrotetrazol-5-one (hereinafter referred to as "Compound 43 of the present invention").

Compound 43 of the present invention

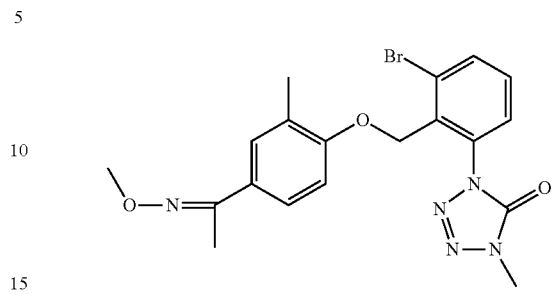

1H-NMR (CDCl3) δ: 7.80 (1H, dd, J=7.85, 1.57 Hz), 7.45-7.36 (4H, m), 6.81 (1H, d, J=8.45 Hz), 5.32 (2H, s), 3.97 (3H, s), 3.60 (3H, s), 2.18 (3H, s), 2.04 (3H, s).

Production Example 44

The same reaction as that of Production Example 2 was carried out except that 1-(2-bromomethyl-3-ethoxyphenyl)-4-methyl-1,4-dihydrotetrazol-5-one described in Reference production example 13 was used in place of 1-(2-bromomethyl-3-methylphenyl)-4-methyl-1,4-dihydrotetrazol-5-one in Production example 2 to obtain 1-{2-[2-methyl-4-(1-methoxyimino-ethyl)phenoxymethyl]-3-ethoxy-phenyl}-4-methyl-1,4-dihydrotetrazol-5-one (hereinafter referred to as "Compound 44 of the present invention").

Compound 44 of the present invention

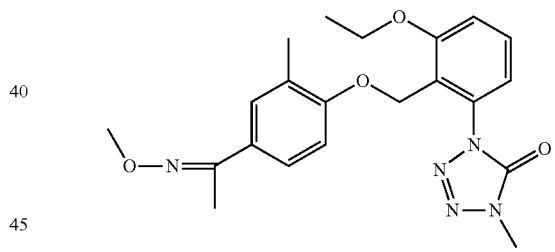

1H-NMR (CDCl3) δ: 7.43 (1H, t, J=8.21 Hz), 7.40-7.38 (1H, m), 7.35 (1H, dd, J=8.57, 2.29 Hz), 7.08-7.03 (2H, m), 6.87 (1H, d, J=8.69 Hz), 5.30 (2H, s), 4.14 (2H, q, J=7.00 Hz), 3.96 (3H, s), 3.59 (3H, s), 2.17 (3H, s), 2.00 (3H, s), 1.44 (3H, t, J=7.00 Hz).

Production Example 45

The same reaction as that of Production Example 2 was carried out except that 1-(2-bromomethyl-3-trifluoromethylphenyl)-4-methyl-1,4-dihydrotetrazol-5-one described in Reference production example 9 was used in place of 1-(2-bromomethyl-3-methylphenyl)-4-methyl-1,4-dihydrotetrazol-5-one in Production example 2 to obtain 1-{2-[2-methyl-4-(1-methoxyimino-ethyl)phenoxymethyl]-3-trifluoromethyl-phenyl}-4-methyl-1,4-dihydrotetrazol-5-one (hereinafter referred to as "Compound 45 of the present invention").

Compound 45 of the present invention

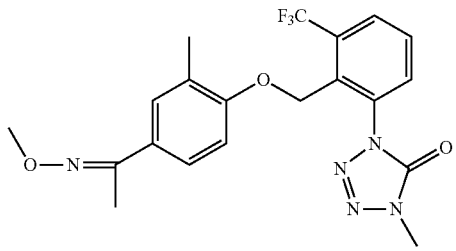 [SMILES: CON=C(C)c1ccc(OCc2c(-n3nnn(C)c3=O)cccc2C(F)(F)F)c(C)c1]

1H-NMR (CDCl3) δ: 7.91 (1H, dd, J=6.52, 2.90 Hz), 7.71-7.65 (2H, m), 7.45-7.41 (1H, m), 7.38 (1H, dd, J=8.45, 2.17 Hz), 6.80 (1H, d, J=8.45 Hz), 5.31 (2H, s), 3.97 (3H, s), 3.53 (3H, s), 2.18 (3H, s), 2.01 (3H, s).

Production Example 46

A mixture of 0.45 g of the compound 43 of the present invention described in Production Example 43, 0.17 g of isopropenylboronic acid pinacol ester, 0.02 g of 1,1'-bis(diphenylphosphino)ferrocene-palladium (II) dichloride-dichloromethane complex, 0.42 g of potassium phosphate, 4 mL of 1,4-dioxane, and 0.4 mL of water was stirred at 80° C. for 4 hr. The reaction mixture was concentrated under reduced pressure and the obtained residue was subjected to silica gel column chromatography to obtain 0.28 g of 1-{2-[2-methyl-4-(1-methoxyimino-ethyl)-phenoxymethyl]-3-isopropenyl-phenyl}-4-methyl-1,4-dihydrotetrazol-5-one (hereinafter referred to as "Compound 46 of the present invention").

Compound 46 of the present invention

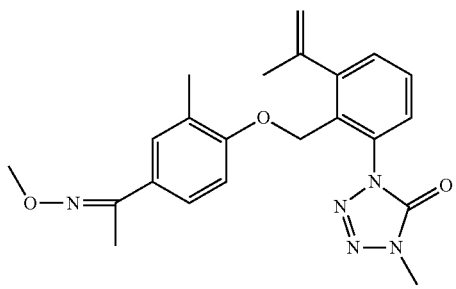 [SMILES: C=C(C)c1cccc(-n2nnn(C)c2=O)c1COc1ccc(C(C)=NOC)cc1C]

1H-NMR (CDCl3) δ: 7.49 (1H, t, J=7.73 Hz), 7.43-7.34 (4H, m), 6.76 (1H, d, J=8.45 Hz), 5.28 (1H, s), 5.13 (2H, s), 4.98 (1H, s), 3.97 (3H, s), 3.55 (3H, s), 2.17 (3H, s), 2.09 (3H, s), 2.03 (3H, s).

Production Example 47

A mixture of 0.20 g of the compound 46 of the present invention described in Production Example 46, 0.02 g of a palladium-fibroin complex, and 10 mL of ethanol was stirred at ambient temperature in a hydrogen atmosphere for 8 hr. The reaction mixture was filtered and the filtrate was concentrated under reduced pressure to obtain 0.19 g of 1-{2-[2-methyl-4-(1-methoxyimino-ethyl)-phenoxymethyl]-3-isopropyl-phenyl}-4-methyl-1,4-dihydrotetrazol-5-one (hereinafter referred to as "Compound 47 of the present invention").

Compound 47 of the present invention

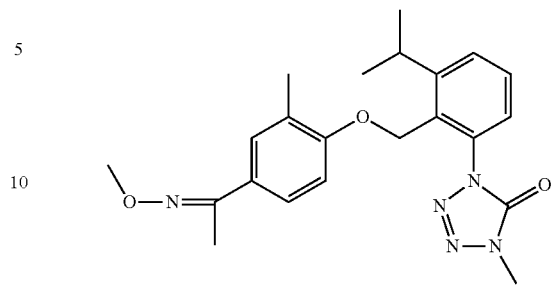

1H-NMR (CDCl3) δ: 7.60-7.35 (4H, m), 7.30-7.25 (1H, m), 6.87-6.81 (1H, m), 5.04 (2H, s), 3.97 (3H, s), 3.59 (3H, s), 3.37-3.26 (1H, m), 2.18 (3H, s), 2.11 (3H, s), 1.29 (6H, s).

Production Example 48

The same reaction as that of Production Example 2 was carried out except that 2,5-dimethyl-4-(1-methoxyimino-ethyl)phenol described in Reference production example 50 was used in place of 2-methyl-4-(1-methoxyimino-ethyl)phenol in Production example 2 to obtain 1-{2-[2,5-dimethyl-4-(1-methoxyimino-ethyl)-phenoxymethyl]-3-methyl-phenyl}-4-methyl-1,4-dihydrotetrazol-5-one (hereinafter referred to as "Compound 48 of the present invention").

Compound 48 of the present invention

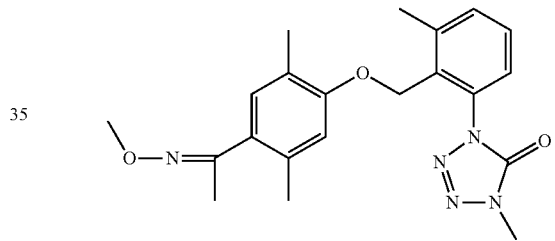

1H-NMR (CDCl3) δ: 7.45-7.35 (2H, m), 7.28-7.25 (1H, m), 6.96 (1H, s), 6.64 (1H, s), 5.01 (2H, s), 3.94 (3H, s), 3.65 (3H, s), 2.49 (3H, s), 2.31 (3H, s), 2.12 (3H, s), 2.04 (3H, s).

Production Example 49

The same reaction as that of Production Example 2 was carried out except that 3-methyl-4-(1-methoxyimino-ethyl)phenol described in Reference production example 90 was used in place of 2-methyl-4-(1-methoxyimino-ethyl)phenol in Production example 2 to obtain 1-{2-[3-methyl-4-(1-methoxyimino-ethyl)-phenoxymethyl]-3-methyl-phenyl}-4-methyl-1,4-dihydrotetrazol-5-one (hereinafter referred to as "Compound 49 of the present invention").

Compound 49 of the present invention

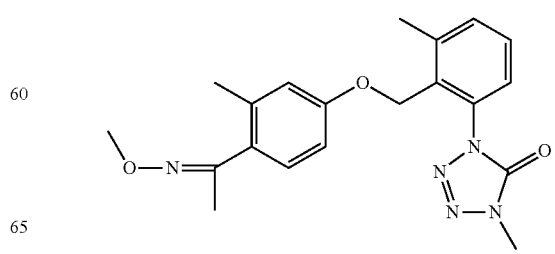

1H-NMR (CDCl3) δ: 7.44-7.42 (2H, m), 7.27 (1H, dd, J=7.10, 2.06 Hz), 7.13 (1H, d, J=9.16 Hz), 6.75-6.68 (2H, m), 5.00 (2H, s), 3.95 (3H, s), 3.64 (3H, s), 2.48 (3H, s), 2.32 (3H, s), 2.14 (3H, s).

Production Example 50

The same reaction as that of Production Example 6 was carried out except that 2,5-dimethyl-4-(1-methoxyimino-ethyl)phenol described in Reference production example 50 was used in place of 2-methyl-4-(1-methoxyimino-ethyl)phenol in Production example 6 to obtain 1-{2-[2,5-dimethyl-4-(1-methoxyimino-ethyl)-phenoxymethyl]-3-methoxy-phenyl}-4-methyl-1,4-dihydrotetrazol-5-one (hereinafter referred to as "Compound 50 of the present invention").

Compound 50 of the present invention

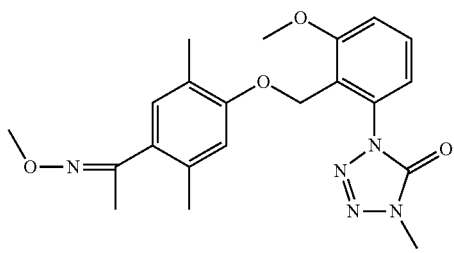 [SMILES: CON=C(C)c1cc(C)c(OCc2c(OC)cccc2-n2nnn(C)c2=O)cc1C]

1H-NMR (CDCl3) δ: 7.46 (1H, t, J=8.24 Hz), 7.10-7.05 (2H, m), 6.92 (1H, s), 6.70 (1H, s), 5.24 (2H, s), 3.94 (3H, s), 3.93 (3H, s), 3.62 (3H, s), 2.29 (3H, s), 2.11 (3H, s), 1.94 (3H, s).

Production Example 50-2

The same reaction as that of Production Example 6 was carried out except that 2-methyl-4-{1-(tert-butoxy)imino-ethyl)phenol described in Reference production example 59 was used in place of 2-methyl-4-(1-methoxyimino-ethyl)phenol in Production example 6 to obtain 1-{2-[2-methyl-4-{1-(tert-butoxy)imino-ethyl)-phenoxymethyl]-3-methoxy-phenyl}-4-methyl-1,4-dihydrotetrazol-5-one (hereinafter referred to as "Compound 50 of the present invention).

Compound 50 of the present invention

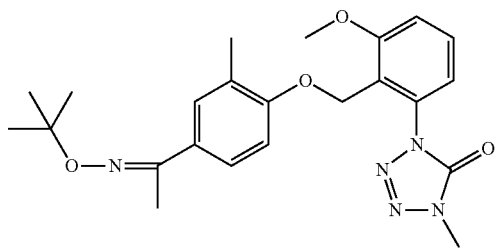 [SMILES: COc1cccc(-n2nnn(C)c2=O)c1COc1ccc(C(C)=NOC(C)(C)C)cc1C]

1H-NMR (CDCl3) δ: 7.46 (1H, t, J=8.13 Hz), 7.41-7.38 (2H, m), 7.10-7.05 (2H, m), 6.84 (1H, d, J=8.24 Hz), 5.28 (2H, s), 3.93 (3H, s), 3.59 (3H, s), 2.15 (3H, s), 2.01 (3H, s), 1.34 (9H, s).

Production Example 51

The same reaction as that of Production Example 12 was carried out except that 2-trifluoromethyl-4-(1-methoxyimino-ethyl)phenol described in Reference production example 89 was used in place of 2-methyl-4-(1-methoxyimino-ethyl)phenol in Production example 12 to obtain 1-{2-[2-methyl-4-(1-methoxyimino-ethyl)-phenoxymethyl]-3-ethyl-phenyl}-4-trifluoromethyl-1,4-dihydrotetrazol-5-one (hereinafter referred to as "Compound 51 of the present invention").

Compound 51 of the present invention

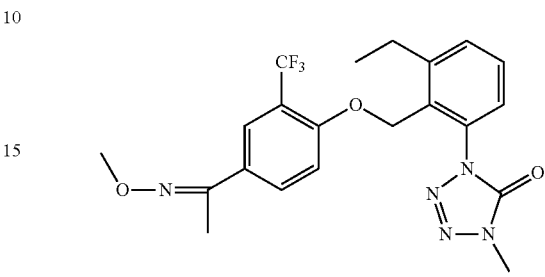

1H-NMR (CDCl3) δ: 7.85-7.83 (1H, m), 7.73 (1H, dd, J=8.70, 2.29 Hz), 7.51-7.42 (2H, m), 7.30 (1H, dd, J=7.56, 1.60 Hz), 6.96 (1H, d, J=8.70 Hz), 5.21 (2H, s), 3.98 (3H, s), 3.65 (3H, s), 2.85 (2H, q, J=7.56 Hz), 2.19 (3H, s), 1.27 (3H, t, J=7.56 Hz).

Production Example 52

The same reaction as that of Production Example 13 was carried out except that 2,5-dimethyl-4-(1-methoxyimino-ethyl)phenol described in Reference production example 50 was used in place of 2-methyl-4-(1-methoxyimino-ethyl)phenol in Production example 13 to obtain 1-{2-[2,5-dimethyl-4-(1-methoxyimino-ethyl)-phenoxymethyl]-3-methoxy-phenyl}-4-methyl-1,4-dihydrotetrazol-5-one (hereinafter referred to as "Compound 52 of the present invention").

Compound 52 of the present invention

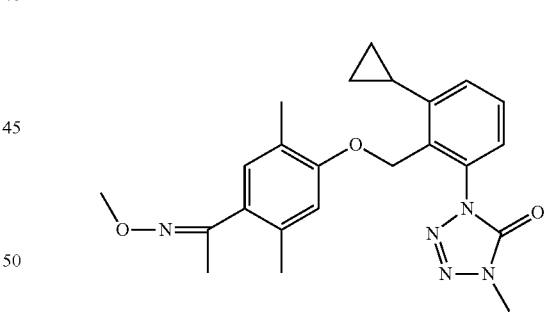

1H-NMR (CDCl3) δ: 7.43 (1H, t, J=7.90 Hz), 7.28-7.24 (2H, m), 6.96 (1H, s), 6.69 (1H, s), 5.23 (2H, s), 3.95 (3H, s), 3.64 (3H, s), 2.32 (3H, s), 2.13 (3H, s), 2.11-2.08 (1H, m), 2.03 (3H, s), 1.01-0.95 (2H, m), 0.78-0.73 (2H, m).

Production Example 53

The same reaction as that of Production Example 2 was carried out except that 2-methyl-4-(1-methoxyimino-1-cyclopropyl-methyl)phenol described in Reference production example 24 was used in place of 2-methyl-4-(1-methoxyimino-ethyl)phenol in Production example 2 to obtain 1-{2-[2-methyl-4-(1-methoxyimino-1-cyclopropyl-methyl)-phenoxymethyl]-3-methyl-phenyl}-4-methyl-1,4- dihydrotetrazol-5-one (hereinafter referred to as "Compound 53 of the present invention").

Compound 53 of the present invention

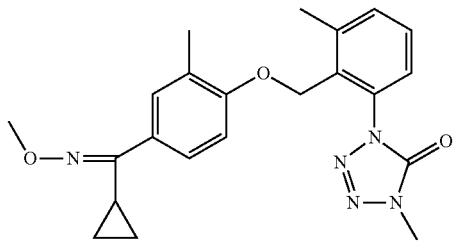 [SMILES: CON=C(c1ccc(OCc2c(C)cccc2-n2nnn(C)c2=O)c(C)c1)C1CC1]

1H-NMR (CDCl3) δ: 7.45-7.38 (2.4H, m), 7.29-7.21 (1H, m), 7.15-7.12 (1.6H, m), 6.85 (0.4H, d, J=8.47 Hz), 6.79 (0.6H, d, J=8.24 Hz), 5.03 (0.8H, s), 5.01 (1.2H, s), 3.95 (2H, s), 3.79 (1H, s), 3.64 (2H, s), 3.64 (1H, s), 2.50-2.48 (3H, m), 2.24-2.20 (1H, m), 2.10-2.07 (3H, m), 0.91-0.87 (1.2H, m), 0.81-0.76 (1.6H, m), 0.63-0.58 (1.2H, m).

Production Example 54

The same reaction as that of Production Example 6 was carried out except that 2-methyl-4-(1-methoxyimino-1-cyclopropyl-methyl)phenol described in Reference production example 24 was used in place of 2-methyl-4-(1-methoxyimino-ethyl)phenol in Production example 6 to obtain 1-{2-[2-methyl-4-(1-methoxyimino-1-cyclopropyl-methyl)-phenoxymethyl]-3-methoxy-phenyl}-4-methyl-1,4-dihydrotetrazol-5-one (hereinafter referred to as "Compound 54 of the present invention").

Compound 54 of the present invention

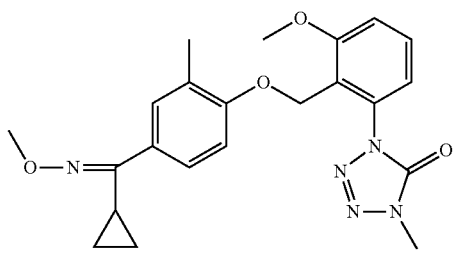 [SMILES: CON=C(c1ccc(OCc2c(OC)cccc2-n2nnn(C)c2=O)c(C)c1)C1CC1]

1H-NMR (CDCl3) δ: 7.50-7.43 (1.2H, m), 7.25-7.17 (0.6H, m), 7.11-7.05 (3.2H, m), 6.88 (0.4H, d, J=8.47 Hz), 6.82 (0.6H, d, J=8.24 Hz), 5.25 (0.8H, s), 5.24 (1.2H, s), 3.95 (2H, s), 3.93-3.91 (3H, m), 3.78 (1H, s), 3.61 (1H, s), 3.60 (2H, s), 2.25-2.17 (1H, m), 2.00 (1.2H, s), 1.97 (1.8H, s), 0.90-0.84 (1.3H, m), 0.80-0.76 (1.5H, m), 0.61-0.55 (1.2H, m).

Production Example 55

The same reaction as that of Production Example 13 was carried out except that 2-methyl-4-(1-methoxyimino-1-cyclopropyl-methyl)phenol described in Reference production example 24 was used in place of 2-methyl-4-(1-methoxyimino-ethyl)phenol in Production example 13 to obtain 1-{2-[2-methyl-4-(1-methoxyimino-1-cyclopropyl-methyl)-phenoxymethyl]-3-cyclopropyl-phenyl}-4-methyl-1,4-dihydrotetrazol-5-one (hereinafter referred to as "Compound 55 of the present invention").

Compound 55 of the present invention

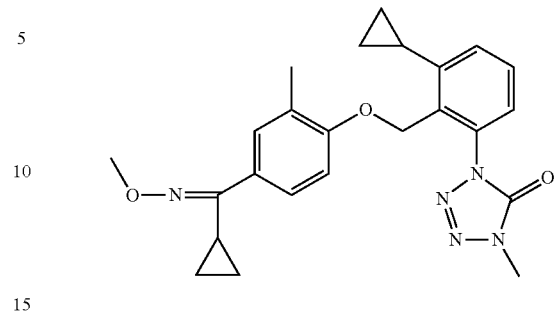

1H-NMR (CDCl3) δ: 7.47-7.39 (1H, m), 7.32-7.21 (3H, m), 7.17-7.09 (1H, m), 6.89 (0.3H, d, J=8.47 Hz), 6.83 (0.7H, d, J=8.24 Hz), 5.25 (0.7H, s), 5.23 (1.3H, s), 3.95 (2H, s), 3.79 (1H, s), 3.64-3.60 (3H, m), 2.24-2.20 (1H, m), 2.11-2.04 (4H, m), 1.02-0.95 (2H, m), 0.93-0.85 (1.3H, m), 0.83-0.73 (3.4H, m), 0.64-0.58 (1.3H, m).

Production Example 56

The same reaction as that of Production Example 2 was carried out except that 2-methyl-4-(1-methoxyimino-propyl)phenol described in Reference production example 21 was used in place of 2-methyl-4-(1-methoxyimino-ethyl)phenol in Production example 2 to obtain 1-{2-[2-methyl-4-(1-methoxyimino-propyl)-phenoxymethyl]-3-methyl-phenyl}-4-methyl-1,4-dihydrotetrazol-5-one (hereinafter referred to as "Compound 56 of the present invention").

Compound 56 of the present invention

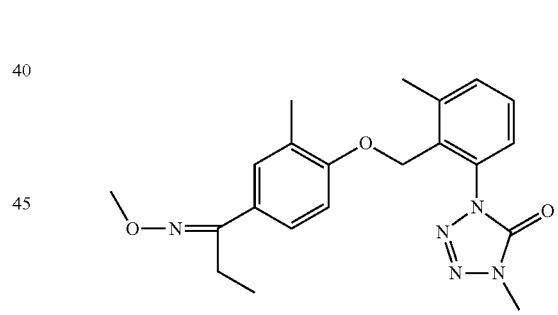

1H-NMR (CDCl3) δ: 7.44-7.35 (4H, m), 7.27 (1H, dd, J=7.10, 2.06 Hz), 6.81 (1H, d, J=8.47 Hz), 5.05 (2H, s), 3.95 (3H, s), 3.62 (3H, s), 2.70 (2H, q, J=7.56 Hz), 2.50 (3H, s), 2.10 (3H, s), 1.11 (3H, t, J=7.56 Hz).

Production Example 57

The same reaction as that of Production Example 6 was carried out except that 2-methyl-4-(1-methoxyimino-propyl)phenol described in Reference production example 21 was used in place of 2-methyl-4-(1-methoxyimino-ethyl)phenol in Production example 6 to obtain 1-{2-[2-methyl-4-(1-methoxyimino-propyl)-phenoxymethyl]-3-methoxy-phenyl}-4-methyl-1,4-dihydrotetrazol-5-one (hereinafter referred to as "Compound 57 of the present invention").

Compound 57 of the present invention

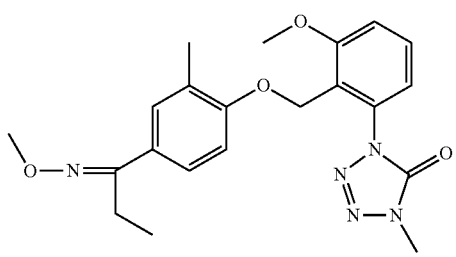 [SMILES: CCC(=NOC)c1ccc(OCc2c(OC)cccc2-n2nnn(C)c2=O)c(C)c1]

1H-NMR (CDCl3) δ: 7.46 (1H, t, J=8.13 Hz), 7.39-7.37 (1H, m), 7.34 (1H, dd, J=8.47, 2.29 Hz), 7.10-7.04 (2H, m), 6.85 (1H, d, J=8.47 Hz), 5.28 (2H, s), 3.94 (3H, s), 3.92 (3H, s), 3.59 (3H, s), 2.68 (2H, q, J=7.67 Hz), 2.00 (3H, s), 1.10 (3H, t, J=7.67 Hz).

Production Example 58

The same reaction as that of Production Example 13 was carried out except that 2-methyl-4-(1-methoxyimino-ethyl)phenol described in Reference production example 21 was used in place of 2-methyl-4-(1-methoxyimino-ethyl)phenol in Production example 13 to obtain 1-{2-[2-methyl-4-(1-methoxyimino-propyl)-phenoxymethyl]-3-cyclopropyl-phenyl}-4-methyl-1,4-dihydrotetrazol-5-one (hereinafter referred to as "Compound 58 of the present invention").

Compound 58 of the present invention

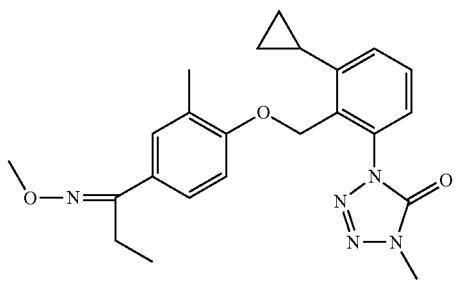 [SMILES: CCC(=NOC)c1ccc(OCc2c(C3CC3)cccc2-n2nnn(C)c2=O)c(C)c1]

1H-NMR (CDCl3) δ: 7.45-7.41 (2H, m), 7.38 (1H, dd, J=8.47, 2.29 Hz), 7.28-7.25 (2H, m), 6.86 (1H, d, J=8.47 Hz), 5.27 (2H, s), 3.95 (3H, s), 3.61 (3H, s), 2.70 (2H, q, J=7.67 Hz), 2.15-2.08 (1H, m), 2.09 (3H, s), 1.11 (3H, t, J=7.67 Hz), 1.01-0.95 (2H, m), 0.78-0.73 (2H, m).

Production Example 59

The same reaction as that of Production Example 2 was carried out except that 2-bromo-4-(1-methoxyimino-3,3-dimethyl-butyl)phenol described in Reference production example 56 was used in place of 2-methyl-4-(1-methoxyimino-ethyl)phenol in Production example 2 to obtain 1-{2-[2-bromo-4-(1-methoxyimino-3,3-dimethyl-butyl)-phenoxymethyl]-3-methyl-phenyl}-4-methyl-1,4-dihydrotetrazol-5-one (hereinafter referred to as "Compound 59 of the present invention").

Compound 59 of the present invention

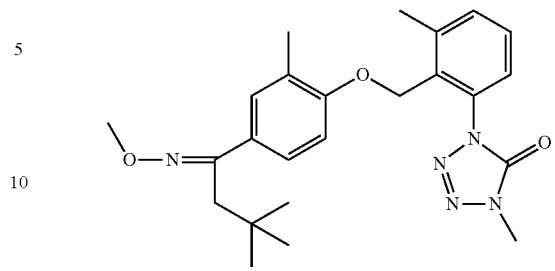

1H-NMR (CDCl3) δ: 7.45-7.38 (2H, m), 7.34-7.32 (1H, m), 7.32-7.25 (2H, m), 6.79 (1H, d, J=8.47 Hz), 5.03 (2H, s), 3.91 (3H, s), 3.62 (3H, s), 2.70 (2H, s), 2.49 (3H, s), 2.09 (3H, s), 0.86 (9H, s).

Production Example 60

The same reaction as that of Production Example 6 was carried out except that 2-bromo-4-(1-methoxyimino-3,3-dimethyl-butyl)phenol described in Reference production example 56 was used in place of 2-methyl-4-(1-methoxyimino-ethyl)phenol in Production example 6 to obtain 1-{2-[2-bromo-4-(1-methoxyimino-3,3-dimethyl-butyl)-phenoxymethyl]-3-methoxy-phenyl}-4-methyl-1,4-dihydrotetrazol-5-one (hereinafter referred to as "Compound 60 of the present invention").

Compound 60 of the present invention

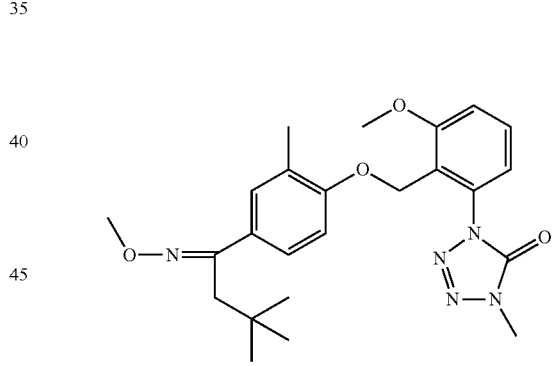

1H-NMR (CDCl3) δ: 7.46 (1H, t, J=8.13 Hz), 7.30-7.24 (2H, m), 7.10-7.05 (2H, m), 6.83 (1H, d, J=8.24 Hz), 5.26 (2H, s), 3.92 (3H, s), 3.90 (3H, s), 3.57 (3H, s), 2.69 (2H, s), 2.00 (3H, s), 0.85 (9H, s).

Production Example 61

The same reaction as that of Production Example 13 was carried out except that 2-bromo-4-(1-methoxyimino-3,3-dimethyl-butyl)phenol described in Reference production example 56 was used in place of 2-methyl-4-(1-methoxyimino-ethyl)phenol in Production example 13 to obtain 1-{2-[2-bromo-4-(1-methoxyimino-3,3-dimethyl-butyl)-phenoxymethyl]-3-cyclopropyl-phenyl}-4-methyl-1,4-dihydrotetrazol-5-one (hereinafter referred to as "Compound 61 of the present invention").

Compound 61 of the present invention

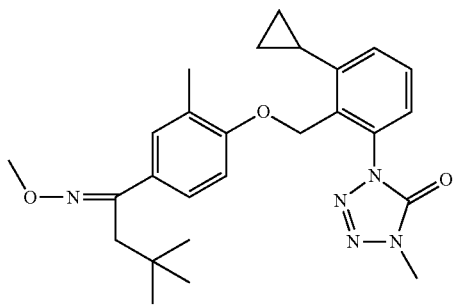 [SMILES: CON=C(CC(C)(C)C)c1ccc(OCc2c(C3CC3)cccc2-n2nnn(C)c2=O)c(C)c1]

1H-NMR (CDCl3) δ: 7.43 (1H, t, J=7.90 Hz), 7.34-7.32 (1H, m), 7.30 (1H, dd, J=8.36, 2.18 Hz), 7.28-7.24 (2H, m), 6.84 (1H, d, J=8.47 Hz), 5.26 (2H, s), 3.91 (3H, s), 3.60 (3H, s), 2.71 (2H, s), 2.14-2.06 (4H, m), 1.00-0.94 (2H, m), 0.86 (9H, s), 0.78-0.73 (2H, m).

Production Example 62

The same reaction as that of Production Example 2 was carried out except that 2-methyl-4-(1-methoxyimino-1-phenyl-methyl)phenol described in Reference production example 36 was used in place of 2-methyl-4-(1-methoxyimino-ethyl)phenol in Production example 2 to obtain 1-{2-[2-methyl-4-(1-methoxyimino-1-phenyl-methyl)-phenoxy methyl]-3-methyl-phenyl}-4-methyl-1,4-dihydrotetrazol-5-one (hereinafter referred to as "Compound 62 of the present invention").

Compound 62 of the present invention

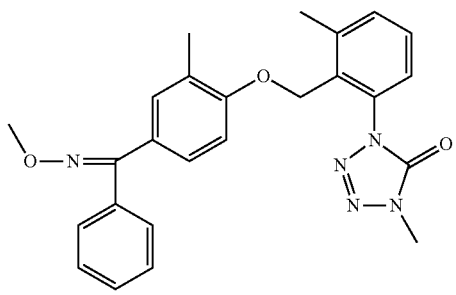 [SMILES: CON=C(c1ccccc1)c1ccc(OCc2c(C)cccc2-n2nnn(C)c2=O)c(C)c1]

1H-NMR (CDCl3) δ: 7.50-7.46 (1H, m), 7.45-7.37 (3.5H, m), 7.36-7.30 (3H, m), 7.29-7.26 (1H, m), 7.19 (0.5H, dd, J=8.45, 2.17 Hz), 7.17-7.11 (1H, m), 6.88 (0.5H, d, J=8.45 Hz), 6.75 (0.5H, d, J=8.45 Hz), 5.06 (0.9H, s), 5.03 (1.1H, s), 3.98 (1.3H, s), 3.94 (1.7H, s), 3.66 (1.3H, s), 3.63 (1.7H, s), 2.52 (1.3H, s), 2.49 (1.7H, s), 2.09 (1.3H, s), 2.06 (1.7H, s).

Production Example 63

The same reaction as that of Production Example 2 was carried out except that 2-methyl-4-(1-methoxyimino-2-methyl-propyl)phenol described in Reference production example 27 was used in place of 2-methyl-4-(1-methoxyimino-ethyl)phenol in Production example 2 to obtain 1-{2-[2-methyl-4-(1-methoxyimino-2-methyl-propyl)-phenoxy methyl]-3-methyl-phenyl}-4-methyl-1,4-dihydrotetrazol-5-one (hereinafter referred to as "Compound 63 of the present invention").

Compound 63 of the present invention

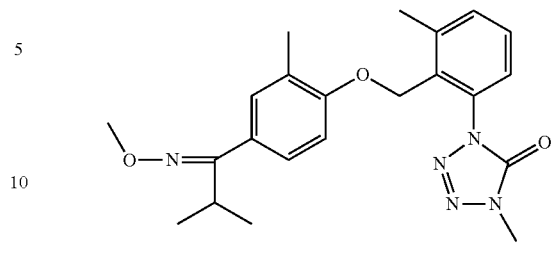

1H-NMR (CDCl3) δ: 7.46-7.39 (2H, m), 7.30-7.25 (1H, m), 7.20-7.15 (1H, m), 7.04 (0.5H, dd, J=8.24, 2.06 Hz), 7.00-6.98 (0.5H, m), 6.86 (0.5H, d, J=8.24 Hz), 6.81 (0.5H, d, J=8.24 Hz), 5.03 (2H, s), 3.92 (1.5H, s), 3.80 (1.5H, s), 3.66-3.63 (3H, m), 3.50-3.42 (0.5H, m), 2.81-2.74 (0.5H, m), 2.51 (1.5H, s), 2.50 (1.5H, s), 2.10 (3H, s), 1.18 (3H, d, J=7.10 Hz), 1.11 (3H, d, J=6.87 Hz).

Production Example 64

The same reaction as that of Production Example 6 was carried out except that 2-methyl-4-(1-methoxyimino-2-methyl-propyl)phenol described in Reference production example 27 was used in place of 2-methyl-4-(1-methoxyimino-ethyl)phenol in Production example 6 to obtain 1-{2-[2-methyl-4-(1-methoxyimino-2-methyl-propyl)-phenoxy methyl]-3-methoxy-phenyl}-4-methyl-1,4-dihydrotetrazol-5-one (hereinafter referred to as "Compound 64 of the present invention").

Compound 64 of the present invention

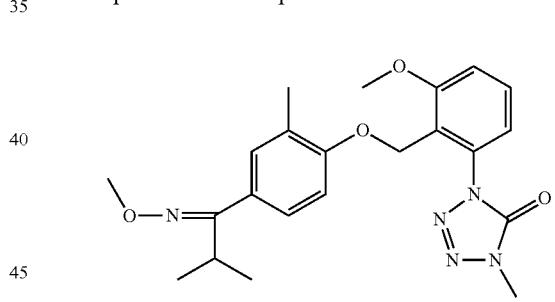

1H-NMR (CDCl3) δ: 7.49-7.43 (1H, m), 7.16-7.04 (3H, m), 7.00 (0.5H, dd, J=8.33, 2.05 Hz), 6.96-6.93 (0.5H, m), 6.88 (0.5H, d, J=8.45 Hz), 6.83 (0.5H, d, J=8.45 Hz), 5.26 (1H, s), 5.25 (1H, s), 3.93-3.91 (3H, m), 3.90 (1.5H, s), 3.78 (1.5H, s), 3.60 (1.5H, s), 3.60 (1.5H, s), 3.47-3.40 (0.5H, m), 2.79-2.72 (0.5H, m), 2.00 (1.5H, s), 1.99 (1.5H, s), 1.16 (3H, d, J=7.00 Hz), 1.09 (3H, d, J=6.76 Hz).

Production Example 65

The same reaction as that of Production Example 13 was carried out except that 2-methyl-4-(1-methoxyimino-2-methyl-propyl)phenol described in Reference production example 27 was used in place of 2-methyl-4-(1-methoxyimino-ethyl)phenol in Production example 13 to obtain 1-{2-[2-methyl-4-(1-methoxyimino-2-methyl-propyl)-phenoxy methyl]-3-cyclohexyl-phenyl}-4-methyl-1,4-dihydro-tetrazol-5-one (hereinafter referred to as "Compound 65 of the present invention").

Compound 65 of the present invention

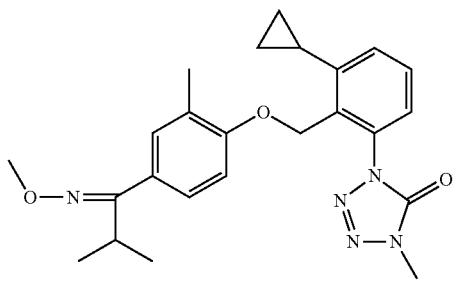 [SMILES: CON=C(c1ccc(OCc2c(C3CC3)cccc2-n2nnn(C)c2=O)c(C)c1)C(C)C]

1H-NMR (CDCl3) δ: 7.48-7.44 (1H, m), 7.32-7.27 (2H, m), 7.23-7.18 (1H, m), 7.07 (0.5H, dd, J=8.36, 2.18 Hz), 7.03-7.01 (0.5H, m), 6.92 (0.5H, d, J=8.47 Hz), 6.88 (0.5H, d, J=8.24 Hz), 5.28 (2H, s), 3.95 (1.5H, s), 3.83 (1.5H, s), 3.65 (3H, s), 3.52-3.45 (0.5H, m), 2.83-2.77 (0.5H, m), 2.18-2.10 (4H, m), 1.22-1.18 (3H, m), 1.13 (3H, d, J=6.87 Hz), 1.05-0.98 (2H, m), 0.82-0.77 (2H, m).

Production Example 66

The same reaction as that of Production Example 2 was carried out except that 2-methyl-4-(1-methoxyimino-1-cyclohexyl-methyl)phenol described in Reference production example 30 was used in place of 2-methyl-4-(1-methoxyimino-ethyl)phenol in Production example 2 to obtain 1-{2-[2-methyl-4-(1-methoxyimino-1-cyclohexyl-methyl)-phenoxymethyl]-3-methyl-phenyl}-4-methyl-1,4-dihydrotetrazol-5-one (hereinafter referred to as "Compound 66 of the present invention").

Compound 66 of the present invention

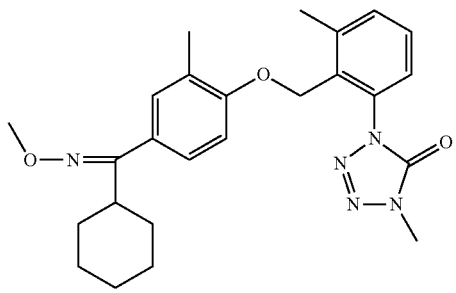 [SMILES: CON=C(c1ccc(OCc2c(C)cccc2-n2nnn(C)c2=O)c(C)c1)C1CCCCC1]

1H-NMR (CDCl3) δ: 7.46-7.38 (2H, m), 7.30-7.25 (1H, m), 7.17-7.10 (1H, m), 7.01 (0.5H, dd, J=8.24, 2.06 Hz), 6.98-6.96 (0.5H, m), 6.85 (0.5H, d, J=8.24 Hz), 6.80 (0.5H, d, J=8.24 Hz), 5.02 (2H, s), 3.91 (1.4H, s), 3.79 (1.6H, s), 3.65 (1.6H, s), 3.64 (1.4H, s), 3.23-3.11 (0.5H, m), 2.50 (1.6H, s), 2.49 (1.4H, s), 2.47-2.34 (0.5H, m), 2.11-2.08 (3H, m), 1.84-1.62 (5H, m), 1.48-1.24 (5H, m).

Production Example 67

The same reaction as that of Production Example 2 was carried out except that 2-methyl-4-(1-butoxyimino-ethyl)phenol described in Reference production example 62 was used in place of 2-methyl-4-(1-methoxyimino-ethyl)phenol in Production example 2 to obtain 1-{2-[2-methyl-4-(1-butoxyimino-ethyl)-phenoxymethyl]-3-methyl-phenyl}-4-methyl-1,4-dihydrotetrazol-5-one (hereinafter referred to as "Compound 67 of the present invention").

Compound 67 of the present invention

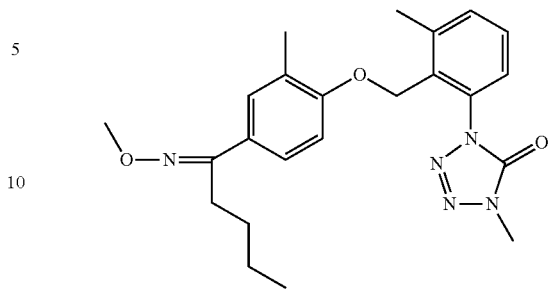

1H-NMR (CDCl3) δ: 7.44-7.35 (4H, m), 7.27 (1H, dd, J=7.21, 2.18 Hz), 6.81 (1H, d, J=8.47 Hz), 5.04 (2H, d, J=6.64 Hz), 3.94 (3H, s), 3.63 (3H, s), 2.69 (2H, t, J=7.79 Hz), 2.49 (3H, s), 2.10 (3H, s), 1.51-1.42 (2H, m), 1.41-1.31 (2H, m), 0.91 (3H, t, J=7.23 Hz).

Production Example 68

0.05 mL of hydrochloric acid (12 M) was added to a mixture of 0.35 g of 1-{2-(2-methyl-4-acetyl-phenoxymethyl)-3-methyl-phenyl}-4-methyl-1,4-dihydro-tetrazole-5-one described in Reference production example 65, 0.25 g of O-(2,3,4,5,6-pentafluorobenzyl)hydroxyamine hydrochloride, 4 mL of ethanol and the mixture was stirred at ambient temperature for 4 hr. Saturated sodium bicarbonate water was added to the reaction mixture and the mixture was extracted three times with chloroform and washed with saturated saline. The obtained solution was dried by sodium sulfate and filtered, and then, the filtrate was concentrated. The obtained residue was subjected to silica gel chromatograph to obtain 1-{2-[2-methyl-4-{1-(2,3,4,5,6-pentafluorobenzyloxy)imino-ethyl)-phenoxymethyl]-3-methylphenyl}-4-methyl-1,4-dihydrotetrazol-5-one (hereinafter referred to as "compound 68 of the present invention).

Compound 68 of the present invention

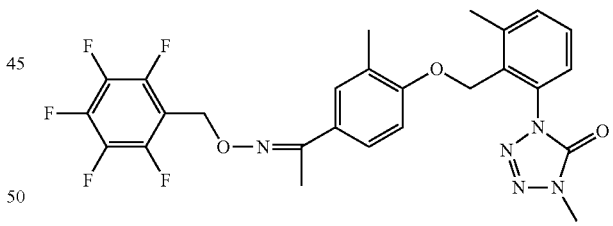

1H-NMR (CDCl3) δ: 7.45-7.36 (4H, m), 7.31-7.25 (1H, m), 6.80 (1H, d, J=8.47 Hz), 5.25 (2H, s), 5.04 (2H, s), 3.62 (3H, s), 2.49 (3H, s), 2.15 (3H, s), 2.09 (3H, s).

Production Example 69

The same reaction as that of Production Example 6 was carried out except that 2-methyl-4-(1-methoxyimino-1-phenyl-methyl)phenol described in Reference production example 36 was used in place of 2-methyl-4-(1-methoxyimino-ethyl)phenol in Production example 6 to obtain 1-{2-[2-methyl-4-(1-methoxyimino-1-phenyl-methyl)-phenoxymethyl]-3-methoxy-phenyl}-4-methyl-1,4-dihydrotetrazol-5-one (hereinafter referred to as "Compound 69 of the present invention").

Compound 69 of the present invention

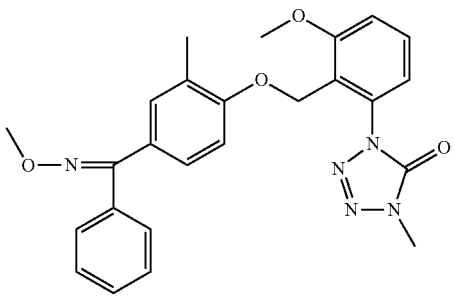 [SMILES: CON=C(c1ccccc1)c1ccc(OCc2c(OC)cccc2-n2nnn(C)c2=O)c(C)c1]

1H-NMR (CDCl3) δ: 7.50-7.28 (7H, m), 7.16 (0.5H, dd, J=8.47, 2.06 Hz), 7.11-7.05 (2.5H, m), 6.92 (0.4H, d, J=8.47 Hz), 6.78 (0.6H, d, J=8.70 Hz), 5.29 (0.8H, s), 5.28 (1.2H, s), 3.98 (1.3H, s), 3.93 (1.7H, s), 3.93 (1.3H, s), 3.92 (1.7H, s), 3.64 (1.3H, s), 3.61 (1.7H, s), 2.00 (1.3H, s), 1.96 (1.7H, s).

Production Example 70

The same reaction as that of Production Example 13 was carried out except that 2-methyl-4-(1-methoxyimino-1-phenyl-methyl)phenol described in Reference production example 36 was used in place of 2-methyl-4-(1-methoxyimino-ethyl)phenol in Production example 13 to obtain 1-{2-[2-methyl-4-(1-methoxyimino-1-phenyl-methyl)-phenoxy methyl]-3-cyclopropyl-phenyl}-4-methyl-1,4-dihydrotetrazol-5-one (hereinafter referred to as "Compound 70 of the present invention").

Compound 70 of the present invention

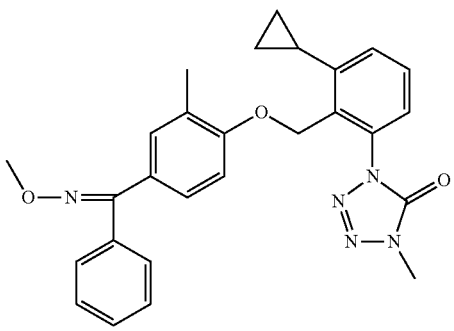 [SMILES: CON=C(c1ccccc1)c1ccc(OCc2c(C3CC3)cccc2-n2nnn(C)c2=O)c(C)c1]

1H-NMR (CDCl3) δ: 7.50-7.38 (3.5H, m), 7.37-7.31 (3H, m), 7.28-7.25 (2H, m), 7.22-7.19 (0.5H, m), 7.16-7.12 (1H, m), 6.93 (0.4H, d, J=8.47 Hz), 6.80 (0.6H, d, J=8.47 Hz), 5.28 (0.9H, s), 5.26 (1.1H, s), 3.99 (1.3H, s), 3.95 (1.7H, s), 3.65 (1.3H, s), 3.62 (1.7H, s), 2.20-2.08 (2.3H, m), 2.06 (1.7H, s), 1.03-0.95 (2H, m), 0.80-0.73 (2H, m).

Production Example 71

The same reaction as that of Production Example 68 was carried out except that O-(2-chlorobenzyl)hydroxylamine hydrochloride was used in place of O-phenylhydroxyamine hydrochloride in Production example 68 to obtain 1-{2-[1-(2-chlorobenzyloxy)imino-ethyl)-phenoxymethyl]-3-methyl-phenyl}-4-methyl-1,4-dihydrotetrazol-5-one (hereinafter referred to as "Compound 71 of the present invention").

Compound 71 of the present invention

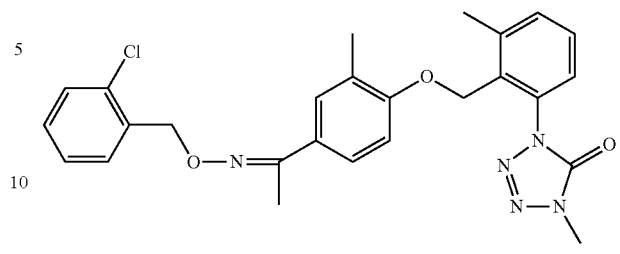

1H-NMR (CDCl3) δ: 7.47-7.36 (6H, m), 7.30-7.22 (3H, m), 6.80 (1H, d, J=8.47 Hz), 5.33 (2H, s), 5.05 (2H, s), 3.62 (3H, s), 2.49 (3H, s), 2.27 (3H, s), 2.09 (3H, s).

Production Example 72

The same reaction as that of Production Example 2 was carried out except that 2-methyl-4-{1-methoxyimino-1-(2-chlorophenyl)-methyl}phenol described in Reference production example 41 was used in place of 2-methyl-4-(1-methoxyimino-ethyl)phenol in Production example 2 to obtain 1-{2-[2-methyl-4-(1-methoxyimino-1-(2-chlorophenyl)-methyl)-phenoxymethyl]-3-methyl-phenyl}-4-methyl-1,4-dihydrotetrazol-5-one (hereinafter referred to as "Compound 72 of the present invention").

Compound 72 of the present invention

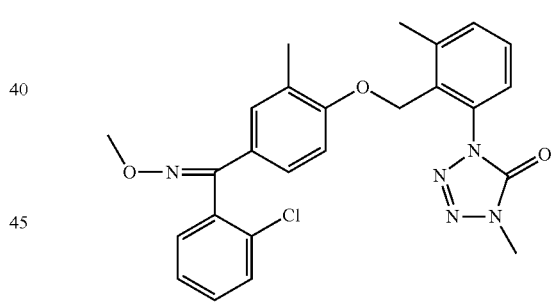

1H-NMR (CDCl3) δ: 7.50-7.46 (1H, m), 7.44-7.31 (5H, m), 7.28-7.25 (1H, m), 7.18-7.15 (1H, m), 7.09 (1H, dd, J=8.59, 2.19 Hz), 6.75 (1H, d, J=8.70 Hz), 5.03 (2H, s), 3.95 (3H, s), 3.62 (3H, s), 2.48 (3H, s), 2.07 (3H, s).

Production Example 73

The same reaction as that of Production Example 2 was carried out except that 2-methyl-4-(1-methoxyimino-1-(3-chlorophenyl)-methyl)phenol described in Reference production example 44 was used in place of 2-methyl-4-(1-methoxyimino-ethyl)phenol in Production example 2 to obtain 1-{2-[2-methyl-4-{1-methoxyimino-1-(3-chlorophenyl)-methyl}-phenoxymethyl]-3-methyl-phenyl}-4-methyl-1,4-dihydrotetrazol-5-one (hereinafter referred to as "Compound 73 of the present invention").

Compound 73 of the present invention

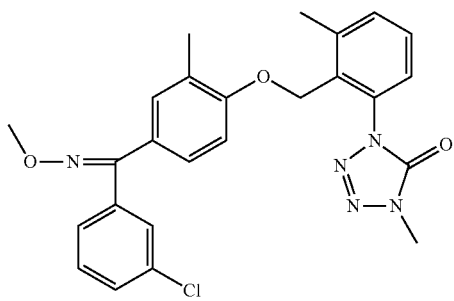 [SMILES: CON=C(c1cccc(Cl)c1)c1ccc(OCc2c(C)cccc2-n2nnn(C)c2=O)c(C)c1]

1H-NMR (CDCl3) δ: 7.50 (0.5H, t, J=1.72 Hz), 7.45-7.24 (6.5H, m), 7.21-7.10 (2H, m), 6.90 (0.5H, d, J=8.47 Hz), 6.76 (0.5H, d, J=8.47 Hz), 5.07 (1H, s), 5.04 (1H, s), 3.99 (1.5H, s), 3.95 (1.5H, s), 3.67 (1.5H, s), 3.64 (1.5H, s), 2.53 (1.5H, s), 2.49 (1.5H, s), 2.11 (1.5H, s), 2.08 (1.5H, s).

Production Example 74

The same reaction as that of Production Example 2 was carried out except that 2-methyl-4-{1-methoxyimino-1-(4-chlorophenyl)-methyl}phenol described in Reference production example 47 was used in place of 2-methyl-4-(1-methoxyimino-ethyl)phenol in Production example 2 to obtain 1-{2-[2-methyl-4-(1-methoxyimino-1-(4-chlorophenyl)-methyl)-phenoxymethyl]-3-methyl-phenyl}-4-methyl-1,4-dihydrotetrazol-5-one (hereinafter referred to as "Compound 74 of the present invention").

Compound 74 of the present invention

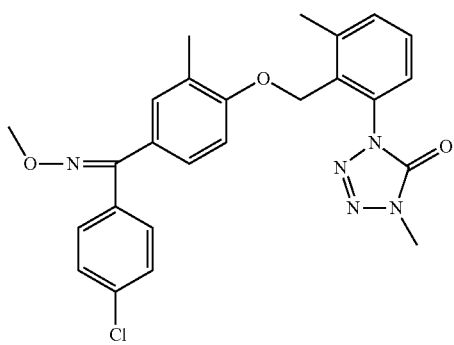 [SMILES: CON=C(c1ccc(Cl)cc1)c1ccc(OCc2c(C)cccc2-n2nnn(C)c2=O)c(C)c1]

1H-NMR (CDCl3) δ: 7.45-7.39 (4.0H, m), 7.32-7.26 (3.6H, m), 7.19-7.08 (1.4H, m), 6.89 (0.4H, d, J=8.47 Hz), 6.76 (0.6H, d, J=8.70 Hz), 5.06 (0.8H, s), 5.04 (1.2H, s), 3.98 (1.2H, s), 3.95 (1.8H, s), 3.67 (1.2H, s), 3.64 (1.8H, s), 2.53 (1.2H, s), 2.49 (1.8H, s), 2.10 (1.2H, s), 2.07 (1.8H, s).

Production Example 75

The same reaction as that of Production Example 68 was carried out except that O-(3-chlorobenzyl)hydroxylamine hydrochloride was used in place of O-phenylhydroxyamine hydrochloride in Production example 68 to obtain 1-{2-[1-(3-chlorobenzyloxy)imino-ethyl]-phenoxymethyl]-3methyl-phenyl}-4-methyl-1,4-dihydrotetrazol-5-one (hereinafter referred to as "Compound 75 of the present invention").

Compound 75 of the present invention

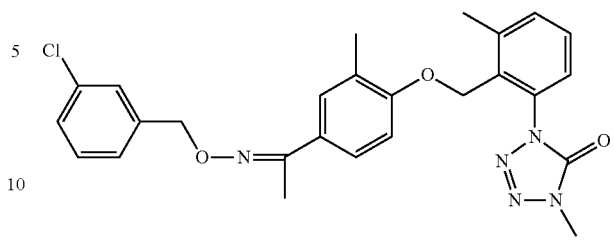

1H-NMR (CDCl3) δ: 7.45-7.37 (5H, m), 7.29-7.25 (4H, m), 6.81 (1H, d, J=8.47 Hz), 5.18 (2H, s), 5.05 (2H, s), 3.62 (3H, s), 2.49 (3H, s), 2.24 (3H, s), 2.10 (3H, s).

Production Example 76

The same reaction as that of Production Example 68 was carried out except that O-(4-chlorobenzyl)hydroxylamine hydrochloride was used in place of O-phenylhydroxyamine hydrochloride in Production example 68 to obtain 1-{2-[1-(4-chlorobenzyloxy)imino-ethyl]-phenoxymethyl]-3-methyl-phenyl]-4-methyl-1,4-dihydrotetrazol-5-one (hereinafter referred to as "Compound 76 of the present invention").

Compound 76 of the present invention

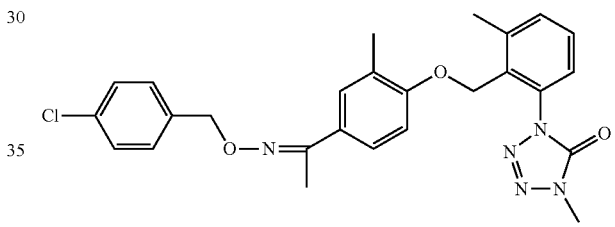

1H-NMR (CDCl3) δ: 7.43-7.28 (9H, m), 6.80 (1H, d, J=8.47 Hz), 5.17 (2H, s), 5.05 (2H, s), 3.62 (3H, s), 2.49 (3H, s), 2.22 (3H, s), 2.09 (3H, s).

Production Example 77

The same reaction as that of Production Example 68 was carried out except that O-(3-trifluoromethylbenzyl)hydroxylamine hydrochloride was used in place of O-phenylhydroxyamine hydrochloride in Production example 68 to obtain 1-{2-[1-(3-trifluoromethylbenzyloxy)imino-ethyl]-phenoxymethyl]-3-methyl-phenyl}-4-methyl-1,4-dihydrotetrazol-5-one (hereinafter referred to as "Compound 77 of the present invention").

Compound 77 of the present invention

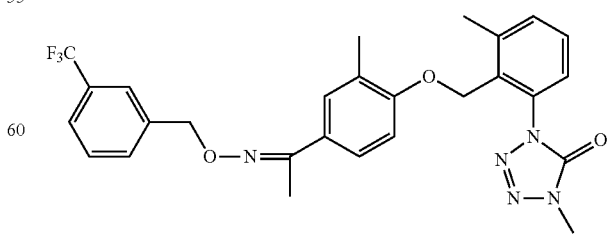

1H-NMR (CDCl3) δ: 7.67 (1H, s), 7.61-7.54 (2H, m), 7.49 (1H, d, J=7.6 Hz), 7.46-7.36 (4H, m), 7.29-7.26 (1H, m), 6.81 (1H, d, J=8.7 Hz), 5.25 (2H, s), 5.05 (2H, s), 3.62 (3H, s), 2.49 (3H, s), 2.24 (3H, s), 2.09 (3H, s).

Production Example 78

The same reaction as that of Production Example 2 was carried out except that 2-methyl-4-{1-methoxyimino-1-(3-methylphenyl)-methyl}phenol described in Reference production example 96 was used in place of 2-methyl-4-(1-methoxyimino-ethyl)phenol in Production example 2 to obtain 1-{2-[2-methyl-4-{1-methoxyimino-1-(3-methylphenyl)-methyl}-phenoxymethyl]-3-methyl-phenyl}-4-methyl-1,4-dihydrotetrazol-5-one (hereinafter referred to as "Compound 78 of the present invention").

Compound 78 of the present invention

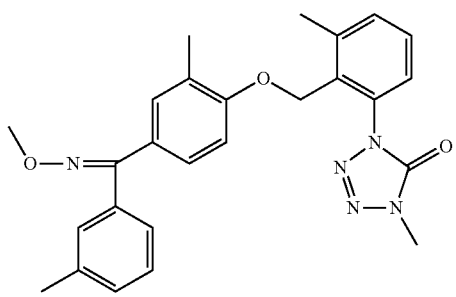 [SMILES: CON=C(c1cccc(C)c1)c1ccc(OCc2c(C)cccc2-n2nnn(C)c2=O)c(C)c1]

1H-NMR (CDCl3) δ: 7.46-7.37 (2.0H, m), 7.36-7.27 (3.0H, m), 7.23-7.14 (2.0H, m), 7.13-7.10 (2.0H, m), 6.88 (0.4H, d, J=8.5 Hz), 6.75 (0.6H, d, J=8.5 Hz), 5.06 (0.9H, s), 5.03 (1.1H, s), 3.98 (1.3H, s), 3.94 (1.7H, s), 3.66 (1.3H, s), 3.63 (1.7H, s), 2.52 (1.3H, s), 2.49 (1.7H, s), 2.37 (1.7H, s), 2.35 (1.3H, s), 2.09 (1.3H, s), 2.07 (1.7H, s).

Production Example 79

The same reaction as that of Production Example 2 was carried out except that 2-methyl-4-{1-methoxyimino-1-(3-methylphenyl)-methyl}phenol described in Reference production example 97 was used in place of 2-methyl-4-(1-methoxyimino-ethyl)phenol in Production example 2 to obtain 1-{2-[2-methyl-4-{1-methoxyimino-1-(3-methoxyphenyl)-methyl}-phenoxymethyl]-3-methyl-phenyl}-4-methyl-1,4-dihydrotetrazol-5-one (hereinafter referred to as "Compound 79 of the present invention").

Compound 79 of the present invention

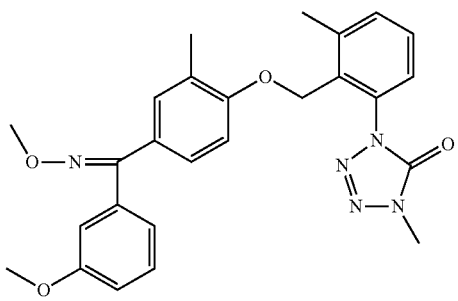 [SMILES: CON=C(c1cccc(OC)c1)c1ccc(OCc2c(C)cccc2-n2nnn(C)c2=O)c(C)c1]

1H-NMR (CDCl3) δ: 7.46-7.37 (2.0H, m), 7.36-7.27 (3.0H, m), 7.23-7.14 (2.0H, m), 7.13-7.10 (2.0H, m), 6.88 (0.4H, d, J=8.5 Hz), 6.75 (0.6H, d, J=8.5 Hz), 5.06 (0.9H, s), 5.03 (1.1H, s), 3.98 (1.3H, s), 3.94 (1.7H, s), 3.66 (1.3H, s), 3.63 (1.7H, s), 2.52 (1.3H, s), 2.49 (1.7H, s), 2.37 (1.7H, s), 2.35 (1.3H, s), 2.09 (1.3H, s), 2.07 (1.7H, s).

Production Example 80

The same reaction as that of Production Example 2 was carried out except that 2-cyano-4-(1-methoxyimino-ethyl)phenol described in Reference production example 100 was used in place of 2-methyl-4-(1-methoxyimino-ethyl)phenol in Production example 2 to obtain 1-{2-[2-methyl-4-{1-methoxyimino-ethyl}-phenoxymethyl]-3-methyl-phenyl}-4-methyl-1,4-dihydrotetrazol-5-one (hereinafter referred to as "Compound 80 of the present invention").

Compound 80 of the present invention

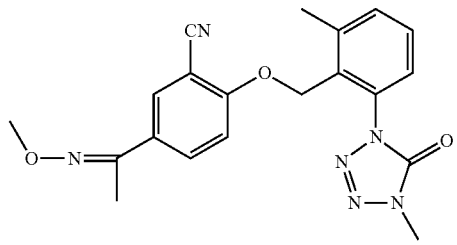 [SMILES: CON=C(C)c1ccc(OCc2c(C)cccc2-n2nnn(C)c2=O)c(C#N)c1]

1H-NMR (CDCl3) δ: 7.82 (1H, d, J=2.3 Hz), 7.76 (1H, dd, J=8.9, 2.3 Hz), 7.44-7.38 (2H, m), 7.30-7.26 (1H, m), 6.83 (1H, d, J=8.9 Hz), 5.27 (2H, s), 3.97 (3H, s), 3.71 (3H, s), 2.55 (3H, s), 2.15 (3H, s).

Next, reference production examples will be shown to explain the production of production intermediates of the compounds of the present invention.

Reference Production Example 1

1-(2-bromomethyl-3-fluorophenyl)-4-methyl-1,4-dihydrotetrazol-5-one was produced in the following steps (1) to (3).

<Step (1)>

21.9 g of anhydrous aluminum trichloride was added to 250 mL of N,N-dimethylformamide under ice cooling and the mixture was stirred for 15 min. 10.7 g of sodium azide was added to the mixture, which was then stirred for 15 min. Then, 22.5 g of 1-fluoro-3-isocyanate-2-methylbenzene was added to the reaction mixture, which was then stirred at 80° C. for 3.5 hr. After the reaction mixture was cooled, it was added in a mixture of 34 g of sodium nitrite, 2 L of water, and 500 g of ice with stirring. The mixture was made acidic by adding 10% hydrochloric acid and then extracted with ethyl acetate. The organic phase was washed with water and saturated saline, dried by magnesium sulfate anhydride, and then, concentrated under reduced pressure to obtain 27.5 g of 1-(2-methyl-3-fluorophenyl)-1,4-dihydrotetrazol-5-one.

1-(2-methyl-3-fluorophenyl)-1,4-dihydrotetrazol-5-one

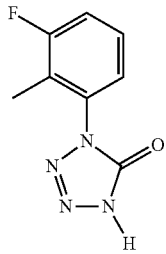

¹H-NMR (CDCl₃) δ: 12.93 (1H, s), 7.07-7.36 (3H, m), 2.21 (3H, s).

<Step (2)>

2.47 g of 55% sodium hydride was added under ice cooling to a mixture of 10.00 g of the above 1-(2-methyl-3-fluorophenyl)-1,4-dihydrotetrazol-5-one and 100 mL of N,N-dimethylformamide. The mixture was heated to ambient temperature and stirred for 1 hr. 3.5 mL of methyl iodide was added to the reaction mixture under ice cooling. The mixture was heated to ambient temperature and stirred for 14 hr. Water was added to the reaction mixture to extract the mixture with ethyl acetate. The organic phase was washed with 10% hydrochloric acid, water, and saturated saline, dried by magnesium sulfate anhydride, and concentrated under reduced pressure. The obtained residue was subjected to silica gel column chromatography to obtain 2.19 g of 1-(2-methyl-3-fluorophenyl)-4-methyl-1,4-dihydrotetrazol-5-one.

1-(2-methyl-3-fluorophenyl)-4-methyl-1,4-dihydrotetrazol-5-one

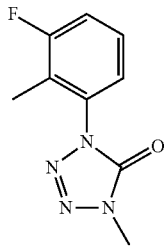

¹H-NMR (CDCl₃) δ: 7.29 (1H, dt, J=5.9, 8.3 Hz), 7.16-7.20 (2H, m), 3.70 (3H, s), 2.19 (3H, s).

<Step (3)>

A mixture of 2.19 g of the above 1-(2-methyl-3-fluorophenyl)-4-methyl-1,4-dihydrotetrazol-5-one, 0.52 g of 1,1'-azobis(cyclohexane-1-carbonitrile), 2.16 g of N-bromosuccinimide, and 40 mL of chlorobenzene was refluxed under heating with stirring for 5 hr. After the reaction mixture was cooled, water was poured into the mixture to extract the mixture with ethyl acetate. The organic phase was washed with water and saturated saline, dried by magnesium sulfate anhydride, and then, concentrated under reduced pressure. The obtained residue was subjected to silica gel column chromatography to obtain 2.36 g of 1-(2-bromomethyl-3-fluorophenyl)-4-methyl-1,4-dihydrotetrazol-5-one.

1-(2-bromomethyl-3-fluorophenyl)-4-methyl-1,4-dihydrotetrazol-5-one

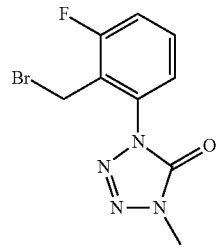 [SMILES: Cn1nnn(-c2cccc(F)c2CBr)c1=O]

¹H-NMR (CDCl₃) δ: 7.47 (1H, dt, J=5.9, 8.0 Hz), 7.23-7.30 (2H, m), 4.64 (2H, s), 3.75 (3H, s).

Reference Production Example 2

1-(2-bromomethyl-3-chlorophenyl)-4-methyl-1,4-dihydrotetrazol-5-one was produced in the following steps (1) to (3).

<Step (1)>

21.9 g of anhydrous aluminum trichloride was added to 250 mL of N,N-dimethylformamide under ice cooling and the mixture was stirred for 15 min. 10.7 g of sodium azide was added to the mixture, which was then stirred for 15 min. Then, 25.0 g of 1-chloro-3-isocyanate-2-methylbenzene was added to the reaction mixture, which was then heated at 80° C. for 5 hr. After the reaction mixture was cooled, it was added in a mixture of 35 g of sodium nitrite, 2 L of water, and 500 g of ice with stirring. The mixture was made acidic by adding 10% hydrochloric acid and then extracted with ethyl acetate. The organic phase was washed with water and saturated saline, dried by magnesium sulfate anhydride, and then, concentrated under reduced pressure to obtain 17.0 g of 1-(2-methyl-3-chlorophenyl)-1,4-dihydrotetrazol-5-one.

1-(2-methyl-3-chlorophenyl)-1,4-dihydrotetrazol-5-one

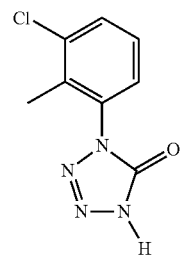

¹H-NMR (CDCl₃) δ: 13.08 (1H, s), 7.57 (1H, dd, J=6.8, 2.2 Hz), 7.28-7.36 (2H, m), 2.32 (3H, s).

<Step (2)>

2.30 g of 55% sodium hydride was added under ice cooling to a mixture of 10.00 g of the above 1-(2-methyl-3-chlorophenyl)-1,4-dihydrotetrazol-5-one and 100 mL of N,N-dimethylformamide. The mixture was heated to ambient temperature and stirred for 1 hr. 3.2 mL of methyl iodide was added to the reaction mixture under ice cooling. The mixture was heated to ambient temperature and stirred for 14 hr. Water was added to the reaction mixture to extract the mixture with ethyl acetate. The organic phase was washed with 10% hydrochloric acid, water, and saturated saline, dried by magnesium sulfate anhydride, and concentrated under reduced pressure. The obtained residue was subjected to silica gel column chromatography to obtain 1.56 g of 1-(2-methyl-3-chlorophenyl)-4-methyl-1,4-dihydrotetrazol-5-one.

1-(2-methyl-3-chlorophenyl)-4-methyl-1,4-dihydrotetrazol-5-one

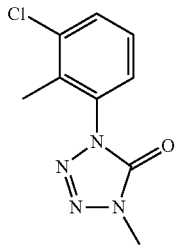

$^1$H-NMR (CDCl$_3$) δ: 7.52 (1H, dd, J=2.7, 6.8 Hz), 7.28 (1H, d, J=7.1 Hz), 7.27 (1H, d, J=2.7 Hz), 3.73 (3H, s), 2.30 (3H, s).

<Step (3)>

A mixture of 1.56 g of the above 1-(2-methyl-3-chlorophenyl)-4-methyl-1,4-dihydrotetrazol-5-one, 0.34 g of 1,1'-azobis(cyclohexane-1-carbonitrile), 1.42 g of N-bromosuccinimide, and 30 mL of chlorobenzene was refluxed under heating with stirring for 5 hr. After the reaction mixture was cooled, water was poured into the mixture to extract the mixture with ethyl acetate. The organic phase was washed with water and saturated saline, dried by magnesium sulfate anhydride, and then, concentrated under reduced pressure. The obtained residue was subjected to silica gel column chromatography to obtain 1.94 g of 1-(2-bromomethyl-3-chlorophenyl)-4-methyl-1,4-dihydrotetrazol-5-one.

1-(2-bromomethyl-3-chlorophenyl)-4-methyl-1,4-dihydrotetrazol-5-one

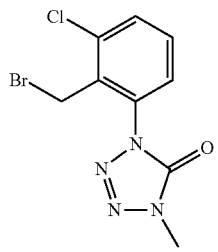 [SMILES: Cn1nnn(-c2cccc(Cl)c2CBr)c1=O]

$^1$H-NMR (CDCl$_3$) δ: 7.58 (1H, dd, J=1.2, 8.1 Hz), 7.43 (1H, t, J=8.1 Hz), 7.35 (1H, dd, J=1.2, 8.1 Hz), 4.69 (2H, s), 3.76 (3H, s).

Reference Production Example 3

A mixture of 21.5 g of 3-chloro-2-methylbenzoic acid, 17.6 g of oxalyl dichloride, about 50 mg of N,N-dimethylformamide, and 300 mL of tetrahydrofuran was stirred at 25° C. for 1 hr. The reaction mixture was concentrated under reduced pressure to obtain 3-chloro-2-methylbenzoic acid chloride.

A mixture of 33.6 g of aluminum chloride, 49.2 g of sodium azide, and 100 mL of tetrahydrofuran was refluxed under heating with stirring for 2 hr. After the reaction mixture was ice-cooled, a mixture of 3-chloro-2-methylbenzoic acid chloride, and 100 mL of tetrahydrofuran was added to the reaction mixture, which was then refluxed under heating with stirring for 10 hr. After the reaction mixture was cooled, it was added in a mixture of 75.6 g of sodium nitrite and 500 mL of water with stirring. The mixture was made acidic by adding concentrated hydrochloric acid and then, extracted with ethyl acetate. After the organic phase was dried by sodium sulfate anhydride, it was concentrated under reduced pressure to obtain 1-(2-methyl-3-chlorophenyl)-1,4-dihydrotetrazol-5-one.

A mixture of the above 1-(2-methyl-3-chlorophenyl)-1,4-dihydrotetrazol-5-one, 57.5 g of potassium carbonate, 19.1 g of dimethylsulfuric acid, and 150 mL of N,N-dimethylformamide was stirred at 25° C. for 1 hr. Saturated sodium bicarbonate water was added to the reaction mixture and the mixture was extracted with ethyl acetate. The organic phase was washed with saturated sodium bicarbonate water and then dried by sodium sulfate anhydride.

The residue was concentrated under reduced pressure to obtain 21.6 g of 1-(2-methyl-3-chlorophenyl)-4-methyl-1,4-dihydrotetrazol-5-one.

5.00 g of 3-amino-1-chloro-2-methylbenzene was added dropwise to a mixture of 30 mL of methyl chloroformate and 50 mL of tetrahydrofuran under ice cooling and the mixture was stirred at 25° C. for 0.5 hr. Water was added to the reaction mixture to extract the mixture with ethyl acetate. The organic phase was washed with saturated sodium bicarbonate water and dried by sodium sulfate anhydride. After the mixture was concentrated under reduced pressure, 5.80 g of 1-chloro-2-methyl-3-methoxycarbonylaminobenzene was obtained.

A mixture of 5.80 g of 1-chloro-2-methyl-3-methoxycarbonylaminobenzene, 7.53 g of phosphorous pentachloride, and 50 mL of chlorobenzene was refluxed under heating with stirring for 1 hr. After the reaction mixture was concentrated under reduced pressure, 1-chloro-3-isocyanate-2-methyl-benzene was obtained.

A mixture of 4.71 g of aluminum chloride, 6.89 g of sodium azide, and 100 mL of tetrahydrofuran was refluxed under heating with stirring for 1 hr. After the reaction mixture was ice-cooled, a mixture of 1-chloro-3-isocyanate-2-methyl-benzene, and 10 mL of tetrahydrofuran was added to the reaction mixture, which was then refluxed under heating with stirring for 5 hr. After the reaction mixture was cooled, it was added in a mixture of 10.59 g of sodium nitrite and 300 mL of water with stirring. The mixture was made acidic by adding concentrated hydrochloric acid and then, extracted with ethyl acetate. After the organic phase was dried by sodium sulfate anhydride, it was concentrated under reduced pressure to obtain 1-(2-methyl-3-chlorophenyl)-1,4-dihydrotetrazol-5-one.

A mixture of 1-(2-methyl-3-chlorophenyl)-1,4-dihydrotetrazol-5-one, 16.11 g of potassium carbonate, 5.34 g of dimethylsulfuric acid, and 150 mL of N, N-dimethylformamide was stirred at 25° C. for 1 hr. Saturated sodium bicarbonate water was added to the reaction mixture and the mixture was extracted with ethyl acetate. The organic phase was washed with saturated sodium bicarbonate water and then dried by sodium sulfate anhydride. The residue was concentrated under reduced pressure to obtain 4.80 g of 1-(2-methyl-3-chlorophenyl)-4-methyl-1,4-dihydrotetrazol-5-one.

Reference Production Example 5

1-(2-bromomethyl-3-bromophenyl)-4-methyl-1,4-dihydrotetrazol-5-one was produced in the following steps (1) to (4).

<Step (1)>

A mixture of 25.0 g of 1-bromo-2-methyl-3-aminobenzene, 60.0 g of triphosgene, and 400 mL of toluene was refluxed under heating with stirring for 3 hr. The reaction mixture which was allowed to cool was concentrated under reduced pressure to obtain 30.3 g of 1-bromo-3-isocyanate-2-methylbenzene.

1-bromo-3-isocyanate-2-methylbenzene

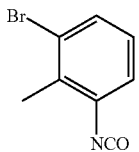

$^1$H-NMR (CDCl$_3$) δ: 7.39 (1H, dd, J=1.5, 7.7 Hz), 7.05 (1H, dd, J=1.7, 8.0 Hz), 7.00 (1H, dt, J=0.5, 8.0 Hz), 2.42 (3H, s).

<Step (2)>

19.7 g of aluminum trichloride anhydride was added to 220 mL of N,N-dimethylformamide under ice cooling and the mixture was stirred for 15 min. 9.6 g of sodium azide was added to the mixture, which was stirred for 15 min and then, 30.3 g of the above 1-bromo-3-isocyanate-2-methylbenzene was added to the mixture and heated at 80° C. for 5 hr. After the reaction mixture was cooled, the reaction mixture was added in a mixture of 33 g of sodium nitrite, 2 L of water, and 500 g of ice with stirring. The mixture was made acidic by adding 10% hydrochloric acid and then extracted with ethyl acetate. The organic phase was washed with 10% hydrochloric acid, water, and saturated saline, dried by magnesium sulfate anhydride, and concentrated under reduced pressure to obtain 31.4 g of 1-(2-methyl-3-bromophenyl)-1,4-dihydrotetrazol-5-one.

1-(2-methyl-3-bromophenyl)-1,4-dihydrotetrazol-5-one

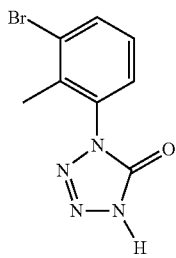

$^1$H-NMR (DMSO-d$_6$) δ: 14.72 (1H, s), 7.82 (1H, dd, J=8.0, 1.0 Hz), 7.49 (1H, dd, J=8.2, 1.1 Hz), 7.34 (1H, t, J=7.2 Hz), 2.22 (3H, s).

<Step (3)>

5.90 g of 60% sodium hydride was added under ice cooling to a mixture of 31.40 g of the above 1-(2-methyl-3-bromophenyl)-1,4-dihydrotetrazol-5-one and 250 mL of N,N-dimethylformamide. The mixture was heated to ambient temperature and stirred for 1 hr. 8.4 mL of methyl iodide was added to the reaction mixture under ice cooling. The mixture was heated to ambient temperature and stirred for 14 hr. Water was added to the reaction mixture to extract the mixture with ethyl acetate. The organic phase was washed with 10% hydrochloric acid, water, and saturated saline, dried by magnesium sulfate anhydride, and concentrated under reduced pressure. The obtained residue was subjected to silica gel column chromatography to obtain 8.47 g of 1-(2-methyl-3-bromophenyl)-4-methyl-1,4-dihydrotetrazol-5-one.

1-(2-methyl-3-bromophenyl)-4-methyl-1,4-dihydrotetrazol-5-one

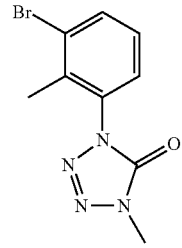

$^1$H-NMR (CDCl$_3$) δ: 7.71 (1H, dd, J=1.2, 8.3 Hz), 7.30 (1H, dd, J=1.0, 8.0 Hz), 7.21 (1H, dt, J=0.5, 7.8 Hz), 3.73 (3H, s), 2.33 (3H, s).

<Step (4)>

A mixture of 8.47 g of the above 1-(2-methyl-3-bromophenyl)-4-methyl-1,4-dihydrotetrazol-5-one, 1.54 g of 1,1'-azobis(cyclohexane-1-carbonitrile), 6.44 g of N-bromosuccinimide, and 125 mL of chlorobenzene was refluxed under heating with stirring for 5 hr. After the reaction mixture was cooled, water was poured into the mixture to extract the mixture with ethyl acetate. The organic phase was washed with water and saturated saline, dried by magnesium sulfate anhydride, and then, concentrated under reduced pressure. The obtained residue was subjected to silica gel column chromatography to obtain 7.52 g of 1-(2-bromomethyl-3-bromophenyl)-4-methyl-1,4-dihydrotetrazol-5-one.

1-(2-bromomethyl-3-bromophenyl)-4-methyl-1,4-dihydrotetrazol-5-one

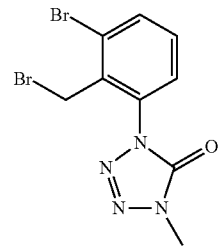

$^1$H-NMR (CDCl$_3$) δ: 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Production Example 6

A mixture of 146.0 g of 3-bromo-2-methylbenzoic acid, 94.8 g of oxalyl dichloride, about 15 mg of N,N-dimethylformamide, and 500 mL of tetrahydrofuran was stirred at 25° C. for 1 hr. The reaction mixture was concentrated under reduced pressure to obtain 3-bromo-2-methylbenzoic acid chloride.

A mixture of 181.0 g of aluminum chloride, 265.0 g of sodium azide, and 300 mL of tetrahydrofuran was refluxed under heating with stirring for 2 hr. After the reaction mixture was ice-cooled, a mixture of 3-bromo-2-methylbenzoic acid chloride, and 200 mL of tetrahydrofuran was added to the reaction mixture, which was then refluxed under heating with stirring for 10 hr. After the reaction mixture was cooled, it was added in a mixture of 407 g of sodium nitrite and 1500 mL of water with stirring. The mixture was made acidic by adding concentrated hydrochloric acid and then, extracted with ethyl acetate. After the organic phase was dried by sodium sulfate anhydride, it was concentrated under reduced pressure to obtain 1-(2-methyl-3-bromophenyl)-1,4-dihydrotetrazol-5-one.

A mixture of the above 1-(2-methyl-3-bromophenyl)-1,4-dihydrotetrazol-5-one, 310.0 g of potassium carbonate, 103.0 g of dimethylsulfuric acid, and 500 mL of N,N-dimethylformamide was stirred at 25° C. for 1 hr. Saturated sodium bicarbonate water was added to the reaction mixture and the mixture was extracted with ethyl acetate. The organic phase was washed with saturated sodium bicarbonate water and then dried by sodium sulfate anhydride. The residue was concentrated under reduced pressure to obtain 142.0 g of 1-(2-methyl-3-bromophenyl)-4-methyl-1,4-dihydrotetrazol-5-one.

Reference Production Example 7

1-(2-bromomethyl-3-iodophenyl)-4-methyl-1,4-dihydro tetrazol-5-one was produced in the following steps (1) and (2).
<Step (1)>
A mixture of 10.00 g of 3-iodo-2-methylbenzoic acid, 5.33 g of oxalyl dichloride, 5 drops of N,N-dimethylformamide, and 200 mL of tetrahydrofuran was stirred at 25° C. for 1 hr. The reaction mixture was concentrated under reduced pressure to obtain 3-iodo-2-methylbenzoic acid chloride.

A mixture of 10.20 g of aluminum trichloride, 14.90 g of sodium azide, and 100 mL of tetrahydrofuran was refluxed under heating with stirring for 2 hr. After the reaction mixture was ice-cooled, a mixture of 3-iodo-2-methylbenzoic acid chloride, and 100 mL of tetrahydrofuran was added to the reaction mixture, which was then refluxed under heating with stirring for 10 hr. After the reaction mixture was cooled, it was added in a mixture of 22.90 g of sodium nitrite and 200 mL of water with stirring. The mixture was made acidic by adding concentrated hydrochloric acid and then, extracted with ethyl acetate. After the organic phase was dried by sodium sulfate anhydride, it was concentrated under reduced pressure to obtain 1-(2-methyl-3-iodophenyl)-1,4-dihydrotetrazol-5-one.

A mixture of the above 1-(2-methyl-3-iodophenyl)-1,4-dihydrotetrazol-5-one, 17.40 g of potassium carbonate, 5.78 g of dimethylsulfuric acid, and 150 mL of N, N-dimethylformamide was stirred at 25° C. for 1 hr. Saturated sodium bicarbonate water was added to the reaction mixture and the mixture was extracted with ethyl acetate. The organic phase was washed with saturated sodium bicarbonate water and then dried by sodium sulfate anhydride. The residue was concentrated under reduced pressure to obtain 8.10 g of 1-(2-methyl-3-iodophenyl)-4-methyl-1,4-dihydrotetrazol-5-one.

1-(2-methyl-3-iodophenyl)-4-methyl-1,4-dihydrotetrazol-5-one

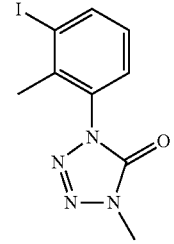

$^1$H-NMR (CDCl$_3$) δ: 2.37 (3H, s), 3.72 (3H, s), 7.04 (1H, t, J=8.0 Hz), 7.32 (1H, d, J=7.7 Hz), 7.99 (1H, d, 8.0 Hz).
<Step (2)>
A mixture of 8.10 g of the above 1-(2-methyl-3-iodophenyl)-4-methyl-1,4-dihydrotetrazol-5-one, 1.25 g of 1,1'-azobis(cyclohexane-1-carbonitrile), 5.24 g of N-bromosuccinimide, and 100 mL of chlorobenzene was refluxed under heating with stirring for 5 hr. After the reaction mixture was cooled, water was poured into the reaction mixture to extract the mixture with ethyl acetate. The organic phase was washed with water and saturated saline, dried by magnesium sulfate anhydride, and then, concentrated under reduced pressure. The obtained residue was subjected to silica gel column chromatography to obtain 3.11 g of 1-(2-bromomethyl-3-iodophenyl)-4-methyl-1,4-dihydrotetrazol-5-one.

1-(2-bromomethyl-3-iodophenyl)-4-methyl-1,4-dihydrotetrazol-5-one

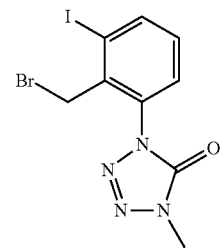

$^1$H-NMR (CDCl$_3$) δ: 3.75 (3H, s), 4.71 (2H, s), 7.17 (1H, t, J=8.0 Hz), 7.39 (1H, d, J=8.0 Hz), 8.04 (1H, J=8.0 Hz).

Reference Production Example 8

1-(2-bromomethyl-3-methoxyphenyl)-4-methyl-1,4-dihydrotetrazol-5-one was produced in the following steps (1) to (4).
<Step (1)>
A mixture of 15.0 g of 3-amino-1-methoxy-2-methylbenzene, 48.7 g of triphosgene, and 350 mL of toluene was refluxed under heating with stirring for 3 hr. The reaction mixture which was allowed to cool was concentrated under reduced pressure to obtain 17.0 g of 1-methoxy-3-isocyanate-2-methylbenzene.

1-methoxy-3-isocyanate-2-methylbenzene

¹H-NMR (CDCl₃) δ: 2.19 (3H, s), 3.82 (3H, s), 6.69 (1H, d, J=8.2 Hz), 6.72 (1H, dd, J=0.5, 8.0 Hz), 7.09 (1H, t, J=8.2 Hz).

<Step (2)>

16.0 g of aluminum trichloride anhydride was added to 180 mL of N,N-dimethylformamide under ice cooling and the mixture was stirred for 15 min. 7.8 g of sodium azide was added to the mixture, which was stirred for 15 min and then, 17.0 g of the above 1-methoxy-3-isocyanate-2-methylbenzene was added to the mixture and heated at 80° C. for 4.5 hr. After the reaction mixture was cooled, the reaction mixture was added in a mixture of 25 g of sodium nitrite, 2 L of water, and 500 g of ice with stirring. The mixture was made acidic by adding 10% hydrochloric acid and then extracted with ethyl acetate. The organic phase was washed with water and saturated saline, dried by magnesium sulfate anhydride, and concentrated under reduced pressure, to obtain 16.2 g of 1-(2-methyl-3-methoxyphenyl)-1,4-dihydrotetrazol-5-one.

1-(2-methyl-3-methoxyphenyl)-1,4-dihydrotetrazol-5-one

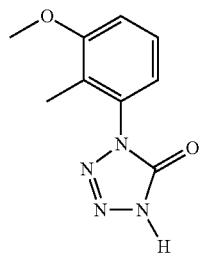

¹H-NMR (DMSO-d₆) δ: 1.99 (3H, s), 3.87 (3H, s), 7.01 (1H, d, J=8.1 Hz), 7.17 (1H, d, J=8.1 Hz), 7.36 (1H, t, J=8.3 Hz), 14.63 (1H, s).

<Step (3)>

2.47 g of 55% sodium hydride was added under ice cooling to a mixture of 10.00 g of the above 1-(2-methyl-3-methoxyphenyl)-1,4-dihydrotetrazol-5-one and 100 mL of N,N-dimethylformamide. The mixture was heated to ambient temperature and stirred for 1 hr. 3.5 mL of methyl iodide was added to the reaction mixture under ice cooling. The mixture was heated to ambient temperature and stirred for 14 hr. Water was added to the reaction mixture to extract the mixture with ethyl acetate. The organic phase was washed with 10% hydrochloric acid, water, and saturated saline, dried by magnesium sulfate anhydride, and concentrated under reduced pressure. The obtained residue was subjected to silica gel column chromatography to obtain 2.19 g of 1-(2-methyl-3-methoxyphenyl)-4-methyl-1,4-dihydrotetrazol-5-one.

1-(2-methyl-3-methoxyphenyl)-4-methyl-1,4-dihydrotetrazol-5-one

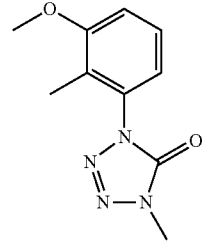 [SMILES: COc1cccc(-n2nnn(C)c2=O)c1C]

¹H-NMR (CDCl₃) δ: 2.11 (3H, s), 3.72 (3H, s), 3.88 (3H, s), 6.95 (1H, d, J=8.2 Hz), 6.98 (1H, d, J=8.5 Hz), 7.29 (1H, t, J=8.2 Hz)

<Step (4)>

A mixture of 2.19 g of the above 1-(2-methyl-3-methoxyphenyl)-4-methyl-1,4-dihydrotetrazol-5-one, 0.52 g of 1,1'-azobis(cyclohexane-1-carbonitrile), 2.16 g of N-bromosuccinimide, and 40 mL of chlorobenzene was refluxed under heating with stirring for 5 hr. After the reaction mixture was cooled, water was poured into the mixture to extract the mixture with ethyl acetate. The organic phase was washed with water and saturated saline, dried by magnesium sulfate anhydride, and then, concentrated under reduced pressure. The obtained residue was subjected to silica gel column chromatography to obtain 2.36 g of 1-(2-bromomethyl-3-methoxyphenyl)-4-methyl-1,4-dihydrotetrazol-5-one.

1-(2-bromomethyl-3-methoxyphenyl)-4-methyl-1,4-dihydrotetrazol-5-one

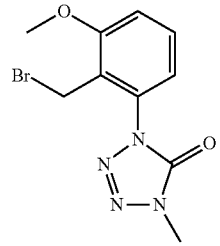

¹H-NMR (CDCl₃) δ: 3.74 (3H, s), 3.96 (3H, s), 4.93 (2H, s), 7.02 (1H, dd, J=1.0, 8.5 Hz), 7.04 (1H, d, J=9.0 Hz), 7.43 (1H, t, J=8.1 Hz).

Reference Production Example 9

1-(2-bromomethyl-3-trifluoromethylphenyl)-4-methyl-1,4-dihydrotetrazol-5-one was produced in the following steps (1) and (2).

<Step (1)>

A mixture of 5.00 g of 3-trifluoromethyl-2-methylbenzoic acid, 3.42 g of oxalyl dichloride, about 50 mg of N,N- dimethylformamide, and 200 mL of tetrahydrofuran was stirred at 25° C. for 1 hr. The reaction mixture was concentrated under reduced pressure to obtain 3-trifluoromethyl-2-methylbenzoic acid chloride.

A mixture of 6.53 g of aluminum trichloride, 9.55 g of sodium azide, and 100 mL of tetrahydrofuran was refluxed under heating with stirring for 2 hr. After the reaction mixture was ice-cooled, a mixture of the above 3-trifluoromethyl-2-methylbenzoic acid chloride and 100 mL of tetrahydrofuran was added to the reaction mixture, which was then refluxed under heating with stirring for 10 hr. After the reaction mixture was cooled, it was added in a mixture of 14.7 g of sodium nitrite and 200 mL of water with stirring. The mixture was made acidic by adding concentrated hydrochloric acid and then, extracted with ethyl acetate. After the organic phase was dried by sodium sulfate anhydride, it was concentrated under reduced pressure to obtain a crude product of 1-(2-methyl-3-trifluoromethylphenyl)-1,4-dihydrotetrazol-5-one.

A mixture of the above crude product of 1-(2-methyl-3-trifluoromethylphenyl)-1,4-dihydrotetrazol-5-one, 11.20 g of potassium carbonate, 3.71 g of dimethylsulfuric acid, and 150 mL of N,N-dimethylformamide was stirred at 25° C. for 1 hr. Saturated sodium bicarbonate water was added to the reaction mixture and the mixture was extracted with ethyl acetate. The organic phase was washed with saturated sodium bicarbonate water and then dried by sodium sulfate anhydride. The residue was concentrated under reduced pressure to obtain 5.13 g of 1-(2-methyl-3-trifluoromethylphenyl)-4-methyl-1,4-dihydro tetrazol-5-one.

1-(2-methyl-3-trifluoromethylphenyl)-4-methyl-1,4-dihydro tetrazol-5-one

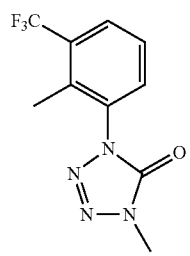

$^1$H-NMR (CDCl$_3$) δ: 2.42 (3H, s), 3.75 (3H, s), 7.52 (1H, t, J=8.2 Hz), 7.62 (1H, dd, J=1.2, 7.7 Hz), 8.02 (1H, dd, J=1.2, 8.2 Hz).

<Step (2)>

A mixture of 1.00 g of the above 1-(2-methyl-3-trifluoromethylphenyl)-4-methyl-1,4-dihydro tetrazol-5-one, 0.38 g of 1,1'-azobis(cyclohexane-1-carbonitrile), 0.79 g of N-bromosuccinimide, and 30 mL of chlorobenzene was refluxed under heating with stirring for 5 hr. After the reaction mixture was cooled, water was poured into the reaction mixture to extract the mixture with ethyl acetate. The organic phase was washed with water and saturated saline, dried by magnesium sulfate anhydride, and then, concentrated under reduced pressure. The obtained residue was subjected to silica gel column chromatography to obtain 1.21 g of 1-(2-bromomethyl-3-trifluoromethylphenyl)-4-methyl-1,4-dihydrotetrazol-5-one.

1-(2-bromomethyl-3-trifluoromethylphenyl)-4-methyl-1,4-dihydrotetrazol-5-one

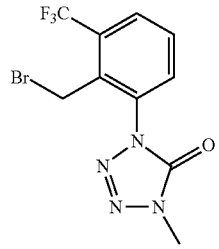

$^1$H-NMR (CDCl$_3$) δ: 3.77 (3H, s), 4.75 (2H, s), 7.62 (1H, d, J=5.5 Hz), 7.63 (1H, d, J=3.4 Hz), 7.85 (1H, dd, J=3.6, 5.8 Hz).

Reference Production Example 10

1-(2-bromomethyl-3-nitrophenyl)-4-methyl-1,4-dihydrotetrazol-5-one was produced in the following steps (1) and (2).

<Step (1)>

A mixture of 5.0 g of 3-nitro-2-methylbenzoic acid, 3.9 g of oxalyl dichloride, about 50 mg of N,N-dimethylformamide, and 200 mL of tetrahydrofuran was stirred at 25° C. for 1 hr. The reaction mixture was concentrated under reduced pressure to obtain 3-nitro-2-methylbenzoic acid chloride.

A mixture of 7.4 g of aluminum trichloride, 11.0 g of sodium azide, and 100 mL of tetrahydrofuran was refluxed under heating with stirring for 2 hr. After the reaction mixture was ice-cooled, a mixture of the above 3-nitro-2-methylbenzoic acid chloride and 100 mL of tetrahydrofuran was added to the reaction mixture, which was then refluxed under heating with stirring for 10 hr. After the reaction mixture was cooled, it was added in a mixture of 16.6 g of sodium nitrite and 200 mL of water with stirring. The mixture was made acidic by adding concentrated hydrochloric acid and then, extracted with ethyl acetate. After the organic phase was dried by sodium sulfate anhydride, it was concentrated under reduced pressure to obtain 1-(2-methyl-3-nitrophenyl)-1,4-dihydrotetrazol-5-one.

A mixture of the above 1-(2-methyl-3-nitrophenyl)-1,4-dihydrotetrazol-5-one, 12.6 g of potassium carbonate, 13.8 g of dimethylsulfuric acid, and 150 mL of N,N-dimethylformamide was stirred at 25° C. for 1 hr. Saturated sodium bicarbonate water was added to the reaction mixture and the mixture was extracted with ethyl acetate. The organic phase was washed with saturated sodium bicarbonate water and then dried by sodium sulfate anhydride. The residue was concentrated under reduced pressure to obtain 5.3 g of 1-(2-methyl-3-nitrophenyl)-4-methyl-1,4-dihydrotetrazol-5-one.

1-(2-methyl-3-nitrophenyl)-4-methyl-1,4-dihydrotetrazol-5-one

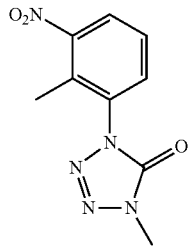 [SMILES: Cc1c(-n2nnn(C)c2=O)cccc1[N+](=O)[O-]]

$^1$H-NMR (CDCl$_3$) δ: 2.42 (3H, s), 3.75 (3H, s), 7.52 (1H, t, J=8.2 Hz), 7.62 (1H, dd, J=1.2, 7.7 Hz), 8.02 (1H, d, J=1.2, 8.2 Hz).

<Step (2)>

A mixture of 1.00 g of the above 1-(2-methyl-3-nitrophenyl)-4-methyl-1,4-dihydrotetrazol-5-one, 0.42 g of 1,1'-azobis(cyclohexane-1-carbonitrile), 0.87 g of N-bromosuccinimide, and 30 mL of chlorobenzene was refluxed under heating with stirring for 5 hr. After the resulting mixture was cooled, water was poured into the reaction mixture to extract the mixture with ethyl acetate. The organic phase was washed with water and saturated sodium bicarbonate, dried by magnesium sulfate anhydride, and then, concentrated under reduced pressure. The obtained residue was subjected to silica gel column chromatography to obtain 1.00 g of 1-(2-bromomethyl-3-nitrophenyl)-4-methyl-1,4-dihydrotetrazol-5-one.

1-(2-bromomethyl-3-nitrophenyl)-4-methyl-1,4-dihydrotetrazol-5-one

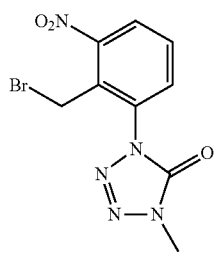

$^1$H-NMR (CDCl$_3$) δ: 3.72 (3H, s), 5.63 (2H, s), 7.61 (1H, t, J=8.0 Hz), 7.70 (1H, d, J=8.1 Hz), 7.97 (1H, d, J=8.1 Hz).

Reference Production Example 11

1-(2-bromomethyl-3-methylphenyl)-4-methyl-1,4-dihydrotetrazol-5-one was produced in the following steps (1) to (3).

<Step (1)>

A mixture of 45.0 g of the above 1-(2-bromomethyl-3-bromophenyl)-4-methyl-1,4-dihydrotetrazol-5-one described in Reference production example 5, 37.4 g of sodium methoxide, and 600 mL of tetrahydrofuran was stirred at 25° C. for 3 hr. Saturated sodium bicarbonate water was poured into the reaction mixture, which was then extracted with ethyl acetate. The organic phase was washed with saturated sodium bicarbonate water and dried by sodium sulfate anhydride. The residue was concentrated under reduced pressure to obtain 1-(2-methoxymethyl-3-bromophenyl)-4-methyl-1,4-dihydrotetrazol-5-one.

1-(2-methoxymethyl-3-bromophenyl)-4-methyl-1,4-dihydrotetrazol-5-one

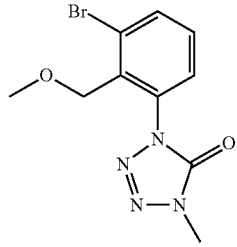 [SMILES: COCc1c(Br)cccc1-n1nnn(C)c1=O]

$^1$H-NMR (CDCl$_3$) δ: 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

<Step (2)>

A mixture of 23.2 g of the obtained 1-(2-methoxymethyl-3-bromophenyl)-4-methyl-1,4-dihydrotetrazol-5-one, 23.2 g of methylboronic acid, 66.7 g of cesium fluoride, 10.6 g of a dichlorometnane adduct of [1,1']-bis(diphenylphosphino)ferrocene]palladium (II) dichloride, and 500 mL of dioxane was stirred at 90° C. for 5.5 hr. After the resulting mixture was cooled, it was filtered and the filtrate was concentrated under reduced pressure. The obtained residue was subjected to silica gel column chromatography to obtain 1-(2-methoxymethyl-3-methylphenyl)-4-methyl-1,4-dihydrotetrazol-5-one.

1-(2-methoxymethyl-3-methylphenyl)-4-methyl-1,4-dihydrotetrazol-5-one

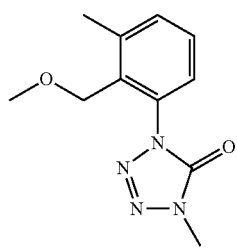 [SMILES: COCc1c(C)cccc1-n1nnn(C)c1=O]

$^1$H-NMR (CDCl$_3$) δ: 2.48 (3H, s), 3.23 (3H, s), 3.72 (3H, s), 4.42 (2H, s), 7.21 (1H, t, J=5.1 Hz), 7.35 (2H, d, J=4.8 Hz).

<Step (3)>

A mixture of the above 1-(2-methoxymethyl-3-methylphenyl)-4-methyl-1,4-dihydrotetrazol-5-one, 50 mL of acetic acid, and 50 mL of 25% hydrogen bromide-acetic acid solution was stirred at 65° C. for 1 hr. Saturated sodium bicarbonate water was added to the reaction mixture and the mixture was extracted with ethyl acetate. The organic phase was washed with saturated sodium bicarbonate water and then dried by sodium sulfate anhydride. The residue was concentrated under reduced pressure to obtain 27.9 g of 1-(2-bromomethyl-3-methylphenyl)-4-methyl-1,4-dihydrotetrazol-5-one.

1-(2-bromomethyl-3-methylphenyl)-4-methyl-1,4-dihydrotetrazol-5-one

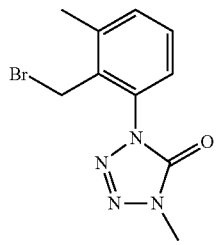

$^1$H-NMR (CDCl$_3$) δ: 2.51 (3H, s), 3.75 (3H, s), 4.51 (2H, s), 7.22-7.24 (1H, m), 7.36-7.39 (2H, m).

Reference Production Example 12

1-(2-bromomethyl-3-methylphenyl)-4-methyl-1,4-dihydrotetrazol-5-one described in Reference production example 11 can also be produced in the following steps (1) to (5).

<Step (1)>

2.0 M diethyl ether solution of trimethylsilyldiazomethane was added under ice cooling to a mixture of 15.1 g of 2-amino-6-methylbenzoic acid, 150 mL of ethyl acetate, 150 mL of ethanol. After the mixture was stirred at ambient temperature for 4 hr, the reaction mixture was concentrated under reduced pressure to obtain 16.5 g of methyl 2-amino-6-methyl benzoate.

Methyl 2-amino-6-methylbenzoate

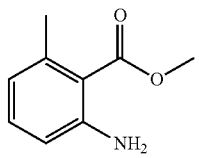

$^1$H-NMR (CDCl$_3$) δ: 6.94 (1H, t, J=8.0 Hz), 6.40-6.38 (2H, m), 4.96 (2H, s), 3.75 (3H, s), 2.29 (3H, s).

<Step (2)>

44.5 g of triphosgene was added in the mixture of 16.5 g of the obtained methyl 2-amino-6-methylbenzoate and 300 mL of toluene and the mixture was refluxed under heating with stirring for 2.5 hr. The reaction mixture was concentrated under reduced pressure to obtain methyl 2-isocyanate-6-methylbenzoate.

Methyl 2-isocyanate-6-methylbenzoate

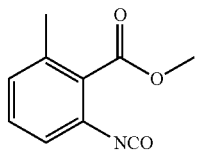

$^1$H-NMR (CDCl$_3$) δ: 7.28-7.24 (1H, m), 7.07-7.04 (1H, m), 6.98-6.95 (1H, m), 3.97 (3H, s), 2.36 (3H, s).

<Step (3)>

16.0 g of aluminum trichloride was added to 200 mL of N,N-dimethylformamide under ice cooling and the mixture was stirred for 0.5 hr. 7.2 g of sodium azide was added to the mixture, which was stirred for 0.5 hr and then, the above methyl 2-isocyanate-6-methylbenzoate was added to the mixture and heated at 80° C. with stirring for 8 hr. After the reaction mixture was cooled, the reaction mixture was added in a mixture of 11.5 g of sodium nitrite and 300 mL of ice water. The mixture was made acidic by adding 10% hydrochloric acid and then extracted with ethyl acetate. The organic phase was washed with water and saturated saline, dried by magnesium sulfate anhydride, and concentrated under reduced pressure, to obtain methyl 2-methyl-6-(5-oxo-4,5-dihydro-tetrazole-1-yl-benzoate.

42.0 g of potassium carbonate and 18.9 g of dimethylsulfuric acid were added to a mixture of methyl 2-methyl-6-(5-oxo-4,5-dihydro-tetrazole-1-yl-benzoate and 300 mL of N,N-dimethylformamide at ambient temperature and the mixture was stirred for 24 hr. Water was poured into the reaction mixture to extract the mixture with ethyl acetate. The organic phase was washed with water and saturated sodium bicarbonate water, dried by magnesium sulfate anhydride, and then, concentrated under reduced pressure. The obtained residue was subjected to silica gel column chromatography to obtain 13.9 g of methyl 2-methyl-6-(4-methyl-5-oxo-4,5-dihydro-tetrazole-1-yl-benzoate.

Methyl 2-methyl-6-(4-methyl-5-oxo-4,5-dihydro-tetrazole-1-yl-benzoate

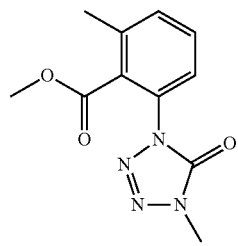 [SMILES: COC(=O)c1c(C)cccc1-n1nnn(C)c1=O]

$^1$H-NMR (CDCl$_3$) δ: 7.50-7.46 (2H, m), 7.35-7.33 (1H, m), 3.83 (3H, s), 3.69 (3H, s), 2.48 (3H, s).

<Step (4)>

201 mL of 1.0 M tetrahydrofuran solution of lithium triethylborane hydride was added at 0° C. to a mixture of 25 g of the above 2-methyl-6-(4-methyl-5-oxo-4,5-dihydro-tetrazole-1-yl-benzoate and 300 mL of tetrahydrofuran and the mixture was stirred at ambient temperature for 0.5 hr. Water was poured into the reaction mixture, which was then made acidic by adding an aqueous 10% hydrochloric acid solution and extracted with ethyl acetate. The organic phase was washed with water, dried by magnesium sulfate anhydride, and then, concentrated under reduced pressure to obtain 21.2 g of 1-(2-hydroxymethyl-3-methylphenyl)-4-methyl-1,4-dihydrotetrazol-5-one.

1-(2-hydroxymethyl-3-methylphenyl)-4-methyl-1,4-dihydrotetrazol-5-one

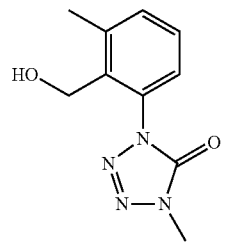 [SMILES: Cc1cccc(-n2nnn(C)c2=O)c1CO]

¹H-NMR (CDCl₃) δ: 7.39-7.34 (2H, m), 7.21 (1H, dd, J=6.5, 2.8 Hz), 4.48 (2H, s), 3.75 (3H, s), 2.57 (3H, s), 1.59 (1H, br s).

<Step (5)>

52.1 g of phosphorous tribromide was added to a mixture of 21.2 g of the above 1-(2-hydroxymethyl-3-methylphenyl)-4-methyl-1,4-dihydrotetrazol-5-one and 300 mL of chloroform and the mixture was stirred at ambient temperature for 1 hr. 200 mL of ice water was poured into the reaction mixture, which was then extracted with ethyl acetate. The organic phase was washed with water and saline, dried by magnesium sulfate anhydride, and concentrated under reduced pressure to obtain 26.0 g of 1-(2-bromomethyl-3-methylphenyl)-4-methyl-1,4-dihydrotetrazol-5-one.

Reference Production Example 13

1-(2-bromomethyl-3-ethoxyphenyl)-4-methyl-1,4-dihydrotetrazol-5-one was produced in the following steps (1) to (6).

<Step (1)>

A mixture of 33.5 g of 2-methyl-3-nitrophenol, 41 g of iodoethane, 90 g of potassium carbonate, and 400 mL of acetone was refluxed under heating with stirring for 10 hr. The mixture was cooled to ambient temperature, and filtered, and the filtrate was concentrated. The concentrated filtrate was extracted with ethyl acetate. The organic phase was washed with water and saturated saline, dried by magnesium sulfate anhydride, and concentrated under reduced pressure. The obtained residue was subjected to silica gel column chromatography to obtain 39.9 g of 1-ethoxy-2-methyl-3-nitrobenzene.

1-ethoxy-2-methyl-3-nitrobenzene

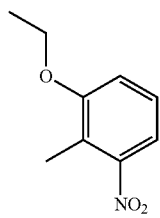

¹H-NMR (CDCl₃) δ: 7.39 (1H, dd, J=8.2, 1.0 Hz), 7.24 (1H, t, J=8.3 Hz), 7.02 (1H, d, J=8.2 Hz), 4.08 (2H, q, J=7.0 Hz), 2.37 (3H, s), 1.50-1.42 (3H, m).

<Step (2)>

A mixture of 39.9 g of the above 1-ethoxy-2-methyl-3-nitrobenzene, 4 g of palladium-carbon (palladium: 5%), and 200 mL of ethanol was stirred at ambient temperature in a hydrogen atmosphere for 18 hr. The mixture was filtered and the filtrate was concentrated to obtain 33.0 g of 3-ethoxy-2-methylaniline.

3-ethoxy-2-methylaniline

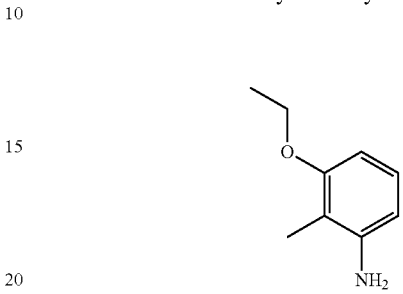

¹H-NMR (CDCl₃) δ: 6.95 (1H, t, J=8.1 Hz), 6.35 (1H, d, J=2.9 Hz), 6.33 (1H, d, J=3.1 Hz), 4.02-3.97 (2H, m), 3.61 (2H, br s), 2.05 (3H, s), 1.40 (3H, t, J=7.1 Hz).

<Step (3)>

25 g of triphosgene was added to a mixture of 33.0 g of the above 3-ethoxy-2-methyl-aniline and 400 mL of toluene at ambient temperature and the mixture was refluxed under heating with stirring for 4 hr. The mixture was concentrated under reduced pressure to obtain 37.2 g of 1-ethoxy-3-isocyanate-2-methylbenzene.

1-ethoxy-3-isocyanate-2-methylbenzene

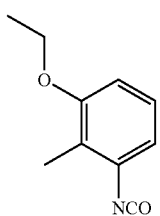

¹H-NMR (CDCl₃) δ: 7.07 (1H, t, J=8.2 Hz), 6.70 (1H, d, J=7.7 Hz), 6.68 (1H, d, J=8.2 Hz), 4.02 (2H, q, J=7.0 Hz), 2.20 (3H, s), 1.42 (3H, t, J=7.0 Hz).

<Step (4)>

15 g of sodium azide was added at 0° C. to a mixture of 350 mL of N,N-dimethylformamide and 33.6 g of aluminum trichloride and the mixture was stirred for 1 hr. After that, 37.2 g of the above 1-ethoxy-3-isocyanate-2-methylbenzene was added to the reaction mixture which was then heated to 80° C. and stirred for 5 hr. The mixture was cooled and 100 mL of ice water was added to the reaction mixture while keeping a temperature of 0° C. A mixture of 23 g of sodium nitrite and 150 mL of water was added to the mixture and then, the mixture was adjusted to pH about 4 by adding an aqueous 10% hydrochloric acid solution. The mixture was extracted with ethyl acetate. The organic phase was washed with water and saturated saline, dried by magnesium sulfate anhydride, and then, concentrated under reduced pressure. The obtained residue was subjected to silica gel column chromatography to obtain 39.0 g of 1-(3-ethoxy-2-methylphenyl)-1,4-dihydrotetrazol-5-one.

1-(3-ethoxy-2-methylphenyl)-1,4-dihydrotetrazol-5-one

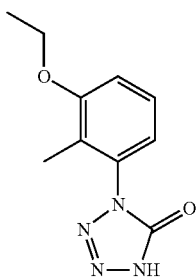 [SMILES: CCOc1cccc(-n2nn[nH]c2=O)c1C]

$^1$H-NMR (CDCl$_3$) δ: 7.30 (1H, t, J=8.1 Hz), 6.99 (1H, d, J=8.5 Hz), 6.96 (1H, d, J=8.0 Hz), 4.10 (2H, q, J=6.9 Hz), 2.13 (3H, s), 1.46 (3H, t, J=7.0 Hz).
<Step (5)>
44.7 g of dimethyl sulfate was added to a mixture of 400 mL of N,N-dimethylformamide, 39.0 g of the above 1-(3-ethoxy-2-methylphenyl)-1,4-dihydrotetrazol-5-one, 36.7 g of potassium carbonate, and 400 mL of N,N-dimethylformamide at 0° C. and the mixture was heated to ambient temperature, followed by stirring for 7 hr. 100 mL of water was added to the mixture, which was extracted with ethyl acetate. The organic phase was washed with water and saturated saline, dried by magnesium sulfate anhydride, and concentrated under reduced pressure. The obtained residue was subjected to silica gel column chromatography to obtain 38.2 g of 1-(3-ethoxy-2-methylphenyl)-4-methyl-1,4-dihydrotetrazol-5-one.

1-(3-ethoxy-2-methylphenyl)-4-methyl-1,4-dihydrotetrazol-5-one

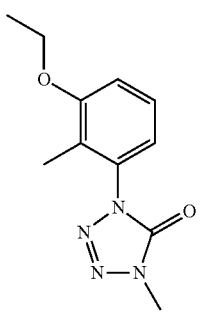 [SMILES: CCOc1cccc(-n2nnn(C)c2=O)c1C]

$^1$H-NMR (CDCl$_3$) δ: 7.29-7.23 (1H, m), 6.96 (1H, d, J=8.2 Hz), 6.93 (1H, d, J=8.2 Hz), 4.08 (2H, q, J=6.9 Hz), 3.72 (3H, s), 2.11 (3H, s), 1.45 (3H, t, J=7.1 Hz).
<Step (6)>
A mixture of 38.2 g of the above 1-(3-ethoxy-2-methylphenyl)-4-methyl-1,4-dihydrotetrazol-5-one, 7.95 g of 1,1'-azobis(cyclohexane-1-carbonitrile), 33.4 g of N-bromosuccinimide, and 380 mL of chlorobenzene was stirred at 120° C. for 5 hr. After the reaction solution was cooled, water was poured into the reaction solution to extract the solution with ethyl acetate. The organic phase was washed with water and saturated saline, dried by magnesium sulfate anhydride, and then, concentrated under reduced pressure. The obtained residue was subjected to silica gel column chromatography to obtain 38.2 g of 1-(3-ethoxy-2-bromomethylphenyl)-4-methyl-1,4-dihydrotetrazol-5-one.

1-(2-bromomethyl-3-ethoxyphenyl)-4-methyl-1,4-dihydrotetrazol-5-one

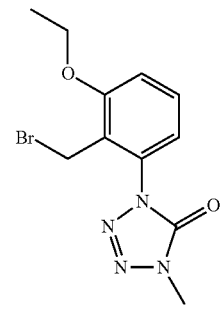

$^1$H-NMR (CDCl$_3$) δ: 7.40 (1H, t, J=8.2 Hz), 7.01 (2H, t, J=8.3 Hz), 4.64 (2H, s), 4.17 (2H, q, J=7.0 Hz), 3.74 (3H, s), 1.49 (3H, t, J=6.9 Hz).

Reference Production Example 14

1-(2-bromomethyl-3-ethylphenyl)-4-methyl-1,4-dihydrotetrazol-5-one was produced in the following steps (1) to (3).
<Step (1)>
A mixture of 29.8 g of the above 1-(2-methoxymethyl-3-bromophenyl)-4-methyl-1,4-dihydrotetrazol-5-one described in Reference production example 11, 35.2 g of tributylvinyltin, 11.6 g of tetrakistriphenylphosphine palladium, and 500 mL of toluene was refluxed under heating with stirring for 14 hr. After the reaction mixture was cooled, an aqueous saturated ammonium chloride solution was poured into the reaction solution and the reaction solution was extracted with ethyl acetate. The organic phase was washed with water and saturated saline, dried by sodium sulfate anhydride, and then, concentrated under reduced pressure. The obtained residue was subjected to silica gel column chromatography to obtain 19.7 g of 1-(2-methoxymethyl-3-ethenylphenyl)-4-methyl-1,4-dihydrotetrazol-5-one.

1-(2-methoxymethyl-3-ethenylphenyl)-4-methyl-1,4-dihydrotetrazol-5-one

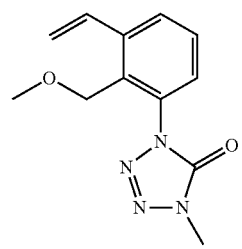 [SMILES: C=Cc1cccc(-n2nnn(C)c2=O)c1COC]

$^1$H-NMR (CDCl$_3$) δ: 7.67 (1H, dd, J=7.8, 1.3 Hz), 7.44 (1H, t, J=7.8 Hz), 7.29 (1H, dd, J=7.8, 1.3 Hz), 7.11 (1H, dd, J=17.4, 11.1 Hz), 5.72 (1H, dd, J=17.4, 1.3 Hz), 5.44 (1H, dd, J=11.1, 1.3 Hz), 4.45 (2H, s), 3.72 (3H, s), 3.23 (3H, s).
<Step (2)>
A mixture of 19.7 g of the obtained 1-(2-methoxymethyl-3-ethenylphenyl)-4-methyl-1,4-dihydrotetrazol-5-one, 3.02 g of a palladium-fibroin complex, and 1 L of methanol was stirred at ambient temperature for 11 hr in a hydrogen atmosphere. The reaction mixture was filtered and the filtrate was concentrated under reduced pressure. The obtained residue was subjected to silica gel column chromatography to obtain 19.3 g of 1-(2-methoxymethyl-3-ethylphenyl)-4-methyl-1,4-dihydrotetrazol-5-one.

1-(2-methoxymethyl-3-ethylphenyl)-4-methyl-1,4-dihydrotetrazol-5-one

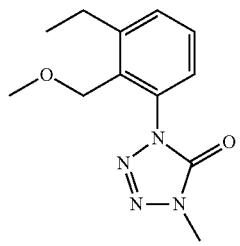 [SMILES: CCc1cccc(-n2nnn(C)c2=O)c1COC]

$^1$H-NMR (CDCl$_3$) δ: 7.42-7.38 (2H, m), 7.23-7.20 (1H, m), 4.44 (2H, s), 3.72 (3H, s), 3.22 (3H, s), 2.82 (2H, q, J=7.6 Hz), 1.27 (3H, t, J=7.6 Hz).

<Step (3)>

A mixture of 19.3 g of the obtained 1-(2-methoxymethyl-3-ethylphenyl)-4-methyl-1,4-dihydrotetrazol-5-one, 40 mL of acetic acid, and 40 mL of 25% hydrogen bromide-acetic acid solution was stirred at 65° C. for 1.5 hr. Saturated saline was poured into the reaction mixture and the mixture was extracted with ethyl acetate. The organic phase was washed with saturated sodium bicarbonate water and then dried by sodium sulfate anhydride. The residue was concentrated under reduced pressure to obtain 23.3 g of 1-(2-bromomethyl-3-ethylphenyl)-4-methyl-1,4-dihydrotetrazol-5-one.

1-(2-bromomethyl-3-ethylphenyl)-4-methyl-1,4-dihydrotetrazol-5-one

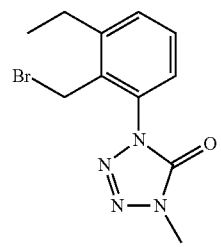

$^1$H-NMR (CDCl$_3$) δ: 7.44-7.37 (2H, m), 7.23 (1H, dd, J=7.1, 2.0 Hz), 4.56 (2H, s), 3.75 (3H, s), 2.85 (2H, q, J=7.6 Hz), 1.33 (3H, t, J=7.6 Hz).

Reference Production Example 15

1-(2-bromomethyl-3-difluoromethylphenyl)-4-methyl-1,4-dihydrotetrazol-5-one was produced in the following steps (1) to (8).

<Step (1)>

A mixture of 9.4 g of sodium borohydride and 150 mL of tetrahydrofuran was stirred at 25° C. for 30 min. 30.8 g of 2-methyl-3-nitrobenzoic acid was added to the mixture, which was further stirred at 25° C. for 30 min. This mixture solution was ice-cooled and 11.0 mL of methanesulfonic acid was gradually added to the mixture over 45 min. The reaction mixture was stirred at 25° C. for 3 days. Water was poured into the reaction mixture to extract the mixture with ethyl acetate. The organic phase was washed with an aqueous 10% hydrochloric acid solution and saturated saline, dried by magnesium sulfate anhydride, and then, concentrated under reduced pressure to obtain 27.0 g of 3-hydroxymethyl-2-methyl-1-nitrobenzene.

3-hydroxymethyl-2-methyl-1-nitrobenzene

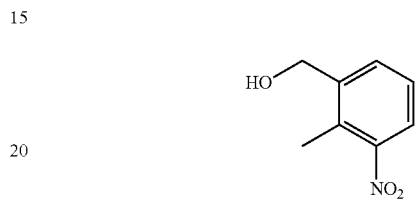

$^1$H-NMR (CDCl$_3$) δ: 1.81 (1H, s), 2.44 (3H, s), 4.79 (2H, s), 7.34 (1H, t, J=7.8 Hz), 7.65 (1H, d, 7.6 Hz), 7.72 (1H, d, J=8.1 Hz).

<Step (2)>

A mixture of 17.0 g of the above 3-hydroxymethyl-2-methyl-1-nitrobenzene, 65.0 g of manganese dioxide, and 170 mL of chloroform was refluxed under heating with stirring for 5 hr. The reaction mixture which was allowed to cool was filtered by celite and concentrated under reduced pressure to obtain 14.0 g of 3-formyl-2-methyl-1-nitrobenzene.

3-formyl-2-methyl-1-nitrobenzene

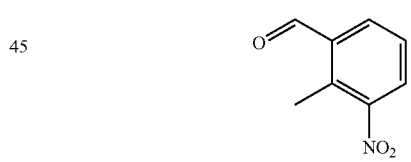

$^1$H-NMR (CDCl$_3$) δ: 2.78 (3H, s), 7.53 (1H, t, J=8.1 Hz), 7.97 (1H, dd, J=1.5, 8.1 Hz), 8.06 (1H, dd, J=1.5, 7.8 Hz), 10.39 (1H, s).

<Step (3)>

A mixture of 13.0 g of the above 3-formyl-2-methyl-1-nitrobenzene and 200 mL of chloroform was cooled to −78° C. at which 31.7 g of N,N-dimethylaminosulfur trifluoride was added dropwise to the mixture, which was then stirred at 25° C. for 16 hr. Water was added to the reaction mixture to extract the mixture with chloroform. The organic phase was washed with saturated saline, dried by magnesium sulfate anhydride, and then, concentrated under reduced pressure. The resulting residue was subjected to silica gel column chromatography to obtain 6.8 g of 3-difluoromethyl-2-methyl-1-nitrobenzene.

3-difluoromethyl-2-methyl-1-nitrobenzene

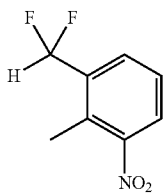

$^1$H-NMR (CDCl$_3$) δ: 2.54 (3H, s), 6.84 (1H, t, J=54.6 Hz), 7.45 (1H, t, J=7.7 Hz), 7.78 (1H, d, J=7.7 Hz), 7.89 (1H, d, J=8.0 Hz)

<Step (4)>

A mixture of 6.80 g of the above 3-difluoromethyl-2-methyl-1-nitrobenzene, 0.30 g of 5% platinum-activated carbon, and 50 mL of methanol was stirred at 35° C. for 8 hr in a hydrogen atmosphere. The reaction mixture was filtered by celite and the filtrate was concentrated under reduced pressure. The obtained residue was subjected to silica gel column chromatography to obtain 3.87 g of 3-difluoromethy-2-methyl-1-aminobenzene.

3-difluoromethy-2-methyl-1-aminobenzene

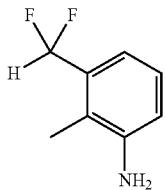

$^1$H-NMR (CDCl$_3$) δ: 2.20 (3H, s), 3.71 (2H, s), 6.72 (1H, t, J=55.5 Hz), 6.79 (1H, d, J=8.0 Hz), 6.92 (1H, d, J=7.7 Hz), 7.09 (1H, t, J=7.7 Hz).

<Step (5)>

A mixture of 3.87 g of the above 3-difluoromethy-2-methyl-1-aminobenzene, 10.96 g of triphosgene, and 80 mL of toluene was refluxed under heating with stirring for 3.5 hr. The reaction mixture which was allowed to cool was concentrated under reduced pressure to obtain 3-difluoromethyl-2-methyl-1-isocyanatebenzene.

3-difluoromethyl-2-methyl-1-isocyanatebenzene

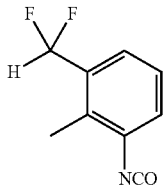

$^1$H-NMR (CDCl$_3$) δ: 2.39 (3H, s), 6.74 (1H, t, J=55.1 Hz), 7.21-7.27 (2H, m), 7.34 (1H, d, J=7.2 Hz).

<Step (6)>

3.62 g of aluminum trichloride anhydride was added to 40 mL of N,N-dimethylformamide under ice cooling, followed by stirring for 20 min. 1.76 g of sodium azide was added to the mixture, which was then stirred for 15 min and then, the above 3-difluoromethyl-2-methyl-1-isocyanatebenzene was added to the mixture, which was then heated at 80° C. for 4 hr. After the reaction mixture was cooled, it was added to a mixture of 6 g of sodium nitrite, 0.5 L of water, and 100 g of ice with stirring. The mixture was made acidic by adding 10% hydrochloric acid and then extracted with ethyl acetate. The organic phase was washed with water and saturated saline, dried by magnesium sulfate anhydride, and then, concentrated under reduced pressure to obtain 3.22 g of 1-(2-methyl-3-difluoromethylphenyl)-1,4-dihydrotetrazol-5-one.

1-(2-methyl-3-difluoromethylphenyl)-1,4-dihydrotetrazol-5-one

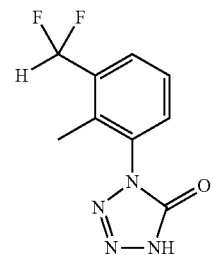

<Step (7)>

A mixture of 3.22 g of the above 1-(2-methyl-3-difluoromethylphenyl)-1,4-dihydrotetrazol-5-one, 3.93 g of potassium carbonate, 4.04 g of methyl iodide, and 70 mL of N,N-dimethylformamide was stirred at 25° C. for 5 hr. Water was added to the reaction mixture, which was then extracted with ethyl acetate. The organic phase was washed with 10% hydrochloric acid, water, and saturated saline, dried by magnesium sulfate anhydride, and concentrated under reduced pressure. The obtained residue was subjected to silica gel column chromatography to obtain 1.14 g of 1-(2-methyl-3-difluoromethylphenyl)-4-methyl-1,4-dihydrotetrazol-5-one.

1-(2-methyl-3-difluoromethylphenyl)-4-methyl-1,4-dihydrotetrazol-5-one

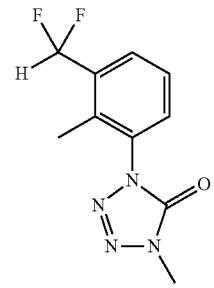

$^1$H-NMR (CDCl$_3$) δ: 2.31 (3H, s), 3.73 (3H, s), 6.83 (1H, t, J=55.1 Hz), 7.44-7.46 (2H, m), 7.68-7.71 (1H, m).

<Step (8)>

A mixture of 1.14 g of the above 1-(2-methyl-3-difluoromethylphenyl)-4-methyl-1,4-dihydrotetrazol-5-one, 0.23 g of 1,1'-azobis[cyclohexane-1-carbonitrile], 0.97 g of N-bromosuccinimide, and 20 mL of chlorobenzene was refluxed under heating with stirring for 5 hr. After the reaction mixture was cooled, water was added to the reaction mixture, which was then extracted with ethyl acetate. The organic phase was washed with water and saturated saline, dried by magnesium sulfate anhydride, then, concentrated under reduced pressure. The obtained residue was subjected to silica gel column chromatography to obtain 1.21 g of 1-(2-bromomethyl-3-difluoromethylphenyl)-4-methyl-1,4-dihydrotetrazol-5-one.

1-(2-bromomethyl-3-difluoromethylphenyl)-4-methyl-1,4-dihydrotetrazol-5-one

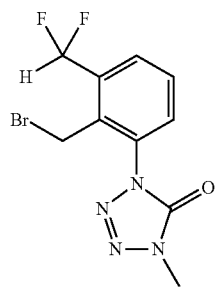

$^1$H-NMR (CDCl$_3$) δ: 3.76 (3H, s), 4.66 (2H, s), 6.99 (1H, t, J=54.8 Hz), 7.55 (1H, d, J=8.0 Hz), 7.60 (1H, t, J=7.7 Hz), 7.56 (1H, d, J=7.5 Hz).

Reference Production Example 16

1-(2-bromomethyl-3-difluoromethoxyphenyl)-4-methyl-1,4-dihydrotetrazol-5-one was produced in the following steps (1) to (5).

<Step (1)>
A mixture of 7.17 g of 2-methyl-3-nitrophenol, 27 g of potassium hydroxide, 25 g of bromodifluoromethyl-diethylphosphonate, 100 mL of water, and 100 mL of acetanilile was stirred at ambient temperature for 24 hr. The reaction mixture was extracted with ethyl acetate. The organic phase was washed with water and saturated saline, dried by magnesium sulfate anhydride, and concentrated under reduced pressure. The obtained residue was subjected to silica gel column chromatography to obtain 7.50 g of 1-difluoromethoxy-2-methyl-3-nitrobenzene.

1-difluoromethoxy-2-methyl-3-nitrobenzene

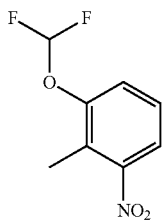

$^1$H-NMR (CDCl$_3$) δ: 7.74 (1H, dd, J=7.6, 1.8 Hz), 7.40-7.32 (2H, m), 6.56 (1H, t, J=72.4 Hz), 2.46 (3H, s).

<Step (2)>
A mixture of 7.50 g of the above 1-difluoromethoxy-2-methyl-3-nitrobenzene, 0.8 g of palladium-carbon (palladium: 5%), and 80 mL of ethanol was stirred at ambient temperature in a hydrogen atmosphere for 8 hr. The mixture was filtered and the filtrate was concentrated to obtain 6.4 g of 3-difluoromethoxy-2-methylaniline.

3-difluoromethoxy-2-methylaniline

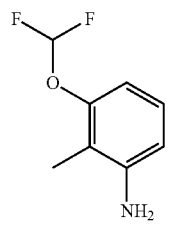

$^1$H-NMR (CDCl$_3$) δ: 6.99 (1H, t, J=8.1 Hz), 6.55 (1H, d, J=8.0 Hz), 6.51 (1H, d, J=8.2 Hz), 6.46 (1H, td, J=74.4, 0.4 Hz), 3.72 (2H, br s), 2.09 (3H, s).

<Step (3)>
5.48 g of triphosgene was added to a mixture of 6.4 g of the above 3-difluoromethoxy-2-methylaniline and 100 mL of toluene at ambient temperature and the mixture was refluxed under heating with stirring for 1 hr. The mixture was concentrated under reduced pressure to obtain 7.36 g of 1-difluoromethoxy-3-isocyanate-2-methylbenzene.

1-difluoromethoxy-3-isocyanate-2-methylbenzene

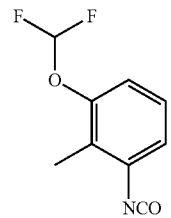

$^1$H-NMR (CDCl$_3$) δ: 7.14 (1H, t, J=8.1 Hz), 6.97 (2H, t, J=8.5 Hz), 6.50 (1H, td, J=73.6, 0.4 Hz), 2.27 (3H, s).

<Step (4)>
2.64 g of sodium azide was added to a mixture of 200 mL of N,N-dimethylformamide and 5.91 g of aluminum chloride anhydride and the mixture was stirred for 1 hr. After that, 7.36 g of the above 1-difluoromethoxy-3-isocyanate-2-methylbenzene was added to the reaction mixture, which was then heated to 75° C. and stirred for 9 hr. The mixture was cooled and 50 mL of ice water was added to the reaction mixture under ice cooling. A mixture of 4.1 g of sodium nitrite and 100 mL of water was added to the reaction mixture and then, the mixture was adjusted to pH about 4 by adding concentrated hydrochloric acid. The mixture was extracted with ethyl acetate. The organic phase was washed with water and saturated saline, dried by magnesium sulfate anhydride, and then, concentrated under reduced pressure. 100 mL of N,N-dimethylformamide, 7.66 g of potassium carbonate, and 9.32 g of dimethyl sulfate were added to the obtained residue containing 1-(2-methyl-3-difluoromethoxyphenyl)-1,4-dihydrotetrazol-5-one, and the mixture was stirred at ambient temperature for 4 hr. 100 mL of water was added to the mixture to extract the mixture with ethyl acetate. The organic phase was washed with water and saturated saline, dried by magnesium sulfate anhydride, and then, concentrated under reduced pressure. The obtained residue was subjected to silica gel column chromatography to obtain 1.0 g of 1-(2-methyl-3-difluoromethoxyphenyl)-4-methyl-1,4-dihydro tetrazol-5-one.

1-(2-methyl-3-difluoromethoxyphenyl)-4-methyl-1,4-dihydrotetrazol-5-one

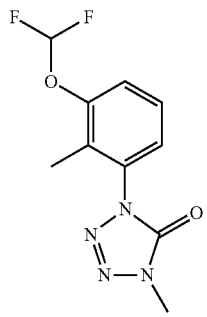 [SMILES: Cc1c(OC(F)F)cccc1-n1nnn(C)c1=O]

$^1$H-NMR (CDCl$_3$) δ: 7.34 (1H, t, J=8.1 Hz), 7.30-7.23 (2H, m), 6.55 (1H, t, J=72.8 Hz), 3.73 (3H, d, J=0.5 Hz), 2.21 (3H, s).

<Step (5)>

A mixture of 1.0 g of the above 1-(2-methyl-3-difluoromethoxyphenyl)-4-methyl-1,4-dihydro tetrazol-5-one, 0.19 g of 1,1'-azobis(cyclohexane-1-carbonitrile), 0.80 g of N-bromosuccinimide, and 50 mL of chlorobenzene was refluxed under heating with stirring for 8 hr. After the reaction solution was cooled, water was added to the reaction solution, which was then extracted with ethyl acetate. The organic phase was washed with water and saturated saline, dried by magnesium sulfate anhydride, and concentrated under reduced pressure. The obtained residue was subjected to silica gel column chromatography to obtain 1.1 g of 1-(2-bromomethyl-3-difluoromethoxyphenyl)-4-methyl-1,4-dihydrotetrazol-5-one.

1-(2-bromomethyl-3-difluoromethoxyphenyl)-4-methyl-1,4-dihydrotetrazol-5-one

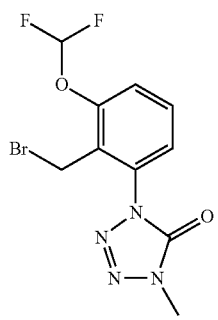 [SMILES: Cn1nnn(-c2cccc(OC(F)F)c2CBr)c1=O]

$^1$H-NMR (CDCl$_3$) δ: 7.50 (1H, t, J=8.2 Hz), 7.34 (2H, d, J=8.2 Hz), 6.62 (1H, t, J=72.8 Hz), 4.65 (2H, s), 3.76 (3H, d, J=0.5 Hz).

Reference Production Example 17

1-(2-bromomethyl-3-cyclopropylphenyl)-4-methyl-1,4-dihydrotetrazol-5-one was produced in the following steps (1) to (2).
<Step (1)>

A mixture of 30.1 g of 1-(2-methoxymethyl-3-bromophenyl)-4-methyl-1,4-dihydrotetrazol-5-one described in Reference production example 11, 12.9 g of cyclopropylboronic acid, 46.2 g of cesium fluoride, 8.2 g of a dichlorometnane adduct of [1,1']-bis(diphenylphosphino)ferrocene]palladium (II) dichloride, and 680 mL of dioxane was stirred at 90° C. for 4 hr. After the resulting mixture was cooled, it was filtered and the filtrate was concentrated under reduced pressure. The obtained residue was subjected to silica gel column chromatography to obtain 26.0 g of 1-(2-methoxymethyl-3-cyclopropylphenyl)-4-methyl-1,4-dihydrotetrazol-5-one.

1-(2-methoxymethyl-3-cyclopropylphenyl)-4-methyl-1,4-dihydrotetrazol-5-one

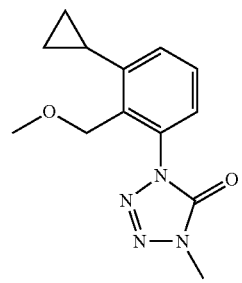 [SMILES: COCc1c(C2CC2)cccc1-n1nnn(C)c1=O]

$^1$H-NMR (CDCl$_3$) δ: 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).
<Step (2)>

A mixture of 26.0 g of the above 1-(2-methoxymethyl-3-cyclopropylphenyl)-4-methyl-1,4-dihydrotetrazol-5-one, 40 mL of acetic acid, and 40 mL of a 25% hydrogen bromide-acetic acid solution was stirred at 65° C. for 2 hr. Saturated saline was poured into the reaction mixture, which was then extracted with ethyl acetate. The organic phase was washed with saturated sodium bicarbonate water and dried by sodium sulfate anhydride. The residue was concentrated under reduced pressure to obtain 30.8 g of 1-(2-bromomethyl-3-cyclopropylphenyl)-4-methyl-1,4-dihydrotetrazol-5-one.

1-(2-bromomethyl-3-cyclopropylphenyl)-4-methyl-1,4-dihydrotetrazol-5-one

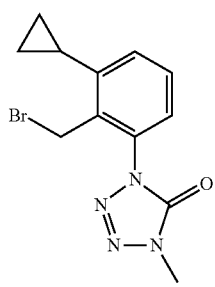

¹H-NMR (CDCl₃) δ: 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Production Example 18

1-(2-bromomethyl-3-methylphenyl)-4-methyl-1,4-dihydrotetrazol-5-one was produced in the following steps (1) to (3).

<Step (1)>

0.63 g of 60% sodium hydride was added under ice cooling to a mixture of 4.99 g of triisopropylsilanethiol and 30 mL of toluene and the mixture was stirred for 30 min. 2.82 g of 1-(2-methyl-3-bromophenyl)-4-methyl-1,4-dihydrotetrazol-5-one described in Reference production example 5 and 0.856 g of a dichlorometnane adduct of [1,1']-bis(diphenylphosphino)ferrocene]palladium (II) dichloride were added to the reaction mixture and the mixture was heated to 90° C. and stirred for 4 hr. After the reaction mixture was cooled, water was added to the reaction mixture to extract the mixture with ethyl acetate. The organic phase was washed with water and saturated saline, dried by magnesium sulfate anhydride, and concentrated under reduced pressure. The obtained residue was subjected to silica gel column chromatography to obtain 3.64 g of 1-(2-methyl-3-triisopropylsilanylthiophenyl)-4-methyl-1,4-dihydrotetrazol-5-one.

1-(2-methyl-3-triisopropylsilanylthiophenyl)-4-methyl-1,4-dihydrotetrazol-5-one

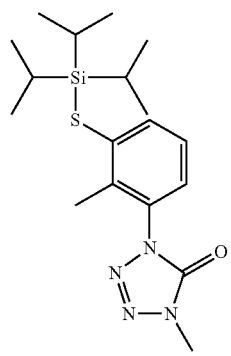 [SMILES: Cc1c(S[Si](C(C)C)(C(C)C)C(C)C)cccc1-n1nnn(C)c1=O]

¹H-NMR (CDCl₃) δ: 1.09 (18H, d, J=6.6 Hz), 1.31 (3H, q, J=6.6 Hz), 2.45 (3H, s), 3.71 (3H, s), 7.16-7.21 (2H, m), 7.64 (1H, dd, J=6.6, 2.7 Hz).

<Step (2)>

A mixture of 3.63 g of the above 1-(2-methyl-3-triisopropylsilanylthiophenyl)-4-methyl-1,4-dihydrotetrazol-5-one, 2.91 g of cesium fluoride, and 10 mL of N,N-dimethylformamide was stirred at ambient temperature for 30 min. 2.72 g of methyl iodide was added to the reaction mixture, which was then stirred at ambient temperature for 3 hr. Water was added to the mixture, which was then extracted with ethyl acetate. The organic phase was washed with water and saturated saline, dried by magnesium sulfate anhydride, and then, concentrated under reduced pressure. The obtained residue was subjected to silica gel column chromatography to obtain 1.65 g of 1-(2-methyl-3-methylthiophenyl)-4-methyl-1,4-dihydrotetrazol-5-one.

1-(2-methyl-3-methylthiophenyl)-4-methyl-1,4-dihydrotetrazol-5-one

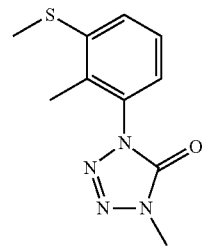

¹H-NMR (CDCl₃) δ: 2.22 (3H, s), 2.51 (3H, s), 3.72 (3H, s), 7.10-7.16 (1H, m), 7.36-7.29 (2H, m).

<Step (3)>

A mixture of 1.50 g of the above 1-(2-methyl-3-methylthiophenyl)-4-methyl-1,4-dihydrotetrazol-5-one, 0.620 g of 1,1'-azobis(cyclohexane-1-carbonitrile), 1.30 g of N-bromosuccinimide, and 15 mL of chlorobenzene was refluxed under heating with stirring for 4 hr. After the resulting mixture was cooled, water was poured into the mixture to extract the mixture with ethyl acetate. The organic phase was washed with water and saturated saline, dried by magnesium sulfate anhydride, and then, concentrated under reduced pressure. The obtained residue was subjected to silica gel column chromatography to obtain 0.400 g of 1-(2-bromomethyl-3-methylphenyl)-4-methyl-1,4-dihydrotetrazol-5-one.

1-(2-bromomethyl-3-methylphenyl)-4-methyl-1,4-dihydrotetrazol-5-one

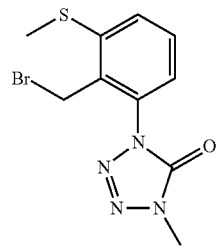

¹H-NMR (CDCl₃) δ: 2.57 (3H, s), 3.75 (3H, s), 4.69 (2H, s), 7.20 (1H, t, J=4.5 Hz), 7.44 (2H, d, J=4.5 Hz).

Reference Production Example 19

6.1 g of propionyl chloride and 22.8 ml of triethylamine were added to a mixture of 5.9 g of o-cresol and 150 mL of chloroform at 0° C. and then, the mixture was heated to ambient temperature, followed by stirring for 2 hr. Then, the mixture was extracted with chloroform. The organic phase was washed with water, dried by magnesium sulfate anhydride, and concentrated under reduced pressure. The obtained residue was subjected to silica gel column chromatography to obtain 8.9 g of 2-methylphenyl propionate.

2-methylphenyl propionate

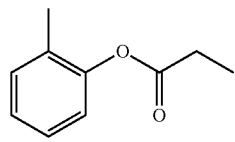

1H-NMR (CDCl3) δ: 7.26-7.18 (2H, m), 7.14 (1H, td, J=7.44, 1.37 Hz), 7.01 (1H, d, J=8.93 Hz), 2.62 (2H, q, J=7.56 Hz), 2.18 (3H, s), 1.30 (3H, t, J=7.56 Hz).

Reference Production Example 20

18 g of aluminum trichloride was added to a mixture of 8.9 g of the above 2-methylphenyl propionate described in Reference production example 19 and 100 mL of nitromethane at 0° C. and the mixture was heated to 50° C. After the mixture was stirred for 12 hr, the reaction mixture was poured into 50 ml of ice water and then extracted with chloroform. The organic phase was washed with water, dried by magnesium sulfate anhydride, and concentrated under reduced pressure. The obtained residue was subjected to silica gel column chromatography to obtain 7.6 g of 1-(4-hydroxy-3-methyl-phenyl)propan-1-one.

1-(4-hydroxy-3-methyl-phenyl)propan-1-one

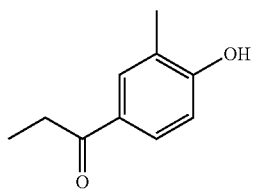

1H-NMR (CDCl3) δ: 7.81-7.79 (1H, m), 7.75 (1H, dd, J=8.47, 2.18 Hz), 6.84 (1H, d, J=8.47 Hz), 6.24 (1H, br s), 2.96 (2H, q, J=7.33 Hz), 2.29 (3H, s), 1.21 (3H, t, J=7.33 Hz).

Reference Production Example 21

0.5 mL of hydrochloric acid (12M) was added to a mixture of 1.6 g of the above 1-(4-hydroxy-3-methyl-phenyl) propane-1-one described in Reference production example 20, 0.84 g of O-methylhydroxyamine hydrochloride, and 20 mL of ethanol and the mixture was stirred at ambient temperature for 4 hr. Saturated sodium bicarbonate was added to the reaction mixture which was then extracted three times with chloroform and washed with saturated saline. The obtained solution was dried by sodium sulfate, filtered, and then, the filtrate was concentrated to obtain 2-methyl-4-(1-methoxyimino-propyl)phenol.

2-methyl-4-(1-methoxyimino-propyl)phenol

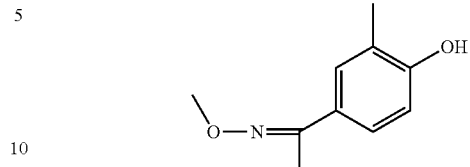

1H-NMR (CDCl3) δ: 7.43 (1H, d, J=2.18 Hz), 7.33 (1H, dd, J=8.24, 2.18 Hz), 6.75 (1H, d, J=8.24 Hz), 5.07 (1H, s), 3.96 (3H, s), 2.71 (2H, q, J=7.56 Hz), 2.26 (3H, s), 1.11 (3H, t, J=7.56 Hz).

Reference Production Example 22

The same reaction as that of Reference production example 19 was carried out except that cyclopropane carbonylchloride was used in place of propionyl chloride in Reference Production Example 19 to obtain 2-methylphenyl cyclopropanecarboxylate.

2-methylphenyl cyclopropanecarboxylate

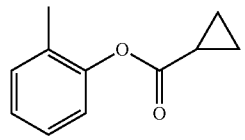

¹H-NMR (CDCl₃) δ: 7.24-7.17 (2H, m), 7.13 (1H, td, J=7.38, 1.26 Hz), 7.01 (1H, dd, J=7.67, 1.26 Hz), 2.19 (3H, s), 1.88 (1H, tt, J=8.01, 3.78 Hz), 1.21-1.16 (2H, m), 1.06-1.00 (2H, m).

Reference Production Example 23

The same reaction as that of Reference production example 20 was carried out except that 2-methylphenyl cyclopropanecarboxylate described in Reference production example 22 was used in place of 2-methylphenyl propionate in Reference production example 20 to obtain cyclopropyl-(4-hydroxy-3-methyl-phenyl)-methanone.

Cyclopropyl-(4-hydroxy-3-methyl-phenyl)-methanone

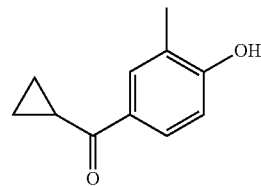

¹H-NMR (CDCl₃) δ: 7.85 (1H, d, J=2.17 Hz), 7.80 (1H, dd, J=8.45, 2.17 Hz), 6.84 (1H, d, J=8.45 Hz), 6.15 (1H, br s), 2.68-2.61 (1H, m), 2.30 (3H, s), 1.25-1.20 (2H, m), 1.04-0.98 (2H, m).

Reference Production Example 24

The same reaction as that of Reference production example 21 was carried out except that cyclopropyl-(4-hydroxy-3-methyl-phenyl)-methanone described in Reference production example 23 was used in place of 1-(4-hydroxy-3-methyl-phenyl)propane-1-one in Reference production example 21 to obtain 2-methyl-4-(1-methoxy-imino-1-cyclopropyl-methyl)phenol.

2-methyl-4-(1-methoxyimino-1-cyclopropyl-methyl)phenol

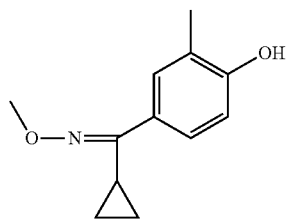

1H-NMR (CDCl3) δ: 7.27-7.24 (0.3H, m), 7.21 (0.3H, d, J=8.24 Hz), 7.13 (0.7H, d, J=2.18 Hz), 7.06 (0.7H, dd, J=8.24, 2.18 Hz), 6.77 (0.3H, d, J=8.24 Hz), 6.71 (0.7H, d, J=8.24 Hz), 6.23 (0.3H, br s), 6.14 (0.7H, s), 3.96 (2H, s), 3.80 (1H, s), 2.26 (1H, s), 2.25-2.19 (3H, m), 0.91-0.86 (1.3H, m), 0.81-0.76 (1.4H, m), 0.64-0.58 (1.3H, m).

Reference Production Example 25

The same reaction as that of Reference production example 19 was carried out except that 2-methylpropionyl chloride was used in place of propionyl chloride Reference production example 19 to obtain 2-methylphenyl 2-methylpropionate.

2-methylphenyl 2-methylpropionate

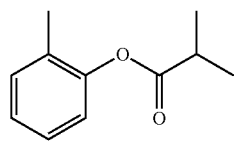

$^1$H-NMR (CDCl$_3$) δ: 7.24-7.17 (2H, m), 7.13 (1H, t, J=7.10 Hz), 6.98 (1H, d, J=7.79 Hz), 2.89-2.80 (1H, m), 2.17 (3H, s), 1.34 (6H, d, J=6.87 Hz).

Reference Production Example 26

The same reaction was that of Reference production example 20 was carried out except that 2-methylphenyl 2-methylpropionate described in Reference production example 25 was used in place of 2-methylphenyl propionate in Reference production example 20 to obtain 1-(4-hydroxy-3-methyl-phenyl)-2-methyl-propane-1-one.

1-(4-hydroxy-3-methyl-phenyl)-2-methyl-propane-1-one

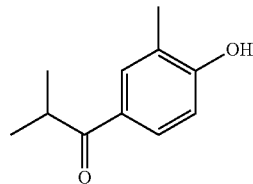

$^1$H-NMR (CDCl$_3$) δ: 7.80 (1H, d, J=2.18 Hz), 7.74 (1H, dd, J=8.24, 2.18 Hz), 6.84 (1H, d, J=8.24 Hz), 6.08 (1H, br s), 3.57-3.49 (1H, m), 2.30 (3H, s), 1.20 (6H, d, J=6.75 Hz).

Reference Production Example 27

The same reaction as that of Reference production example 21 was carried out except that 1-(4-hydroxy-3-methyl-phenyl)-2-methyl-propane-1-one described in Reference production example 26 was used in place of 1-(4-hydroxy-3-methyl-phenyl)-propane-1-one in Reference production example 21 to obtain 2-methyl-4-(1-methoxy-imino-2-methyl-propyl)phenol.

2-methyl-4-(1-methoxyimino-2-methyl-propyl)phenol

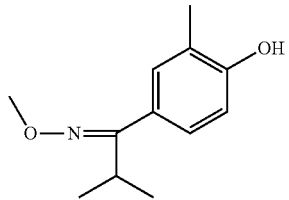

1H-NMR (CDCl3) δ: 7.16 (0.5H, s), 7.11 (0.5H, dd, J=8.21, 2.29 Hz), 7.00 (0.5H, s), 6.97 (0.5H, dd, J=8.21, 2.05 Hz), 6.76 (0.5H, d, J=8.21 Hz), 6.72 (0.5H, d, J=8.21 Hz), 4.90 (1.0H, s), 3.92 (1.5H, s), 3.80 (1.5H, s), 3.46 (0.5H, t, J=7.12 Hz), 2.77 (0.5H, t, J=6.88 Hz), 2.26-2.23 (3.0H, m), 1.17 (3.0H, d, J=6.88 Hz), 1.10 (3.0H, d, J=7.12 Hz).

Reference Production Example 28

The same reaction as that of Reference production example 19 was carried out except that cyclohexanecarbonyl chloride was used in place of propionyl chloride in Reference production example 19 to obtain 2-methylphenyl cyclohexanecarboxylate.

2-methylphenyl cyclohexanecarboxylate

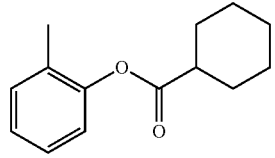 [SMILES: Cc1ccccc1OC(=O)C1CCCCC1]

¹H-NMR (CDCl₃) δ: 7.24-7.17 (2H, m), 7.12 (1H, t, J=7.33 Hz), 6.97 (1H, d, J=8.01 Hz), 2.63-2.55 (1H, m), 2.16 (3H, s), 2.11-2.07 (2H, m), 1.88-1.80 (2H, m), 1.70-1.59 (2H, m), 1.43-1.28 (4H, m).

Reference Production Example 29

The same reaction as that of Reference production example 20 was carried out except that 2-methylphenyl cyclohexanecarboxylate described in Reference production example 28 was used in place of 2-methylphenyl propionate in Reference production example 20 to obtain cyclohexyl-(4-hydroxy-3-methyl-phenyl)-methanone.

Cyclohexyl-(4-hydroxy-3-methyl-phenyl)-methanone

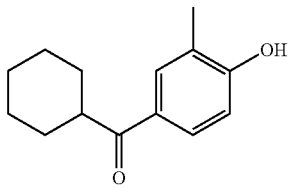 [SMILES: Cc1cc(C(=O)C2CCCCC2)ccc1O]

¹H-NMR (CDCl₃) δ: 7.77 (1H, d, J=2.17 Hz), 7.73 (1H, dd, J=8.45, 2.17 Hz), 6.82 (1H, d, J=8.45 Hz), 3.25-3.19 (1H, m), 2.29 (3H, s), 1.87-1.83 (4H, m), 1.76-1.25 (6H, m).

Reference Production Example 30

The same reaction as that of Reference production example 21 was carried out except that cyclohexyl-(4-hydroxy-3-methyl-phenyl)-methanone described in Reference production example 29 was used in place of 1-(4-hydroxy-3-methyl-phenyl)propan-1-one in Reference production example 21 to obtain 2-methyl-4-(1-methoxyimino-1-cyclohexyl-methyl)phenol.

2-methyl-4-(1-methoxyimino-1-cyclohexyl-methyl) phenol

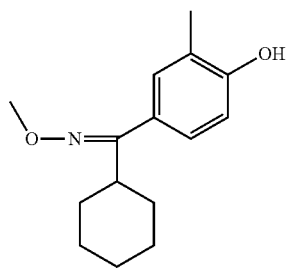 [SMILES: CON=C(c1ccc(O)c(C)c1)C1CCCCC1]

1H-NMR (CDCl3) δ: 7.10 (0.5H, d, J=2.06 Hz), 7.05 (0.5H, dd, J=8.24, 2.06 Hz), 6.97 (0.5H, d, J=1.83 Hz), 6.93 (0.5H, dd, J=8.24, 1.83 Hz), 6.73 (0.5H, d, J=8.24 Hz), 6.67 (0.5H, d, J=8.24 Hz), 3.91 (1.5H, s), 3.78 (1.5H, s), 3.21-3.11 (0.5H, m), 2.44-2.36 (0.5H, m), 2.23 (1.5H, s), 2.22 (1.5H, s), 1.84-1.60 (4H, m), 1.48-1.12 (6H, m).

Reference Production Example 31

The same reaction as that of Reference production example 19 was carried out except that pentanoyl chloride was used in place of propionyl chloride in Reference production example 19 to obtain 2-methylphenyl pentanoate.

2-methylphenyl pentanoate

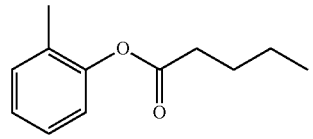

¹H-NMR (CDCl₃) δ: 7.22-7.19 (2H, m), 7.13 (1H, td, J=7.37, 1.09 Hz), 6.99 (1H, dd, J=7.61, 1.09 Hz), 2.58 (2H, t, J=7.61 Hz), 2.18 (3H, s), 1.80-1.73 (2H, m), 1.50-1.42 (2H, m), 0.98 (3H, t, J=7.37 Hz).

Reference Production Example 32

The same reaction as that of Reference production example 20 was carried out except that 2-methylphenyl pentanoate described in Reference production example 31 was used in place of 2-methylphenyl propionate in Reference production example 20 to obtain 1-(4-hydroxy-3-methyl-phenyl)-pentan-1-one.

1-(4-hydroxy-3-methyl-phenyl)-pentan-1-one

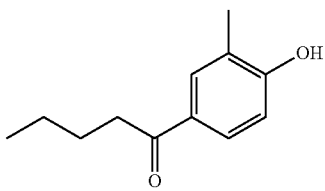

¹H-NMR (CDCl₃) δ: 7.80 (1H, d, J=2.17 Hz), 7.74 (1H, dd, J=8.45, 2.17 Hz), 6.85 (1H, d, J=8.45 Hz), 6.28 (1H, br s), 2.92 (2H, t, J=7.49 Hz), 2.31 (3H, t, J=5.31 Hz), 1.75-1.67 (2H, m), 1.44-1.36 (2H, m), 0.95 (3H, t, J=7.31 Hz).

Reference Production Example 33

The same reaction as that of Reference production example 21 was carried out except that 1-(4-hydroxy-3-methyl-phenyl)-pentan-1-one described in Reference production example 32 was used in place of 1-(4-hydroxy-3-methyl-phenyl)propan-1-one in Reference production example 21 to obtain 2-methyl-4-(1-methoxyimino-pentyl) phenol.

2-methyl-4-(1-methoxyimino-pentyl)phenol

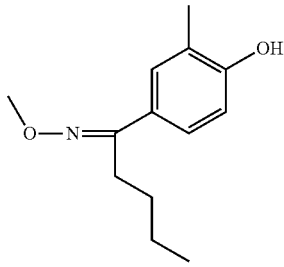 [SMILES: CCCCC(=NOC)c1ccc(O)c(C)c1]

1H-NMR (CDCl3) δ: 7.43 (1H, d, J=2.17 Hz), 7.32 (1H, dd, J=8.45, 2.17 Hz), 6.74 (1H, d, J=8.45 Hz), 4.96 (1H, br s), 3.95 (3H, s), 2.69 (2H, t, J=7.87 Hz), 2.26 (3H, s), 1.53-1.43 (2H, m), 1.41-1.31 (2H, m), 0.91 (3H, t, J=7.24 Hz).

Reference Production Example 34

The same reaction as that of Reference production example 19 was carried out except that benzoic acid chloride was used in place of propionyl chloride in Reference production example 19 to obtain 2-methylphenyl benzoate.

2-methylphenyl benzoate

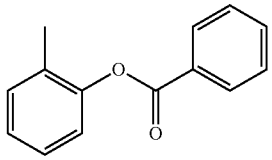 [SMILES: Cc1ccccc1OC(=O)c1ccccc1]

1H-NMR (CDCl3) δ: 8.25-8.21 (2H, m), 7.65 (1H, tt, J=7.44, 1.45 Hz), 7.53 (2H, t, J=7.44 Hz), 7.30-7.23 (2H, m), 7.21-7.13 (2H, m), 2.24 (3H, s).

Reference Production Example 35

The same reaction as that of Reference production example 20 was carried out except that 2-methylphenyl benzoate described in Reference production example 34 was used in place of 2-methylphenyl propionate in Reference production example 20 to obtain (4-hydroxy-3-methyl-phenyl)-phenyl-methanone. was obtained in the same reaction as in Reference production example 20.

(4-hydroxy-3-methyl-phenyl)-phenyl-methanone

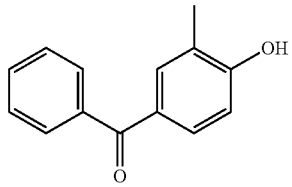 [SMILES: Cc1cc(C(=O)c2ccccc2)ccc1O]

1H-NMR (CDCl3) δ: 7.76-7.72 (2H, m), 7.68 (1H, d, J=1.37 Hz), 7.60-7.53 (2H, m), 7.49-7.43 (2H, m), 6.84 (1H, d, J=8.24 Hz), 6.37 (1H, br s), 2.29 (3H, s).

Reference Production Example 36

2-methyl-4-(methoxyimino-1-phenyl-methyl)phenol was obtained in the same reaction as in Reference production example 21 except that (4-hydroxy-3-methyl-phenyl)-phenyl-methanone described in Reference production example 35 was used in place of 1-(4-hydroxy-3-methyl-phenyl)propan-1-one.

2-methyl-4-(methoxyimino-1-phenyl-methyl)phenol

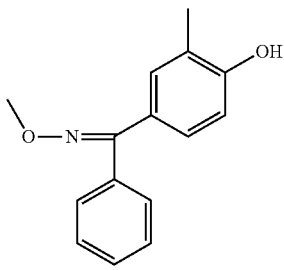 [SMILES: CON=C(c1ccccc1)c1ccc(O)c(C)c1]

1H-NMR (CDCl3) δ: 7.51-7.46 (1H, m), 7.45-7.30 (4.5H, m), 7.17-7.15 (0.5H, m), 7.14-7.10 (1H, m), 6.82 (0.5H, d, J=8.01 Hz), 6.71 (0.5H, d, J=8.47 Hz), 5.94 (1H, br s), 3.99 (1.4H, s), 3.95 (1.6H, s), 2.26 (1.4H, s), 2.23 (1.6H, s).

Reference Production Example 37

The same reaction as that of Reference production example 21 was carried out except that 4-hydroxy-3-methyl-benzaldehyde was used in place of 1-(4-hydroxy-3-methyl-phenyl)propan-1-one in Reference production example 21 to obtain 2-methyl-4-methoxyiminomethylphenol.

2-methyl-4-methoxyiminomethylphenol

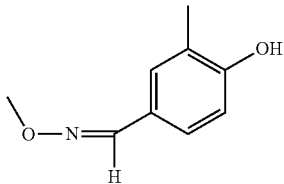

1H-NMR (CDCl3) δ: 7.98 (1H, s), 7.40 (1H, d, J=2.45 Hz), 7.28 (1H, dd, J=8.21, 2.45 Hz), 6.76 (1H, d, J=8.21 Hz), 5.09 (1H, br s), 3.94 (3H, s), 2.25 (3H, s).

Reference Production Example 38

The same reaction as that of Reference production example 21 was carried out except that 4'-hydroxy-3'-methyl-acetophenone was used in place of 1-(4-hydroxy-3-methyl-phenyl)propan-1-one in Reference production example 21 to obtain 2-methyl-4-(1-methoxyimino-ethyl)phenol.

2-methyl-4-(1-methoxyimino-ethyl)phenol

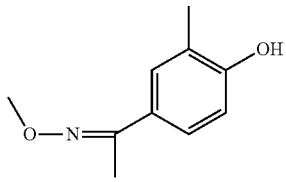

1H-NMR (CDCl3) δ: 7.44 (1H, d, J=2.29 Hz), 7.34 (1H, dd, J=8.45, 2.29 Hz), 6.74 (1H, d, J=8.45 Hz), 5.08 (1H, br s), 3.97 (3H, s), 2.25 (3H, s), 2.19 (3H, s).

Reference Production Example 39

The same reaction as that of Reference production example 19 was carried out except that 2-chlorobenzoic acid chloride was used in place of propionyl chloride in Reference production example 19 to obtain 2-methylphenyl 2-chlorobenzoate.

2-methylphenyl 2-chlorobenzoate

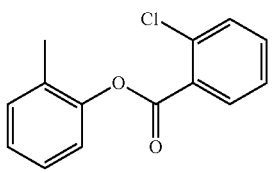 [SMILES: Cc1ccccc1OC(=O)c1ccccc1Cl]

1H-NMR (CDCl3) δ: 8.07 (1H, d, J=7.79 Hz), 7.56-7.48 (2H, m), 7.45-7.38 (1H, m), 7.32-7.25 (2H, m), 7.23-7.19 (1H, m), 7.17 (1H, d, J=7.56 Hz), 2.28 (3H, s).

Reference Production Example 40

The same reaction as that of Reference production example 20 was carried out except that 2-methylphenyl 2-chlorobenzoate described in Reference production example 39 was used in place of 2-methylphenyl propionate in Reference production example 20 to obtain 2-chlorophenyl-(4-hydroxy-3-methyl-phenyl)methanone.

2-chlorophenyl-(4-hydroxy-3-methyl-phenyl)methanone

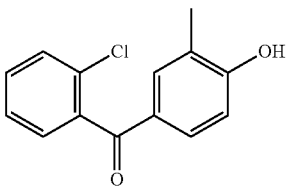 [SMILES: Cc1cc(C(=O)c2ccccc2Cl)ccc1O]

1H-NMR (CDCl3) δ: 7.69-7.67 (1H, m), 7.53 (1H, dd, J=8.36, 2.18 Hz), 7.50-7.37 (2H, m), 7.37-7.33 (2H, m), 6.80 (1H, d, J=8.24 Hz), 5.85 (1H, br s), 2.27 (3H, s).

Reference Production Example 41

The same reaction as that of Reference production example 21 was carried out except that 2-chlorophenyl-(4-hydroxy-3-methyl-phenyl)-methanone described in Reference production example 40 was used in place of 1-(4-hydroxy-3-methyl-phenyl)propan-1-one in Reference production example 21 to obtain 2-methyl-4-{1-methoxy-imino-1-(2-chlorophenyl)-methyl}phenol.

2-methyl-4-{1-methoxyimino-1-(2-chlorophenyl)-methyl}phenol

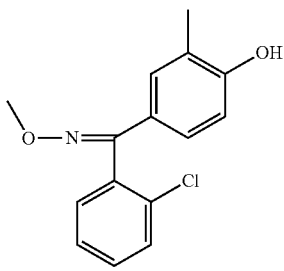 [SMILES: CON=C(c1ccc(O)c(C)c1)c1ccccc1Cl]

1H-NMR (CDCl3) δ: 7.50-7.45 (1H, m), 7.38-7.30 (3H, m), 7.19-7.15 (1H, m), 7.10 (1H, dd, J=8.36, 2.18 Hz), 6.70 (1H, d, J=8.24 Hz), 5.20 (1H, br s), 3.95 (3H, s), 2.23 (3H, s).

Reference Production Example 42

The same reaction as that of Reference production example 19 was carried out except that 3-chlorobenzoic acid chloride was used in place of propionyl chloride in Reference production example 19 to obtain 2-methylphenyl 3-chlorobenzoate.

2-methylphenyl 3-chlorobenzoate

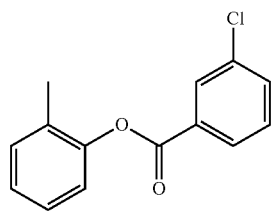 [SMILES: Cc1ccccc1OC(=O)c1cccc(Cl)c1]

1H-NMR (CDCl3) δ: 8.20 (1H, t, J=1.83 Hz), 8.11 (1H, dt, J=7.79, 1.26 Hz), 7.64-7.60 (1H, m), 7.47 (1H, t, J=7.90 Hz), 7.31-7.23 (2H, m), 7.21 (1H, dd, J=7.44, 1.26 Hz), 7.12 (1H, dd, J=7.90, 1.03 Hz), 2.23 (3H, s).

Reference Production Example 43

The same reaction as that of Reference production example 20 was carried out except that 2-methylphenyl 3-chlorobenzoate described in Reference production example 42 was used in place of 2-methylphenyl propionate in Reference production example 20 to obtain 3-chlorophenyl-(4-hydroxy-3-methyl-phenyl)-methanone.

3-chlorophenyl-(4-hydroxy-3-methyl-phenyl)-methanone

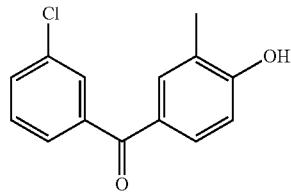 [SMILES: Cc1cc(C(=O)c2cccc(Cl)c2)ccc1O]

1H-NMR (CDCl3) δ: 7.72 (1H, d, J=1.69 Hz), 7.67 (1H, s), 7.63-7.50 (3H, m), 7.44-7.38 (1H, m), 6.84 (1H, d, J=8.21 Hz), 5.61 (1H, br s), 2.30 (3H, s).

Reference Production Example 44

The same reaction as that of Reference production example 21 was carried out except that 3-chlorophenyl-(4-hydroxy-3-methyl-phenyl)-methanone described in Reference production example 43 was used in place of 1-(4-hydroxy-3-methyl-phenyl)propane-1-one in Reference production example 21 to obtain 3-methyl-4-{1-methoxyimino-1-(3-chlorophenyl)-methyl}phenol.

2-methyl-4-{1-methoxyimino-1-(3-chlorophenyl)-methyl}phenol

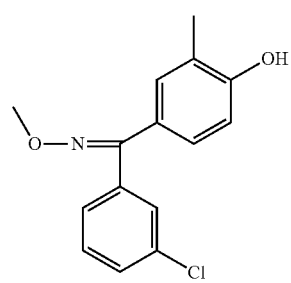 [SMILES: CON=C(c1cccc(Cl)c1)c1ccc(O)c(C)c1]

1H-NMR (CDCl3) δ: 7.50 (0.5H, t, J=1.83 Hz), 7.39-7.28 (2.5H, m), 7.28-7.24 (1.0H, m), 7.22-7.18 (0.5H, m), 7.12 (1.0H, d, J=6.18 Hz), 7.11-7.08 (0.5H, m), 6.82 (0.5H, d, J=8.24 Hz), 6.71 (0.5H, d, J=8.47 Hz), 5.00 (0.5H, s), 4.96 (0.5H, s), 3.99 (1.5H, s), 3.95 (1.5H, s), 2.26 (1.5H, s), 2.23 (1.5H, s).

Reference Production Example 45

The same reaction as that of Reference production example 19 was carried out except that 4-chlorobenzoic acid chloride was used in place of propionylchloride in Reference production example 19 to obtain 2-methylphenyl 4-chlorobenzoate.

2-methylphenyl 4-chlorobenzoate

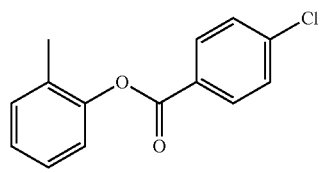 [SMILES: Cc1ccccc1OC(=O)c1ccc(Cl)cc1]

1H-NMR (CDCl3) δ: 8.16 (2H, d, J=8.16 Hz), 7.50 (2H, d, J=8.16 Hz), 7.32-7.23 (2H, m), 7.21 (1H, d, J=7.56 Hz), 7.13 (1H, d, J=7.79 Hz), 2.23 (3H, s).

Reference Production Example 46

The same reaction as that of Reference production example 20 was carried out except that 2-methylphenyl 4-chlorobenzoate described in Reference production example 45 was used in place of 2-methylphenyl propionate to obtain 4-chlorophenyl-(4-hydroxy-3-methyl-phenyl)methanone.

4-chlorophenyl-(4-hydroxy-3-methyl-phenyl)methanone

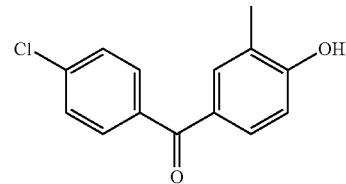 [SMILES: Cc1cc(C(=O)c2ccc(Cl)cc2)ccc1O]

1H-NMR (CDCl3) δ: 7.70 (2H, d, J=8.47 Hz), 7.65 (1H, s), 7.59-7.54 (1H, m), 7.45 (2H, d, J=8.47 Hz), 6.83 (1H, d, J=8.47 Hz), 5.43 (1H, br s), 2.30 (3H, s).

Reference Production Example 47

The same reaction as that of Reference production example 21 was carried out except that 4-chlorophenyl-(4-hydroxy-3-methyl-phenyl)-methanone described in Reference production example 46 was used in place of 1-(4-hydroxy-3-methyl-phenyl)propan-1-one in Reference production example 21 to obtain 3-methyl-4-{1-methoxyimino-1-(4-chlorophenyl)-methyl}phenol.

2-methyl-4-{1-methoxyimino-1-(4-chlorophenyl)-methyl}phenol

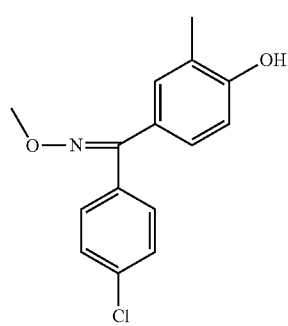 [SMILES: CON=C(c1ccc(Cl)cc1)c1ccc(O)c(C)c1]

1H-NMR (CDCl3) δ: 7.44-7.39 (2.0H, m), 7.32-7.27 (2.5H, m), 7.14-7.08 (1.5H, m), 6.81 (0.5H, d, J=8.01 Hz), 6.71 (0.5H, d, J=8.24 Hz), 5.03 (0.5H, s), 5.00 (0.5H, s), 3.98 (1.5H, s), 3.95 (1.5H, s), 2.25 (1.5H, s), 2.23 (1.5H, s).

Reference Production Example 48

15 g of acetyl chloride and 49 g of triethylamine were added to a mixture of 20 g of 2,5-dimethylphenol and 150 ml of chloroform at 0° C. and the mixture was heated to ambient temperature, followed by stirring for 4 hr. Then, the mixture was extracted with chloroform. The organic phase was washed with water, dried by magnesium sulfate anhydride, and concentrated under reduced pressure. The obtained residue was subjected to silica gel column chromatography to obtain 24 g of 2,5-dimethylphenyl acetate.

2,5-dimethylphenyl acetate

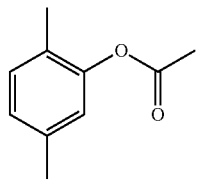

$^1$H-NMR (CDCl$_3$) δ: 7.10 (1H, d, J=7.7 Hz), 6.95 (1H, d, J=7.2 Hz), 6.82 (1H, s), 2.31 (6H, s), 2.13 (3H, s).

Reference Production Example 49

49 g of aluminum trichloride was added to a mixture of 24 g of 2,5-dimethylphenyl acetate described in Reference production example 48 and 200 mL of nitromethane at ambient temperature and the mixture was heated to 50° C. The mixture was stirred for 8.5 hr and then, poured into 300 ml of ice water to extract the mixture with chloroform. The organic phase was washed with water, dried by magnesium sulfate anhydride, and concentrated under reduced pressure. The obtained residue was subjected to silica gel column chromatography to obtain 21 g of 1-(2,5-dimethyl-4-hydroxy-phenyl)-ethanone.

1-(2,5-dimethyl-4-hydroxy-phenyl)-ethanone

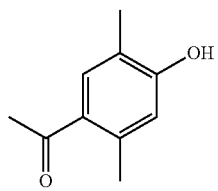

$^1$H-NMR (CDCl$_3$) δ: 7.59 (1H, s), 6.64 (1H, s), 5.56 (1H, s), 2.55 (3H, s), 2.50 (3H, s), 2.26 (3H, s).

Reference Production Example 50

The same reaction as that of Reference production example 21 was carried out except that 1-(2,5-dimethyl-4-hydroxyphenyl)-ethanone described in Reference production example 49 was used in place of 1-(4-hydroxy-3-methyl-phenyl)propan-1-one in Reference production example 21 to obtain 2,5-dimethyl-4-(1-methoxyimino-ethyl)phenol.

2,5-dimethyl-4-(1-methoxyimino-ethyl)phenol

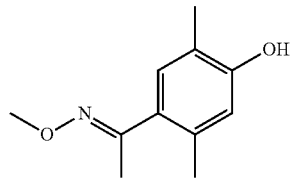

1H-NMR (CDCl3) δ: 6.98 (1H, s), 6.58 (1H, s), 4.92 (1H, br s), 3.96 (3H, s), 2.26 (3H, s), 2.19 (3H, s), 2.13 (3H, s).

Reference Production Example 51

The same reaction as that of Reference production example 48 was carried out except that 2-bromophenol was used in place of 2,5-dimethylphenol in Reference production example 48 to obtain 2-bromophenyl acetate.

2-bromophenyl acetate

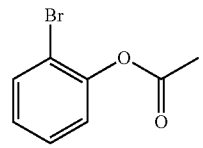

$^1$H-NMR (CDCl$_3$) δ: 7.61 (1H, d, J=7.3 Hz), 7.34 (1H, t, J=7.3 Hz), 7.16-7.10 (2H, m), 2.36 (3H, s).

Reference Production Example 52

The same reaction as that of Reference production example 20 except that 2-bromophenyl acetate described in Reference production example 51 was used in place of 2-methylphenyl propionate in Reference production example 20 to obtain 1-(3-bromo-4-hydroxy-phenyl)-ethanone.

1-(3-bromo-4-hydroxy-phenyl)-ethanone

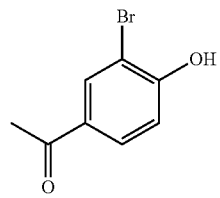

$^1$H-NMR (CDCl$_3$) δ: 7.08 (1H, d, J=8.01 Hz), 6.68-6.60 (2H, m), 5.31 (1H, br s), 2.30 (3H, s).

Reference Production Example 53

The same reaction as that of Reference production example 21 was carried out except that 1-(3-bromo-4- hydroxy-phenyl)-ethanone described in Reference production example 52 was used in place of 1-(4-hydroxy-3-methyl-phenyl)propan-1-one in Reference production example 21 to obtain 2-bromo-4-(1-methoxyimino-ethyl)phenol.

2-bromo-4-(1-methoxyimino-ethyl)phenol

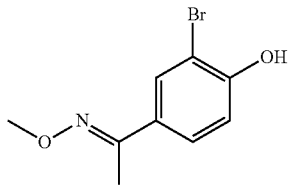

1H-NMR (CDCl3) δ: 7.80 (1H, d, J=2.06 Hz), 7.51 (1H, dd, J=8.47, 2.06 Hz), 7.00 (1H, d, J=8.47 Hz), 5.72 (1H, br s), 3.98 (3H, s), 2.17 (3H, s).

Reference Production Example 54

The same reaction as that of Reference production example 19 was carried out except that 3,3-dimethylbutanoyl chloride was used in place of propionyl chloride in Reference production example 19 to obtain 2-methylphenyl 3,3-dimethybutanoate.

2-methylphenyl 3,3-dimethybutanoate

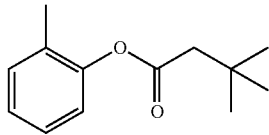

¹H-NMR (CDCl₃) δ: 7.24-7.18 (2H, m), 7.13 (1H, td, J=7.33, 1.37 Hz), 7.00 (1H, d, J=7.33 Hz), 2.48 (2H, s), 2.20 (3H, s), 1.15 (9H, s).

Reference Production Example 55

The same reaction as that of Reference production example 20 was carried out except that 2-methylphenyl 3,3-dimethylbutanoate described in Reference production example 54 was used in place of 2-methylphenyl propionate in Reference production example 20 to obtain 1-(4-hydroxy-3-methyl-pheny)-3,3-dimethylbutan-1-one.

1-(4-hydroxy-3-methyl-pheny)-3,3-dimethylbutan-1-one

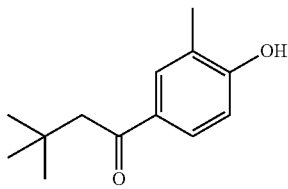

¹H-NMR (CDCl₃) δ: 7.79-7.77 (1H, m), 7.72 (1H, dd, J=8.47, 2.29 Hz), 6.83 (1H, d, J=8.47 Hz), 6.23 (1H, s), 2.80 (2H, s), 2.29 (3H, s), 1.05 (9H, s).

Reference Production Example 56

The same reaction as that of Reference production example 21 was carried out except that 1-(4-hydroxy-3-methyl-phenyl)-3,3-dimethylbutan-1-one described in Reference production example 55 was used in place of 1-(4-hydroxy-3-methyl-phenyl)propan-1-one in Reference production example 21 to obtain 2-methyl-4-(1-methoxyimino-3,3-dimethyl-butyl)phenol.

2-methyl-4-(1-methoxyimino-3,3-dimethyl-butyl)phenol

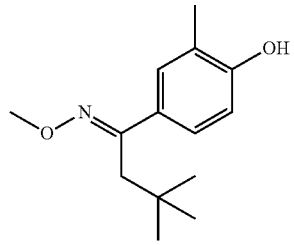 [SMILES: CO/N=C(\CC(C)(C)C)c1ccc(O)c(C)c1]

1H-NMR (CDCl3) δ: 7.34 (1H, d, J=2.18 Hz), 7.23 (1H, dd, J=8.24, 2.18 Hz), 6.71 (1H, d, J=8.24 Hz), 5.01 (1H, br s), 3.91 (3H, s), 2.70 (2H, s), 2.24 (3H, s), 0.85 (9H, s).

Reference Production Example 57

1.0 mL of hydrochloric acid (12M) was added to a mixture of 3.00 g of 4'-hydroxy-3'-methyl-acetophenone, 1.95 g of O-ethylhydroxyamine hydrochloride and 40 mL of ethanol and then, the mixture was stirred at ambient temperature for 4 hr. Saturated sodium bicarbonate was added to the mixture, which was then extracted three times with chloroform and washed with saturated saline. The obtained solution was dried by sodium sulfate and subjected to filtration, and the filtrate was concentrated to obtain 3.08 g of 2-methyl-4-(1-ethoxyimino-ethyl)phenol.

2-methyl-4-(1-ethoxyimino-ethyl)phenol

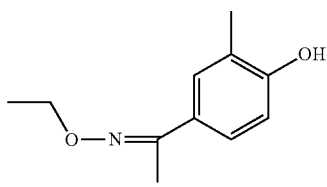

1H-NMR (CDCl3) δ: 7.45 (1H, s), 7.35 (1H, dd, J=8.24, 1.95 Hz), 6.74 (1H, d, J=8.24 Hz), 4.88 (1H, s), 4.22 (2H, q, J=7.10 Hz), 2.26 (3H, s), 2.20 (3H, s), 1.32 (3H, t, J=7.10 Hz).

Reference Production Example 58

The same reaction as that of Reference production example 57 was carried out except that 3'-chloro-4'-hydroxyacetophenone was used in place of 4'-hydroxy-3'-methyl-acetophenone in Reference production example 57 to obtain 2-chloro-4-(1-ethoxyimino-ethyl)phenol.

2-chloro-4-(1-ethoxyimino-ethyl)phenol

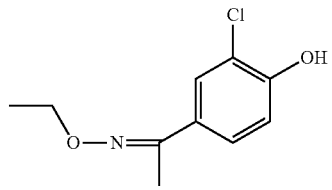

1H-NMR (CDCl3) δ: 7.66 (1H, d, J=2.2 Hz), 7.47 (1H, dd, J=8.5, 2.2 Hz), 6.99 (1H, d, J=8.5 Hz), 5.65 (1H, s), 4.22 (2H, q, J=7.1 Hz), 2.18 (3H, s), 1.32 (3H, t, J=7.1 Hz).

Reference Production Example 59

The same reaction as that of Reference production example 57 was carried out except that O-(tert-butyl)hydroxyamine hydrochloride was used in place of O-ethylhydroxyamine hydrochloride in Reference production example 57 to obtain 2-methyl-4-{1-(tert-butoxy)imino-ethyl}phenol.

2-methyl-4-{1-(tert-butoxy)imino-ethyl}phenol

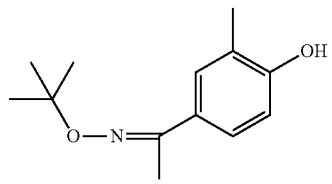 [SMILES: CC(=NOC(C)(C)C)c1ccc(O)c(C)c1]

1H-NMR (CDCl3) δ: 7.47-7.45 (1H, m), 7.40 (1H, dd, J=8.45, 2.29 Hz), 6.74 (1H, d, J=8.45 Hz), 4.77 (1H, br s), 2.27 (3H, s), 2.16 (3H, s), 1.35 (9H, s).

Reference Production Example 60

The same reaction as that of Reference production example 57 was carried out except that O-allylhydroxyamine hydrochloride was used in place of O-ethylhydroxyamine hydrochloride in Reference production example 57 to obtain 2-methyl-4-(1-allyloxyimino-ethyl)phenol.

2-methyl-4-(1-allyloxyimino-ethyl)phenol

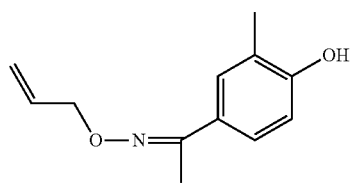

1H-NMR (CDCl3) δ: 7.43 (1H, d, J=2.18 Hz), 7.34 (1H, dd, J=8.47, 2.18 Hz), 6.72 (1H, d, J=8.47 Hz), 6.11-5.99 (1H, m), 5.36-5.29 (1H, m), 5.24-5.19 (1H, m), 4.95 (1H, br s), 4.67 (2H, dt, J=5.72, 1.37 Hz), 2.24 (3H, s), 2.21 (3H, s).

Reference Production Example 61

The same reaction as that of Reference production example 57 was carried out except that O-benzylhydroxyamine hydrochloride was used in place of O-ethylhydroxyamine hydrochloride in Reference production example 57 to obtain 2-methyl-4-(1-benzyloxyimino-ethyl)phenol.

2-methyl-4-(1-benzyloxyimino-ethyl)phenol

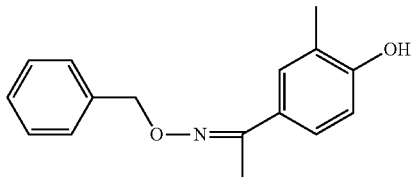 [SMILES: CC(=NOCc1ccccc1)c1ccc(O)c(C)c1]

1H-NMR (CDCl3) δ: 7.44-7.30 (7H, m), 6.73 (1H, d, J=8.45 Hz), 5.22 (2H, s), 5.04 (1H, s), 2.25 (3H, s), 2.23 (3H, s).

Reference Production Example 62

The same reaction as that of Reference production example 57 was carried out except that O-(n-butyl)hydroxyamine described in Reference production example 63 was used in place of O-ethylhydroxyamine hydrochloride in Reference production example 57 to obtain 2-methyl-4-(1-butoxyimino-ethyl)phenol.

2-methyl-4-(1-butoxyimino-ethyl)phenol

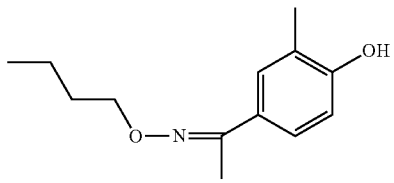 [SMILES: CCCCON=C(C)c1ccc(O)c(C)c1]

1H-NMR (CDCl3) δ: 7.78 (1H, d, J=2.17 Hz), 7.73 (1H, dd, J=8.45, 2.17 Hz), 6.81 (1H, d, J=8.45 Hz), 4.17 (2H, t, J=6.64 Hz), 2.55 (3H, s), 2.19 (3H, s), 1.74-1.66 (2H, m), 1.48-1.38 (2H, m), 0.96 (3H, t, J=7.37 Hz).

Reference Production Example 63

A mixture of 3.62 g of N-butoxyphthalimide described in Reference production example 64, 2.48 g of hydrazine monohydrate, 4.5 mL of methanol, and 45 mL of chloroform was stirred at ambient temperature for 2 hr and the reaction mixture was filtered. The filtrate was washed with saturated saline, dried by magnesium sulfate anhydride, and concentrated under reduced pressure. The obtained residue was subjected to silica gel column chromatography to obtain 0.390 g of O-(n-butyl)hydroxyamine.

O-(n-butyl)hydroxyamine

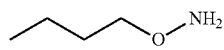

1H-NMR (CDCl3) δ: 5.34 (2H, br s), 3.67 (2H, t, J=6.71 Hz), 1.60-1.52 (2H, m), 1.41-1.31 (2H, m), 0.93 (3H, t, J=7.32 Hz).

Reference Production Example 64

A mixture of 3.26 g of N-hydroxyphthalimide, 2.74 g of 1-bromobutane, 4.05 g of triethylamine, and 40 mL of dimethylformamide was stirred at 80° C. for 4 hr. Water was added to the reaction mixture, which was then extracted three times with chloroform and washed with saturated saline. The obtained solution was dried by magnesium sulfate anhydride, subjected to filtration, and the filtrate was concentrated. The obtained residue was subjected to silica gel column chromatography to obtain 3.79 g of N-butoxyphthalimide.

N-butoxyphthalimide

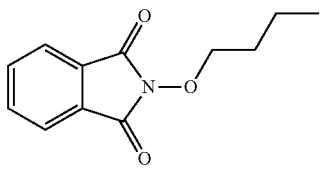 [SMILES: CCCCON1C(=O)c2ccccc2C1=O]

1H-NMR (CDCl3) δ: 7.86-7.82 (2H, m), 7.77-7.73 (2H, m), 4.21 (2H, t, J=6.64 Hz), 1.82-1.74 (2H, m), 1.58-1.48 (2H, m), 0.98 (3H, t, J=7.37 Hz).

Reference Production Example 65

A mixture of 5.66 g of 1-(2-bromomethyl-3-methyl-phenyl)-4-methyl-1,4-dihydrotetrazol-5-one, 3.00 g of 4'-hydroxy-3'-methyl-acetophenone, 5.53 g of potassium carbonate described in Reference production example 11, and 40 mL of acetonitrile was refluxed under heating with stirring for 4 hr. The reaction mixture was cooled to ambient temperature and the reaction mixture was filtered and concentrated. The obtained residue was subjected to silica gel column chromatography to obtain 4.73 g of 1-{2-(2-methyl-4-acetyl-phenoxymethyl)-3-methyl-phenyl}-4-methyl-1,4-dihydrotetrazol-5-one.

1-{2-(2-methyl-4-acetyl-phenoxymethyl)-3-methyl-phenyl}-4-methyl-1,4-dihydrotetrazol-5-one

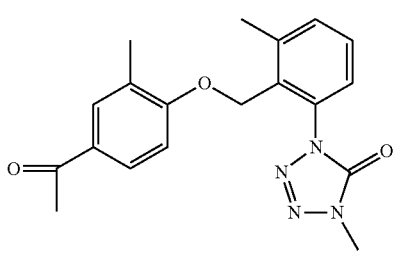 [SMILES: CC(=O)c1ccc(OCc2c(C)cccc2-n2nnn(C)c2=O)c(C)c1]

1H-NMR (CDCl3) δ: 7.79 (1H, dd, J=8.54, 2.24 Hz), 7.75 (1H, d, J=1.46 Hz), 7.46-7.40 (2H, m), 7.29 (1H, dd, J=7.32, 1.95 Hz), 6.86 (1H, d, J=8.54 Hz), 5.11 (2H, s), 3.62 (3H, s), 2.54 (3H, s), 2.50 (3H, s), 2.12 (3H, s).

Reference Production Example 66

The same reaction as that of Reference production example 65 was carried out except that 1-(2-bromomethyl-3-methoxyphenyl)-4-methyl-1,4-dihydrotetrazol-5-one described in Reference production example 8 was used in place of 1-(2-bromomethyl-3-methyl-phenyl)-4-methyl-1,4-dihydrotetrazol-5-one in Reference production example 65 to obtain 1-{2-(2-methyl-4-acetyl-phenoxymethyl)-3-methoxy-phenyl}-4-methyl-1,4-dihydrotetrazol-5-one.

1-{2-(2-methyl-4-acetyl-phenoxymethyl)-3-methoxy-phenyl}-4-methyl-1,4-dihydrotetrazol-5-one

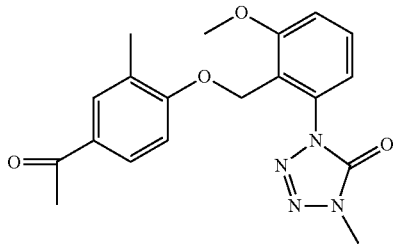 [SMILES: COc1cccc(-n2nnn(C)c2=O)c1COc1ccc(C(C)=O)cc1C]

1H-NMR (CDCl3) δ: 7.76 (1H, dd, J=8.54, 2.29 Hz), 7.72-7.69 (1H, m), 7.48 (1H, t, J=8.21 Hz), 7.12-7.06 (2H, m), 6.91 (1H, d, J=8.54 Hz), 5.35 (2H, s), 3.94 (3H, s), 3.59 (3H, s), 2.52 (3H, s), 2.02 (3H, s).

Reference Production Example 67

The same reaction as that of Reference production example 65 was carried out except that 1-(4-hydroxy-3-methyl-phenyl)-propane-1-one described in Reference production example 20 was used in place of 4'-hydroxy-3'-methyl-acetophenone in Reference production example 65 to obtain 1-[2-(4-propionyl-2-methyl-phenoxymethyl)-3-methoxy-pheny 1]-4-methyl-1,4-dihydrotetrazol-5-one.

1-[2-(4-propionyl-2-methyl-phenoxymethyl)-3-methoxy-pheny 1]-4-methyl-1,4-dihydrotetrazol-5-one

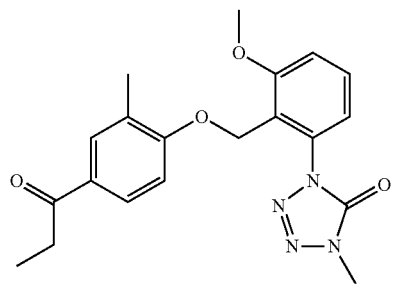 [SMILES: CCC(=O)c1ccc(OCc2c(OC)cccc2-n2nnn(C)c2=O)c(C)c1]

¹H-NMR (CDCl₃) δ: 7.77 (1H, dd, J=8.6, 2.3 Hz), 7.71 (1H, d, J=2.2 Hz), 7.48 (1H, t, J=8.2 Hz), 7.09 (2H, t, J=8.1

Hz), 6.90 (1H, d, J=8.5 Hz), 5.34 (2H, s), 3.94 (3H, s), 3.59 (3H, s), 2.92 (2H, q, J=7.2 Hz), 2.02 (3H, s), 1.19 (3H, t, J=7.2 Hz).

Reference Production Example 68

The same reaction as that of Reference production example 65 was carried out except that 1-(4-hydroxy-3-methyl-phenyl)-2-methyl-propane-1-one described in Reference production example 26 was used in place of 4'-hydroxy-3'-methyl-acetophenone in Reference production example 65 to obtain 1-[2-(4-isobutynyl-2-methyl-phenoxymethyl)-3-methyl-pheny l]-4-methyl-1,4-dihydrotetrazol-5-one.

1-[2-(4-isobutynyl-2-methyl-phenoxymethyl)-3-methyl-pheny l]-4-methyl-1,4-dihydrotetrazol-5-one

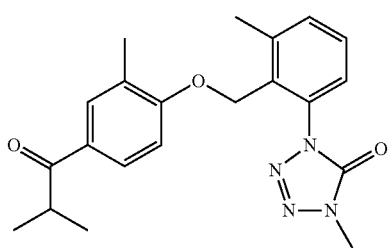 [SMILES: Cc1cc(C(=O)C(C)C)ccc1OCc1c(C)cccc1-n1nnn(C)c1=O]

1H-NMR (CDCl3) δ: 7.81 (1H, d, J=8.70 Hz), 7.78-7.75 (1H, m), 7.47-7.39 (2H, m), 7.30-7.29 (1H, m), 6.88 (1H, d, J=8.70 Hz), 5.12 (2H, s), 3.63 (3H, s), 3.55-3.48 (1H, m), 2.51 (3H, s), 2.13 (3H, s), 1.20 (6H, d, J=6.87 Hz).

Reference Production Example 69

The same reaction as that of Reference production example 66 was carried out except that 1-(4-hydroxy-3-methyl-phenyl)-2-methyl-propane-1-one described in Reference production example 26 was used in place of 4'-hydroxy-3'-methyl-acetophenone in Reference production example 66 to obtain 1-[2-(4-isobutynyl-2-methyl-phenoxymethyl)-3-methoxy-phenyl]-4-methyl-1,4-dihydrotetrazol-5-one.

1-[2-(4-isobutynyl-2-methyl-phenoxymethyl)-3-methoxy-phenyl]-4-methyl-1,4-dihydrotetrazol-5-one

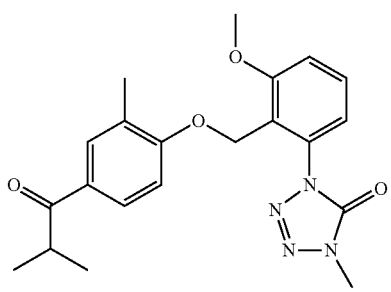 [SMILES: COc1cccc(-n2nnn(C)c2=O)c1COc1ccc(C(=O)C(C)C)cc1C]

$^1$H-NMR (CDCl$_3$) δ: 7.77 (1H, dd, J=8.69, 2.29 Hz), 7.73-7.70 (1H, m), 7.48 (1H, t, J=8.21 Hz), 7.12-7.06 (2H, m), 6.91 (1H, d, J=8.69 Hz), 5.34 (2H, s), 3.94 (3H, s), 3.59 (3H, s), 3.54-3.46 (1H, m), 2.02 (3H, s), 1.18 (6H, d, J=6.76 Hz).

Reference Production Example 70

The same reaction as that of Reference production example 65 was carried out except that 1-(4-hydroxy-3-methyl-phenyl)-propane-1-one described in Reference production example 20 was used in place of 4'-hydroxy-3'-methyl-acetophenone in Reference production example 65 to obtain 1-[2-(2-methyl-4-propionyl-phenoxymethyl)-3-methyl-phenyl]-4-methyl-1,4-dihydrotetrazol-5-one.

1-[2-(2-methyl-4-propionyl-phenoxymethyl)-3-methyl-phenyl]-4-methyl-1,4-dihydrotetrazol-5-one

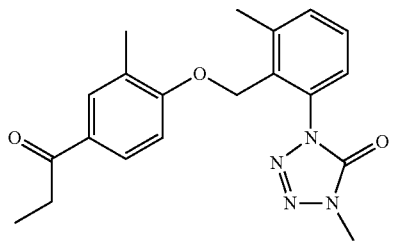 [SMILES: CCC(=O)c1ccc(OCc2c(C)cccc2-n2nnn(C)c2=O)c(C)c1]

$^1$H-NMR (CDCl$_3$) δ: 7.80 (1H, d, J=8.47 Hz), 7.77-7.74 (1H, m), 7.47-7.39 (2H, m), 7.29 (1H, d J=7.33 Hz), 6.86 (1H, d, J=8.47 Hz), 5.11 (2H, s), 3.62 (3H, s), 2.94 (2H, q, J=7.33 Hz), 2.50 (3H, s), 2.12 (3H, s), 1.20 (3H, t, J=7.33 Hz).

Reference Production Example 71

The same reaction as that of Reference production example 65 was carried out except that cyclopropyl-(4-hydroxy-3-methyl-phenyl)methanone described in Reference production example 23 was used in place of 4'-hydroxy-3'-methyl-acetophenone in Reference production example 65 to obtain 1-[2-(4-cyclopropanecarbonyl-2-methyl-phenoxymethyl)-3-methyl-phenyl]-4-methyl-1,4-dihydrotetrazol-5-one.

1-[2-(4-cyclopropanecarbonyl-2-methyl-phenoxymethyl)-3-methyl-phenyl]-4-methyl-1,4-dihydrotetrazol-5-one

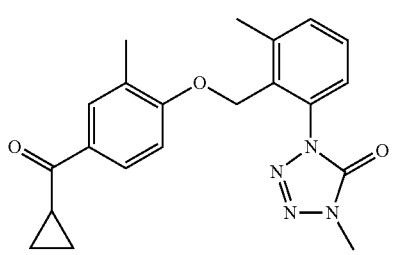 [SMILES: Cc1cc(C(=O)C2CC2)ccc1OCc1c(C)cccc1-n1nnn(C)c1=O]

$^1$H-NMR (CDCl$_3$) δ: 7.88 (1H, dd, J=8.47, 2.06 Hz), 7.83-7.80 (1H, m), 7.47-7.41 (2H, m), 7.29 (1H, dd, J=7.21, 1.72 Hz), 6.89 (1H, d, J=8.47 Hz), 5.12 (2H, s), 3.63 (3H, s), 2.65-2.61 (1H, m), 2.51 (3H, s), 2.13 (3H, s), 1.22-1.18 (2H, m), 1.02-0.96 (2H, m).

Reference Production Example 72

The same reaction as that of Reference production example 65 was carried out except that 1-(4-hydroxy-3-methyl-phenyl)-3,3-dimethyl-butan-1-one described in Reference production example 55 was used in place of 4'-hydroxy-3'-methyl-acetophenone in Reference production example 65 to obtain 1-{2-[4-(3,3-dimethyl-butyryl)-2-methyl-phenoxymethyl]-3-methyl-phenyl}-4-methyl-1,4-dihydro-tetrazol-5-one.

1-{2-[4-(3,3-dimethyl-butyryl)-2-methyl-phenoxymethyl]-3-methyl-phenyl}-4-methyl-1,4-dihydro-tetrazol-5-one

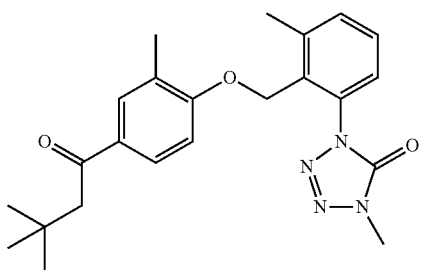 [SMILES: Cc1cc(C(=O)CC(C)(C)C)ccc1OCc1c(C)cccc1-n1nnn(C)c1=O]

¹H-NMR (CDCl₃) δ: 7.77 (1H, dd, J=8.47, 2.06 Hz), 7.75-7.73 (1H, m), 7.47-7.39 (2H, m), 7.29 (1H, dd, J=7.21, 1.72 Hz), 6.85 (1H, d, J=8.47 Hz), 5.10 (2H, s), 3.62 (3H, s), 2.79 (2H, s), 2.50 (3H, s), 2.12 (3H, s), 1.05 (9H, s).

Reference Production Example 73

The same reaction as that of Reference production example 65 was carried out except that cyclohexyl-(4-hydroxy-3-methyl-phenyl)-methanone described in Reference production example 29 was used in place of 4'-hydroxy-3'-methyl-acetophenone in Reference production example 65 to obtain 1-[2-(4-cyclohexanecarbonyl-2-methyl-phenoxymethyl)-3-methyl-phenyl]-4-methyl-1,4-dihydro-tetrazol-5-one.

1-[2-(4-cyclohexanecarbonyl-2-methyl-phenoxymethyl)-3-methyl-phenyl]-4-methyl-1,4-dihydro-tetrazol-5-one

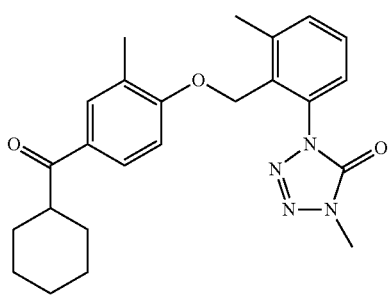 [SMILES: Cc1cc(C(=O)C2CCCCC2)ccc1OCc1c(C)cccc1-n1nnn(C)c1=O]

¹H-NMR (CDCl₃) δ: 7.79 (1H, dd, J=8.45, 2.29 Hz), 7.75-7.72 (1H, m), 7.46-7.36 (2H, m), 7.29 (1H, dd, J=7.24, 1.93 Hz), 6.86 (1H, d, J=8.45 Hz), 5.11 (2H, s), 3.62 (3H, s), 3.24-3.18 (1H, m), 2.50 (3H, s), 2.13 (3H, s), 1.89-1.79 (4H, m), 1.77-1.66 (2H, m), 1.54-1.29 (4H, m).

Reference Production Example 74

The same reaction as that of Reference production example 65 was carried out except that 1-(4-hydroxy-3-methylphenyl)-pentan-1-one described in Reference production example 32 was used in place of 4'-hydroxy-3'-methyl-acetophenone in Reference production example 65 to obtain 1-[2-(2-methyl-4-pentanoyl-phenoxymethyl)-3-methyl-phenyl]-4-methyl-1,4-dihydro-tetrazol-5-one.

1-[2-(2-methyl-4-pentanoyl-phenoxymethyl)-3-methyl-phenyl]-4-methyl-1,4-dihydro-tetrazol-5-one

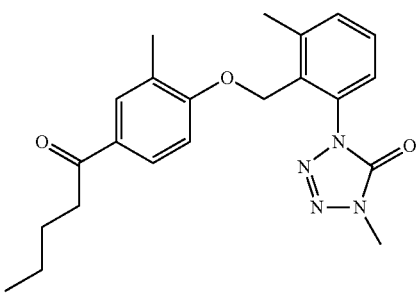 [SMILES: CCCCC(=O)c1ccc(OCc2c(C)cccc2-n2nnn(C)c2=O)c(C)c1]

¹H-NMR (CDCl₃) δ: 7.80 (1H, dd, J=8.47, 2.06 Hz), 7.76-7.74 (1H, m), 7.47-7.39 (2H, m), 7.29 (1H, dd, J=7.21, 1.72 Hz), 6.86 (1H, d, J=8.47 Hz), 5.10 (2H, s), 3.62 (3H, s), 2.89 (2H, t, J=7.44 Hz), 2.50 (3H, s), 2.12 (3H, s), 1.73-1.66 (2H, m), 1.45-1.34 (2H, m), 0.94 (3H, t, J=7.33 Hz)

Reference Production Example 75

The same reaction as that of Reference production example 65 was carried out except that 1-(3-bromo-4-hydroxy-phenyl)-ethanone described in Reference production example 52 was used in place of 4'-hydroxy-3'-methyl-acetophenone in Reference production example 65 to obtain 1-[2-(4-acetyl-2-bromo-phenoxymethyl)-3-methyl-phenyl]-4-methyl-1,4-dihydro-tetrazol-5-one.

1-[2-(4-acetyl-2-bromo-phenoxymethyl)-3-methyl-phenyl]-4-methyl-1,4-dihydro-tetrazol-5-one

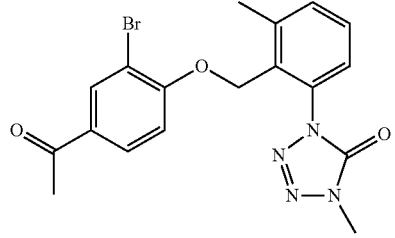 [SMILES: CC(=O)c1ccc(OCc2c(C)cccc2-n2nnn(C)c2=O)c(Br)c1]

$^1$H-NMR (CDCl$_3$) δ: 8.13 (1H, d, J=2.17 Hz), 7.86 (1H, dd, J=8.69, 2.17 Hz), 7.47-7.38 (2H, m), 7.33-7.30 (1H, m), 6.90 (1H, d, J=8.69 Hz), 5.24 (2H, s), 3.67 (3H, s), 2.55-2.53 (6H, m).

Reference Production Example 76

A mixture of 0.4 g of 1-[2-(4-acetyl-2-bromo-phenoxymethyl)-3-methyl-phenyl]-4-methyl-1,4-dihydro-tetrazol-5-one described in Reference production example 75, 0.1 g of cyclopropylboronic acid, 0.08 g of 1,1'-bis(diphenylphosphine)ferrocene-palladium (II) dichloride-dichloromethane complex, 0.3 g of cesium fluoride, and 5 ml of 1,4-dioxane was refluxed under heating with stirring for 4 hr. The mixture was concentrated under reduced pressure and the obtained residue was subjected to silica gel column chromatography to obtain 1-[2-(2-cyclopropyl-4-acetyl-phenoxymethyl)-3-methyl-phenyl]-4-methyl-1,4-dihydro-tetrazol-5-one.

1-[2-(2-cyclopropyl-4-acetyl-phenoxymethyl)-3-methyl-phenyl]-4-methyl-1,4-dihydro-tetrazol-5-one

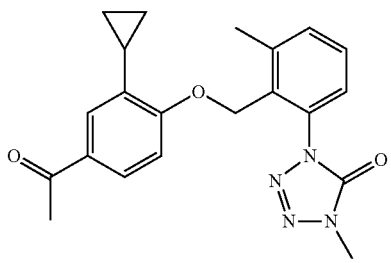 [SMILES: CC(=O)c1ccc(OCc2c(C)cccc2-n2nnn(C)c2=O)c(C2CC2)c1]

$^1$H-NMR (CDCl$_3$) δ: 7.76 (1H, dd, J=8.69, 2.17 Hz), 7.46-7.40 (3H, m), 7.30 (1H, dd, J=7.24, 1.93 Hz), 6.89 (1H, d, J=8.69 Hz), 5.16 (2H, s), 3.63 (3H, s), 3.53-3.45 (1H, m), 2.52 (3H, s), 1.19 (3H, s), 0.90-0.84 (2H, m), 0.65-0.60 (2H, m).

Reference Production Example 77

The same reaction as that of Reference production example 65 was carried out except that (4-hydroxy-3-methyl-phenyl)-phenyl-methanone described in Reference production example 35 was used in place of 4'-hydroxy-3'-methyl-acetophenone in Reference production example 65 to obtain 1-[2-(4-benzoyl-2-methyl-phenoxymethyl)-3-methyl-phenyl]-4-methyl-1,4-dihydro-tetrazol-5-one.

1-[2-(4-benzoyl-2-methyl-phenoxymethyl)-3-methyl-phenyl]-4-methyl-1,4-dihydro-tetrazol-5-one

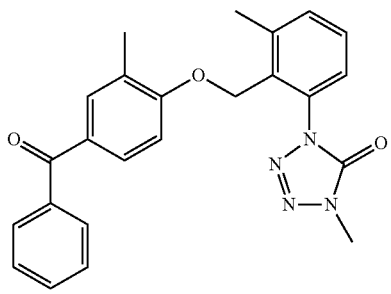 [SMILES: Cc1cc(C(=O)c2ccccc2)ccc1OCc1c(C)cccc1-n1nnn(C)c1=O]

1H-NMR (CDCl3) δ: 7.48 (1H, dd, J=7.97, 1.69 Hz), 7.45-7.37 (3H, m), 7.36-7.30 (3H, m), 7.29-7.25 (1H, m), 7.17-7.11 (2H, m), 6.75 (1H, d, J=8.45 Hz), 5.03 (2H, s), 3.63 (3H, s), 2.49 (3H, s), 2.06 (3H, s).

Reference Production Example 78

The same reaction as that of Reference production example 65 was carried out except that 2-chlorophenyl-(4-hydroxy-3-methyl-phenyl)-methanone described in Reference production example 40 was used in place of 4'-hydroxy-3'-methyl-acetophenone in Reference production example 65 to obtain 1-[2-{4-(2-chloro-benzoyl)-2-methyl-phenoxymethyl}-3-methyl-phenyl]-4-methyl-1,4-dihydro-tetrazol-5-one.

1-[2-{4-(2-chloro-benzoyl)-2-methyl-phenoxymethyl}-3-methyl-phenyl]-4-methyl-1,4-dihydro-tetrazol-5-one

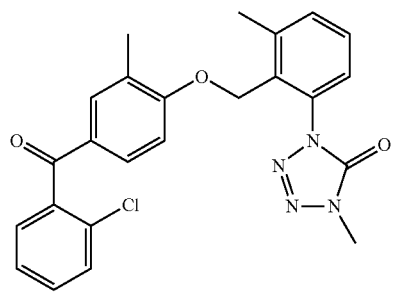 [SMILES: Cc1cc(C(=O)c2ccccc2Cl)ccc1OCc1c(C)cccc1-n1nnn(C)c1=O]

1H-NMR (CDCl3) δ: 7.66 (1H, d, J=2.29 Hz), 7.59 (1H, dd, J=8.47, 2.29 Hz), 7.47-7.37 (4H, m), 7.36-7.32 (2H, m), 7.30-7.27 (1H, m), 6.86 (1H, d, J=8.70 Hz), 5.11 (2H, s), 3.62 (3H, s), 2.50 (3H, s), 2.11 (3H, s).

Reference Production Example 79

The same reaction as that of Reference production example 65 was carried out except that 3-chlorophenyl-(4-hydroxy-3-methyl-phenyl)methanone described in Reference production example 43 was used in place of 4'-hydroxy-3'-methyl-acetophenone in Reference production example 65 to obtain 1-[2-{4-(3-chloro-benzoyl)-2-methyl-phenoxymethyl}-3-methyl-phenyl]-4-methyl-1,4-dihydro-tetrazol-5-one.

1-[2-{4-(3-chloro-benzoyl)-2-methyl-phenoxymethyl}-3-methyl-phenyl]-4-methyl-1,4-dihydro-tetrazol-5-one

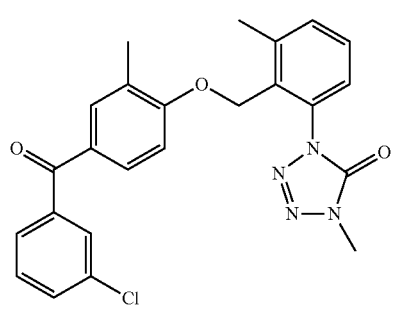 [SMILES: Cc1cc(C(=O)c2cccc(Cl)c2)ccc1OCc1c(C)cccc1-n1nnn(C)c1=O]

1H-NMR (CDCl3) δ: 7.72 (1H, t, J=1.83 Hz), 7.65-7.60 (3H, m), 7.54 (1H, d, J=7.21 Hz), 7.48-7.39 (3H, m), 7.30 (1H, dd, J=7.21, 1.95 Hz), 6.90 (1H, d, J=8.24 Hz), 5.13 (2H, s), 3.65 (3H, s), 2.52 (3H, s), 2.14 (3H, s).

Reference Production Example 80

The same reaction as that of Reference production example 65 was carried out except that 4-chlorophenyl-(4-hydroxy-3-methyl-phenyl)-methanone described in Reference production example 46 was used in place of 4'-hydroxy-3'-methyl-acetophenone in Reference production example 65 to obtain 1-[2-{4-(4-chloro-benzoyl)-2-methyl-phenoxymethyl}-3-methyl-phenyl]-4-methyl-1,4-dihydro-tetrazol-5-one.

1-[2-{4-(4-chloro-benzoyl)-2-methyl-phenoxymethyl}-3-methyl-phenyl]-4-methyl-1,4-dihydro-tetrazol-5-one

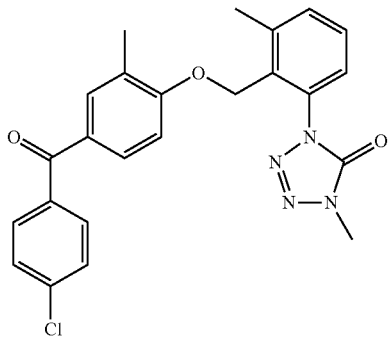 [SMILES: Cc1cc(C(=O)c2ccc(Cl)cc2)ccc1OCc1c(C)cccc1-n1nnn(C)c1=O]

1H-NMR (CDCl3) δ: 7.73-7.68 (2H, m), 7.64-7.59 (2H, m), 7.48-7.40 (4H, m), 7.32-7.25 (1H, m), 6.89 (1H, d, J=8.47 Hz), 5.13 (2H, s), 3.64 (3H, s), 2.51 (3H, s), 2.13 (3H, s).

Reference Production Example 81

The same reaction as that of Reference production example 77 was carried out except that 1-(2-bromomethyl-3-methoxyphenyl)-4-methyl-1,4-dihydrotetrazol-5-one described in Reference production example 8 was used in place of 1-(2-bromomethyl-3-methyl-phenyl)-4-methyl-1,4-dihydrotetrazol-5-one in Reference production example 77 to obtain 1-[2-{4-(4-chloro-benzoyl-2-methyl-phenoxymethyl)-3-methyl-phenyl]-4-methyl-1,4-dihydro-tetrazol-5-one.

1-[2-{4-(4-chloro-benzoyl-2-methyl-phenoxymethyl)-3-methoxy-phenyl]-4-methyl-1,4-dihydro-tetrazol-5-one

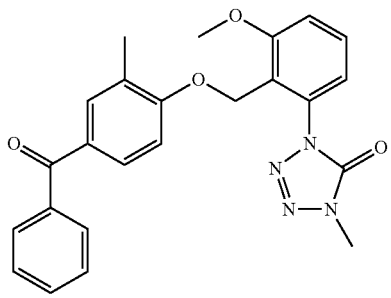 [SMILES: COc1cccc(-n2nnn(C)c2=O)c1COc1ccc(C(=O)c2ccccc2)cc1C]

1H-NMR (CDCl3) δ: 7.73 (2H, d, J=8.15 Hz), 7.64-7.59 (2H, m), 7.59-7.53 (1H, m), 7.52-7.43 (3H, m), 7.11-7.08 (2H, m), 6.93 (1H, d, J=8.93 Hz), 5.37 (2H, s), 3.94 (3H, s), 3.62 (3H, s), 2.03 (3H, s).

Reference Production Example 82

The same reaction as that of Reference production example 71 was carried out except that 1-(2-bromomethyl-3-cyclopropylphenyl)-4-methyl-1,4-dihydrotetrazol-5-one described in Reference production example 17 was used in place of 1-(2-bromomethyl-3-methyl-phenyl)-4-methyl-1,4-dihydrotetrazol-5-one in Reference production example 71 to obtain 1-[2-(4-cyclopropanecarbonyl-2-methyl-phenoxymethyl)-3-cyclopropyl-phenyl]-4-methyl-1,4-dihydro-tetrazol-5-one.

1-[2-(4-cyclopropanecarbonyl-2-methyl-phenoxymethyl)-3-cyclopropyl-phenyl]-4-methyl-1,4-dihydrotetrazol-5-one

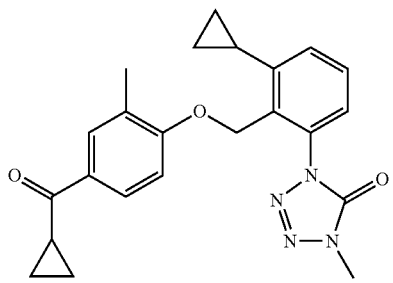 [SMILES: Cc1cc(C(=O)C2CC2)ccc1OCc1c(C2CC2)cccc1-n1nnn(C)c1=O]

1H-NMR (CDCl3) δ: 7.88 (1H, dd, J=8.70, 2.18 Hz), 7.82-7.80 (1H, m), 7.45 (1H, t, J=7.90 Hz), 7.31-7.27 (2H, m), 6.94 (1H, d, J=8.70 Hz), 5.34 (2H, s), 3.61 (3H, s), 2.65-2.61 (1H, m), 2.13-2.07 (4H, m), 1.22-1.16 (2H, m), 1.02-0.97 (4H, m), 0.80-0.74 (2H, m).

Reference Production Example 83

The same reaction as that of Reference production example 71 was carried out except that 1-(2-bromomethyl-3-methoxyphenyl)-4-methyl-1,4-dihydrotetrazol-5-one described in Reference production example 8 was used in place of 1-(2-bromomethyl-3-methyl-phenyl)-4-methyl-1,4-dihydrotetrazol-5-one in Reference production example 71 to obtain 1-[2-(4-cyclopropanecarbonyl-2-methyl-phenoxymethyl)-3-methoxy-phenyl]-4-methyl-1,4-dihydro-tetrazol-5-one.

1-[2-(4-cyclopropanecarbonyl-2-methyl-phenoxymethyl)-3-methoxy-phenyl]-4-methyl-1,4-dihydro-tetrazol-5-one

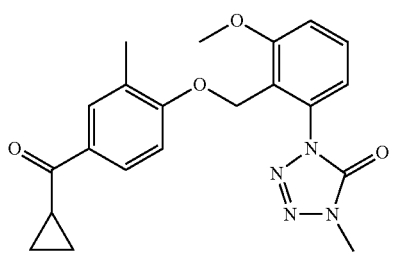 [SMILES: COc1cccc(-n2nnn(C)c2=O)c1COc1ccc(C(=O)C2CC2)cc1C]

1H-NMR (CDCl3) δ: 7.84 (1H, dd, J=8.70, 2.18 Hz), 7.78-7.76 (1H, m), 7.48 (1H, t, J=8.13 Hz), 7.12-7.06 (2H, m), 6.93 (1H, d, J=8.70 Hz), 5.35 (2H, s), 3.94 (3H, s), 3.59 (3H, s), 2.65-2.58 (1H, m), 2.03 (3H, s), 1.20-1.16 (2H, m), 1.00-0.94 (2H, m).

Reference Production Example 84

The same reaction as that of Reference production example 21 was carried out except that 3'-fluoro-4'-hydroxy-acetophenone was used in place of 1-(4-hydroxy-3-methyl-phenyl)propan-1-one in Reference production example 21 to obtain 2-fluoro-4-(1-methoxyimino-ethyl)phenol.

2-fluoro-4-(1-methoxyimino-ethyl)phenol

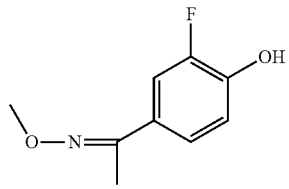

1H-NMR (CDCl3) δ: 7.45 (1H, dd, J=11.95, 2.05 Hz), 7.34-7.29 (1H, m), 6.98 (1H, t, J=8.69 Hz), 5.29 (1H, br s), 3.98 (3H, s), 2.17 (3H, s).

Reference Production Example 85

The same reaction as that of Reference production example 21 was carried out except that 3'-methoxy-4'-hydroxyacetophenone was used in place of 1-(4-hydroxy-3-methyl-phenyl)propan-1-one in Reference production example 21 to obtain 2-methoxy-4-(1-methoxyimino-ethyl)phenol.

2-methoxy-4-(1-methoxyimino-ethyl)phenol

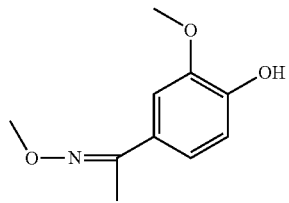

1H-NMR (CDCl3) δ: 7.29 (1H, d, J=1.93 Hz), 7.10 (1H, dd, J=8.21, 1.93 Hz), 6.90 (1H, d, J=8.21 Hz), 3.98 (3H, s), 3.94 (3H, s), 2.20 (3H, s).

Reference Production Example 86

The same reaction as that of Reference production example 21 was carried out except that 3'-nitro-4'-hydroxy-acetophenone was used in place of 1-(4-hydroxy-3-methyl-phenyl)propan-1-one in Reference production example 21 to obtain 2-nitro-4-(1-methoxyimino-ethyl)phenol.

2-nitro-4-(1-methoxyimino-ethyl)phenol

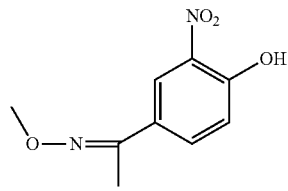

1H-NMR (CDCl3) δ: 10.67 (1H, s), 8.32 (1H, d, J=2.29 Hz), 8.02 (1H, dd, J=8.93, 2.29 Hz), 7.16 (1H, d, J=8.93 Hz), 4.00 (3H, s), 2.22 (3H, s).

Reference Production Example 87

The same reaction as that of Reference production example 21 was carried out except that 3',5'-dimethyl-4'-hydroxyacetophenone was used in place of 1-(4-hydroxy-3-methyl-phenyl)propan-1-one in Reference production example 21 to obtain 2,6-dimethyl-4-(1-methoxyimino-ethyl)phenol.

2,6-dimethyl-4-(1-methoxyimino-ethyl)phenol

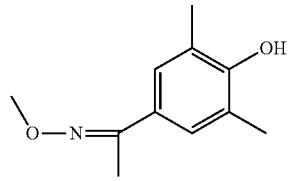

1H-NMR (CDCl3) δ: 7.27 (2H, s), 4.78 (1H, s), 3.97 (3H, s), 2.26 (6H, s), 2.18 (3H, s).

Reference Production Example 88

The same reaction as that of Reference production example 21 was carried out except that 4'-hydroxy-3'-methyl-benzaldehyde was used in place of 1-(4-hydroxy-3-methyl-phenyl)propan-1-one in Reference production example 21 to obtain 2-methyl-4-(1-methoxyimino-methyl)phenol.

2-methyl-4-(1-methoxyimino-methyl)phenol

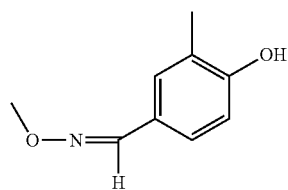

1H-NMR (CDCl3) δ: 7.98 (1H, s), 7.40 (1H, d, J=2.45 Hz), 7.28 (1H, dd, J=8.21, 2.45 Hz), 6.76 (1H, d, J=8.21 Hz), 5.09 (1H, br s), 3.94 (3H, s), 2.25 (3H, s).

Reference Production Example 89

The same reaction as that of Reference production example 21 was carried out except that 3'-trifluoromethyl-4'-hydroxyacetophenone was used in place of 1-(4-hydroxy-3-methyl-phenyl)propan-1-one in Reference production example 21 to obtain 2-trifluoromethyl-4-(1-methoxyimino-ethyl)phenol.

2-trifluoromethyl-4-(1-methoxyimino-ethyl)phenol

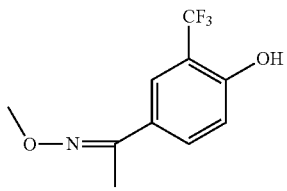 [SMILES: CON=C(C)c1ccc(O)c(C(F)(F)F)c1]

1H-NMR (CDCl3) δ: 7.80 (1H, d, J=2.17 Hz), 7.72 (1H, dd, J=8.69, 2.17 Hz), 6.94 (1H, d, J=8.69 Hz), 5.90 (1H, br s), 3.99 (3H, s), 2.20 (3H, s).

Reference Production Example 90

The same reaction as that of Reference production example 21 was carried out except that 2'-methyl-4'-hydroxyacetophenone was used in place of 1-(4-hydroxy-3-methyl-phenyl)propan-1-one in Reference production example 21 to obtain 3-methyl-4-(1-methoxyimino-ethyl)phenol.

3-methyl-4-(1-methoxyimino-ethyl)phenol

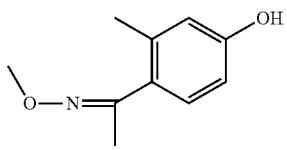

1H-NMR (CDCl3) δ: 7.06 (1H, d, J=8.01 Hz), 6.61-6.55 (2H, m), 3.96 (3H, s), 2.29 (3H, s), 2.14 (3H, s).

Reference Production Example 91

The same reaction as that of Reference production example 21 was carried out except that 3'-chloro-4'-hydroxyacetophenone was used in place of 1-(4-hydroxy-3-methyl-phenyl)propan-1-one in Reference production example 21 to obtain 2-chloro-4-(1-methoxyimino-ethyl)phenol.

2-chloro-4-(1-methoxyimino-ethyl)phenol

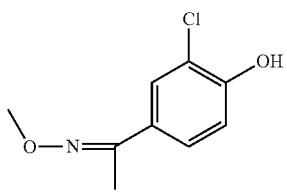

1H-NMR (CDCl3) δ: 7.66 (1H, d, J=2.20 Hz), 7.47 (1H, dd, J=8.66, 2.07 Hz), 7.00 (1H, d, J=8.54 Hz), 5.61 (1H, s), 3.98 (3H, s), 2.17 (3H, s).

Reference Production Example 92

A mixture of 1.78 g of N-propargyloxyphthalimide described in Reference production example 93, 1.32 g of hydrazine monohydrate, 2.4 mL of methanol, and 24 mL of chloroform was stirred at ambient temperature for 2 hr. The reaction mixture was filtered and the filtrate was washed with saturated saline. After 4 mL of hydrochloric acid (12 M) was added to the mixture, the mixture was concentrated under reduced pressure. 0.24 mL of hydrochloric acid (12 M) was added to a mixture obtained by adding 0.71 g of 4'-hydroxy-3'-methyl-acetophenone and 9.4 mL of ethanol to 0.51 g of the obtained residue and the mixture was stirred at ambient temperature for 2 hr. Saturated sodium bicarbonate was added to the mixture, which was then extracted three times with chloroform and then washed with saturated saline. The obtained solution was dried by sodium sulfate, filtered, and then, the filtrate was concentrated to obtain 2-methyl-4-{1-propargyloxyimino-ethyl}phenol.

2-methyl-4-{1-propargyloxyimino-ethyl}phenol

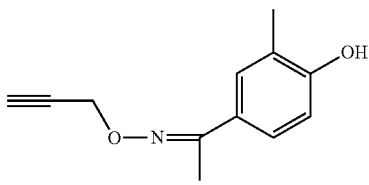

1H-NMR (CDCl3) δ: 7.46 (1H, d, J=2.17 Hz), 7.37 (1H, dd, J=8.21, 2.17 Hz), 6.75 (1H, d, J=8.21 Hz), 5.03 (1H, br s), 4.77 (2H, d, J=2.41 Hz), 2.48 (1H, t, J=2.41 Hz), 2.26 (3H, s), 2.23 (3H, s).

Reference Production Example 93

The same reaction as that of Reference production example 64 was carried out except that 3-bromo-propyne was used in place of 1-bromobutane in Reference production example 64 to obtain N-propargyloxyphthalimide.

N-propargyloxyphthalimide

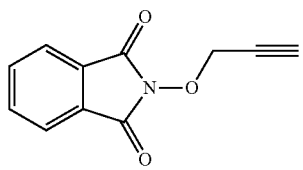

1H-NMR (CDCl3) δ: 7.88-7.85 (2H, m), 7.80-7.77 (2H, m), 4.89 (2H, d, J=2.46 Hz), 2.60 (1H, t, J=2.46 Hz).

Reference Production Example 94

The same reaction as that of Reference production example 19 was carried out except that 3-methylbenzoic acid chloride was used in place of propionyl chloride in Reference production example 19 to obtain 2-methylphenyl 3-methylbenzoate.

2-methylphenyl 3-methylbenzoate

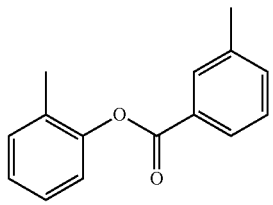 [SMILES: Cc1cccc(C(=O)Oc2ccccc2C)c1]

1H-NMR (CDCl3) δ: 8.04-7.95 (2H, m), 7.51-7.38 (2H, m), 7.29-7.24 (2H, m), 7.22-7.17 (1H, m), 7.14-7.12 (1H, m), 2.46 (3H, s), 2.24 (3H, s).

Reference Production Example 95

The same reaction as that of Reference production example 20 was carried out except that 2-methylphenyl-3-methylbenzoate described in Reference production example 94 was used in place of 2-methylphenyl propionate in Reference production example 20 to obtain 3-methylphenyl-(4-hydroxy-3-methylphenyl)-methanone.

3-methylphenyl-(4-hydroxy-3-methylphenyl)-methanone

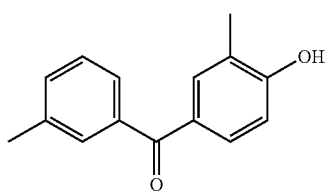 [SMILES: Cc1cccc(C(=O)c2ccc(O)c(C)c2)c1]

1H-NMR (CDCl3) δ: 7.70-7.68 (1H, m), 7.61-7.56 (2H, m), 7.55-7.50 (1H, m), 7.39-7.35 (2H, m), 6.84 (1H, d, J=8.5 Hz), 5.90 (1H, br s), 2.41 (3H, s), 2.29 (3H, s).

Reference Production Example 96

The same reaction as that of Reference production example 21 was carried out except that 3-methylphenyl-(4-hydroxy-3-methylphenyl)-methanone described in Reference production example 94 was used in place of 1-(4-hydroxy-3-methyl-phenyl)propan-1-one in Reference production example 21 to obtain 2-methyl-4-{1-methoxy-imino-1-(3-methylphenyl)methyl}-phenol.

2-methyl-4-{1-methoxyimino-1-(3-methylphenyl)methyl}-phenol

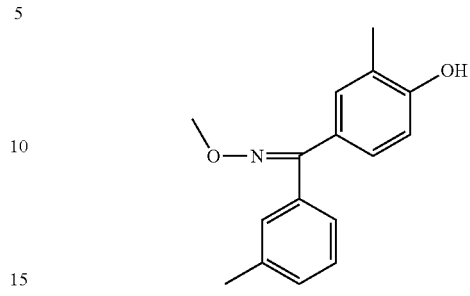

1H-NMR (CDCl3) δ: 7.36-7.30 (2.0H, m), 7.24-7.10 (4.0H, m), 6.80 (0.5H, d, J=8.2 Hz), 6.69 (0.5H, d, J=8.2 Hz), 5.08 (1.0H, br s), 3.99 (1.5H, s), 3.95 (1.5H, s), 2.38 (1.5H, s), 2.34 (1.5H, s), 2.25 (1.5H, s), 2.23 (1.5H, s).

Reference Production Example 97

9.3 g of 3-methoxybenzoic acid chloride and 22.8 ml of triethylamine were added to a mixture of 5.9 g of o-cresol and 150 ml of chloroform at 0° C. and the mixture was heated to 80° C. at which the mixture was stirred for 2 hr. After that, the mixture was extracted with chloroform. The organic phase was washed with water, dried by sodium sulfate anhydride, and then, concentrated under reduced pressure. 100 ml of acetonitrile was added to the obtained residue, to which was then added 18 g of aluminum trichloride at 0° C. The mixture was heated to 50° C. at which the mixture was stirred for 12 hr. The obtained reaction mixture was poured into 50 ml of ice water to extract with chloroform. The organic phase was washed with water, dried by magnesium sulfate anhydride, and then, concentrated under reduced pressure. The obtained residue was subjected to silica gel column chromatography to obtain a crude product. 0.84 g of O-methylhydroxyamine hydrochloride, 1 ml of pyridine, and 20 ml of ethanol were added to the obtained crude product and the mixture was stirred at ambient temperature for 4 hr. Saturated sodium bicarbonate was added to the mixture, which was then extracted three times with chloroform. The mixture was washed with saturated saline and the organic phase was concentrated under reduced pressure. The obtained residue was subjected to silica gel column chromatography to obtain 2-methyl-4-{1-methoxyimino-1-(3-methoxyphenyl)methyl}phenol.

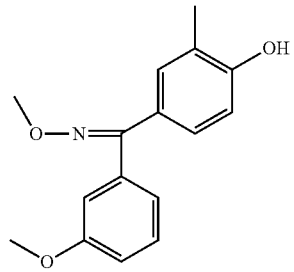 [SMILES: CON=C(c1cccc(OC)c1)c1ccc(O)c(C)c1]

1H-NMR (CDCl3) δ: 7.35-7.30 (2.0H, m), 7.15-7.11 (2.0H, m), 7.08-7.01 (2.0H, m), 6.81 (0.5H, d, J=8.2 Hz), 6.70 (0.5H, d, J=8.2 Hz), 3.98 (1.5H, s), 3.95 (1.5H, s), 3.81 (1.5H, s), 3.80 (1.5H, s), 2.25 (1.5H, s), 2.23 (1.5H, s).

Reference Production Example 98

2.8 g of acetyl chloride and 12.5 ml of triethylamine were added to 3.8 g of 2-cyanophenol and 30 ml of chloroform at 0° C. and the mixture was heated to ambient temperature at which the mixture was stirred for 2 hr. After that, the mixture was extracted with chloroform. The organic phase was washed with water, dried by sodium sulfate anhydride, and then, concentrated under reduced pressure. The obtained residue was subjected to silica gel column chromatography to obtain 4.9 g of 2-cyanophenyl acetate.

2-cyanophenyl acetate

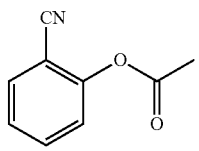

1H-NMR (CDCl3) δ: 7.70-7.67 (1H, m), 7.66-7.61 (1H, m), 7.35 (1H, td, J=7.7, 1.1 Hz), 7.30-7.28 (1H, m), 2.41 (3H, s).

Reference Production Example 99

The same reaction as that of Reference production example 20 was carried out except that 2-cyanophenyl acetate described in Reference production example 98 was used in place of 2-methylphenyl propionate in Reference production example 20 to obtain 4-acetyl-2-cyanophenol.

4-acetyl-2-cyanophenol

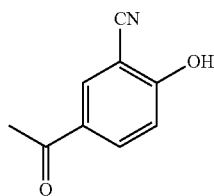

1H-NMR (CDCl3) δ: 8.15 (1H, d, J=2.3 Hz), 8.08 (1H, dd, J=8.7, 2.3 Hz), 7.11 (1H, d, J=8.7 Hz), 2.58 (3H, s).

Reference Production Example 100

The same reaction as that of Reference production example 21 was carried out except that 4-acetyl-2-cyanophenol described in Reference production example 99 was used in place of 1-(4-hydroxy-3-methyl-phenyl)propan-1-one in Reference production example 21 to obtain 2-cyano-4-(1-methoxyimino-ethyl)phenol.

2-cyano-4-(1-methoxyimino-ethyl)phenol

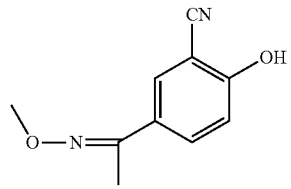

1H-NMR (CDCl3) δ: 7.83-7.78 (2H, m), 6.97 (1H, dd, J=8.6, 0.6 Hz), 3.99 (3H, s), 2.19 (3H, s).

Compounds EP1A-0001~EP1A-2492, EP1B-0001~EP1B-2492, EP1C-0001~EP1C-2492, EP1D-0001~EP1D-2492, EP1E-0001~EP1E-2492, EP1F-0001~EP1F-2492, EP1G-0001~EP1G-2492, EP1H-0001~EP1H-2492, EP2A-0001~EP2A-2492, EP2B-0001~EP2B-2492, EP2C-0001~EP2C-2492, EP2D-0001~EP2D-2492, EP2E-0001~EP2E-2492, EP2F-0001~EP2F-2492, EP2G-0001~EP2G-2492, EP2H-0001~EP2H-2492, EP3A-0001~EP3A-2492, EP3B-0001~EP3B-2492, EP3C-0001~EP3C-2492, EP3D-0001~EP3D-2492, EP3E-0001~EP3E-2492, EP3F-0001~EP3F-2492, EP3G-0001~EP3G-2492, EP3H-0001~EP3H-2492, EP4A-0001~EP4A-2492, EP4B-0001~EP4B-2492, EP4C-0001~EP4C-2492, EP4D-0001~EP4D-2492, EP4E-0001~EP4E-2492, EP4F-0001~EP4F-2492, EP4G-0001~EP4G-2492, EP4H-0001~EP4H-2492, EP5A-0001~EP5A-2492, EP5B-0001~EP5B-2492, EP5C-0001~EP5C-2492, EP5D-0001~EP5D-2492, EP5E-0001~EP5E-2492, EP5F-0001~EP5F-2492, EP5G-0001~EP5G-2492, EP5H-0001~EP5H-2492, EP6A-0001~EP6A-2492, EP6B-0001~EP6B-2492, EP6C-0001~EP6C-2492, EP6D-0001~EP6D-2492, EP6E-0001~EP6E-2492, EP6F-0001~EP6F-2492, EP6G-0001~EP6G-2492, EP6H-0001~EP6H-2492, EP7A-0001~EP7A-2492, EP7B-0001~EP7B-2492, EPIC-0001~EP7C-2492, EP7D-0001~EP7D-2492, EP7E-0001~EP7E-2492, EP7F-0001~EP7F-2492, EP7G-0001~EP7G-2492, EP7H-0001~EP7H-2492, EP8A-0001~EP8A-2492, EP8B-0001~EP8B-2492, EP8C-0001~EP8C-2492, EP8D-0001~EP8D-2492, EP8E-0001~EP8E-2492, EP8F-0001~EP8F-2492, EP8G-0001~EP8G-2492, EP8H-0001~EP8H-2492, EP9A-0001~EP9A-2492, EP9B-0001~EP9B-2492, EP9C-0001~EP9C-2492, EP9D-0001~EP9D-2492, EP9E-0001~EP9E-2492, EP9F-0001~EP9F-2492, EP9G-0001~EP9G-2492, EP9H-0001~EP9H-2492, EP10A-0001~EP10A-2492, EP10B-0001~EP10B-2492, EP10C-0001~EP10C-2492, EP10D-0001~EP10D-2492, EP10E-0001~EP10E-2492, EP10E-0001~EP10E-2492, EP10G-0001~EP10G-2492, EP10H-0001~EP10H-2492, EP11A-0001~EP11A-2492, EP11B-0001~EP11B-2492, EP11C-0001~EP11C-2492, EP11D-0001~EP11D-2492, EP11E-0001~EP11E-2492, EP11F-0001~EP11F-2492, EP11G-0001~EP11G-2492, EP11H-0001~EP11H-2492, EP12A-0001~EP12A-2492, EP12B-0001~EP12B-2492, EP12C-0001~EP12C-2492, EP12D-0001~EP12D-2492, EP12E-0001~EP12E-2492, EP12F-0001~EP12F-2492, EP12G-0001~EP12G-2492, EP12H-0001~EP12H-2492 can be obtained according to the above methods.

The compounds EP1A-0001 to EP1A-2492 are compounds represented by the following formula:

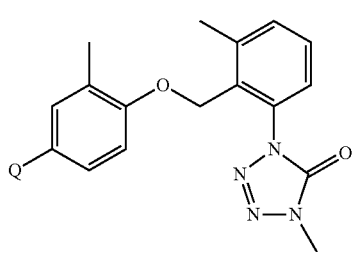
(EP1A)

[in the above formula (EP1A), Q is a compound represented by a substituent corresponding to each of the substituent numbers 1 to 2492 shown below];

The compounds EP1B-0001 to EP1B-2492 are compounds represented by the following formula:

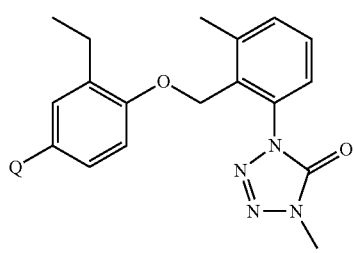
(EP1B)

[in the above formula (EP1B), Q is a compound represented by a substituent corresponding to each of the substituent numbers 1 to 2492 shown below];

The compounds EP1C-0001 to EP1C-2492 are compounds represented by the following formula:

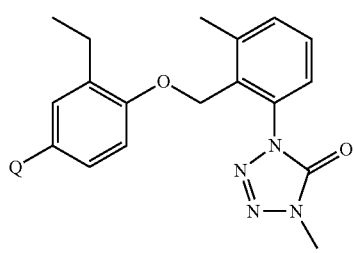
(EP1C)

[in the above formula (EP1C), Q is a compound represented by a substituent corresponding to each of the substituent numbers 1 to 2492 shown below];

The compounds EP1D-0001 to EP1D-2492 are compounds represented by the following formula:

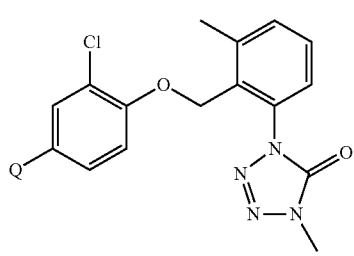
(EP1D)

[in the above formula (EP1D), Q is a compound represented by a substituent corresponding to each of the substituent numbers 1 to 2492 shown below];

The compounds EP1E-0001 to EP1E-2492 are compounds represented by the following formula:

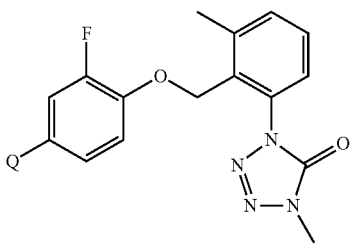
(EP1E)

[in the above formula (EP1E), Q is a compound represented by a substituent corresponding to each of the substituent numbers 1 to 2492 shown below];

The compounds EP1F-0001 to EP1F-2492 are compounds represented by the following formula:

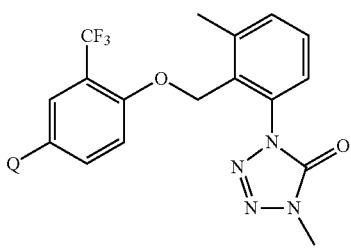
(EP1F)

[in the above formula (EP1F), Q is a compound represented by a substituent corresponding to each of the substituent numbers 1 to 2492 shown below];

The compounds EP1G-0001 to EP1G-2492 are compounds represented by the following formula:

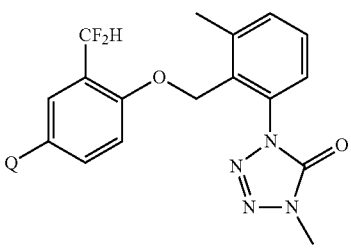
(EP1G)

[in the above formula (EP1G), Q is a compound represented by a substituent corresponding to each of the substituent numbers 1 to 2492 shown below];

The compounds EP1H-0001 to EP1H-2492 are compounds represented by the following formula:

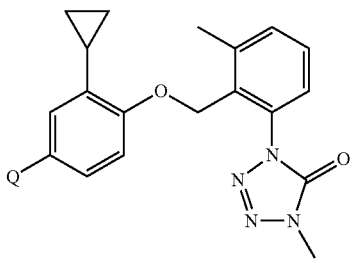
(EP1H)

[in the above formula (EP1H), Q is a compound represented by a substituent corresponding to each of the substituent numbers 1 to 2492 shown below];

The compounds EP2A-0001 to EP2A-2492 are compounds represented by the following formula:

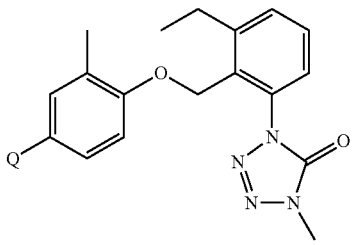
(EP2A)

[in the above formula (EP2A), Q is a compound represented by a substituent corresponding to each of the substituent numbers 1 to 2492 shown below];

The compounds EP2B-0001 to EP2B-2492 are compounds represented by the following formula:

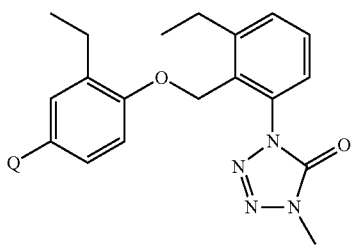
(EP2B)

[in the above formula (EP2B), Q is a compound represented by a substituent corresponding to each of the substituent numbers 1 to 2492 shown below];

The compounds EP2C-0001 to EP2C-2492 are compounds represented by the following formula:

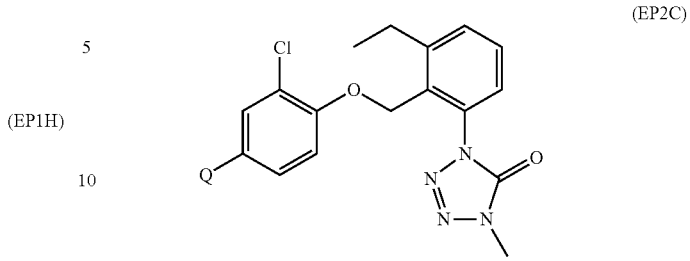
(EP2C)

[in the above formula (EP2C), Q is a compound represented by a substituent corresponding to each of the substituent numbers 1 to 2492 shown below];

The compounds EP2D-0001 to EP2D-2492 are compounds represented by the following formula:

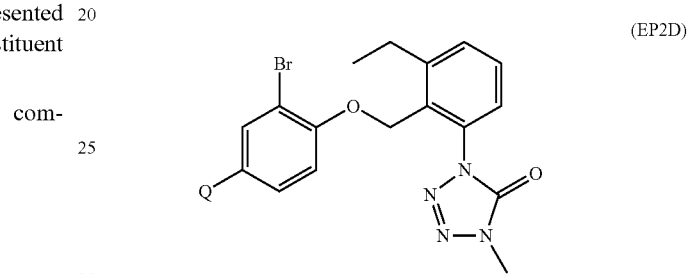
(EP2D)

[in the above formula (EP2D), Q is a compound represented by a substituent corresponding to each of the substituent numbers 1 to 2492 shown below];

The compounds EP2E-0001 to EP2E-2492 are compounds represented by the following formula:

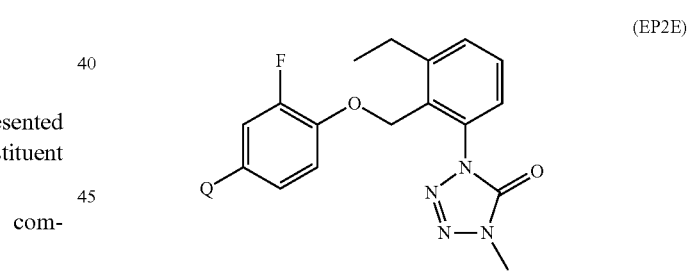
(EP2E)

[in the above formula (EP2E), Q is a compound represented by a substituent corresponding to each of the substituent numbers 1 to 2492 shown below];

The compounds EP2F-0001 to EP2F-2492 are compounds represented by the following formula:

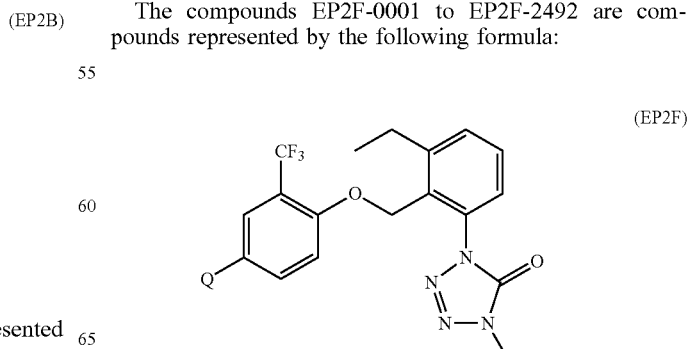
(EP2F)

[in the above formula (EP2F), Q is a compound represented by a substituent corresponding to each of the substituent numbers 1 to 2492 shown below];

The compounds EP2G-0001 to EP2G-2492 are compounds represented by the following formula:

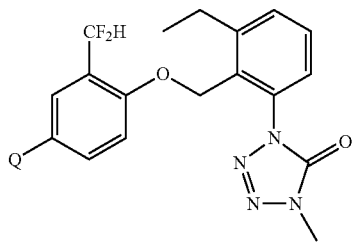
(EP2G)

[in the above formula (EP2G), Q is a compound represented by a substituent corresponding to each of the substituent numbers 1 to 2492 shown below];

The compounds EP2H-0001 to EP2H-2492 are compounds represented by the following formula:

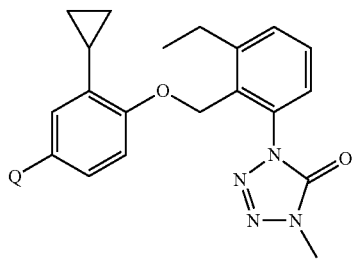
(EP2H)

[in the above formula (EP2H), Q is a compound represented by a substituent corresponding to each of the substituent numbers 1 to 2492 shown below];

The compounds EP3A-0001 to EP3A-2492 are compounds represented by the following formula:

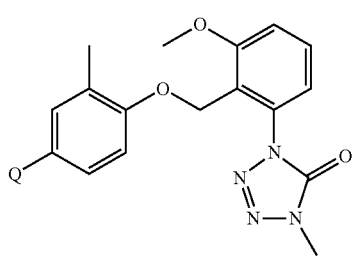
(EP3A)

[in the above formula (EP3A), Q is a compound represented by a substituent corresponding to each of the substituent numbers 1 to 2492 shown below];

The compounds EP3B-0001 to EP3B-2492 are compounds represented by the following formula:

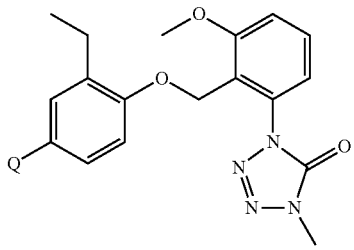
(EP3B)

[in the above formula (EP3B), Q is a compound represented by a substituent corresponding to each of the substituent numbers 1 to 2492 shown below];

The compounds EP3C-0001 to EP3C-2492 are compounds represented by the following formula:

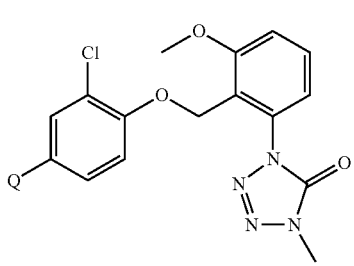
(EP3C)

[in the above formula (EP3C), Q is a compound represented by a substituent corresponding to each of the substituent numbers 1 to 2492 shown below];

The compounds EP3D-0001 to EP3D-2492 are compounds represented by the following formula:

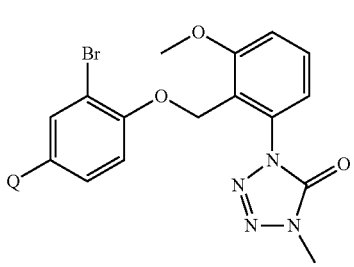
(EP3D)

[in the above formula (EP3D), Q is a compound represented by a substituent corresponding to each of the substituent numbers 1 to 2492 shown below];

The compounds EP3E-0001 to EP3E-2492 are compounds represented by the following formula:

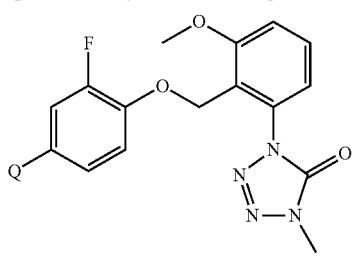
(EP3E)

[in the above formula (EP3E), Q is a compound represented by a substituent corresponding to each of the substituent numbers 1 to 2492 shown below];

The compounds EP3F-0001 to EP3F-2492 are compounds represented by the following formula:

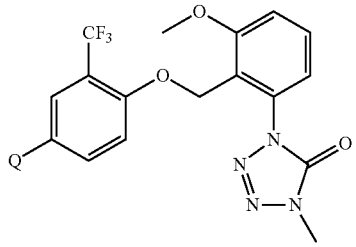
(EP3F)

[in the above formula (EP3F), Q is a compound represented by a substituent corresponding to each of the substituent numbers 1 to 2492 shown below];

The compounds EP3G-0001 to EP3G-2492 are compounds represented by the following formula:

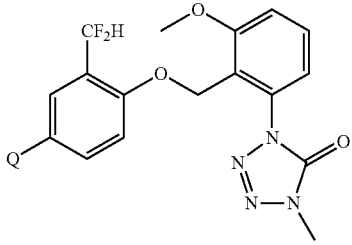
(EP3G)

[in the above formula (EP3G), Q is a compound represented by a substituent corresponding to each of the substituent numbers 1 to 2492 shown below];

The compounds EP3H-0001 to EP3H-2492 are compounds represented by the following formula:

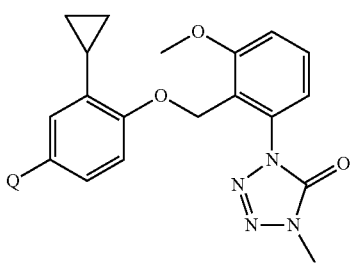
(EP3H)

[in the above formula (EP3H), Q is a compound represented by a substituent corresponding to each of the substituent numbers 1 to 2492 shown below];

The compounds EP4A-0001 to EP4A-2492 are compounds represented by the following formula:

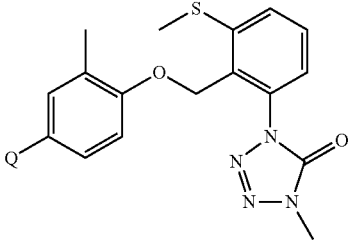
(EP4A)

[in the above formula (EP4A), Q is a compound represented by a substituent corresponding to each of the substituent numbers 1 to 2492 shown below];

The compounds EP4B-0001 to EP4B-2492 are compounds represented by the following formula:

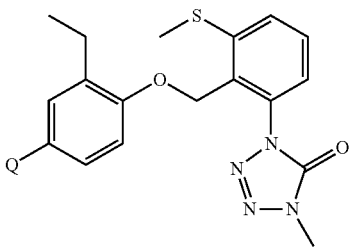
(EP4B)

[in the above formula (EP4B), Q is a compound represented by a substituent corresponding to each of the substituent numbers 1 to 2492 shown below];

The compounds EP4C-0001 to EP4C-2492 are compounds represented by the following formula:

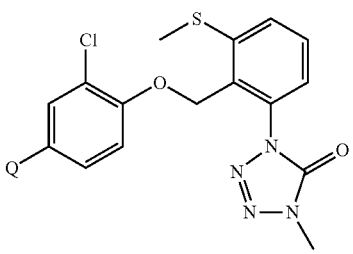
(EP4C)

[in the above formula (EP4C), Q is a compound represented by a substituent corresponding to each of the substituent numbers 1 to 2492 shown below];

The compounds EP4D-0001 to EP4D-2492 are compounds represented by the following formula:

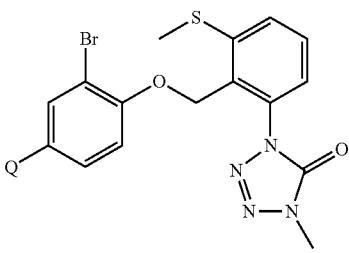
(EP4D)

[in the above formula (EP4D), Q is a compound represented by a substituent corresponding to each of the substituent numbers 1 to 2492 shown below];

The compounds EP4E-0001 to EP4E-2492 are compounds represented by the following formula:

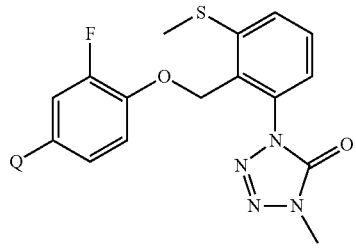
(EP4E)

[in the above formula (EP4E), Q is a compound represented by a substituent corresponding to each of the substituent numbers 1 to 2492 shown below];

The compounds EP4F-0001 to EP4F-2492 are compounds represented by the following formula:

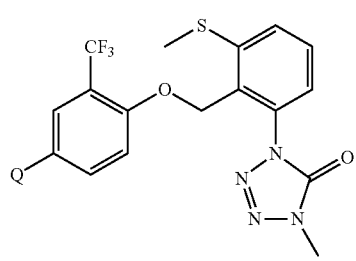
(EP4F)

[in the above formula (EP4F), Q is a compound represented by a substituent corresponding to each of the substituent numbers 1 to 2492 shown below];

The compounds EP4G-0001 to EP4G-2492 are compounds represented by the following formula:

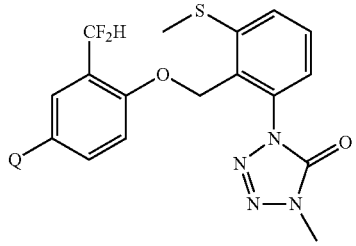
(EP4G)

[in the above formula (EP4G), Q is a compound represented by a substituent corresponding to each of the substituent numbers 1 to 2492 shown below];

The compounds EP4H-0001 to EP4H-2492 are compounds represented by the following formula:

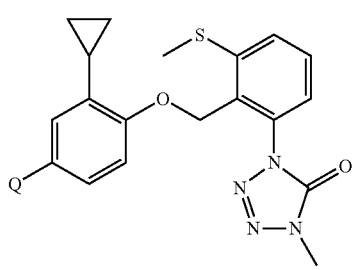
(EP4H)

[in the above formula (EP4H), Q is a compound represented by a substituent corresponding to each of the substituent numbers 1 to 2492 shown below];

The compounds EP5A-0001 to EP5A-2492 are compounds represented by the following formula:

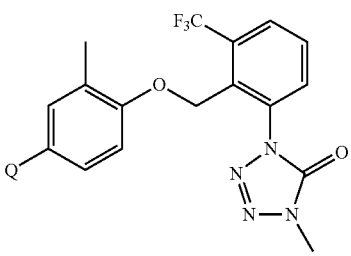
(EP5A)

[in the above formula (EP5A), Q is a compound represented by a substituent corresponding to each of the substituent numbers 1 to 2492 shown below];

The compounds EP5B-0001 to EP5B-2492 are compounds represented by the following formula:

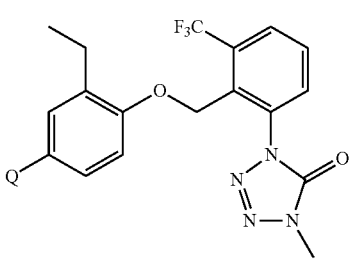
(EP5B)

[in the above formula (EP5B), Q is a compound represented by a substituent corresponding to each of the substituent numbers 1 to 2492 shown below];

The compounds EP5C-0001 to EP5C-2492 are compounds represented by the following formula:

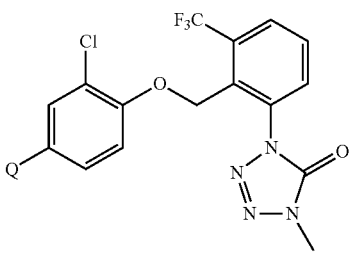
(EP5C)

[in the above formula (EP5C), Q is a compound represented by a substituent corresponding to each of the substituent numbers 1 to 2492 shown below];

The compounds EP5D-0001 to EP5D-2492 are compounds represented by the following formula:

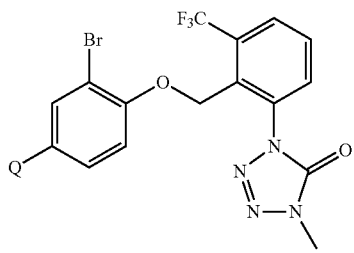
(EP5D)

[in the above formula (EP5D), Q is a compound represented by a substituent corresponding to each of the substituent numbers 1 to 2492 shown below];

The compounds EP5E-0001 to EP5E-2492 are compounds represented by the following formula:

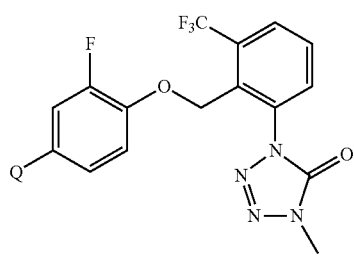
(EP5E)

[in the above formula (EP5E), Q is a compound represented by a substituent corresponding to each of the substituent numbers 1 to 2492 shown below];

The compounds EP5F-0001 to EP5F-2492 are compounds represented by the following formula:

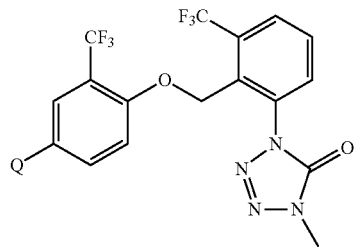
(EP5F)

[in the above formula (EP5F), Q is a compound represented by a substituent corresponding to each of the substituent numbers 1 to 2492 shown below];

The compounds EP5G-0001 to EP5G-2492 are compounds represented by the following formula:

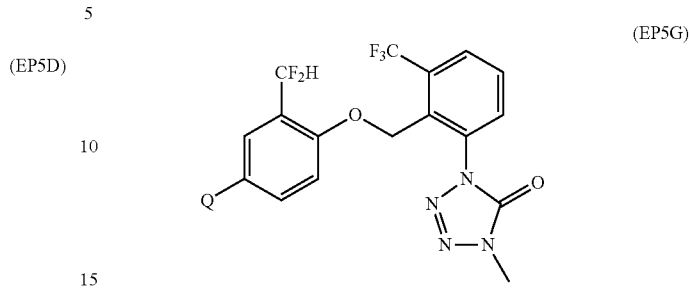
(EP5G)

[in the above formula (EP5G), Q is a compound represented by a substituent corresponding to each of the substituent numbers 1 to 2492 shown below];

The compounds EP5H-0001 to EP5H-2492 are compounds represented by the following formula:

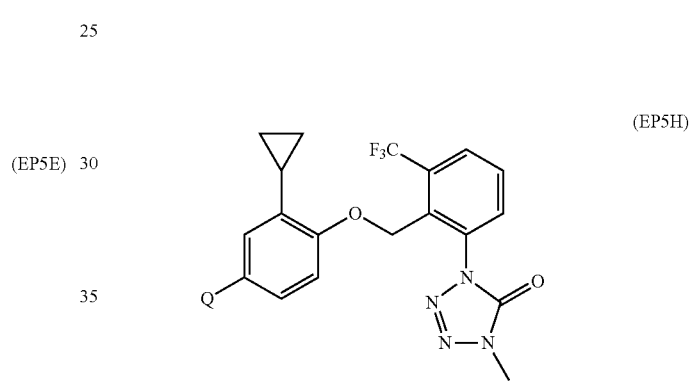
(EP5H)

[in the above formula (EP5H), Q is a compound represented by a substituent corresponding to each of the substituent numbers 1 to 2492 shown below];

The compounds EP6A-0001 to EP6A-2492 are compounds represented by the following formula:

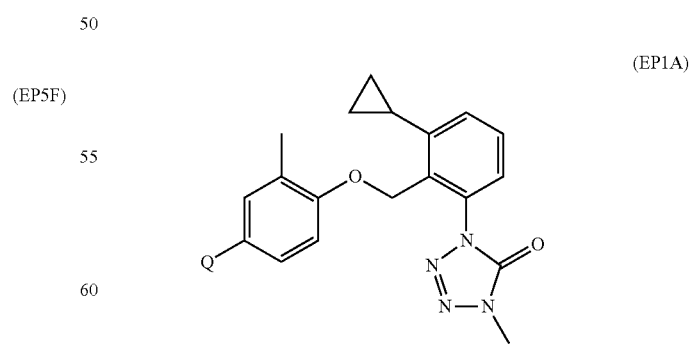
(EP1A)

[in the above formula (EP6A), Q is a compound represented by a substituent corresponding to each of the substituent numbers 1 to 2492 shown below];

The compounds EP6B-0001 to EP6B-2492 are compounds represented by the following formula:

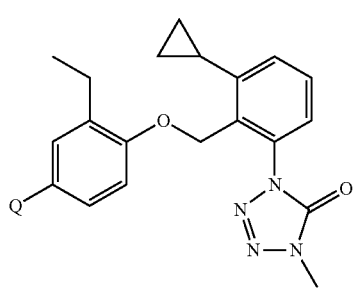
(EP6B)

[in the above formula (EP6B), Q is a compound represented by a substituent corresponding to each of the substituent numbers 1 to 2492 shown below];

The compounds EP6C-0001 to EP6C-2492 are compounds represented by the following formula:

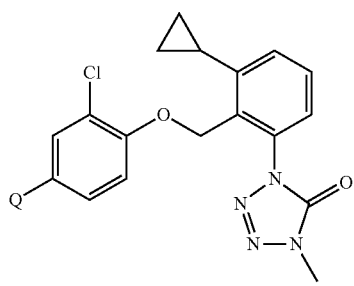
(EP6C)

[in the above formula (EP6C), Q is a compound represented by a substituent corresponding to each of the substituent numbers 1 to 2492 shown below];

The compounds EP6D-0001 to EP6D-2492 are compounds represented by the following formula:

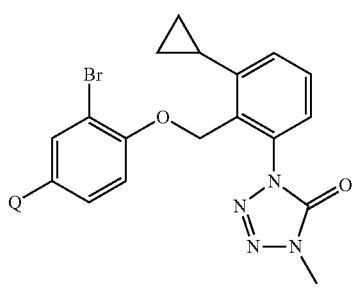
(EP6D)

[in the above formula (EP6D), Q is a compound represented by a substituent corresponding to each of the substituent numbers 1 to 2492 shown below];

The compounds EP6E-0001 to EP6E-2492 are compounds represented by the following formula:

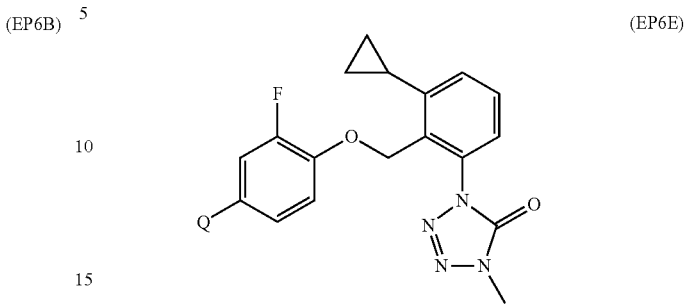
(EP6E)

[in the above formula (EP6E), Q is a compound represented by a substituent corresponding to each of the substituent numbers 1 to 2492 shown below];

The compounds EP6F-0001 to EP6F-2492 are compounds represented by the following formula:

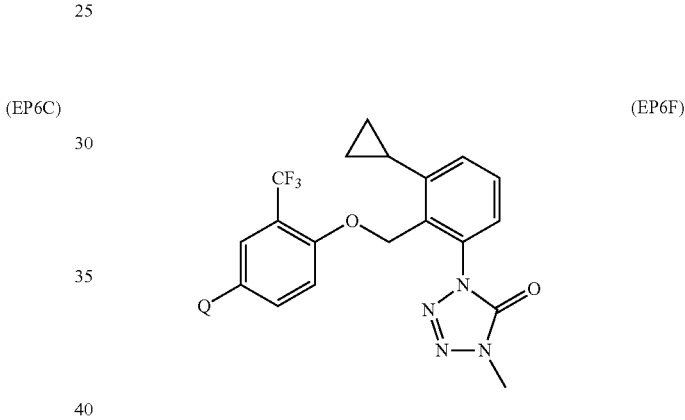
(EP6F)

[in the above formula (EP6F), Q is a compound represented by a substituent corresponding to each of the substituent numbers 1 to 2492 shown below];

The compounds EP6G-0001 to EP6G-2492 are compounds represented by the following formula:

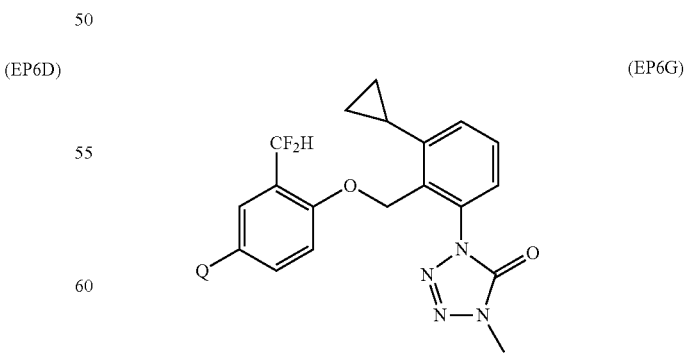
(EP6G)

[in the above formula (EP6G), Q is a compound represented by a substituent corresponding to each of the substituent numbers 1 to 2492 shown below];

The compounds EP6H-0001 to EP6H-2492 are compounds represented by the following formula:

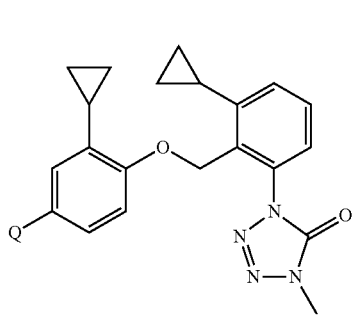

(EP6H)

[in the above formula (EP6H), Q is a compound represented by a substituent corresponding to each of the substituent numbers 1 to 2492 shown below];

The compounds EP7A-0001 to EP7A-2492 are compounds represented by the following formula:

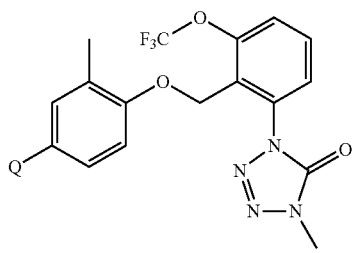

(EP7A)

[in the above formula (EP7A), Q is a compound represented by a substituent corresponding to each of the substituent numbers 1 to 2492 shown below];

The compounds EP7B-0001 to EP7B-2492 are compounds represented by the following formula:

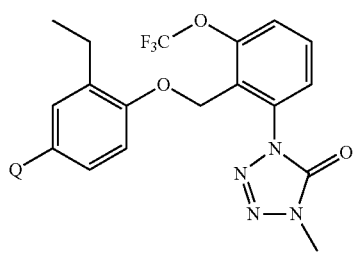

(EP7B)

[in the above formula (EP7B), Q is a compound represented by a substituent corresponding to each of the substituent numbers 1 to 2492 shown below];

The compounds EPIC-0001 to EPIC-2492 are compounds represented by the following formula:

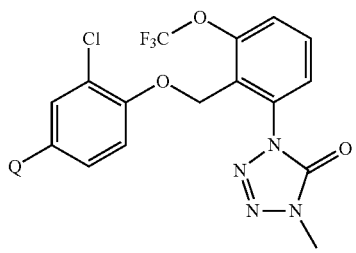

(EP7C)

[in the above formula (EP7C), Q is a compound represented by a substituent corresponding to each of the substituent numbers 1 to 2492 shown below];

The compounds EP7D-0001 to EP7D-2492 are compounds represented by the following formula:

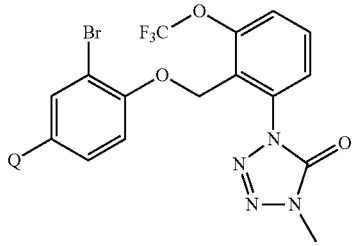

(EP7D)

[in the above formula (EP7D), Q is a compound represented by a substituent corresponding to each of the substituent numbers 1 to 2492 shown below];

The compounds EP7E-0001 to EP7E-2492 are compounds represented by the following formula:

(EP7E)

[in the above formula (EP7E), Q is a compound represented by a substituent corresponding to each of the substituent numbers 1 to 2492 shown below];

The compounds EP7F-0001 to EP7F-2492 are compounds represented by the following formula:

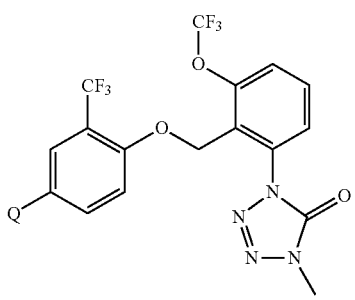
(EP7F)

[in the above formula (EP7F), Q is a compound represented by a substituent corresponding to each of the substituent numbers 1 to 2492 shown below];

The compounds EP7G-0001 to EP7G-2492 are compounds represented by the following formula:

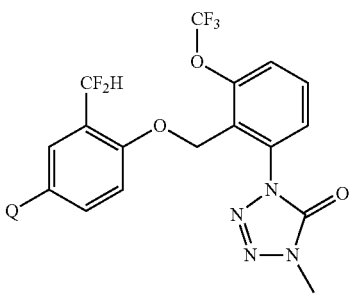
(EP7G)

[in the above formula (EP7G), Q is a compound represented by a substituent corresponding to each of the substituent numbers 1 to 2492 shown below];

The compounds EP7H-0001 to EP7H-2492 are compounds represented by the following formula:

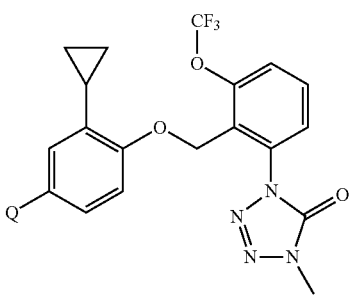
(EP7H)

[in the above formula (EP7H), Q is a compound represented by a substituent corresponding to each of the substituent numbers 1 to 2492 shown below];

The compounds EP8A-0001 to EP8A-2492 are compounds represented by the following formula:

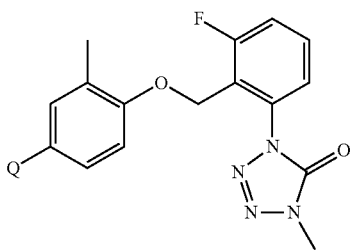
(EP8A)

[in the above formula (EP8A), Q is a compound represented by a substituent corresponding to each of the substituent numbers 1 to 2492 shown below];

The compounds EP8B-0001 to EP8B-2492 are compounds represented by the following formula:

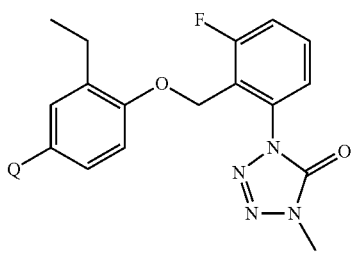
(EP8B)

[in the above formula (EP8B), Q is a compound represented by a substituent corresponding to each of the substituent numbers 1 to 2492 shown below];

The compounds EP8C-0001 to EP8C-2492 are compounds represented by the following formula:

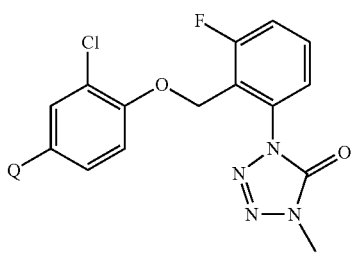
(EP8C)

[in the above formula (EP8C), Q is a compound represented by a substituent corresponding to each of the substituent numbers 1 to 2492 shown below];

The compounds EP8D-0001 to EP8D-2492 are compounds represented by the following formula:

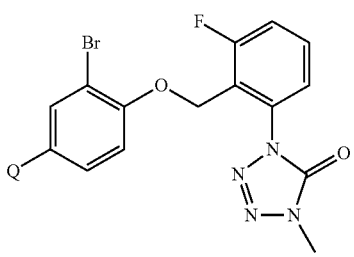
(EP8D)

[in the above formula (EP8D), Q is a compound represented by a substituent corresponding to each of the substituent numbers 1 to 2492 shown below];

The compounds EP8E-0001 to EP8E-2492 are compounds represented by the following formula:

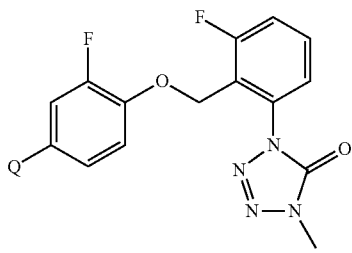
(EP8E)

[in the above formula (EP8E), Q is a compound represented by a substituent corresponding to each of the substituent numbers 1 to 2492 shown below];

The compounds EP8F-0001 to EP8F-2492 are compounds represented by the following formula:

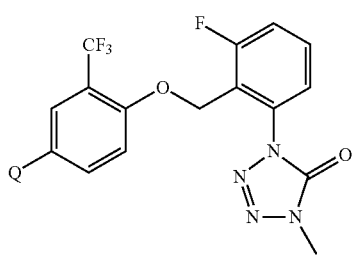
(EP8F)

[in the above formula (EP8F), Q is a compound represented by a substituent corresponding to each of the substituent numbers 1 to 2492 shown below];

The compounds EP8G-0001 to EP8G-2492 are compounds represented by the following formula:

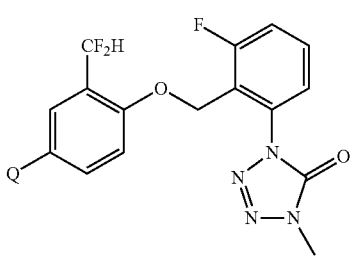
(EP8G)

[in the above formula (EP8G), Q is a compound represented by a substituent corresponding to each of the substituent numbers 1 to 2492 shown below];

The compounds EP8H-0001 to EP8H-2492 are compounds represented by the following formula:

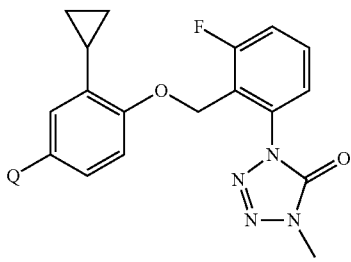
(EP8H)

[in the above formula (EP8H), Q is a compound represented by a substituent corresponding to each of the substituent numbers 1 to 2492 shown below];

The compounds EP9A-0001 to EP9A-2492 are compounds represented by the following formula:

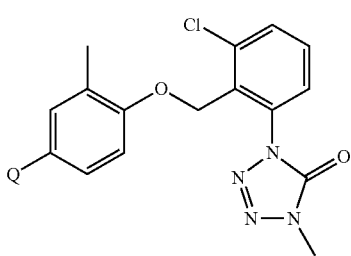
(EP9A)

[in the above formula (EP9A), Q is a compound represented by a substituent corresponding to each of the substituent numbers 1 to 2492 shown below];

The compounds EP9B-0001 to EP9B-2492 are compounds represented by the following formula:

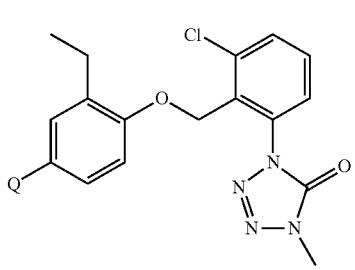
(EP9B)

[in the above formula (EP9B), Q is a compound represented by a substituent corresponding to each of the substituent numbers 1 to 2492 shown below];

The compounds EP9C-0001 to EP9C-2492 are compounds represented by the following formula:

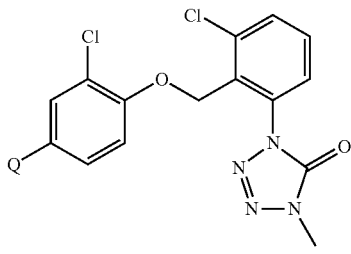
(EP9C)

215

[in the above formula (EP9C), Q is a compound represented by a substituent corresponding to each of the substituent numbers 1 to 2492 shown below];

The compounds EP9D-0001 to EP9D-2492 are compounds represented by the following formula:

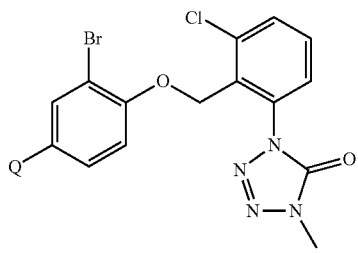
(EP9D)

[in the above formula (EP9D), Q is a compound represented by a substituent corresponding to each of the substituent numbers 1 to 2492 shown below];

The compounds EP9E-0001 to EP9E-2492 are compounds represented by the following formula:

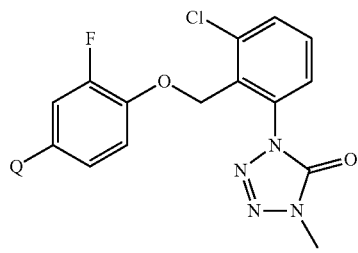
(EP9E)

[in the above formula (EP9E), Q is a compound represented by a substituent corresponding to each of the substituent numbers 1 to 2492 shown below];

The compounds EP9F-0001 to EP9F-2492 are compounds represented by the following formula:

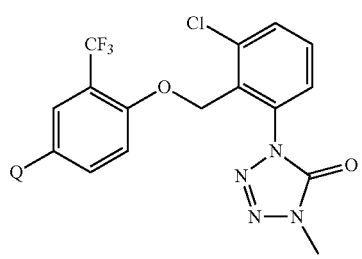
(EP9F)

[in the above formula (EP9F), Q is a compound represented by a substituent corresponding to each of the substituent numbers 1 to 2492 shown below];

The compounds EP9G-0001 to EP9G-2492 are compounds represented by the following formula:

216

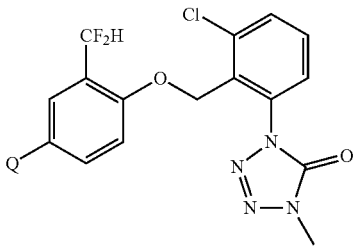
(EP9G)

[in the above formula (EP9G), Q is a compound represented by a substituent corresponding to each of the substituent numbers 1 to 2492 shown below];

The compounds EP9H-0001 to EP9H-2492 are compounds represented by the following formula:

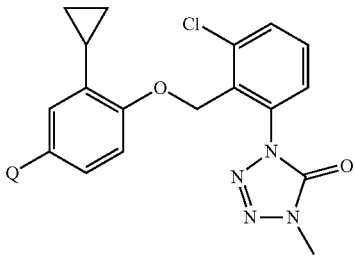
(EP9H)

[in the above formula (EP9H), Q is a compound represented by a substituent corresponding to each of the substituent numbers 1 to 2492 shown below];

The compounds EP10A-0001 to EP10A-2492 are compounds represented by the following formula:

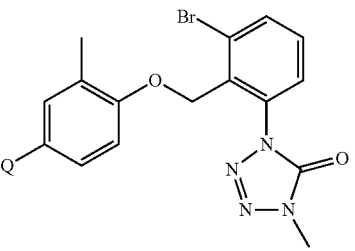
(EP10A)

[in the above formula (EP10A), Q is a compound represented by a substituent corresponding to each of the substituent numbers 1 to 2492 shown below];

The compounds EP10B-0001 to EP10B-2492 are compounds represented by the following formula:

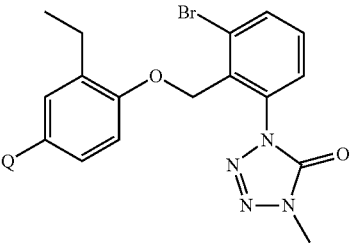
(EP10B)

[in the above formula (EP10B), Q is a compound represented by a substituent corresponding to each of the substituent numbers 1 to 2492 shown below];

The compounds EP10C-0001 to EP10C-2492 are compounds represented by the following formula:

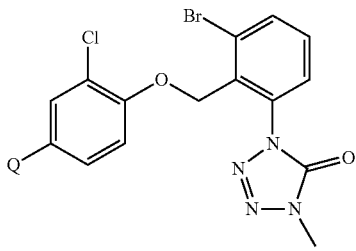
(EP10C)

[in the above formula (EP10C), Q is a compound represented by a substituent corresponding to each of the substituent numbers 1 to 2492 shown below];

The compounds EP10D-0001 to EP10D-2492 are compounds represented by the following formula:

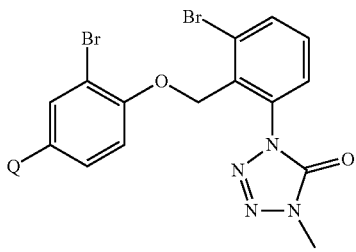
(EP10D)

[in the above formula (EP10D), Q is a compound represented by a substituent corresponding to each of the substituent numbers 1 to 2492 shown below];

The compounds EP10E-0001 to EP10E-2492 are compounds represented by the following formula:

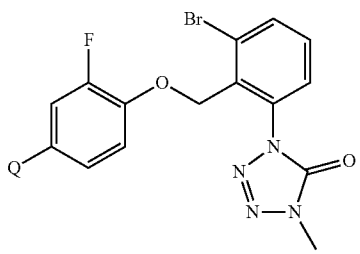
(EP10E)

[in the above formula (EP10E), Q is a compound represented by a substituent corresponding to each of the substituent numbers 1 to 2492 shown below];

The compounds EP10E-0001 to EP10E-2492 are compounds represented by the following formula:

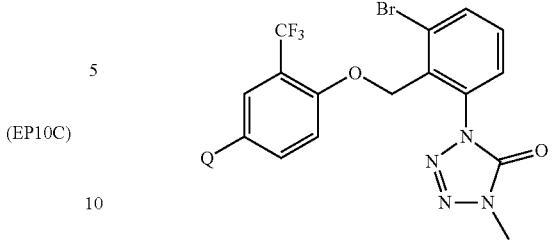
(EP10F)

[in the above formula (EP10F), Q is a compound represented by a substituent corresponding to each of the substituent numbers 1 to 2492 shown below];

The compounds EP10G-0001 to EP10G-2492 are compounds represented by the following formula:

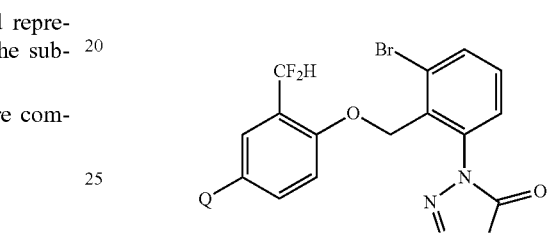
(EP10G)

[in the above formula (EP10G), Q is a compound represented by a substituent corresponding to each of the substituent numbers 1 to 2492 shown below];

The compounds EP10H-0001 to EP10H-2492 are compounds represented by the following formula:

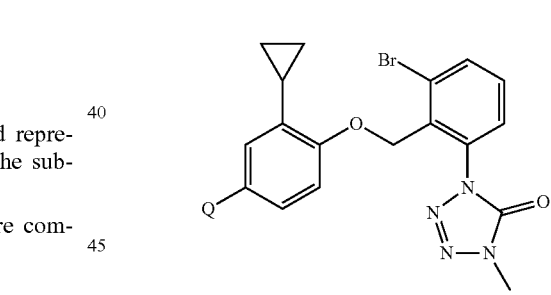
(EP10H)

[in the above formula (EP10H), Q is a compound represented by a substituent corresponding to each of the substituent numbers 1 to 2492 shown below];

The compounds EP11A-0001 to EP11A-2492 are compounds represented by the following formula:

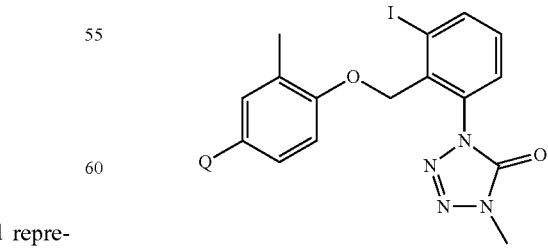
(EP11A)

[in the above formula (EP11A), Q is a compound represented by a substituent corresponding to each of the substituent numbers 1 to 2492 shown below];

The compounds EP11B-0001 to EP11B-2492 are compounds represented by the following formula:

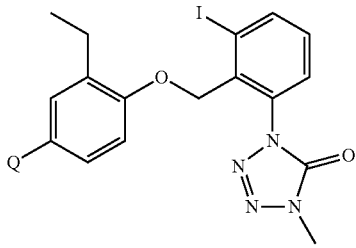

(EP11B)

[in the above formula (EP11B), Q is a compound represented by a substituent corresponding to each of the substituent numbers 1 to 2492 shown below];

The compounds EP11C-0001 to EP11C-2492 are compounds represented by the following formula:

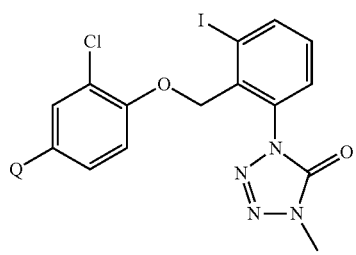

(EP11C)

[in the above formula (EP11C), Q is a compound represented by a substituent corresponding to each of the substituent numbers 1 to 2492 shown below];

The compounds EP11D-0001 to EP11D-2492 are compounds represented by the following formula:

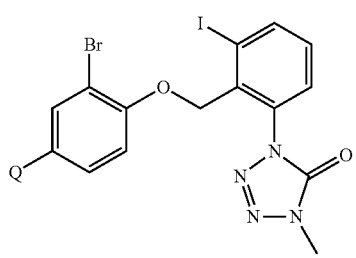

(EP11D)

[in the above formula (EP11D), Q is a compound represented by a substituent corresponding to each of the substituent numbers 1 to 2492 shown below];

The compounds EP11E-0001 to EP11E-2492 are compounds represented by the following formula:

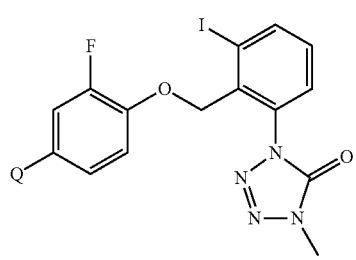

(EP11E)

[in the above formula (EP11E), Q is a compound represented by a substituent corresponding to each of the substituent numbers 1 to 2492 shown below];

The compounds EP11F-0001 to EP11F-2492 are compounds represented by the following formula:

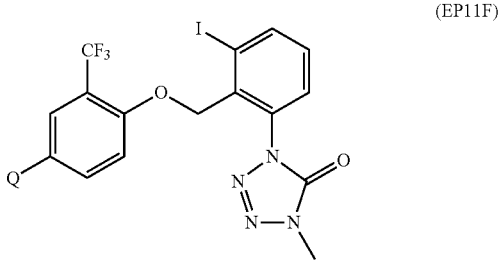

(EP11F)

[in the above formula (EP11F), Q is a compound represented by a substituent corresponding to each of the substituent numbers 1 to 2492 shown below];

The compounds EP11G-0001 to EP11G-2492 are compounds represented by the following formula:

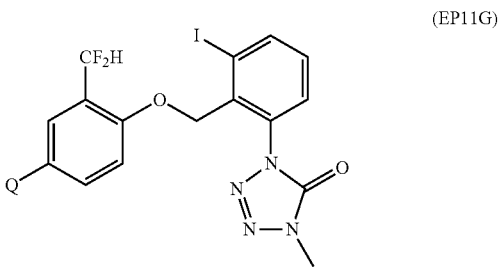

(EP11G)

[in the above formula (EP11G), Q is a compound represented by a substituent corresponding to each of the substituent numbers 1 to 2492 shown below];

The compounds EP11H-0001 to EP11H-2492 are compounds represented by the following formula:

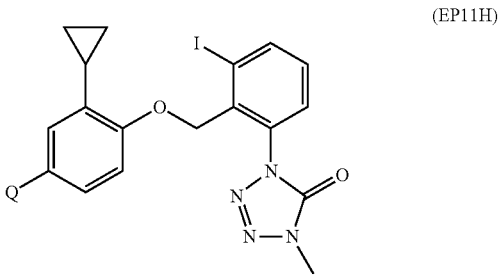

(EP11H)

[in the above formula (EP11H), Q is a compound represented by a substituent corresponding to each of the substituent numbers 1 to 2492 shown below];

The compounds EP12A-0001 to EP12A-2492 are compounds represented by the following formula:

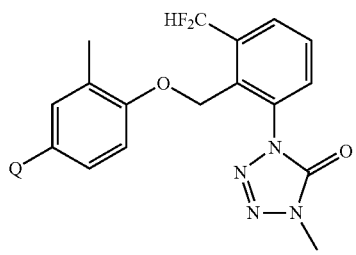
(EP12A)

[in the above formula (EP12A), Q is a compound represented by a substituent corresponding to each of the substituent numbers 1 to 2492 shown below];

The compounds EP12B-0001 to EP12B-2492 are compounds represented by the following formula:

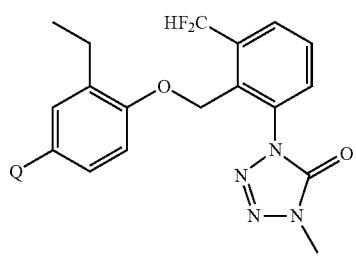
(EP12B)

[in the above formula (EP12B), Q is a compound represented by a substituent corresponding to each of the substituent numbers 1 to 2492 shown below];

The compounds EP12C-0001 to EP12C-2492 are compounds represented by the following formula:

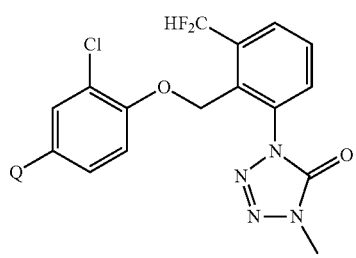
(EP12C)

[in the above formula (EP12C), Q is a compound represented by a substituent corresponding to each of the substituent numbers 1 to 2492 shown below];

The compounds EP12D-0001 to EP12D-2492 are compounds represented by the following formula:

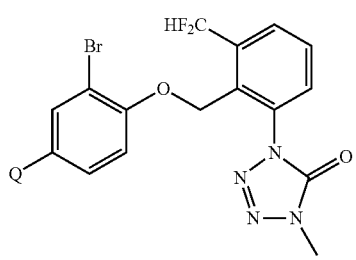
(EP12D)

[in the above formula (EP12D), Q is a compound represented by a substituent corresponding to each of the substituent numbers 1 to 2492 shown below];

The compounds EP12E-0001 to EP12E-2492 are compounds represented by the following formula:

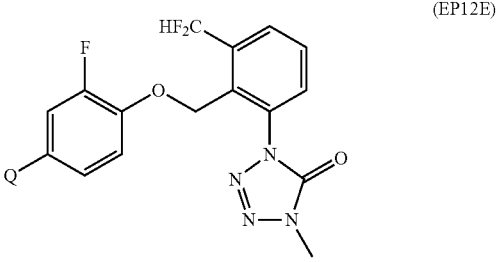
(EP12E)

[in the above formula (EP12E), Q is a compound represented by a substituent corresponding to each of the substituent numbers 1 to 2492 shown below];

The compounds EP12F-0001 to EP12F-2492 are compounds represented by the following formula:

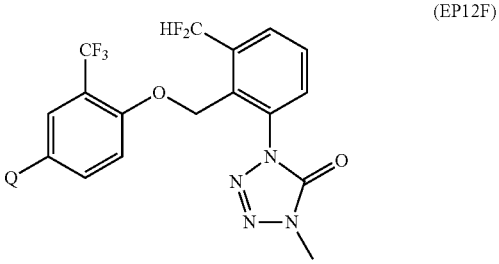
(EP12F)

[in the above formula (EP12F), Q is a compound represented by a substituent corresponding to each of the substituent numbers 1 to 2492 shown below];

The compounds EP12G-0001 to EP12G-2492 are compounds represented by the following formula:

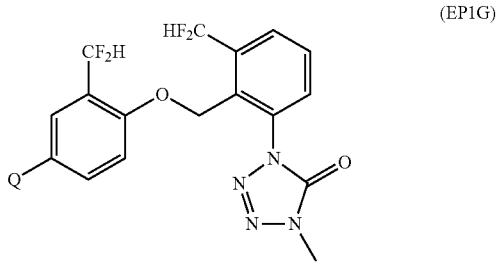
(EP1G)

[in the above formula (EP12G), Q is a compound represented by a substituent corresponding to each of the substituent numbers 1 to 2492 shown below];

The compounds EP12H-0001 to EP12H-2492 are compounds represented by the following formula:

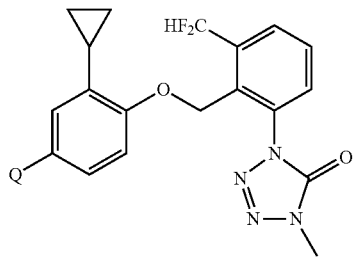

(EP12H)

[in the above formula (EP12H), Q is a compound represented by a substituent corresponding to each of the substituent numbers 1 to 2492 shown below].
Substituent Number; Q
1; 1-(ethoxyimino)propyl group
2; 1-(propyloxyimino)propyl group
3; 1-(n-butoxyimino)propyl group
4; 1-(n-pentyloxyimino)propyl group
5; 1-(n-hexyloxyimino)propyl group
6; 1-(isopropoxyimino)propyl group
7; 1-(tert-butoxyimino)propyl group
8; 1-(sec-butoxyimino)propyl group
9; 1-(cyclopropyloxyimino)propyl group
10; 1-(cyclopentyloxyimino)propyl group
11; 1-(cyclohexyloxyimino)propyl group
12; 1-(3-allyloxyimino)propyl group
13; 1-(4-butenoxyimino)propyl group
14; 1-(3-propynoxyimino)propyl group
15; 1-(4-butynoxyimino)propyl group
16; 1-(1-cyclohexenoxyimino)propyl group
17; 1-(2,2,2-trifluoroethoxyimino)propyl group
18; 1-(benzyloxyimino)propyl group
19; 1-(2-fluorobenzyloxyimino)propyl group
20; 1-(3-fluorobenzyloxyimino)propyl group
21; 1-(4-fluorobenzyloxyimino)propyl group
22; 1-(2-chlorobenzyloxyimino)propyl group
23; 1-(3-chlorobenzyloxyimino)propyl group
24; 1-(4-chlorobenzyloxyimino)propyl group
25; 1-(2-methylbenzyloxyimino)propyl group
26; 1-(3-methylbenzyloxyimino)propyl group
27; 1-(4-methylbenzyloxyimino)propyl group
28; 1-(2-cyanobenzyloxyimino)propyl group
29; 1-(3-cyanobenzyloxyimino)propyl group
Substituent Number; Q
30; 1-(4-cyanobenzyloxyimino)propyl group
31; 1-(2-trifluoromethylbenzyloxyimino)propyl group
32; 1-(3-trifluoromethylbenzyloxyimino)propyl group
33; 1-(4-trifluoromethylbenzyloxyimino)propyl group
34; 1-(2-difluoromethylbenzyloxyimino)propyl group
35; 1-(3-difluoromethylbenzyloxyimino)propyl group
36; 1-(4-difluoromethylbenzyloxyimino)propyl group
37; 1-(2-methoxybenzyloxyimino)propyl group
38; 1-(3-methoxybenzyloxyimino)propyl group
39; 1-(4-methoxybenzyloxyimino)propyl group
40; 1-(2-vinylbenzyloxyimino)propyl group
41; 1-(3-vinylbenzyloxyimino)propyl group
42; 1-(4-vinylbenzyloxyimino)propyl group
43; 1-(2-phenylbenzyloxyimino)propyl group
44; 1-(3-phenylbenzyloxyimino)propyl group
45; 1-(4-phenylbenzyloxyimino)propyl group
46; 1-(2,3-difluorobenzyloxyimino)propyl group
47; 1-(2,4-difluorobenzyloxyimino)propyl group
48; 1-(2,5-difluorobenzyloxyimino)propyl group
49; 1-(2,6-difluorobenzyloxyimino)propyl group
50; 1-(3,4-difluorobenzyloxyimino)propyl group
51; 1-(3,5-difluorobenzyloxyimino)propyl group
52; 1-(2,3,4,5,6-pentafluorobenzyloxyimino)propyl group
53; 1-(3-ethylbenzyloxyimino)propyl group
54; 1-(4-ethylbenzyloxyimino)propyl group
55; 1-(2-trifluoromethoxybenzyloxyimino)propyl group
56; 1-(3-trifluoromethoxybenzyloxyimino)propyl group
57; 1-(4-trifluoromethoxybenzyloxyimino)propyl group
58; 1-(methoxyimino)propyl group
Substituent Number; Q
59; 1-(ethoxyimino)butyl group
60; 1-(propyloxyimino)butyl group
61; 1-(n-butoxyimino)butyl group
62; 1-(n-pentyloxyimino)butyl group
63; 1-(n-hexyloxyimino)butyl group
64; 1-(isopropoxyimino)butyl group
65; 1-(tert-butoxyimino)butyl group
66; 1-(sec-butoxyimino)butyl group
67; 1-(cyclopropyloxyimino)butyl group
68; 1-(cyclopentyloxyimino)butyl group
69; 1-(cyclohexyloxyimino)butyl group
70; 1-(3-allyloxyimino)butyl group
71; 1-(4-butenoxyimino)butyl group
72; 1-(3-propynoxyimino)butyl group
73; 1-(4-butynoxyimino)butyl group
74; 1-(1-cyclohexenoxyimino)butyl group
75; 1-(2,2,2-trifluoroethoxyimino)butyl group
76; 1-(benzyloxyimino)butyl group
77; 1-(2-fluorobenzyloxyimino)butyl group
78; 1-(3-fluorobenzyloxyimino)butyl group
79; 1-(4-fluorobenzyloxyimino)butyl group
80; 1-(2-chlorobenzyloxyimino)butyl group
81; 1-(3-chlorobenzyloxyimino)butyl group
82; 1-(4-chlorobenzyloxyimino)butyl group
83; 1-(2-methylbenzyloxyimino)butyl group
84; 1-(3-methylbenzyloxyimino)butyl group
85; 1-(4-methylbenzyloxyimino)butyl group
86; 1-(2-cyanobenzyloxyimino)butyl group
87; 1-(3-cyanobenzyloxyimino)butyl group
Substituent Number; Q
88; 1-(4-cyanobenzyloxyimino)butyl group
89; 1-(2-trifluoromethylbenzyloxyimino)butyl group
90; 1-(3-trifluoromethylbenzyloxyimino)butyl group
91; 1-(4-trifluoromethylbenzyloxyimino)butyl group
92; 1-(2-difluoromethylbenzyloxyimino)butyl group
93; 1-(3-difluoromethylbenzyloxyimino)butyl group
94; 1-(4-difluoromethylbenzyloxyimino)butyl group
95; 1-(2-methoxybenzyloxyimino)butyl group
96; 1-(3-methoxybenzyloxyimino)butyl group
97; 1-(4-methoxybenzyloxyimino)butyl group
98; 1-(2-vinylbenzyloxyimino)butyl group
99; 1-(3-vinylbenzyloxyimino)butyl group
100; 1-(4-vinylbenzyloxyimino)butyl group
101; 1-(2-penylbenzyloxyimino)butyl group
102; 1-(3-penylbenzyloxyimino)butyl group
103; 1-(4-penylbenzyloxyimino)butyl group
104; 1-(2,3-difluorobenzyloxyimino)butyl group
105; 1-(2,4-difluorobenzyloxyimino)butyl group
106; 1-(2,5-difluorobenzyloxyimino)butyl group
107; 1-(2,6-difluorobenzyloxyimino)butyl group
108; 1-(3,4-difluorobenzyloxyimino)butyl group
109; 1-(3,5-difluorobenzyloxyimino)butyl group
110: 1-(2,3,4,5,6-pentafluorobenzyloxyimino)butyl group
111; 1-(3-ethylbenzyloxyimino)butyl group 112; 1-(4-ethylbenzyloxyimino)butyl group
113; 1-(2-trifluoromethoxybenzyloxyimino)butyl group
114; 1-(3-trifluoromethoxybenzyloxyimino)butyl group
115; 1-(4-trifluoromethoxybenzyloxyimino)butyl group
116; 1-(methoxyimino)butyl group
Substituent Number; Q
117; 1-(ethoxyimino)pentyl group
118; 1-(propyloxyimino)pentyl group
119; 1-(n-butoxyimino)pentyl group
120; 1-(n-pentyloxyimino)pentyl group
121; 1-(n-hexyloxyimino)pentyl group
122; 1-(isopropoxyimino)pentyl group
123; 1-(tert-butoxyimino)pentyl group
124; 1-(sec-butoxyimino)pentyl group
125; 1-(cyclopropyloxyimino)pentyl group
126; 1-(cyclopentyloxyimino)pentyl group
127; 1-(cyclohexyloxyimino)pentyl group
128; 1-(3-allyloxyimino)pentyl group
129; 1-(4-butenoxyimino)pentyl group
130; 1-(3-propynoxyimino)pentyl group
131; 1-(4-butynoxyimino)pentyl group
132; 1-(1-cyclohexenoxyimino)pentyl group
133; 1-(2,2,2-trifluoroethoxyimino)pentyl group
134; 1-(benzyloxyimino)pentyl group
135; 1-(2-fluorobenzyloxyimino)pentyl group
136; 1-(3-fluorobenzyloxyimino)pentyl group
137; 1-(4-fluorobenzyloxyimino)pentyl group
138; 1-(2-chlorobenzyloxyimino)pentyl group
139; 1-(3-chlorobenzyloxyimino)pentyl group
140; 1-(4-chlorobenzyloxyimino)pentyl group
141; 1-(2-methylbenzyloxyimino)pentyl group
142; 1-(3-methylbenzyloxyimino)pentyl group
143; 1-(4-methylbenzyloxyimino)pentyl group
144; 1-(2-cyanobenzyloxyimino)pentyl group
145; 1-(3-cyanobenzyloxyimino)pentyl group
Substituent Number; Q
146; 1-(4-cyanobenzyloxyimino)pentyl group
147; 1-(2-trifluoromethylbenzyloxyimino)pentyl group
148; 1-(3-trifluoromethylbenzyloxyimino)pentyl group
149; 1-(4-trifluoromethylbenzyloxyimino)pentyl group
150; 1-(2-difluoromethylbenzyloxyimino)pentyl group
151; 1-(3-difluoromethylbenzyloxyimino)pentyl group
152; 1-(4-difluoromethylbenzyloxyimino)pentyl group
153; 1-(2-methoxybenzyloxyimino)pentyl group
154; 1-(3-methoxybenzyloxyimino)pentyl group
155; 1-(4-methoxybenzyloxyimino)pentyl group
156; 1-(2-vinylbenzyloxyimino)pentyl group
157; 1-(3-vinylbenzyloxyimino)pentyl group
158; 1-(4-vinylbenzyloxyimino)pentyl group
159; 1-(2-phenylbenzyloxyimino)pentyl group
160; 1-(3-phenylbenzyloxyimino)pentyl group
161; 1-(4-phenylbenzyloxyimino)pentyl group
162; 1-(2,3-difluorobenzyloxyimino)pentyl group
163; 1-(2,4-difluorobenzyloxyimino)pentyl group
164; 1-(2,5-difluorobenzyloxyimino)pentyl group
165; 1-(2,6-difluorobenzyloxyimino)pentyl group
166; 1-(3,4-difluorobenzyloxyimino)pentyl group
167; 1-(3,5-difluorobenzyloxyimino)pentyl group
168; 1-(2,3,4,5,6-pentafluorobenzyloxyimino)pentyl group
169; 1-(3-ethylbenzyloxyimino)pentyl group
170; 1-(4-ethylbenzyloxyimino)pentyl group
171; 1-(2-trifluoromethoxybenzyloxyimino)pentyl group
172; 1-(3-trifluoromethoxybenzyloxyimino)pentyl group
173; 1-(4-trifluoromethoxybenzyloxyimino)pentyl group
174; 1-(methoxyimino)pentyl group
Substituent Number; Q
291; 1-(ethoxyimino)-2-methyl-propyl group
292; 1-(propyloxyimino)-2-methyl-propyl group
293; 1-(n-butoxyimino)-2-methyl-propyl group
294; 1-(n-pentyloxyimino)-2-methyl-propyl group
295; 1-(n-hexyloxyimino)-2-methyl-propyl group
296; 1-(isopropoxyimino)-2-methyl-propyl group
297; 1-(tert-butoxyimino)-2-methyl-propyl group
298; 1-(sec-butoxyimino)-2-methyl-propyl group
299; 1-(cyclopropyloxyimino)-2-methyl-propyl group
300; 1-(cyclopentyloxyimino)-2-methyl-propyl group
301; 1-(cyclohexyloxyimino)-2-methyl-propyl group
302; 1-(3-allyloxyimino)-2-methyl-propyl group
303; 1-(4-butenoxyimino)-2-methyl-propyl group
304; 1-(3-propynoxyimino)-2-methyl-propyl group
305; 1-(4-butynoxyimino)-2-methyl-propyl group
306; 1-(1-cyclohexenoxyimino)-2-methyl-propyl group
307; 1-(2,2,2-trifluoroethoxyimino)-2-methyl-propyl group
308; 1-(benzyloxyimino)-2-methyl-propyl group
309; 1-(2-fluorobenzyloxyimino)-2-methyl-propyl group
310; 1-(3-fluorobenzyloxyimino)-2-methyl-propyl group
311; 1-(4-fluorobenzyloxyimino)-2-methyl-propyl group
312; 1-(2-chlorobenzyloxyimino)-2-methyl-propyl group
313; 1-(3-chlorobenzyloxyimino)-2-methyl-propyl group
314; 1-(4-chlorobenzyloxyimino)-2-methyl-propyl group
315; 1-(2-methylbenzyloxyimino)-2-methyl-propyl group
316; 1-(3-methylbenzyloxyimino)-2-methyl-propyl group
317; 1-(4-methylbenzyloxyimino)-2-methyl-propyl group
318; 1-(2-cyanobenzyloxyimino)-2-methyl-propyl group
319; 1-(3-cyanobenzyloxyimino)-2-methyl-propyl group
Substituent Number; Q
320; 1-(4-cyanobenzyloxyimino)-2-methyl-propyl group
321; 1-(2-trifluoromethylbenzyloxyimino)-2-methyl-propyl group
322; 1-(3-trifluoromethylbenzyloxyimino)-2-methyl-propyl group
323; 1-(4-trifluoromethylbenzyloxyimino)-2-methyl-propyl group
324; 1-(2-difluoromethylbenzyloxyimino)-2-methyl-propyl group
325; 1-(3-difluoromethylbenzyloxyimino)-2-methyl-propyl group
326; 1-(4-difluoromethylbenzyloxyimino)-2-methyl-propyl group
327; 1-(2-methoxybenzyloxyimino)-2-methyl-propyl group
328; 1-(3-methoxybenzyloxyimino)-2-methyl-propyl group
329; 1-(4-methoxybenzyloxyimino)-2-methyl-propyl group
330; 1-(2-vinylbenzyloxyimino)-2-methyl-propyl group
331; 1-(3-vinylbenzyloxyimino)-2-methyl-propyl group
332; 1-(4-vinylbenzyloxyimino)-2-methyl-propyl group
333; 1-(2-phenylbenzyloxyimino)-2-methyl-propyl group
334; 1-(3-phenylbenzyloxyimino)-2-methyl-propyl group
335; 1-(4-phenylbenzyloxyimino)-2-methyl-propyl group
336; 1-(2,3-difluorobenzyloxyimino)-2-methyl-propyl group
337; 1-(2,4-difluorobenzyloxyimino)-2-methyl-propyl group
338; 1-(2,5-difluorobenzyloxyimino)-2-methyl-propyl group
339; 1-(2,6-difluorobenzyloxyimino)-2-methyl-propyl group
340; 1-(3,4-difluorobenzyloxyimino)-2-methyl-propyl group
341; 1-(3,5-difluorobenzyloxyimino)-2-methyl-propyl group
342; 1-(2,3,4,5,6-pentafluorobenzyloxyimino)-2-methyl-propyl group
343; 1-(3-ethylbenzyloxyimino)-2-methyl-propyl group
344; 1-(4-ethylbenzyloxyimino)-2-methyl-propyl group 345; 1-(2-trifluoromethoxybenzyloxyimino)-2-methyl-propyl group
346; 1-(3-trifluoromethoxybenzyloxyimino)-2-methyl-propyl group
347; 1-(4-trifluoromethoxybenzyloxyimino)-2-methyl-propyl group
348; 1-(methoxyimino)-2-methyl-propyl group
Substituent Number; Q
349; 1-(ethoxyimino)-2,2-dimethyl-propyl group
350; 1-(propyloxyimino)-2,2-dimethyl-propyl group
351; 1-(n-butoxyimino)-2,2-dimethyl-propyl group
352; 1-(n-pentyloxyimino)-2,2-dimethyl-propyl group
353; 1-(n-hexyloxyimino)-2,2-dimethyl-propyl group
354; 1-(isopropoxyimino)-2,2-dimethyl-propyl group
355; 1-(tert-butoxyimino)-2,2-dimethyl-propyl group
356; 1-(sec-butoxyimino)-2,2-dimethyl-propyl group
357; 1-(cyclopropyloxyimino)-2,2-dimethyl-propyl group
358; 1-(cyclopentyloxyimino)-2,2-dimethyl-propyl group
359; 1-(cyclohexyloxyimino)-2,2-dimethyl-propyl group
360; 1-(3-allyloxyimino)-2,2-dimethyl-propyl group
361; 1-(4-butenoxyimino)-2,2-dimethyl-propyl group
362; 1-(3-propynoxyimino)-2,2-dimethyl-propyl group
363; 1-(4-butynoxyimino)-2,2-dimethyl-propyl group
364; 1-(1-cyclohexenoxyimino)-2,2-dimethyl-propyl group
365; 1-(2,2,2-trifluoroethoxyimino)-2,2-dimethyl-propyl group
366; 1-(benzyloxyimino)-2,2-dimethyl-propyl group
367; 1-(2-fluorobenzyloxyimino)-2,2-dimethyl-propyl group
368; 1-(3-fluorobenzyloxyimino)-2,2-dimethyl-propyl group
369; 1-(4-fluorobenzyloxyimino)-2,2-dimethyl-propyl group
370; 1-(2-chlorobenzyloxyimino)-2,2-dimethyl-propyl group
371; 1-(3-chlorobenzyloxyimino)-2,2-dimethyl-propyl group
372; 1-(4-chlorobenzyloxyimino)-2,2-dimethyl-propyl group
373; 1-(2-methylbenzyloxyimino)-2,2-dimethyl-propyl group
374; 1-(3-methylbenzyloxyimino)-2,2-dimethyl-propyl group
375; 1-(4-methylbenzyloxyimino)-2,2-dimethyl-propyl group
376; 1-(2-cyanobenzyloxyimino)-2,2-dimethyl-propyl group
377; 1-(3-cyanobenzyloxyimino)-2,2-dimethyl-propyl group
Substituent Number; Q
378; 1-(4-cyanobenzyloxyimino)-2,2-dimethyl-propyl group
379; 1-(2-trifluoromethylbenzyloxyimino)-2,2-dimethyl-propyl group
380; 1-(3-trifluoromethylbenzyloxyimino)-2,2-dimethyl-propyl group
381; 1-(4-trifluoromethylbenzyloxyimino)-2,2-dimethyl-propyl group
382; 1-(2-difluoromethylbenzyloxyimino)-2,2-dimethyl-propyl group
383; 1-(3-difluoromethylbenzyloxyimino)-2,2-dimethyl-propyl group
384; 1-(4-difluoromethylbenzyloxyimino)-2,2-dimethyl-propyl group
385; 1-(2-methoxybenzyloxyimino)-2,2-dimethyl-propyl group
386; 1-(3-methoxybenzyloxyimino)-2,2-dimethyl-propyl group
387; 1-(4-methoxybenzyloxyimino)-2,2-dimethyl-propyl group
388; 1-(2-vinylbenzyloxyimino)-2,2-dimethyl-propyl group
389; 1-(3-vinylbenzyloxyimino)-2,2-dimethyl-propyl group
390; 1-(4-vinylbenzyloxyimino)-2,2-dimethyl-propyl group
391; 1-(2-phenylbenzyloxyimino)-2,2-dimethyl-propyl group
392; 1-(3-phenylbenzyloxyimino)-2,2-dimethyl-propyl group
393; 1-(4-phenylbenzyloxyimino)-2,2-dimethyl-propyl group
394; 1-(2,3-difluorobenzyloxyimino)-2,2-dimethyl-propyl group
395; 1-(2,4-difluorobenzyloxyimino)-2,2-dimethyl-propyl group
396; 1-(2,5-difluorobenzyloxyimino)-2,2-dimethyl-propyl group
397; 1-(2,6-difluorobenzyloxyimino)-2,2-dimethyl-propyl group
398; 1-(3,4-difluorobenzyloxyimino)-2,2-dimethyl-propyl group
399; 1-(3,5-difluorobenzyloxyimino)-2,2-dimethyl-propyl group
400; 1-(2,3,4,5,6-pentafluorobenzyloxyimino)-2,2-dimethyl-propyl group
401; 1-(3-ethylbenzyloxyimino)-2,2-dimethyl-propyl group
402; 1-(4-ethylbenzyloxyimino)-2,2-dimethyl-propyl group
403; 1-(2-trifluoromethoxybenzyloxyimino)-2,2-dimethyl-propyl group
404; 1-(3-trifluoromethoxybenzyloxyimino)-2,2-dimethyl-propyl group
405; 1-(4-trifluoromethoxybenzyloxyimino)-2,2-dimethyl-propyl group
406; 1-(methoxyimino)-2,2-dimethyl-propyl group
Substituent Number; Q
407; 1-(ethoxyimino)-1-cyclopropyl-methyl group
408; 1-(propyloxyimino)-1-cyclopropyl-methyl group
409; 1-(n-butoxyimino)-1-cyclopropyl-methyl group
410; 1-(n-pentyloxyimino)-1-cyclopropyl-methyl group
411; 1-(n-hexyloxyimino)-1-cyclopropyl-methyl group
412; 1-(isopropoxyimino)-1-cyclopropyl-methyl group
413; 1-(tert-butoxyimino)-1-cyclopropyl-methyl group
414; 1-(sec-butoxyimino)-1-cyclopropyl-methyl group
415; 1-(cyclopropyloxyimino)-1-cyclopropyl-methyl group
416; 1-(cyclopentyloxyimino)-1-cyclopropyl-methyl group
417; 1-(cyclohexyloxyimino)-1-cyclopropyl-methyl group
418; 1-(3-allyloxyimino)-1-cyclopropyl-methyl group
419; 1-(4-butenoxyimino)-1-cyclopropyl-methyl group
420; 1-(3-propynoxyimino)-1-cyclopropyl-methyl group
421; 1-(4-butynoxyimino)-1-cyclopropyl-methyl group
422; 1-(1-cyclohexenoxyimino)-1-cyclopropyl-methyl group
423; 1-(2,2,2-trifluoroethoxyimino)-1-cyclopropyl-methyl group
424; 1-(benzyloxyimino)-1-cyclopropyl-methyl group
425; 1-(2-fluorobenzyloxyimino)-1-cyclopropyl-methyl group
426; 1-(3-fluorobenzyloxyimino)-1-cyclopropyl-methyl group
427; 1-(4-fluorobenzyloxyimino)-1-cyclopropyl-methyl group
428; 1-(2-chlorobenzyloxyimino)-1-cyclopropyl-methyl group
429; 1-(3-chlorobenzyloxyimino)-1-cyclopropyl-methyl group 430; 1-(4-chlorobenzyloxyimino)-1-cyclopropyl-methyl group
431; 1-(2-methylbenzyloxyimino)-1-cyclopropyl-methyl group
432; 1-(3-methylbenzyloxyimino)-1-cyclopropyl-methyl group
433; 1-(4-methylbenzyloxyimino)-1-cyclopropyl-methyl group
434; 1-(2-cyanobenzyloxyimino)-1-cyclopropyl-methyl group
435; 1-(3-cyanobenzyloxyimino)-1-cyclopropyl-methyl group
Substituent Number; Q
436; 1-(4-cyanobenzyloxyimino)-1-cyclopropyl-methyl group
437; 1-(2-trifluoromethylbenzyloxyimino)-1-cyclopropyl-methyl group
438; 1-(3-trifluoromethylbenzyloxyimino)-1-cyclopropyl-methyl group
439; 1-(4-trifluoromethylbenzyloxyimino)-1-cyclopropyl-methyl group
440; 1-(2-difluoromethylbenzyloxyimino)-1-cyclopropyl-methyl group
441; 1-(3-difluoromethylbenzyloxyimino)-1-cyclopropyl-methyl group
442; 1-(4-difluoromethylbenzyloxyimino)-1-cyclopropyl-methyl group
443; 1-(2-methoxybenzyloxyimino)-1-cyclopropyl-methyl group
444; 1-(3-methoxybenzyloxyimino)-1-cyclopropyl-methyl group
445; 1-(4-methoxybenzyloxyimino)-1-cyclopropyl-methyl group
446; 1-(2-vinylbenzyloxyimino)-1-cyclopropyl-methyl group
447; 1-(3-vinylbenzyloxyimino)-1-cyclopropyl-methyl group
448; 1-(4-vinylbenzyloxyimino)-1-cyclopropyl-methyl group
449; 1-(2-phenylbenzyloxyimino)-1-cyclopropyl-methyl group
450; 1-(3-phenylbenzyloxyimino)-1-cyclopropyl-methyl group
451; 1-(4-phenylbenzyloxyimino)-1-cyclopropyl-methyl group
452; 1-(2,3-difluorobenzyloxyimino)-1-cyclopropyl-methyl group
453; 1-(2,4-difluorobenzyloxyimino)-1-cyclopropyl-methyl group
454; 1-(2,5-difluorobenzyloxyimino)-1-cyclopropyl-methyl group
455; 1-(2,6-difluorobenzyloxyimino)-1-cyclopropyl-methyl group
456; 1-(3,4-difluorobenzyloxyimino)-1-cyclopropyl-methyl group
457; 1-(3,5-difluorobenzyloxyimino)-1-cyclopropyl-methyl group
458; 1-(2,3,4,5,6-pentafluorobenzyloxyimino)-1-cyclopropyl-methyl group
459; 1-(3-ethylbenzyloxyimino)-1-cyclopropyl-methyl group
460; 1-(4-ethylbenzyloxyimino)-1-cyclopropyl-methyl group
461; 1-(2-trifluoromethoxybenzyloxyimino)-1-cyclopropyl-methyl group
462; 1-(3-trifluoromethoxybenzyloxyimino)-1-cyclopropyl-methyl group
463; 1-(4-trifluoromethoxybenzyloxyimino)-1-cyclopropyl-methyl group
464; 1-(methoxyimino)-1-cyclopropyl-methyl group
Substituent Number; Q
465; 1-(ethoxyimino)-1-cyclobutyl-methyl group
466; 1-(propyloxyimino)-1-cyclobutyl-methyl group
467; 1-(n-butoxyimino)-1-cyclobutyl-methyl group
468; 1-(n-pentyloxyimino)-1-cyclobutyl-methyl group
469; 1-(n-hexyloxyimino)-1-cyclobutyl-methyl group
470; 1-(isopropoxyimino)-1-cyclobutyl-methyl group
471; 1-(tert-butoxyimino)-1-cyclobutyl-methyl group
472; 1-(sec-butoxyimino)-1-cyclobutyl-methyl group
473; 1-(cyclopropyloxyimino)-1-cyclobutyl-methyl group
474; 1-(cyclopentyloxyimino)-1-cyclobutyl-methyl group
475; 1-(cyclohexyloxyimino)-1-cyclobutyl-methyl group
476; 1-(3-allyloxyimino)-1-cyclobutyl-methyl group
478; 1-(4-butenoxyimino)-1-cyclobutyl-methyl group
479; 1-(3-propynoxyimino)-1-cyclobutyl-methyl group
480; 1-(4-butynoxyimino)-1-cyclobutyl-methyl group
481; 1-(1-cyclohexenoxyimino)-1-cyclobutyl-methyl group
482; 1-(2,2,2-trifluoroethoxyimino)-1-cyclobutyl-methyl group
483; 1-(benzyloxyimino)-1-cyclobutyl-methyl group
484; 1-(2-fluorobenzyloxyimino)-1-cyclobutyl-methyl group
485; 1-(3-fluorobenzyloxyimino)-1-cyclobutyl-methyl group
486; 1-(4-fluorobenzyloxyimino)-1-cyclobutyl-methyl group
487; 1-(2-chlorobenzyloxyimino)-1-cyclobutyl-methyl group
488; 1-(3-chlorobenzyloxyimino)-1-cyclobutyl-methyl group
489; 1-(4-chlorobenzyloxyimino)-1-cyclobutyl-methyl group
490; 1-(2-methylbenzyloxyimino)-1-cyclobutyl-methyl group
491; 1-(3-methylbenzyloxyimino)-1-cyclobutyl-methyl group
492; 1-(4-methylbenzyloxyimino)-1-cyclobutyl-methyl group
493; 1-(2-cyanobenzyloxyimino)-1-cyclobutyl-methyl group
494; 1-(3-cyanobenzyloxyimino)-1-cyclobutyl-methyl group
Substituent Number; Q
495; 1-(4-cyanobenzyloxyimino)-1-cyclobutyl-methyl group
496; 1-(2-trifluoromethylbenzyloxyimino)-1-cyclobutyl-methyl group
497; 1-(3-trifluoromethylbenzyloxyimino)-1-cyclobutyl-methyl group
498; 1-(4-trifluoromethylbenzyloxyimino)-1-cyclobutyl-methyl group
499; 1-(2-difluoromethylbenzyloxyimino)-1-cyclobutyl-methyl group
500; 1-(3-difluoromethylbenzyloxyimino)-1-cyclobutyl-methyl group
501; 1-(4-difluoromethylbenzyloxyimino)-1-cyclobutyl-methyl group
502; 1-(2-methoxybenzyloxyimino)-1-cyclobutyl-methyl group
503; 1-(3-methoxybenzyloxyimino)-1-cyclobutyl-methyl group
504; 1-(4-methoxybenzyloxyimino)-1-cyclobutyl-methyl group
505; 1-(2-vinylbenzyloxyimino)-1-cyclobutyl-methyl group 506; 1-(3-vinylbenzyloxyimino)-1-cyclobutyl-methyl group
507; 1-(4-vinylbenzyloxyimino)-1-cyclobutyl-methyl group
508; 1-(2-phenylbenzyloxyimino)-1-cyclobutyl-methyl group
509; 1-(3-phenylbenzyloxyimino)-1-cyclobutyl-methyl group
510; 1-(4-phenylbenzyloxyimino)-1-cyclobutyl-methyl group
511; 1-(2,3-difluorobenzyloxyimino)-1-cyclobutyl-methyl group
512; 1-(2,4-difluorobenzyloxyimino)-1-cyclobutyl-methyl group
513; 1-(2,5-difluorobenzyloxyimino)-1-cyclobutyl-methyl group
514; 1-(2,6-difluorobenzyloxyimino)-1-cyclobutyl-methyl group
515; 1-(3,4-difluorobenzyloxyimino)-1-cyclobutyl-methyl group
516; 1-(3,5-difluorobenzyloxyimino)-1-cyclobutyl-methyl group
517; 1-(2,3,4,5,6-pentafluorobenzyloxyimino)-1-cyclobutyl-methyl group
518; 1-(3-ethylbenzyloxyimino)-1-cyclobutyl-methyl group
519; 1-(4-ethylbenzyloxyimino)-1-cyclobutyl-methyl group
520; 1-(2-trifluoromethoxybenzyloxyimino)-1-cyclobutyl-methyl group
521; 1-(3-trifluoromethoxybenzyloxyimino)-1-cyclobutyl-methyl group
522; 1-(4-trifluoromethoxybenzyloxyimino)-1-cyclobutyl-methyl group
523; 1-(methoxyimino)-1-cyclobutyl-methyl group
Substituent Number; Q
524; 1-(ethoxyimino)-1-cyclopentyl-methyl group
525; 1-(propyloxyimino)-1-cyclopentyl-methyl group
526; 1-(n-butoxyimino)-1-cyclopentyl-methyl group
527; 1-(n-pentyloxyimino)-1-cyclopentyl-methyl group
528; 1-(n-hexyloxyimino)-1-cyclopentyl-methyl group
529; 1-(isopropoxyimino)-1-cyclopentyl-methyl group
530; 1-(tert-butoxyimino)-1-cyclopentyl-methyl group
531; 1-(sec-butoxyimino)-1-cyclopentyl-methyl group
532; 1-(cyclopropyloxyimino)-1-cyclopentyl-methyl group
533; 1-(cyclopentyloxyimino)-1-cyclopentyl-methyl group
534; 1-(cyclohexyloxyimino)-1-cyclopentyl-methyl group
535; 1-(3-allyloxyimino)-1-cyclopentyl-methyl group
536; 1-(4-butenoxyimino)-1-cyclopentyl-methyl group
537; 1-(3-propynoxyimino)-1-cyclopentyl-methyl group
538; 1-(4-butynoxyimino)-1-cyclopentyl-methyl group
539; 1-(1-cyclohexenoxyimino)-1-cyclopentyl-methyl group
540; 1-(2,2,2-trifluoroethoxyimino)-1-cyclopentyl-methyl group
541; 1-(benzyloxyimino)-1-cyclopentyl-methyl group
542; 1-(2-fluorobenzyloxyimino)-1-cyclopentyl-methyl group
543; 1-(3-fluorobenzyloxyimino)-1-cyclopentyl-methyl group
544; 1-(4-fluorobenzyloxyimino)-1-cyclopentyl-methyl group
545; 1-(2-chlorobenzyloxyimino)-1-cyclopentyl-methyl group
546; 1-(3-chlorobenzyloxyimino)-1-cyclopentyl-methyl group
547; 1-(4-chlorobenzyloxyimino)-1-cyclopentyl-methyl group
548; 1-(2-methylbenzyloxyimino)-1-cyclopentyl-methyl group
549; 1-(3-methylbenzyloxyimino)-1-cyclopentyl-methyl group
550; 1-(4-methylbenzyloxyimino)-1-cyclopentyl-methyl group
551; 1-(2-cyanobenzyloxyimino)-1-cyclopentyl-methyl group
552; 1-(3-cyanobenzyloxyimino)-1-cyclopentyl-methyl group
Substituent Number; Q
553; 1-(4-cyanobenzyloxyimino)-1-cyclopentyl-methyl group
554; 1-(2-trifluoromethylbenzyloxyimino)-1-cyclopentyl-methyl group
555; 1-(3-trifluoromethylbenzyloxyimino)-1-cyclopentyl-methyl group
556; 1-(4-trifluoromethylbenzyloxyimino)-1-cyclopentyl-methyl group
557; 1-(2-difluoromethylbenzyloxyimino)-1-cyclopentyl-methyl group
558; 1-(3-difluoromethylbenzyloxyimino)-1-cyclopentyl-methyl group
559; 1-(4-difluoromethylbenzyloxyimino)-1-cyclopentyl-methyl group
560; 1-(2-methoxybenzyloxyimino)-1-cyclopentyl-methyl group
561; 1-(3-methoxybenzyloxyimino)-1-cyclopentyl-methyl group
562; 1-(4-methoxybenzyloxyimino)-1-cyclopentyl-methyl group
563; 1-(2-vinylbenzyloxyimino)-1-cyclopentyl-methyl group
564; 1-(3-vinylbenzyloxyimino)-1-cyclopentyl-methyl group
565; 1-(4-vinylbenzyloxyimino)-1-cyclopentyl-methyl group
566; 1-(2-phenylbenzyloxyimino)-1-cyclopentyl-methyl group
567; 1-(3-phenylbenzyloxyimino)-1-cyclopentyl-methyl group
568; 1-(4-phenylbenzyloxyimino)-1-cyclopentyl-methyl group
569; 1-(2,3-difluorobenzyloxyimino)-1-cyclopentyl-methyl group
570; 1-(2,4-difluorobenzyloxyimino)-1-cyclopentyl-methyl group
571; 1-(2,5-difluorobenzyloxyimino)-1-cyclopentyl-methyl group
572; 1-(2,6-difluorobenzyloxyimino)-1-cyclopentyl-methyl group
573; 1-(3,4-difluorobenzyloxyimino)-1-cyclopentyl-methyl group
574; 1-(3,5-difluorobenzyloxyimino)-1-cyclopentyl-methyl group
575; 1-(2,3,4,5,6-pentafluorobenzyloxyimino)-1-cyclopentyl-methyl group
576; 1-(3-ethylbenzyloxyimino)-1-cyclopentyl-methyl group
577; 1-(4-ethylbenzyloxyimino)-1-cyclopentyl-methyl group
578; 1-(2-trifluoromethoxybenzyloxyimino)-1-cyclopentyl-methyl group
579; 1-(3-trifluoromethoxybenzyloxyimino)-1-cyclopentyl-methyl group
580; 1-(4-trifluoromethoxybenzyloxyimino)-1-cyclopentyl-methyl group
581; 1-(methoxyimino)-1-cyclopentyl-methyl group Substituent Number; Q
582; 1-(ethoxyimino)-1-cyclohexyl-methyl group
583; 1-(propyloxyimino)-1-cyclohexyl-methyl group
584; 1-(n-butoxyimino)-1-cyclohexyl-methyl group
585; 1-(n-pentyloxyimino)-1-cyclohexyl-methyl group
586; 1-(n-hexyloxyimino)-1-cyclohexyl-methyl group
587; 1-(isopropoxyimino)-1-cyclohexyl-methyl group
588; 1-(tert-butoxyimino)-1-cyclohexyl-methyl group
589; 1-(sec-butoxyimino)-1-cyclohexyl-methyl group
590; 1-(cyclopropyloxyimino)-1-cyclohexyl-methyl group
591; 1-(cyclopentyloxyimino)-1-cyclohexyl-methyl group
592; 1-(cyclohexyloxyimino)-1-cyclohexyl-methyl group
593; 1-(3-allyloxyimino)-1-cyclohexyl-methyl group
594; 1-(4-butenoxyimino)-1-cyclohexyl-methyl group
595; 1-(3-propynoxyimino)-1-cyclohexyl-methyl group
596; 1-(4-butynoxyimino)-1-cyclohexyl-methyl group
597; 1-(1-cyclohexenoxyimino)-1-cyclohexyl-methyl group
598; 1-(2,2,2-trifluoroethoxyimino)-1-cyclohexyl-methyl group
599; 1-(benzyloxyimino)-1-cyclohexyl-methyl group
600; 1-(2-fluorobenzyloxyimino)-1-cyclohexyl-methyl group
601; 1-(3-fluorobenzyloxyimino)-1-cyclohexyl-methyl group
602; 1-(4-fluorobenzyloxyimino)-1-cyclohexyl-methyl group
603; 1-(2-chlorobenzyloxyimino)-1-cyclohexyl-methyl group
604; 1-(3-chlorobenzyloxyimino)-1-cyclohexyl-methyl group
605; 1-(4-chlorobenzyloxyimino)-1-cyclohexyl-methyl group
606; 1-(2-methylbenzyloxyimino)-1-cyclohexyl-methyl group
607; 1-(3-methylbenzyloxyimino)-1-cyclohexyl-methyl group
608; 1-(4-methylbenzyloxyimino)-1-cyclohexyl-methyl group
609; 1-(2-cyanobenzyloxyimino)-1-cyclohexyl-methyl group
610; 1-(3-cyanobenzyloxyimino)-1-cyclohexyl-methyl group
Substituent Number; Q
617; 1-(4-cyanobenzyloxyimino)-1-cyclohexyl-methyl group
618; 1-(2-trifluoromethylbenzyloxyimino)-1-cyclohexyl-methyl group
619; 1-(3-trifluoromethylbenzyloxyimino)-1-cyclohexyl-methyl group
620; 1-(4-trifluoromethylbenzyloxyimino)-1-cyclohexyl-methyl group
621; 1-(2-difluoromethylbenzyloxyimino)-1-cyclohexyl-methyl group
622; 1-(3-difluoromethylbenzyloxyimino)-1-cyclohexyl-methyl group
623; 1-(4-difluoromethylbenzyloxyimino)-1-cyclohexyl-methyl group
624; 1-(2-methoxybenzyloxyimino)-1-cyclohexyl-methyl group
625; 1-(3-methoxybenzyloxyimino)-1-cyclohexyl-methyl group
626; 1-(4-methoxybenzyloxyimino)-1-cyclohexyl-methyl group
627; 1-(2-vinylbenzyloxyimino)-1-cyclohexyl-methyl group
628; 1-(3-vinylbenzyloxyimino)-1-cyclohexyl-methyl group
629; 1-(4-vinylbenzyloxyimino)-1-cyclohexyl-methyl group
630; 1-(2-phenylbenzyloxyimino)-1-cyclohexyl-methyl group
631; 1-(3-phenylbenzyloxyimino)-1-cyclohexyl-methyl group
632; 1-(4-phenylbenzyloxyimino)-1-cyclohexyl-methyl group
633; 1-(2,3-difluorobenzyloxyimino)-1-cyclohexyl-methyl group
634; 1-(2,4-difluorobenzyloxyimino)-1-cyclohexyl-methyl group
635; 1-(2,5-difluorobenzyloxyimino)-1-cyclohexyl-methyl group
636; 1-(2,6-difluorobenzyloxyimino)-1-cyclohexyl-methyl group
637; 1-(3,4-difluorobenzyloxyimino)-1-cyclohexyl-methyl group
638; 1-(3,5-difluorobenzyloxyimino)-1-cyclohexyl-methyl group
639; 1-(2,3,4,5,6-pentafluorobenzyloxyimino)-1-cyclohexyl-methyl group
640; 1-(3-ethylbenzyloxyimino)-1-cyclohexyl-methyl group
642; 1-(4-ethylbenzyloxyimino)-1-cyclohexyl-methyl group
643; 1-(2-trifluoromethoxybenzyloxyimino)-1-cyclohexyl-methyl group
644; 1-(3-trifluoromethoxybenzyloxyimino)-1-cyclohexyl-methyl group
645; 1-(4-trifluoromethoxybenzyloxyimino)-1-cyclohexyl-methyl group
646; 1-(methoxyimino)-1-cyclohexyl-methyl group
Substituent Number; Q
647; 1-(ethoxyimino)-1-(1-cyclohexenyl)-methyl group
648; 1-(propyloxyimino)-1-(1-cyclohexenyl)-methyl group
649; 1-(n-butoxyimino)-1-(1-cyclohexenyl)-methyl group
650; 1-(n-pentyloxyimino)-1-(1-cyclohexenyl)-methyl group
651; 1-(n-hexyloxyimino)-1-(1-cyclohexenyl)-methyl group
652; 1-(isopropoxyimino)-1-(1-cyclohexenyl)-methyl group
653; 1-(tert-butoxyimino)-1-(1-cyclohexenyl)-methyl group
654; 1-(sec-butoxyimino)-1-(1-cyclohexenyl)-methyl group
655; 1-(cyclopropyloxyimino)-1-(1-cyclohexenyl)-methyl group
656; 1-(cyclopentyloxyimino)-1-(1-cyclohexenyl)-methyl group
657; 1-(cyclohexyloxyimino)-1-(1-cyclohexenyl)-methyl group
658; 1-(3-allyloxyimino)-1-(1-cyclohexenyl)-methyl group
659; 1-(4-butenoxyimino)-1-(1-cyclohexenyl)-methyl group
660; 1-(3-propynoxyimino)-1-(1-cyclohexenyl)-methyl group
661; 1-(4-butynoxyimino)-1-(1-cyclohexenyl)-methyl group
662; 1-(1-cyclohexenoxyimino)-1-(1-cyclohexenyl)-methyl group
663; 1-(2,2,2-trifluoroethoxyimino)-1-(1-cyclohexenyl)-methyl group
664; 1-(benzyloxyimino)-1-(1-cyclohexenyl)-methyl group
665; 1-(2-fluorobenzyloxyimino)-1-(1-cyclohexenyl)-methyl group
666; 1-(3-fluorobenzyloxyimino)-1-(1-cyclohexenyl)-methyl group
667; 1-(4-fluorobenzyloxyimino)-1-(1-cyclohexenyl)-methyl group 668; 1-(2-chlorobenzyloxyimino)-1-(1-cyclohexenyl)-methyl group
669; 1-(3-chlorobenzyloxyimino)-1-(1-cyclohexenyl)-methyl group
670; 1-(4-chlorobenzyloxyimino)-1-(1-cyclohexenyl)-methyl group
671; 1-(2-methylbenzyloxyimino)-1-(1-cyclohexenyl)-methyl group
672; 1-(3-methylbenzyloxyimino)-1-(1-cyclohexenyl)-methyl group
673; 1-(4-methylbenzyloxyimino)-1-(1-cyclohexenyl)-methyl group
674; 1-(2-cyanobenzyloxyimino)-1-(1-cyclohexenyl)-methyl group
675; 1-(3-cyanobenzyloxyimino)-1-(1-cyclohexenyl)-methyl group
Substituent Number; Q
676; 1-(4-cyanobenzyloxyimino)-1-(1-cyclohexenyl)-methyl group
677; 1-(2-trifluoromethylbenzyloxyimino)-1-(1-cyclohexenyl)-methyl group
678; 1-(3-trifluoromethylbenzyloxyimino)-1-(1-cyclohexenyl)-methyl group
679; 1-(4-trifluoromethylbenzyloxyimino)-1-(1-cyclohexenyl)-methyl group
680; 1-(2-difluoromethylbenzyloxyimino)-1-(1-cyclohexenyl)-methyl group
681; 1-(3-difluoromethylbenzyloxyimino)-1-(1-cyclohexenyl)-methyl group
682; 1-(4-difluoromethylbenzyloxyimino)-1-(1-cyclohexenyl)-methyl group
683; 1-(2-methoxybenzyloxyimino)-1-(1-cyclohexenyl)-methyl group
684; 1-(3-methoxybenzyloxyimino)-1-(1-cyclohexenyl)-methyl group
685; 1-(4-methoxybenzyloxyimino)-1-(1-cyclohexenyl)-methyl group
686; 1-(2-vinylbenzyloxyimino)-1-(1-cyclohexenyl)-methyl group
687; 1-(3-vinylbenzyloxyimino)-1-(1-cyclohexenyl)-methyl group
688; 1-(4-vinylbenzyloxyimino)-1-(1-cyclohexenyl)-methyl group
689; 1-(2-phenylbenzyloxyimino)-1-(1-cyclohexenyl)-methyl group
690; 1-(3-phenylbenzyloxyimino)-1-(1-cyclohexenyl)-methyl group
691; 1-(4-phenylbenzyloxyimino)-1-(1-cyclohexenyl)-methyl group
692; 1-(2,3-difluorobenzyloxyimino)-1-(1-cyclohexenyl)-methyl group
693; 1-(2,4-difluorobenzyloxyimino)-1-(1-cyclohexenyl)-methyl group
694; 1-(2,5-difluorobenzyloxyimino)-1-(1-cyclohexenyl)-methyl group
695; 1-(2,6-difluorobenzyloxyimino)-1-(1-cyclohexenyl)-methyl group
696; 1-(3,4-difluorobenzyloxyimino)-1-(1-cyclohexenyl)-methyl group
697; 1-(3,5-difluorobenzyloxyimino)-1-(1-cyclohexenyl)-methyl group
698; 1-(2,3,4,5,6-pentafluorobenzyloxyimino)-1-(1-cyclohexenyl)-methyl group-1-(1-cyclohexyl)-methyl group;
699; 1-(3-ethylbenzyloxyimino)-1-(1-cyclohexenyl)-methyl group
700; 1-(4-ethylbenzyloxyimino)-1-(1-cyclohexenyl)-methyl group
701; 1-(2-trifluoromethoxybenzyloxyimino)-1-(1-cyclohexenyl)-methyl group
702; 1-(3-trifluoromethoxybenzyloxyimino)-1-(1-cyclohexenyl)-methyl group
703; 1-(4-trifluoromethoxybenzyloxyimino)-1-(1-cyclohexenyl)-methyl group
704; 1-(methoxyimino)-1-(1-cyclohexenyl)-methyl group
Substituent Number; Q
705; 1-(ethoxyimino)-1-phenyl-methyl group
706; 1-(propyloxyimino)-1-phenyl-methyl group
707; 1-(n-butoxyimino)-1-phenyl-methyl group
708; 1-(n-pentyloxyimino)-1-phenyl-methyl group
709; 1-(n-hexyloxyimino)-1-phenyl-methyl group
710; 1-(isopropoxyimino)-1-phenyl-methyl group
711; 1-(tert-butoxyimino)-1-phenyl-methyl group
712; 1-(sec-butoxyimino)-1-phenyl-methyl group
713; 1-(cyclopropyloxyimino)-1-phenyl-methyl group
714; 1-(cyclopentyloxyimino)-1-phenyl-methyl group
715; 1-(cyclohexyloxyimino)-1-phenyl-methyl group
716; 1-(3-allyloxyimino)-1-phenyl-methyl group
717; 1-(4-butenoxyimino)-1-phenyl-methyl group
718; 1-(3-propynoxyimino)-1-phenyl-methyl group
719; 1-(4-butynoxyimino)-1-phenyl-methyl group
720; 1-(1-cyclohexenoxyimino)-1-phenyl-methyl group
721; 1-(2,2,2-trifluoroethoxyimino)-1-phenyl-methyl group
722; 1-(benzyloxyimino)-1-phenyl-methyl group
723; 1-(2-fluorobenzyloxyimino)-1-phenyl-methyl group
224; 1-(3-fluorobenzyloxyimino)-1-phenyl-methyl group
725; 1-(4-fluorobenzyloxyimino)-1-phenyl-methyl group
726; 1-(2-chlorobenzyloxyimino)-1-phenyl-methyl group
727; 1-(3-chlorobenzyloxyimino)-1-phenyl-methyl group
728; 1-(4-chlorobenzyloxyimino)-1-phenyl-methyl group
729; 1-(2-methylbenzyloxyimino)-1-phenyl-methyl group
730; 1-(3-methylbenzyloxyimino)-1-phenyl-methyl group
731; 1-(4-methylbenzyloxyimino)-1-phenyl-methyl group
732; 1-(2-cyanobenzyloxyimino)-1-phenyl-methyl group
733; 1-(3-cyanobenzyloxyimino)-1-phenyl-methyl group
Substituent Number; Q
734; 1-(4-cyanobenzyloxyimino)-1-phenyl-methyl group
735; 1-(2-trifluoromethylbenzyloxyimino)-1-phenyl-methyl group
736; 1-(3-trifluoromethylbenzyloxyimino)-1-phenyl-methyl group
737; 1-(4-trifluoromethylbenzyloxyimino)-1-phenyl-methyl group
738; 1-(2-difluoromethylbenzyloxyimino)-1-phenyl-methyl group
739; 1-(3-difluoromethylbenzyloxyimino)-1-phenyl-methyl group
740; 1-(4-difluoromethylbenzyloxyimino)-1-phenyl-methyl group
741; 1-(2-methoxybenzyloxyimino)-1-phenyl-methyl group
742; 1-(3-methoxybenzyloxyimino)-1-phenyl-methyl group
743; 1-(4-methoxybenzyloxyimino)-1-phenyl-methyl group
744; 1-(2-vinylbenzyloxyimino)-1-phenyl-methyl group
745; 1-(3-vinylbenzyloxyimino)-1-phenyl-methyl group
746; 1-(4-vinylbenzyloxyimino)-1-phenyl-methyl group
747; 1-(2-phenylbenzyloxyimino)-1-phenyl-methyl group
748; 1-(3-phenylbenzyloxyimino)-1-phenyl-methyl group
749; 1-(4-phenylbenzyloxyimino)-1-phenyl-methyl group
750; 1-(2,3-difluorobenzyloxyimino)-1-phenyl-methyl group
751; 1-(2,4-difluorobenzyloxyimino)-1-phenyl-methyl group
752; 1-(2,5-difluorobenzyloxyimino)-1-phenyl-methyl group 753; 1-(2,6-difluorobenzyloxyimino)-1-phenyl-methyl group
754; 1-(3,4-difluorobenzyloxyimino)-1-phenyl-methyl group
755; 1-(3,5-difluorobenzyloxyimino)-1-phenyl-methyl group
756; 1-(2,3,4,5,6-pentafluorobenzyloxyimino)-1-phenyl-methyl group
757; 1-(3-ethylbenzyloxyimino)-1-phenyl-methyl group
758; 1-(4-ethylbenzyloxyimino)-1-phenyl-methyl group
759; 1-(2-trifluoromethoxybenzyloxyimino)-1-phenyl-methyl group
760; 1-(3-trifluoromethoxybenzyloxyimino)-1-phenyl-methyl group
761; 1-(4-trifluoromethoxybenzyloxyimino)-1-phenyl-methyl group
762; 1-(methoxyimino)-1-phenyl-methyl group
Substituent Number; Q
763; 1-(ethoxyimino)-1-(2-chlorophenyl)-methyl group
764; 1-(propyloxyimino)-1-(2-chlorophenyl)-methyl group
765; 1-(n-butoxyimino)-1-(2-chlorophenyl)-methyl group
766; 1-(n-pentyloxyimino)-1-(2-chlorophenyl)-methyl group
767; 1-(n-hexyloxyimino)-1-(2-chlorophenyl)-methyl group
768; 1-(isopropoxyimino)-1-(2-chlorophenyl)-methyl group
769; 1-(tert-butoxyimino)-1-(2-chlorophenyl)-methyl group
770; 1-(sec-butoxyimino)-1-(2-chlorophenyl)-methyl group
771; 1-(cyclopropyloxyimino)-1-(2-chlorophenyl)-methyl group
772; 1-(cyclopentyloxyimino)-1-(2-chlorophenyl)-methyl group
773; 1-(cyclohexyloxyimino)-1-(2-chlorophenyl)-methyl group
774; 1-(3-allyloxyimino)-1-(2-chlorophenyl)-methyl group
775; 1-(4-butenoxyimino)-1-(2-chlorophenyl)-methyl group
776; 1-(3-propynoxyimino)-1-(2-chlorophenyl)-methyl group
777; 1-(4-butynoxyimino)-1-(2-chlorophenyl)-methyl group
778; 1-(1-cyclohexenoxyimino)-1-(2-chlorophenyl)-methyl group
779; 1-(2,2,2-trifluoroethoxyimino)-1-(2-chlorophenyl)-methyl group
780; 1-(benzyloxyimino)-1-(2-chlorophenyl)-methyl group
781; 1-(2-fluorobenzyloxyimino)-1-(2-chlorophenyl)-methyl group
782; 1-(3-fluorobenzyloxyimino)-1-(2-chlorophenyl)-methyl group
783; 1-(4-fluorobenzyloxyimino)-1-(2-chlorophenyl)-methyl group
784; 1-(2-chlorobenzyloxyimino)-1-(2-chlorophenyl)-methyl group
785; 1-(3-chlorobenzyloxyimino)-1-(2-chlorophenyl)-methyl group
786; 1-(4-chlorobenzyloxyimino)-1-(2-chlorophenyl)-methyl group
787; 1-(2-methylbenzyloxyimino)-1-(2-chlorophenyl)-methyl group
788; 1-(3-methylbenzyloxyimino)-1-(2-chlorophenyl)-methyl group
789; 1-(4-methylbenzyloxyimino)-1-(2-chlorophenyl)-methyl group
790; 1-(2-cyanobenzyloxyimino)-1-(2-chlorophenyl)-methyl group
791; 1-(3-cyanobenzyloxyimino)-1-(2-chlorophenyl)-methyl group
Substituent Number; Q
792; 1-(4-cyanobenzyloxyimino)-1-(2-chlorophenyl)-methyl group
793; 1-(2-trifluoromethylbenzyloxyimino)-1-(2-chlorophenyl)-methyl group
794; 1-(3-trifluoromethylbenzyloxyimino)-1-(2-chlorophenyl)-methyl group
795; 1-(4-trifluoromethylbenzyloxyimino)-1-(2-chlorophenyl)-methyl group
796; 1-(2-difluoromethylbenzyloxyimino)-1-(2-chlorophenyl)-methyl group
797; 1-(3-difluoromethylbenzyloxyimino)-1-(2-chlorophenyl)-methyl group
798; 1-(4-difluoromethylbenzyloxyimino)-1-(2-chlorophenyl)-methyl group
799; 1-(2-methoxybenzyloxyimino)-1-(2-chlorophenyl)-methyl group
800; 1-(3-methoxybenzyloxyimino)-1-(2-chlorophenyl)-methyl group
801; 1-(4-methoxybenzyloxyimino)-1-(2-chlorophenyl)-methyl group
802; 1-(2-vinylbenzyloxyimino)-1-(2-chlorophenyl)-methyl group
803; 1-(3-vinylbenzyloxyimino)-1-(2-chlorophenyl)-methyl group
804; 1-(4-vinylbenzyloxyimino)-1-(2-chlorophenyl)-methyl group
805; 1-(2-phenylbenzyloxyimino)-1-(2-chlorophenyl)-methyl group
806; 1-(3-phenylbenzyloxyimino)-1-(2-chlorophenyl)-methyl group
807; 1-(4-phenylbenzyloxyimino)-1-(2-chlorophenyl)-methyl group
808; 1-(2,3-difluorobenzyloxyimino)-1-(2-chlorophenyl)-methyl group
809; 1-(2,4-difluorobenzyloxyimino)-1-(2-chlorophenyl)-methyl group
800; 1-(2,5-difluorobenzyloxyimino)-1-(2-chlorophenyl)-methyl group
801; 1-(2,6-difluorobenzyloxyimino)-1-(2-chlorophenyl)-methyl group
802; 1-(3,4-difluorobenzyloxyimino)-1-(2-chlorophenyl)-methyl group
803; 1-(3,5-difluorobenzyloxyimino)-1-(2-chlorophenyl)-methyl group
804; 1-(2,3,4,5,6-pentafluorobenzyloxyimino)-1-(2-chlorophenyl)-methyl group
805; 1-(3-ethylbenzyloxyimino)-1-(2-chlorophenyl)-methyl group
806; 1-(4-ethylbenzyloxyimino)-1-(2-chlorophenyl)-methyl group
807; 1-(2-trifluoromethoxybenzyloxyimino)-1-(2-chlorophenyl)-methyl group
808; 1-(3-trifluoromethoxybenzyloxyimino)-1-(2-chlorophenyl)-methyl group
809; 1-(4-trifluoromethoxybenzyloxyimino)-1-(2-chlorophenyl)-methyl group
810; 1-(methoxyimino)-1-(2-chlorophenyl)-methyl group
Substituent Number; Q
811; 1-(ethoxyimino)-1-(3-chlorophenyl)-methyl group
812; 1-(propyloxyimino)-1-(3-chlorophenyl)-methyl group
813; 1-(n-butoxyimino)-1-(3-chlorophenyl)-methyl group
814; 1-(n-pentyloxyimino)-1-(3-chlorophenyl)-methyl group
815; 1-(n-hexyloxyimino)-1-(3-chlorophenyl)-methyl group
816; 1-(isopropoxyimino)-1-(3-chlorophenyl)-methyl group
817; 1-(tert-butoxyimino)-1-(3-chlorophenyl)-methyl group
818; 1-(sec-butoxyimino)-1-(3-chlorophenyl)-methyl group 819; 1-(cyclopropyloxyimino)-1-(3-chlorophenyl)-methyl group
820; 1-(cyclopentyloxyimino)-1-(3-chlorophenyl)-methyl group
821; 1-(cyclohexyloxyimino)-1-(3-chlorophenyl)-methyl group
822; 1-(3-allyloxyimino)-1-(3-chlorophenyl)-methyl group
823; 1-(4-butenoxyimino)-1-(3-chlorophenyl)-methyl group
824; 1-(3-propynoxyimino)-1-(3-chlorophenyl)-methyl group
825; 1-(4-butynoxyimino)-1-(3-chlorophenyl)-methyl group
826; 1-(1-cyclohexenoxyimino)-1-(3-chlorophenyl)-methyl group
827; 1-(2,2,2-trifluoroethoxyimino)-1-(3-chlorophenyl)-methyl group
828; 1-(benzyloxyimino)-1-(3-chlorophenyl)-methyl group
829; 1-(2-fluorobenzyloxyimino)-1-(3-chlorophenyl)-methyl group
830; 1-(3-fluorobenzyloxyimino)-1-(3-chlorophenyl)-methyl group
831; 1-(4-fluorobenzyloxyimino)-1-(3-chlorophenyl)-methyl group
832; 1-(2-chlorobenzyloxyimino)-1-(3-chlorophenyl)-methyl group
833; 1-(3-chlorobenzyloxyimino)-1-(3-chlorophenyl)-methyl group
834; 1-(4-chlorobenzyloxyimino)-1-(3-chlorophenyl)-methyl group
835; 1-(2-methylbenzyloxyimino)-1-(3-chlorophenyl)-methyl group
836; 1-(3-methylbenzyloxyimino)-1-(3-chlorophenyl)-methyl group
837; 1-(4-methylbenzyloxyimino)-1-(3-chlorophenyl)-methyl group
838; 1-(2-cyanobenzyloxyimino)-1-(3-chlorophenyl)-methyl group
839; 1-(3-cyanobenzyloxyimino)-1-(3-chlorophenyl)-methyl group
Substituent Number; Q
840; 1-(4-cyanobenzyloxyimino)-1-(3-chlorophenyl)-methyl group
841; 1-(2-trifluoromethylbenzyloxyimino)-1-(3-chlorophenyl)-methyl group
842; 1-(3-trifluoromethylbenzyloxyimino)-1-(3-chlorophenyl)-methyl group
843; 1-(4-trifluoromethylbenzyloxyimino)-1-(3-chlorophenyl)-methyl group
844; 1-(2-difluoromethylbenzyloxyimino)-1-(3-chlorophenyl)-methyl group
845; 1-(3-difluoromethylbenzyloxyimino)-1-(3-chlorophenyl)-methyl group
846; 1-(4-difluoromethylbenzyloxyimino)-1-(3-chlorophenyl)-methyl group
847; 1-(2-methoxybenzyloxyimino)-1-(3-chlorophenyl)-methyl group
848; 1-(3-methoxybenzyloxyimino)-1-(3-chlorophenyl)-methyl group
849; 1-(4-methoxybenzyloxyimino)-1-(3-chlorophenyl)-methyl group
850; 1-(2-vinylbenzyloxyimino)-1-(3-chlorophenyl)-methyl group
851; 1-(3-vinylbenzyloxyimino)-1-(3-chlorophenyl)-methyl group
852; 1-(4-vinylbenzyloxyimino)-1-(3-chlorophenyl)-methyl group
853; 1-(2-phenylbenzyloxyimino)-1-(3-chlorophenyl)-methyl group
854; 1-(3-phenylbenzyloxyimino)-1-(3-chlorophenyl)-methyl group
855; 1-(4-phenylbenzyloxyimino)-1-(3-chlorophenyl)-methyl group
856; 1-(2,3-difluorobenzyloxyimino)-1-(3-chlorophenyl)-methyl group
857; 1-(2,4-difluorobenzyloxyimino)-1-(3-chlorophenyl)-methyl group
858; 1-(2,5-difluorobenzyloxyimino)-1-(3-chlorophenyl)-methyl group
859; 1-(2,6-difluorobenzyloxyimino)-1-(3-chlorophenyl)-methyl group
860; 1-(3,4-difluorobenzyloxyimino)-1-(3-chlorophenyl)-methyl group
861; 1-(3,5-difluorobenzyloxyimino)-1-(3-chlorophenyl)-methyl group
862; 1-(2,3,4,5,6-pentafluorobenzyloxyimino)-1-(3-chlorophenyl)-methyl group
863; 1-(3-ethylbenzyloxyimino)-1-(3-chlorophenyl)-methyl group
864; 1-(4-ethylbenzyloxyimino)-1-(3-chlorophenyl)-methyl group
865; 1-(2-trifluoromethoxybenzyloxyimino)-1-(3-chlorophenyl)-methyl group
866; 1-(3-trifluoromethoxybenzyloxyimino)-1-(3-chlorophenyl)-methyl group
867; 1-(4-trifluoromethoxybenzyloxyimino)-1-(3-chlorophenyl)-methyl group
868; 1-(methoxyimino)-1-(3-chlorophenyl)-methyl group
Substituent Number; Q
869; 1-(ethoxyimino)-1-(4-chlorophenyl)-methyl group
870; 1-(propyloxyimino)-1-(4-chlorophenyl)-methyl group
871; 1-(n-butoxyimino)-1-(4-chlorophenyl)-methyl group
872; 1-(n-pentyloxyimino)-1-(4-chlorophenyl)-methyl group
873; 1-(n-hexyloxyimino)-1-(4-chlorophenyl)-methyl group
874; 1-(isopropoxyimino)-1-(4-chlorophenyl)-methyl group
875; 1-(tert-butoxyimino)-1-(4-chlorophenyl)-methyl group
876; 1-(sec-butoxyimino)-1-(4-chlorophenyl)-methyl group
877; 1-(cyclopropyloxyimino)-1-(4-chlorophenyl)-methyl group
878; 1-(cyclopentyloxyimino)-1-(4-chlorophenyl)-methyl group
879; 1-(cyclohexyloxyimino)-1-(4-chlorophenyl)-methyl group
880; 1-(3-allyloxyimino)-1-(4-chlorophenyl)-methyl group
881; 1-(4-butenoxyimino)-1-(4-chlorophenyl)-methyl group
882; 1-(3-propynoxyimino)-1-(4-chlorophenyl)-methyl group
883; 1-(4-butynoxyimino)-1-(4-chlorophenyl)-methyl group
884; 1-(1-cyclohexenoxyimino)-1-(4-chlorophenyl)-methyl group
885; )-1-(4-chlorophenyl)-methyl group
886; 1-(benzyloxyimino)-1-(4-chlorophenyl)-methyl group
887; 1-(2-fluorobenzyloxyimino)-1-(4-chlorophenyl)-methyl group
888; 1-(3-fluorobenzyloxyimino)-1-(4-chlorophenyl)-methyl group
889; 1-(4-fluorobenzyloxyimino)-1-(4-chlorophenyl)-methyl group
890; 1-(2-chlorobenzyloxyimino)-1-(4-chlorophenyl)-methyl group
891; 1-(3-chlorobenzyloxyimino)-1-(4-chlorophenyl)-methyl group 892; 1-(4-chlorobenzyloxyimino)-1-(4-chlorophenyl)-methyl group
893; 1-(2-methylbenzyloxyimino)-1-(4-chlorophenyl)-methyl group
894; 1-(3-methylbenzyloxyimino)-1-(4-chlorophenyl)-methyl group
895; 1-(4-methylbenzyloxyimino)-1-(4-chlorophenyl)-methyl group
896; 1-(2-cyanobenzyloxyimino)-1-(4-chlorophenyl)-methyl group
897; 1-(3-cyanobenzyloxyimino)-1-(4-chlorophenyl)-methyl group
Substituent Number; Q
898; 1-(4-cyanobenzyloxyimino)-1-(4-chlorophenyl)-methyl group
899; 1-(2-trifluoromethylbenzyloxyimino)-1-(4-chlorophenyl)-methyl group
900; 1-(3-trifluoromethylbenzyloxyimino)-1-(4-chlorophenyl)-methyl group
901; 1-(4-trifluoromethylbenzyloxyimino)-1-(4-chlorophenyl)-methyl group
902; 1-(2-difluoromethylbenzyloxyimino)-1-(4-chlorophenyl)-methyl group
903; 1-(3-difluoromethylbenzyloxyimino)-1-(4-chlorophenyl)-methyl group
904; 1-(4-difluoromethylbenzyloxyimino)-1-(4-chlorophenyl)-methyl group
905; 1-(2-methoxybenzyloxyimino)-1-(4-chlorophenyl)-methyl group
906; 1-(3-methoxybenzyloxyimino)-1-(4-chlorophenyl)-methyl group
907; 1-(4-methoxybenzyloxyimino)-1-(4-chlorophenyl)-methyl group
908; 1-(2-vinylbenzyloxyimino)-1-(4-chlorophenyl)-methyl group
909; 1-(3-vinylbenzyloxyimino)-1-(4-chlorophenyl)-methyl group
910; 1-(4-vinylbenzyloxyimino)-1-(4-chlorophenyl)-methyl group
911; 1-(2-phenylbenzyloxyimino)-1-(4-chlorophenyl)-methyl group
912; 1-(3-phenylbenzyloxyimino)-1-(4-chlorophenyl)-methyl group
913; 1-(4-phenylbenzyloxyimino)-1-(4-chlorophenyl)-methyl group
914; 1-(2,3-difluorobenzyloxyimino)-1-(4-chlorophenyl)-methyl group
915; 1-(2,4-difluorobenzyloxyimino)-1-(4-chlorophenyl)-methyl group
916; 1-(2,5-difluorobenzyloxyimino)-1-(4-chlorophenyl)-methyl group
917; 1-(2,6-difluorobenzyloxyimino)-1-(4-chlorophenyl)-methyl group
918; 1-(3,4-difluorobenzyloxyimino)-1-(4-chlorophenyl)-methyl group
919; 1-(3,5-difluorobenzyloxyimino)-1-(4-chlorophenyl)-methyl group
920; 1-(2,3,4,5,6-pentafluorobenzyloxyimino)-1-(4-chlorophenyl)-methyl group
921; 1-(3-ethylbenzyloxyimino)-1-(4-chlorophenyl)-methyl group
922; 1-(4-ethylbenzyloxyimino)-1-(4-chlorophenyl)-methyl group
923; 1-(2-trifluoromethoxybenzyloxyimino)-1-(4-chlorophenyl)-methyl group
924; 1-(3-trifluoromethoxybenzyloxyimino)-1-(4-chlorophenyl)-methyl group
925; 1-(4-trifluoromethoxybenzyloxyimino)-1-(4-chlorophenyl)-methyl group
926; 1-(methoxyimino)-1-(4-chlorophenyl)-methyl group
Substituent Number; Q
927; 1-(ethoxyimino)-1-(2-fluorophenyl)-methyl group
928; 1-(propyloxyimino)-1-(2-fluorophenyl)-methyl group
929; 1-(n-butoxyimino)-1-(2-fluorophenyl)-methyl group
930; 1-(n-pentyloxyimino)-1-(2-fluorophenyl)-methyl group
931; 1-(n-hexyloxyimino)-1-(2-fluorophenyl)-methyl group
932; 1-(isopropoxyimino)-1-(2-fluorophenyl)-methyl group
933; 1-(tert-butoxyimino)-1-(2-fluorophenyl)-methyl group
934; 1-(sec-butoxyimino)-1-(2-fluorophenyl)-methyl group
935; 1-(cyclopropyloxyimino)-1-(2-fluorophenyl)-methyl group
936; 1-(cyclopentyloxyimino)-1-(2-fluorophenyl)-methyl group
937; 1-(cyclohexyloxyimino)-1-(2-fluorophenyl)-methyl group
938; 1-(3-allyloxyimino)-1-(2-fluorophenyl)-methyl group
939; 1-(4-butenoxyimino)-1-(2-fluorophenyl)-methyl group
940; 1-(3-propynoxyimino)-1-(2-fluorophenyl)-methyl group
941; 1-(4-butynoxyimino)-1-(2-fluorophenyl)-methyl group
942; 1-(1-cyclohexenoxyimino)-1-(2-fluorophenyl)-methyl group
943; 1-(2,2,2-trifluoroethoxyimino)-1-(2-fluorophenyl)-methyl group
944; 1-(benzyloxyimino)-1-(2-fluorophenyl)-methyl group
945; 1-(2-fluorobenzyloxyimino)-1-(2-fluorophenyl)-methyl group
946; 1-(3-fluorobenzyloxyimino)-1-(2-fluorophenyl)-methyl group
947; 1-(4-fluorobenzyloxyimino)-1-(2-fluorophenyl)-methyl group
948; 1-(2-chlorobenzyloxyimino)-1-(2-fluorophenyl)-methyl group
949; 1-(3-chlorobenzyloxyimino)-1-(2-fluorophenyl)-methyl group
950; 1-(4-chlorobenzyloxyimino)-1-(2-fluorophenyl)-methyl group
951; 1-(2-methylbenzyloxyimino)-1-(2-fluorophenyl)-methyl group
952; 1-(3-methylbenzyloxyimino)-1-(2-fluorophenyl)-methyl group
953; 1-(4-methylbenzyloxyimino)-1-(2-fluorophenyl)-methyl group
954; 1-(2-cyanobenzyloxyimino)-1-(2-fluorophenyl)-methyl group
955; 1-(3-cyanobenzyloxyimino)-1-(2-fluorophenyl)-methyl group
Substituent Number; Q
956; 1-(4-cyanobenzyloxyimino)-1-(2-fluorophenyl)-methyl group
957; 1-(2-trifluoromethylbenzyloxyimino)-1-(2-fluorophenyl)-methyl group
958; 1-(3-trifluoromethylbenzyloxyimino)-1-(2-fluorophenyl)-methyl group
959; 1-(4-trifluoromethylbenzyloxyimino)-1-(2-fluorophenyl)-methyl group
960; 1-(2-difluoromethylbenzyloxyimino)-1-(2-fluorophenyl)-methyl group
961; 1-(3-difluoromethylbenzyloxyimino)-1-(2-fluorophenyl)-methyl group
962; 1-(4-difluoromethylbenzyloxyimino)-1-(2-fluorophenyl)-methyl group 963; 1-(2-methoxybenzyloxyimino)-1-(2-fluorophenyl)-methyl group
964; 1-(3-methoxybenzyloxyimino)-1-(2-fluorophenyl)-methyl group
965; 1-(4-methoxybenzyloxyimino)-1-(2-fluorophenyl)-methyl group
966; 1-(2-vinylbenzyloxyimino)-1-(2-fluorophenyl)-methyl group
967; 1-(3-vinylbenzyloxyimino)-1-(2-fluorophenyl)-methyl group
968; 1-(4-vinylbenzyloxyimino)-1-(2-fluorophenyl)-methyl group
969; 1-(2-phenylbenzyloxyimino)-1-(2-fluorophenyl)-methyl group
970; 1-(3-phenylbenzyloxyimino)-1-(2-fluorophenyl)-methyl group
971; 1-(4-phenylbenzyloxyimino)-1-(2-fluorophenyl)-methyl group
972; 1-(2,3-difluorobenzyloxyimino)-1-(2-fluorophenyl)-methyl group
973; 1-(2,4-difluorobenzyloxyimino)-1-(2-fluorophenyl)-methyl group
974; 1-(2,5-difluorobenzyloxyimino)-1-(2-fluorophenyl)-methyl group
975; 1-(2,6-difluorobenzyloxyimino)-1-(2-fluorophenyl)-methyl group
976; 1-(3,4-difluorobenzyloxyimino)-1-(2-fluorophenyl)-methyl group
977; 1-(3,5-difluorobenzyloxyimino)-1-(2-fluorophenyl)-methyl group
978; 1-(2,3,4,5,6-pentafluorobenzyloxyimino)-1-(2-fluorophenyl)-methyl group
979; 1-(3-ethylbenzyloxyimino)-1-(2-fluorophenyl)-methyl group
980; 1-(4-ethylbenzyloxyimino)-1-(2-fluorophenyl)-methyl group
981; 1-(2-trifluoromethoxybenzyloxyimino)-1-(2-fluorophenyl)-methyl group
982; 1-(3-trifluoromethoxybenzyloxyimino)-1-(2-fluorophenyl)-methyl group
983; 1-(4-trifluoromethoxybenzyloxyimino)-1-(2-fluorophenyl)-methyl group
984; 1-(methoxyimino)-1-(2-fluorophenyl)-methyl group
Substituent Number; Q
985; 1-(ethoxyimino)-1-(3-fluorophenyl)-methyl group
986; 1-(propyloxyimino)-1-(3-fluorophenyl)-methyl group
987; 1-(n-butoxyimino)-1-(3-fluorophenyl)-methyl group
988; 1-(n-pentyloxyimino)-1-(3-fluorophenyl)-methyl group
989; 1-(n-hexyloxyimino)-1-(3-fluorophenyl)-methyl group
990; 1-(isopropoxyimino)-1-(3-fluorophenyl)-methyl group
991; 1-(tert-butoxyimino)-1-(3-fluorophenyl)-methyl group
992; 1-(sec-butoxyimino)-1-(3-fluorophenyl)-methyl group
993; 1-(cyclopropyloxyimino)-1-(3-fluorophenyl)-methyl group
994; 1-(cyclopentyloxyimino)-1-(3-fluorophenyl)-methyl group
995; 1-(cyclohexyloxyimino)-1-(3-fluorophenyl)-methyl group
996; 1-(3-allyloxyimino)-1-(3-fluorophenyl)-methyl group
997; 1-(4-butenoxyimino)-1-(3-fluorophenyl)-methyl group
998; 1-(3-propynoxyimino)-1-(3-fluorophenyl)-methyl group
999; 1-(4-butynoxyimino)-1-(3-fluorophenyl)-methyl group
1000; 1-(1-cyclohexenoxyimino)-1-(3-fluorophenyl)-methyl group
1001; 1-(2,2,2-trifluoroethoxyimino)-1-(3-fluorophenyl)-methyl group
1002; 1-(benzyloxyimino)-1-(3-fluorophenyl)-methyl group
1003; 1-(2-fluorobenzyloxyimino)-1-(3-fluorophenyl)-methyl group
1004; 1-(3-fluorobenzyloxyimino)-1-(3-fluorophenyl)-methyl group
1005; 1-(4-fluorobenzyloxyimino)-1-(3-fluorophenyl)-methyl group
1006; 1-(2-chlorobenzyloxyimino)-1-(3-fluorophenyl)-methyl group
1007; 1-(3-chlorobenzyloxyimino)-1-(3-fluorophenyl)-methyl group
1008; 1-(4-chlorobenzyloxyimino)-1-(3-fluorophenyl)-methyl group
1009; 1-(2-methylbenzyloxyimino)-1-(3-fluorophenyl)-methyl group
1010; 1-(3-methylbenzyloxyimino)-1-(3-fluorophenyl)-methyl group
1011; 1-(4-methylbenzyloxyimino)-1-(3-fluorophenyl)-methyl group
1012; 1-(2-cyanobenzyloxyimino)-1-(3-fluorophenyl)-methyl group
1013; 1-(3-cyanobenzyloxyimino)-1-(3-fluorophenyl)-methyl group
Substituent Number; Q
1014; 1-(4-cyanobenzyloxyimino)-1-(3-fluorophenyl)-methyl group
1015; 1-(2-trifluoromethylbenzyloxyimino)-1-(3-fluorophenyl)-methyl group
1016; 1-(3-trifluoromethylbenzyloxyimino)-1-(3-fluorophenyl)-methyl group
1017; 1-(4-trifluoromethylbenzyloxyimino)-1-(3-fluorophenyl)-methyl group
1018; 1-(2-difluoromethylbenzyloxyimino)-1-(3-fluorophenyl)-methyl group
1019; 1-(3-difluoromethylbenzyloxyimino)-1-(3-fluorophenyl)-methyl group
1020; 1-(4-difluoromethylbenzyloxyimino)-1-(3-fluorophenyl)-methyl group
1021; 1-(2-methoxybenzyloxyimino)-1-(3-fluorophenyl)-methyl group
1022; 1-(3-methoxybenzyloxyimino)-1-(3-fluorophenyl)-methyl group
1023; 1-(4-methoxybenzyloxyimino)-1-(3-fluorophenyl)-methyl group
1024; 1-(2-vinylbenzyloxyimino)-1-(3-fluorophenyl)-methyl group
1025; 1-(3-vinylbenzyloxyimino)-1-(3-fluorophenyl)-methyl group
1026; 1-(4-vinylbenzyloxyimino)-1-(3-fluorophenyl)-methyl group
1027; 1-(2-phenylbenzyloxyimino)-1-(3-fluorophenyl)-methyl group
1028; 1-(3-phenylbenzyloxyimino)-1-(3-fluorophenyl)-methyl group
1029; 1-(4-phenylbenzyloxyimino)-1-(3-fluorophenyl)-methyl group
1030; 1-(2,3-difluorobenzyloxyimino)-1-(3-fluorophenyl)-methyl group
1031; 1-(2,4-difluorobenzyloxyimino)-1-(3-fluorophenyl)-methyl group
1032; 1-(2,5-difluorobenzyloxyimino)-1-(3-fluorophenyl)-methyl group
1033; 1-(2,6-difluorobenzyloxyimino)-1-(3-fluorophenyl)-methyl group 1034; 1-(3,4-difluorobenzyloxyimino)-1-(3-fluorophenyl)-methyl group
1035; 1-(3,5-difluorobenzyloxyimino)-1-(3-fluorophenyl)-methyl group
1036; 1-(2,3,4,5,6-pentafluorobenzyloxyimino)-1-(3-fluorophenyl)-methyl group
1037; 1-(3-ethylbenzyloxyimino)-1-(3-fluorophenyl)-methyl group
1038; 1-(4-ethylbenzyloxyimino)-1-(3-fluorophenyl)-methyl group
1039; 1-(2-trifluoromethoxybenzyloxyimino)-1-(3-fluorophenyl)-methyl group
1040; 1-(3-trifluoromethoxybenzyloxyimino)-1-(3-fluorophenyl)-methyl group
1041; 1-(4-trifluoromethoxybenzyloxyimino)-1-(3-fluorophenyl)-methyl group
1042; 1-(methoxyimino)-1-(3-fluorophenyl)-methyl group
Substituent Number; Q
1043; 1-(ethoxyimino)-1-(4-fluorophenyl)-methyl group
1044; 1-(propyloxyimino)-1-(4-fluorophenyl)-methyl group
1045; 1-(n-butoxyimino)-1-(4-fluorophenyl)-methyl group
1046; 1-(n-pentyloxyimino)-1-(4-fluorophenyl)-methyl group
1047; 1-(n-hexyloxyimino)-1-(4-fluorophenyl)-methyl group
1048; 1-(isopropoxyimino)-1-(4-fluorophenyl)-methyl group
1049; 1-(tert-butoxyimino)-1-(4-fluorophenyl)-methyl group
1050; 1-(sec-butoxyimino)-1-(4-fluorophenyl)-methyl group
1051; 1-(cyclopropyloxyimino)-1-(4-fluorophenyl)-methyl group
1052; 1-(cyclopentyloxyimino)-1-(4-fluorophenyl)-methyl group
1053; 1-(cyclohexyloxyimino)-1-(4-fluorophenyl)-methyl group
1054; 1-(3-allyloxyimino)-1-(4-fluorophenyl)-methyl group
1055; 1-(4-butenoxyimino)-1-(4-fluorophenyl)-methyl group
1056; 1-(3-propynoxyimino)-1-(4-fluorophenyl)-methyl group
1057; 1-(4-butynoxyimino)-1-(4-fluorophenyl)-methyl group
1058; 1-(1-cyclohexenoxyimino)-1-(4-fluorophenyl)-methyl group
1059; 1-(2,2,2-trifluoroethoxyimino)-1-(4-fluorophenyl)-methyl group
1060; 1-(benzyloxyimino)-1-(4-fluorophenyl)-methyl group
1061; 1-(2-fluorobenzyloxyimino)-1-(4-fluorophenyl)-methyl group
1062; 1-(3-fluorobenzyloxyimino)-1-(4-fluorophenyl)-methyl group
1063; 1-(4-fluorobenzyloxyimino)-1-(4-fluorophenyl)-methyl group
1064; 1-(2-chlorobenzyloxyimino)-1-(4-fluorophenyl)-methyl group
1065; 1-(3-chlorobenzyloxyimino)-1-(4-fluorophenyl)-methyl group
1066; 1-(4-chlorobenzyloxyimino)-1-(4-fluorophenyl)-methyl group
1067; 1-(2-methylbenzyloxyimino)-1-(4-fluorophenyl)-methyl group
1068; 1-(3-methylbenzyloxyimino)-1-(4-fluorophenyl)-methyl group
1069; 1-(4-methylbenzyloxyimino)-1-(4-fluorophenyl)-methyl group
1070; 1-(2-cyanobenzyloxyimino)-1-(4-fluorophenyl)-methyl group
1071; 1-(3-cyanobenzyloxyimino)-1-(4-fluorophenyl)-methyl group
Substituent Number; Q
1072; 1-(4-cyanobenzyloxyimino)-1-(4-fluorophenyl)-methyl group
1073; 1-(2-trifluoromethylbenzyloxyimino)-1-(4-fluorophenyl)-methyl group
1074; 1-(3-trifluoromethylbenzyloxyimino)-1-(4-fluorophenyl)-methyl group
1075; 1-(4-trifluoromethylbenzyloxyimino)-1-(4-fluorophenyl)-methyl group
1076; 1-(2-difluoromethylbenzyloxyimino)-1-(4-fluorophenyl)-methyl group
1077; 1-(3-difluoromethylbenzyloxyimino)-1-(4-fluorophenyl)-methyl group
1078; 1-(4-difluoromethylbenzyloxyimino)-1-(4-fluorophenyl)-methyl group
1079; 1-(2-methoxybenzyloxyimino)-1-(4-fluorophenyl)-methyl group
1080; 1-(3-methoxybenzyloxyimino)-1-(4-fluorophenyl)-methyl group
1081; 1-(4-methoxybenzyloxyimino)-1-(4-fluorophenyl)-methyl group
1082; 1-(2-vinylbenzyloxyimino)-1-(4-fluorophenyl)-methyl group
1083; 1-(3-vinylbenzyloxyimino)-1-(4-fluorophenyl)-methyl group
1084; 1-(4-vinylbenzyloxyimino)-1-(4-fluorophenyl)-methyl group
1085; 1-(2-phenylbenzyloxyimino)-1-(4-fluorophenyl)-methyl group
1086; 1-(3-phenylbenzyloxyimino)-1-(4-fluorophenyl)-methyl group
1087; 1-(4-phenylbenzyloxyimino)-1-(4-fluorophenyl)-methyl group
1088; 1-(2,3-difluorobenzyloxyimino)-1-(4-fluorophenyl)-methyl group-1-(4-fluorophenyl)-methyl group
1089; 1-(2,4-difluorobenzyloxyimino)-1-(4-fluorophenyl)-methyl group
1090; 1-(2,5-difluorobenzyloxyimino)-1-(4-fluorophenyl)-methyl group
1091; 1-(2,6-difluorobenzyloxyimino)-1-(4-fluorophenyl)-methyl group
1092; 1-(3,4-difluorobenzyloxyimino)-1-(4-fluorophenyl)-methyl group
1093; 1-(3,5-difluorobenzyloxyimino)-1-(4-fluorophenyl)-methyl group
1094; 1-(2,3,4,5,6-pentafluorobenzyloxyimino)-1-(4-fluorophenyl)-methyl group
1095; 1-(3-ethylbenzyloxyimino)-1-(4-fluorophenyl)-methyl group
1096; 1-(4-ethylbenzyloxyimino)-1-(4-fluorophenyl)-methyl group
1097; 1-(2-trifluoromethoxybenzyloxyimino)-1-(4-fluorophenyl)-methyl group
1098; 1-(3-trifluoromethoxybenzyloxyimino)-1-(4-fluorophenyl)-methyl group
1099; 1-(4-trifluoromethoxybenzyloxyimino)-1-(4-fluorophenyl)-methyl group
1100; 1-(methoxyimino)-1-(4-fluorophenyl)-methyl group
Substituent Number; Q
1101; 1-(ethoxyimino)-1-(4-fluorophenyl)-methyl group
1102; 1-(propyloxyimino)-1-(2-bromophenyl)-methyl group
1103; 1-(n-butoxyimino)-1-(2-bromophenyl)-methyl group 1104; 1-(n-pentyloxyimino)-1-(2-bromophenyl)-methyl group
1105; 1-(n-hexyloxyimino)-1-(2-bromophenyl)-methyl group
1106; 1-(isopropoxyimino)-1-(2-bromophenyl)-methyl group
1107; 1-(tert-butoxyimino)-1-(2-bromophenyl)-methyl group
1108; 1-(sec-butoxyimino)-1-(2-bromophenyl)-methyl group
1109; 1-(cyclopropyloxyimino)-1-(2-bromophenyl)-methyl group
1110; 1-(cyclopentyloxyimino)-1-(2-bromophenyl)-methyl group
1111; 1-(cyclohexyloxyimino)-1-(2-bromophenyl)-methyl group
1112; 1-(3-allyloxyimino)-1-(2-bromophenyl)-methyl group
1113; 1-(4-butenoxyimino)-1-(2-bromophenyl)-methyl group
1114; 1-(3-propynoxyimino)-1-(2-bromophenyl)-methyl group
1115; 1-(4-butynoxyimino)-1-(2-bromophenyl)-methyl group
1116; 1-(1-cyclohexenoxyimino)-1-(2-bromophenyl)-methyl group
1117; 1-(2,2,2-trifluoroethoxyimino)-1-(2-bromophenyl)-methyl group
1118; 1-(benzyloxyimino)-1-(2-bromophenyl)-methyl group
1119; 1-(2-fluorobenzyloxyimino)-1-(2-bromophenyl)-methyl group
1120; 1-(3-fluorobenzyloxyimino)-1-(2-bromophenyl)-methyl group
1121; 1-(4-fluorobenzyloxyimino)-1-(2-bromophenyl)-methyl group
1122; 1-(2-chlorobenzyloxyimino)-1-(2-bromophenyl)-methyl group
1123; 1-(3-chlorobenzyloxyimino)-1-(2-bromophenyl)-methyl group
1124; 1-(4-chlorobenzyloxyimino)-1-(2-bromophenyl)-methyl group
1125; 1-(2-methylbenzyloxyimino)-1-(2-bromophenyl)-methyl group
1126; 1-(3-methylbenzyloxyimino)-1-(2-bromophenyl)-methyl group
1127; 1-(4-methylbenzyloxyimino)-1-(2-bromophenyl)-methyl group
1128; 1-(2-cyanobenzyloxyimino)-1-(2-bromophenyl)-methyl group
1129; 1-(3-cyanobenzyloxyimino)-1-(2-bromophenyl)-methyl group
Substituent Number; Q
1130; 1-(4-cyanobenzyloxyimino)-1-(2-bromophenyl)-methyl group
1131; 1-(2-trifluoromethylbenzyloxyimino)-1-(2-bromophenyl)-methyl group
1132; 1-(3-trifluoromethylbenzyloxyimino)-1-(2-bromophenyl)-methyl group
1133; 1-(4-trifluoromethylbenzyloxyimino)-1-(2-bromophenyl)-methyl group
1134; 1-(2-difluoromethylbenzyloxyimino)-1-(2-bromophenyl)-methyl group
1135; 1-(3-difluoromethylbenzyloxyimino)-1-(2-bromophenyl)-methyl group
1136; 1-(4-difluoromethylbenzyloxyimino)-1-(2-bromophenyl)-methyl group
1137; 1-(2-methoxybenzyloxyimino)-1-(2-bromophenyl)-methyl group
1138; 1-(3-methoxybenzyloxyimino)-1-(2-bromophenyl)-methyl group
1139; 1-(4-methoxybenzyloxyimino)-1-(2-bromophenyl)-methyl group
1140; 1-(2-vinylbenzyloxyimino)-1-(2-bromophenyl)-methyl group
1141; 1-(3-vinylbenzyloxyimino)-1-(2-bromophenyl)-methyl group
1142; 1-(4-vinylbenzyloxyimino)-1-(2-bromophenyl)-methyl group
1143; 1-(2-phenylbenzyloxyimino)-1-(2-bromophenyl)-methyl group
1144; 1-(3-phenylbenzyloxyimino)-1-(2-bromophenyl)-methyl group
1145; 1-(4-phenylbenzyloxyimino)-1-(2-bromophenyl)-methyl group
1146; 1-(2,3-difluorobenzyloxyimino)-1-(2-bromophenyl)-methyl group
1147; 1-(2,4-difluorobenzyloxyimino)-1-(2-bromophenyl)-methyl group
1148; 1-(2,5-difluorobenzyloxyimino)-1-(2-bromophenyl)-methyl group
1149; 1-(2,6-difluorobenzyloxyimino)-1-(2-bromophenyl)-methyl group
1150; 1-(3,4-difluorobenzyloxyimino)-1-(2-bromophenyl)-methyl group
1151; 1-(3,5-difluorobenzyloxyimino)-1-(2-bromophenyl)-methyl group
1152; 1-(2,3,4,5,6-pentafluorobenzyloxyimino)-1-(2-bromophenyl)-methyl group
1153; 1-(3-ethylbenzyloxyimino)-1-(2-bromophenyl)-methyl group
1154; 1-(4-ethylbenzyloxyimino)-1-(2-bromophenyl)-methyl group
1155; 1-(2-trifluoromethoxybenzyloxyimino)-1-(2-bromophenyl)-methyl group
1156; 1-(3-trifluoromethoxybenzyloxyimino)-1-(2-bromophenyl)-methyl group
1157; 1-(4-trifluoromethoxybenzyloxyimino)-1-(2-bromophenyl)-methyl group
1158; 1-(methoxyimino)-1-(2-bromophenyl)-methyl group
Substituent Number; Q
1159; 1-(ethoxyimino)-1-(3-bromophenyl)-methyl group
1160; 1-(propyloxyimino)-1-(3-bromophenyl)-methyl group
1161; 1-(n-butoxyimino)-1-(3-bromophenyl)-methyl group
1162; 1-(n-pentyloxyimino)-1-(3-bromophenyl)-methyl group
1163; 1-(n-hexyloxyimino)-1-(3-bromophenyl)-methyl group
1164; 1-(isopropoxyimino)-1-(3-bromophenyl)-methyl group
1165; 1-(tert-butoxyimino)-1-(3-bromophenyl)-methyl group
1166; 1-(sec-butoxyimino)-1-(3-bromophenyl)-methyl group
1167; 1-(cyclopropyloxyimino)-1-(3-bromophenyl)-methyl group
1168; 1-(cyclopentyloxyimino)-1-(3-bromophenyl)-methyl group
1169; 1-(cyclohexyloxyimino)-1-(3-bromophenyl)-methyl group
1170; 1-(3-allyloxyimino)-1-(3-bromophenyl)-methyl group 1171; 1-(4-butenoxyimino)-1-(3-bromophenyl)-methyl group
1172; 1-(3-propynoxyimino)-1-(3-bromophenyl)-methyl group
1173; 1-(4-butynoxyimino)-1-(3-bromophenyl)-methyl group
1174; 1-(1-cyclohexenoxyimino)-1-(3-bromophenyl)-methyl group
1175; 1-(2,2,2-trifluoroethoxyimino)-1-(3-bromophenyl)-methyl group
1176; 1-(benzyloxyimino)-1-(3-bromophenyl)-methyl group
1177; 1-(2-fluorobenzyloxyimino)-1-(3-bromophenyl)-methyl group
1178; 1-(3-fluorobenzyloxyimino)-1-(3-bromophenyl)-methyl group
1179; 1-(4-fluorobenzyloxyimino)-1-(3-bromophenyl)-methyl group
1180; 1-(2-chlorobenzyloxyimino)-1-(3-bromophenyl)-methyl group
1181; 1-(3-chlorobenzyloxyimino)-1-(3-bromophenyl)-methyl group
1182; 1-(4-chlorobenzyloxyimino)-1-(3-bromophenyl)-methyl group
1183; 1-(2-methylbenzyloxyimino)-1-(3-bromophenyl)-methyl group
1184; 1-(3-methylbenzyloxyimino)-1-(3-bromophenyl)-methyl group
1185; 1-(4-methylbenzyloxyimino)-1-(3-bromophenyl)-methyl group
1186; 1-(2-cyanobenzyloxyimino)-1-(3-bromophenyl)-methyl group
1187; 1-(3-cyanobenzyloxyimino)-1-(3-bromophenyl)-methyl group
Substituent Number; Q
1188; 1-(4-cyanobenzyloxyimino)-1-(3-bromophenyl)-methyl group
1189; 1-(2-trifluoromethylbenzyloxyimino)-1-(3-bromophenyl)-methyl group
1190; 1-(3-trifluoromethylbenzyloxyimino)-1-(3-bromophenyl)-methyl group
1191; 1-(4-trifluoromethylbenzyloxyimino)-1-(3-bromophenyl)-methyl group
1192; 1-(2-difluoromethylbenzyloxyimino)-1-(3-bromophenyl)-methyl group
1193; 1-(3-difluoromethylbenzyloxyimino)-1-(3-bromophenyl)-methyl group
1194; 1-(4-difluoromethylbenzyloxyimino)-1-(3-bromophenyl)-methyl group
1195; 1-(2-methoxybenzyloxyimino)-1-(3-bromophenyl)-methyl group
1196; 1-(3-methoxybenzyloxyimino)-1-(3-bromophenyl)-methyl group
1197; 1-(4-methoxybenzyloxyimino)-1-(3-bromophenyl)-methyl group
1198; 1-(2-vinylbenzyloxyimino)-1-(3-bromophenyl)-methyl group
1199; 1-(3-vinylbenzyloxyimino)-1-(3-bromophenyl)-methyl group
1200; 1-(4-vinylbenzyloxyimino)-1-(3-bromophenyl)-methyl group
1201; 1-(2-phenylbenzyloxyimino)-1-(3-bromophenyl)-methyl group
1202; 1-(3-phenylbenzyloxyimino)-1-(3-bromophenyl)-methyl group
1203; 1-(4-phenylbenzyloxyimino)-1-(3-bromophenyl)-methyl group
1204; 1-(2,3-difluorobenzyloxyimino)-1-(3-bromophenyl)-methyl group
1205; 1-(2,4-difluorobenzyloxyimino)-1-(3-bromophenyl)-methyl group
1206; 1-(2,5-difluorobenzyloxyimino)-1-(3-bromophenyl)-methyl group
1207; 1-(2,6-difluorobenzyloxyimino)-1-(3-bromophenyl)-methyl group
1208; 1-(3,4-difluorobenzyloxyimino)-1-(3-bromophenyl)-methyl group
1209; 1-(3,5-difluorobenzyloxyimino)-1-(3-bromophenyl)-methyl group
1210; 1-(2,3,4,5,6-pentafluorobenzyloxyimino)-1-(3-bromophenyl)-methyl group
1211; 1-(3-ethylbenzyloxyimino)-1-(3-bromophenyl)-methyl group
1212; 1-(4-ethylbenzyloxyimino)-1-(3-bromophenyl)-methyl group
1213; 1-(2-trifluoromethoxybenzyloxyimino)-1-(3-bromophenyl)-methyl group
1214; 1-(3-trifluoromethoxybenzyloxyimino)-1-(3-bromophenyl)-methyl group
1215; 1-(4-trifluoromethoxybenzyloxyimino)-1-(3-bromophenyl)-methyl group
1216; 1-(methoxyimino)-1-(3-bromophenyl)-methyl group
Substituent Number; Q
1217; 1-(ethoxyimino)-1-(4-bromophenyl)-methyl group
1218; 1-(propyloxyimino)-1-(4-bromophenyl)-methyl group
1219; 1-(n-butoxyimino)-1-(4-bromophenyl)-methyl group
1220; 1-(n-pentyloxyimino)-1-(4-bromophenyl)-methyl group
1221; 1-(n-hexyloxyimino)-1-(4-bromophenyl)-methyl group
1222; 1-(isopropoxyimino)-1-(4-bromophenyl)-methyl group
1223; 1-(tert-butoxyimino)-1-(4-bromophenyl)-methyl group
1224; 1-(sec-butoxyimino)-1-(4-bromophenyl)-methyl group
1225; 1-(cyclopropyloxyimino)-1-(4-bromophenyl)-methyl group
1226; 1-(cyclopentyloxyimino)-1-(4-bromophenyl)-methyl group
1227; 1-(cyclohexyloxyimino)-1-(4-bromophenyl)-methyl group
1228; 1-(3-allyloxyimino)-1-(4-bromophenyl)-methyl group
1229; 1-(4-butenoxyimino)-1-(4-bromophenyl)-methyl group
1230; 1-(3-propynoxyimino)-1-(4-bromophenyl)-methyl group
1231; 1-(4-butynoxyimino)-1-(4-bromophenyl)-methyl group
1232; 1-(1-cyclohexenoxyimino)-1-(4-bromophenyl)-methyl group
1233; 1-(2,2,2-trifluoroethoxyimino)-1-(4-bromophenyl)-methyl group
1234; 1-(benzyloxyimino)-1-(4-bromophenyl)-methyl group
1235; 1-(2-fluorobenzyloxyimino)-1-(4-bromophenyl)-methyl group
1236; 1-(3-fluorobenzyloxyimino)-1-(4-bromophenyl)-methyl group
1237; 1-(4-fluorobenzyloxyimino)-1-(4-bromophenyl)-methyl group 1238; 1-(2-chlorobenzyloxyimino)-1-(4-bromophenyl)-methyl group
1239; 1-(3-chlorobenzyloxyimino)-1-(4-bromophenyl)-methyl group
1240; 1-(4-chlorobenzyloxyimino)-1-(4-bromophenyl)-methyl group
1241; 1-(2-methylbenzyloxyimino)-1-(4-bromophenyl)-methyl group
1242; 1-(3-methylbenzyloxyimino)-1-(4-bromophenyl)-methyl group
1243; 1-(4-methylbenzyloxyimino)-1-(4-bromophenyl)-methyl group
1244; 1-(2-cyanobenzyloxyimino)-1-(4-bromophenyl)-methyl group
1245; 1-(3-cyanobenzyloxyimino)-1-(4-bromophenyl)-methyl group
Substituent Number; Q
1246; 1-(4-cyanobenzyloxyimino)-1-(4-bromophenyl)-methyl group
1247; 1-(2-trifluoromethylbenzyloxyimino)-1-(4-bromophenyl)-methyl group
1248; 1-(3-trifluoromethylbenzyloxyimino)-1-(4-bromophenyl)-methyl group
1249; 1-(4-trifluoromethylbenzyloxyimino)-1-(4-bromophenyl)-methyl group
1250; 1-(2-difluoromethylbenzyloxyimino)-1-(4-bromophenyl)-methyl group
1251; 1-(3-difluoromethylbenzyloxyimino)-1-(4-bromophenyl)-methyl group
1252; 1-(4-difluoromethylbenzyloxyimino)-1-(4-bromophenyl)-methyl group
1253; 1-(2-methoxybenzyloxyimino)-1-(4-bromophenyl)-methyl group
1254; 1-(3-methoxybenzyloxyimino)-1-(4-bromophenyl)-methyl group
1255; 1-(4-methoxybenzyloxyimino)-1-(4-bromophenyl)-methyl group
1256; 1-(2-vinylbenzyloxyimino)-1-(4-bromophenyl)-methyl group
1257; 1-(3-vinylbenzyloxyimino)-1-(4-bromophenyl)-methyl group
1258; 1-(4-vinylbenzyloxyimino)-1-(4-bromophenyl)-methyl group
1259; 1-(2-phenylbenzyloxyimino)-1-(4-bromophenyl)-methyl group
1260; 1-(3-phenylbenzyloxyimino)-1-(4-bromophenyl)-methyl group
1261; 1-(4-phenylbenzyloxyimino)-1-(4-bromophenyl)-methyl group
1262; 1-(2,3-difluorobenzyloxyimino)-1-(4-bromophenyl)-methyl group
1263; 1-(2,4-difluorobenzyloxyimino)-1-(4-bromophenyl)-methyl group
1264; 1-(2,5-difluorobenzyloxyimino)-1-(4-bromophenyl)-methyl group
1265; 1-(2,6-difluorobenzyloxyimino)-1-(4-bromophenyl)-methyl group
1266; 1-(3,4-difluorobenzyloxyimino)-1-(4-bromophenyl)-methyl group
1267; 1-(3,5-difluorobenzyloxyimino)-1-(4-bromophenyl)-methyl group
1268; 1-(2,3,4,5,6-pentafluorobenzyloxyimino)-1-(4-bromophenyl)-methyl group
1269; 1-(3-ethylbenzyloxyimino)-1-(4-bromophenyl)-methyl group
1270; 1-(4-ethylbenzyloxyimino)-1-(4-bromophenyl)-methyl group
1271; 1-(2-trifluoromethoxybenzyloxyimino)-1-(4-bromophenyl)-methyl group
1272; 1-(3-trifluoromethoxybenzyloxyimino)-1-(4-bromophenyl)-methyl group
1273; 1-(4-trifluoromethoxybenzyloxyimino)-1-(4-bromophenyl)-methyl group
1274; 1-(methoxyimino)-1-(4-bromophenyl)-methyl group
Substituent Number; Q
1275; 1-(ethoxyimino)-1-(2-methylphenyl)-methyl group
1276; 1-(propyloxyimino)-1-(2-methylphenyl)-methyl group
1277; 1-(n-butoxyimino)-1-(2-methylphenyl)-methyl group
1278; 1-(n-pentyloxyimino)-1-(2-methylphenyl)-methyl group
1279; 1-(n-hexyloxyimino)-1-(2-methylphenyl)-methyl group
1280; 1-(isopropoxyimino)-1-(2-methylphenyl)-methyl group
1281; 1-(tert-butoxyimino)-1-(2-methylphenyl)-methyl group
1282; 1-(sec-butoxyimino)-1-(2-methylphenyl)-methyl group
1283; 1-(cyclopropyloxyimino)-1-(2-methylphenyl)-methyl group
1284; 1-(cyclopentyloxyimino)-1-(2-methylphenyl)-methyl group
1285; 1-(cyclohexyloxyimino)-1-(2-methylphenyl)-methyl group
1286; 1-(3-allyloxyimino)-1-(2-methylphenyl)-methyl group
1287; 1-(4-butenoxyimino)-1-(2-methylphenyl)-methyl group
1288; 1-(3-propynoxyimino)-1-(2-methylphenyl)-methyl group
1289; 1-(4-butynoxyimino)-1-(2-methylphenyl)-methyl group
1290; 1-(1-cyclohexenoxyimino)-1-(2-methylphenyl)-methyl group
1291; 1-(2,2,2-trifluoroethoxyimino)-1-(2-methylphenyl)-methyl group
1292; 1-(benzyloxyimino)-1-(2-methylphenyl)-methyl group
1293; 1-(2-fluorobenzyloxyimino)-1-(2-methylphenyl)-methyl group
1294; 1-(3-fluorobenzyloxyimino)-1-(2-methylphenyl)-methyl group
1295; 1-(4-fluorobenzyloxyimino)-1-(2-methylphenyl)-methyl group
1296; 1-(2-chlorobenzyloxyimino)-1-(2-methylphenyl)-methyl group
1297; 1-(3-chlorobenzyloxyimino)-1-(2-methylphenyl)-methyl group
1298; 1-(4-chlorobenzyloxyimino)-1-(2-methylphenyl)-methyl group
1299; 1-(2-methylbenzyloxyimino)-1-(2-methylphenyl)-methyl group
1300; 1-(3-methylbenzyloxyimino)-1-(2-methylphenyl)-methyl group
1301; 1-(4-methylbenzyloxyimino)-1-(2-methylphenyl)-methyl group
1302; 1-(2-cyanobenzyloxyimino)-1-(2-methylphenyl)-methyl group
1303; 1-(3-cyanobenzyloxyimino)-1-(2-methylphenyl)-methyl group
Substituent Number; Q
1304; 1-(4-cyanobenzyloxyimino)-1-(2-methylphenyl)-methyl group 1305; 1-(2-trifluoromethylbenzyloxyimino)-1-(2-methylphenyl)-methyl group
1306; 1-(3-trifluoromethylbenzyloxyimino)-1-(2-methylphenyl)-methyl group
1307; 1-(4-trifluoromethylbenzyloxyimino)-1-(2-methylphenyl)-methyl group
1308; 1-(2-difluoromethylbenzyloxyimino)-1-(2-methylphenyl)-methyl group
1309; 1-(3-difluoromethylbenzyloxyimino)-1-(2-methylphenyl)-methyl group
1310; 1-(4-difluoromethylbenzyloxyimino)-1-(2-methylphenyl)-methyl group
1311; 1-(2-methoxybenzyloxyimino)-1-(2-methylphenyl)-methyl group
1312; 1-(3-methoxybenzyloxyimino)-1-(2-methylphenyl)-methyl group
1313; 1-(4-methoxybenzyloxyimino)-1-(2-methylphenyl)-methyl group
1314; 1-(2-vinylbenzyloxyimino)-1-(2-methylphenyl)-methyl group
1315; 1-(3-vinylbenzyloxyimino)-1-(2-methylphenyl)-methyl group
1316; 1-(4-vinylbenzyloxyimino)-1-(2-methylphenyl)-methyl group
1317; 1-(2-phenylbenzyloxyimino)-1-(2-methylphenyl)-methyl group
1318; 1-(3-phenylbenzyloxyimino)-1-(2-methylphenyl)-methyl group
1319; 1-(4-phenylbenzyloxyimino)-1-(2-methylphenyl)-methyl group
1320; 1-(2,3-difluorobenzyloxyimino)-1-(2-methylphenyl)-methyl group
1321; 1-(2,4-difluorobenzyloxyimino)-1-(2-methylphenyl)-methyl group
1322; 1-(2,5-difluorobenzyloxyimino)-1-(2-methylphenyl)-methyl group
1323; 1-(2,6-difluorobenzyloxyimino)-1-(2-methylphenyl)-methyl group
1324; 1-(3,4-difluorobenzyloxyimino)-1-(2-methylphenyl)-methyl group
1325; 1-(3,5-difluorobenzyloxyimino)-1-(2-methylphenyl)-methyl group
1326; 1-(2,3,4,5,6-pentafluorobenzyloxyimino)-1-(2-methylphenyl)-methyl group
1327; 1-(3-ethylbenzyloxyimino)-1-(2-methylphenyl)-methyl group
1328; 1-(4-ethylbenzyloxyimino)-1-(2-methylphenyl)-methyl group
1329; 1-(2-trifluoromethoxybenzyloxyimino)-1-(2-methylphenyl)-methyl group
1330; 1-(3-trifluoromethoxybenzyloxyimino)-1-(2-methylphenyl)-methyl group
1331; 1-(4-trifluoromethoxybenzyloxyimino)-1-(2-methylphenyl)-methyl group
1332; 1-(methoxyimino)-1-(2-methylphenyl)-methyl group
Substituent Number; Q
1333; 1-(ethoxyimino)-1-(3-methylphenyl)-methyl group
1334; 1-(propyloxyimino)-1-(3-methylphenyl)-methyl group
1335; 1-(n-butoxyimino)-1-(3-methylphenyl)-methyl group
1336; 1-(n-pentyloxyimino)-1-(3-methylphenyl)-methyl group
1337; 1-(n-hexyloxyimino)-1-(3-methylphenyl)-methyl group
1338; 1-(isopropoxyimino)-1-(3-methylphenyl)-methyl group
1339; 1-(tert-butoxyimino)-1-(3-methylphenyl)-methyl group
1340; 1-(sec-butoxyimino)-1-(3-methylphenyl)-methyl group
1341; 1-(cyclopropyloxyimino)-1-(3-methylphenyl)-methyl group
1342; 1-(cyclopentyloxyimino)-1-(3-methylphenyl)-methyl group
1343; 1-(cyclohexyloxyimino)-1-(3-methylphenyl)-methyl group
1344; 1-(3-allyloxyimino)-1-(3-methylphenyl)-methyl group
1345; 1-(4-butenoxyimino)-1-(3-methylphenyl)-methyl group
1346; 1-(3-propynoxyimino)-1-(3-methylphenyl)-methyl group
1347; 1-(4-butynoxyimino)-1-(3-methylphenyl)-methyl group
1348; 1-(1-cyclohexenoxyimino)-1-(3-methylphenyl)-methyl group
1349; 1-(2,2,2-trifluoroethoxyimino)-1-(3-methylphenyl)-methyl group
1350; 1-(benzyloxyimino)-1-(3-methylphenyl)-methyl group
1351; 1-(2-fluorobenzyloxyimino)-1-(3-methylphenyl)-methyl group
1352; 1-(3-fluorobenzyloxyimino)-1-(3-methylphenyl)-methyl group
1353; 1-(4-fluorobenzyloxyimino)-1-(3-methylphenyl)-methyl group
1354; 1-(2-chlorobenzyloxyimino)-1-(3-methylphenyl)-methyl group
1355; 1-(3-chlorobenzyloxyimino)-1-(3-methylphenyl)-methyl group
1356; 1-(4-chlorobenzyloxyimino)-1-(3-methylphenyl)-methyl group
1357; 1-(2-methylbenzyloxyimino)-1-(3-methylphenyl)-methyl group
1358; 1-(3-methylbenzyloxyimino)-1-(3-methylphenyl)-methyl group
1359; 1-(4-methylbenzyloxyimino)-1-(3-methylphenyl)-methyl group
1360; 1-(2-cyanobenzyloxyimino)-1-(3-methylphenyl)-methyl group
1361; 1-(3-cyanobenzyloxyimino)-1-(3-methylphenyl)-methyl group
Substituent Number; Q
1362; 1-(4-cyanobenzyloxyimino)-1-(3-methylphenyl)-methyl group
1363; 1-(2-trifluoromethylbenzyloxyimino)-1-(3-methylphenyl)-methyl group
1364; 1-(3-trifluoromethylbenzyloxyimino)-1-(3-methylphenyl)-methyl group
1365; 1-(4-trifluoromethylbenzyloxyimino)-1-(3-methylphenyl)-methyl group
1366; 1-(2-difluoromethylbenzyloxyimino)-1-(3-methylphenyl)-methyl group
1367; 1-(3-difluoromethylbenzyloxyimino)-1-(3-methylphenyl)-methyl group
1368; 1-(4-difluoromethylbenzyloxyimino)-1-(3-methylphenyl)-methyl group
1369; 1-(2-methoxybenzyloxyimino)-1-(3-methylphenyl)-methyl group
1370; 1-(3-methoxybenzyloxyimino)-1-(3-methylphenyl)-methyl group
1371; 1-(4-methoxybenzyloxyimino)-1-(3-methylphenyl)-methyl group 1372; 1-(2-vinylbenzyloxyimino)-1-(3-methylphenyl)-methyl group
1373; 1-(3-vinylbenzyloxyimino)-1-(3-methylphenyl)-methyl group
1374; 1-(4-vinylbenzyloxyimino)-1-(3-methylphenyl)-methyl group
1375; 1-(2-phenylbenzyloxyimino)-1-(3-methylphenyl)-methyl group
1376; 1-(3-phenylbenzyloxyimino)-1-(3-methylphenyl)-methyl group
1377; 1-(4-phenylbenzyloxyimino)-1-(3-methylphenyl)-methyl group
1378; 1-(2,3-difluorobenzyloxyimino)-1-(3-methylphenyl)-methyl group
1379; 1-(2,4-difluorobenzyloxyimino)-1-(3-methylphenyl)-methyl group
1380; 1-(2,5-difluorobenzyloxyimino)-1-(3-methylphenyl)-methyl group
1381; 1-(2,6-difluorobenzyloxyimino)-1-(3-methylphenyl)-methyl group
1382; 1-(3,4-difluorobenzyloxyimino)-1-(3-methylphenyl)-methyl group
1383; 1-(3,5-difluorobenzyloxyimino)-1-(3-methylphenyl)-methyl group
1384; 1-(2,3,4,5,6-pentafluorobenzyloxyimino)-1-(3-methylphenyl)-methyl group
1385; 1-(3-ethylbenzyloxyimino)-1-(3-methylphenyl)-methyl group
1386; 1-(4-ethylbenzyloxyimino)-1-(3-methylphenyl)-methyl group
1387; 1-(2-trifluoromethoxybenzyloxyimino)-1-(3-methylphenyl)-methyl group
1388; 1-(3-trifluoromethoxybenzyloxyimino)-1-(3-methylphenyl)-methyl group
1389; 1-(4-trifluoromethoxybenzyloxyimino)-1-(3-methylphenyl)-methyl group
1390; 1-(methoxyimino)-1-(3-methylphenyl)-methyl group
Substituent Number; Q
1391; 1-(ethoxyimino)-1-(4-methylphenyl)-methyl group
1392; 1-(propyloxyimino)-1-(4-methylphenyl)-methyl group
1393; 1-(n-butoxyimino)-1-(4-methylphenyl)-methyl group
1394; 1-(n-pentyloxyimino)-1-(4-methylphenyl)-methyl group
1395; 1-(n-hexyloxyimino)-1-(4-methylphenyl)-methyl group
1396; 1-(isopropoxyimino)-1-(4-methylphenyl)-methyl group
1397; 1-(tert-butoxyimino)-1-(4-methylphenyl)-methyl group
1398; 1-(sec-butoxyimino)-1-(4-methylphenyl)-methyl group
1399; 1-(cyclopropyloxyimino)-1-(4-methylphenyl)-methyl group
1400; 1-(cyclopentyloxyimino)-1-(4-methylphenyl)-methyl group
1401; 1-(cyclohexyloxyimino)-1-(4-methylphenyl)-methyl group
1402; 1-(3-allyloxyimino)-1-(4-methylphenyl)-methyl group
1403; 1-(4-butenoxyimino)-1-(4-methylphenyl)-methyl group
1404; 1-(3-propynoxyimino)-1-(4-methylphenyl)-methyl group
1405; 1-(4-butynoxyimino)-1-(4-methylphenyl)-methyl group
1406; 1-(1-cyclohexenoxyimino)-1-(4-methylphenyl)-methyl group
1407; 1-(2,2,2-trifluoroethoxyimino)-1-(4-methylphenyl)-methyl group
1408; 1-(benzyloxyimino)-1-(4-methylphenyl)-methyl group
1409; 1-(2-fluorobenzyloxyimino)-1-(4-methylphenyl)-methyl group
1410; 1-(3-fluorobenzyloxyimino)-1-(4-methylphenyl)-methyl group
1411; 1-(4-fluorobenzyloxyimino)-1-(4-methylphenyl)-methyl group
1412; 1-(2-chlorobenzyloxyimino)-1-(4-methylphenyl)-methyl group
1413; 1-(3-chlorobenzyloxyimino)-1-(4-methylphenyl)-methyl group
1414; 1-(4-chlorobenzyloxyimino)-1-(4-methylphenyl)-methyl group
1415; 1-(2-methylbenzyloxyimino)-1-(4-methylphenyl)-methyl group
1416; 1-(3-methylbenzyloxyimino)-1-(4-methylphenyl)-methyl group
1417; 1-(4-methylbenzyloxyimino)-1-(4-methylphenyl)-methyl group
1418; 1-(2-cyanobenzyloxyimino)-1-(4-methylphenyl)-methyl group
1419; 1-(3-cyanobenzyloxyimino)-1-(4-methylphenyl)-methyl group
Substituent Number; Q
1420; 1-(4-cyanobenzyloxyimino)-1-(4-methylphenyl)-methyl group
1421; 1-(2-trifluoromethylbenzyloxyimino)-1-(4-methylphenyl)-methyl group
1422; 1-(3-trifluoromethylbenzyloxyimino)-1-(4-methylphenyl)-methyl group
1423; 1-(4-trifluoromethylbenzyloxyimino)-1-(4-methylphenyl)-methyl group
1424; 1-(2-difluoromethylbenzyloxyimino)-1-(4-methylphenyl)-methyl group
1425; 1-(3-difluoromethylbenzyloxyimino)-1-(4-methylphenyl)-methyl group
1426; 1-(4-difluoromethylbenzyloxyimino)-1-(4-methylphenyl)-methyl group
1427; 1-(2-methoxybenzyloxyimino)-1-(4-methylphenyl)-methyl group
1428; 1-(3-methoxybenzyloxyimino)-1-(4-methylphenyl)-methyl group
1429; 1-(4-methoxybenzyloxyimino)-1-(4-methylphenyl)-methyl group
1430; 1-(2-vinylbenzyloxyimino)-1-(4-methylphenyl)-methyl group
1431; 1-(3-vinylbenzyloxyimino)-1-(4-methylphenyl)-methyl group
1432; 1-(4-vinylbenzyloxyimino)-1-(4-methylphenyl)-methyl group
1433; 1-(2-phenylbenzyloxyimino)-1-(4-methylphenyl)-methyl group
1434; 1-(3-phenylbenzyloxyimino)-1-(4-methylphenyl)-methyl group
1435; 1-(4-phenylbenzyloxyimino)-1-(4-methylphenyl)-methyl group
1436; 1-(2,3-difluorobenzyloxyimino)-1-(4-methylphenyl)-methyl group
1437; 1-(2,4-difluorobenzyloxyimino)-1-(4-methylphenyl)-methyl group
1438; 1-(2,5-difluorobenzyloxyimino)-1-(4-methylphenyl)-methyl group 1439; 1-(2,6-difluorobenzyloxyimino)-1-(4-methylphenyl)-methyl group
1440; 1-(3,4-difluorobenzyloxyimino)-1-(4-methylphenyl)-methyl group
1441; 1-(3,5-difluorobenzyloxyimino)-1-(4-methylphenyl)-methyl group
1442; 1-(2,3,4,5,6-pentafluorobenzyloxyimino)-1-(4-methylphenyl)-methyl group
1443; 1-(3-ethylbenzyloxyimino)-1-(4-methylphenyl)-methyl group
1444; 1-(4-ethylbenzyloxyimino)-1-(4-methylphenyl)-methyl group
1445; 1-(2-trifluoromethoxybenzyloxyimino)-1-(4-methylphenyl)-methyl group
1446; 1-(3-trifluoromethoxybenzyloxyimino)-1-(4-methylphenyl)-methyl group
1447; 1-(4-trifluoromethoxybenzyloxyimino)-1-(4-methylphenyl)-methyl group
1448; 1-(methoxyimino)-1-(4-methylphenyl)-methyl group
Substituent Number; Q
1449; 1-(ethoxyimino)-1-(2-ethylphenyl)-methyl group
1450; 1-(propyloxyimino)-1-(2-ethylphenyl)-methyl group
1451; 1-(n-butoxyimino)-1-(2-ethylphenyl)-methyl group
1452; 1-(n-pentyloxyimino)-1-(2-ethylphenyl)-methyl group
1453; 1-(n-hexyloxyimino)-1-(2-ethylphenyl)-methyl group
1454; 1-(isopropoxyimino)-1-(2-ethylphenyl)-methyl group
1455; 1-(tert-butoxyimino)-1-(2-ethylphenyl)-methyl group
1456; 1-(sec-butoxyimino)-1-(2-ethylphenyl)-methyl group
1457; 1-(cyclopropyloxyimino)-1-(2-ethylphenyl)-methyl group
1458; 1-(cyclopentyloxyimino)-1-(2-ethylphenyl)-methyl group
1459; 1-(cyclohexyloxyimino)-1-(2-ethylphenyl)-methyl group
1460; 1-(3-allyloxyimino)-1-(2-ethylphenyl)-methyl group
1461; 1-(4-butenoxyimino)-1-(2-ethylphenyl)-methyl group
1462; 1-(3-propynoxyimino)-1-(2-ethylphenyl)-methyl group
1463; 1-(4-butynoxyimino)-1-(2-ethylphenyl)-methyl group
1464; 1-(1-cyclohexenoxyimino)-1-(2-ethylphenyl)-methyl group
1465; 1-(2,2,2-trifluoroethoxyimino)-1-(2-ethylphenyl)-methyl group
1466; 1-(benzyloxyimino)-1-(2-ethylphenyl)-methyl group
1467; 1-(2-fluorobenzyloxyimino)-1-(2-ethylphenyl)-methyl group
1468; 1-(3-fluorobenzyloxyimino)-1-(2-ethylphenyl)-methyl group
1469; 1-(4-fluorobenzyloxyimino)-1-(2-ethylphenyl)-methyl group
1470; 1-(2-chlorobenzyloxyimino)-1-(2-ethylphenyl)-methyl group
1471; 1-(3-chlorobenzyloxyimino)-1-(2-ethylphenyl)-methyl group
1472; 1-(4-chlorobenzyloxyimino)-1-(2-ethylphenyl)-methyl group
1473; 1-(2-methylbenzyloxyimino)-1-(2-ethylphenyl)-methyl group
1474; 1-(3-methylbenzyloxyimino)-1-(2-ethylphenyl)-methyl group
1475; 1-(4-methylbenzyloxyimino)-1-(2-ethylphenyl)-methyl group
1476; 1-(2-cyanobenzyloxyimino)-1-(2-ethylphenyl)-methyl group
1477; 1-(3-cyanobenzyloxyimino)-1-(2-ethylphenyl)-methyl group
Substituent Number; Q
1478; 1-(4-cyanobenzyloxyimino)-1-(2-ethylphenyl)-methyl group
1479; 1-(2-trifluoromethylbenzyloxyimino)-1-(2-ethylphenyl)-methyl group
1480; 1-(3-trifluoromethylbenzyloxyimino)-1-(2-ethylphenyl)-methyl group
1481; 1-(4-trifluoromethylbenzyloxyimino)-1-(2-ethylphenyl)-methyl group
1482; 1-(2-difluoromethylbenzyloxyimino)-1-(2-ethylphenyl)-methyl group
1483; 1-(3-difluoromethylbenzyloxyimino)-1-(2-ethylphenyl)-methyl group
1484; 1-(4-difluoromethylbenzyloxyimino)-1-(2-ethylphenyl)-methyl group
1485; 1-(2-methoxybenzyloxyimino)-1-(2-ethylphenyl)-methyl group
1486; 1-(3-methoxybenzyloxyimino)-1-(2-ethylphenyl)-methyl group
1487; 1-(4-methoxybenzyloxyimino)-1-(2-ethylphenyl)-methyl group
1488; 1-(2-vinylbenzyloxyimino)-1-(2-ethylphenyl)-methyl group
1489; 1-(3-vinylbenzyloxyimino)-1-(2-ethylphenyl)-methyl group
1490; 1-(4-vinylbenzyloxyimino)-1-(2-ethylphenyl)-methyl group
1491; 1-(2-phenylbenzyloxyimino)-1-(2-ethylphenyl)-methyl group
1492; 1-(3-phenylbenzyloxyimino)-1-(2-ethylphenyl)-methyl group
1493; 1-(4-phenylbenzyloxyimino)-1-(2-ethylphenyl)-methyl group
1494; 1-(2,3-difluorobenzyloxyimino)-1-(2-ethylphenyl)-methyl group
1495; 1-(2,4-difluorobenzyloxyimino)-1-(2-ethylphenyl)-methyl group
1496; 1-(2,5-difluorobenzyloxyimino)-1-(2-ethylphenyl)-methyl group
1497; 1-(2,6-difluorobenzyloxyimino)-1-(2-ethylphenyl)-methyl group
1498; 1-(3,4-difluorobenzyloxyimino)-1-(2-ethylphenyl)-methyl group
1499; 1-(3,5-difluorobenzyloxyimino)-1-(2-ethylphenyl)-methyl group
1500; 1-(2,3,4,5,6-pentafluorobenzyloxyimino)-1-(2-ethylphenyl)-methyl group
1501; 1-(3-ethylbenzyloxyimino)-1-(2-ethylphenyl)-methyl group
1502; 1-(4-ethylbenzyloxyimino)-1-(2-ethylphenyl)-methyl group
1503; 1-(2-trifluoromethoxybenzyloxyimino)-1-(2-ethylphenyl)-methyl group
1504; 1-(3-trifluoromethoxybenzyloxyimino)-1-(2-ethylphenyl)-methyl group
1505; 1-(4-trifluoromethoxybenzyloxyimino)-1-(2-ethylphenyl)-methyl group
1506; 1-(methoxyimino)-1-(2-ethylphenyl)-methyl group
Substituent Number; Q
1507; 1-(ethoxyimino)-1-(3-ethylphenyl)-methyl group
1508; 1-(propyloxyimino)-1-(3-ethylphenyl)-methyl group
1509; 1-(n-butoxyimino)-1-(3-ethylphenyl)-methyl group
1510; 1-(n-pentyloxyimino)-1-(3-ethylphenyl)-methyl group
1511; 1-(n-hexyloxyimino)-1-(3-ethylphenyl)-methyl group
1512; 1-(isopropoxyimino)-1-(3-ethylphenyl)-methyl group
1513; 1-(tert-butoxyimino)-1-(3-ethylphenyl)-methyl group 1514; 1-(sec-butoxyimino)-1-(3-ethylphenyl)-methyl group
1515; 1-(cyclopropyloxyimino)-1-(3-ethylphenyl)-methyl group
1516; 1-(cyclopentyloxyimino)-1-(3-ethylphenyl)-methyl group
1517; 1-(cyclohexyloxyimino)-1-(3-ethylphenyl)-methyl group
1518; 1-(3-allyloxyimino)-1-(3-ethylphenyl)-methyl group
1519; 1-(4-butenoxyimino)-1-(3-ethylphenyl)-methyl group
1520; 1-(3-propynoxyimino)-1-(3-ethylphenyl)-methyl group
1521; 1-(4-butynoxyimino)-1-(3-ethylphenyl)-methyl group
1522; 1-(1-cyclohexenoxyimino)-1-(3-ethylphenyl)-methyl group
1523; 1-(2,2,2-trifluoroethoxyimino)-1-(3-ethylphenyl)-methyl group
1524; 1-(benzyloxyimino)-1-(3-ethylphenyl)-methyl group
1525; 1-(2-fluorobenzyloxyimino)-1-(3-ethylphenyl)-methyl group
1526; 1-(3-fluorobenzyloxyimino)-1-(3-ethylphenyl)-methyl group
1527; 1-(4-fluorobenzyloxyimino)-1-(3-ethylphenyl)-methyl group
1528; 1-(2-chlorobenzyloxyimino)-1-(3-ethylphenyl)-methyl group
1529; 1-(3-chlorobenzyloxyimino)-1-(3-ethylphenyl)-methyl group
1530; 1-(4-chlorobenzyloxyimino)-1-(3-ethylphenyl)-methyl group
1531; 1-(2-methylbenzyloxyimino)-1-(3-ethylphenyl)-methyl group
1532; 1-(3-methylbenzyloxyimino)-1-(3-ethylphenyl)-methyl group
1533; 1-(4-methylbenzyloxyimino)-1-(3-ethylphenyl)-methyl group
1534; 1-(2-cyanobenzyloxyimino)-1-(3-ethylphenyl)-methyl group
1535; 1-(3-cyanobenzyloxyimino)-1-(3-ethylphenyl)-methyl group
Substituent Number; Q
1536; 1-(4-cyanobenzyloxyimino)-1-(3-ethylphenyl)-methyl group
1537; 1-(2-trifluoromethylbenzyloxyimino)-1-(3-ethylphenyl)-methyl group
1538; 1-(3-trifluoromethylbenzyloxyimino)-1-(3-ethylphenyl)-methyl group
1539; 1-(4-trifluoromethylbenzyloxyimino)-1-(3-ethylphenyl)-methyl group
1540; 1-(2-difluoromethylbenzyloxyimino)-1-(3-ethylphenyl)-methyl group
1541; 1-(3-difluoromethylbenzyloxyimino)-1-(3-ethylphenyl)-methyl group
1542; 1-(4-difluoromethylbenzyloxyimino)-1-(3-ethylphenyl)-methyl group
1543; 1-(2-methoxybenzyloxyimino)-1-(3-ethylphenyl)-methyl group
1544; 1-(3-methoxybenzyloxyimino)-1-(3-ethylphenyl)-methyl group
1545; 1-(4-methoxybenzyloxyimino)-1-(3-ethylphenyl)-methyl group
1546; 1-(2-vinylbenzyloxyimino)-1-(3-ethylphenyl)-methyl group
1547; 1-(3-vinylbenzyloxyimino)-1-(3-ethylphenyl)-methyl group
1548; 1-(4-vinylbenzyloxyimino)-1-(3-ethylphenyl)-methyl group
1549; 1-(2-phenylbenzyloxyimino)-1-(3-ethylphenyl)-methyl group
1550; 1-(3-phenylbenzyloxyimino)-1-(3-ethylphenyl)-methyl group
1551; 1-(4-phenylbenzyloxyimino)-1-(3-ethylphenyl)-methyl group
1552; 1-(2,3-difluorobenzyloxyimino)-1-(3-ethylphenyl)-methyl group
1553; 1-(2,4-difluorobenzyloxyimino)-1-(3-ethylphenyl)-methyl group
1554; 1-(2,5-difluorobenzyloxyimino)-1-(3-ethylphenyl)-methyl group
1555; 1-(2,6-difluorobenzyloxyimino)-1-(3-ethylphenyl)-methyl group
1556; 1-(3,4-difluorobenzyloxyimino)-1-(3-ethylphenyl)-methyl group
1557; 1-(3,5-difluorobenzyloxyimino)-1-(3-ethylphenyl)-methyl group
1558; 1-(2,3,4,5,6-pentafluorobenzyloxyimino)-1-(3-ethylphenyl)-methyl group
1559; 1-(3-ethylbenzyloxyimino)-1-(3-ethylphenyl)-methyl group
1560; 1-(4-ethylbenzyloxyimino)-1-(3-ethylphenyl)-methyl group
1561; 1-(2-trifluoromethoxybenzyloxyimino)-1-(3-ethylphenyl)-methyl group
1562; 1-(3-trifluoromethoxybenzyloxyimino)-1-(3-ethylphenyl)-methyl group
1563; 1-(4-trifluoromethoxybenzyloxyimino)-1-(3-ethylphenyl)-methyl group
1564; 1-(methoxyimino)-1-(3-ethylphenyl)-methyl group
Substituent Number; Q
1565; 1-(ethoxyimino)-1-(4-ethylphenyl)-methyl group
1566; 1-(propyloxyimino)-1-(4-ethylphenyl)-methyl group
1567; 1-(n-butoxyimino)-1-(4-ethylphenyl)-methyl group
1568; 1-(n-pentyloxyimino)-1-(4-ethylphenyl)-methyl group
1569; 1-(n-hexyloxyimino)-1-(4-ethylphenyl)-methyl group
1570; 1-(isopropoxyimino)-1-(4-ethylphenyl)-methyl group
1571; 1-(tert-butoxyimino)-1-(4-ethylphenyl)-methyl group
1572; 1-(sec-butoxyimino)-1-(4-ethylphenyl)-methyl group
1573; 1-(cyclopropyloxyimino)-1-(4-ethylphenyl)-methyl group
1574; 1-(cyclopentyloxyimino)-1-(4-ethylphenyl)-methyl group
1575; 1-(cyclohexyloxyimino)-1-(4-ethylphenyl)-methyl group
1576; 1-(3-allyloxyimino)-1-(4-ethylphenyl)-methyl group
1577; 1-(4-butenoxyimino)-1-(4-ethylphenyl)-methyl group
1578; 1-(3-propynoxyimino)-1-(4-ethylphenyl)-methyl group
1579; 1-(4-butynoxyimino)-1-(4-ethylphenyl)-methyl group
1580; 1-(1-cyclohexenoxyimino)-1-(4-ethylphenyl)-methyl group
1581; 1-(2,2,2-trifluoroethoxyimino)-1-(4-ethylphenyl)-methyl group
1582; 1-(benzyloxyimino)-1-(4-ethylphenyl)-methyl group
1583; 1-(2-fluorobenzyloxyimino)-1-(4-ethylphenyl)-methyl group
1584; 1-(3-fluorobenzyloxyimino)-1-(4-ethylphenyl)-methyl group
1585; 1-(4-fluorobenzyloxyimino)-1-(4-ethylphenyl)-methyl group
1586; 1-(2-chlorobenzyloxyimino)-1-(4-ethylphenyl)-methyl group
1587; 1-(3-chlorobenzyloxyimino)-1-(4-ethylphenyl)-methyl group 1588; 1-(4-chlorobenzyloxyimino)-1-(4-ethylphenyl)-methyl group
1589; 1-(2-methylbenzyloxyimino)-1-(4-ethylphenyl)-methyl group
1590; 1-(3-methylbenzyloxyimino)-1-(4-ethylphenyl)-methyl group
1591; 1-(4-methylbenzyloxyimino)-1-(4-ethylphenyl)-methyl group
1592; 1-(2-cyanobenzyloxyimino)-1-(4-ethylphenyl)-methyl group
1593; 1-(3-cyanobenzyloxyimino)-1-(4-ethylphenyl)-methyl group
Substituent Number; Q
1594; 1-(4-cyanobenzyloxyimino)-1-(4-ethylphenyl)-methyl group
1595; 1-(2-trifluoromethylbenzyloxyimino)-1-(4-ethylphenyl)-methyl group
1596; 1-(3-trifluoromethylbenzyloxyimino)-1-(4-ethylphenyl)-methyl group
1597; 1-(4-trifluoromethylbenzyloxyimino)-1-(4-ethylphenyl)-methyl group
1598; 1-(2-difluoromethylbenzyloxyimino)-1-(4-ethylphenyl)-methyl group
1599; 1-(3-difluoromethylbenzyloxyimino)-1-(4-ethylphenyl)-methyl group
1600; 1-(4-difluoromethylbenzyloxyimino)-1-(4-ethylphenyl)-methyl group
1601; 1-(2-methoxybenzyloxyimino)-1-(4-ethylphenyl)-methyl group
1602; 1-(3-methoxybenzyloxyimino)-1-(4-ethylphenyl)-methyl group
1603; 1-(4-methoxybenzyloxyimino)-1-(4-ethylphenyl)-methyl group
1604; 1-(2-vinylbenzyloxyimino)-1-(4-ethylphenyl)-methyl group
1605; 1-(3-vinylbenzyloxyimino)-1-(4-ethylphenyl)-methyl group
1606; 1-(4-vinylbenzyloxyimino)-1-(4-ethylphenyl)-methyl group
1607; 1-(2-phenylbenzyloxyimino)-1-(4-ethylphenyl)-methyl group
1608; 1-(3-phenylbenzyloxyimino)-1-(4-ethylphenyl)-methyl group
1609; 1-(4-phenylbenzyloxyimino)-1-(4-ethylphenyl)-methyl group
1610; 1-(2,3-difluorobenzyloxyimino)-1-(4-ethylphenyl)-methyl group
1611; 1-(2,4-difluorobenzyloxyimino)-1-(4-ethylphenyl)-methyl group
1612; 1-(2,5-difluorobenzyloxyimino)-1-(4-ethylphenyl)-methyl group
1613; 1-(2,6-difluorobenzyloxyimino)-1-(4-ethylphenyl)-methyl group
1614; 1-(3,4-difluorobenzyloxyimino)-1-(4-ethylphenyl)-methyl group
1615; 1-(3,5-difluorobenzyloxyimino)-1-(4-ethylphenyl)-methyl group
1616; 1-(2,3,4,5,6-pentafluorobenzyloxyimino)-1-(4-ethylphenyl)-methyl group
1617; 1-(3-ethylbenzyloxyimino)-1-(4-ethylphenyl)-methyl group
1618; 1-(4-ethylbenzyloxyimino)-1-(4-ethylphenyl)-methyl group
1619; 1-(2-trifluoromethoxybenzyloxyimino)-1-(4-ethylphenyl)-methyl group
1620; 1-(3-trifluoromethoxybenzyloxyimino)-1-(4-ethylphenyl)-methyl group
1621; 1-(4-trifluoromethoxybenzyloxyimino)-1-(4-ethylphenyl)-methyl group
1622; 1-(methoxyimino)-1-(4-ethylphenyl)-methyl group
Substituent Number; Q
1623; 1-(ethoxyimino)-1-(2-trifluoromethylphenyl)-methyl group
1624; 1-(propyloxyimino)-1-(2-trifluoromethylphenyl)-methyl group
1625; 1-(n-butoxyimino)-1-(2-trifluoromethylphenyl)-methyl group
1626; 1-(n-pentyloxyimino)-1-(2-trifluoromethylphenyl)-methyl group
1627; 1-(n-hexyloxyimino)-1-(2-trifluoromethylphenyl)-methyl group
1628; 1-(isopropoxyimino)-1-(2-trifluoromethylphenyl)-methyl group
1629; 1-(tert-butoxyimino)-1-(2-trifluoromethylphenyl)-methyl group
1630; 1-(sec-butoxyimino)-1-(2-trifluoromethylphenyl)-methyl group
1631; 1-(cyclopropyloxyimino)-1-(2-trifluoromethylphenyl)-methyl group
1632; 1-(cyclopentyloxyimino)-1-(2-trifluoromethylphenyl)-methyl group
1633; 1-(cyclohexyloxyimino)-1-(2-trifluoromethylphenyl)-methyl group
1634; 1-(3-allyloxyimino)-1-(2-trifluoromethylphenyl)-methyl group
1635; 1-(4-butenoxyimino)-1-(2-trifluoromethylphenyl)-methyl group
1636; 1-(3-propynoxyimino)-1-(2-trifluoromethylphenyl)-methyl group
1637; 1-(4-butynoxyimino)-1-(2-trifluoromethylphenyl)-methyl group
1638; 1-(1-cyclohexenoxyimino)-1-(2-trifluoromethylphenyl)-methyl group
1639; 1-(2,2,2-trifluoroethoxyimino)-1-(2-trifluoromethylphenyl)-methyl group
1640; 1-(benzyloxyimino)-1-(2-trifluoromethylphenyl)-methyl group
1641; 1-(2-fluorobenzyloxyimino)-1-(2-trifluoromethylphenyl)-methyl group
1642; 1-(3-fluorobenzyloxyimino)-1-(2-trifluoromethylphenyl)-methyl group
1643; 1-(4-fluorobenzyloxyimino)-1-(2-trifluoromethylphenyl)-methyl group
1644; 1-(2-chlorobenzyloxyimino)-1-(2-trifluoromethylphenyl)-methyl group
1645; 1-(3-chlorobenzyloxyimino)-1-(2-trifluoromethylphenyl)-methyl group
1646; 1-(4-chlorobenzyloxyimino)-1-(2-trifluoromethylphenyl)-methyl group
1647; 1-(2-methylbenzyloxyimino)-1-(2-trifluoromethylphenyl)-methyl group
1648; 1-(3-methylbenzyloxyimino)-1-(2-trifluoromethylphenyl)-methyl group
1649; 1-(4-methylbenzyloxyimino)-1-(2-trifluoromethylphenyl)-methyl group
1650; 1-(2-cyanobenzyloxyimino)-1-(2-trifluoromethylphenyl)-methyl group
1651; 1-(3-cyanobenzyloxyimino)-1-(2-trifluoromethylphenyl)-methyl group
Substituent Number; Q
1652; 1-(4-cyanobenzyloxyimino)-1-(2-trifluoromethylphenyl)-methyl group
1653; 1-(2-trifluoromethylbenzyloxyimino)-1-(2-trifluoromethylphenyl)-methyl group 1654; 1-(3-trifluoromethylbenzyloxyimino)-1-(2-trifluoromethylphenyl)-methyl group
1655; 1-(4-trifluoromethylbenzyloxyimino)-1-(2-trifluoromethylphenyl)-methyl group
1656; 1-(2-difluoromethylbenzyloxyimino)-1-(2-trifluoromethylphenyl)-methyl group
1657; 1-(3-difluoromethylbenzyloxyimino)-1-(2-trifluoromethylphenyl)-methyl group
1658; 1-(4-difluoromethylbenzyloxyimino)-1-(2-trifluoromethylphenyl)-methyl group
1659; 1-(2-methoxybenzyloxyimino)-1-(2-trifluoromethylphenyl)-methyl group
1660; 1-(3-methoxybenzyloxyimino)-1-(2-trifluoromethylphenyl)-methyl group
1661; 1-(4-methoxybenzyloxyimino)-1-(2-trifluoromethylphenyl)-methyl group
1662; 1-(2-vinylbenzyloxyimino)-1-(2-trifluoromethylphenyl)-methyl group
1663; 1-(3-vinylbenzyloxyimino)-1-(2-trifluoromethylphenyl)-methyl group
1664; 1-(4-vinylbenzyloxyimino)-1-(2-trifluoromethylphenyl)-methyl group
1665; 1-(2-phenylbenzyloxyimino)-1-(2-trifluoromethylphenyl)-methyl group
1666; 1-(3-phenylbenzyloxyimino)-1-(2-trifluoromethylphenyl)-methyl group
1667; 1-(4-phenylbenzyloxyimino)-1-(2-trifluoromethylphenyl)-methyl group
1668; 1-(2,3-difluorobenzyloxyimino)-1-(2-trifluoromethylphenyl)-methyl group
1669; 1-(2,4-difluorobenzyloxyimino)-1-(2-trifluoromethylphenyl)-methyl group
1670; 1-(2,5-difluorobenzyloxyimino)-1-(2-trifluoromethylphenyl)-methyl group
1671; 1-(2,6-difluorobenzyloxyimino)-1-(2-trifluoromethylphenyl)-methyl group
1672; 1-(3,4-difluorobenzyloxyimino)-1-(2-trifluoromethylphenyl)-methyl group
1673; 1-(3,5-difluorobenzyloxyimino)-1-(2-trifluoromethylphenyl)-methyl group
1674; 1-(2,3,4,5,6-pentafluorobenzyloxyimino)-1-(2-trifluoromethylphenyl)-methyl group
1675; 1-(3-ethylbenzyloxyimino)-1-(2-trifluoromethylphenyl)-methyl group
1676; 1-(4-ethylbenzyloxyimino)-1-(2-trifluoromethylphenyl)-methyl group
1677; 1-(2-trifluoromethoxybenzyloxyimino)-1-(2-trifluoromethyl phenyl)-methyl group
1678; 1-(3-trifluoromethoxybenzyloxyimino)-1-(2-trifluoromethyl phenyl)-methyl group
1679; 1-(4-trifluoromethoxybenzyloxyimino)-1-(2-trifluoromethyl phenyl)-methyl group
1680; 1-(methoxyimino)-1-(2-trifluoromethylphenyl)-methyl group
Substituent Number; Q
1681; 1-(ethoxyimino)-1-(3-trifluoromethylphenyl)-methyl group
1682; 1-(propyloxyimino)-1-(3-trifluoromethylphenyl)-methyl group
1683; 1-(n-butoxyimino)-1-(3-trifluoromethylphenyl)-methyl group
1684; 1-(n-pentyloxyimino)-1-(3-trifluoromethylphenyl)-methyl group
1685; 1-(n-hexyloxyimino)-1-(3-trifluoromethylphenyl)-methyl group
1686; 1-(isopropoxyimino)-1-(3-trifluoromethylphenyl)-methyl group
1687; 1-(tert-butoxyimino)-1-(3-trifluoromethylphenyl)-methyl group
1688; 1-(sec-butoxyimino)-1-(3-trifluoromethylphenyl)-methyl group
1689; 1-(cyclopropyloxyimino)-1-(3-trifluoromethylphenyl)-methyl group
1690; 1-(cyclopentyloxyimino)-1-(3-trifluoromethylphenyl)-methyl group
1691; 1-(cyclohexyloxyimino)-1-(3-trifluoromethylphenyl)-methyl group
1692; 1-(3-allyloxyimino)-1-(3-trifluoromethylphenyl)-methyl group
1693; 1-(4-butenoxyimino)-1-(3-trifluoromethylphenyl)-methyl group
1694; 1-(3-propynoxyimino)-1-(3-trifluoromethylphenyl)-methyl group
1695; 1-(4-butynoxyimino)-1-(3-trifluoromethylphenyl)-methyl group
1696; 1-(1-cyclohexenoxyimino)-1-(3-trifluoromethylphenyl)-methyl group
1697; 1-(2,2,2-trifluoroethoxyimino)-1-(3-trifluoromethylphenyl)-methyl group
1698; 1-(benzyloxyimino)-1-(3-trifluoromethylphenyl)-methyl group
1699; 1-(2-fluorobenzyloxyimino)-1-(3-trifluoromethylphenyl)-methyl group
1700; 1-(3-fluorobenzyloxyimino)-1-(3-trifluoromethylphenyl)-methyl group
1701; 1-(4-fluorobenzyloxyimino)-1-(3-trifluoromethylphenyl)-methyl group
1702; 1-(2-chlorobenzyloxyimino)-1-(3-trifluoromethylphenyl)-methyl group
1703; 1-(3-chlorobenzyloxyimino)-1-(3-trifluoromethylphenyl)-methyl group
1704; 1-(4-chlorobenzyloxyimino)-1-(3-trifluoromethylphenyl)-methyl group
1705; 1-(2-methylbenzyloxyimino)-1-(3-trifluoromethylphenyl)-methyl group
1706; 1-(3-methylbenzyloxyimino)-1-(3-trifluoromethylphenyl)-methyl group
1707; 1-(4-methylbenzyloxyimino)-1-(3-trifluoromethylphenyl)-methyl group
1708; 1-(2-cyanobenzyloxyimino)-1-(3-trifluoromethylphenyl)-methyl group
1709; 1-(3-cyanobenzyloxyimino)-1-(3-trifluoromethylphenyl)-methyl group
Substituent Number; Q
1710; 1-(4-cyanobenzyloxyimino)-1-(3-trifluoromethylphenyl)-methyl group
1711; 1-(2-trifluoromethylbenzyloxyimino)-1-(3-trifluoromethylphenyl)-methyl group
1712; 1-(3-trifluoromethylbenzyloxyimino)-1-(3-trifluoromethylphenyl)-methyl group
1713; 1-(4-trifluoromethylbenzyloxyimino)-1-(3-trifluoromethylphenyl)-methyl group
1714; 1-(2-difluoromethylbenzyloxyimino)-1-(3-trifluoromethylphenyl)-methyl group
1715; 1-(3-difluoromethylbenzyloxyimino)-1-(3-trifluoromethylphenyl)-methyl group
1716; 1-(4-difluoromethylbenzyloxyimino)-1-(3-trifluoromethylphenyl)-methyl group
1717; 1-(2-methoxybenzyloxyimino)-1-(3-trifluoromethylphenyl)-methyl group
1718; 1-(3-methoxybenzyloxyimino)-1-(3-trifluoromethylphenyl)-methyl group
1719; 1-(4-methoxybenzyloxyimino)-1-(3-trifluoromethylphenyl)-methyl group 1720; 1-(2-vinylbenzyloxyimino)-1-(3-trifluoromethylphenyl)-methyl group
1721; 1-(3-vinylbenzyloxyimino)-1-(3-trifluoromethylphenyl)-methyl group
1722; 1-(4-vinylbenzyloxyimino)-1-(3-trifluoromethylphenyl)-methyl group
1723; 1-(2-phenylbenzyloxyimino)-1-(3-trifluoromethylphenyl)-methyl group
1724; 1-(3-phenylbenzyloxyimino)-1-(3-trifluoromethylphenyl)-methyl group
1725; 1-(4-phenylbenzyloxyimino)-1-(3-trifluoromethylphenyl)-methyl group
1726; 1-(2,3-difluorobenzyloxyimino)-1-(3-trifluoromethylphenyl)-methyl group
1727; 1-(2,4-difluorobenzyloxyimino)-1-(3-trifluoromethylphenyl)-methyl group
1728; 1-(2,5-difluorobenzyloxyimino)-1-(3-trifluoromethylphenyl)-methyl group
1729; 1-(2,6-difluorobenzyloxyimino)-1-(3-trifluoromethylphenyl)-methyl group
1730; 1-(3,4-difluorobenzyloxyimino)-1-(3-trifluoromethylphenyl)-methyl group
1731; 1-(3,5-difluorobenzyloxyimino)-1-(3-trifluoromethylphenyl)-methyl group
1732; 1-(2,3,4,5,6-pentafluorobenzyloxyimino)-1-(3-trifluoromethylphenyl)-methyl group
1733; 1-(3-ethylbenzyloxyimino)-1-(3-trifluoromethylphenyl)-methyl group
1734; 1-(4-ethylbenzyloxyimino)-1-(3-trifluoromethylphenyl)-methyl group
1735; 1-(2-trifluoromethoxybenzyloxyimino)-1-(3-trifluoromethyl phenyl)-methyl group
1736; 1-(3-trifluoromethoxybenzyloxyimino)-1-(3-trifluoromethyl phenyl)-methyl group
1737; 1-(4-trifluoromethoxybenzyloxyimino)-1-(3-trifluoromethyl phenyl)-methyl group
1738; 1-(methoxyimino)-1-(3-trifluoromethylphenyl)-methyl group
Substituent Number; Q
1739; 1-(ethoxyimino)-1-(4-trifluoromethylphenyl)-methyl group
1740; 1-(propyloxyimino)-1-(4-trifluoromethylphenyl)-methyl group
1741; 1-(n-butoxyimino)-1-(4-trifluoromethylphenyl)-methyl group
1742; 1-(n-pentyloxyimino)-1-(4-trifluoromethylphenyl)-methyl group
1743; 1-(n-hexyloxyimino)-1-(4-trifluoromethylphenyl)-methyl group
1744; 1-(isopropoxyimino)-1-(4-trifluoromethylphenyl)-methyl group
1745; 1-(tert-butoxyimino)-1-(4-trifluoromethylphenyl)-methyl group
1746; 1-(sec-butoxyimino)-1-(4-trifluoromethylphenyl)-methyl group
1747; 1-(cyclopropyloxyimino)-1-(4-trifluoromethylphenyl)-methyl group
1748; 1-(cyclopentyloxyimino)-1-(4-trifluoromethylphenyl)-methyl group
1749; 1-(cyclohexyloxyimino)-1-(4-trifluoromethylphenyl)-methyl group
1750; 1-(3-allyloxyimino)-1-(4-trifluoromethylphenyl)-methyl group
1751; 1-(4-butenoxyimino)-1-(4-trifluoromethylphenyl)-methyl group
1752; 1-(3-propynoxyimino)-1-(4-trifluoromethylphenyl)-methyl group
1753; 1-(4-butynoxyimino)-1-(4-trifluoromethylphenyl)-methyl group
1754; 1-(1-cyclohexenoxyimino)-1-(4-trifluoromethylphenyl)-methyl group
1755; 1-(2,2,2-trifluoroethoxyimino)-1-(4-trifluoromethylphenyl)-methyl group
1756; 1-(benzyloxyimino)-1-(4-trifluoromethylphenyl)-methyl group
1757; 1-(2-fluorobenzyloxyimino)-1-(4-trifluoromethylphenyl)-methyl group
1758; 1-(3-fluorobenzyloxyimino)-1-(4-trifluoromethylphenyl)-methyl group
1759; 1-(4-fluorobenzyloxyimino)-1-(4-trifluoromethylphenyl)-methyl group
1760; 1-(2-chlorobenzyloxyimino)-1-(4-trifluoromethylphenyl)-methyl group
1761; 1-(3-chlorobenzyloxyimino)-1-(4-trifluoromethylphenyl)-methyl group
1762; 1-(4-chlorobenzyloxyimino)-1-(4-trifluoromethylphenyl)-methyl group
1763; 1-(2-methylbenzyloxyimino)-1-(4-trifluoromethylphenyl)-methyl group
1764; 1-(3-methylbenzyloxyimino)-1-(4-trifluoromethylphenyl)-methyl group
1765; 1-(4-methylbenzyloxyimino)-1-(4-trifluoromethylphenyl)-methyl group
1766; 1-(2-cyanobenzyloxyimino)-1-(4-trifluoromethylphenyl)-methyl group
1767; 1-(3-cyanobenzyloxyimino)-1-(4-trifluoromethylphenyl)-methyl group
Substituent Number; Q
1768; 1-(4-cyanobenzyloxyimino)-1-(2-difluoromethylphenyl)-methyl group
1769; 1-(2-trifluoromethylbenzyloxyimino)-1-(2-difluoromethylphenyl)-methyl group
1770; 1-(3-trifluoromethylbenzyloxyimino)-1-(2-difluoromethylphenyl)-methyl group
1771; 1-(4-trifluoromethylbenzyloxyimino)-1-(2-difluoromethylphenyl)-methyl group
1772; 1-(2-difluoromethylbenzyloxyimino)-1-(2-difluoromethylphenyl)-methyl group
1773; 1-(3-difluoromethylbenzyloxyimino)-1-(2-difluoromethylphenyl)-methyl group
1774; 1-(4-difluoromethylbenzyloxyimino)-1-(2-difluoromethylphenyl)-methyl group
1775; 1-(2-methoxybenzyloxyimino)-1-(2-difluoromethylphenyl)-methyl group
1776; 1-(3-methoxybenzyloxyimino)-1-(2-difluoromethylphenyl)-methyl group
1777; 1-(4-methoxybenzyloxyimino)-1-(2-difluoromethylphenyl)-methyl group
1778; 1-(2-vinylbenzyloxyimino)-1-(2-difluoromethylphenyl)-methyl group
1779; 1-(3-vinylbenzyloxyimino)-1-(2-difluoromethylphenyl)-methyl group
1780; 1-(4-vinylbenzyloxyimino)-1-(2-difluoromethylphenyl)-methyl group
1781; 1-(2-phenylbenzyloxyimino)-1-(2-difluoromethylphenyl)-methyl group
1782; 1-(3-phenylbenzyloxyimino)-1-(2-difluoromethylphenyl)-methyl group
1783; 1-(4-phenylbenzyloxyimino)-1-(2-difluoromethylphenyl)-methyl group
1784; 1-(2,3-difluorobenzyloxyimino)-1-(2-difluoromethylphenyl)-methyl group
1785; 1-(2,4-difluorobenzyloxyimino)-1-(2-difluoromethylphenyl)-methyl group 1786; 1-(2,5-difluorobenzyloxyimino)-1-(2-difluoromethylphenyl)-methyl group
1787; 1-(2,6-difluorobenzyloxyimino)-1-(2-difluoromethylphenyl)-methyl group
1788; 1-(3,4-difluorobenzyloxyimino)-1-(2-difluoromethylphenyl)-methyl group
1789; 1-(3,5-difluorobenzyloxyimino)-1-(2-difluoromethylphenyl)-methyl group
1790; 1-(2,3,4,5,6-pentafluorobenzyloxyimino)-1-(2-difluoromethylphenyl)-methyl group
1791; 1-(3-ethylbenzyloxyimino)-1-(2-difluoromethylphenyl)-methyl group
1792; 1-(4-ethylbenzyloxyimino)-1-(2-difluoromethylphenyl)-methyl group
1793; 1-(2-trifluoromethoxybenzyloxyimino)-1-(2-difluoromethylphenyl)-methyl group
1794; 1-(3-trifluoromethoxybenzyloxyimino)-1-(2-difluoromethylphenyl)-methyl group
1795; 1-(4-trifluoromethoxybenzyloxyimino)-1-(2-difluoromethylphenyl)-methyl group
1796; 1-(methoxyimino)-1-(2-difluoromethylphenyl)-methyl group
Substituent Number; Q
1797; 1-(ethoxyimino)-1-(2-difluoromethylphenyl)-methyl group
1798; 1-(propyloxyimino)-1-(2-difluoromethylphenyl)-methyl group
1799; 1-(n-butoxyimino)-1-(2-difluoromethylphenyl)-methyl group
1800; 1-(n-pentyloxyimino)-1-(2-difluoromethylphenyl)-methyl group
1801; 1-(n-hexyloxyimino)-1-(2-difluoromethylphenyl)-methyl group
1802; 1-(isopropoxyimino)-1-(2-difluoromethylphenyl)-methyl group
1803; 1-(tert-butoxyimino)-1-(2-difluoromethylphenyl)-methyl group
1804; 1-(sec-butoxyimino)-1-(2-difluoromethylphenyl)-methyl group
1805; 1-(cyclopropyloxyimino)-1-(2-difluoromethylphenyl)-methyl group
1806; 1-(cyclopentyloxyimino)-1-(2-difluoromethylphenyl)-methyl group
1807; 1-(cyclohexyloxyimino)-1-(2-difluoromethylphenyl)-methyl group
1808; 1-(3-allyloxyimino)-1-(2-difluoromethylphenyl)-methyl group
1809; 1-(4-butenoxyimino)-1-(2-difluoromethylphenyl)-methyl group
1810; 1-(3-propynoxyimino)-1-(2-difluoromethylphenyl)-methyl group
1811; 1-(4-butynoxyimino)-1-(2-difluoromethylphenyl)-methyl group
1812; 1-(1-cyclohexenoxyimino)-1-(2-difluoromethylphenyl)-methyl group
1813; 1-(2,2,2-trifluoroethoxyimino)-1-(2-difluoromethylphenyl)-methyl group
1814; 1-(benzyloxyimino)-1-(2-difluoromethylphenyl)-methyl group
1815; 1-(2-fluorobenzyloxyimino)-1-(2-difluoromethylphenyl)-methyl group
1816; 1-(3-fluorobenzyloxyimino)-1-(2-difluoromethylphenyl)-methyl group
1817; 1-(4-fluorobenzyloxyimino)-1-(2-difluoromethylphenyl)-methyl group
1818; 1-(2-chlorobenzyloxyimino)-1-(2-difluoromethylphenyl)-methyl group
1819; 1-(3-chlorobenzyloxyimino)-1-(2-difluoromethylphenyl)-methyl group
1820; 1-(4-chlorobenzyloxyimino)-1-(2-difluoromethylphenyl)-methyl group
1821; 1-(2-methylbenzyloxyimino)-1-(2-difluoromethylphenyl)-methyl group
1822; 1-(3-methylbenzyloxyimino)-1-(2-difluoromethylphenyl)-methyl group
1823; 1-(4-methylbenzyloxyimino)-1-(2-difluoromethylphenyl)-methyl group
1824; 1-(2-cyanobenzyloxyimino)-1-(2-difluoromethylphenyl)-methyl group
1825; 1-(3-cyanobenzyloxyimino)-1-(2-difluoromethylphenyl)-methyl group
Substituent Number; Q
1826; 1-(4-cyanobenzyloxyimino)-1-(2-difluoromethylphenyl)-methyl group
1827; 1-(2-trifluoromethylbenzyloxyimino)-1-(2-difluoromethylphenyl)-methyl group
1828; 1-(3-trifluoromethylbenzyloxyimino)-1-(2-difluoromethylphenyl)-methyl group
1829; 1-(4-trifluoromethylbenzyloxyimino)-1-(2-difluoromethylphenyl)-methyl group
1830; 1-(2-difluoromethylbenzyloxyimino)-1-(2-difluoromethylphenyl)-methyl group
1831; 1-(3-difluoromethylbenzyloxyimino)-1-(2-difluoromethylphenyl)-methyl group
1832; 1-(4-difluoromethylbenzyloxyimino)-1-(2-difluoromethylphenyl)-methyl group
1833; 1-(2-methoxybenzyloxyimino)-1-(2-difluoromethylphenyl)-methyl group
1834; 1-(3-methoxybenzyloxyimino)-1-(2-difluoromethylphenyl)-methyl group
1835; 1-(4-methoxybenzyloxyimino)-1-(2-difluoromethylphenyl)-methyl group
1836; 1-(2-vinylbenzyloxyimino)-1-(2-difluoromethylphenyl)-methyl group
1837; 1-(3-vinylbenzyloxyimino)-1-(2-difluoromethylphenyl)-methyl group
1838; 1-(4-vinylbenzyloxyimino)-1-(2-difluoromethylphenyl)-methyl group
1839; 1-(2-phenylbenzyloxyimino)-1-(2-difluoromethylphenyl)-methyl group
1840; 1-(3-phenylbenzyloxyimino)-1-(2-difluoromethylphenyl)-methyl group
1841; 1-(4-phenylbenzyloxyimino)-1-(2-difluoromethylphenyl)-methyl group
1842; 1-(2,3-difluorobenzyloxyimino)-1-(2-difluoromethylphenyl)-methyl group
1843; 1-(2,4-difluorobenzyloxyimino)-1-(2-difluoromethylphenyl)-methyl group
1844; 1-(2,5-difluorobenzyloxyimino)-1-(2-difluoromethylphenyl)-methyl group
1845 1-(2,6-difluorobenzyloxyimino)-1-(2-difluoromethylphenyl)-methyl group
1846; 1-(3,4-difluorobenzyloxyimino)-1-(2-difluoromethylphenyl)-methyl group
1847; 1-(3,5-difluorobenzyloxyimino)-1-(2-difluoromethylphenyl)-methyl group
1848; 1-(2,3,4,5,6-pentafluorobenzyloxyimino)-1-(2-difluoromethylphenyl)-methyl group
1849; 1-(3-ethylbenzyloxyimino)-1-(2-difluoromethylphenyl)-methyl group
1850; 1-(4-ethylbenzyloxyimino)-1-(2-difluoromethylphenyl)-methyl group
1851; 1-(2-trifluoromethoxybenzyloxyimino)-1-(2-difluoromethylphenyl)-methyl group 1852; 1-(3-trifluoromethoxybenzyloxyimino)-1-(2-difluoromethylphenyl)-methyl group
1853; 1-(4-trifluoromethoxybenzyloxyimino)-1-(2-difluoromethylphenyl)-methyl group
1854; 1-(methoxyimino)-1-(2-difluoromethylphenyl)-methyl group Substituent Number; Q
1855; 1-(ethoxyimino)-1-(3-difluoromethylphenyl)-methyl group
1856; 1-(propyloxyimino)-1-(3-difluoromethylphenyl)-methyl group
1857; 1-(n-butoxyimino)-1-(3-difluoromethylphenyl)-methyl group
1858; 1-(n-pentyloxyimino)-1-(3-difluoromethylphenyl)-methyl group
1859; 1-(n-hexyloxyimino)-1-(3-difluoromethylphenyl)-methyl group
1860; 1-(isopropoxyimino)-1-(3-difluoromethylphenyl)-methyl group
1861; 1-(tert-butoxyimino)-1-(3-difluoromethylphenyl)-methyl group
1862; 1-(sec-butoxyimino)-1-(3-difluoromethylphenyl)-methyl group
1863; 1-(cyclopropyloxyimino)-1-(3-difluoromethylphenyl)-methyl group
1864; 1-(cyclopentyloxyimino)-1-(3-difluoromethylphenyl)-methyl group
1865; 1-(cyclohexyloxyimino)-1-(3-difluoromethylphenyl)-methyl group
1866; 1-(3-allyloxyimino)-1-(3-difluoromethylphenyl)-methyl group
1867; 1-(4-butenoxyimino)-1-(3-difluoromethylphenyl)-methyl group
1868; 1-(3-propynoxyimino)-1-(3-difluoromethylphenyl)-methyl group
1869; 1-(4-butynoxyimino)-1-(3-difluoromethylphenyl)-methyl group
1870; 1-(1-cyclohexenoxyimino)-1-(3-difluoromethylphenyl)-methyl group
1871; 1-(2,2,2-trifluoroethoxyimino)-1-(3-difluoromethylphenyl)-methyl group
1872; 1-(benzyloxyimino)-1-(3-difluoromethylphenyl)-methyl group
1873; 1-(2-fluorobenzyloxyimino)-1-(3-difluoromethylphenyl)-methyl group
1874; 1-(3-fluorobenzyloxyimino)-1-(3-difluoromethylphenyl)-methyl group
1875; 1-(4-fluorobenzyloxyimino)-1-(3-difluoromethylphenyl)-methyl group
1876; 1-(2-chlorobenzyloxyimino)-1-(3-difluoromethylphenyl)-methyl group
1877; 1-(3-chlorobenzyloxyimino)-1-(3-difluoromethylphenyl)-methyl group
1878; 1-(4-chlorobenzyloxyimino)-1-(3-difluoromethylphenyl)-methyl group
1879; 1-(2-methylbenzyloxyimino)-1-(3-difluoromethylphenyl)-methyl group
1880; 1-(3-methylbenzyloxyimino)-1-(3-difluoromethylphenyl)-methyl group
1881; 1-(4-methylbenzyloxyimino)-1-(3-difluoromethylphenyl)-methyl group
1882; 1-(2-cyanobenzyloxyimino)-1-(3-difluoromethylphenyl)-methyl group
1883; 1-(3-cyanobenzyloxyimino)-1-(3-difluoromethylphenyl)-methyl group Substituent Number; Q
1884; 1-(4-cyanobenzyloxyimino)-1-(3-difluoromethylphenyl)-methyl group-1-(3-difluoromethylphenyl)-methyl group
1885; 1-(2-trifluoromethylbenzyloxyimino)-1-(3-difluoromethylphenyl)-methyl group
1886; 1-(3-trifluoromethylbenzyloxyimino)-1-(3-difluoromethylphenyl)-methyl group
1887; 1-(4-trifluoromethylbenzyloxyimino)-1-(3-difluoromethylphenyl)-methyl group
1888; 1-(2-difluoromethylbenzyloxyimino)-1-(3-difluoromethylphenyl)-methyl group
1889; 1-(3-difluoromethylbenzyloxyimino)-1-(3-difluoromethylphenyl)-methyl group
1890; 1-(4-difluoromethylbenzyloxyimino)-1-(3-difluoromethylphenyl)-methyl group
1891; 1-(2-methoxybenzyloxyimino)-1-(3-difluoromethylphenyl)-methyl group
1892; 1-(3-methoxybenzyloxyimino)-1-(3-difluoromethylphenyl)-methyl group
1893; 1-(4-methoxybenzyloxyimino)-1-(3-difluoromethylphenyl)-methyl group
1894; 1-(2-vinylbenzyloxyimino)-1-(3-difluoromethylphenyl)-methyl group
1895; 1-(3-vinylbenzyloxyimino)-1-(3-difluoromethylphenyl)-methyl group
1896; 1-(4-vinylbenzyloxyimino)-1-(3-difluoromethylphenyl)-methyl group
1897; 1-(2-phenylbenzyloxyimino)-1-(3-difluoromethylphenyl)-methyl group
1898; 1-(3-phenylbenzyloxyimino)-1-(3-difluoromethylphenyl)-methyl group
1899; 1-(4-phenylbenzyloxyimino)-1-(3-difluoromethylphenyl)-methyl group
1900; 1-(2,3-difluorobenzyloxyimino)-1-(3-difluoromethylphenyl)-methyl group
1901; 1-(2,4-difluorobenzyloxyimino)-1-(3-difluoromethylphenyl)-methyl group
1902; 1-(2,5-difluorobenzyloxyimino)-1-(3-difluoromethylphenyl)-methyl group
1903; 1-(2,6-difluorobenzyloxyimino)-1-(3-difluoromethylphenyl)-methyl group
1904; 1-(3,4-difluorobenzyloxyimino)-1-(3-difluoromethylphenyl)-methyl group
1905; 1-(3,5-difluorobenzyloxyimino)-1-(3-difluoromethylphenyl)-methyl group
1906; 1-(2,3,4,5,6-pentafluorobenzyloxyimino)-1-(3-difluoromethylphenyl)-methyl group
1907; 1-(3-ethylbenzyloxyimino)-1-(3-difluoromethylphenyl)-methyl group
1908; 1-(4-ethylbenzyloxyimino)-1-(3-difluoromethylphenyl)-methyl group
1909; 1-(2-trifluoromethoxybenzyloxyimino)-1-(3-difluoromethylphenyl)-methyl group
1910; 1-(3-trifluoromethoxybenzyloxyimino)-1-(3-difluoromethylphenyl)-methyl group
1911; 1-(4-trifluoromethoxybenzyloxyimino)-1-(3-difluoromethylphenyl)-methyl group
1912; 1-(methoxyimino)-1-(3-difluoromethylphenyl)-methyl group Substituent Number; Q
1913; 1-(ethoxyimino)-1-(4-difluoromethylphenyl)-methyl group
1914; 1-(propyloxyimino)-1-(4-difluoromethylphenyl)-methyl group
1915; 1-(n-butoxyimino)-1-(4-difluoromethylphenyl)-methyl group 1916; 1-(n-pentyloxyimino)-1-(4-difluoromethylphenyl)-methyl group
1917; 1-(n-hexyloxyimino)-1-(4-difluoromethylphenyl)-methyl group
1918; 1-(isopropoxyimino)-1-(4-difluoromethylphenyl)-methyl group
1919; 1-(tert-butoxyimino)-1-(4-difluoromethylphenyl)-methyl group
1920; 1-(sec-butoxyimino)-1-(4-difluoromethylphenyl)-methyl group
1921; 1-(cyclopropyloxyimino)-1-(4-difluoromethylphenyl)-methyl group
1922; 1-(cyclopentyloxyimino)-1-(4-difluoromethylphenyl)-methyl group
1923; 1-(cyclohexyloxyimino)-1-(4-difluoromethylphenyl)-methyl group
1924; 1-(3-allyloxyimino)-1-(4-difluoromethylphenyl)-methyl group
1925; 1-(4-butenoxyimino)-1-(4-difluoromethylphenyl)-methyl group
1926; 1-(3-propynoxyimino)-1-(4-difluoromethylphenyl)-methyl group
1927; 1-(4-butynoxyimino)-1-(4-difluoromethylphenyl)-methyl group
1928; 1-(1-cyclohexenoxyimino)-1-(4-difluoromethylphenyl)-methyl group
1929; 1-(2,2,2-trifluoroethoxyimino)-1-(4-difluoromethylphenyl)-methyl group
1930; 1-(benzyloxyimino)-1-(4-difluoromethylphenyl)-methyl group
1931; 1-(2-fluorobenzyloxyimino)-1-(4-difluoromethylphenyl)-methyl group
1932; 1-(3-fluorobenzyloxyimino)-1-(4-difluoromethylphenyl)-methyl group
1933; 1-(4-fluorobenzyloxyimino)-1-(4-difluoromethylphenyl)-methyl group
1934; 1-(2-chlorobenzyloxyimino)-1-(4-difluoromethylphenyl)-methyl group
1935; 1-(3-chlorobenzyloxyimino)-1-(4-difluoromethylphenyl)-methyl group
1936; 1-(4-chlorobenzyloxyimino)-1-(4-difluoromethylphenyl)-methyl group
1937; 1-(2-methylbenzyloxyimino)-1-(4-difluoromethylphenyl)-methyl group
1938; 1-(3-methylbenzyloxyimino)-1-(4-difluoromethylphenyl)-methyl group
1939; 1-(4-methylbenzyloxyimino)-1-(4-difluoromethylphenyl)-methyl group
1940; 1-(2-cyanobenzyloxyimino)-1-(4-difluoromethylphenyl)-methyl group
1941; 1-(3-cyanobenzyloxyimino)-1-(4-difluoromethylphenyl)-methyl group
Substituent Number; Q
1942; 1-(4-cyanobenzyloxyimino)-1-(4-difluoromethylphenyl)-methyl group
1943; 1-(2-trifluoromethylbenzyloxyimino)-1-(4-difluoromethylphenyl)-methyl group
1944; 1-(3-trifluoromethylbenzyloxyimino)-1-(4-difluoromethylphenyl)-methyl group
1945; 1-(4-trifluoromethylbenzyloxyimino)-1-(4-difluoromethylphenyl)-methyl group
1946; 1-(2-difluoromethylbenzyloxyimino)-1-(4-difluoromethylphenyl)-methyl group
1947; 1-(3-difluoromethylbenzyloxyimino)-1-(4-difluoromethylphenyl)-methyl group
1948; 1-(4-difluoromethylbenzyloxyimino)-1-(4-difluoromethylphenyl)-methyl group
1949; 1-(2-methoxybenzyloxyimino)-1-(4-difluoromethylphenyl)-methyl group
1950; 1-(3-methoxybenzyloxyimino)-1-(4-difluoromethylphenyl)-methyl group
1951; 1-(4-methoxybenzyloxyimino)-1-(4-difluoromethylphenyl)-methyl group
1952; 1-(2-vinylbenzyloxyimino)-1-(4-difluoromethylphenyl)-methyl group
1953; 1-(3-vinylbenzyloxyimino)-1-(4-difluoromethylphenyl)-methyl group
1954; 1-(4-vinylbenzyloxyimino)-1-(4-difluoromethylphenyl)-methyl group
1955; 1-(2-phenylbenzyloxyimino)-1-(4-difluoromethylphenyl)-methyl group
1956; 1-(3-phenylbenzyloxyimino)-1-(4-difluoromethylphenyl)-methyl group
1957; 1-(4-phenylbenzyloxyimino)-1-(4-difluoromethylphenyl)-methyl group
1958; 1-(2,3-difluorobenzyloxyimino)-1-(4-difluoromethylphenyl)-methyl group
1959; 1-(2,4-difluorobenzyloxyimino)-1-(4-difluoromethylphenyl)-methyl group
1960; 1-(2,5-difluorobenzyloxyimino)-1-(4-difluoromethylphenyl)-methyl group
1961; 1-(2,6-difluorobenzyloxyimino)-1-(4-difluoromethylphenyl)-methyl group
1962; 1-(3,4-difluorobenzyloxyimino)-1-(4-difluoromethylphenyl)-methyl group
1963; 1-(3,5-difluorobenzyloxyimino)-1-(4-difluoromethylphenyl)-methyl group
1964; 1-(2,3,4,5,6-pentafluorobenzyloxyimino)-1-(4-difluoromethylphenyl)-methyl group
1965; 1-(3-ethylbenzyloxyimino)-1-(4-difluoromethylphenyl)-methyl group
1966; 1-(4-ethylbenzyloxyimino)-1-(4-difluoromethylphenyl)-methyl group
1967; 1-(2-trifluoromethoxybenzyloxyimino)-1-(4-difluoromethylphenyl)-methyl group
1968; 1-(3-trifluoromethoxybenzyloxyimino)-1-(4-difluoromethylphenyl)-methyl group
1969; 1-(4-trifluoromethoxybenzyloxyimino)-1-(4-difluoromethylphenyl)-methyl group
1970; 1-(methoxyimino)-1-(4-difluoromethylphenyl)-methyl group
Substituent Number; Q
1971; 1-(ethoxyimino)-1-(2-methoxyphenyl)-methyl group
1972; 1-(propyloxyimino)-1-(2-methoxyphenyl)-methyl group
1973; 1-(n-butoxyimino)-1-(2-methoxyphenyl)-methyl group
1974; 1-(n-pentyloxyimino)-1-(2-methoxyphenyl)-methyl group
1975; 1-(n-hexyloxyimino)-1-(2-methoxyphenyl)-methyl group
1976; 1-(isopropoxyimino)-1-(2-methoxyphenyl)-methyl group
1977; 1-(tert-butoxyimino)-1-(2-methoxyphenyl)-methyl group
1978; 1-(sec-butoxyimino)-1-(2-methoxyphenyl)-methyl group
1979; 1-(cyclopropyloxyimino)-1-(2-methoxyphenyl)-methyl group
1980; 1-(cyclopentyloxyimino)-1-(2-methoxyphenyl)-methyl group
1981; 1-(cyclohexyloxyimino)-1-(2-methoxyphenyl)-methyl group 1982; 1-(3-allyloxyimino)-1-(2-methoxyphenyl)-methyl group
1983; 1-(4-butenoxyimino)-1-(2-methoxyphenyl)-methyl group
1984; 1-(3-propynoxyimino)-1-(2-methoxyphenyl)-methyl group
1985; 1-(4-butynoxyimino)-1-(2-methoxyphenyl)-methyl group
1986; 1-(1-cyclohexenoxyimino)-1-(2-methoxyphenyl)-methyl group
1987; 1-(2,2,2-trifluoroethoxyimino)-1-(2-methoxyphenyl)-methyl group
1988; 1-(benzyloxyimino)-1-(2-methoxyphenyl)-methyl group
1989; 1-(2-fluorobenzyloxyimino)-1-(2-methoxyphenyl)-methyl group
1990; 1-(3-fluorobenzyloxyimino)-1-(2-methoxyphenyl)-methyl group
1991; 1-(4-fluorobenzyloxyimino)-1-(2-methoxyphenyl)-methyl group
1992; 1-(2-chlorobenzyloxyimino)-1-(2-methoxyphenyl)-methyl group
1993; 1-(3-chlorobenzyloxyimino)-1-(2-methoxyphenyl)-methyl group
1994; 1-(4-chlorobenzyloxyimino)-1-(2-methoxyphenyl)-methyl group
1995; 1-(2-methylbenzyloxyimino)-1-(2-methoxyphenyl)-methyl group
1996; 1-(3-methylbenzyloxyimino)-1-(2-methoxyphenyl)-methyl group
1997; 1-(4-methylbenzyloxyimino)-1-(2-methoxyphenyl)-methyl group
1998; 1-(2-cyanobenzyloxyimino)-1-(2-methoxyphenyl)-methyl group
1999; 1-(3-cyanobenzyloxyimino)-1-(2-methoxyphenyl)-methyl group
Substituent Number; Q
2000; 1-(4-cyanobenzyloxyimino)-1-(2-methoxyphenyl)-methyl group
2001; 1-(2-trifluoromethylbenzyloxyimino)-1-(2-methoxyphenyl)-methyl group
2002; 1-(3-trifluoromethylbenzyloxyimino)-1-(2-methoxyphenyl)-methyl group
2003; 1-(4-trifluoromethylbenzyloxyimino)-1-(2-methoxyphenyl)-methyl group
2004; 1-(2-difluoromethylbenzyloxyimino)-1-(2-methoxyphenyl)-methyl group
2005; 1-(3-difluoromethylbenzyloxyimino)-1-(2-methoxyphenyl)-methyl group
2006; 1-(4-difluoromethylbenzyloxyimino)-1-(2-methoxyphenyl)-methyl group
2007; 1-(2-methoxybenzyloxyimino)-1-(2-methoxyphenyl)-methyl group
2008; 1-(3-methoxybenzyloxyimino)-1-(2-methoxyphenyl)-methyl group
2009; 1-(4-methoxybenzyloxyimino)-1-(2-methoxyphenyl)-methyl group
2010; 1-(2-vinylbenzyloxyimino)-1-(2-methoxyphenyl)-methyl group
2011; 1-(3-vinylbenzyloxyimino)-1-(2-methoxyphenyl)-methyl group
2012; 1-(4-vinylbenzyloxyimino)-1-(2-methoxyphenyl)-methyl group
2013; 1-(2-phenylbenzyloxyimino)-1-(2-methoxyphenyl)-methyl group
2014; 1-(3-phenylbenzyloxyimino)-1-(2-methoxyphenyl)-methyl group
2015; 1-(4-phenylbenzyloxyimino)-1-(2-methoxyphenyl)-methyl group
2016; 1-(2,3-difluorobenzyloxyimino)-1-(2-methoxyphenyl)-methyl group
2017; 1-(2,4-difluorobenzyloxyimino)-1-(2-methoxyphenyl)-methyl group
2018; 1-(2,5-difluorobenzyloxyimino)-1-(2-methoxyphenyl)-methyl group
2019; 1-(2,6-difluorobenzyloxyimino)-1-(2-methoxyphenyl)-methyl group
2020; 1-(3,4-difluorobenzyloxyimino)-1-(2-methoxyphenyl)-methyl group
2021; 1-(3,5-difluorobenzyloxyimino)-1-(2-methoxyphenyl)-methyl group
2022; 1-(2,3,4,5,6-pentafluorobenzyloxyimino)-1-(2-methoxyphenyl)-methyl group
2023; 1-(3-ethylbenzyloxyimino)-1-(2-methoxyphenyl)-methyl group
2024; 1-(4-ethylbenzyloxyimino)-1-(2-methoxyphenyl)-methyl group
2025; 1-(2-trifluoromethoxybenzyloxyimino)-1-(2-methoxyphenyl)-methyl group
2026; 1-(3-trifluoromethoxybenzyloxyimino)-1-(2-methoxyphenyl)-methyl group
2027; 1-(4-trifluoromethoxybenzyloxyimino)-1-(2-methoxyphenyl)-methyl group
2028; 1-(methoxyimino)-1-(2-methoxyphenyl)-methyl group
Substituent Number; Q
2029; 1-(ethoxyimino)-1-(3-methoxyphenyl)-methyl group
2030; 1-(propyloxyimino)-1-(3-methoxyphenyl)-methyl group
2031; 1-(n-butoxyimino)-1-(3-methoxyphenyl)-methyl group
2032; 1-(n-pentyloxyimino)-1-(3-methoxyphenyl)-methyl group
2033; 1-(n-hexyloxyimino)-1-(3-methoxyphenyl)-methyl group
2034; 1-(isopropoxyimino)-1-(3-methoxyphenyl)-methyl group
2035; 1-(tert-butoxyimino)-1-(3-methoxyphenyl)-methyl group
2036; 1-(sec-butoxyimino)-1-(3-methoxyphenyl)-methyl group
2037; 1-(cyclopropyloxyimino)-1-(3-methoxyphenyl)-methyl group
2038; 1-(cyclopentyloxyimino)-1-(3-methoxyphenyl)-methyl group
2039; 1-(cyclohexyloxyimino)-1-(3-methoxyphenyl)-methyl group
2040; 1-(3-allyloxyimino)-1-(3-methoxyphenyl)-methyl group
2041; 1-(4-butenoxyimino)-1-(3-methoxyphenyl)-methyl group
2042; 1-(3-propynoxyimino)-1-(3-methoxyphenyl)-methyl group
2043; 1-(4-butynoxyimino)-1-(3-methoxyphenyl)-methyl group
2044; 1-(1-cyclohexenoxyimino)-1-(3-methoxyphenyl)-methyl group
2045; 1-(2,2,2-trifluoroethoxyimino)-1-(3-methoxyphenyl)-methyl group
2046; 1-(benzyloxyimino)-1-(3-methoxyphenyl)-methyl group
2047; 1-(2-fluorobenzyloxyimino)-1-(3-methoxyphenyl)-methyl group 2048; 1-(3-fluorobenzyloxyimino)-1-(3-methoxyphenyl)-methyl group
2049; 1-(4-fluorobenzyloxyimino)-1-(3-methoxyphenyl)-methyl group
2050; 1-(2-chlorobenzyloxyimino)-1-(3-methoxyphenyl)-methyl group
2051; 1-(3-chlorobenzyloxyimino)-1-(3-methoxyphenyl)-methyl group
2052; 1-(4-chlorobenzyloxyimino)-1-(3-methoxyphenyl)-methyl group
2053; 1-(2-methylbenzyloxyimino)-1-(3-methoxyphenyl)-methyl group
2054; 1-(3-methylbenzyloxyimino)-1-(3-methoxyphenyl)-methyl group
2055; 1-(4-methylbenzyloxyimino)-1-(3-methoxyphenyl)-methyl group
2056; 1-(2-cyanobenzyloxyimino)-1-(3-methoxyphenyl)-methyl group
2057; 1-(3-cyanobenzyloxyimino)-1-(3-methoxyphenyl)-methyl group
Substituent Number; Q
2058; 1-(4-cyanobenzyloxyimino)-1-(3-methoxyphenyl)-methyl group
2059; 1-(2-trifluoromethylbenzyloxyimino)-1-(3-methoxyphenyl)-methyl group
2060; 1-(3-trifluoromethylbenzyloxyimino)-1-(3-methoxyphenyl)-methyl group
2061; 1-(4-trifluoromethylbenzyloxyimino)-1-(3-methoxyphenyl)-methyl group
2062; 1-(2-difluoromethylbenzyloxyimino)-1-(3-methoxyphenyl)-methyl group
2063; 1-(3-difluoromethylbenzyloxyimino)-1-(3-methoxyphenyl)-methyl group
2064; 1-(4-difluoromethylbenzyloxyimino)-1-(3-methoxyphenyl)-methyl group
2065; 1-(2-methoxybenzyloxyimino)-1-(3-methoxyphenyl)-methyl group
2066; 1-(3-methoxybenzyloxyimino)-1-(3-methoxyphenyl)-methyl group
2067; 1-(4-methoxybenzyloxyimino)-1-(3-methoxyphenyl)-methyl group
2068; 1-(2-vinylbenzyloxyimino)-1-(3-methoxyphenyl)-methyl group
2069; 1-(3-vinylbenzyloxyimino)-1-(3-methoxyphenyl)-methyl group
2070; 1-(4-vinylbenzyloxyimino)-1-(3-methoxyphenyl)-methyl group
2071; 1-(2-phenylbenzyloxyimino)-1-(3-methoxyphenyl)-methyl group
2072; 1-(3-phenylbenzyloxyimino)-1-(3-methoxyphenyl)-methyl group
2073; 1-(4-phenylbenzyloxyimino)-1-(3-methoxyphenyl)-methyl group
2074; 1-(2,3-difluorobenzyloxyimino)-1-(3-methoxyphenyl)-methyl group
2075; 1-(2,4-difluorobenzyloxyimino)-1-(3-methoxyphenyl)-methyl group
2076; 1-(2,5-difluorobenzyloxyimino)-1-(3-methoxyphenyl)-methyl group
2077; 1-(2,6-difluorobenzyloxyimino)-1-(3-methoxyphenyl)-methyl group
2078; 1-(3,4-difluorobenzyloxyimino)-1-(3-methoxyphenyl)-methyl group
2079; 1-(3,5-difluorobenzyloxyimino)-1-(3-methoxyphenyl)-methyl group
2080; 1-(2,3,4,5,6-pentafluorobenzyloxyimino)-1-(3-methoxyphenyl)-methyl group
2081; 1-(3-ethylbenzyloxyimino)-1-(3-methoxyphenyl)-methyl group
2082; 1-(4-ethylbenzyloxyimino)-1-(3-methoxyphenyl)-methyl group
2083; 1-(2-trifluoromethoxybenzyloxyimino)-1-(3-methoxyphenyl)-methyl group
2084; 1-(3-trifluoromethoxybenzyloxyimino)-1-(3-methoxyphenyl)-methyl group
2085; 1-(4-trifluoromethoxybenzyloxyimino)-1-(3-methoxyphenyl)-methyl group
2086; 1-(methoxyimino)-1-(3-methoxyphenyl)-methyl group
Substituent Number; Q
2087; 1-(ethoxyimino)-1-(4-methoxyphenyl)-methyl group
2088; 1-(propyloxyimino)-1-(4-methoxyphenyl)-methyl group
2089; 1-(n-butoxyimino)-1-(4-methoxyphenyl)-methyl group
2090; 1-(n-pentyloxyimino)-1-(4-methoxyphenyl)-methyl group
2091; 1-(n-hexyloxyimino)-1-(4-methoxyphenyl)-methyl group
2092; 1-(isopropoxyimino)-1-(4-methoxyphenyl)-methyl group
2093; 1-(tert-butoxyimino)-1-(4-methoxyphenyl)-methyl group
2094; 1-(sec-butoxyimino)-1-(4-methoxyphenyl)-methyl group
2095; 1-(cyclopropyloxyimino)-1-(4-methoxyphenyl)-methyl group
2096; 1-(cyclopentyloxyimino)-1-(4-methoxyphenyl)-methyl group
2097; 1-(cyclohexyloxyimino)-1-(4-methoxyphenyl)-methyl group
2098; 1-(3-allyloxyimino)-1-(4-methoxyphenyl)-methyl group
2099; 1-(4-butenoxyimino)-1-(4-methoxyphenyl)-methyl group
2100; 1-(3-propynoxyimino)-1-(4-methoxyphenyl)-methyl group
2101; 1-(4-butynoxyimino)-1-(4-methoxyphenyl)-methyl group
2102; 1-(1-cyclohexenoxyimino)-1-(4-methoxyphenyl)-methyl group
2103; 1-(2,2,2-trifluoroethoxyimino)-1-(4-methoxyphenyl)-methyl group
2104; 1-(benzyloxyimino)-1-(4-methoxyphenyl)-methyl group
2105; 1-(2-fluorobenzyloxyimino)-1-(4-methoxyphenyl)-methyl group
2106; 1-(3-fluorobenzyloxyimino)-1-(4-methoxyphenyl)-methyl group
2107; 1-(4-fluorobenzyloxyimino)-1-(4-methoxyphenyl)-methyl group
2108; 1-(2-chlorobenzyloxyimino)-1-(4-methoxyphenyl)-methyl group
2109; 1-(3-chlorobenzyloxyimino)-1-(4-methoxyphenyl)-methyl group
2110; 1-(4-chlorobenzyloxyimino)-1-(4-methoxyphenyl)-methyl group
2111; 1-(2-methylbenzyloxyimino)-1-(4-methoxyphenyl)-methyl group
2112; 1-(3-methylbenzyloxyimino)-1-(4-methoxyphenyl)-methyl group
2113; 1-(4-methylbenzyloxyimino)-1-(4-methoxyphenyl)-methyl group 2114; 1-(2-cyanobenzyloxyimino)-1-(4-methoxyphenyl)-methyl group
2115; 1-(3-cyanobenzyloxyimino)-1-(4-methoxyphenyl)-methyl group
Substituent Number; Q
2116; 1-(4-cyanobenzyloxyimino)-1-(4-methoxyphenyl)-methyl group
2117; 1-(2-trifluoromethylbenzyloxyimino)-1-(4-methoxyphenyl)-methyl group
2118; 1-(3-trifluoromethylbenzyloxyimino)-1-(4-methoxyphenyl)-methyl group
2119; 1-(4-trifluoromethylbenzyloxyimino)-1-(4-methoxyphenyl)-methyl group
2120; 1-(2-difluoromethylbenzyloxyimino)-1-(4-methoxyphenyl)-methyl group
2121; 1-(3-difluoromethylbenzyloxyimino)-1-(4-methoxyphenyl)-methyl group
2122; 1-(4-difluoromethylbenzyloxyimino)-1-(4-methoxyphenyl)-methyl group
2123; 1-(2-methoxybenzyloxyimino)-1-(4-methoxyphenyl)-methyl group
2124; 1-(3-methoxybenzyloxyimino)-1-(4-methoxyphenyl)-methyl group
2125; 1-(4-methoxybenzyloxyimino)-1-(4-methoxyphenyl)-methyl group
2126; 1-(2-vinylbenzyloxyimino)-1-(4-methoxyphenyl)-methyl group
2127; 1-(3-vinylbenzyloxyimino)-1-(4-methoxyphenyl)-methyl group
2128; 1-(4-vinylbenzyloxyimino)-1-(4-methoxyphenyl)-methyl group
2129; 1-(2-phenylbenzyloxyimino)-1-(4-methoxyphenyl)-methyl group
2130; 1-(3-phenylbenzyloxyimino)-1-(4-methoxyphenyl)-methyl group
2131; 1-(4-phenylbenzyloxyimino)-1-(4-methoxyphenyl)-methyl group
2132; 1-(2,3-difluorobenzyloxyimino)-1-(4-methoxyphenyl)-methyl group
2133; 1-(2,4-difluorobenzyloxyimino)-1-(4-methoxyphenyl)-methyl group
2134; 1-(2,5-difluorobenzyloxyimino)-1-(4-methoxyphenyl)-methyl group
2135; 1-(2,6-difluorobenzyloxyimino)-1-(4-methoxyphenyl)-methyl group
2136; 1-(3,4-difluorobenzyloxyimino)-1-(4-methoxyphenyl)-methyl group
2137; 1-(3,5-difluorobenzyloxyimino)-1-(4-methoxyphenyl)-methyl group
2138; 1-(2,3,4,5,6-pentafluorobenzyloxyimino)-1-(4-methoxyphenyl)-methyl group
2139; 1-(3-ethylbenzyloxyimino)-1-(4-methoxyphenyl)-methyl group
2140; 1-(4-ethylbenzyloxyimino)-1-(4-methoxyphenyl)-methyl group
2141; 1-(2-trifluoromethoxybenzyloxyimino)-1-(4-methoxyphenyl)-methyl group
2142; 1-(3-trifluoromethoxybenzyloxyimino)-1-(4-methoxyphenyl)-methyl group
2143; 1-(4-trifluoromethoxybenzyloxyimino)-1-(4-methoxyphenyl)-methyl group
2144; 1-(methoxyimino)-1-(4-methoxyphenyl)-methyl group
Substituent Number; Q
2145; 1-(ethoxyimino)-1-(2-cyclohexylphenyl)-methyl group
2146; 1-(propyloxyimino)-1-(2-cyclohexylphenyl)-methyl group
2147; 1-(n-butoxyimino)-1-(2-cyclohexylphenyl)-methyl group
2148; 1-(n-pentyloxyimino)-1-(2-cyclohexylphenyl)-methyl group
2149; 1-(n-hexyloxyimino)-1-(2-cyclohexylphenyl)-methyl group
2150; 1-(isopropoxyimino)-1-(2-cyclohexylphenyl)-methyl group
2151; 1-(tert-butoxyimino)-1-(2-cyclohexylphenyl)-methyl group
2152; 1-(sec-butoxyimino)-1-(2-cyclohexylphenyl)-methyl group
2153; 1-(cyclopropyloxyimino)-1-(2-cyclohexylphenyl)-methyl group
2154; 1-(cyclopentyloxyimino)-1-(2-cyclohexylphenyl)-methyl group
2155; 1-(cyclohexyloxyimino)-1-(2-cyclohexylphenyl)-methyl group
2156; 1-(3-allyloxyimino)-1-(2-cyclohexylphenyl)-methyl group
2157; 1-(4-butenoxyimino)-1-(2-cyclohexylphenyl)-methyl group
2158; 1-(3-propynoxyimino)-1-(2-cyclohexylphenyl)-methyl group
2159; 1-(4-butynoxyimino)-1-(2-cyclohexylphenyl)-methyl group
2160; 1-(1-cyclohexenoxyimino)-1-(2-cyclohexylphenyl)-methyl group
2161; 1-(2,2,2-trifluoroethoxyimino)-1-(2-cyclohexylphenyl)-methyl group
2162; 1-(benzyloxyimino)-1-(2-cyclohexylphenyl)-methyl group
2163; 1-(2-fluorobenzyloxyimino)-1-(2-cyclohexylphenyl)-methyl group
2164; 1-(3-fluorobenzyloxyimino)-1-(2-cyclohexylphenyl)-methyl group
2165; 1-(4-fluorobenzyloxyimino)-1-(2-cyclohexylphenyl)-methyl group
2166; 1-(2-chlorobenzyloxyimino)-1-(2-cyclohexylphenyl)-methyl group
2167; 1-(3-chlorobenzyloxyimino)-1-(2-cyclohexylphenyl)-methyl group
2168; 1-(4-chlorobenzyloxyimino)-1-(2-cyclohexylphenyl)-methyl group
2169; 1-(2-methylbenzyloxyimino)-1-(2-cyclohexylphenyl)-methyl group
2170; 1-(3-methylbenzyloxyimino)-1-(2-cyclohexylphenyl)-methyl group
2171; 1-(4-methylbenzyloxyimino)-1-(2-cyclohexylphenyl)-methyl group
2172; 1-(2-cyanobenzyloxyimino)-1-(2-cyclohexylphenyl)-methyl group
2173; 1-(3-cyanobenzyloxyimino)-1-(2-cyclohexylphenyl)-methyl group
Substituent Number; Q
2174; 1-(4-cyanobenzyloxyimino)-1-(2-cyclohexylphenyl)-methyl group
2175; 1-(2-trifluoromethylbenzyloxyimino)-1-(2-cyclohexylphenyl)-methyl group
2176; 1-(3-trifluoromethylbenzyloxyimino)-1-(2-cyclohexylphenyl)-methyl group
2177; 1-(4-trifluoromethylbenzyloxyimino)-1-(2-cyclohexylphenyl)-methyl group
2178; 1-(2-difluoromethylbenzyloxyimino)

2179; 1-(3-difluoromethylbenzyloxyimino)-1-(2-cyclohexylphenyl)-methyl group
2180; 1-(4-difluoromethylbenzyloxyimino)-1-(2-cyclohexylphenyl)-methyl group
2181; 1-(2-methoxybenzyloxyimino)-1-(2-cyclohexylphenyl)-methyl group
2182; 1-(3-methoxybenzyloxyimino)-1-(2-cyclohexylphenyl)-methyl group
2183; 1-(4-methoxybenzyloxyimino)-1-(2-cyclohexylphenyl)-methyl group
2184; 1-(2-vinylbenzyloxyimino)-1-(2-cyclohexylphenyl)-methyl group
2185; 1-(3-vinylbenzyloxyimino)-1-(2-cyclohexylphenyl)-methyl group
2186; 1-(4-vinylbenzyloxyimino)-1-(2-cyclohexylphenyl)-methyl group
2187; 1-(2-phenylbenzyloxyimino)-1-(2-cyclohexylphenyl)-methyl group
2188; 1-(3-phenylbenzyloxyimino)-1-(2-cyclohexylphenyl)-methyl group
2189; 1-(4-phenylbenzyloxyimino)-1-(2-cyclohexylphenyl)-methyl group
2190; 1-(2,3-difluorobenzyloxyimino)-1-(2-cyclohexylphenyl)-methyl group
2191; 1-(2,4-difluorobenzyloxyimino)-1-(2-cyclohexylphenyl)-methyl group
2192; 1-(2,5-difluorobenzyloxyimino)-1-(2-cyclohexylphenyl)-methyl group
2193; 1-(2,6-difluorobenzyloxyimino)-1-(2-cyclohexylphenyl)-methyl group
2194; 1-(3,4-difluorobenzyloxyimino)-1-(2-cyclohexylphenyl)-methyl group
2195; 1-(3,5-difluorobenzyloxyimino)-1-(2-cyclohexylphenyl)-methyl group
2196; 1-(2,3,4,5,6-pentafluorobenzyloxyimino)-1-(2-cyclohexylphenyl)-methyl group
2197; 1-(3-ethylbenzyloxyimino)-1-(2-cyclohexylphenyl)-methyl group
2198; 1-(4-ethylbenzyloxyimino)-1-(2-cyclohexylphenyl)-methyl group
2199; 1-(2-trifluoromethoxybenzyloxyimino)-1-(2-cyclohexylphenyl)-methyl group
2200; 1-(3-trifluoromethoxybenzyloxyimino)-1-(2-cyclohexylphenyl)-methyl group
2201; 1-(4-trifluoromethoxybenzyloxyimino)-1-(2-cyclohexylphenyl)-methyl group
2202; 1-(methoxyimino)-1-(2-cyclohexylphenyl)-methyl group
Substituent Number; Q
2203; 1-(ethoxyimino)-1-(3-cyclohexylphenyl)-methyl group
2204; 1-(propyloxyimino)-1-(3-cyclohexylphenyl)-methyl group
2205; 1-(n-butoxyimino)-1-(3-cyclohexylphenyl)-methyl group
2206; 1-(n-pentyloxyimino)-1-(3-cyclohexylphenyl)-methyl group
2207; 1-(n-hexyloxyimino)-1-(3-cyclohexylphenyl)-methyl group
2208; 1-(isopropoxyimino)-1-(3-cyclohexylphenyl)-methyl group
2209; 1-(tert-butoxyimino)-1-(3-cyclohexylphenyl)-methyl group
2210; 1-(sec-butoxyimino)-1-(3-cyclohexylphenyl)-methyl group
2211; 1-(cyclopropyloxyimino)-1-(3-cyclohexylphenyl)-methyl group
2212; 1-(cyclopentyloxyimino)-1-(3-cyclohexylphenyl)-methyl group
2213; 1-(cyclohexyloxyimino)-1-(3-cyclohexylphenyl)-methyl group
2214; 1-(3-allyloxyimino)-1-(3-cyclohexylphenyl)-methyl group
2215; 1-(4-butenoxyimino)-1-(3-cyclohexylphenyl)-methyl group
2216; 1-(3-propynoxyimino)-1-(3-cyclohexylphenyl)-methyl group
2217; 1-(4-butynoxyimino)-1-(3-cyclohexylphenyl)-methyl group
2218; 1-(1-cyclohexenoxyimino)-1-(3-cyclohexylphenyl)-methyl group
2219; 1-(2,2,2-trifluoroethoxyimino)-1-(3-cyclohexylphenyl)-methyl group
2220; 1-(benzyloxyimino)-1-(3-cyclohexylphenyl)-methyl group
2221; 1-(2-fluorobenzyloxyimino)-1-(3-cyclohexylphenyl)-methyl group
2222; 1-(3-fluorobenzyloxyimino)-1-(3-cyclohexylphenyl)-methyl group
2223; 1-(4-fluorobenzyloxyimino)-1-(3-cyclohexylphenyl)-methyl group
2224; 1-(2-chlorobenzyloxyimino)-1-(3-cyclohexylphenyl)-methyl group
2225; 1-(3-chlorobenzyloxyimino)-1-(3-cyclohexylphenyl)-methyl group
2226; 1-(4-chlorobenzyloxyimino)-1-(3-cyclohexylphenyl)-methyl group
2227; 1-(2-methylbenzyloxyimino)-1-(3-cyclohexylphenyl)-methyl group
2228; 1-(3-methylbenzyloxyimino)-1-(3-cyclohexylphenyl)-methyl group
2229; 1-(4-methylbenzyloxyimino)-1-(3-cyclohexylphenyl)-methyl group
2230; 1-(2-cyanobenzyloxyimino)-1-(3-cyclohexylphenyl)-methyl group
2231; 1-(3-cyanobenzyloxyimino)-1-(3-cyclohexylphenyl)-methyl group
Substituent Number; Q
2232; 1-(4-cyanobenzyloxyimino)-1-(3-cyclohexylphenyl)-methyl group
2233; 1-(2-trifluoromethylbenzyloxyimino)-1-(3-cyclohexylphenyl)-methyl group
2234; 1-(3-trifluoromethylbenzyloxyimino)-1-(3-cyclohexylphenyl)-methyl group
2235; 1-(4-trifluoromethylbenzyloxyimino)-1-(3-cyclohexylphenyl)-methyl group
2236; 1-(2-difluoromethylbenzyloxyimino)-1-(3-cyclohexylphenyl)-methyl group
2237; 1-(3-difluoromethylbenzyloxyimino)-1-(3-cyclohexylphenyl)-methyl group
2238; 1-(4-difluoromethylbenzyloxyimino)-1-(3-cyclohexylphenyl)-methyl group
2239; 1-(2-methoxybenzyloxyimino)-1-(3-cyclohexylphenyl)-methyl group
2240; 1-(3-methoxybenzyloxyimino)-1-(3-cyclohexylphenyl)-methyl group
2241; 1-(4-methoxybenzyloxyimino)-1-(3-cyclohexylphenyl)-methyl group
2242; 1-(2-vinylbenzyloxyimino)-1-(3-cyclohexylphenyl)-methyl group
2243; 1-(3-vinylbenzyloxyimino)-1-(3-cyclohexylphenyl)-methyl group
2244; 1-(4-vinylbenzyloxyimino)-1-(3-cyclohexylphenyl)-methyl group 2245; 1-(2-phenylbenzyloxyimino)-1-(3-cyclohexylphenyl)-methyl group
2246; 1-(3-phenylbenzyloxyimino)-1-(3-cyclohexylphenyl)-methyl group
2247; 1-(4-phenylbenzyloxyimino)-1-(3-cyclohexylphenyl)-methyl group
2248; 1-(2,3-difluorobenzyloxyimino)-1-(3-cyclohexylphenyl)-methyl group
2249; 1-(2,4-difluorobenzyloxyimino)-1-(3-cyclohexylphenyl)-methyl group
2250; 1-(2,5-difluorobenzyloxyimino)-1-(3-cyclohexylphenyl)-methyl group
2251; 1-(2,6-difluorobenzyloxyimino)-1-(3-cyclohexylphenyl)-methyl group
2252; 1-(3,4-difluorobenzyloxyimino)-1-(3-cyclohexylphenyl)-methyl group
2253; 1-(3,5-difluorobenzyloxyimino)-1-(3-cyclohexylphenyl)-methyl group
2254; 1-(2,3,4,5,6-pentafluorobenzyloxyimino)-1-(3-cyclohexylphenyl)-methyl group
2255; 1-(3-ethylbenzyloxyimino)-1-(3-cyclohexylphenyl)-methyl group
2256; 1-(4-ethylbenzyloxyimino)-1-(3-cyclohexylphenyl)-methyl group
2257; 1-(2-trifluoromethoxybenzyloxyimino)-1-(3-cyclohexylphenyl)-methyl group
2258; 1-(3-trifluoromethoxybenzyloxyimino)-1-(3-cyclohexylphenyl)-methyl group
2259; 1-(4-trifluoromethoxybenzyloxyimino)-1-(3-cyclohexylphenyl)-methyl group
2260; 1-(methoxyimino)-1-(3-cyclohexylphenyl)-methyl group
Substituent Number; Q
2261; 1-(ethoxyimino)-1-(4-cyclohexylphenyl)-methyl group
2262; 1-(propyloxyimino)-1-(4-cyclohexylphenyl)-methyl group
2263; 1-(n-butoxyimino)-1-(4-cyclohexylphenyl)-methyl group
2264; 1-(n-pentyloxyimino)-1-(4-cyclohexylphenyl)-methyl group
2265; 1-(n-hexyloxyimino)-1-(4-cyclohexylphenyl)-methyl group
2266; 1-(isopropoxyimino)-1-(4-cyclohexylphenyl)-methyl group
2267; 1-(tert-butoxyimino)-1-(4-cyclohexylphenyl)-methyl group
2268; 1-(sec-butoxyimino)-1-(4-cyclohexylphenyl)-methyl group
2269; 1-(cyclopropyloxyimino)-1-(4-cyclohexylphenyl)-methyl group
2270; 1-(cyclopentyloxyimino)-1-(4-cyclohexylphenyl)-methyl group
2271; 1-(cyclohexyloxyimino)-1-(4-cyclohexylphenyl)-methyl group
2272; 1-(3-allyloxyimino)-1-(4-cyclohexylphenyl)-methyl group
2273; 1-(4-butenoxyimino)-1-(4-cyclohexylphenyl)-methyl group
2274; 1-(3-propynoxyimino)-1-(4-cyclohexylphenyl)-methyl group
2275; 1-(4-butynoxyimino)-1-(4-cyclohexylphenyl)-methyl group
2276; 1-(1-cyclohexenoxyimino)-1-(4-cyclohexylphenyl)-methyl group
2277; 1-(2,2,2-trifluoroethoxyimino)-1-(4-cyclohexylphenyl)-methyl group
2278; 1-(benzyloxyimino)-1-(4-cyclohexylphenyl)-methyl group
2279; 1-(2-fluorobenzyloxyimino)-1-(4-cyclohexylphenyl)-methyl group
2280; 1-(3-fluorobenzyloxyimino)-1-(4-cyclohexylphenyl)-methyl group
2281; 1-(4-fluorobenzyloxyimino)-1-(4-cyclohexylphenyl)-methyl group
2282; 1-(2-chlorobenzyloxyimino)-1-(4-cyclohexylphenyl)-methyl group
2283; 1-(3-chlorobenzyloxyimino)-1-(4-cyclohexylphenyl)-methyl group
2284; 1-(4-chlorobenzyloxyimino)-1-(4-cyclohexylphenyl)-methyl group
2285; 1-(2-methylbenzyloxyimino)-1-(4-cyclohexylphenyl)-methyl group
2286; 1-(3-methylbenzyloxyimino)-1-(4-cyclohexylphenyl)-methyl group
2287; 1-(4-methylbenzyloxyimino)-1-(4-cyclohexylphenyl)-methyl group
2288; 1-(2-cyanobenzyloxyimino)-1-(4-cyclohexylphenyl)-methyl group
2289; 1-(3-cyanobenzyloxyimino)-1-(4-cyclohexylphenyl)-methyl group
Substituent Number; Q
2290; 1-(4-cyanobenzyloxyimino)-1-(4-cyclohexylphenyl)-methyl group
2291; 1-(2-trifluoromethylbenzyloxyimino)-1-(4-cyclohexylphenyl)-methyl group
2292; 1-(3-trifluoromethylbenzyloxyimino)-1-(4-cyclohexylphenyl)-methyl group
2293; 1-(4-trifluoromethylbenzyloxyimino)-1-(4-cyclohexylphenyl)-methyl group
2294; 1-(2-difluoromethylbenzyloxyimino)-1-(4-cyclohexylphenyl)-methyl group
2295; 1-(3-difluoromethylbenzyloxyimino)-1-(4-cyclohexylphenyl)-methyl group
2296; 1-(4-difluoromethylbenzyloxyimino)-1-(4-cyclohexylphenyl)-methyl group
2297; 1-(2-methoxybenzyloxyimino)-1-(4-cyclohexylphenyl)-methyl group
2298; 1-(3-methoxybenzyloxyimino)-1-(4-cyclohexylphenyl)-methyl group
2299; 1-(4-methoxybenzyloxyimino)-1-(4-cyclohexylphenyl)-methyl group
2300; 1-(2-vinylbenzyloxyimino)-1-(4-cyclohexylphenyl)-methyl group
2301; 1-(3-vinylbenzyloxyimino)-1-(4-cyclohexylphenyl)-methyl group
2302; 1-(4-vinylbenzyloxyimino)-1-(4-cyclohexylphenyl)-methyl group
2303; 1-(2-phenylbenzyloxyimino)-1-(4-cyclohexylphenyl)-methyl group
2304; 1-(3-phenylbenzyloxyimino)-1-(4-cyclohexylphenyl)-methyl group
2305; 1-(4-phenylbenzyloxyimino)-1-(4-cyclohexylphenyl)-methyl group
2306; 1-(2,3-difluorobenzyloxyimino)-1-(4-cyclohexylphenyl)-methyl group
2307; 1-(2,4-difluorobenzyloxyimino)-1-(4-cyclohexylphenyl)-methyl group
2308; 1-(2,5-difluorobenzyloxyimino)-1-(4-cyclohexylphenyl)-methyl group
2309; 1-(2,6-difluorobenzyloxyimino)-1-(4-cyclohexylphenyl)-methyl group
2310; 1-(3,4-difluorobenzyloxyimino)-1-(4-cyclohexylphenyl)-methyl group 2311; 1-(3,5-difluorobenzyloxyimino)-1-(4-cyclohexylphenyl)-methyl group
2312; 1-(2,3,4,5,6-pentafluorobenzyloxyimino)-1-(4-cyclohexylphenyl)-methyl group
2313; 1-(3-ethylbenzyloxyimino)-1-(4-cyclohexylphenyl)-methyl group
2314; 1-(4-ethylbenzyloxyimino)-1-(4-cyclohexylphenyl)-methyl group
2315; 1-(2-trifluoromethoxybenzyloxyimino)-1-(4-cyclohexylphenyl)-methyl group
2316; 1-(3-trifluoromethoxybenzyloxyimino)-1-(4-cyclohexylphenyl)-methyl group
2317; 1-(4-trifluoromethoxybenzyloxyimino)-1-(4-cyclohexylphenyl)-methyl group
2318; 1-(methoxyimino)-1-(4-cyclohexylphenyl)-methyl group
Substituent Number; Q
2319; 1-(ethoxyimino)-1-(2-cyanophenyl)-methyl group
2320; 1-(propyloxyimino)-1-(2-cyanophenyl)-methyl group
2321; 1-(n-butoxyimino)-1-(2-cyanophenyl)-methyl group
2322; 1-(n-pentyloxyimino)-1-(2-cyanophenyl)-methyl group
2323; 1-(n-hexyloxyimino)-1-(2-cyanophenyl)-methyl group
2324; 1-(isopropoxyimino)-1-(2-cyanophenyl)-methyl group
2325; 1-(tert-butoxyimino)-1-(2-cyanophenyl)-methyl group
2326; 1-(sec-butoxyimino)-1-(2-cyanophenyl)-methyl group
2327; 1-(cyclopropyloxyimino)-1-(2-cyanophenyl)-methyl group
2328; 1-(cyclopentyloxyimino)-1-(2-cyanophenyl)-methyl group
2329; 1-(cyclohexyloxyimino)-1-(2-cyanophenyl)-methyl group
2330; 1-(3-allyloxyimino)-1-(2-cyanophenyl)-methyl group
2331; 1-(4-butenoxyimino)-1-(2-cyanophenyl)-methyl group
2332; 1-(3-propynoxyimino)-1-(2-cyanophenyl)-methyl group
2333; 1-(4-butynoxyimino)-1-(2-cyanophenyl)-methyl group
2334; 1-(1-cyclohexenoxyimino)-1-(2-cyanophenyl)-methyl group
2335; 1-(2,2,2-trifluoroethoxyimino)-1-(2-cyanophenyl)-methyl group
2336; 1-(benzyloxyimino)-1-(2-cyanophenyl)-methyl group
2337; 1-(2-fluorobenzyloxyimino)-1-(2-cyanophenyl)-methyl group
2338; 1-(3-fluorobenzyloxyimino)-1-(2-cyanophenyl)-methyl group
2339; 1-(4-fluorobenzyloxyimino)-1-(2-cyanophenyl)-methyl group
2340; 1-(2-chlorobenzyloxyimino)-1-(2-cyanophenyl)-methyl group
2341; 1-(3-chlorobenzyloxyimino)-1-(2-cyanophenyl)-methyl group
2342; 1-(4-chlorobenzyloxyimino)-1-(2-cyanophenyl)-methyl group
2343; 1-(2-methylbenzyloxyimino)-1-(2-cyanophenyl)-methyl group
2344; 1-(3-methylbenzyloxyimino)-1-(2-cyanophenyl)-methyl group
2345; 1-(4-methylbenzyloxyimino)-1-(2-cyanophenyl)-methyl group
2346; 1-(2-cyanobenzyloxyimino)-1-(2-cyanophenyl)-methyl group
2347; 1-(3-cyanobenzyloxyimino)-1-(2-cyanophenyl)-methyl group
Substituent Number; Q
2348; 1-(4-cyanobenzyloxyimino)-1-(2-cyanophenyl)-methyl group
2349; 1-(2-trifluoromethylbenzyloxyimino)-1-(2-cyanophenyl)-methyl group
2350; 1-(3-trifluoromethylbenzyloxyimino)-1-(2-cyanophenyl)-methyl group
2351; 1-(4-trifluoromethylbenzyloxyimino)-1-(2-cyanophenyl)-methyl group
2352; 1-(2-difluoromethylbenzyloxyimino)-1-(2-cyanophenyl)-methyl group
2353; 1-(3-difluoromethylbenzyloxyimino)-1-(2-cyanophenyl)-methyl group
2354; 1-(4-difluoromethylbenzyloxyimino)-1-(2-cyanophenyl)-methyl group
2355; 1-(2-methoxybenzyloxyimino)-1-(2-cyanophenyl)-methyl group
2356; 1-(3-methoxybenzyloxyimino)-1-(2-cyanophenyl)-methyl group
2357; 1-(4-methoxybenzyloxyimino)-1-(2-cyanophenyl)-methyl group
2358; 1-(2-vinylbenzyloxyimino)-1-(2-cyanophenyl)-methyl group
2359; 1-(3-vinylbenzyloxyimino)-1-(2-cyanophenyl)-methyl group
2360; 1-(4-vinylbenzyloxyimino)-1-(2-cyanophenyl)-methyl group
2361; 1-(2-phenylbenzyloxyimino)-1-(2-cyanophenyl)-methyl group
2362; 1-(3-phenylbenzyloxyimino)-1-(2-cyanophenyl)-methyl group
2363; 1-(4-phenylbenzyloxyimino)-1-(2-cyanophenyl)-methyl group
2364; 1-(2,3-difluorobenzyloxyimino)-1-(2-cyanophenyl)-methyl group
2365; 1-(2,4-difluorobenzyloxyimino)-1-(2-cyanophenyl)-methyl group
2366; 1-(2,5-difluorobenzyloxyimino)-1-(2-cyanophenyl)-methyl group
2367; 1-(2,6-difluorobenzyloxyimino)-1-(2-cyanophenyl)-methyl group
2368; 1-(3,4-difluorobenzyloxyimino)-1-(2-cyanophenyl)-methyl group
2369; 1-(3,5-difluorobenzyloxyimino)-1-(2-cyanophenyl)-methyl group
2370; 1-(2,3,4,5,6-pentafluorobenzyloxyimino)-1-(2-cyanophenyl)-methyl group
2371; 1-(3-ethylbenzyloxyimino)-1-(2-cyanophenyl)-methyl group
2372; 1-(4-ethylbenzyloxyimino)-1-(2-cyanophenyl)-methyl group
2373; 1-(2-trifluoromethoxybenzyloxyimino)-1-(2-cyanophenyl)-methyl group
2374; 1-(3-trifluoromethoxybenzyloxyimino)-1-(2-cyanophenyl)-methyl group
2375; 1-(4-trifluoromethoxybenzyloxyimino)-1-(2-cyanophenyl)-methyl group
2376; 1-(methoxyimino)-1-(2-cyanophenyl)-methyl group
Substituent Number; Q
2377; 1-(ethoxyimino)-1-(3-cyanophenyl)-methyl group
2378; 1-(propyloxyimino)-1-(3-cyanophenyl)-methyl group
2379; 1-(n-butoxyimino)-1-(3-cyanophenyl)-methyl group 2380; 1-(n-pentyloxyimino)-1-(3-cyanophenyl)-methyl group
2381; 1-(n-hexyloxyimino)-1-(3-cyanophenyl)-methyl group
2382; 1-(isopropoxyimino)-1-(3-cyanophenyl)-methyl group
2383; 1-(tert-butoxyimino)-1-(3-cyanophenyl)-methyl group
2384; 1-(sec-butoxyimino)-1-(3-cyanophenyl)-methyl group
2385; 1-(cyclopropyloxyimino)-1-(3-cyanophenyl)-methyl group
2386; 1-(cyclopentyloxyimino)-1-(3-cyanophenyl)-methyl group
2387; 1-(cyclohexyloxyimino)-1-(3-cyanophenyl)-methyl group
2388; 1-(3-allyloxyimino)-1-(3-cyanophenyl)-methyl group
2389; 1-(4-butenoxyimino)-1-(3-cyanophenyl)-methyl group
2390; 1-(3-propynoxyimino)-1-(3-cyanophenyl)-methyl group
2391; 1-(4-butynoxyimino)-1-(3-cyanophenyl)-methyl group
2392; 1-(1-cyclohexenoxyimino)-1-(3-cyanophenyl)-methyl group
2393; 1-(2,2,2-trifluoroethoxyimino)-1-(3-cyanophenyl)-methyl group
2394; 1-(benzyloxyimino)-1-(3-cyanophenyl)-methyl group
2395; 1-(2-fluorobenzyloxyimino)-1-(3-cyanophenyl)-methyl group
2396; 1-(3-fluorobenzyloxyimino)-1-(3-cyanophenyl)-methyl group
2397; 1-(4-fluorobenzyloxyimino)-1-(3-cyanophenyl)-methyl group
2398; 1-(2-chlorobenzyloxyimino)-1-(3-cyanophenyl)-methyl group
2399; 1-(3-chlorobenzyloxyimino)-1-(3-cyanophenyl)-methyl group
2400; 1-(4-chlorobenzyloxyimino)-1-(3-cyanophenyl)-methyl group
2401; 1-(2-methylbenzyloxyimino)-1-(3-cyanophenyl)-methyl group
2402; 1-(3-methylbenzyloxyimino)-1-(3-cyanophenyl)-methyl group
2403; 1-(4-methylbenzyloxyimino)-1-(3-cyanophenyl)-methyl group
2404; 1-(2-cyanobenzyloxyimino)-1-(3-cyanophenyl)-methyl group
2405; 1-(3-cyanobenzyloxyimino)-1-(3-cyanophenyl)-methyl group
Substituent Number; Q
2406; 1-(4-cyanobenzyloxyimino)-1-(3-cyanophenyl)-methyl group
2407; 1-(2-trifluoromethylbenzyloxyimino)-1-(3-cyanophenyl)-methyl group
2408; 1-(3-trifluoromethylbenzyloxyimino)-1-(3-cyanophenyl)-methyl group
2409; 1-(4-trifluoromethylbenzyloxyimino)-1-(3-cyanophenyl)-methyl group
2410; 1-(2-difluoromethylbenzyloxyimino)-1-(3-cyanophenyl)-methyl group
2411; 1-(3-difluoromethylbenzyloxyimino)-1-(3-cyanophenyl)-methyl group
2412; 1-(4-difluoromethylbenzyloxyimino)-1-(3-cyanophenyl)-methyl group
2413; 1-(2-methoxybenzyloxyimino)-1-(3-cyanophenyl)-methyl group
2414; 1-(3-methoxybenzyloxyimino)-1-(3-cyanophenyl)-methyl group
2415; 1-(4-methoxybenzyloxyimino)-1-(3-cyanophenyl)-methyl group
2416; 1-(2-vinylbenzyloxyimino)-1-(3-cyanophenyl)-methyl group
2417; 1-(3-vinylbenzyloxyimino)-1-(3-cyanophenyl)-methyl group
2418; 1-(4-vinylbenzyloxyimino)-1-(3-cyanophenyl)-methyl group
2419; 1-(2-phenylbenzyloxyimino)-1-(3-cyanophenyl)-methyl group
2420; 1-(3-phenylbenzyloxyimino)-1-(3-cyanophenyl)-methyl group
2421; 1-(4-phenylbenzyloxyimino)-1-(3-cyanophenyl)-methyl group
2422; 1-(2,3-difluorobenzyloxyimino)-1-(3-cyanophenyl)-methyl group
2423; 1-(2,4-difluorobenzyloxyimino)-1-(3-cyanophenyl)-methyl group
2424; 1-(2,5-difluorobenzyloxyimino)-1-(3-cyanophenyl)-methyl group
2425; 1-(2,6-difluorobenzyloxyimino)-1-(3-cyanophenyl)-methyl group
2426; 1-(3,4-difluorobenzyloxyimino)-1-(3-cyanophenyl)-methyl group
2427; 1-(3,5-difluorobenzyloxyimino)-1-(3-cyanophenyl)-methyl group
2428; 1-(2,3,4,5,6-pentafluorobenzyloxyimino)-1-(3-cyanophenyl)-methyl group
2429; 1-(3-ethylbenzyloxyimino)-1-(3-cyanophenyl)-methyl group
2430; 1-(4-ethylbenzyloxyimino)-1-(3-cyanophenyl)-methyl group
2431; 1-(2-trifluoromethoxybenzyloxyimino)-1-(3-cyanophenyl)-methyl group
2432; 1-(3-trifluoromethoxybenzyloxyimino)-1-(3-cyanophenyl)-methyl group
2433; 1-(4-trifluoromethoxybenzyloxyimino)-1-(3-cyanophenyl)-methyl group
2434; 1-(methoxyimino)-1-(3-cyanophenyl)-methyl group
Substituent Number; Q
2435; 1-(ethoxyimino)-1-(4-cyanophenyl)-methyl group
2436; 1-(propyloxyimino)-1-(4-cyanophenyl)-methyl group
2437; 1-(n-butoxyimino)-1-(4-cyanophenyl)-methyl group
2438; 1-(n-pentyloxyimino)-1-(4-cyanophenyl)-methyl group
2439; 1-(n-hexyloxyimino)-1-(4-cyanophenyl)-methyl group
2440; 1-(isopropoxyimino)-1-(4-cyanophenyl)-methyl group
2441; 1-(tert-butoxyimino)-1-(4-cyanophenyl)-methyl group
2442; 1-(sec-butoxyimino)-1-(4-cyanophenyl)-methyl group
2443; 1-(cyclopropyloxyimino)-1-(4-cyanophenyl)-methyl group
2444; 1-(cyclopentyloxyimino)-1-(4-cyanophenyl)-methyl group
2445; 1-(cyclohexyloxyimino)-1-(4-cyanophenyl)-methyl group
2446; 1-(3-allyloxyimino)-1-(4-cyanophenyl)-methyl group
2447; 1-(4-butenoxyimino)-1-(4-cyanophenyl)-methyl group
2448; 1-(3-propynoxyimino)-1-(4-cyanophenyl)-methyl group 2449; 1-(4-butynoxyimino)-1-(4-cyanophenyl)-methyl group
2450; 1-(1-cyclohexenoxyimino)-1-(4-cyanophenyl)-methyl group
2451; 1-(2,2,2-trifluoroethoxyimino)-1-(4-cyanophenyl)-methyl group
2452; 1-(benzyloxyimino)-1-(4-cyanophenyl)-methyl group
2453; 1-(2-fluorobenzyloxyimino)-1-(4-cyanophenyl)-methyl group
2454; 1-(3-fluorobenzyloxyimino)-1-(4-cyanophenyl)-methyl group
2455; 1-(4-fluorobenzyloxyimino)-1-(4-cyanophenyl)-methyl group
2456; 1-(2-chlorobenzyloxyimino)-1-(4-cyanophenyl)-methyl group
2457; 1-(3-chlorobenzyloxyimino)-1-(4-cyanophenyl)-methyl group
2458; 1-(4-chlorobenzyloxyimino)-1-(4-cyanophenyl)-methyl group
2459; 1-(2-methylbenzyloxyimino)-1-(4-cyanophenyl)-methyl group
2460; 1-(3-methylbenzyloxyimino)-1-(4-cyanophenyl)-methyl group
2461; 1-(4-methylbenzyloxyimino)-1-(4-cyanophenyl)-methyl group
2462; 1-(2-cyanobenzyloxyimino)-1-(4-cyanophenyl)-methyl group
2463; 1-(3-cyanobenzyloxyimino)-1-(4-cyanophenyl)-methyl group Substituent Number; Q 2464; 1-(4-cyanobenzyloxyimino)-1-(4-cyanophenyl)-methyl group
2465; 1-(2-trifluoromethylbenzyloxyimino)-1-(4-cyanophenyl)-methyl group
2466; 1-(3-trifluoromethylbenzyloxyimino)-1-(4-cyanophenyl)-methyl group
2467; 1-(4-trifluoromethylbenzyloxyimino)-1-(4-cyanophenyl)-methyl group
2468; 1-(2-difluoromethylbenzyloxyimino)-1-(4-cyanophenyl)-methyl group
2469; 1-(3-difluoromethylbenzyloxyimino)-1-(4-cyanophenyl)-methyl group
2470; 1-(4-difluoromethylbenzyloxyimino)-1-(4-cyanophenyl)-methyl group
2471; 1-(2-methoxybenzyloxyimino)-1-(4-cyanophenyl)-methyl group
2472; 1-(3-methoxybenzyloxyimino)-1-(4-cyanophenyl)-methyl group
2473; 1-(4-methoxybenzyloxyimino)-1-(4-cyanophenyl)-methyl group
2474; 1-(2-vinylbenzyloxyimino)-1-(4-cyanophenyl)-methyl group
2475; 1-(3-vinylbenzyloxyimino)-1-(4-cyanophenyl)-methyl group
2476; 1-(4-vinylbenzyloxyimino)-1-(4-cyanophenyl)-methyl group
2477; 1-(2-phenylbenzyloxyimino)-1-(4-cyanophenyl)-methyl group
2478; 1-(3-phenylbenzyloxyimino)-1-(4-cyanophenyl)-methyl group
2479; 1-(4-phenylbenzyloxyimino)-1-(4-cyanophenyl)-methyl group
2480; 1-(2,3-difluorobenzyloxyimino)-1-(4-cyanophenyl)-methyl group
2481; 1-(2,4-difluorobenzyloxyimino)-1-(4-cyanophenyl)-methyl group
2482; 1-(2,5-difluorobenzyloxyimino)-1-(4-cyanophenyl)-methyl group
2483; 1-(2,6-difluorobenzyloxyimino)-1-(4-cyanophenyl)-methyl group
2484; 1-(3,4-difluorobenzyloxyimino)-1-(4-cyanophenyl)-methyl group
2485; 1-(3,5-difluorobenzyloxyimino)-1-(4-cyanophenyl)-methyl group
2486; 1-(2,3,4,5,6-pentafluorobenzyloxyimino)-1-(4-cyanophenyl)-methyl group
2487; 1-(3-ethylbenzyloxyimino)-1-(4-cyanophenyl)-methyl group
2488; 1-(4-ethylbenzyloxyimino)-1-(4-cyanophenyl)-methyl group
2489; 1-(2-trifluoromethoxybenzyloxyimino)-1-(4-cyanophenyl)-methyl group
2490; 1-(3-trifluoromethoxybenzyloxyimino)-1-(4-cyanophenyl)-methyl group
2491; 1-(4-trifluoromethoxybenzyloxyimino)-1-(4-cyanophenyl)-methyl group
2492; 1-(methoxyimino)-1-(4-cyanophenyl)-methyl group The following explanations are furnished as to preparation examples. In the following examples, the term "parts" represents "parts by weight".

Preparation Example 1

50 parts of any one of the compounds 1 to 76 of the present invention, 3 parts of calcium ligninsulfonate, 2 parts of magnesium laurylsulfate, and 45 parts of synthetic silicon oxide hydrate are thoroughly milled and mixed to obtain a preparation.

Preparation Example 2

20 parts of any one of the compounds 1 to 76 of the present invention and 1.5 parts of sorbitan trioleate are mixed in 28.5 parts of an aqueous solution containing 2 parts of polyvinyl alcohol and the mixture is pulverized by a wet milling method. Then, 40 parts of an aqueous solution containing 0.05 parts of xanthan gum and 0.1 parts of aluminum-magnesium silicate is added and 10 parts of propylene glycol is further added to the mixture, which is then mixed with stirring to obtain a preparation.

Preparation Example 3

2 parts of anyone of the compounds 1 to 76 of the present invention, 88 parts of kaolin clay, and 10 parts of talc are thoroughly milled and mixed to obtain a preparation.

Preparation Example 4

5 parts of anyone of the compounds 1 to 76 of the present invention, 14 parts of polyoxyethylenestyryl phenyl ether, 6 parts of calcium dodecylbenzene sulfonate, and 75 parts of xylene are thoroughly mixed to obtain a preparation.

Preparation Example 5

2 parts of anyone of the compounds 1 to 76 of the present invention, 1 part of synthetic silicon oxide hydrate, 2 parts of calcium ligninsulfonate, 30 parts of bentonite, and 65 parts of kaolin clay are thoroughly milled and mixed and water is added to the mixture, which is then thoroughly kneaded, followed by granulating and drying to obtain a preparation.

Preparation Example 6

10 parts of any one of the compounds 1 to 76 of the present invention; 35 parts of white carbon containing 50 parts of polyoxyethylene alkyl ether sulfate ammonium salt; and 55 parts of water are mixed and pulverized by a wet milling method to obtain a preparation.

When the control agent of the present invention is blended with other sterilizers, pesticides, acaricides, nematicides, or plant growth regulators prior to use, it may be specifically used in the following forms.

A plant disease control composition including any one of the compounds 1 to 81 of the present invention and prothioconazole in a ratio of 0.1:1;

A plant disease control composition including any one of the compounds 1 to 81 of the present invention, the compound 1 of the present invention, or the compound 81 of the present invention, and prothioconazole in a ratio of 1:1;

A plant disease control composition including any one of the compounds 1 to 81 of the present invention, the compound 1 of the present invention, or the compound 81 of the present invention, and prothioconazole in a ratio of 10:1;

A plant disease control composition including any one of the compounds 1 to 81 of the present invention, the compound 1 of the present invention, or the compound 81 of the present invention, and bromuconazole in a ratio of 0.1:1;

A plant disease control composition including any one of the compounds 1 to 81 of the present invention, the compound 1 of the present invention, or the compound 81 of the present invention, and bromuconazole in a ratio of 1:1;

A plant disease control composition including any one of the compounds 1 to 81 of the present invention, the compound 1 of the present invention, or the compound 81 of the present invention, and bromuconazole in a ratio of 10:1;

A plant disease control composition including any one of the compounds 1 to 81 of the present invention, the compound 1 of the present invention, or the compound 81 of the present invention, and metconazole in a ratio of 0.1:1;

A plant disease control composition including any one of the compounds 1 to 81 of the present invention, the compound 1 of the present invention, or the compound 81 of the present invention, and metconazole in a ratio of 1:1;

A plant disease control composition including any one of the compounds 1 to 81 of the present invention, the compound 1 of the present invention, or the compound 81 of the present invention, and metconazole in a ratio of 10:1;

A plant disease control composition including any one of the compounds 1 to 81 of the present invention, the compound 1 of the present invention, or the compound 81 of the present invention, and tebuconazole in a ratio of 0.1:1;

A plant disease control composition including any one of the compounds 1 to 81 of the present invention, the compound 1 of the present invention, or the compound 81 of the present invention, and tebuconazole in a ratio of 1:1;

A plant disease control composition including any one of the compounds 1 to 81 of the present invention, the compound 1 of the present invention, or the compound 81 of the present invention, and tebuconazole in a ratio of 10:1;

A plant disease control composition including any one of the compounds 1 to 81 of the present invention, the compound 1 of the present invention, or the compound 81 of the present invention, and tetraconazole in a ratio of 0.1:1;

A plant disease control composition including any one of the compounds 1 to 81 of the present invention, the compound 1 of the present invention, or the compound 81 of the present invention, and tetraconazole in a ratio of 1:1;

A plant disease control composition including any one of the compounds 1 to 81 of the present invention, the compound 1 of the present invention, or the compound 81 of the present invention, and tetraconazole in a ratio of 10:1;

A plant disease control composition including any one of the compounds 1 to 81 of the present invention, the compound 1 of the present invention, or the compound 81 of the present invention, and cyproconazole in a ratio of 0.1:1;

A plant disease control composition including any one of the compounds 1 to 81 of the present invention, the compound 1 of the present invention, or the compound 81 of the present invention, and cyproconazole in a ratio of 1:1;

A plant disease control composition including any one of the compounds 1 to 81 of the present invention, the compound 1 of the present invention, or the compound 81 of the present invention, and cyproconazole in a ratio of 10:1;

A plant disease control composition including any one of the compounds 1 to 81 of the present invention, the compound 1 of the present invention, or the compound 81 of the present invention, and flusilazole in a ratio of 0.1:1;

A plant disease control composition including any one of the compounds 1 to 81 of the present invention, the compound 1 of the present invention, or the compound 81 of the present invention, and flusilazole in a ratio of 1:1;

A plant disease control composition including any one of the compounds 1 to 81 of the present invention, the compound 1 of the present invention, or the compound 81 of the present invention, and flusilazole in a ratio of 10:1;

A plant disease control composition including any one of the compounds 1 to 81 of the present invention, the compound 1 of the present invention, or the compound 81 of the present invention, and prochloraz in a ratio of 0.1:1;

A plant disease control composition including any one of the compounds 1 to 81 of the present invention, the compound 1 of the present invention, or the compound 81 of the present invention, and prochloraz in a ratio of 1:1;

A plant disease control composition including any one of the compounds 1 to 81 of the present invention, the compound 1 of the present invention, or the compound 81 of the present invention, and prochloraz in a ratio of 10:1;

A plant disease control composition including any one of the compounds 1 to 81 of the present invention, the compound 1 of the present invention, or the compound 81 of the present invention, and azoxystrobin in a ratio of 0.1:1;

A plant disease control composition including any one of the compounds 1 to 81 of the present invention, the compound 1 of the present invention, or the compound 81 of the present invention, and azoxystrobin in a ratio of 1:1;

A plant disease control composition including any one of the compounds 1 to 81 of the present invention, the compound 1 of the present invention, or the compound 81 of the present invention, and azoxystrobin in a ratio of 10:1;

A plant disease control composition including any one of the compounds 1 to 81 of the present invention, the compound 1 of the present invention, or the compound 81 of the present invention, and pyraclostrobin in a ratio of 0.1:1;

A plant disease control composition including any one of the compounds 1 to 81 of the present invention, the compound 1 of the present invention, or the compound 81 of the present invention, and pyraclostrobin in a ratio of 1:1;

A plant disease control composition including any one of the compounds 1 to 81 of the present invention, the compound 1 of the present invention, or the compound 81 of the present invention, and pyraclostrobin in a ratio of 10:1;

A plant disease control composition including any one of the compounds 1 to 81 of the present invention, the compound 1 of the present invention, or the compound 81 of the present invention, and picoxystrobin in a ratio of 0.1:1;

A plant disease control composition including any one of the compounds 1 to 81 of the present invention, the compound 1 of the present invention, or the compound 81 of the present invention, and picoxystrobin in a ratio of 1:1;

A plant disease control composition including any one of the compounds 1 to 81 of the present invention, the compound 1 of the present invention, or the compound 81 of the present invention, and picoxystrobin in a ratio of 10:1;

A plant disease control composition including any one of the compounds 1 to 81 of the present invention, the compound 1 of the present invention, or the compound 81 of the present invention, and fluoxastrobin in a ratio of 0.1:1;

A plant disease control composition including any one of the compounds 1 to 81 of the present invention, the compound 1 of the present invention, or the compound 81 of the present invention, and fluoxastrobin in a ratio of 1:1;

A plant disease control composition including any one of the compounds 1 to 81 of the present invention, the compound 1 of the present invention, or the compound 81 of the present invention, and fluoxastrobin in a ratio of 10:1;

A plant disease control composition including any one of the compounds 1 to 81 of the present invention, the compound 1 of the present invention, or the compound 81 of the present invention, and trifloxystrobin in a ratio of 0.1:1;

A plant disease control composition including any one of the compounds 1 to 81 of the present invention, the compound 1 of the present invention, or the compound 81 of the present invention, and trifloxystrobin in a ratio of 1:1;

A plant disease control composition including any one of the compounds 1 to 81 of the present invention, the compound 1 of the present invention, or the compound 81 of the present invention, and trifloxystrobin in a ratio of 10:1;

A plant disease control composition including any one of the compounds 1 to 81 of the present invention, the compound 1 of the present invention, or the compound 81 of the present invention, and mandestrobin in a ratio of 0.1:1;

A plant disease control composition including any one of the compounds 1 to 81 of the present invention, the compound 1 of the present invention, or the compound 81 of the present invention, and mandestrobin in a ratio of 1:1;

A plant disease control composition including any one of the compounds 1 to 81 of the present invention, the compound 1 of the present invention, or the compound 81 of the present invention, and mandestrobin in a ratio of 10:1;

A plant disease control composition including any one of the compounds 1 to 81 of the present invention, the compound 1 of the present invention, or the compound 81 of the present invention, and fluoxastrobin in a ratio of 0.1:1;

A plant disease control composition including any one of the compounds 1 to 81 of the present invention, the compound 1 of the present invention, or the compound 81 of the present invention, and fluoxastrobin in a ratio of 1:1;

A plant disease control composition including any one of the compounds 1 to 81 of the present invention, the compound 1 of the present invention, or the compound 81 of the present invention, and fluoxastrobin in a ratio of 10:1;

A plant disease control composition including any one of the compounds 1 to 81 of the present invention, the compound 1 of the present invention, or the compound 81 of the present invention, and bixafen in a ratio of 0.1:1;

A plant disease control composition including any one of the compounds 1 to 81 of the present invention, the compound 1 of the present invention, or the compound 81 of the present invention, and bixafen in a ratio of 1:1;

A plant disease control composition including any one of the compounds 1 to 81 of the present invention, the compound 1 of the present invention, or the compound 81 of the present invention, and bixafen in a ratio of 10:1;

A plant disease control composition including any one of the compounds 1 to 81 of the present invention, the compound 1 of the present invention, or the compound 81 of the present invention, and isopyrazam in a ratio of 0.1:1;

A plant disease control composition including any one of the compounds 1 to 81 of the present invention, the compound 1 of the present invention, or the compound 81 of the present invention, and isopyrazam in a ratio of 1:1;

A plant disease control composition including any one of the compounds 1 to 81 of the present invention, the compound 1 of the present invention, or the compound 81 of the present invention, and isopyrazam in a ratio of 10:1;

A plant disease control composition including any one of the compounds 1 to 81 of the present invention, the compound 1 of the present invention, or the compound 81 of the present invention, and fluopyram in a ratio of 0.1:1;

A plant disease control composition including any one of the compounds 1 to 81 of the present invention, the compound 1 of the present invention, or the compound 81 of the present invention, and fluopyram in a ratio of 1:1;

A plant disease control composition including any one of the compounds 1 to 81 of the present invention, the compound 1 of the present invention, or the compound 81 of the present invention, and fluopyram in a ratio of 10:1;

A plant disease control composition including any one of the compounds 1 to 81 of the present invention, the compound 1 of the present invention, or the compound 81 of the present invention, and penthiopyrad in a ratio of 0.1:1;

A plant disease control composition including any one of the compounds 1 to 81 of the present invention, the compound 1 of the present invention, or the compound 81 of the present invention, and penthiopyrad in a ratio of 1:1;

A plant disease control composition including any one of the compounds 1 to 81 of the present invention, the compound 1 of the present invention, or the compound 81 of the present invention, and penthiopyrad in a ratio of 10:1;

A plant disease control composition including any one of the compounds 1 to 81 of the present invention, the compound 1 of the present invention, or the compound 81 of the present invention, and benzovindiflupyr in a ratio of 0.1:1;

A plant disease control composition including any one of the compounds 1 to 81 of the present invention, the compound 1 of the present invention, or the compound 81 of the present invention, and benzovindiflupyr in a ratio of 1:1;

A plant disease control composition including any one of the compounds 1 to 81 of the present invention, the compound 1 of the present invention, or the compound 81 of the present invention, and benzovindiflupyr in a ratio of 10:1;

A plant disease control composition including any one of the compounds 1 to 81 of the present invention, the compound 1 of the present invention, or the compound 81 of the present invention, and fluxapyroxad in a ratio of 0.1:1;

A plant disease control composition including any one of the compounds 1 to 81 of the present invention, the compound 1 of the present invention, or the compound 81 of the present invention, and fluxapyroxad in a ratio of 1:1;

A plant disease control composition including any one of the compounds 1 to 81 of the present invention, the compound 1 of the present invention, or the compound 81 of the present invention, and fluxapyroxad in a ratio of 10:1;

A plant disease control composition including any one of the compounds 1 to 81 of the present invention, the compound 1 of the present invention, or the compound 81 of the present invention, and boscalid in a ratio of 0.1:1;

A plant disease control composition including any one of the compounds 1 to 81 of the present invention, the compound 1 of the present invention, or the compound 81 of the present invention, and boscalid in a ratio of 1:1;

A plant disease control composition including any one of the compounds 1 to 81 of the present invention, the compound 1 of the present invention, or the compound 81 of the present invention, and boscalid in a ratio of 10:1;

A plant disease control composition including any one of the compounds 1 to 81 of the present invention, the compound 1 of the present invention, or the compound 81 of the present invention, and N-[2-(3,4-difluorophenyl)phenyl]-3-trifluoromethyl pyrazine-2-carboxylic acid amide in a ratio of 0.1:1;

A plant disease control composition including any one of the compounds 1 to 81 of the present invention, the compound 1 of the present invention, or the compound 81 of the present invention, and N-[2-(3,4-difluorophenyl)phenyl]-3-trifluoromethyl pyrazine-2-carboxylic acid amide in a ratio of 1:1;

A plant disease control composition including any one of the compounds 1 to 81 of the present invention, the compound 1 of the present invention, or the compound 81 of the present invention, and N-[2-(3,4-difluorophenyl)phenyl]-3-trifluoromethyl pyrazine-2-carboxylic acid amide in a ratio of 10:1;

A plant disease control composition including any one of the compounds 1 to 81 of the present invention, the compound 1 of the present invention, or the compound 81 of the present invention, and (R)-(−)-N-(1,1,3-trimethylindane-4-yl)-1-methyl-3-difluoromethylpyrazole-4-carboxylic acid amide in a ratio of 0.1:1;

A plant disease control composition including any one of the compounds 1 to 81 of the present invention, the compound 1 of the present invention, or the compound 81 of the present invention, and (R)-(−)-N-(1,1,3-trimethylindane-4-yl)-1-methyl-3-difluoromethylpyrazole-4-carboxylic acid amide in a ratio of 1:1;

A plant disease control composition including any one of the compounds 1 to 81 of the present invention, the compound 1 of the present invention, or the compound 81 of the present invention, and (R)-(−)-N-(1,1,3-trimethylindane-4-yl)-1-methyl-3-difluoromethylpyrazole-4-carboxylic acid amide in a ratio of 10:1;

A plant disease control composition including any one of the compounds 1 to 81 of the present invention, the compound 1 of the present invention, or the compound 81 of the present invention, and 3-chloro-4-(2,6-difluorophenyl)-6-methyl-5-phenylpyridazine in a ratio of 0.1:1;

A plant disease control composition including any one of the compounds 1 to 81 of the present invention, the compound 1 of the present invention, or the compound 81 of the present invention, and 3-chloro-4-(2,6-difluorophenyl)-6-methyl-5-phenylpyridazine in a ratio of 1:1;

A plant disease control composition including any one of the compounds 1 to 81 of the present invention, the compound 1 of the present invention, or the compound 81 of the present invention, and 3-chloro-4-(2,6-difluorophenyl)-6-methyl-5-phenylpyridazine in a ratio of 10:1;

A plant disease control composition including any one of the compounds 1 to 81 of the present invention, the compound 1 of the present invention, or the compound 81 of the present invention, and 3-cyano-4-(2,6-difluorophenyl)-6-methyl-5-phenylpyridanzine in a ratio of 0.1:1;

A plant disease control composition including any one of the compounds 1 to 81 of the present invention, the compound 1 of the present invention, or the compound 81 of the present invention, and 3-cyano-4-(2,6-difluorophenyl)-6-methyl-5-phenylpyridanzine in a ratio of 1:1;

A plant disease control composition including any one of the compounds 1 to 81 of the present invention, the compound 1 of the present invention, or the compound 81 of the present invention, and 3-cyano-4-(2,6-difluorophenyl)-6-methyl-5-phenylpyridanzine in a ratio of 10:1;

A plant disease control composition including any one of the compounds 1 to 81 of the present invention, the compound 1 of the present invention, or the compound 81 of the present invention, and fenpropimorph in a ratio of 0.1:1;

A plant disease control composition including any one of the compounds 1 to 81 of the present invention, the compound 1 of the present invention, or the compound 81 of the present invention, and fenpropimorph in a ratio of 1:1;

A plant disease control composition including any one of the compounds 1 to 81 of the present invention, the compound 1 of the present invention, or the compound 81 of the present invention, and fenpropimorph in a ratio of 10:1;

A plant disease control composition including any one of the compounds 1 to 81 of the present invention, the compound 1 of the present invention, or the compound 81 of the present invention, and fenpropidine in a ratio of 0.1:1;

A plant disease control composition including any one of the compounds 1 to 81 of the present invention, the compound 1 of the present invention, or the compound 81 of the present invention, and fenpropidine in a ratio of 1:1;

A plant disease control composition including any one of the compounds 1 to 81 of the present invention, the compound 1 of the present invention, or the compound 81 of the present invention, and fenpropidine in a ratio of 10:1;

A plant disease control composition including any one of the compounds 1 to 81 of the present invention, the compound 1 of the present invention, or the compound 81 of the present invention, and spiroxamine in a ratio of 0.1:1;

A plant disease control composition including any one of the compounds 1 to 81 of the present invention, the compound 1 of the present invention, or the compound 81 of the present invention, and spiroxamine in a ratio of 1:1;

A plant disease control composition including any one of the compounds 1 to 81 of the present invention, the compound 1 of the present invention, or the compound 81 of the present invention, and spiroxamine in a ratio of 10:1;

A plant disease control composition including any one of the compounds 1 to 81 of the present invention, the compound 1 of the present invention, or the compound 81 of the present invention, and cyprodinil in a ratio of 0.1:1;

A plant disease control composition including any one of the compounds 1 to 81 of the present invention, the compound 1 of the present invention, or the compound 81 of the present invention, and cyprodinil in a ratio of 1:1;

A plant disease control composition including any one of the compounds 1 to 81 of the present invention, the compound 1 of the present invention, or the compound 81 of the present invention, and cyprodinil in a ratio of 10:1;

A plant disease control composition including any one of the compounds 1 to 81 of the present invention, the compound 1 of the present invention, or the compound 81 of the present invention, and pyrimethanil in a ratio of 0.1:1;

A plant disease control composition including any one of the compounds 1 to 81 of the present invention, the compound 1 of the present invention, or the compound 81 of the present invention, and pyrimethanil in a ratio of 1:1;

A plant disease control composition including any one of the compounds 1 to 81 of the present invention, the compound 1 of the present invention, or the compound 81 of the present invention, and pyrimethanil in a ratio of 10:1;

A plant disease control composition including any one of the compounds 1 to 81 of the present invention, the compound 1 of the present invention, or the compound 81 of the present invention, and fludioxonil in a ratio of 0.1:1;

A plant disease control composition including any one of the compounds 1 to 81 of the present invention, the compound 1 of the present invention, or the compound 81 of the present invention, and fludioxonil in a ratio of 1:1;

A plant disease control composition including any one of the compounds 1 to 81 of the present invention, the compound 1 of the present invention, or the compound 81 of the present invention, and fludioxonil in a ratio of 10:1;

A plant disease control composition including any one of the compounds 1 to 81 of the present invention, the compound 1 of the present invention, or the compound 81 of the present invention, and procymidone in a ratio of 0.1:1;

A plant disease control composition including any one of the compounds 1 to 81 of the present invention, the compound 1 of the present invention, or the compound 81 of the present invention, and procymidone in a ratio of 1:1;

A plant disease control composition including any one of the compounds 1 to 81 of the present invention, the compound 1 of the present invention, or the compound 81 of the present invention, and procymidone in a ratio of 10:1;

A plant disease control composition including any one of the compounds 1 to 81 of the present invention, the compound 1 of the present invention, or the compound 81 of the present invention, and iprodione in a ratio of 0.1:1;

A plant disease control composition including any one of the compounds 1 to 81 of the present invention, the compound 1 of the present invention, or the compound 81 of the present invention, and iprodione in a ratio of 1:1;

A plant disease control composition including any one of the compounds 1 to 81 of the present invention, the compound 1 of the present invention, or the compound 81 of the present invention, and iprodione in a ratio of 10:1;

A plant disease control composition including any one of the compounds 1 to 81 of the present invention, the compound 1 of the present invention, or the compound 81 of the present invention, and thiophanate methyl in a ratio of 0.1:1;

A plant disease control composition including any one of the compounds 1 to 81 of the present invention, the compound 1 of the present invention, or the compound 81 of the present invention, and thiophanate methyl in a ratio of 1:1;

A plant disease control composition including any one of the compounds 1 to 81 of the present invention, the compound 1 of the present invention, or the compound 81 of the present invention, and thiophanate methyl in a ratio of 10:1;

A plant disease control composition including any one of the compounds 1 to 81 of the present invention, the compound 1 of the present invention, or the compound 81 of the present invention, and carbendazim in a ratio of 0.1:1;

A plant disease control composition including any one of the compounds 1 to 81 of the present invention, the compound 1 of the present invention, or the compound 81 of the present invention, and carbendazim in a ratio of 1:1;

A plant disease control composition including any one of the compounds 1 to 81 of the present invention, the compound 1 of the present invention, or the compound 81 of the present invention, and carbendazim in a ratio of 10:1;

A plant disease control composition including any one of the compounds 1 to 81 of the present invention, the compound 1 of the present invention, or the compound 81 of the present invention, and diethofencarb in a ratio of 0.1:1;

A plant disease control composition including any one of the compounds 1 to 81 of the present invention, the compound 1 of the present invention, or the compound 81 of the present invention, and diethofencarb in a ratio of 1:1;

A plant disease control composition including any one of the compounds 1 to 81 of the present invention, the compound 1 of the present invention, or the compound 81 of the present invention, and diethofencarb in a ratio of 10:1;

A plant disease control composition including any one of the compounds 1 to 81 of the present invention, the compound 1 of the present invention, or the compound 81 of the present invention, and fenpyrazamine in a ratio of 0.1:1;

A plant disease control composition including any one of the compounds 1 to 81 of the present invention, the compound 1 of the present invention, or the compound 81 of the present invention, and fenpyrazamine in a ratio of 1:1;

A plant disease control composition including any one of the compounds 1 to 81 of the present invention, the compound 1 of the present invention, or the compound 81 of the present invention, and fenpyrazamine in a ratio of 10:1;

A plant disease control composition including any one of the compounds 1 to 81 of the present invention, the compound 1 of the present invention, or the compound 81 of the present invention, and chlorothalonil in a ratio of 0.1:1;

A plant disease control composition including any one of the compounds 1 to 81 of the present invention, the compound 1 of the present invention, or the compound 81 of the present invention, and chlorothalonil in a ratio of 1:1;

A plant disease control composition including any one of the compounds 1 to 81 of the present invention, the compound 1 of the present invention, or the compound 81 of the present invention, and chlorothalonil in a ratio of 10:1;

A plant disease control composition including any one of the compounds 1 to 81 of the present invention, the compound 1 of the present invention, or the compound 81 of the present invention, and manzeb in a ratio of 0.1:1;

A plant disease control composition including any one of the compounds 1 to 81 of the present invention, the compound 1 of the present invention, or the compound 81 of the present invention, and manzeb in a ratio of 1:1;

A plant disease control composition including any one of the compounds 1 to 81 of the present invention, the compound 1 of the present invention, or the compound 81 of the present invention, and manzeb in a ratio of 10:1;

A plant disease control composition including any one of the compounds 1 to 81 of the present invention, the compound 1 of the present invention, or the compound 81 of the present invention, and folpet in a ratio of 0.1:1;

A plant disease control composition including any one of the compounds 1 to 81 of the present invention, the compound 1 of the present invention, or the compound 81 of the present invention, and folpet in a ratio of 1:1;

A plant disease control composition including any one of the compounds 1 to 81 of the present invention, the compound 1 of the present invention, or the compound 81 of the present invention, and folpet in a ratio of 10:1;

A plant disease control composition including any one of the compounds 1 to 81 of the present invention, the compound 1 of the present invention, or the compound 81 of the present invention, and metiram in a ratio of 0.1:1;

A plant disease control composition including any one of the compounds 1 to 81 of the present invention, the compound 1 of the present invention, or the compound 81 of the present invention, and metiram in a ratio of 1:1;

A plant disease control composition including any one of the compounds 1 to 81 of the present invention, the compound 1 of the present invention, or the compound 81 of the present invention, and metiram in a ratio of 10:1;

A plant disease control composition including any one of the compounds 1 to 81 of the present invention, the compound 1 of the present invention, or the compound 81 of the present invention, and clothianidin in a ratio of 1:1;

A plant disease control composition including any one of the compounds 1 to 81 of the present invention, the compound 1 of the present invention, or the compound 81 of the present invention, and clothianidin in a ratio of 1:10;

A plant disease control composition including any one of the compounds 1 to 81 of the present invention, the compound 1 of the present invention, or the compound 81 of the present invention, and clothianidin in a ratio of 1:50;

A plant disease control composition including any one of the compounds 1 to 81 of the present invention, the compound 1 of the present invention, or the compound 81 of the present invention, and imidacloprid in a ratio of 1:1;

A plant disease control composition including any one of the compounds 1 to 81 of the present invention, the compound 1 of the present invention, or the compound 81 of the present invention, and imidacloprid in a ratio of 1:10;

A plant disease control composition including any one of the compounds 1 to 81 of the present invention, the compound 1 of the present invention, or the compound 81 of the present invention, and imidacloprid in a ratio of 1:50;

A plant disease control composition including any one of the compounds 1 to 81 of the present invention, the compound 1 of the present invention, or the compound 81 of the present invention, and thiametoxam in a ratio of 1:1;

A plant disease control composition including any one of the compounds 1 to 81 of the present invention, the compound 1 of the present invention, or the compound 81 of the present invention, and thiametoxam in a ratio of 1:10;

A plant disease control composition including any one of the compounds 1 to 81 of the present invention, the compound 1 of the present invention, or the compound 81 of the present invention, and thiametoxam in a ratio of 1:50;

A plant disease control composition including any one of the compounds 1 to 81 of the present invention, the compound 1 of the present invention, or the compound 81 of the present invention, and dinotefuran in a ratio of 1:1;

A plant disease control composition including any one of the compounds 1 to 81 of the present invention, the compound 1 of the present invention, or the compound 81 of the present invention, and dinotefuran in a ratio of 1:10;

A plant disease control composition including any one of the compounds 1 to 81 of the present invention, the compound 1 of the present invention, or the compound 81 of the present invention, and dinotefuran in a ratio of 1:50;

A plant disease control composition including any one of the compounds 1 to 81 of the present invention, the compound 1 of the present invention, or the compound 81 of the present invention, and sulfoxaflor in a ratio of 1:1;

A plant disease control composition including any one of the compounds 1 to 81 of the present invention, the compound 1 of the present invention, or the compound 81 of the present invention, and sulfoxaflor in a ratio of 1:10;

A plant disease control composition including any one of the compounds 1 to 81 of the present invention, the compound 1 of the present invention, or the compound 81 of the present invention, and sulfoxaflor in a ratio of 1:50;

A plant disease control composition including any one of the compounds 1 to 81 of the present invention, the compound 1 of the present invention, or the compound 81 of the present invention, and chlorantraniliprole in a ratio of 1:1;

A plant disease control composition including any one of the compounds 1 to 81 of the present invention, the compound 1 of the present invention, or the compound 81 of the present invention, and chlorantraniliprole in a ratio of 1:10;

A plant disease control composition including any one of the compounds 1 to 81 of the present invention, the compound 1 of the present invention, or the compound 81 of the present invention, and chlorantraniliprole in a ratio of 1:50;

A plant disease control composition including any one of the compounds 1 to 81 of the present invention, the compound 1 of the present invention, or the compound 81 of the present invention, and cyantraniliprole in a ratio of 1:1;

A plant disease control composition including any one of the compounds 1 to 81 of the present invention, the compound 1 of the present invention, or the compound 81 of the present invention, and cyantraniliprole in a ratio of 1:10;

A plant disease control composition including any one of the compounds 1 to 81 of the present invention, the compound 1 of the present invention, or the compound 81 of the present invention, and cyantraniliprole in a ratio of 1:50;

A plant disease control composition including any one of the compounds 1 to 81 of the present invention, the compound 1 of the present invention, or the compound 81 of the present invention, and cyclaniliprole in a ratio of 1:1;

A plant disease control composition including any one of the compounds 1 to 81 of the present invention, the compound 1 of the present invention, or the compound 81 of the present invention, and cyclaniliprole in a ratio of 1:10;

A plant disease control composition including any one of the compounds 1 to 81 of the present invention, the compound 1 of the present invention, or the compound 81 of the present invention, and cyclaniliprole in a ratio of 1:50;

A plant disease control composition including any one of the compounds 1 to 81 of the present invention, the compound 1 of the present invention, or the compound 81 of the present invention, and abamectin in a ratio of 1:1;

A plant disease control composition including any one of the compounds 1 to 81 of the present invention, the compound 1 of the present invention, or the compound 81 of the present invention, and abamectin in a ratio of 1:10;

A plant disease control composition including any one of the compounds 1 to 81 of the present invention, the compound 1 of the present invention, or the compound 81 of the present invention, and abamectin in a ratio of 1:50;

A plant disease control composition including any one of the compounds 1 to 81 of the present invention, the compound 1 of the present invention, or the compound 81 of the present invention, and 4-oxo-4-(2-phenylethyl)aminobutyric acid in a ratio of 5:1;

A plant disease control composition including any one of the compounds 1 to 81 of the present invention, the compound 1 of the present invention, or the compound 81 of the present invention, and 4-oxo-4-(2-phenylethyl)aminobutyric acid in a ratio of 1:10;

A plant disease control composition including any one of the compounds 1 to 81 of the present invention, the compound 1 of the present invention, or the compound 81 of the present invention, and 4-oxo-4-(2-phenylethyl)aminobutyric acid in a ratio of 1:50;

A plant disease control composition including any one of the compounds 1 to 81 of the present invention, the compound 1 of the present invention, or the compound 81 of the present invention, and methyl 5-(trifluoromethyl)benzo[b]thiophene-2-carboxylate in a ratio of 5:1;

A plant disease control composition including any one of the compounds 1 to 81 of the present invention, the compound 1 of the present invention, or the compound 81 of the present invention, and methyl 5-(trifluoromethyl)benzo[b]thiophene-2-carboxylate in a ratio of 1:10;

A plant disease control composition including any one of the compounds 1 to 81 of the present invention, the compound 1 of the present invention, or the compound 81 of the present invention, and methyl 5-(trifluoromethyl)benzo[b]thiophene-2-carboxylate in a ratio of 1:50;

A plant disease control composition including any one of the compounds 1 to 81 of the present invention, the compound 1 of the present invention, or the compound 81 of the present invention, and 5-(trifluoromethyl)benzo[b]thiophene-2-carboxylic acid in a ratio of 5:1;

A plant disease control composition including any one of the compounds 1 to 81 of the present invention, the compound 1 of the present invention, or the compound 81 of the present invention, and 5-(trifluoromethyl)benzo[b]thiophene-2-carboxylic acid in a ratio of 1:10;

A plant disease control composition including any one of the compounds 1 to 81 of the present invention, the compound 1 of the present invention, or the compound 81 of the present invention, and 5-(trifluoromethyl)benzo[b]thiophene-2-carboxylic acid in a ratio of 1:50;

Next, the followings are test examples showing that the compound of the present invention is useful for controlling plant diseases.

In the test, the area of lesions on a test plant was visually observed in the examination and the area of lesions on a plant treated by the compound of the present invention was compared with the area of lesions on an untreated plant to evaluate the control effect of the compound. In this case, the untreated plant was one subjected to the test in the same condition as that of the test example except that a water-diluted solution of a formulation containing the compound of the present invention was not sprayed on stem and leaves.

Test Example 1

A plastic pot was filled with soil and rice seeds (Cultivar: Nipponbare) were planted in it to grow the seeds for 20 days in a greenhouse. Then, the compounds 2, 3, 4, 6, 7, 12, 13, 17, 30, 43, and 48 of the present invention were each made into a preparation according to the above preparation examples and each preparation was diluted with water to prepare a solution having a predetermined concentration (500 ppm). The solution was sprayed on stem and leaf so as to apply sufficiently to the surface of the rice leaf. After the application, the plant was air-dried, and the treated rice plant and rice seedling (Cultivar:Nipponbare) infected with *Magnaporthe grisea* were allowed to stand while the both were in contact with each other in the condition of 24° C. in the daytime and 20° C. in the nighttime under high humidity for 6 days to examine an infected area. As a result, the infected area of the plant treated with any one of the compounds 2, 3, 4, 6, 7, 12, 13, 17, 30, 43, and 48 of the present invention was 30% or less of that of the untreated plant.

Test Example 2

A plastic pot was filled with soil and wheat seeds (Cultivar:Shirogane) were planted in it to grow the seeds for 9 days in a greenhouse. Then, the compounds 2, 3, 4, 6, 7, 12, 13, 17, 30, 43, 48, 53, 54, 55, 56, 57, 58, 59, 60, 61, 62, 63, 64, and 65 of the present invention were each made into a preparation according to the above preparation examples and each preparation was diluted with water to prepare a solution having a predetermined concentration (500 ppm). The solution was sprayed on stem and leaf so as to apply sufficiently to the surface of the wheat leaf. After the application, the plant was air-dried and cultivated at 20° C. under illumination for 5 days. Then, the plant was inoculated with spores of *Puccinia recondita* by sprinkling the spores. After the inoculation, the plant was allowed to stand at 23° C. in a dark and highly humid atmosphere for one day and then, cultivated at 20° C. under illumination for 8 days to examine an infected area. As a result, the infected area of the plant treated with any one of the compounds 2, 3, 4, 6, 7, 12, 13, 17, 30, 43, 48, 53, 54, 55, 56, 57, 58, 59, 60, 61, 62, 63, 64, and 65 of the present invention was 30% or less of that of the untreated plant.

Test Example 3

A plastic pot was filled with soil and barley seeds (Cultivar:Mikamo Golden) were planted in it to grow the seeds for 7 days in a greenhouse. Then, the compounds 1, 2, 3, 4, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, and 81 of the present invention were each made into a preparation according to the above preparation examples and each preparation was diluted with water to prepare a solution having a predetermined concentration (500 ppm). The solution was sprayed on stem and leaf so as to apply sufficiently to the surface of the barley leaf. After the application, the plant was air-dried and was, after two days, inoculated with an aqueous suspension of spores of *Pyrenophora teres* by spraying. After the inoculation, the plant was allowed to stand under high humidity in a greenhouse kept at 23° C. in the daytime and at 20° C. in the nighttime for 3 days and then, cultivated in a greenhouse for 7 days to examine an infected area. As a result, the infected area of the plant treated with any one of the compounds 1, 2, 3, 4, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, and 81 of the present invention was 30% or less of that of the untreated plant.

Test Example 4

A plastic pot was filled with soil and kidney bean seeds (Cultivar:Nagauzura Saito) were planted in it to grow the seeds for 8 days in a greenhouse. Then, the compounds 2, 3, 4, 6, 7, 12, 13, 17, 30, 43, and 48 of the present invention were each made into a preparation according to the above preparation examples and each preparation was diluted with water to prepare a solution having a predetermined concentration (500 ppm). The solution was sprayed on stem and leaf so as to apply sufficiently to the surface of the bean leaf. After the application, the plant was air-dried and a PDA medium containing hyphae of *Sclerotinia sclerotiorum* was laid on a kidney bean leaf. After the inoculation, all kidney beans were placed under high humidity only in the nighttime to examine an infected area four days after the inoculation. As a result, the infected area of the plant treated with any one of the compounds 2, 3, 4, 6, 7, 12, 13, 17, 30, 43, and 48 of the present invention was 30% or less of that of the untreated plant.

Test Example 5

A plastic pot was filled with soil and wheat seeds (Cultivar:Apogee) were planted in it to grow the seeds for 10 days in a greenhouse. Then, the compounds 2, 3, 4, 6, 7, 12, 13, 17, 30, 43, 48, 53, 54, 55, 56, 57, 58, 59, 60, 61, 62, 63, 64, 65, 66, 67, 68, 69, 70, 71, 72, 73, 76, 77, 78, 79, and 81 of the present invention were each made into a preparation according to the above preparation examples and each preparation was diluted with water to prepare a solution having a predetermined concentration (500 ppm). The solution was sprayed on stem and leaf so as to apply sufficiently to the surface of the wheat leaf. After the application, the plant was air-dried and was, after four days, inoculated with an aqueous suspension of spores of *Septoria tritici* by spraying. After the inoculation, the plant was allowed to stand at 18° C. under high humidity for 3 days and then, placed under illumination for 14 to 18 days to examine an infected area. As a result, the infected area of the plant treated with any one of the compounds 2, 3, 4, 6, 7, 12, 13, 17, 30, 43, 48, 53, 54, 55, 56, 57, 58, 59, 60, 61, 62, 63, 64, 65, 66, 67, 68, 69, 70, 71, 72, 73, 76, 77, 78, 79, and 81 of the present invention was 30% or less of that of the untreated plant.

Test Example 6

A plastic pot was filled with soil and cucumber seeds (Cultivar:Sagami hanjiro) were planted in it to grow the seeds for 12 days in a greenhouse. Then, the compounds 2, 3, 4, 6, 7, 12, 13, 17, 30, 43, 48, 66, 67, 68, 69, 70, 71, 72, 73, 74, 75, 76, 77, 78, 79, and 81 of the present invention were each made into a preparation according to the above preparation examples and each preparation was diluted with water to prepare a solution having a predetermined concentration (500 ppm). The solution was sprayed on stem and leaf so as to apply sufficiently to the surface of the cucumber leaf. After the application, the plant was air-dried and was inoculated with spores of *Sphaerotheca fuliginea* by sprinkling. The plant was cultivated in a greenhouse kept at 24° C. in the daytime and at 20° C. in the nighttime for 8 days to examine an infected area. As a result, the infected area of the plant treated with any one of the compounds 2, 3, 4, 6, 7, 12, 13, 17, 30, 43, 48, 66, 67, 68, 69, 70, 71, 72, 73, 74, 75, 76, 77, 78, 79, and 81 of the present invention was 30% or less of that of the untreated plant.

Test Example 7

A plastic pot was filled with soil and rice seeds (Cultivar: Nipponbare) were planted in it to grow the seeds for 20 days in a greenhouse. Then, the compounds 2, 3, 4, 6, 7, 12, 13, 17, 30, 43, and 48 of the present invention were each made into a preparation according to the above preparation examples and each preparation was diluted with water to prepare a solution having a predetermined concentration (200 ppm). The solution was sprayed on stem and leaf so as to apply sufficiently to the surface of the rice leaf. After the application, the plant was air-dried, and the treated rice plant and rice seedling (Cultivar:Nipponbare) infected with *Magnaporthe grisea* were allowed to stand while the both were in contact with each other in the condition of 24° C. in the daytime and 20° C. in the nighttime under high humidity for 6 days to examine an infected area. As a result, the infected area of the plant treated with any one of the compounds 2, 3, 4, 6, 7, 12, 13, 17, 30, 43, and 48 of the present invention was 30% or less of that of the untreated plant.

Test Example 8

A plastic pot was filled with soil and wheat seeds (Cultivar:Shirogane) were planted in it to grow the seeds for 9 days in a greenhouse. Then, the compounds 53, 54, 55, 56, 57, 58, 59, 60, 61, 62, 63, 64, and 65 of the present invention were each made into a preparation according to the above preparation examples and each preparation was diluted with water to prepare a solution having a predetermined concentration (200 ppm). The solution was sprayed on stem and leaf so as to apply sufficiently to the surface of the wheat leaf. After the application, the plant was air-dried and cultivated at 20° C. under illumination for 5 days. Then, the plant was inoculated with spores of *Puccinia recondita* by sprinkling the spores. After the inoculation, the plant was allowed to stand at 23° C. in a dark and highly humid atmosphere for one day and then, cultivated at 20° C. under illumination for 8 days to examine an infected area. As a result, the infected area of the plant treated with any one of the compounds 53, 54, 55, 56, 57, 58, 59, 60, 61, 62, 63, 64, and 65 of the present invention was 30% or less of that of the untreated plant.

Test Example 9

A plastic pot was filled with soil and barley seeds (Cultivar:Mikamo Golden) were planted in it to grow the seeds for 7 days in a greenhouse. Then, the compounds 2, 3, 4, 6, 7, 12, 13, 17, 30, 43, 48, 53, 54, 55, 56, 57, 58, 59, 60, 61, 62, 63, 64, and 65 of the present invention were each made into a preparation according to the above preparation examples and each preparation was diluted with water to prepare a solution having a predetermined concentration (200 ppm). The solution was sprayed on stem and leaf so as to apply sufficiently to the surface of the barley leaf. After the application, the plant was air-dried and was, after two days, inoculated with an aqueous suspension of spores of *Pyrenophora teres* by spraying. After the inoculation, the plant was allowed to stand under high humidity in a greenhouse kept at 23° C. in the daytime and at 20° C. in the nighttime for 3 days and then, cultivated in a greenhouse for 7 days to examine an infected area. As a result, the infected area of the plant treated with any one of the compounds 2, 3, 4, 6, 7, 12, 13, 17, 30, 43, 48, 53, 54, 55, 56, 57, 58, 59, 60, 61, 62, 63, 64, and 65 of the present invention was 30% or less of that of the untreated plant.

Test Example 10

A plastic pot was filled with soil and kidney bean seeds (Cultivar:Nagauzura Saito) were planted in it to grow the seeds 8 days in a greenhouse. Then, the compounds 1, 2, 3, 4, 6, 7, 12, 13, 17, 30, 43, and 48 of the present invention were each made into a preparation according to the above preparation examples and each preparation was diluted with water to prepare a solution having a predetermined concentration (200 ppm). The solution was sprayed on stem and leaf so as to apply sufficiently to the surface of the bean leaf. After the application, the plant was air-dried and a PDA medium containing hyphae of *Sclerotinia sclerotiorum* was laid on a kidney bean leaf. After the inoculation, all kidney beans were placed under high humidity only in the nighttime to examine an infected area four days after the inoculation. As a result, the infected area of the plant treated with any one of the compounds 1, 2, 3, 4, 6, 7, 12, 13, 17, 30, 43, and 48 of the present invention was 30% or less of that of the untreated plant.

Test Example 11

A plastic pot was filled with soil and wheat seeds (Cultivar:Apogee) were planted in it to grow the seeds for 10 days in a greenhouse. Then, the compounds 2, 3, 4, 6, 7, 12, 13, 17, 30, 43, 48, 53, 54, 55, 56, 57, 58, 59, 60, 61, 62, 63, 64 and 65 of the present invention were each made into a preparation according to the above preparation examples and each preparation was diluted with water to prepare a solution having a predetermined concentration (200 ppm). The solution was sprayed on stem and leaf so as to apply sufficiently to the surface of the wheat leaf. After the application, the plant was air-dried and was, after four days, inoculated with an aqueous suspension of spores of *Septoria tritici* by spraying. After the inoculation, the plant was allowed to stand at 18° C. under high humidity for 3 days and then, placed under illumination for 14 to 18 days to examine an infected area. As a result, the infected area of the plant treated with any one of the compounds 2, 3, 4, 6, 7, 12, 13, 17, 30, 43, 48, 53, 54, 55, 56, 57, 58, 59, 60, 61, 62, 63, 64 and 65 of the present invention was 30% or less of that of the untreated plant.

Test Example 12

A plastic pot was filled with soil and cucumber seeds (Cultivar:Sagami hanjiro) were planted in it to grow the seeds for 12 days in a greenhouse. Then, the compounds 1, 2, 3, 4, 6, 7, 12, 13, 17, 30, 43, and 48 of the present invention were each made into a preparation according to the above preparation examples and each preparation was diluted with water to prepare a solution having a predetermined concentration (200 ppm). The solution was sprayed on stem and leaf so as to apply sufficiently to the surface of the cucumber leaf. After the application, the plant was air-dried and was inoculated with spores of *Sphaerotheca fuliginea* by sprinkling. The plant was cultivated in a greenhouse kept at 24° C. in the daytime and at 20° C. in the nighttime for 8 days to examine an infected area. As a result, the infected area of the plant treated with any one of the compounds 1, 2, 3, 4, 6, 7, 12, 13, 17, 30, 43, and 48 of the present invention was 30% or less of that of the untreated plant.

Test Example 13

A plastic pot was filled with soil and soybean seeds (Cultivar:Kurosengoku) were planted in it to grow the seeds for 13 days in a greenhouse. Then, the compounds 53, 54, 55, 56, 57, 58, 59, 60, 61, 62, 63, 64, and 65 of the present invention were each made into a preparation according to the above preparation examples and each preparation was diluted with water to prepare a solution having a predetermined concentration (200 ppm). The solution was sprayed on stem and leaf so as to apply sufficiently to the surface of the soybean leaf. After the application, the plant was air-dried and was, after two days, inoculated with an aqueous suspension of spores of *Phakopsora pachyrhizi* by spraying. After the inoculation, the plant was allowed to stand under high humidity for 3 days in a greenhouse kept at 23° C. in the daytime and at 20° C. in the nighttime and then, cultivated in a greenhouse for 14 days to examine an infected area. As a result, the infected area of the plant treated with any one of the compounds 53, 54, 55, 56, 57, 58, 59, 60, 61, 62, 63, 64, and 65 of the present invention was 30% or less of that of the untreated plant.

Test Example 14

A plastic pot was filled with soil and barley seeds (Cultivar:Mikamo Golden) were planted in it to grow the seeds for 7 days in a greenhouse. Then, the compounds 2, 3, 4, 6, 7, 12, 13, 17, 30, 43, 48, 53, 54, 55, 56, 57, 58, 59, 60, 61, 62, 63, 64, 65, 66, 67, 68, 69, 70, 71, 72, 73, 74, 75, 76, 77, 78, 79, and 81 of the present invention were each made into a preparation according to the above preparation examples and each preparation was diluted with water to prepare a solution having a predetermined concentration (200 ppm). The solution was sprayed on stem and leaf so as to apply sufficiently to the surface of the barley leaf. After the application, the plant was air-dried and was, after two days, inoculated with an aqueous suspension of spores of *Rhynchosporium secalis* by spraying. After the inoculation, the plant was allowed to stand under high humidity in a greenhouse kept at 23° C. in the daytime and at 20° C. in the nighttime for 3 days and then, cultivated in a greenhouse for 7 days to examine an infected area. As a result, the infected area of the plant treated with any one of the compounds 2, 3, 4, 6, 7, 12, 13, 17, 30, 43, 48, 53, 54, 55, 56, 57, 58, 59, 60, 61, 62, 63, 64, 65, 66, 67, 68, 69, 70, 71, 72, 73, 74, 75, 76, 77, 78, 79, and 81 of the present invention was 30% or less of that of the untreated plant.

The invention claimed is:
1. A tetrazolinone compound represented by the formula (1):

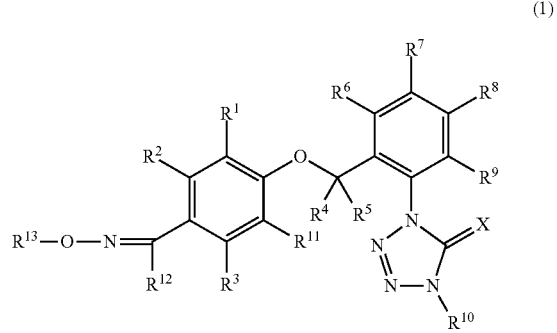

wherein
$R^1$, $R^2$, $R^3$, and $R^{11}$ each represent a hydrogen atom, a halogen atom, a cyano group, a nitro group, an amino group, a hydroxy group, a thiol group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a C3-C12 trialkylsilyl group, a C2-C6 alkylcarbonyl group, a C2-C6 alkoxycarbonyl group, or a C2-C9 alkylaminocarbonyl group,
a C1-C6 alkyl group which may have a group selected from the group $P^1$, or
a C3-C6 cycloalkyl group which may have a group selected from the group $P^1$;

$R^4$ and $R^5$ each represent a hydrogen atom, a halogen atom, or a C1-C3 alkyl group;

$R^6$ represents a C1-C4 alkyl group which may have a halogen atom(s), a halogen atom, a C1-C4 alkoxy group which may have a halogen atom(s), a C2-C4 alkenyl group, a C2-C4 haloalkenyl group, a C2-C4 alkynyl group, a C2-C4 haloalkynyl group, a C1-C4 alkylthio group, a C1-C4 haloalkylthio group, a C3-C6 cycloalkyl group, a C3-C6 halocycloalkyl group, a cyano group, a nitro group, a C1-C4 alkylsulfinyl group, a C1-C4 alkylsulfonyl group, a C1-C4 haloalkylsulfinyl group, a C1-C4 haloalkylsulfonyl group, a C1-C6 alkylamino group, or a C1-C6 haloalkylamino group;

$R^7$, $R^8$, and $R^9$ each represent a hydrogen atom, a halogen atom, a C1-C3 alkyl group, a C1-C3 haloalkyl group, a C2-C3 alkenyl group, a C2-C3 haloalkenyl group, a C1-C3 alkoxy group, or a C1-C3 haloalkoxy group;

$R^{10}$ represents a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group, or a C3-C5 halocycloalkyl group;

X represents an oxygen atom or a sulfur atom;

$R^{12}$ represents a C1-C6 alkyl group which may have a group selected from the group $P^1$, a C3-C6 cycloalkyl group which may have a group selected from the group $P^1$, a phenyl group which may have a group selected from the group $P^2$, a hydrogen atom, a halogen atom, a cyano group, a nitro group, an amino group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C6 cycloalkenyl group, a C3-C6 halocycloalkenyl group, a C1-C8 alkylamino group, a C3-C12 trialkylsilyl group, a C2-C6 alkylcarbonyl group, a C2-C6 alkoxycarbonyl group, or a C2-C9 alkylaminocarbonyl group;

$R^{13}$ represents a C1-C8 alkyl group, a C1-C8 haloalkyl group, a C2-C6 alkenyl group, a C2-C6 haloalkenyl group, a C2-C6 alkynyl group, a C2-C6 haloalkynyl group, a C3-C6 cycloalkyl group, a C3-C6 halocycloalkyl group, a C3-C6 cycloalkenyl group, or a C3-C6 halocycloalkenyl group, or a benzyl group which may have a group selected from the group $P^2$;

Group $P^1$: Group consisting of a halogen atom, cyano group, C3-C6 cycloalkyl group, C3-C6 halocycloalkyl group, C1-C4 alkoxy group, C1-C4 haloalkoxy group, C1-C4 alkylthio group, and C1-C4 haloalkylthio group; and Group $P^2$: Group consisting of a halogen atom, cyano group, amino group, hydroxy group, thiol group, C1-C6 alkyl group, C1-C6 haloalkyl group, C3-C6 cycloalkyl group, C3-C6 halocycloalkyl group, C2-C6 alkenyl group, C2-C6 haloalkenyl group, C2-C6 alkynyl group, C1-C6 alkoxy group, C1-C6 haloalkoxy group, C1-C8 alkylamino group, C1-C6 alkylthio group, C1-C6 haloalkylthio group, C1-C6 alkylsulfinyl group, C1-C6 alkylsulfonyl group, pentafluorosulfanyl group, C3-C12 trialkylsilyl group, C2-C6 alkylcarbonyl group, C2-C6 alkoxycarbonyl group, and C2-C9 alkylaminocarbonyl group.

2. The tetrazolinone compound according to claim 1, wherein $R^1$ is a C1-C3 alkyl group which may have a halogen atom(s), a halogen atom, a C3-C5 cycloalkyl group, a C1-C3 alkoxy group, a C2-C3 alkynyl group, a C2-C3 haloalkynyl group, a C3-C5 halocycloalkyl group, or a C1-C3 haloalkoxy group, $R^2$, $R^4$, $R^5$, $R^7$, $R^8$, $R^9$, and $R^{11}$ are each a hydrogen atom;

$R^3$ is a halogen atom, a C1-C3 alkyl group, a C1-C3 haloalkyl group, or a hydrogen atom;

$R^6$ is a C1-C3 alkyl group which may have a halogen atom(s), a halogen atom, a C1-C3 alkoxy group which may have a halogen atom(s), a C2-C4 alkenyl group, a C2-C4 haloalkenyl group, a C2-C4 alkynyl group, a C2-C4 haloalkynyl group, a C1-C4 alkylthio group, a C1-C4 haloalkyl thio group, a C3-C6 cycloalkyl group, or a C3-C6 halocycloalkyl group;

$R^{10}$ is a methyl group; and

X is an oxygen atom.

3. The tetrazolinone compound according to claim 1, wherein $R^{12}$ is a C1-C6 alkyl group which may have a halogen atom(s), a C3-C6 cycloalkyl group which may have a halogen atom(s), a phenyl group which may have a group selected from the group $P^3$, a C2-C6 alkenyl group, a C2-C6 haloalkynyl group, a C1-C6 alkoxy group, a C1-C6 haloalkoxy group, or a C3-C6 halocycloalkyl group; and Group $P^3$: Group consisting of a hydrogen atom, halogen atom, C1-C3 alkyl group, and C1-C3 haloalkyl group.

4. The tetrazolinone compound according to claim 1, wherein $R^{13}$ is a C1-C6 alkyl group which may have a halogen atom(s), a C2-C6 alkenyl group, a C2-C6 haloalkenyl group, a C2-C6 alkynyl group, a C2-C6 haloalkynyl group, a C3-C6 cycloalkyl group, a C3-C6 cycloalkenyl group, or a benzyl group which may have a group selected from the group $P^3$.

5. The tetrazolinone compound according to claim 1, wherein $R^{12}$ is a C1-C6 alkyl group which may have a halogen atom(s), a C3-C6 cycloalkyl group which may have a halogen atom(s), a phenyl group, or a hydrogen atom.

6. The tetrazolinone compound according to claim 1, wherein $R^{13}$ is a C1-C6 alkyl group which may have a halogen atom(s), a C2-C6 alkenyl group, a C2-C6 alkynyl group, a benzyl group, or a C3-C6 cycloalkyl group.

7. The tetrazolinone compound according to claim 1, wherein $R^1$ is a C1-C3 alkyl group which may have a halogen atom(s) or a halogen atom;

$R^3$ is a hydrogen atom or a methyl group; and $R^6$ is a C1-C3 alkyl group which may have a halogen atom(s), a C1-C3 alkoxy group which may have a halogen atom(s), a cyclopropyl group, or a halogen atom.

8. A pest control agent comprising:

the tetrazolinone compound as defined in claim 1.

9. A pest control method comprising:

treating plants or soils with an effective amount of the tetrazolinone compound as defined in claim 1.

* * * * *